United States Patent
Lerchen et al.

(10) Patent No.: US 12,059,472 B2
(45) Date of Patent: Aug. 13, 2024

(54) PRODRUGS OF CYTOTOXIC ACTIVE AGENTS HAVING ENZYMATICALLY CLEAVABLE GROUPS

(71) Applicants: Bayer Aktiengesellschaft, Leverkusen (DE); Bayer Pharma Aktiengesellschaft, Berlin (DE)

(72) Inventors: Hans-Georg Lerchen, Leverkusen (DE); Anne-Sophie Rebstock, Champagne au Mont d'Or (FR); Leo Marx, Wuppertal (DE); Sarah Anna Liesa Johannes, Hilden (DE); Beatrix Stelte-Ludwig, Wülfrath (DE); Lisa Dietz, Wuppertal (DE); Hannah Joerissen, Heiligenhaus (DE); Christoph Mahlert, Wuppertal (DE); Simone Greven, Dormagen (DE); Anette Sommer, Berlin (DE)

(73) Assignees: BAYER AKTIENGESELLSCHAFT, Leverkusen (DE); BAYER PHARMA AKTIENGESELLSCHAFT, Berlin (DE)

( * ) Notice: Subject to any disclaimer, the term of this patent is extended or adjusted under 35 U.S.C. 154(b) by 1062 days.

(21) Appl. No.: 16/472,634

(22) PCT Filed: Dec. 18, 2017

(86) PCT No.: PCT/EP2017/083305
§ 371 (c)(1),
(2) Date: Jun. 21, 2019

(87) PCT Pub. No.: WO2018/114798
PCT Pub. Date: Jun. 28, 2018

(65) Prior Publication Data
US 2019/0351066 A1    Nov. 21, 2019

(30) Foreign Application Priority Data

Dec. 21, 2016 (EP) .................................. 16205935

(51) Int. Cl.
A61K 47/68 (2017.01)
A61K 31/402 (2006.01)
(Continued)

(52) U.S. Cl.
CPC ........ *A61K 47/6803* (2017.08); *A61K 31/402* (2013.01); *A61K 47/65* (2017.08);
(Continued)

(58) Field of Classification Search
CPC ................ A61K 47/6803; A61K 47/65; A61K 47/6849; A61K 47/6855; A61K 31/402; A61P 35/00; C07D 207/335
See application file for complete search history.

(56) References Cited

U.S. PATENT DOCUMENTS

| | | | |
|---|---|---|---|
| 4,399,216 A | 8/1983 | Axel et al. | |
| 4,474,893 A | 10/1984 | Reading | |

(Continued)

FOREIGN PATENT DOCUMENTS

| | | | | |
|---|---|---|---|---|
| CA | 2934617 | * | 7/2015 | ........... C07D 403/12 |
| CA | 3018630 A1 | | 9/2017 | |

(Continued)

OTHER PUBLICATIONS

Domain, E. (2014) Modifications of the Self-Immolative Spacer PABOH in Antibody Drug Conjugates A Major Qualifying Project Report; Worchester Polytechnic Institute pp. 1-42 (Year: 2014).*

(Continued)

*Primary Examiner* — Scarlett Y Goon
*Assistant Examiner* — Audrey L Buttice
(74) *Attorney, Agent, or Firm* — WILSON SONSINI GOODRICH & ROSATI

(57) ABSTRACT

The invention relates to novel prodrugs or conjugates of the general formula (Ia)

(Continued)

in which La, n, R and D have the definitions given in the description and which have a structural motif reduced to an asparagine derivative as cleavage site for tumour-associated proteases such as legumain, in which cytotoxic drugs, for example kinesin spindle protein inhibitors, are released by legumain cleavage, and to the use of these prodrugs or conjugates for treatment and/or prevention of diseases, and to the use of these prodrugs or conjugates for production of medicaments for treatment and/or prevention of diseases, especially of hyperproliferative and/or angiogenic disorders, for example cancers. Reduction of the legumain-cleavable substrate peptide sequence to an asparagine derivative as structural motif, as a result of slowed legumain cleavage, achieves an increase in stability in the lysosomes of healthy organs while simultaneously maintaining the high anti-tumour effect.

15 Claims, 31 Drawing Sheets

Specification includes a Sequence Listing.

(51) Int. Cl.
*A61K 47/65* (2017.01)
*A61P 35/00* (2006.01)
*C07D 207/335* (2006.01)

(52) U.S. Cl.
CPC ...... *A61K 47/6849* (2017.08); *A61K 47/6855* (2017.08); *A61P 35/00* (2018.01); *C07D 207/335* (2013.01)

(56) References Cited

U.S. PATENT DOCUMENTS

| | | |
|---|---|---|
| 4,510,245 A | 4/1985 | Cousens et al. |
| 4,634,665 A | 1/1987 | Axel et al. |
| 4,714,681 A | 12/1987 | Reading |
| 4,816,397 A | 3/1989 | Boss et al. |
| 4,816,567 A | 3/1989 | Cabilly et al. |
| 4,925,648 A | 5/1990 | Hansen et al. |
| 4,968,615 A | 11/1990 | Koszinowski et al. |
| 5,168,062 A | 12/1992 | Stinski |
| 5,179,017 A | 1/1993 | Axel et al. |
| 5,270,163 A | 12/1993 | Gold et al. |
| 5,573,920 A | 11/1996 | Randle |
| 5,601,819 A | 2/1997 | Wong et al. |
| 6,177,078 B1 | 1/2001 | Lopez |
| 7,318,924 B2 | 1/2008 | McKenzie et al. |
| 7,465,449 B2 | 12/2008 | Violette et al. |
| 7,598,350 B2 | 10/2009 | Liu et al. |
| 7,628,986 B2 | 12/2009 | Weber et al. |
| 8,470,330 B2 | 6/2013 | Maddon et al. |
| 10,022,453 B2 | 7/2018 | Lerchen et al. |
| 10,485,880 B2 | 11/2019 | Lerchen et al. |
| 10,744,205 B2 | 8/2020 | Lerchen et al. |
| 10,973,923 B2 | 4/2021 | Lerchen et al. |
| 11,478,554 B2 | 10/2022 | Lerchen et al. |
| 2007/0264253 A1 | 11/2007 | Liu et al. |
| 2009/0175796 A1 | 7/2009 | Raitano et al. |
| 2010/0028947 A1 | 2/2010 | Goletz et al. |
| 2015/0343083 A1 | 12/2015 | Chu |
| 2018/0169256 A1 | 6/2018 | Lerchen |
| 2019/0077752 A1 | 3/2019 | Lerchen et al. |
| 2019/0328897 A1 | 10/2019 | Lerchen et al. |
| 2019/0330357 A1 | 10/2019 | Lerchen et al. |
| 2019/0365916 A1 | 12/2019 | Lerchen et al. |
| 2020/0138970 A1 | 5/2020 | Lerchen et al. |
| 2021/0015806 A1 | 1/2021 | Scholz |
| 2021/0230284 A1 | 7/2021 | Lerchen et al. |
| 2021/0386864 A1 | 12/2021 | Lerchen et al. |
| 2022/0267457 A1 | 8/2022 | Lerchen et al. |
| 2022/0362392 A1 | 11/2022 | Lerchen et al. |
| 2023/0338559 A1 | 10/2023 | Lerchen et al. |
| 2023/0399411 A1 | 12/2023 | Lerchen et al. |
| 2024/0043379 A1 | 2/2024 | Lerchen et al. |

FOREIGN PATENT DOCUMENTS

| | | |
|---|---|---|
| EP | 0719859 A1 | 7/1996 |
| EP | 1735348 A1 | 12/2006 |
| EP | 1900750 A1 | 3/2008 |
| EP | 1911766 A1 | 4/2008 |
| EP | 2073842 A2 | 7/2009 |
| EP | 2121008 A2 | 11/2009 |
| EP | 2426148 B1 | 8/2015 |
| EP | 3184540 A1 | 6/2017 |
| WO | WO-9000786 A1 | 1/1990 |
| WO | WO-9100360 A1 | 1/1991 |
| WO | WO-9105871 A1 | 5/1991 |
| WO | WO-9205793 A1 | 4/1992 |
| WO | WO-9208802 A1 | 5/1992 |
| WO | WO-9215683 A1 | 9/1992 |
| WO | WO-9317715 A1 | 9/1993 |
| WO | WO-9708320 A1 | 3/1997 |
| WO | WO-9735616 A1 | 10/1997 |
| WO | WO-9947554 A1 | 9/1999 |
| WO | WO-0109192 A1 | 2/2001 |
| WO | WO-0162931 A2 | 8/2001 |
| WO | WO-0188138 A1 | 11/2001 |
| WO | WO-0212501 A2 | 2/2002 |
| WO | WO-02077033 A1 | 10/2002 |
| WO | WO-02088170 A2 | 11/2002 |
| WO | WO-02092771 A2 | 11/2002 |
| WO | WO-02100348 A1 | 12/2002 |
| WO | WO-03034903 A2 | 5/2003 |
| WO | WO-03083041 A2 | 10/2003 |
| WO | WO-03106495 A2 | 12/2003 |
| WO | WO-2004056847 A2 | 7/2004 |
| WO | WO-2004091375 A2 | 10/2004 |
| WO | WO-2005009369 A2 | 2/2005 |
| WO | WO-2005010151 A2 | 2/2005 |
| WO | WO-2005056606 A2 | 6/2005 |
| WO | WO-2005081711 A2 | 9/2005 |
| WO | WO-2005081854 A2 | 9/2005 |
| WO | WO-2005090407 A2 | 9/2005 |
| WO | WO-2006062779 A2 | 6/2006 |
| WO | WO-2006074418 A2 | 7/2006 |
| WO | WO-2006089232 A2 | 8/2006 |
| WO | WO-2007002222 A2 | 1/2007 |
| WO | WO-2007024536 A2 | 3/2007 |
| WO | WO-2007038637 A2 | 4/2007 |
| WO | WO2007064759 A2 | 6/2007 |
| WO | WO-2007070538 A2 | 6/2007 |
| WO | WO-2008004834 A1 | 1/2008 |
| WO | WO-2008028686 A2 | 3/2008 |
| WO | WO-2008031056 A2 | 3/2008 |
| WO | WO-2008036688 A2 | 3/2008 |
| WO | WO-2008047242 A2 | 4/2008 |
| WO | WO-2008070593 A2 | 6/2008 |
| WO | WO-2008092117 A2 | 7/2008 |
| WO | WO-2008140603 A2 | 11/2008 |
| WO | WO-2009020933 A2 | 11/2008 |
| WO | WO-2009023265 A2 | 2/2009 |
| WO | WO-2009026274 A1 | 2/2009 |
| WO | WO-2009032661 A1 | 3/2009 |
| WO | WO-2009033094 A2 | 3/2009 |
| WO | WO-2009068204 A1 | 6/2009 |
| WO | WO-2009070844 A1 | 6/2009 |
| WO | WO-2009080829 A1 | 7/2009 |
| WO | WO-2009080830 A1 | 7/2009 |
| WO | WO-2009123894 A2 | 10/2009 |
| WO | WO-2009140177 A2 | 11/2009 |
| WO | WO-2010022736 A2 | 3/2010 |
| WO | WO-2010112413 A1 | 10/2010 |
| WO | WO-2011009400 A1 | 1/2011 |
| WO | WO-2011044368 A1 | 4/2011 |
| WO | WO-2012021934 A1 | 2/2012 |
| WO | WO-2012112363 A1 | 8/2012 |
| WO | WO-2012143499 A2 | 10/2012 |
| WO | WO-2013076186 A1 | 5/2013 |

(56) References Cited

FOREIGN PATENT DOCUMENTS

| WO | WO-2013092983 A2 | 6/2013 |
| WO | WO-2013092998 A1 | 6/2013 |
| WO | WO-2014061277 A1 | 4/2014 |
| WO | WO-2014198817 A1 | 12/2014 |
| WO | WO-2015096982 A1 | 7/2015 |
| WO | WO-2015189143 A1 | 12/2015 |
| WO | WO2016026458 A1 | 2/2016 |
| WO | WO2016096610 A1 | 6/2016 |
| WO | WO2016207089 A1 | 12/2016 |
| WO | WO2016207090 A2 | 12/2016 |
| WO | WO2017162663 A1 | 9/2017 |
| WO | WO-2018114798 A1 | 6/2018 |
| WO | WO-2019243159 A1 | 12/2019 |

OTHER PUBLICATIONS

Poreba, M., et al.(2016) Counter Selection Substrate Library Strategy for Developing Specific Protease Substrates and Probes Cell Chem Biol 23(8); 1023-1035 (Year: 2016).*

Sexton, K.B., et al.(2007) Design of cell-permeable, fluorescent activity-based probes for the lysosomal cysteine protease asparaginyl endopeptidase (AEP)/legumain Bioorganic & Medicinal Chemistry Letters 17; 649-653 (Year: 2007).*

Agarwal et al. Site-specific antibody-drug conjugates: the nexus of bioorthogonal chemistry, protein engineering, and drug development. Bioconjug. Chem. 26:176-192 (2015).

Ahrens et al. Peptides and peptide conjugates: therapeutics on the upward path. Future Med. Chem. 4:1567-1586 (2012).

Amir et al. Prodrug activation gated by a molecular "OR" logic trigger. Angew Chem. Inter. Ed. 44:4378-4381 (2005).

Bebbington et al. High-level expression of a recombinant antibody from myeloma cells using a glutamine synthetase gene as an amplifiable selectable marker. Biotechnology 10(2):169-75 (1992).

Beck et al. Strategies and challenges for the next generation of antibody—drug conjugates. Nature Reviews. Drug Discovery 16(5):315-337. (2017).

Behrens, et al. Methods for site-specific drug conjugation to antibodies. MAbs. Jan.-Feb. 2014;6(1):46-53.

Bencharit et al. Structural insights into CPT-11 activation by mammalian carboxylesterases. Nat. Struct. Biol., 9:337-342 (2002).

Berger. Isolation of Cytoplamic RNA: Ribonucleoside-Vanadyl Complexes. Methods in Enzymology 152:227-234 (1987).

Böhme. Drug delivery and release systems for targetd tumor therapy. J. Pept. Sci. 21:186-200 (2015).

Boger, CBI Prodrug Analogs of CC-1065 and the Duocarmycins. Synthesis 1999(S1):1505-1509 (1999).

Cal et al. Cysteine-selective reactions for antibody conjugation. Angewandte Chemi International Edition 53:10585-10587 (2014).

Chen et al. Cloning, isolation, and characterization of mammalian legumain, an asparaginyl endopeptidase. J. Biol. Chem. 272:8090-8098 (1997).

Chothia et al. Canonical structures for the hypervariable regions of immunoglobulins. J Mol Biol 196:901-917 (1987).

Clackson et al. Making antibody fragments using phage display libraries. Nature 352(6336):624-628 (1991).

Co-pending U.S. Appl. No. 17/166,713, inventors Lerchen; Hans-Georg et al., filed Mar. 3, 2021.

Co-pending U.S. Appl. No. 17/253,086, inventors Johannes; Sarah Anna Liesa et al., filed Dec. 16, 2020.

Co-pending U.S. Appl. No. 17/374,756, inventors Lerchen; Hans-Georg et al., filed Jul. 13, 2021.

Damen et al. Synthesis of novel paclitaxel prodrugs designed for bioreductive activation in hypoxic tumour tissue. Bioorg. Med. Chem. 10:71-77 (2002).

Dennler et al. Chapter 12: Antibody Drug Conjuagtes (Ducry, L., Ed.), pp. 205-215, Humana Press. (2013).

Deshmukh et al., A Series of α-Amino Acid Ester Prodrugs of Camptothecin: In Vitro Hydrolysis and A549 Human Lung Carcinoma Cell Cytotoxicity. J Med Chem 53(3): 1043; 1038-1047 (2010).

Doronina et al. Development of potent monoclonal antibody auristatin conjugates for cancer therapy. Nat Biotechnol 21:778-784 (2003).

Dorsch et al. Identification and optimization of pyridazinones as potent and selective c-Met kinase inhibitors. Bioorg. Med. Chem. Lett. 7:1597-1602 (1999).

Dubowchik et al. Cathepsin B-labile dipeptide linkers for lysosomal release of doxorubicin from internalizing immunoconjugates: model studies of enzymatic drug release and antigen-specific in vitro anticancer activity. Bioconjugate Chem. 13:855-869 (2002).

Dubowchik et al. Cathepsin B-sensitive dipeptide prodrugs. 1. A model study of structural requirements for efficient release of doxorubicin. Bioorg Med Chem Lett 8:3341-3346 (1998).

Ducry et al. Antibody-drug conjugates: linking cytotoxic payloads to monoclonal antibodies. Bioconjug Chem. 21(1):5-13 (2010).

Durocher et al., High-level and high-throughput recombinant protein production by transient transfection of suspension-growing human HEK293-EBNA1 cells. Nucleic acids research, 30(2):e9 (2002).

Fan et al. Improving the efficiency of CHO cell line generation using glutamine synthetase gene knockout cells. Biotechnol Bioeng. 109(4):1007-15 (2012).

Gebauer et al. Engineered protein scaffolds as next-generation antibody therapeutics. Curr. Opinion in Chem. Biol. 13:245-255 (2009).

Gruendker et al. Effective targeted chemotherapy using AEZS-108 (AN-152) for LHRH receptor-positive pancreatic cancers. Oncology Reports 26:629-635 (2011).

Harlow, et al. Using Antibodies: A Laboratory Manual. Cold Spring Harbor Laboratory, Cold Spring Harbor, N.Y. 1999.

Ishii. Legumain: asparaginyl endopeptidase . Methods Enzymol. 244:604-615 (1994).

Jeger et al. Site-specific and stoichiometric modification of antibodies by bacterial transglutaminase. Ange Chem Int. Ed. Engl 49:9995-9997 (2010).

Jeger, S., Site-specific conjugation of tumour-targeting antibodies using transglutaminase. PhD Thesis, Univ. Zurich (2009).

Josten et al. Use of microbial transglutaminase for the enzymatic biotinylation of antibodies. J. Immunol. Methods 240:47-54 (2000).

Junutula et al. Site-specific conjugation of a cytotoxic drug to an antibody improves the therapeutic index. Nat Biotechnol. 26(8):925-32 (2008).

Kabat et al. Sequences of proteins of immunological interest. NIH Publ. No. 91-3242 1:647-669 (1991).

Kaufman, et al. Amplification and expression of sequences cotransfected with a modular dihydrofolate reductase complementary dna gene. J Mol Biol. Aug. 25, 1982;159(4):601-21.

Keefe et al. Aptamers as therapeutics. Nat. Rev. Drug Discov. 9:537-550 (2010).

Kim et al. Genipin Enhances the Therapeutic Effects of Oxaliplatin by Upregulating BIM in Colorectal Cancer. Mol. Cancer. Ther. 4:751-761 (2005).

Kohchi et al. Design and synthesis of novel prodrugs of 2'-deoxy-2'-methylidenecytidine activated by membrane dipeptidase overexpressed in tumor tissues. Bioorg. Med. Chem. Lett. 17:2241-2245 (2007).

Kostelny et al. Formation of a bispecific antibody by the use of leucine zippers. J. Immunol. 148(5):1547-1553 (1992).

Kumar et al. Modulating paclitaxel bioavailability for targeting prostate cancer. Bioorg. Med. Chem. 15:4973-4984 (2007).

Kuo et al. Antibody internalization after cell surface antigen binding is critical for immunotoxin development. Bioconjug Chem. 20(10):1975-82 (2009).

Lai et al. Molecular basis of prodrug activation by human valacyclovirase, an alpha-amino acid ester hydrolase. J. Biol. Chem. 283:9318-9327 (2008).

Lang et al. Cellular Incorporation of Unnatural Amino Acids and Bioorthogonal Labeling of Proteins, Chem.Rev. 114:4764-4806 (2014).

Langer et al. Novel peptide conjugates for tumor-specific chemotherapy. J. Med. Chem. 44:1341-1348 (2001).

(56) References Cited

OTHER PUBLICATIONS

Lhospice et al. Site-Specific Conjugation of Monomethyl Auristatin E to Anti-CD30 Antibodies Improves Their Pharmacokinetics and Therapeutic Index in Rodent Models. Mol Pharm 12:1863-1871 (2015).
Lonberg et al. Human antibodies from transgenic mice. Int Rev Immunol. 13(1):65-93 (1995).
Maltais et al. In vitro and in vivo isotope effects with hepatitis C protease inhibitors: enhanced plasma exposure of deuterated telaprevir versus telaprevir in rats. J. Med. Chem. 52:7993 (2009).
Mindt et al. Modification of different IgG1 antibodies via glutamine and lysine using bacterial and human tissue transglutaminase. Bioconjugate Chem. 19:271-278 (2008).
Nakayama et al. Characterization of murine TWEAK and its receptor (Fn14) by monoclonal antibodies. Biochem Biophy Res Comm 306:819-825 (2003).
Nuttall et al. Display scaffolds: protein engineering for novel therapeutics. Curr. Opinion in Pharmacology 8:609-615 (2008).
Olsson et al. Human-human monoclonal antibody-producing hybridomas: Technical aspects. Meth Enzymol. 92:3-16 (1983).
Panowski et al. Site-specific antibody drug conjugates for cancer therapy MAbs 6:34-45 (2014).
Peterson et al. Cathepsin substrates as cleavable peptide linkers in bioconjugates, selected from a fluorescence quench combinatorial library. Bioconjugate Chem. 9:618-626 (1998).
Polson et al. Antibody-drug conjugates for the treatment of non-Hodgkin's lymphoma: target and linker-drug selection. Cancer Res. 69(6):2358-64 (2009).
Polson et al. Antibody-drug conjugates targeted to CD79 for the treatment of non-Hodgkin lymphoma. Blood 110(2):616-623 (2007).
Queen et al. A humanized antibody that binds to the interleukin 2 receptor. PNAS USA 86:10029-10032 (1989).
Rashidian et al. Enzymatic labeling of proteins: techniques and approaches. Bioconjugate Chem. 24:1277-1294 (2013).
Rawale et al. Synthesis and biological activity of the prodrug of class I major histocompatibility peptide GILGFVFTL activated by beta-glucuronidase. J. Med. Chem. 45:937-943 (2002).
Rosman et al., Isotopic composition of the elements 1997. Pure and Applied Chemistry 70(1):217-235 (1998).
Schinkel et al. Absence of the mdr1a P-Glycoprotein in mice affects tissue distribution and pharmacokinetics of dexamethasone, digoxin, and cyclosporin A. J. Clin. Invest. 96:1698-1705 (1995).
SSchmidt et al. Prodrug Mono Therapy: synthesis and biological evaluation of an etoposide glucuronide-prodrug. Bioorg. Med. Chem. 11:2277-2283 (2003).
Schwab et al. Comparison of in vitro P-glycoprotein screening assays: recommendations for their use in drug discovery. J. Med. Chem. 46:1716-1725 (2003).
Söderlind et al. Recombining germline-derived CDR sequences for creating diverse single-framework antibody libraries. Nature Biotechnology 18:852-856 (Aug. 1, 2000).
Sharma et al. Nevirapine bioactivation and covalent binding in the skin. Chem. Res. Toxicol. 26:410-421 (2013).
Sochaj et al. Current methods for the synthesis of homogeneous antibody-drug conjugates. Biotechnology Advances 33:775-784 (2015).
Soudy et al. Novel peptide-doxorubicin conjugates for targeting breast cancer cells including the multidrug resistant cells. J. Med. Chem. 56:7564-7573 (2013).
Stern, L. et al., A novel antitumor prodrug platform designed to be cleaved by the endoprotease legumain, Bioconj. Chem., 20: 500-510 (2009).
Strop et al. Location matters: site of conjugation modulates stability and pharmacokinetics of antibody drug conjugates. Chem Biol 20(2):161-167 (2013).
Sun et al. Monoclonal antibody 7G3 recognizes the N-terminal domain of the human interleukin-3 (IL-3) receptor alpha-chain and functions as a specific IL-3 receptor antagonist. Blood 87(1):83-92 (1996).
Tai et al. Development of a peptide-drug conjugate for prostate cancer therapy. Molecular Pharmaceutics, vol. 8, No. 3, pp. 901-912, Jun. 6, 2011.
Tom et al. Transient expression in HEK293-EBNA1 cells, in Expression Systems: Methods Express, Dyson, M.R. et al. eds., Scion Publishing Ltd.: Oxfordshire, pp. 204-223 (2007).
Tranoy-Opalinski et al. Design of self-immolative linkers for tumour-activated prodrug therapy. Anticancer Agents in Medicinal Chemistry 8:618-637 (2008).
Troutman et al. Novel experimental parameters to quantify the modulation of absorptive and secretory transport of compounds by P-glycoprotein in cell culture models of intestinal epithelium. Pharm. Res. 20(8):1210-1224 (2003).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Ueki et al. Selective cancer targeting with prodrugs activated by histone deacetylases and a tumour-associated protease. Nat. Commun. 4:2735 (2013).
Umlauf et al. Identification of a novel lysosomal trafficking peptide using phage display biopanning coupled with endocytic selection pressure. Bioconjug Chem 25(10):1829-37 (2014).
Urlaub et al. Deletion of the diploid dihydrofolate reductase locus from cultured mammalian cells. Cell 33(2):405-12 (1983).
Urlaub et al. Isolation of Chinese hamster cell mutants deficient in dihydrofolate reductase activity, PNAS USA 77:4216-4220 (1980).
Wenthur et al. Discovery of (R)-(2-fluoro-4-((-4-methoxyphenyl)ethynyl)phenyl) (3-hydroxypiperidin-1-yl)methanone (ML337), an mGlu3 selective and CNS penetrant negative allosteric modulator (NAM). J. Med. Chem. 56:5208-5212 (2013).
Wu et al. Targeting cell-impermeable prodrug activation to tumor microenvironment eradicates multiple drug-resistant neoplasms. Cancer Res. 66:970-980 (2006).
Zhou et al. The TWEAK Receptor Fn14 is a Novel Therapeutic Target in Melanoma: Immunotoxins Targeting Fn14 Receptor for Malignant Melanoma Treatment. J. Invest Dermatol. 133(4):1052-1062 (2013).
Bajjuri, K. et al. (2011). "The Legumain Protease-Activated Auristatin Prodrugs Suppress Tumor Growth and Metastasis without Toxicity," Chem Med Chem 6(1):54-59.
International Search Report and Written Opinion dated Apr. 19, 2018, for International Application No. PCT/EP2017/083305, filed Dec. 18, 2017 10 pages.
Liu Y. et al. (Jan. 1, 2012) "Targeting Cell Surface Alpha(v)beta(3) Integrins Increases Therapeutic Efficacies of a Legumain Protease-Activated Auristatin Prodrug," Mol. Pharm. 9(1):168-175.
Wang Y. et al. (2014) "Protease-Activatable Hybrid Nanoprobe for Tumor Imaging," Adv. Funct. Mater. 24:5443-5453.
El Tayar et al. The lipophilicity of deuterium atoms. A comparison of shake-flask and HPLC methods. Int. J. Pharm. 19(3):271-281 (1984).
Lerchen et al. Tailored Linker Chemistries for the Efficient and Selective Activation of ADCs with KSPi Payloads. Bioconjug Chem. 31(8):1893-1898 (2020).
Mutlib et al. The species-dependent metabolism of efavirenz produces a nephrotoxic glutathione conjugate in rats. Toxicol. Appl. Pharmacol. 169:102-113 (2000).
Perrin et al. Secondary deuterium isotope effects on the acidity of carboxylic acids and phenols. J. Am. Chem. Soc. 129:4490-4497 (2007).
Perrin et al. Stereochemistry of beta-deuterium isotope effects on amine basicity. J. Am. Chem. Soc. 127:9641-9647 (2005).
Schmeider et al. Enhanced plasma concentration by selective deuteration of rofecoxib in rats. Arzneimittelforschung 56:295-300 (2006).
Velikyan et al. Convenient preparation of 68Ga-based PET-radiopharmaceuticals at room temperature. Bioconjug Chem 19:569-578 (2014).
Co-pending U.S. Appl. No. 17/812,095, inventors Lerchen; Hans-Georg et al., filed Jul. 12, 2022.

(56) References Cited

OTHER PUBLICATIONS

Ruan et al. Synthesis and Antitumor Activity Study of Tetrahydrocarboline Kinesin Spindle Protein Inhibitors. Acta Pharmaceutica Sinica 48(7):1119-1123 (2013) (Abstract Only).
Co-pending U.S. Appl. No. 18/175,265, inventors Lerchen; Hans-Georg et al., filed Feb. 27, 2023.
Co-pending U.S. Appl. No. 18/182,093, inventors Lerchen; Hans-Georg et al., filed Mar. 10, 2023.

* cited by examiner

Fig. 2A

```
>TPP-981 VH (PRT)
QVQLKQSGPGLVQPSQSLSITCTVSGFSLTNYGVHWVRQSPGKGLEWLGVIWSGGNTDYNTPFTSRLSINKDNSKSQVFF
                           |---|                  |----HCDR2-----|
                           HCDR1

KMNSLQSNDTAIYYCARALTYYDYEFAYWGQGTLVTVSA
              |--HCDR3--|

>TPP-981 VL (PRT)
DILLTQSPVILSVSPGERVSFSCRASQSIGTNIHWYQQRTNGSPRLLIKYASESISGIPSRFSGSGSGTDFTLSINSVES
                         |--LCDR1--|              |-----|
                                                    LCDR2

EDIADYYCQQNNNWPTTFGAGTKLELK
         |-LCDR3-|

>TPP-981 Heavy Chain (PRT)
QVQLKQSGPGLVQPSQSLSITCTVSGFSLTNYGVHWVRQSPGKGLEWLGVIWSGGNTDYNTPFTSRLSINKDNSKSQVFF
|----------------------------------------------------VH--------------------
                           |---|                  |----HCDR2-----|
                           HCDR1

KMNSLQSNDTAIYYCARALTYYDYEFAYWGQGTLVTVSASTKGPSVFPLAPSSKSTSGGTAALGCLVKDYFPEPVTVSW
-----------------------------------------|
              |--HCDR3--|

NSGALTSGVHTFPAVLQSSGLYSLSSVVTVPSSSLGTQTYICNVNHKPSNTKVDKRVEPKSCDKTHTCPPCPAPELLGGP

SVFLFPPKPKDTLMISRTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWESNGQPENNYKTTPPVL

DSDGSFFLYSKLTVDKSRWQQGNVFSCSVMHEALHNHYTQKSLSLSPGK

>TPP-981 Light Chain (PRT)
DILLTQSPVILSVSPGERVSFSCRASQSIGTNIHWYQQRTNGSPRLLIKYASESISGIPSRFSGSGSGTDFTLSINSVES
|----------------------------------------------VL--------------------------
                         |--LCDR1--|              |-----|
                                                    LCDR2

EDIADYYCQQNNNWPTTFGAGTKLELKRTVAAPSVFIFPPSDEQLKSGTASVVCLLNNFYPREAKVQWKVDNALQSGNSQ
--------------------------|
         |-LCDR3-|

ESVTEQDSKDSTYSLSSTLTLSKADYEKHKVYACEVTHQGLSSPVTKSFNRGEC
```

Fig. 2B

```
>TPP-1015 VH (PRT)
EVQLVESGGGLVQPGGSLRLSCAASGFNIKDTYIHWVRQAPGKGLEWVARIYPTNGYTRYADSVKGRFTISADTSKNTAY
                              |---|              |-----HCDR2-----|
                              HCDR1

LQMNSLRAEDTAVYYCSRWGGDGFYAMDYWGQGTLVTVSS
                |--HCDR3--|

>TPP-1015 VL (PRT)
DIQMTQSPSSLSASVGDRVTITCRASQDVNTAVAWYQQKPGKAPKLLIYSASFLYSGVPSRFSGSRSGTDFTLTISSLQP
                     |--LCDR1--|             |-----|
                                              LCDR2

EDFATYYCQQHYTTPPTFGQGTKVEIK
        |-LCDR3-|

>TPP-1015 Heavy Chain (PRT)
EVQLVESGGGLVQPGGSLRLSCAASGFNIKDTYIHWVRQAPGKGLEWVARIYPTNGYTRYADSVKGRFTISADTSKNTAY
|------------------------------------------------------------VH----------------
                              |---|              |-----HCDR2-----|
                              HCDR1

LQMNSLRAEDTAVYYCSRWGGDGFYAMDYWGQGTLVTVSSASTKGPSVFPLAPSSKSTSGGTAALGCLVKDYFPEPVTVS
----------------------------------------|
                |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK
```

Fig. 2C

```
>TPP-1015 Light Chain (PRT)
DIQMTQSPSSLSASVGDRVTITCRASQDVNTAVAWYQQKPGKAPKLLIYSASFLYSGVPSRFSGSRSGTDFTLTISSLQP
|------------------------------------------------VL--------------------------
                   |--LCDR1--|                       |-----|
                                                      LCDR2

EDFATYYCQQHYTTPPTFGQGTKVEIKRTVAAPSVFIFPPSDEQLKSGTASVVCLLNNFYPREAKVQWKVDNALQSGNSQ
------------------------|
         |-LCDR3-|

ESVTEQDSKDSTYSLSSTLTLSKADYEKHKVYACEVTHQGLSSPVTKSFNRGEC

>TPP-2090 VH (PRT)
EVQLLESGGGLVQPGGSLRLSCAASGFTFSPYPMIWVRQAPGKGLEWVSYISPSGGSTHYADSVKGRFTISRDNSKNTLY
                          |---|                  |-----HCDR2-----|
                          HCDR1

LQMNSLRAEDTAVYYCARGGDTYFDYFDYWGQGTLVTVSS
             |--HCDR3--|

>TPP-2090 VL (PRT)
DIQMTQSPSSLSASVGDRVTITCRASQSISGYLNWYQQKPGKAPKLLIYQASSLQSGVPSRFSGSGSGTDFTLTISSLQP
                   |--LCDR1--|                       |-----|
                                                      LCDR2

EDFATYYCQQSYTSPFITFGQGTKVEIK
        |-LCDR3--|

>TPP-2090 Heavy Chain (PRT)
EVQLLESGGGLVQPGGSLRLSCAASGFTFSPYPMIWVRQAPGKGLEWVSYISPSGGSTHYADSVKGRFTISRDNSKNTLY
|------------------------------------------------VH--------------------------
                          |---|                  |-----HCDR2-----|
                          HCDR1

LQMNSLRAEDTAVYYCARGGDTYFDYFDYWGQGTLVTVSSASTKGPSVFPLAPSSKSTSGGTAALGCLVKDYFPEPVTVS
-----------------------------------------|
             |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPGK
```

Fig. 2D

```
>TPP-2090 Light Chain (PRT)
DIQMTQSPSSLSASVGDRVTITCRASQSISGYLNWYQQKPGKAPKLLIYQASSLQSGVPSRFSGSGSGTDFTLTISSLQP
|-------------------------------------------------VL--------------------------
                        |--LCDR1--|                      |-----|
                                                         LCDR2

EDFATYYCQQSYTSPFITFGQGTKVEIKRTVAAPSVFIFPPSDEQLKSGTASVVCLLNNFYPREAKVQWKVDNALQSGNS
--------------------------|
        |-LCDR3--|

QESVTEQDSKDSTYSLSSTLTLSKADYEKHKVYACEVTHQGLSSPVTKSFNRGEC

>TPP-2658 VH (PRT)
EVQLLESGGGLVQPGGSLRLSCAASGFTFSPYPMIWVRQAPGKGLEWVSYISPSGGSTHYADSVKGRFTISRDNSKNTLY
                        |---|                  |-----HCDR2-----|
                        HCDR1

LQMNSLRAEDTAVYYCARGGDTYFDYFDYWGQGTLVTVSS
            |--HCDR3--|

>TPP-2658 VL (PRT)
DIQMTQSPSSLSASVGDRVTITCRASQSISGYLNWYQQKPGKAPKLLIYQASSLQSGVPSRFSGSGSGTDFTLTISSLQP
                        |--LCDR1--|                      |-----|
                                                          LCDR2

EDFATYYCQQSYTSPFITFGQGTKVEIK
        |-LCDR3--|
```

Fig. 2E

```
>TPP-2658 Heavy Chain (PRT)
EVQLLESGGGLVQPGGSLRLSCAASGFTFSPYPMIWVRQAPGKGLEWVSYISPSGGSTHYADSVKGRFTISRDNSKNTLY
|----------------------------------------------------------------VH--------------------
                          |---|                         |------HCDR2-----|
                          HCDR1

LQMNSLRAEDTAVYYCARGGDTYFDYFDYWGQGTLVTVSSASTKGPSVFPLAPSSKSTSGGTAALGCLVKDYFPEPVTVS
---------------------------------------|
             |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-2658 Light Chain (PRT)
DIQMTQSPSSLSASVGDRVTITCRASQSISGYLNWYQQKPGKAPKLLIYQASSLQSGVPSRFSGSGSGTDFTLTISSLQP
|-----------------------------------------------------------VL--------------------------
                     |--LCDR1--|                        |-----|
                                                         LCDR2

EDFATYYCQQSYTSPFITFGQGTKVEIKRTVAAPSVFIFPPSDEQLKSGTASVVCLLNNFYPREAKVQWKVDNALQSGNS
-------------------------------|
         |-LCDR3--|

QESVTEQDSKDSTYSLSSTLTLSKADYEKHKVYACEVTHQGLSSPVTKSFNRGEC

>TPP-5442 VH (PRT)
EVQLLESGGGLVQPGGSLRLSCAASGFTFSPYPMIWVRQAPGKGLEWVSYISPSGGSTHYADSVKGRFTISRDNSKNTLY
                          |---|                         |-----HCDR2-----|
                          HCDR1

LQMNSLRAEDTAVYYCARGGDTYFDYFDYWGQGTLVTVSS
             |--HCDR3--|
```

Fig. 2F

```
>TPP-5442 VL (PRT)
DIQMTQSPSSLSASVGDRVTITCRASQSISGYLNWYQQKPGKAPKLLIYQASSLQSGVPSRFSGSGSGTDFTLTISSLQP
                        |--LCDR1--|                    |-----|
                                                        LCDR2

EDFATYYCQQSYTSPFITFGQGTKVEIK
        |-LCDR3--|

>TPP-5442 Heavy Chain (PRT)
EVQLLESGGGLVQPGGSLRLSCAASGFTFSPYPMIWVRQAPGKGLEWVSYISPSGGSTHYADSVKGRFTISRDNSKNTLY
|------------------------------------------------------VH------------------
                         |---|               |-----HCDR2-----|
                         HCDR1

LQMNSLRAEDTAVYYCARGGDTYFDYFDYWGQGTLVTVSSASTKGPSVFPLAPSSKSTSGGTAALGCLVKDYFPEPVTVS
-------------------------------------|
           |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYQSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-5442 Light Chain (PRT)
DIQMTQSPSSLSASVGDRVTITCRASQSISGYLNWYQQKPGKAPKLLIYQASSLQSGVPSRFSGSGSGTDFTLTISSLQP
|-----------------------------------------------------VL------------------
                        |--LCDR1--|                    |-----|
                                                        LCDR2

EDFATYYCQQSYTSPFITFGQGTKVEIKRTVAAPSVFIFPPSDEQLKSGTASVVCLLNNFYPREAKVQWKVDNALQSGNS
---------------------------|
        |-LCDR3--|

QESVTEQDSKDSTYSLSSTLTLSKADYEKHKVYACEVTHQGLSSPVTKSFNRGEC
```

Fig. 2G

```
>TPP-7006 VH (PRT)
QVQLQQSGPELVKPGASVKMSCKASGYTFTDFIIAWVKQRTGQGLEWIGEIYPGTGRTYYSEKFRGKATLTADKSSNTAY
                         |---|                   |-----HCDR2-----|
                         HCDR1

MQLSSLTSVDSAVYFCARRTIYYDYDGDYWGQGTTLTVSS
              |--HCDR3--|

>TPP-7006 VL (PRT)
DIVMTQAAFSNPVTLGTSASISCRSSKSLLHSNGITYLYWYLQKPGQSPQLLIYQMSNLASGVPDRFSSSGSGTDFTLRI
                     |----LCDR1-----|                        |-----|
                                                                LCDR2

SRVEAEDVGVYYCAHNLELPWTFGGGTKLELK
            |-LCDR3-|

>TPP-7006 Heavy Chain (PRT)
QVQLQQSGPELVKPGASVKMSCKASGYTFTDFIIAWVKQRTGQGLEWIGEIYPGTGRTYYSEKFRGKATLTADKSSNTAY
|---------------------------------------------------------------VH----------------
                         |---|                   |-----HCDR2-----|
                         HCDR1

MQLSSLTSVDSAVYFCARRTIYYDYDGDYWGQGTTLTVSSASTKGPSVFPLAPSSKSTSGGTAALGCLVKDYFPEPVTVS
----------------------------------------|
              |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-7006 Light Chain (PRT)
DIVMTQAAFSNPVTLGTSASISCRSSKSLLHSNGITYLYWYLQKPGQSPQLLIYQMSNLASGVPDRFSSSGSGTDFTLRI
|---------------------------------------------------------------VL----------------
                     |----LCDR1-----|                        |-----|
                                                                LCDR2

SRVEAEDVGVYYCAHNLELPWTFGGGTKLELKRTVAAPSVFIFPPSDEQLKSGTASVVCLLNNFYPREAKVQWKVDNALQ
-------------------------------|
            |-LCDR3-|

SGNSQESVTEQDSKDSTYSLSSTLTLSKADYEKHKVYACEVTHQGLSSPVTKSFNRGEC
```

Fig. 2H

```
>TPP-7007 VH (PRT)
QVQLVQSGAEVKKPGASVKVSCKASGYTFTDFIIAWVKQAPGQGLEWIGEIYPGTGRTYYSEKFRGKATLTADTSTSTAY
                          |---|                 |-----HCDR2-----|
                          HCDR1

MELSSLRSEDTAVYFCARRTIYYDYDGDYWGQGTLVTVSS
                |--HCDR3--|

>TPP-7007 VL (PRT)
DIVMTQSPLSLPVTPGEPASISCRSSKSLLHSNGITYLYWYLQKPGQSPQLLIYQMSNLASGVPDRFSGSGSGTDFTLKI
                       |----LCDR1-----|                       |-----|
                                                               LCDR2

SRVEAEDVGVYYCAHNLELPWTFGQGTKVEIK
             |-LCDR3-|

>TPP-7007 Heavy Chain (PRT)
QVQLVQSGAEVKKPGASVKVSCKASGYTFTDFIIAWVKQAPGQGLEWIGEIYPGTGRTYYSEKFRGKATLTADTSTSTAY
|----------------------------------------------------------------VH---------------
                          |---|                 |-----HCDR2-----|
                          HCDR1

MELSSLRSEDTAVYFCARRTIYYDYDGDYWGQGTLVTVSSASTKGPSVFPLAPSSKSTSGGTAALGCLVKDYFPEPVTVS
---------------------------------------|
                |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-7007 Light Chain (PRT)
DIVMTQSPLSLPVTPGEPASISCRSSKSLLHSNGITYLYWYLQKPGQSPQLLIYQMSNLASGVPDRFSGSGSGTDFTLKI
|---------------------------------------------------------------VL----------------
                       |----LCDR1-----|                       |-----|
                                                               LCDR2

SRVEAEDVGVYYCAHNLELPWTFGQGTKVEIKRTVAAPSVFIFPPSDEQLKSGTASVVCLLNNFYPREAKVQWKVDNALQ
-------------------------------|
             |-LCDR3-|

SGNSQESVTEQDSKDSTYSLSSTLTLSKADYEKHKVYACEVTHQGLSSPVTKSFNRGEC
```

Fig. 2I

```
>TPP-7510 VH (PRT)
EVQLVESGGGLVQPGGSLRLSCAASGFNIKDTYIHWVRQAPGKGLEWVARIYPTNGYTRYADSVKGRFTISADTSKNTAY
                         |---|               |-----HCDR2-----|
                         HCDR1

LQMNSLRAEDTAVYYCSRWGGDGFYAMDYWGQGTLVTVSS
             |--HCDR3--|

>TPP-7510 VL (PRT)
DIQMTQSPSSLSASVGDRVTITCRASQDVNTAVAWYQQKPGKAPKLLIYSASFLYSGVPSRFSGSRSGTDFTLTISSLQP
                      |--LCDR1--|              |-----|
                                                 LCDR2

EDFATYYCQQHYTTPPTFGQGTKVEIK
        |-LCDR3-|

>TPP-7510 Heavy Chain (PRT)
EVQLVESGGGLVQPGGSLRLSCAASGFNIKDTYIHWVRQAPGKGLEWVARIYPTNGYTRYADSVKGRFTISADTSKNTAY
|-------------------------------------------------------------VH------------------
                         |---|               |-----HCDR2-----|
                         HCDR1

LQMNSLRAEDTAVYYCSRWGGDGFYAMDYWGQGTLVTVSSASTKGPSVFPLAPSSKSTSGGTAALGCLVKDYFPEPVTVS
----------------------------------------|
             |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-7510 Light Chain (PRT)
DIQMTQSPSSLSASVGDRVTITCRASQDVNTAVAWYQQKPGKAPKLLIYSASFLYSGVPSRFSGSRSGTDFTLTISSLQP
|-----------------------------------------------VL----------------------------
                      |--LCDR1--|              |-----|
                                                 LCDR2

EDFATYYCQQHYTTPPTFGQGTKVEIKRTVAAPSVFIFPPSDEQLKSGTASVVCLLNNFYPREAKVQWKVDNALQSGNSQ
-------------------------|
        |-LCDR3-|

ESVTEQDSKDSTYSLSSTLTLSKADYEKHKVYACEVTHQGLSSPVTKSFNRGEC
```

Fig. 2J

```
>TPP-7511 VH (PRT)
EVQLVESGGGLVQPGGSLRLSCAASGFNIKDTYIHWVRQAPGKGLEWVARIYPTNGYTRYADSVKGRFTISADTSKNTAY
                            |---|                   |-----HCDR2-----|
                            HCDR1

LQMNSLRAEDTAVYYCSRWGGDGFYAMDYWGQGTLVTVSS
                |--HCDR3--|

>TPP-7511 VL (PRT)
DIQMTQSPSSLSASVGDRVTITCRASQDVNTAVAWYQQKPGKAPKLLIYSASFLYSGVPSRFSGSRSGTDFTLTISSLQP
                        |--LCDR1--|               |-----|
                                                   LCDR2

EDFATYYCQQHYTTPPTFGQGTKVEIK
        |-LCDR3-|

>TPP-7511 Heavy Chain (PRT)
EVQLVESGGGLVQPGGSLRLSCAASGFNIKDTYIHWVRQAPGKGLEWVARIYPTNGYTRYADSVKGRFTISADTSKNTAY
|----------------------------------------------------------------VH----------------------
                            |---|                   |-----HCDR2-----|
                            HCDR1

LQMNSLRAEDTAVYYCSRWGGDGFYAMDYWGQGTLVTVSSASTKGPSVFPLAPSSKSTSGGTAALGCLVKDYFPEPVTVS
-----------------------------------------|
                |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYQSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-7511 (PRT)
DIQMTQSPSSLSASVGDRVTITCRASQDVNTAVAWYQQKPGKAPKLLIYSASFLYSGVPSRFSGSRSGTDFTLTISSLQP
|----------------------------------------------------------------VL----------------------
                        |--LCDR1--|               |-----|
                                                   LCDR2

EDFATYYCQQHYTTPPTFGQGTKVEIKRTVAAPSVFIFPPSDEQLKSGTASVVCLLNNFYPREAKVQWKVDNALQSGNSQ
---------------------------|
        |-LCDR3-|

ESVTEQDSKDSTYSLSSTLTLSKADYEKHKVYACEVTHQGLSSPVTKSFNRGEC
```

Fig. 2K

```
>TPP-8382 VH (PRT)
EVQLLESGGGLVQPGGSLRLSCAASGFTFSSYAMSWVRQAPGKGLEWVSSISGSGGSTLYADSVKGRFTISRDNSKNTLY
                      |---|                  |-----HCDR2-----|
                      HCDR1

LQMNSLRAEDTAVYYCAKLTGTSFDYWGQGTLVTVSS
                |------|
                HCDR3

>TPP-8382 VL (PRT)
QSVLTQPPSASGTPGQRVTISCSGSSSNIGSNPVNWYQQLPGTAPKLLIYSNNQRPSGVPDRFSGSKSGTSASLAITGLQ
                    |---LCDR1---|                     |-----|
                                                        LCDR2

SEDEADYYCQSFDSSLKKVFGGGTKLTVL
        |-LCDR3--|

>TPP-8382 Heavy Chain (PRT)
EVQLLESGGGLVQPGGSLRLSCAASGFTFSSYAMSWVRQAPGKGLEWVSSISGSGGSTLYADSVKGRFTISRDNSKNTLY
|-----------------------------------------------------------------VH-------------------
                      |---|                  |-----HCDR2-----|
                      HCDR1

LQMNSLRAEDTAVYYCAKLTGTSFDYWGQGTLVTVSSASTKGPSVFPLAPSSKSTSGGTAALGCLVKDYFPEPVTVSWNS
--------------------------------------|
                |------|
                HCDR3

GALTSGVHTFPAVLQSSGLYSLSSVVTVPSSSLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAKTKPREEQYNSTYRVVSVLTVLHQDWLNGKEYK

CKVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

>TPP-8382 Light Chain (PRT)
QSVLTQPPSASGTPGQRVTISCSGSSSNIGSNPVNWYQQLPGTAPKLLIYSNNQRPSGVPDRFSGSKSGTSASLAITGLQ
|-------------------------------------------------------VL-------------------------
                    |---LCDR1---|                     |-----|
                                                        LCDR2

SEDEADYYCQSFDSSLKKVFGGGTKLTVLGQPKAAPSVTLFPPSSEELQANKATLVCLISDFYPGAVTVAWKADSSPVKA
---------------------------|
        |-LCDR3--|

GVETTTPSKQSNNKYAASSYLSLTPEQWKSHRSYSCQVTHEGSTVEKTVAPTECS
```

Fig. 2L

```
>TPP-8567 VH (PRT)
EVQLLESGGGLVQPGGSLRLSCAASGFTFSSYAMSWVRQAPGKGLEWVSSISGSGGSTLYADSVKGRFTISRDNSKNTLY
                              |---|                   |-----HCDR2-----|
                              HCDR1

LQMNSLRAEDTAVYYCAKLTGTSFDYWGQGTLVTVSS
                |------|
                HCDR3

>TPP-8567 VL (PRT)
QSVLTQPPSASGTPGQRVTISCSGSSSNIGSNPVNWYQQLPGTAPKLLIYSNNQRPSGVPDRFSGSKSGTSASLAITGLQ
                    |---LCDR1---|                    |-----|
                                                      LCDR2

SEDEADYYCQSFDSSLKKVFGGGTKLTVL
        |-LCDR3--|

>TPP-8567 Heavy Chain (PRT)
EVQLLESGGGLVQPGGSLRLSCAASGFTFSSYAMSWVRQAPGKGLEWVSSISGSGGSTLYADSVKGRFTISRDNSKNTLY
|------------------------------------------------------------VH-------------------
                              |---|                   |-----HCDR2-----|
                              HCDR1

LQMNSLRAEDTAVYYCAKLTGTSFDYWGQGTLVTVSSASTKGPSVFPLAPSSKSTSGGTAALGCLVKDYFPEPVTVSWNS
-------------------------------------|
                |------|
                HCDR3

GALTSGVHTFPAVLQSSGLYSLSSVVTVPSSSLGTQTYICNVNHKPSNTKVDKKVEPKSCDKTHTCPPCPAPELLGGPSV

FLFPPKPKDTLMISRTPEVTCVVVDVSHEDPEVKFNWYVDGVEVHNAKTKPREEQYQSTYRVVSVLTVLHQDWLNGKEYK

CKVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

>TPP-8567 Light Chain (PRT)
QSVLTQPPSASGTPGQRVTISCSGSSSNIGSNPVNWYQQLPGTAPKLLIYSNNQRPSGVPDRFSGSKSGTSASLAITGLQ
|------------------------------------------------------VL------------------------
                    |---LCDR1---|                    |-----|
                                                      LCDR2

SEDEADYYCQSFDSSLKKVFGGGTKLTVLGQPKAAPSVTLFPPSSEELQANKATLVCLISDFYPGAVTVAWKADSSPVKA
-------------------------------|
        |-LCDR3--|

GVETTTPSKQSNNKYAASSYLSLTPEQWKSHRSYSCQVTHEGSTVEKTVAPTECS
```

Fig. 2M

```
>TPP-8825 VH (PRT)
EVQLLESGGGLVQPGGSLRLSCAASGFTFSPYPMIWVRQAPGKGLEWVSYISPSGGSTHYADSVKGRFTISRDNSKNTLY
                        |---|                      |-----HCDR2-----|
                        HCDR1

LQMNSLRAEDTAVYYCARGGDTYFDYFDYWGQTLVTVSS
              |--HCDR3--|

>TPP-8825 VL (PRT)
DIQMTQSPSSLSASVGDRVTITCRASQSISGYLNWYQQKPGKAPKLLIYQASSLQSGVPSRFSGSGSGTDFTLTISSLQP
                    |--LCDR1--|              |-----|
                                              LCDR2

EDFATYYCQQSYTSPFITFGQGTKVEIK
        |-LCDR3--|

>TPP-8825 Heavy Chain (PRT)
EVQLLESGGGLVQPGGSLRLSCAASGFTFSPYPMIWVRQAPGKGLEWVSYISPSGGSTHYADSVKGRFTISRDNSKNTLY
|----------------------------------------------------------------VH---------------------
                        |---|                      |-----HCDR2-----|
                        HCDR1

LQMNSLRAEDTAVYYCARGGDTYFDYFDYWGQTLVTVSSASTKGPSVFPLAPSSKSTSGGTAALGCLVKDYFPEPVTVS
---------------------------------------|
              |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREENYQSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-8825 Light Chain (PRT)
DIQMTQSPSSLSASVGDRVTITCRASQSISGYLNWYQQKPGKAPKLLIYQASSLQSGVPSRFSGSGSGTDFTLTISSLQP
|----------------------------------------------------------------VL---------------------
                    |--LCDR1--|              |-----|
                                              LCDR2

EDFATYYCQQSYTSPFITFGQGTKVEIKRTVAAPSVFIFPPSDEQLKSGTASVVCLLNNFYPREAKVQWKVDNALQSGNS
---------------------------|
        |-LCDR3--|

QESVTEQDSKDSTYSLSSTLTLSKADYEKHKVYACEVTHQGLSSPVTKSFNRGEC
```

Fig. 2N

```
>TPP-10334 VH (PRT)
QVQLVQSGAEVKKPGASVKVSCKASGYTFTDFIIAWVKQAPGQGLEWIGEIYPGTGRTYYSEKFRGKATLTADTSTSTAY
                |---|                      |-----HCDR2-----|
                HCDR1

MELSSLRSEDTAVYFCARRTIYYDYDGDYWGQGTLVTVSS
              |--HCDR3--|

>TPP-10334 VL (PRT)
DIVMTQSPLSLPVTPGEPASISCRSSQSLLHSNGITYLYWYLQKPGQSPQLLIYQMSNRASGVPDRFSGSGSGTDFTLKI
                    |----LCDR1-----|                   |-----|
                                                        LCDR2

SRVEAEDVGVYYCAHNLELPWTFGQGTKVEIK
            |-LCDR3-|

>TPP-10334 Heavy Chain (PRT)
QVQLVQSGAEVKKPGASVKVSCKASGYTFTDFIIAWVKQAPGQGLEWIGEIYPGTGRTYYSEKFRGKATLTADTSTSTAY
|-----------------------------------------------------------VH-----------------
                |---|                      |-----HCDR2-----|
                HCDR1

MELSSLRSEDTAVYFCARRTIYYDYDGDYWGQGTLVTVSSASTKGPSVFPLAPSSKSTSGGTAALGCLVKDYFPEPVTVS
---------------------------------------|
              |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-10334 Light Chain (PRT)
DIVMTQSPLSLPVTPGEPASISCRSSQSLLHSNGITYLYWYLQKPGQSPQLLIYQMSNRASGVPDRFSGSGSGTDFTLKI
|-----------------------------------------------------------VL-----------------
                    |----LCDR1-----|                   |-----|
                                                        LCDR2

SRVEAEDVGVYYCAHNLELPWTFGQGTKVEIKRTVAAPSVFIFPPSDEQLKSGTASVVCLLNNFYPREAKVQWKVDNALQ
--------------------------------|
            |-LCDR3-|

SGNSQESVTEQDSKDSTYSLSSTLTLSKADYEKHKVYACEVTHQGLSSPVTKSFNRGEC
```

Fig. 2O

```
>TPP-10335 VH (PRT)
QVQLVQSGAEVKKPGASVKVSCKASGYTFTDFIIAWVKQAPGQGLEWIGEIYPGTGRTYYSEKFRGKATLTADTSTSTAY
                    |---|                      |-----HCDR2-----|
                    HCDR1

MELSSLRSEDTAVYFCARRTIYYDYDGDYWGQGTLVTVSS
              |--HCDR3--|

>TPP-10335 VL (PRT)
DIVMTQSPLSLPVTPGEPASISCRSSQSLLHSNGINYLYWYLQKPGQSPQLLIYQMSNRASGVPDRFSGSGSGTDFTLKI
                    |----LCDR1-----|                    |-----|
                                                          LCDR2

SRVEAEDVGVYYCAHNLELPWTFGQGTKVEIK
            |-LCDR3-|

>TPP-10335 Heavy Chain (PRT)
QVQLVQSGAEVKKPGASVKVSCKASGYTFTDFIIAWVKQAPGQGLEWIGEIYPGTGRTYYSEKFRGKATLTADTSTSTAY
|------------------------------------------------------------VH----------------
                    |---|                      |-----HCDR2-----|
                    HCDR1

MELSSLRSEDTAVYFCARRTIYYDYDGDYWGQGTLVTVSSASTKGPSVFPLAPSSKSTSGGTAALGCLVKDYFPEPVTVS
----------------------------------------|
              |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-10335 Light Chain (PRT)
DIVMTQSPLSLPVTPGEPASISCRSSQSLLHSNGINYLYWYLQKPGQSPQLLIYQMSNRASGVPDRFSGSGSGTDFTLKI
|------------------------------------------------------------VL----------------
                    |----LCDR1-----|                    |-----|
                                                          LCDR2

SRVEAEDVGVYYCAHNLELPWTFGQGTKVEIKRTVAAPSVFIFPPSDEQLKSGTASVVCLLNNFYPREAKVQWKVDNALQ
--------------------------------|
            |-LCDR3-|

SGNSQESVTEQDSKDSTYSLSSTLTLSKADYEKHKVYACEVTHQGLSSPVTKSFNRGEC
```

Fig. 2P

```
>TPP-10336 VH (PRT)
QVQLVQSGAEVKKPGASVKVSCKASGYTFTDFIIAWVKQAPGQGLEWIGEIYPGTGRTYYSEKFRGKATLTADTSTSTAY
                      |---|                    |-----HCDR2-----|
                      HCDR1

MELSSLRSEDTAVYFCARRTIYYDYDGDYWGQGTLVTVSS
             |--HCDR3--|

>TPP-10336 VL (PRT)
DIVMTQSPLSLPVTPGEPASISCRSSQSLLHSNWINYLYWYLQKPGQSPQLLIYQMSNRASGVPDRFSGSGSGTDFTLKI
                   |----LCDR1-----|                    |-----|
                                                          LCDR2

SRVEAEDVGVYYCAHNLELPWTFGQGTKVEIK
           |-LCDR3-|

>TPP-10336 Heavy Chain (PRT)
QVQLVQSGAEVKKPGASVKVSCKASGYTFTDFIIAWVKQAPGQGLEWIGEIYPGTGRTYYSEKFRGKATLTADTSTSTAY
|-----------------------------------------------------------------VH----------------------
                      |---|                    |-----HCDR2-----|
                      HCDR1

MELSSLRSEDTAVYFCARRTIYYDYDGDYWGQGTLVTVSSASTKGPSVFPLAPSSKSTSGGTAALGCLVKDYFPEPVTVS
-----------------------------------------|
             |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-10336 Light Chain (PRT)
DIVMTQSPLSLPVTPGEPASISCRSSQSLLHSNWINYLYWYLQKPGQSPQLLIYQMSNRASGVPDRFSGSGSGTDFTLKI
|--------------------------------------------------------VL-----------------------
                   |----LCDR1-----|                    |-----|
                                                          LCDR2

SRVEAEDVGVYYCAHNLELPWTFGQGTKVEIKRTVAAPSVFIFPPSDEQLKSGTASVVCLLNNFYPREAKVQWKVDNALQ
--------------------------------|
           |-LCDR3-|

SGNSQESVTEQDSKDSTYSLSSTLTLSKADYEKHKVYACEVTHQGLSSPVTKSFNRGEC
```

Fig. 2Q

```
>TPP-10337 VH (PRT)
QVQLVQSGAEVKKPGASVKVSCKASGYTFTDFIIAWVKQAPGQGLEWIGEIYPGTGRTYYSEKFRGKATLTADTSTSTAY
                        |---|                   |-----HCDR2-----|
                        HCDR1

MELSSLRSEDTAVYFCARRTIYYDYDGDYWGQGTLVTVSS
              |--HCDR3--|

>TPP-10337 VL (PRT)
DIVMTQSPLSLPVTPGEPASISCRSSQSLLHSNWINYLYWYLQKPGQSPQLLIYQGSNRASGVPDRFSGSGSGTDFTLKI
                      |----LCDR1-----|                     |-----|
                                                              LCDR2

SRVEAEDVGVYYCAHNLELPWTFGQGTKVEIK
            |-LCDR3-|

>TPP-10337 Heavy Chain (PRT)
QVQLVQSGAEVKKPGASVKVSCKASGYTFTDFIIAWVKQAPGQGLEWIGEIYPGTGRTYYSEKFRGKATLTADTSTSTAY
|-----------------------------------------------------------VH-------------------
                        |---|                   |-----HCDR2-----|
                        HCDR1

MELSSLRSEDTAVYFCARRTIYYDYDGDYWGQGTLVTVSSASTKGPSVFPLAPSSKSTSGGTAALGCLVKDYFPEPVTVS
----------------------------------------|
              |--HCDR3--|

WNSGALTSGVHTFPAVLQSSGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEWESNGQPENNYKTTPPV

LDSDGSFFLYSKLTVDKSRWQQGNVFSCSVMHEALHNHYTQKSLSLSPG

>TPP-10337 Light Chain (PRT)
DIVMTQSPLSLPVTPGEPASISCRSSQSLLHSNWINYLYWYLQKPGQSPQLLIYQGSNRASGVPDRFSGSGSGTDFTLKI
|-----------------------------------------------------------VL-------------------
                      |----LCDR1-----|                     |-----|
                                                              LCDR2

SRVEAEDVGVYYCAHNLELPWTFGQGTKVEIKRTVAAPSVFIFPPSDEQLKSGTASVVCLLNNFYPREAKVQWKVDNALQ
--------------------------------|
            |-LCDR3-|

SGNSQESVTEQDSKDSTYSLSSTLTLSKADYEKHKVYACEVTHQGLSSPVTKSFNRGEC
```

Fig. 3A

<SEQ ID NO:1>
QVQLKQSGPGLVQPSQSLSITCTVSGFSLTNYGVHWVRQSPGKGLEWLGVIWSGGNTDYNTPFTSRLSINKDNSK
SQVFFKMNSLQSNDTAIYYCARALTYYDYEFAYWGQGTLVTVSA

<SEQ ID NO:2>
NYGVH

<SEQ ID NO:3>
VIWSGGNTDYNTPFTS

<SEQ ID NO:4>
ALTYYDYEFAY

<SEQ ID NO:5>
DILLTQSPVILSVSPGERVSFSCRASQSIGTNIHWYQQRTNGSPRLLIKYASESISGIPSRFSGSGSGTDFTLSI
NSVESEDIADYYCQQNNNWPTTFGAGTKLELK

<SEQ ID NO:6>
RASQSIGTNIH

<SEQ ID NO:7>
YASESIS

<SEQ ID NO:8>
QQNNNWPTT

<SEQ ID NO:9>
QVQLKQSGPGLVQPSQSLSITCTVSGFSLTNYGVHWVRQSPGKGLEWLGVIWSGGNTDYNTPFTSRLSINKDNSK
SQVFFKMNSLQSNDTAIYYCARALTYYDYEFAYWGQGTLVTVSASTKGPSVFPLAPSSKSTSGGTAALGCLVKD
YFPEPVTVSWNSGALTSGVHTFPAVLQSSGLYSLSSVVTVPSSSLGTQTYICNVNHKPSNTKVDKRVEPKSCDKT
HTCPPCPAPELLGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSREEMTKNQVSLTCLVKGFY
PSDIAVEWESNGQPENNYKTTPPVLDSDGSFFLYSKLTVDKSRWQQGNVFSCSVMHEALHNHYTQKSLSLSPGK

<SEQ ID NO:10>
DILLTQSPVILSVSPGERVSFSCRASQSIGTNIHWYQQRTNGSPRLLIKYASESISGIPSRFSGSGSGTDFTLSI
NSVESEDIADYYCQQNNNWPTTFGAGTKLELKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC

<SEQ ID NO:11>
EVQLVESGGGLVQPGGSLRLSCAASGFNIKDTYIHWVRQAPGKGLEWVARIYPTNGYTRYADSVKGRFTISADTS
KNTAYLQMNSLRAEDTAVYYCSRWGGDGFYAMDYWGQGTLVTVSS

<SEQ ID NO:12>
DTYIH

<SEQ ID NO:13>
RIYPTNGYTRYADSVKG

<SEQ ID NO:14>
WGGDGFYAMDY

<SEQ ID NO:15>
DIQMTQSPSSLSASVGDRVTITCRASQDVNTAVAWYQQKPGKAPKLLIYSASFLYSGVPSRFSGSRSGTDFTLTI
SSLQPEDFATYYCQQHYTTPPTFGQGTKVEIK

Fig. 3B

<SEQ ID NO:16>
RASQDVNTAVA

<SEQ ID NO:17>
SASFLYS

<SEQ ID NO:18>
QQHYTTPPT

<SEQ ID NO:19>
EVQLVESGGGLVQPGGSLRLSCAASGFNIKDTYIHWVRQAPGKGLEWVARIYPTNGYTRYADSVKGRFTISADTS
KNTAYLQMNSLRAEDTAVYYCSRWGGDGFYAMDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFSCSVMHEALHNHYTQKSLSLSPGK

<SEQ ID NO:20>
DIQMTQSPSSLSASVGDRVTITCRASQDVNTAVAWYQQKPGKAPKLLIYSASFLYSGVPSRFSGSRSGTDFTLTI
SSLQPEDFATYYCQQHYTTPPTFGQGTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC

<SEQ ID NO:21>
EVQLLESGGGLVQPGGSLRLSCAASGFTFSPYPMIWVRQAPGKGLEWVSYISPSGGSTHYADSVKGRFTISRDNS
KNTLYLQMNSLRAEDTAVYYCARGGDTYFDYFDYWGQGTLVTVSS

<SEQ ID NO:22>
PYPMI

<SEQ ID NO:23>
YISPSGGSTHYADSVKG

<SEQ ID NO:24>
GGDTYFDYFDY

<SEQ ID NO:25>
DIQMTQSPSSLSASVGDRVTITCRASQSISGYLNWYQQKPGKAPKLLIYQASSLQSGVPSRFSGSGSGTDFTLTI
SSLQPEDFATYYCQQSYTSPFITFGQGTKVEIK

<SEQ ID NO:26>
RASQSISGYLN

<SEQ ID NO:27>
QASSLQS

<SEQ ID NO:28>
QQSYTSPFIT

<SEQ ID NO:29>
EVQLLESGGGLVQPGGSLRLSCAASGFTFSPYPMIWVRQAPGKGLEWVSYISPSGGSTHYADSVKGRFTISRDNS
KNTLYLQMNSLRAEDTAVYYCARGGDTYFDYFDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPGK

Fig. 3C

<SEQ ID NO:30>
DIQMTQSPSSLSASVGDRVTITCRASQSISGYLNWYQQKPGKAPKLLIYQASSLQSGVPSRFSGSGSGTDFTLTI
SSLQPEDFATYYCQQSYTSPFITFGQGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC

<SEQ ID NO:31>
EVQLLESGGGLVQPGGSLRLSCAASGFTFSPYPMIWVRQAPGKGLEWVSYISPSGGSTHYADSVKGRFTISRDNS
KNTLYLQMNSLRAEDTAVYYCARGGDTYFDYFDYWGQGTLVTVSS

<SEQ ID NO:32>
PYPMI

<SEQ ID NO:33>
YISPSGGSTHYADSVKG

<SEQ ID NO:34>
GGDTYFDYFDY

<SEQ ID NO:35>
DIQMTQSPSSLSASVGDRVTITCRASQSISGYLNWYQQKPGKAPKLLIYQASSLQSGVPSRFSGSGSGTDFTLTI
SSLQPEDFATYYCQQSYTSPFITFGQGTKVEIK

<SEQ ID NO:36>
RASQSISGYLN

<SEQ ID NO:37>
QASSLQS

<SEQ ID NO:38>
QQSYTSPFIT

<SEQ ID NO:39>
EVQLLESGGGLVQPGGSLRLSCAASGFTFSPYPMIWVRQAPGKGLEWVSYISPSGGSTHYADSVKGRFTISRDNS
KNTLYLQMNSLRAEDTAVYYCARGGDTYFDYFDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG

<SEQ ID NO:40>
DIQMTQSPSSLSASVGDRVTITCRASQSISGYLNWYQQKPGKAPKLLIYQASSLQSGVPSRFSGSGSGTDFTLTI
SSLQPEDFATYYCQQSYTSPFITFGQGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC

<SEQ ID NO:41>
EVQLLESGGGLVQPGGSLRLSCAASGFTFSPYPMIWVRQAPGKGLEWVSYISPSGGSTHYADSVKGRFTISRDNS
KNTLYLQMNSLRAEDTAVYYCARGGDTYFDYFDYWGQGTLVTVSS

<SEQ ID NO:42>
PYPMI

<SEQ ID NO:43>
YISPSGGSTHYADSVKG

<SEQ ID NO:44>
GGDTYFDYFDY

Fig. 3D

<SEQ ID NO:45>
DIQMTQSPSSLSASVGDRVTITCRASQSISGYLNWYQQKPGKAPKLLIYQASSLQSGVPSRFSGSGSGTDFTLTI
SSLQPEDFATYYCQQSYTSPFITFGQGTKVEIK

<SEQ ID NO:46>
RASQSISGYLN

<SEQ ID NO:47>
QASSLQS

<SEQ ID NO:48>
QQSYTSPFIT

<SEQ ID NO:49>
EVQLLESGGGLVQPGGSLRLSCAASGFTFSPYPMIWVRQAPGKGLEWVSYISPSGGSTHYADSVKGRFTISRDNS
KNTLYLQMNSLRAEDTAVYYCARGGDTYFDYFDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREEQYQ
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG

<SEQ ID NO:50>
DIQMTQSPSSLSASVGDRVTITCRASQSISGYLNWYQQKPGKAPKLLIYQASSLQSGVPSRFSGSGSGTDFTLTI
SSLQPEDFATYYCQQSYTSPFITFGQGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC

<SEQ ID NO:51>
QVQLQQSGPELVKPGASVKMSCKASGYTFTDFIIAWVKQRTGQGLEWIGEIYPGTGRTYYSEKFRGKATLTADKS
SNTAYMQLSSLTSVDSAVYFCARRTIYYDYDGDYWGQGTTLTVSS

<SEQ ID NO:52>
DFIIA

<SEQ ID NO:53>
EIYPGTGRTYYSEKFRG

<SEQ ID NO:54>
RTIYYDYDGDY

<SEQ ID NO:55>
DIVMTQAAFSNPVTLGTSASISCRSSKSLLHSNGITYLYWYLQKPGQSPQLLIYQMSNLASGVPDRFSSSGSGTD
FTLRISRVEAEDVGVYYCAHNLELPWTFGGGTKLELK

<SEQ ID NO:56>
RSSKSLLHSNGITYLY

<SEQ ID NO:57>
QMSNLAS

<SEQ ID NO:58>
AHNLELPWT

Fig. 3E

```
<SEQ ID NO:59>
QVQLQQSGPELVKPGASVKMSCKASGYTFTDFIIAWVKQRTGQGLEWIGEIYPGTGRTYYSEKFRGKATLTADKS
SNTAYMQLSSLTSVDSAVYFCARRTIYYDYDGDYWGQGTTLTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG

<SEQ ID NO:60>
DIVMTQAAFSNPVTLGTSASISCRSSKSLLHSNGITYLYWYLQKPGQSPQLLIYQMSNLASGVPDRFSSSGSGTD
FTLRISRVEAEDVGVYYCAHNLELPWTFGGGTKLELKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSFNRGEC

<SEQ ID NO:61>
QVQLVQSGAEVKKPGASVKVSCKASGYTFTDFIIAWVKQAPGQGLEWIGEIYPGTGRTYYSEKFRGKATLTADTS
TSTAYMELSSLRSEDTAVYFCARRTIYYDYDGDYWGQGTLVTVSS

<SEQ ID NO:62>
DFIIA

<SEQ ID NO:63>
EIYPGTGRTYYSEKFRG

<SEQ ID NO:64>
RTIYYDYDGDY

<SEQ ID NO:65>
DIVMTQSPLSLPVTPGEPASISCRSSKSLLHSNGITYLYWYLQKPGQSPQLLIYQMSNLASGVPDRFSGSGSGTD
FTLKISRVEAEDVGVYYCAHNLELPWTFGQGTKVEIK

<SEQ ID NO:66>
RSSKSLLHSNGITYLY

<SEQ ID NO:67>
QMSNLAS

<SEQ ID NO:68>
AHNLELPWT

<SEQ ID NO:69>
QVQLVQSGAEVKKPGASVKVSCKASGYTFTDFIIAWVKQAPGQGLEWIGEIYPGTGRTYYSEKFRGKATLTADTS
TSTAYMELSSLRSEDTAVYFCARRTIYYDYDGDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG

<SEQ ID NO:70>
DIVMTQSPLSLPVTPGEPASISCRSSKSLLHSNGITYLYWYLQKPGQSPQLLIYQMSNLASGVPDRFSGSGSGTD
FTLKISRVEAEDVGVYYCAHNLELPWTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSFNRGEC

<SEQ ID NO:71>
EVQLVESGGGLVQPGGSLRLSCAASGFNIKDTYIHWVRQAPGKGLEWVARIYPTNGYTRYADSVKGRFTISADTS
KNTAYLQMNSLRAEDTAVYYCSRWGGDGFYAMDYWGQGTLVTVSS
```

Fig. 3F

<SEQ ID NO:72>
DTYIH

<SEQ ID NO:73>
RIYPTNGYTRYADSVKG

<SEQ ID NO:74>
WGGDGFYAMDY

<SEQ ID NO:75>
DIQMTQSPSSLSASVGDRVTITCRASQDVNTAVAWYQQKPGKAPKLLIYSASFLYSGVPSRFSGSRSGTDFTLTI
SSLQPEDFATYYCQQHYTTPPTFGQGTKVEIK

<SEQ ID NO:76>
RASQDVNTAVA

<SEQ ID NO:77>
SASFLYS

<SEQ ID NO:78>
QQHYTTPPT

<SEQ ID NO:79>
EVQLVESGGGLVQPGGSLRLSCAASGFNIKDTYIHWVRQAPGKGLEWVARIYPTNGYTRYADSVKGRFTISADTS
KNTAYLQMNSLRAEDTAVYYCSRWGGDGFYAMDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREEQYA
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG

<SEQ ID NO:80>
DIQMTQSPSSLSASVGDRVTITCRASQDVNTAVAWYQQKPGKAPKLLIYSASFLYSGVPSRFSGSRSGTDFTLTI
SSLQPEDFATYYCQQHYTTPPTFGQGTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC

<SEQ ID NO:81>
EVQLVESGGGLVQPGGSLRLSCAASGFNIKDTYIHWVRQAPGKGLEWVARIYPTNGYTRYADSVKGRFTISADTS
KNTAYLQMNSLRAEDTAVYYCSRWGGDGFYAMDYWGQGTLVTVSS

<SEQ ID NO:82>
DTYIH

<SEQ ID NO:83>
RIYPTNGYTRYADSVKG

<SEQ ID NO:84>
WGGDGFYAMDY

<SEQ ID NO:85>
DIQMTQSPSSLSASVGDRVTITCRASQDVNTAVAWYQQKPGKAPKLLIYSASFLYSGVPSRFSGSRSGTDFTLTI
SSLQPEDFATYYCQQHYTTPPTFGQGTKVEIK

<SEQ ID NO:86>
RASQDVNTAVA

Fig. 3G

<SEQ ID NO:87>
SASFLYS

<SEQ ID NO:88>
QQHYTTPPT

<SEQ ID NO:89>
EVQLVESGGGLVQPGGSLRLSCAASGFNIKDTYIHWVRQAPGKGLEWVARIYPTNGYTRYADSVKGRFTISADTS
KNTAYLQMNSLRAEDTAVYYCSRWGGDGFYAMDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREEQYQ
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG

<SEQ ID NO:90>
DIQMTQSPSSLSASVGDRVTITCRASQDVNTAVAWYQQKPGKAPKLLIYSASFLYSGVPSRFSGSRSGTDFTLTI
SSLQPEDFATYYCQQHYTTPPTFGQGTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQGLSSPVTKSFNRGEC

<SEQ ID NO:91>
EVQLLESGGGLVQPGGSLRLSCAASGFTFSSYAMSWVRQAPGKGLEWVSSISGSGGSTLYADSVKGRFTISRDNS
KNTLYLQMNSLRAEDTAVYYCAKLTGTSFDYWGQGTLVTVSS

<SEQ ID NO:92>
SYAMS

<SEQ ID NO:93>
SISGSGGSTLYADSVKG

<SEQ ID NO:94>
LTGTSFDY

<SEQ ID NO:95>
QSVLTQPPSASGTPGQRVTISCSGSSSNIGSNPVNWYQQLPGTAPKLLIYSNNQRPSGVPDRFSGSKSGTSASLA
ITGLQSEDEADYYCQSFDSSLKKVFGGGTKLTVL

<SEQ ID NO:96>
SGSSSNIGSNPVN

<SEQ ID NO:97>
SNNQRPS

<SEQ ID NO:98>
QSFDSSLKKV

<SEQ ID NO:99>
EVQLLESGGGLVQPGGSLRLSCAASGFTFSSYAMSWVRQAPGKGLEWVSSISGSGGSTLYADSVKGRFTISRDNS
KNTLYLQMNSLRAEDTAVYYCAKLTGTSFDYWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKSLSLSPG

Fig. 3H

<SEQ ID NO:100>
QSVLTQPPSASGTPGQRVTISCSGSSSNIGSNPVNWYQQLPGTAPKLLIYSNNQRPSGVPDRFSGSKSGTSASLA
ITGLQSEDEADYYCQSFDSSLKKVFGGGTKLTVLGQPKAAPSVTLFPPSSEELQANKATLVCLISDFYPGAVTVA
WKADSSPVKAGVETTTPSKQSNNKYAASSYLSLTPEQWKSHRSYSCQVTHEGSTVEKTVAPTECS

<SEQ ID NO:101>
EVQLLESGGGLVQPGGSLRLSCAASGFTFSSYAMSWVRQAPGKGLEWVSSISGSGGSTLYADSVKGRFTISRDNS
KNTLYLQMNSLRAEDTAVYYCAKLTGTSFDYWGQGTLVTVSS

<SEQ ID NO:102>
SYAMS

<SEQ ID NO:103>
SISGSGGSTLYADSVKG

<SEQ ID NO:104>
LTGTSFDY

<SEQ ID NO:105>
QSVLTQPPSASGTPGQRVTISCSGSSSNIGSNPVNWYQQLPGTAPKLLIYSNNQRPSGVPDRFSGSKSGTSASLA
ITGLQSEDEADYYCQSFDSSLKKVFGGGTKLTVL

<SEQ ID NO:106>
SGSSSNIGSNPVN

<SEQ ID NO:107>
SNNQRPS

<SEQ ID NO:108>
QSFDSSLKKV

<SEQ ID NO:109>
EVQLLESGGGLVQPGGSLRLSCAASGFTFSSYAMSWVRQAPGKGLEWVSSISGSGGSTLYADSVKGRFTISRDNS
KNTLYLQMNSLRAEDTAVYYCAKLTGTSFDYWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHT
CPPCPAPELLGGPSVFLFPPKPKDTLMISRTPEVTCVVVDVSHEDPEVKFNWYVDGVEVHNAKTKPREEQYQSTY
RVVSVLTVLHQDWLNGKEYKCKVSNKALPAPIEKTISKAKGQPREPQVYTLPPSRDELTKNQVSLTCLVKGFYPS
DIAVEWESNGQPENNYKTTPPVLDSDGSFFLYSKLTVDKSRWQQGNVFSCSVMHEALHNHYTQKSLSLSPG

<SEQ ID NO:110>
QSVLTQPPSASGTPGQRVTISCSGSSSNIGSNPVNWYQQLPGTAPKLLIYSNNQRPSGVPDRFSGSKSGTSASLA
ITGLQSEDEADYYCQSFDSSLKKVFGGGTKLTVLGQPKAAPSVTLFPPSSEELQANKATLVCLISDFYPGAVTVA
WKADSSPVKAGVETTTPSKQSNNKYAASSYLSLTPEQWKSHRSYSCQVTHEGSTVEKTVAPTECS

<SEQ ID NO:111>
EVQLLESGGGLVQPGGSLRLSCAASGFTFSPYPMIWVRQAPGKGLEWVSYISPSGGSTHYADSVKGRFTISRDNS
KNTLYLQMNSLRAEDTAVYYCARGGDTYFDYFDYWGQGTLVTVSS

<SEQ ID NO:112>
PYPMI

<SEQ ID NO:113>
YISPSGGSTHYADSVKG

<SEQ ID NO:114>
GGDTYFDYFDY

Fig. 3I

<SEQ ID NO:115>
DIQMTQSPSSLSASVGDRVTITCRASQSISGYLNWYQQKPGKAPKLLIYQASSLQSGVPSRFSGSGSGTDFTLTI
SSLQPEDFATYYCQQSYTSPFITFGQGTKVEIK

<SEQ ID NO:116>
RASQSISGYLN

<SEQ ID NO:117>
QASSLQS

<SEQ ID NO:118>
QQSYTSPFIT

<SEQ ID NO:119>
EVQLLESGGGLVQPGGSLRLSCAASGFTFSPYPMIWVRQAPGKGLEWVSYISPSGGSTHYADSVKGRFTISRDNS
KNTLYLQMNSLRAEDTAVYYCARGGDTYFDYFDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREENYQ
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG

<SEQ ID NO:120>
DIQMTQSPSSLSASVGDRVTITCRASQSISGYLNWYQQKPGKAPKLLIYQASSLQSGVPSRFSGSGSGTDFTLTI
SSLQPEDFATYYCQQSYTSPFITFGQGTKVEIKRTVAAPSVFIFPPSDEQLKSGTASVVCLLNNFYPREAKVQWK
VDNALQSGNSQESVTEQDSKDSTYSLSSTLTLSKADYEKHKVYACEVTHQGLSSPVTKSFNRGEC

<SEQ ID NO:121>
QVQLVQSGAEVKKPGASVKVSCKASGYTFTDFIIAWVKQAPGQGLEWIGEIYPGTGRTYYSEKFRGKATLTADTS
TSTAYMELSSLRSEDTAVYFCARRTIYYDYDGDYWGQGTLVTVSS

<SEQ ID NO:122>
DFIIA

<SEQ ID NO:123>
EIYPGTGRTYYSEKFRG

<SEQ ID NO:124>
RTIYYDYDGDY

<SEQ ID NO:125>
DIVMTQSPLSLPVTPGEPASISCRSSQSLLHSNGITYLWYLQKPGQSPQLLIYQMSNRASGVPDRFSGSGSGTD
FTLKISRVEAEDVGVYYCAHNLELPWTFGQGTKVEIK

<SEQ ID NO:126>
RSSQSLLHSNGITYLY

<SEQ ID NO:127>
QMSNRAS

<SEQ ID NO:128>
AHNLELPWT

Fig. 3J

<SEQ ID NO:129>
QVQLVQSGAEVKKPGASVKVSCKASGYTFTDFIIAWVKQAPGQGLEWIGEIYPGTGRTYYSEKFRGKATLTADTS
TSTAYMELSSLRSEDTAVYFCARRTIYYDYDGDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG

<SEQ ID NO:130>
DIVMTQSPLSLPVTPGEPASISCRSSQSLLHSNGITYLYWYLQKPGQSPQLLIYQMSNRASGVPDRFSGSGSGTD
FTLKISRVEAEDVGVYYCAHNLELPWTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSFNRGEC

<SEQ ID NO:131>
QVQLVQSGAEVKKPGASVKVSCKASGYTFTDFIIAWVKQAPGQGLEWIGEIYPGTGRTYYSEKFRGKATLTADTS
TSTAYMELSSLRSEDTAVYFCARRTIYYDYDGDYWGQGTLVTVSS

<SEQ ID NO:132>
DFIIA

<SEQ ID NO:133>
EIYPGTGRTYYSEKFRG

<SEQ ID NO:134>
RTIYYDYDGDY

<SEQ ID NO:135>
DIVMTQSPLSLPVTPGEPASISCRSSQSLLHSNGINYLYWYLQKPGQSPQLLIYQMSNRASGVPDRFSGSGSGTD
FTLKISRVEAEDVGVYYCAHNLELPWTFGQGTKVEIK

<SEQ ID NO:136>
RSSQSLLHSNGINYLY

<SEQ ID NO:137>
QMSNRAS

<SEQ ID NO:138>
AHNLELPWT

<SEQ ID NO:139>
QVQLVQSGAEVKKPGASVKVSCKASGYTFTDFIIAWVKQAPGQGLEWIGEIYPGTGRTYYSEKFRGKATLTADTS
TSTAYMELSSLRSEDTAVYFCARRTIYYDYDGDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG

<SEQ ID NO:140>
DIVMTQSPLSLPVTPGEPASISCRSSQSLLHSNGINYLYWYLQKPGQSPQLLIYQMSNRASGVPDRFSGSGSGTD
FTLKISRVEAEDVGVYYCAHNLELPWTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSFNRGEC

<SEQ ID NO:141>
QVQLVQSGAEVKKPGASVKVSCKASGYTFTDFIIAWVKQAPGQGLEWIGEIYPGTGRTYYSEKFRGKATLTADTS
TSTAYMELSSLRSEDTAVYFCARRTIYYDYDGDYWGQGTLVTVSS

Fig. 3K

<SEQ ID NO:142>
DFIIA

<SEQ ID NO:143>
EIYPGTGRTYYSEKFRG

<SEQ ID NO:144>
RTIYYDYDGDY

<SEQ ID NO:145>
DIVMTQSPLSLPVTPGEPASISCRSSQSLLHSNWINYLYWYLQKPGQSPQLLIYQMSNRASGVPDRFSGSGSGTD
FTLKISRVEAEDVGVYYCAHNLELPWTFGQGTKVEIK

<SEQ ID NO:146>
RSSQSLLHSNWINYLY

<SEQ ID NO:147>
QMSNRAS

<SEQ ID NO:148>
AHNLELPWT

<SEQ ID NO:149>
QVQLVQSGAEVKKPGASVKVSCKASGYTFTDFIIAWVKQAPGQGLEWIGEIYPGTGRTYYSEKFRGKATLTADTS
TSTAYMELSSLRSEDTAVYFCARRTIYYDYDGDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG

<SEQ ID NO:150>
DIVMTQSPLSLPVTPGEPASISCRSSQSLLHSNWINYLYWYLQKPGQSPQLLIYQMSNRASGVPDRFSGSGSGTD
FTLKISRVEAEDVGVYYCAHNLELPWTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSFNRGEC

<SEQ ID NO:151>
QVQLVQSGAEVKKPGASVKVSCKASGYTFTDFIIAWVKQAPGQGLEWIGEIYPGTGRTYYSEKFRGKATLTADTS
TSTAYMELSSLRSEDTAVYFCARRTIYYDYDGDYWGQGTLVTVSS

<SEQ ID NO:152>
DFIIA

<SEQ ID NO:153>
EIYPGTGRTYYSEKFRG

<SEQ ID NO:154>
RTIYYDYDGDY

<SEQ ID NO:155>
DIVMTQSPLSLPVTPGEPASISCRSSQSLLHSNWINYLYWYLQKPGQSPQLLIYQGSNRASGVPDRFSGSGSGTD
FTLKISRVEAEDVGVYYCAHNLELPWTFGQGTKVEIK

<SEQ ID NO:156>
RSSQSLLHSNWINYLY

Fig. 3L

<SEQ ID NO:157>
QGSNRAS

<SEQ ID NO:158>
AHNLELPWT

<SEQ ID NO:159>
QVQLVQSGAEVKKPGASVKVSCKASGYTFTDFIIAWVKQAPGQGLEWIGEIYPGTGRTYYSEKFRGKATLTADTS
TSTAYMELSSLRSEDTAVYFCARRTIYYDYDGDYWGQGTLVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPSNTKVDKKVEPKSCDK
THTCPPCPAPELLGGPSVFLFPPKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTLPPSRDELTKNQVSLTCLVKGF
YPSDIAVEWESNGQPENNYKTTPPVLDSDGSFFLYSKLTVDKSRWQQGNVFSCSVMHEALHNHYTQKSLSLSPG

<SEQ ID NO:160>
DIVMTQSPLSLPVTPGEPASISCRSSQSLLHSNWINYLYWYLQKPGQSPQLLIYQGSNRASGVPDRFSGSGSGTD
FTLKISRVEAEDVGVYYCAHNLELPWTFGQGTKVEIKRTVAAPSVFIFPPSDEQLKSGTASVVCLLNNFYPREAK
VQWKVDNALQSGNSQESVTEQDSKDSTYSLSSTLTLSKADYEKHKVYACEVTHQGLSSPVTKSFNRGEC

<SEQ ID NO:161>
HSDAVFTDNYTRLRKQMAVKKYLNSILN

<SEQ ID NO:162>
ATEPRKQYATPRVFWTDAPG

<SEQ ID NO:163>
LQWRRDDNVHNFGVWARYRL

<SEQ ID NO:164>
MARGSLRRLLRLLVLGLWLALLRSVAGEQAPGTAPCSRGSSWSADLDKCMDCASCRARPHSDFCLGCAAAPPAPF
RLLWPILGGALSLTFVLGLLSGFLVWRRCRRREKFTTPIEETGGEGCPAVALIQ

<SEQ ID NO:165>
MLRRGSPGMGVHVGAALGALWFCLTGALEVQVPEDPVVALVGTDATLCCSFSPEPGFSLAQLNLIWQLTDTKQL
VHSFAEGQDQGSAYANRTALFPDLLAQGNASLRLQRVRVADEGSFTCFVSIRDFGSAAVSLQVAAPYSKPSMTLE
PNKDLRPGDTVTITCSSYQGYPEAEVFWQDGQGVPLTGNVTTSQMANEQGLFDVHSILRVVLGANGTYSCLVRNP
VLQQDAHSSVTITPQRSPTGAVEVQVPEDPVVALVGTDATLRCSFSPEPGFSLAQLNLIWQLTDTKQLVHSFTEG
RDQGSAYANRTALFPDLLAQGNASLRLQRVRVADEGSFTCFVSIRDFGSAAVSLQVAAPYSKPSMTLEPNKDLRP
GDTVTITCSSYRGYPEAEVFWQDGQGVPLTGNVTTSQMANEQGLFDVHSVLRVVLGANGTYSCLVRNPVLQQDAH
GSVTITGQPMTFPPEALWVTVGLSVCLIALLVALAFVCWRKIKQSCEEENAGAEDQDGEGEGSKTALQPLKHSDS
KEDDGQEIA

Fig. 3M

<SEQ ID NO:166>
MELAALCRWGLLLALLPPGAASTQVCTGTDMKLRLPASPETHLDMLRHLYQGCQVVQGNLELTYLPTNASLSFLQ
DIQEVQGYVLIAHNQVRQVPLQRLRIVRGTQLFEDNYALAVLDNGDPLNNTTPVTGASPGGLRELQLRSLTEILK
GGVLIQRNPQLCYQDTILWKDIFHKNNQLALTLIDTNRSRACHPCSPMCKGSRCWGESSEDCQSLTRTVCAGGCA
RCKGPLPTDCCHEQCAAGCTGPKHSDCLACLHFNHSGICELHCPALVTYNTDTFESMPNPEGRYTFGASCVTACP
YNYLSTDVGSCTLVCPLHNQEVTAEDGTQRCEKCSKPCARVCYGLGMEHLREVRAVTSANIQEFAGCKKIFGSLA
FLPESFDGDPASNTAPLQPEQLQVFETLEEITGYLYISAWPDSLPDLSVFQNLQVIRGRILHNGAYSLTLQGLGI
SWLGLRSLRELGSGLALIHHNTHLCFVHTVPWDQLFRNPHQALLHTANRPEDECVGEGLACHQLCARGHCWGPGP
TQCVNCSQFLRGQECVEECRVLQGLPREYVNARHCLPCHPECQPQNGSVTCFGPEADQCVACAHYKDPPFCVARC
PSGVKPDLSYMPIWKFPDEEGACQPCPINCTHSCVDLDDKGCPAEQRASPLTSIISAVVGILLVVVLGVVFGILI
KRRQQKIRKYTMRRLLQETELVEPLTPSGAMPNQAQMRILKETELRKVKVLGSGAFGTVYKGIWIPDGENVKIPV
AIKVLRENTSPKANKEILDEAYVMAGVGSPYVSRLLGICLTSTVQLVTQLMPYGCLLDHVRENRGRLGSQDLLNW
CMQIAKGMSYLEDVRLVHRDLAARNVLVKSPNHVKITDFGIARLLDIDETEYHADGGKVPIKWMALESILRRRFT
HQSDVWSYGVTVWELMTFGAKPYDGIPAREIPDLLEKGERLPQPPICTIDVYMIMVKCWMIDSECRPRFRELVSE
FSRMARDPQRFVVIQNEDLGPASPLDSTFYRSLLEDDDMGDLVDAEEYLVPQQGFFCPDPAPGAGGMVHHRHRSS
STRSGGGDLTLGLEPSEEEAPRSPLAPSEGAGSDVFDGDLGMGAAKGLQSLPTHDPSPLQRYSEDPTVPLPSETD
GYVAPLTCSPQPEYVNQPDVRPQPPSPREGPLPAARPAGATLERPKTLSPGKNGVVKDVFAFGGAVENPEYLTPQ
GGAAPQPHPPPAFSPAFDNLYYWDQDPPERGAPPSTFKGTPTAENPEYLGLDVPV

<SEQ ID NO:167>
MRPSGTAGAALLALLAALCPASRALEEKKVCQGTSNKLTQLGTFEDHFLSLQRMFNNCEVVLGNLEITYVQRNYD
LSFLKTIQEVAGYVLIALNTVERIPLENLQIIRGNMYYENSYALAVLSNYDANKTGLKELPMRNLQEILHGAVRF
SNNPALCNVESIQWRDIVSSDFLSNMSMDFQNHLGSCQKCDPSCPNGSCWGAGEENCQKLTKIICAQQCSGRCRG
KSPSDCCHNQCAAGCTGPRESDCLVCRKFRDEATCKDTCPPLMLYNPTTYQMDVNPEGKYSFGATCVKKCPRNYV
VTDHGSCVRACGADSYEMEEDGVRKCKKCEGPCRKVCNGIGIGEFKDSLSINATNIKHFKNCTSISGDLHILPVA
FRGDSFTHTPPLDPQELDILKTVKEITGFLLIQAWPENRTDLHAFENLEIIRGRTKQHGQFSLAVVSLNITSLGL
RSLKEISDGDVIISGNKNLCYANTINWKKLFGTSGQKTKIISNRGENSCKATGQVCHALCSPEGCWGPEPRDCVS
CRNVSRGRECVDKCNLLEGEPREFVENSECIQCHPECLPQAMNITCTGRGPDNCIQCAHYIDGPHCVKTCPAGVM
GENNTLVWKYADAGHVCHLCHPNCTYGCTGPGLEGCPTNGPKIPSIATGMVGALLLLLVVALGIGLFMRRRHIVR
KRTLRRLLQERELVEPLTPSGEAPNQALLRILKETEFKKIKVLGSGAFGTVYKGLWIPEGEKVKIPVAIKELREA
TSPKANKEILDEAYVMASVDNPHVCRLLGICLTSTVQLITQLMPFGCLLDYVREHKDNIGSQYLLNWCVQIAKGM
NYLEDRRLVHRDLAARNVLVKTPQHVKITDFGLAKLLGAEEKEYHAEGGKVPIKWMALESILHRIYTHQSDVWSY
GVTVWELMTFGSKPYDGIPASEISSILEKGERLPQPPICTIDVYMIMVKCWMIDADSRPKFRELIIEFSKMARDP
QRYLVIQGDERMHLPSPTDSNFYRALMDEEDMDDVVDADEYLIPQQGFFSSPSTSRTPLLSSLSATSNNSTVACI
DRNGLQSCPIKEDSFLQRYSSDPTGALTEDSIDDTFLPVPEYINQSVPKRPAGSVQNPVYHNQPLNPAPSRDPHY
QDPHSTAVGNPEYLNTVQPTCVNSTFDSPAHWAQKGSHQISLDNPDYQQDFFPKEAKPNGIFKGSTAENAEYLRV
APQSSEFIGA

SEQUENCE LISTING

```
<160> NUMBER OF SEQ ID NOS: 167

<210> SEQ ID NO 1
<211> LENGTH: 119
<212> TYPE: PRT
<213> ORGANISM: Artificial Sequence
<220> FEATURE:
<223> OTHER INFORMATION: Antibody sequence

<400> SEQUENCE: 1

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 2
<211> LENGTH: 5
<212> TYPE: PRT
<213> ORGANISM: Artificial Sequence
<220> FEATURE:
```

```
<223> OTHER INFORMATION: Antibody sequence

<400> SEQUENCE: 2

Asn Tyr Gly Val His
1               5

<210> SEQ ID NO 3
<211> LENGTH: 16
<212> TYPE: PRT
<213> ORGANISM: Artificial Sequence
<220> FEATURE:
<223> OTHER INFORMATION: Antibody sequence

<400> SEQUENCE: 3

Val Ile Trp Ser Gly Gly Asn Thr Asp Tyr Asn Thr Pro Phe Thr Ser
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Antibody sequence

<400> SEQUENCE: 4

Ala Leu Thr Tyr Tyr Asp Tyr Glu Phe Ala Tyr
1               5                   10

<210> SEQ ID NO 5
<211> LENGTH: 107
<212> TYPE: PRT
<213> ORGANISM: Artificial Sequence
<220> FEATURE:
<223> OTHER INFORMATION: Antibody sequence

<400> SEQUENCE: 5

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: Antibody sequence

<400> SEQUENCE: 6

Arg Ala Ser Gln Ser Ile Gly Thr Asn Ile His
1               5                   10

<210> SEQ ID NO 7
```

```
<211> LENGTH: 7
<212> TYPE: PRT
<213> ORGANISM: Artificial Sequence
<220> FEATURE:
<223> OTHER INFORMATION: Antibody sequence

<400> SEQUENCE: 7

Tyr Ala Ser Glu Ser Ile Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Antibody sequence

<400> SEQUENCE: 8

Gln Gln Asn Asn Asn Trp Pro Thr Thr
1               5

<210> SEQ ID NO 9
<211> LENGTH: 449
<212> TYPE: PRT
<213> ORGANISM: Artificial Sequence
<220> FEATURE:
<223> OTHER INFORMATION: Antibody sequence

<400> SEQUENCE: 9

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 10
<211> LENGTH: 214
<212> TYPE: PRT
<213> ORGANISM: Artificial Sequence
<220> FEATURE:
<223> OTHER INFORMATION: Antibody sequence

<400> SEQUENCE: 10

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

```
                145                 150                 155                 160
Glu Ser Val Thr Glu Gln Asp Ser Lys Asp Ser Thr Tyr Ser Leu Ser
                    165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 11
<211> LENGTH: 120
<212> TYPE: PRT
<213> ORGANISM: Artificial Sequence
<220> FEATURE:
<223> OTHER INFORMATION: Antibody sequence

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 12
<211> LENGTH: 5
<212> TYPE: PRT
<213> ORGANISM: Artificial Sequence
<220> FEATURE:
<223> OTHER INFORMATION: Antibody sequence

<400> SEQUENCE: 12

Asp Thr Tyr Ile His
1               5

<210> SEQ ID NO 13
<211> LENGTH: 17
<212> TYPE: PRT
<213> ORGANISM: Artificial Sequence
<220> FEATURE:
<223> OTHER INFORMATION: Antibody sequence

<400> SEQUENCE: 13

Arg Ile Tyr Pro Thr Asn Gly Tyr Thr Arg Tyr Ala Asp Ser Val Lys
1               5                   10                  15

Gly

<210> SEQ ID NO 14
<211> LENGTH: 11
```

```
<212> TYPE: PRT
<213> ORGANISM: Artificial Sequence
<220> FEATURE:
<223> OTHER INFORMATION: Antibody sequence

<400> SEQUENCE: 14

Trp Gly Gly Asp Gly Phe Tyr Ala Met Asp Tyr
1               5                   10

<210> SEQ ID NO 15
<211> LENGTH: 107
<212> TYPE: PRT
<213> ORGANISM: Artificial Sequence
<220> FEATURE:
<223> OTHER INFORMATION: Antibody sequence

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 16
<211> LENGTH: 11
<212> TYPE: PRT
<213> ORGANISM: Artificial Sequence
<220> FEATURE:
<223> OTHER INFORMATION: Antibody sequence

<400> SEQUENCE: 16

Arg Ala Ser Gln Asp Val Asn Thr Ala Val Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Antibody sequence

<400> SEQUENCE: 17

Ser Ala Ser Phe Leu Tyr Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Antibody sequence

<400> SEQUENCE: 18

Gln Gln His Tyr Thr Thr Pro Pro Thr
1               5
```

<210> SEQ ID NO 19
<211> LENGTH: 450
<212> TYPE: PRT
<213> ORGANISM: Artificial Sequence
<220> FEATURE:
<223> OTHER INFORMATION: Antibody sequence

<400> SEQUENCE: 19

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365
```

```
Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 20
<211> LENGTH: 214
<212> TYPE: PRT
<213> ORGANISM: Artificial Sequence
<220> FEATURE:
<223> OTHER INFORMATION: Antibody sequence

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 120
<212> TYPE: PRT
<213> ORGANISM: Artificial Sequence
<220> FEATURE:
<223> OTHER INFORMATION: Antibody sequence
```

```
<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser
        115                 120

<210> SEQ ID NO 22
<211> LENGTH: 5
<212> TYPE: PRT
<213> ORGANISM: Artificial Sequence
<220> FEATURE:
<223> OTHER INFORMATION: Antibody sequence

<400> SEQUENCE: 22

Pro Tyr Pro Met Ile
1               5

<210> SEQ ID NO 23
<211> LENGTH: 17
<212> TYPE: PRT
<213> ORGANISM: Artificial Sequence
<220> FEATURE:
<223> OTHER INFORMATION: Antibody sequence

<400> SEQUENCE: 23

Tyr Ile Ser Pro Ser Gly Gly Ser Thr His Tyr Ala Asp Ser Val Lys
1               5                   10                  15

Gly

<210> SEQ ID NO 24
<211> LENGTH: 11
<212> TYPE: PRT
<213> ORGANISM: Artificial Sequence
<220> FEATURE:
<223> OTHER INFORMATION: Antibody sequence

<400> SEQUENCE: 24

Gly Gly Asp Thr Tyr Phe Asp Tyr Phe Asp Tyr
1               5                   10

<210> SEQ ID NO 25
<211> LENGTH: 108
<212> TYPE: PRT
<213> ORGANISM: Artificial Sequence
<220> FEATURE:
<223> OTHER INFORMATION: Antibody sequence

<400> SEQUENCE: 25

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys
            100                 105

<210> SEQ ID NO 26
<211> LENGTH: 11
<212> TYPE: PRT
<213> ORGANISM: Artificial Sequence
<220> FEATURE:
<223> OTHER INFORMATION: Antibody sequence

<400> SEQUENCE: 26

Arg Ala Ser Gln Ser Ile Ser Gly Tyr Leu Asn
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Antibody sequence

<400> SEQUENCE: 27

Gln Ala Ser Ser Leu Gln Ser
1               5

<210> SEQ ID NO 28
<211> LENGTH: 10
<212> TYPE: PRT
<213> ORGANISM: Artificial Sequence
<220> FEATURE:
<223> OTHER INFORMATION: Antibody sequence

<400> SEQUENCE: 28

Gln Gln Ser Tyr Thr Ser Pro Phe Ile Thr
1               5                   10

<210> SEQ ID NO 29
<211> LENGTH: 450
<212> TYPE: PRT
<213> ORGANISM: Artificial Sequence
<220> FEATURE:
<223> OTHER INFORMATION: Antibody sequence

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
450

<210> SEQ ID NO 30
<211> LENGTH: 215

```
<212> TYPE: PRT
<213> ORGANISM: Artificial Sequence
<220> FEATURE:
<223> OTHER INFORMATION: Antibody sequence

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 31
<211> LENGTH: 120
<212> TYPE: PRT
<213> ORGANISM: Artificial Sequence
<220> FEATURE:
<223> OTHER INFORMATION: Antibody sequence

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110
```

```
Gly Thr Leu Val Thr Val Ser Ser
        115             120

<210> SEQ ID NO 32
<211> LENGTH: 5
<212> TYPE: PRT
<213> ORGANISM: Artificial Sequence
<220> FEATURE:
<223> OTHER INFORMATION: Antibody sequence

<400> SEQUENCE: 32

Pro Tyr Pro Met Ile
1               5

<210> SEQ ID NO 33
<211> LENGTH: 17
<212> TYPE: PRT
<213> ORGANISM: Artificial Sequence
<220> FEATURE:
<223> OTHER INFORMATION: Antibody sequence

<400> SEQUENCE: 33

Tyr Ile Ser Pro Ser Gly Gly Ser Thr His Tyr Ala Asp Ser Val Lys
1               5                   10                  15

Gly

<210> SEQ ID NO 34
<211> LENGTH: 11
<212> TYPE: PRT
<213> ORGANISM: Artificial Sequence
<220> FEATURE:
<223> OTHER INFORMATION: Antibody sequence

<400> SEQUENCE: 34

Gly Gly Asp Thr Tyr Phe Asp Tyr Phe Asp Tyr
1               5                   10

<210> SEQ ID NO 35
<211> LENGTH: 108
<212> TYPE: PRT
<213> ORGANISM: Artificial Sequence
<220> FEATURE:
<223> OTHER INFORMATION: Antibody sequence

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys
            100                 105

<210> SEQ ID NO 36
<211> LENGTH: 11
```

```
<212> TYPE: PRT
<213> ORGANISM: Artificial Sequence
<220> FEATURE:
<223> OTHER INFORMATION: Antibody sequence

<400> SEQUENCE: 36

Arg Ala Ser Gln Ser Ile Ser Gly Tyr Leu Asn
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Antibody sequence

<400> SEQUENCE: 37

Gln Ala Ser Ser Leu Gln Ser
1               5

<210> SEQ ID NO 38
<211> LENGTH: 10
<212> TYPE: PRT
<213> ORGANISM: Artificial Sequence
<220> FEATURE:
<223> OTHER INFORMATION: Antibody sequence

<400> SEQUENCE: 38

Gln Gln Ser Tyr Thr Ser Pro Phe Ile Thr
1               5                   10

<210> SEQ ID NO 39
<211> LENGTH: 449
<212> TYPE: PRT
<213> ORGANISM: Artificial Sequence
<220> FEATURE:
<223> OTHER INFORMATION: Antibody sequence

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

-continued

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 40
<211> LENGTH: 215
<212> TYPE: PRT
<213> ORGANISM: Artificial Sequence
<220> FEATURE:
<223> OTHER INFORMATION: Antibody sequence

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe

```
                    85                  90                  95
Ile Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 41
<211> LENGTH: 120
<212> TYPE: PRT
<213> ORGANISM: Artificial Sequence
<220> FEATURE:
<223> OTHER INFORMATION: Antibody sequence

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
                20                  25                  30

Pro Met Ile Trp Val Arg Gln Ala Pro Gly Lys Gly Leu Glu Trp Val
            35                  40                  45

Ser Tyr Ile Ser Pro Ser Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
                100                 105                 110

Gly Thr Leu Val Thr Val Ser Ser
            115                 120

<210> SEQ ID NO 42
<211> LENGTH: 5
<212> TYPE: PRT
<213> ORGANISM: Artificial Sequence
<220> FEATURE:
<223> OTHER INFORMATION: Antibody sequence

<400> SEQUENCE: 42

Pro Tyr Pro Met Ile
1               5

<210> SEQ ID NO 43
<211> LENGTH: 17
<212> TYPE: PRT
<213> ORGANISM: Artificial Sequence
<220> FEATURE:
```

<223> OTHER INFORMATION: Antibody sequence

<400> SEQUENCE: 43

Tyr Ile Ser Pro Ser Gly Gly Ser Thr His Tyr Ala Asp Ser Val Lys
1               5                   10                  15

Gly

<210> SEQ ID NO 44
<211> LENGTH: 11
<212> TYPE: PRT
<213> ORGANISM: Artificial Sequence
<220> FEATURE:
<223> OTHER INFORMATION: Antibody sequence

<400> SEQUENCE: 44

Gly Gly Asp Thr Tyr Phe Asp Tyr Phe Asp Tyr
1               5                   10

<210> SEQ ID NO 45
<211> LENGTH: 108
<212> TYPE: PRT
<213> ORGANISM: Artificial Sequence
<220> FEATURE:
<223> OTHER INFORMATION: Antibody sequence

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
                20                  25                  30

Leu Asn Trp Tyr Gln Gln Lys Pro Gly Lys Ala Pro Lys Leu Leu Ile
            35                  40                  45

Tyr Gln Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys
            100                 105

<210> SEQ ID NO 46
<211> LENGTH: 11
<212> TYPE: PRT
<213> ORGANISM: Artificial Sequence
<220> FEATURE:
<223> OTHER INFORMATION: Antibody sequence

<400> SEQUENCE: 46

Arg Ala Ser Gln Ser Ile Ser Gly Tyr Leu Asn
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Antibody sequence

<400> SEQUENCE: 47

Gln Ala Ser Ser Leu Gln Ser
1               5

<210> SEQ ID NO 48
<211> LENGTH: 10
<212> TYPE: PRT
<213> ORGANISM: Artificial Sequence
<220> FEATURE:
<223> OTHER INFORMATION: Antibody sequence

<400> SEQUENCE: 48

```
Gln Gln Ser Tyr Thr Ser Pro Phe Ile Thr
1               5                   10
```

<210> SEQ ID NO 49
<211> LENGTH: 449
<212> TYPE: PRT
<213> ORGANISM: Artificial Sequence
<220> FEATURE:
<223> OTHER INFORMATION: Antibody sequence

<400> SEQUENCE: 49

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300
```

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly

<210> SEQ ID NO 50
<211> LENGTH: 215
<212> TYPE: PRT
<213> ORGANISM: Artificial Sequence
<220> FEATURE:
<223> OTHER INFORMATION: Antibody sequence

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Phe
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

```
Ser Phe Asn Arg Gly Glu Cys
    210                 215
```

<210> SEQ ID NO 51
<211> LENGTH: 120
<212> TYPE: PRT
<213> ORGANISM: Artificial Sequence
<220> FEATURE:
<223> OTHER INFORMATION: Antibody sequence

<400> SEQUENCE: 51

```
Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Phe
            20                  25                  30

Ile Ile Ala Trp Val Lys Gln Arg Thr Gly Gln Gly Leu Glu Trp Ile
        35                  40                  45

Gly Glu Ile Tyr Pro Gly Thr Gly Arg Thr Tyr Tyr Ser Glu Lys Phe
    50                  55                  60

Arg Gly Lys Ala Thr Leu Thr Ala Asp Lys Ser Ser Asn Thr Ala Tyr
65                  70                  75                  80

Met Gln Leu Ser Ser Leu Thr Ser Val Asp Ser Ala Val Tyr Phe Cys
                85                  90                  95

Ala Arg Arg Thr Ile Tyr Tyr Asp Tyr Asp Gly Asp Tyr Trp Gly Gln
            100                 105                 110

Gly Thr Thr Leu Thr Val Ser Ser
        115                 120
```

<210> SEQ ID NO 52
<211> LENGTH: 5
<212> TYPE: PRT
<213> ORGANISM: Artificial Sequence
<220> FEATURE:
<223> OTHER INFORMATION: Antibody sequence

<400> SEQUENCE: 52

```
Asp Phe Ile Ile Ala
1               5
```

<210> SEQ ID NO 53
<211> LENGTH: 17
<212> TYPE: PRT
<213> ORGANISM: Artificial Sequence
<220> FEATURE:
<223> OTHER INFORMATION: Antibody sequence

<400> SEQUENCE: 53

```
Glu Ile Tyr Pro Gly Thr Gly Arg Thr Tyr Tyr Ser Glu Lys Phe Arg
1               5                   10                  15

Gly
```

<210> SEQ ID NO 54
<211> LENGTH: 11
<212> TYPE: PRT
<213> ORGANISM: Artificial Sequence
<220> FEATURE:
<223> OTHER INFORMATION: Antibody sequence

<400> SEQUENCE: 54

```
Arg Thr Ile Tyr Tyr Asp Tyr Asp Gly Asp Tyr
1               5                   10
```

<210> SEQ ID NO 55
<211> LENGTH: 112
<212> TYPE: PRT
<213> ORGANISM: Artificial Sequence
<220> FEATURE:
<223> OTHER INFORMATION: Antibody sequence

<400> SEQUENCE: 55

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gly Gly Thr Lys Leu Glu Leu Lys
            100                 105                 110

<210> SEQ ID NO 56
<211> LENGTH: 16
<212> TYPE: PRT
<213> ORGANISM: Artificial Sequence
<220> FEATURE:
<223> OTHER INFORMATION: Antibody sequence

<400> SEQUENCE: 56

Arg Ser Ser Lys Ser Leu Leu His Ser Asn Gly Ile Thr Tyr Leu Tyr
1               5                   10                  15

<210> SEQ ID NO 57
<211> LENGTH: 7
<212> TYPE: PRT
<213> ORGANISM: Artificial Sequence
<220> FEATURE:
<223> OTHER INFORMATION: Antibody sequence

<400> SEQUENCE: 57

Gln Met Ser Asn Leu Ala Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Antibody sequence

<400> SEQUENCE: 58

Ala His Asn Leu Glu Leu Pro Trp Thr
1               5

<210> SEQ ID NO 59
<211> LENGTH: 449
<212> TYPE: PRT
<213> ORGANISM: Artificial Sequence
<220> FEATURE:
<223> OTHER INFORMATION: Antibody sequence

<400> SEQUENCE: 59

-continued

```
Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Phe
            20                  25                  30

Ile Ile Ala Trp Val Lys Gln Arg Thr Gly Gln Gly Leu Glu Trp Ile
        35                  40                  45

Gly Glu Ile Tyr Pro Gly Thr Gly Arg Thr Tyr Tyr Ser Glu Lys Phe
    50                  55                  60

Arg Gly Lys Ala Thr Leu Thr Ala Asp Lys Ser Asn Thr Ala Tyr
65                  70                  75                  80

Met Gln Leu Ser Ser Leu Thr Ser Val Asp Ser Ala Val Tyr Phe Cys
                85                  90                  95

Ala Arg Arg Thr Ile Tyr Tyr Asp Tyr Asp Gly Asp Tyr Trp Gly Gln
            100                 105                 110

Gly Thr Thr Leu Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
```

```
                420                 425                 430
Glu Ala Leu His Asn His Tyr Thr Gln Lys Ser Leu Ser Leu Ser Pro
            435                 440                 445
Gly

<210> SEQ ID NO 60
<211> LENGTH: 219
<212> TYPE: PRT
<213> ORGANISM: Artificial Sequence
<220> FEATURE:
<223> OTHER INFORMATION: Antibody sequence

<400> SEQUENCE: 60

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gly Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 61
<211> LENGTH: 120
<212> TYPE: PRT
<213> ORGANISM: Artificial Sequence
<220> FEATURE:
<223> OTHER INFORMATION: Antibody sequence

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ile Ile Ala Trp Val Lys Gln Ala Pro Gly Gln Gly Leu Glu Trp Ile
        35                  40                  45

Gly Glu Ile Tyr Pro Gly Thr Gly Arg Thr Tyr Tyr Ser Glu Lys Phe
```

```
                    50                  55                  60
Arg Gly Lys Ala Thr Leu Thr Ala Asp Thr Ser Thr Ser Thr Ala Tyr
 65                  70                  75                  80

Met Glu Leu Ser Ser Leu Arg Ser Glu Asp Thr Ala Val Tyr Phe Cys
                     85                  90                  95

Ala Arg Arg Thr Ile Tyr Tyr Asp Tyr Asp Gly Asp Tyr Trp Gly Gln
                100                 105                 110

Gly Thr Leu Val Thr Val Ser Ser
            115                 120
```

<210> SEQ ID NO 62
<211> LENGTH: 5
<212> TYPE: PRT
<213> ORGANISM: Artificial Sequence
<220> FEATURE:
<223> OTHER INFORMATION: Antibody sequence

<400> SEQUENCE: 62

```
Asp Phe Ile Ile Ala
 1               5
```

<210> SEQ ID NO 63
<211> LENGTH: 17
<212> TYPE: PRT
<213> ORGANISM: Artificial Sequence
<220> FEATURE:
<223> OTHER INFORMATION: Antibody sequence

<400> SEQUENCE: 63

```
Glu Ile Tyr Pro Gly Thr Gly Arg Thr Tyr Tyr Ser Glu Lys Phe Arg
 1               5                  10                  15

Gly
```

<210> SEQ ID NO 64
<211> LENGTH: 11
<212> TYPE: PRT
<213> ORGANISM: Artificial Sequence
<220> FEATURE:
<223> OTHER INFORMATION: Antibody sequence

<400> SEQUENCE: 64

```
Arg Thr Ile Tyr Tyr Asp Tyr Asp Gly Asp Tyr
 1               5                  10
```

<210> SEQ ID NO 65
<211> LENGTH: 112
<212> TYPE: PRT
<213> ORGANISM: Artificial Sequence
<220> FEATURE:
<223> OTHER INFORMATION: Antibody sequence

<400> SEQUENCE: 65

```
Asp Ile Val Met Thr Gln Ser Pro Leu Ser Leu Pro Val Thr Pro Gly
 1               5                  10                  15

Glu Pro Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
        50                  55                  60

Asp Arg Phe Ser Gly Ser Gly Ser Gly Thr Asp Phe Thr Leu Lys Ile
 65                  70                  75                  80
```

-continued

```
Ser Arg Val Glu Ala Glu Asp Val Gly Val Tyr Tyr Cys Ala His Asn
            85                  90                  95

Leu Glu Leu Pro Trp Thr Phe Gly Gln Gly Thr Lys Val Glu Ile Lys
           100                 105                 110

<210> SEQ ID NO 66
<211> LENGTH: 16
<212> TYPE: PRT
<213> ORGANISM: Artificial Sequence
<220> FEATURE:
<223> OTHER INFORMATION: Antibody sequence

<400> SEQUENCE: 66

Arg Ser Ser Lys Ser Leu Leu His Ser Asn Gly Ile Thr Tyr Leu Tyr
1               5                   10                  15

<210> SEQ ID NO 67
<211> LENGTH: 7
<212> TYPE: PRT
<213> ORGANISM: Artificial Sequence
<220> FEATURE:
<223> OTHER INFORMATION: Antibody sequence

<400> SEQUENCE: 67

Gln Met Ser Asn Leu Ala Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Antibody sequence

<400> SEQUENCE: 68

Ala His Asn Leu Glu Leu Pro Trp Thr
1               5

<210> SEQ ID NO 69
<211> LENGTH: 449
<212> TYPE: PRT
<213> ORGANISM: Artificial Sequence
<220> FEATURE:
<223> OTHER INFORMATION: Antibody sequence

<400> SEQUENCE: 69

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ile Ile Ala Trp Val Lys Gln Ala Pro Gly Gln Gly Leu Glu Trp Ile
            35                  40                  45

Gly Glu Ile Tyr Pro Gly Thr Gly Arg Thr Tyr Tyr Ser Glu Lys Phe
        50                  55                  60

Arg Gly Lys Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
            85                  90                  95

Ala Arg Arg Thr Ile Tyr Tyr Asp Tyr Asp Gly Asp Tyr Trp Gly Gln
           100                 105                 110

Gly Thr Leu Val Thr Val Ser Ser Ala Ser Thr Lys Gly Pro Ser Val
           115                 120                 125
```

```
Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 70
<211> LENGTH: 219
<212> TYPE: PRT
<213> ORGANISM: Artificial Sequence
<220> FEATURE:
<223> OTHER INFORMATION: Antibody sequence

<400> SEQUENCE: 70

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30
```

```
Asn Gly Ile Thr Tyr Leu Tyr Trp Tyr Leu Gln Lys Pro Gly Gln Ser
             35                  40                  45

Pro Gln Leu Leu Ile Tyr Gln Met Ser Asn Leu Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ala His Asn
                 85                  90                  95

Leu Glu Leu Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 71
<211> LENGTH: 120
<212> TYPE: PRT
<213> ORGANISM: Artificial Sequence
<220> FEATURE:
<223> OTHER INFORMATION: Antibody sequence

<400> SEQUENCE: 71

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
             20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
            115                 120

<210> SEQ ID NO 72
<211> LENGTH: 5
<212> TYPE: PRT
<213> ORGANISM: Artificial Sequence
<220> FEATURE:
<223> OTHER INFORMATION: Antibody sequence

<400> SEQUENCE: 72
```

Asp Thr Tyr Ile His
1               5

<210> SEQ ID NO 73
<211> LENGTH: 17
<212> TYPE: PRT
<213> ORGANISM: Artificial Sequence
<220> FEATURE:
<223> OTHER INFORMATION: Antibody sequence

<400> SEQUENCE: 73

Arg Ile Tyr Pro Thr Asn Gly Tyr Thr Arg Tyr Ala Asp Ser Val Lys
1               5                   10                  15

Gly

<210> SEQ ID NO 74
<211> LENGTH: 11
<212> TYPE: PRT
<213> ORGANISM: Artificial Sequence
<220> FEATURE:
<223> OTHER INFORMATION: Antibody sequence

<400> SEQUENCE: 74

Trp Gly Gly Asp Gly Phe Tyr Ala Met Asp Tyr
1               5                   10

<210> SEQ ID NO 75
<211> LENGTH: 107
<212> TYPE: PRT
<213> ORGANISM: Artificial Sequence
<220> FEATURE:
<223> OTHER INFORMATION: Antibody sequence

<400> SEQUENCE: 75

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 76
<211> LENGTH: 11
<212> TYPE: PRT
<213> ORGANISM: Artificial Sequence
<220> FEATURE:
<223> OTHER INFORMATION: Antibody sequence

<400> SEQUENCE: 76

Arg Ala Ser Gln Asp Val Asn Thr Ala Val Ala
1               5                   10

<210> SEQ ID NO 77
<211> LENGTH: 7

```
<212> TYPE: PRT
<213> ORGANISM: Artificial Sequence
<220> FEATURE:
<223> OTHER INFORMATION: Antibody sequence

<400> SEQUENCE: 77

Ser Ala Ser Phe Leu Tyr Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Antibody sequence

<400> SEQUENCE: 78

Gln Gln His Tyr Thr Thr Pro Pro Thr
1               5

<210> SEQ ID NO 79
<211> LENGTH: 449
<212> TYPE: PRT
<213> ORGANISM: Artificial Sequence
<220> FEATURE:
<223> OTHER INFORMATION: Antibody sequence

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
```

```
                            245                 250                 255
Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 80
<211> LENGTH: 214
<212> TYPE: PRT
<213> ORGANISM: Artificial Sequence
<220> FEATURE:
<223> OTHER INFORMATION: Antibody sequence

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 81
<211> LENGTH: 120
<212> TYPE: PRT
<213> ORGANISM: Artificial Sequence
<220> FEATURE:
<223> OTHER INFORMATION: Antibody sequence

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 82
<211> LENGTH: 5
<212> TYPE: PRT
<213> ORGANISM: Artificial Sequence
<220> FEATURE:
<223> OTHER INFORMATION: Antibody sequence

<400> SEQUENCE: 82

Asp Thr Tyr Ile His
1               5

<210> SEQ ID NO 83
<211> LENGTH: 17
<212> TYPE: PRT
<213> ORGANISM: Artificial Sequence
<220> FEATURE:
<223> OTHER INFORMATION: Antibody sequence

<400> SEQUENCE: 83

Arg Ile Tyr Pro Thr Asn Gly Tyr Thr Arg Tyr Ala Asp Ser Val Lys
1               5                   10                  15

Gly

<210> SEQ ID NO 84
<211> LENGTH: 11
<212> TYPE: PRT

```
<213> ORGANISM: Artificial Sequence
<220> FEATURE:
<223> OTHER INFORMATION: Antibody sequence

<400> SEQUENCE: 84

Trp Gly Gly Asp Gly Phe Tyr Ala Met Asp Tyr
1               5                   10

<210> SEQ ID NO 85
<211> LENGTH: 107
<212> TYPE: PRT
<213> ORGANISM: Artificial Sequence
<220> FEATURE:
<223> OTHER INFORMATION: Antibody sequence

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 86
<211> LENGTH: 11
<212> TYPE: PRT
<213> ORGANISM: Artificial Sequence
<220> FEATURE:
<223> OTHER INFORMATION: Antibody sequence

<400> SEQUENCE: 86

Arg Ala Ser Gln Asp Val Asn Thr Ala Val Ala
1               5                   10

<210> SEQ ID NO 87
<211> LENGTH: 7
<212> TYPE: PRT
<213> ORGANISM: Artificial Sequence
<220> FEATURE:
<223> OTHER INFORMATION: Antibody sequence

<400> SEQUENCE: 87

Ser Ala Ser Phe Leu Tyr Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Antibody sequence

<400> SEQUENCE: 88

Gln Gln His Tyr Thr Thr Pro Pro Thr
1               5
```

```
<210> SEQ ID NO 89
<211> LENGTH: 449
<212> TYPE: PRT
<213> ORGANISM: Artificial Sequence
<220> FEATURE:
<223> OTHER INFORMATION: Antibody sequence

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 90
<211> LENGTH: 214
<212> TYPE: PRT
<213> ORGANISM: Artificial Sequence
<220> FEATURE:
<223> OTHER INFORMATION: Antibody sequence

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 91
<211> LENGTH: 117
<212> TYPE: PRT
<213> ORGANISM: Artificial Sequence
<220> FEATURE:
<223> OTHER INFORMATION: Antibody sequence

<400> SEQUENCE: 91
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Gly Ser Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Thr Ser Phe Asp Tyr Trp Gly Gln Gly Thr Leu
            100                 105                 110

Val Thr Val Ser Ser
            115
```

<210> SEQ ID NO 92
<211> LENGTH: 5
<212> TYPE: PRT
<213> ORGANISM: Artificial Sequence
<220> FEATURE:
<223> OTHER INFORMATION: Antibody sequence

<400> SEQUENCE: 92

```
Ser Tyr Ala Met Ser
1               5
```

<210> SEQ ID NO 93
<211> LENGTH: 17
<212> TYPE: PRT
<213> ORGANISM: Artificial Sequence
<220> FEATURE:
<223> OTHER INFORMATION: Antibody sequence

<400> SEQUENCE: 93

```
Ser Ile Ser Gly Ser Gly Gly Ser Thr Leu Tyr Ala Asp Ser Val Lys
1               5                   10                  15

Gly
```

<210> SEQ ID NO 94
<211> LENGTH: 8
<212> TYPE: PRT
<213> ORGANISM: Artificial Sequence
<220> FEATURE:
<223> OTHER INFORMATION: Antibody sequence

<400> SEQUENCE: 94

```
Leu Thr Gly Thr Ser Phe Asp Tyr
1               5
```

<210> SEQ ID NO 95
<211> LENGTH: 109
<212> TYPE: PRT
<213> ORGANISM: Artificial Sequence
<220> FEATURE:
<223> OTHER INFORMATION: Antibody sequence

<400> SEQUENCE: 95

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
```

```
                20                  25                  30
Pro Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Phe Asp Ser Ser Leu
                85                  90                  95

Lys Lys Val Phe Gly Gly Gly Thr Lys Leu Thr Val Leu
            100                 105
```

<210> SEQ ID NO 96
<211> LENGTH: 13
<212> TYPE: PRT
<213> ORGANISM: Artificial Sequence
<220> FEATURE:
<223> OTHER INFORMATION: Antibody sequence

<400> SEQUENCE: 96

```
Ser Gly Ser Ser Ser Asn Ile Gly Ser Asn Pro Val Asn
1               5                   10
```

<210> SEQ ID NO 97
<211> LENGTH: 7
<212> TYPE: PRT
<213> ORGANISM: Artificial Sequence
<220> FEATURE:
<223> OTHER INFORMATION: Antibody sequence

<400> SEQUENCE: 97

```
Ser Asn Asn Gln Arg Pro Ser
1               5
```

<210> SEQ ID NO 98
<211> LENGTH: 10
<212> TYPE: PRT
<213> ORGANISM: Artificial Sequence
<220> FEATURE:
<223> OTHER INFORMATION: Antibody sequence

<400> SEQUENCE: 98

```
Gln Ser Phe Asp Ser Ser Leu Lys Lys Val
1               5                   10
```

<210> SEQ ID NO 99
<211> LENGTH: 446
<212> TYPE: PRT
<213> ORGANISM: Artificial Sequence
<220> FEATURE:
<223> OTHER INFORMATION: Antibody sequence

<400> SEQUENCE: 99

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Gly Ser Thr Tyr Ala Asp Ser Val
        50                  55                  60

Lys Gly Arg Phe Thr Ile Ser Arg Asp Asn Ser Lys Asn Thr Leu Tyr
```

```
            65                  70                  75                  80
Leu Gln Met Asn Ser Leu Arg Ala Glu Asp Thr Ala Val Tyr Tyr Cys
                    85                  90                  95

Ala Lys Leu Thr Gly Thr Ser Phe Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
                275                 280                 285

Thr Lys Pro Arg Glu Glu Gln Tyr Asn Ser Thr Tyr Arg Val Val Ser
                290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 100
<211> LENGTH: 215
<212> TYPE: PRT
<213> ORGANISM: Artificial Sequence
<220> FEATURE:
<223> OTHER INFORMATION: Antibody sequence
```

<400> SEQUENCE: 100

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Phe Asp Ser Ser Leu
                85                  90                  95

Lys Lys Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
            115                 120                 125

Gln Ala Asn Lys Ala Thr Leu Val Cys Leu Ile Ser Asp Phe Tyr Pro
130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
        210                 215

<210> SEQ ID NO 101
<211> LENGTH: 117
<212> TYPE: PRT
<213> ORGANISM: Artificial Sequence
<220> FEATURE:
<223> OTHER INFORMATION: Antibody sequence

<400> SEQUENCE: 101

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ser Ile Ser Gly Ser Gly Gly Ser Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Thr Ser Phe Asp Tyr Trp Gly Gln Gly Thr Leu
            100                 105                 110

Val Thr Val Ser Ser
        115

```
<210> SEQ ID NO 102
<211> LENGTH: 5
<212> TYPE: PRT
<213> ORGANISM: Artificial Sequence
<220> FEATURE:
<223> OTHER INFORMATION: Antibody sequence

<400> SEQUENCE: 102

Ser Tyr Ala Met Ser
1               5

<210> SEQ ID NO 103
<211> LENGTH: 17
<212> TYPE: PRT
<213> ORGANISM: Artificial Sequence
<220> FEATURE:
<223> OTHER INFORMATION: Antibody sequence

<400> SEQUENCE: 103

Ser Ile Ser Gly Ser Gly Gly Ser Thr Leu Tyr Ala Asp Ser Val Lys
1               5                   10                  15

Gly

<210> SEQ ID NO 104
<211> LENGTH: 8
<212> TYPE: PRT
<213> ORGANISM: Artificial Sequence
<220> FEATURE:
<223> OTHER INFORMATION: Antibody sequence

<400> SEQUENCE: 104

Leu Thr Gly Thr Ser Phe Asp Tyr
1               5

<210> SEQ ID NO 105
<211> LENGTH: 109
<212> TYPE: PRT
<213> ORGANISM: Artificial Sequence
<220> FEATURE:
<223> OTHER INFORMATION: Antibody sequence

<400> SEQUENCE: 105

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
                20                  25                  30

Pro Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Phe Asp Ser Ser Leu
                85                  90                  95

Lys Lys Val Phe Gly Gly Gly Thr Lys Leu Thr Val Leu
            100                 105

<210> SEQ ID NO 106
<211> LENGTH: 13
<212> TYPE: PRT
<213> ORGANISM: Artificial Sequence
<220> FEATURE:
<223> OTHER INFORMATION: Antibody sequence
```

-continued

<400> SEQUENCE: 106

Ser Gly Ser Ser Ser Asn Ile Gly Ser Asn Pro Val Asn
1               5                   10

<210> SEQ ID NO 107
<211> LENGTH: 7
<212> TYPE: PRT
<213> ORGANISM: Artificial Sequence
<220> FEATURE:
<223> OTHER INFORMATION: Antibody sequence

<400> SEQUENCE: 107

Ser Asn Asn Gln Arg Pro Ser
1               5

<210> SEQ ID NO 108
<211> LENGTH: 10
<212> TYPE: PRT
<213> ORGANISM: Artificial Sequence
<220> FEATURE:
<223> OTHER INFORMATION: Antibody sequence

<400> SEQUENCE: 108

Gln Ser Phe Asp Ser Ser Leu Lys Lys Val
1               5                   10

<210> SEQ ID NO 109
<211> LENGTH: 446
<212> TYPE: PRT
<213> ORGANISM: Artificial Sequence
<220> FEATURE:
<223> OTHER INFORMATION: Antibody sequence

<400> SEQUENCE: 109

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Gly Ser Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Thr Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

```
Thr Lys Val Asp Lys Lys Val Glu Pro Lys Ser Cys Asp Lys Thr His
    210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Gln Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
        435                 440                 445

<210> SEQ ID NO 110
<211> LENGTH: 215
<212> TYPE: PRT
<213> ORGANISM: Artificial Sequence
<220> FEATURE:
<223> OTHER INFORMATION: Antibody sequence

<400> SEQUENCE: 110

Gln Ser Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ser Asn
                20                  25                  30
Pro Val Asn Trp Tyr Gln Gln Leu Pro Gly Thr Ala Pro Lys Leu Leu
            35                  40                  45
Ile Tyr Ser Asn Asn Gln Arg Pro Ser Gly Val Pro Asp Arg Phe Ser
        50                  55                  60
Gly Ser Lys Ser Gly Thr Ser Ala Ser Leu Ala Ile Thr Gly Leu Gln
65                  70                  75                  80
Ser Glu Asp Glu Ala Asp Tyr Tyr Cys Gln Ser Phe Asp Ser Ser Leu
                85                  90                  95
Lys Lys Val Phe Gly Gly Gly Thr Lys Leu Thr Val Leu Gly Gln Pro
            100                 105                 110
Lys Ala Ala Pro Ser Val Thr Leu Phe Pro Pro Ser Ser Glu Glu Leu
        115                 120                 125
```

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 111
<211> LENGTH: 120
<212> TYPE: PRT
<213> ORGANISM: Artificial Sequence
<220> FEATURE:
<223> OTHER INFORMATION: Antibody sequence

<400> SEQUENCE: 111

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Pro Met Ile Trp Val Arg Gln Ala Pro Gly Lys Gly Leu Glu Trp Val
        35                  40                  45

Ser Tyr Ile Ser Pro Ser Gly Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser
        115                 120

<210> SEQ ID NO 112
<211> LENGTH: 5
<212> TYPE: PRT
<213> ORGANISM: Artificial Sequence
<220> FEATURE:
<223> OTHER INFORMATION: Antibody sequence

<400> SEQUENCE: 112

Pro Tyr Pro Met Ile
1               5

<210> SEQ ID NO 113
<211> LENGTH: 17
<212> TYPE: PRT
<213> ORGANISM: Artificial Sequence
<220> FEATURE:
<223> OTHER INFORMATION: Antibody sequence

<400> SEQUENCE: 113

Tyr Ile Ser Pro Ser Gly Gly Ser Thr His Tyr Ala Asp Ser Val Lys
1               5                   10                  15

Gly

<210> SEQ ID NO 114
<211> LENGTH: 11
<212> TYPE: PRT
<213> ORGANISM: Artificial Sequence
<220> FEATURE:
<223> OTHER INFORMATION: Antibody sequence

<400> SEQUENCE: 114

Gly Gly Asp Thr Tyr Phe Asp Tyr Phe Asp Tyr
1               5                   10

<210> SEQ ID NO 115
<211> LENGTH: 108
<212> TYPE: PRT
<213> ORGANISM: Artificial Sequence
<220> FEATURE:
<223> OTHER INFORMATION: Antibody sequence

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys
            100                 105

<210> SEQ ID NO 116
<211> LENGTH: 11
<212> TYPE: PRT
<213> ORGANISM: Artificial Sequence
<220> FEATURE:
<223> OTHER INFORMATION: Antibody sequence

<400> SEQUENCE: 116

Arg Ala Ser Gln Ser Ile Ser Gly Tyr Leu Asn
1               5                   10

<210> SEQ ID NO 117
<211> LENGTH: 7
<212> TYPE: PRT
<213> ORGANISM: Artificial Sequence
<220> FEATURE:
<223> OTHER INFORMATION: Antibody sequence

<400> SEQUENCE: 117

Gln Ala Ser Ser Leu Gln Ser
1               5

<210> SEQ ID NO 118
<211> LENGTH: 10
<212> TYPE: PRT
<213> ORGANISM: Artificial Sequence
<220> FEATURE:
<223> OTHER INFORMATION: Antibody sequence

<400> SEQUENCE: 118

Gln Gln Ser Tyr Thr Ser Pro Phe Ile Thr
1               5                   10

<210> SEQ ID NO 119
<211> LENGTH: 449
<212> TYPE: PRT
<213> ORGANISM: Artificial Sequence
<220> FEATURE:
<223> OTHER INFORMATION: Antibody sequence

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
                20                  25                  30

Pro Met Ile Trp Val Arg Gln Ala Pro Gly Lys Gly Leu Glu Trp Val
            35                  40                  45

Ser Tyr Ile Ser Pro Ser Gly Gly Ser Thr His Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Thr Tyr Phe Asp Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Asn Tyr Gln Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 120
<211> LENGTH: 215
<212> TYPE: PRT
<213> ORGANISM: Artificial Sequence
<220> FEATURE:
<223> OTHER INFORMATION: Antibody sequence

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gly Tyr
            20                  25                  30

Leu Asn Trp Tyr Gln Gln Lys Pro Gly Lys Ala Pro Lys Leu Leu Ile
        35                  40                  45

Tyr Gln Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Pro Phe
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 121
<211> LENGTH: 120
<212> TYPE: PRT

```
<213> ORGANISM: Artificial Sequence
<220> FEATURE:
<223> OTHER INFORMATION: Antibody sequence

<400> SEQUENCE: 121

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ile Ile Ala Trp Val Lys Gln Ala Pro Gly Gln Gly Leu Glu Trp Ile
        35                  40                  45

Gly Glu Ile Tyr Pro Gly Thr Gly Arg Thr Tyr Tyr Ser Glu Lys Phe
    50                  55                  60

Arg Gly Lys Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Arg Thr Ile Tyr Tyr Asp Tyr Asp Gly Asp Tyr Trp Gly Gln
            100                 105                 110

Gly Thr Leu Val Thr Val Ser Ser
        115                 120

<210> SEQ ID NO 122
<211> LENGTH: 5
<212> TYPE: PRT
<213> ORGANISM: Artificial Sequence
<220> FEATURE:
<223> OTHER INFORMATION: Antibody sequence

<400> SEQUENCE: 122

Asp Phe Ile Ile Ala
1               5

<210> SEQ ID NO 123
<211> LENGTH: 17
<212> TYPE: PRT
<213> ORGANISM: Artificial Sequence
<220> FEATURE:
<223> OTHER INFORMATION: Antibody sequence

<400> SEQUENCE: 123

Glu Ile Tyr Pro Gly Thr Gly Arg Thr Tyr Tyr Ser Glu Lys Phe Arg
1               5                   10                  15

Gly

<210> SEQ ID NO 124
<211> LENGTH: 11
<212> TYPE: PRT
<213> ORGANISM: Artificial Sequence
<220> FEATURE:
<223> OTHER INFORMATION: Antibody sequence

<400> SEQUENCE: 124

Arg Thr Ile Tyr Tyr Asp Tyr Asp Gly Asp Tyr
1               5                   10

<210> SEQ ID NO 125
<211> LENGTH: 112
<212> TYPE: PRT
<213> ORGANISM: Artificial Sequence
<220> FEATURE:
<223> OTHER INFORMATION: Antibody sequence
```

```
<400> SEQUENCE: 125

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ala His Asn
                85                  90                  95

Leu Glu Leu Pro Trp Thr Phe Gly Gln Gly Thr Lys Val Glu Ile Lys
            100                 105                 110

<210> SEQ ID NO 126
<211> LENGTH: 16
<212> TYPE: PRT
<213> ORGANISM: Artificial Sequence
<220> FEATURE:
<223> OTHER INFORMATION: Antibody sequence

<400> SEQUENCE: 126

Arg Ser Ser Gln Ser Leu Leu His Ser Asn Gly Ile Thr Tyr Leu Tyr
1               5                   10                  15

<210> SEQ ID NO 127
<211> LENGTH: 7
<212> TYPE: PRT
<213> ORGANISM: Artificial Sequence
<220> FEATURE:
<223> OTHER INFORMATION: Antibody sequence

<400> SEQUENCE: 127

Gln Met Ser Asn Arg Ala Ser
1               5

<210> SEQ ID NO 128
<211> LENGTH: 9
<212> TYPE: PRT
<213> ORGANISM: Artificial Sequence
<220> FEATURE:
<223> OTHER INFORMATION: Antibody sequence

<400> SEQUENCE: 128

Ala His Asn Leu Glu Leu Pro Trp Thr
1               5

<210> SEQ ID NO 129
<211> LENGTH: 449
<212> TYPE: PRT
<213> ORGANISM: Artificial Sequence
<220> FEATURE:
<223> OTHER INFORMATION: Antibody sequence

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ile Ile Ala Trp Val Lys Gln Ala Pro Gly Gln Gly Leu Glu Trp Ile
```

```
            35                  40                  45
Gly Glu Ile Tyr Pro Gly Thr Gly Arg Thr Tyr Tyr Ser Glu Lys Phe
 50                  55                  60

Arg Gly Lys Ala Thr Leu Thr Ala Asp Thr Ser Thr Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Arg Thr Ile Tyr Tyr Asp Tyr Asp Gly Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly
```

<210> SEQ ID NO 130
<211> LENGTH: 219
<212> TYPE: PRT
<213> ORGANISM: Artificial Sequence
<220> FEATURE:
<223> OTHER INFORMATION: Antibody sequence

<400> SEQUENCE: 130

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 131
<211> LENGTH: 120
<212> TYPE: PRT
<213> ORGANISM: Artificial Sequence
<220> FEATURE:
<223> OTHER INFORMATION: Antibody sequence

<400> SEQUENCE: 131

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ile Ile Ala Trp Val Lys Gln Ala Pro Gly Gln Gly Leu Glu Trp Ile
        35                  40                  45

Gly Glu Ile Tyr Pro Gly Thr Gly Arg Thr Tyr Tyr Ser Glu Lys Phe
    50                  55                  60

Arg Gly Lys Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95
```

```
Ala Arg Arg Thr Ile Tyr Tyr Asp Tyr Asp Gly Asp Tyr Trp Gly Gln
                100                 105                 110

Gly Thr Leu Val Thr Val Ser Ser
        115                 120

<210> SEQ ID NO 132
<211> LENGTH: 5
<212> TYPE: PRT
<213> ORGANISM: Artificial Sequence
<220> FEATURE:
<223> OTHER INFORMATION: Antibody sequence

<400> SEQUENCE: 132

Asp Phe Ile Ile Ala
1               5

<210> SEQ ID NO 133
<211> LENGTH: 17
<212> TYPE: PRT
<213> ORGANISM: Artificial Sequence
<220> FEATURE:
<223> OTHER INFORMATION: Antibody sequence

<400> SEQUENCE: 133

Glu Ile Tyr Pro Gly Thr Gly Arg Thr Tyr Tyr Ser Glu Lys Phe Arg
1               5                   10                  15

Gly

<210> SEQ ID NO 134
<211> LENGTH: 11
<212> TYPE: PRT
<213> ORGANISM: Artificial Sequence
<220> FEATURE:
<223> OTHER INFORMATION: Antibody sequence

<400> SEQUENCE: 134

Arg Thr Ile Tyr Tyr Asp Tyr Asp Gly Asp Tyr
1               5                   10

<210> SEQ ID NO 135
<211> LENGTH: 112
<212> TYPE: PRT
<213> ORGANISM: Artificial Sequence
<220> FEATURE:
<223> OTHER INFORMATION: Antibody sequence

<400> SEQUENCE: 135

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Ile Asn Tyr Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gln Gly Thr Lys Val Glu Ile Lys
            100                 105                 110
```

-continued

```
<210> SEQ ID NO 136
<211> LENGTH: 16
<212> TYPE: PRT
<213> ORGANISM: Artificial Sequence
<220> FEATURE:
<223> OTHER INFORMATION: Antibody sequence

<400> SEQUENCE: 136

Arg Ser Ser Gln Ser Leu Leu His Ser Asn Gly Ile Asn Tyr Leu Tyr
1               5                   10                  15

<210> SEQ ID NO 137
<211> LENGTH: 7
<212> TYPE: PRT
<213> ORGANISM: Artificial Sequence
<220> FEATURE:
<223> OTHER INFORMATION: Antibody sequence

<400> SEQUENCE: 137

Gln Met Ser Asn Arg Ala Ser
1               5

<210> SEQ ID NO 138
<211> LENGTH: 9
<212> TYPE: PRT
<213> ORGANISM: Artificial Sequence
<220> FEATURE:
<223> OTHER INFORMATION: Antibody sequence

<400> SEQUENCE: 138

Ala His Asn Leu Glu Leu Pro Trp Thr
1               5

<210> SEQ ID NO 139
<211> LENGTH: 449
<212> TYPE: PRT
<213> ORGANISM: Artificial Sequence
<220> FEATURE:
<223> OTHER INFORMATION: Antibody sequence

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
                20                  25                  30

Ile Ile Ala Trp Val Lys Gln Ala Pro Gly Gln Gly Leu Glu Trp Ile
            35                  40                  45

Gly Glu Ile Tyr Pro Gly Thr Gly Arg Thr Tyr Tyr Ser Glu Lys Phe
        50                  55                  60

Arg Gly Lys Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Arg Thr Ile Tyr Tyr Asp Tyr Asp Gly Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

-continued

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 140
<211> LENGTH: 219
<212> TYPE: PRT
<213> ORGANISM: Artificial Sequence
<220> FEATURE:
<223> OTHER INFORMATION: Antibody sequence

<400> SEQUENCE: 140

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Ile Asn Tyr Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile

-continued

```
                65                  70                  75                  80
        Ser Arg Val Glu Ala Glu Asp Val Gly Val Tyr Tyr Cys Ala His Asn
                        85                  90                  95

Leu Glu Leu Pro Trp Thr Phe Gly Gln Gly Thr Lys Val Glu Ile Lys
                        100                 105                 110

Arg Thr Val Ala Ala Pro Ser Val Phe Ile Phe Pro Pro Ser Asp Glu
                        115                 120                 125

Gln Leu Lys Ser Gly Thr Ala Ser Val Val Cys Leu Leu Asn Asn Phe
                        130                 135                 140

Tyr Pro Arg Glu Ala Lys Val Gln Trp Lys Val Asp Asn Ala Leu Gln
        145                 150                 155                 160

Ser Gly Asn Ser Gln Glu Ser Val Thr Glu Gln Asp Ser Lys Asp Ser
                        165                 170                 175

Thr Tyr Ser Leu Ser Ser Thr Leu Thr Leu Ser Lys Ala Asp Tyr Glu
                        180                 185                 190

Lys His Lys Val Tyr Ala Cys Glu Val Thr His Gln Gly Leu Ser Ser
                        195                 200                 205

Pro Val Thr Lys Ser Phe Asn Arg Gly Glu Cys
                        210                 215

<210> SEQ ID NO 141
<211> LENGTH: 120
<212> TYPE: PRT
<213> ORGANISM: Artificial Sequence
<220> FEATURE:
<223> OTHER INFORMATION: Antibody sequence

<400> SEQUENCE: 141

Gln Val Gln Leu Val Gln Ser Gly Ala Glu Val Lys Lys Pro Gly Ala
        1               5                   10                  15

Ser Val Lys Val Ser Cys Lys Ala Ser Gly Tyr Thr Phe Thr Asp Phe
                        20                  25                  30

Ile Ile Ala Trp Val Lys Gln Ala Pro Gly Gln Gly Leu Glu Trp Ile
                        35                  40                  45

Gly Glu Ile Tyr Pro Gly Thr Gly Arg Thr Tyr Tyr Ser Glu Lys Phe
                        50                  55                  60

Arg Gly Lys Ala Thr Leu Thr Ala Asp Thr Ser Thr Ser Thr Ala Tyr
        65                  70                  75                  80

Met Glu Leu Ser Ser Leu Arg Ser Glu Asp Thr Ala Val Tyr Phe Cys
                        85                  90                  95

Ala Arg Arg Thr Ile Tyr Tyr Asp Tyr Asp Gly Asp Tyr Trp Gly Gln
                        100                 105                 110

Gly Thr Leu Val Thr Val Ser Ser
                        115                 120

<210> SEQ ID NO 142
<211> LENGTH: 5
<212> TYPE: PRT
<213> ORGANISM: Artificial Sequence
<220> FEATURE:
<223> OTHER INFORMATION: Antibody sequence

<400> SEQUENCE: 142

Asp Phe Ile Ile Ala
        1               5

<210> SEQ ID NO 143
<211> LENGTH: 17
```

```
<212> TYPE: PRT
<213> ORGANISM: Artificial Sequence
<220> FEATURE:
<223> OTHER INFORMATION: Antibody sequence

<400> SEQUENCE: 143

Glu Ile Tyr Pro Gly Thr Gly Arg Thr Tyr Tyr Ser Glu Lys Phe Arg
1               5                   10                  15

Gly

<210> SEQ ID NO 144
<211> LENGTH: 11
<212> TYPE: PRT
<213> ORGANISM: Artificial Sequence
<220> FEATURE:
<223> OTHER INFORMATION: Antibody sequence

<400> SEQUENCE: 144

Arg Thr Ile Tyr Tyr Asp Tyr Asp Gly Asp Tyr
1               5                   10

<210> SEQ ID NO 145
<211> LENGTH: 112
<212> TYPE: PRT
<213> ORGANISM: Artificial Sequence
<220> FEATURE:
<223> OTHER INFORMATION: Antibody sequence

<400> SEQUENCE: 145

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Trp Ile Asn Tyr Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gln Gly Thr Lys Val Glu Ile Lys
            100                 105                 110

<210> SEQ ID NO 146
<211> LENGTH: 16
<212> TYPE: PRT
<213> ORGANISM: Artificial Sequence
<220> FEATURE:
<223> OTHER INFORMATION: Antibody sequence

<400> SEQUENCE: 146

Arg Ser Ser Gln Ser Leu Leu His Ser Asn Trp Ile Asn Tyr Leu Tyr
1               5                   10                  15

<210> SEQ ID NO 147
<211> LENGTH: 7
<212> TYPE: PRT
<213> ORGANISM: Artificial Sequence
<220> FEATURE:
<223> OTHER INFORMATION: Antibody sequence

<400> SEQUENCE: 147
```

Gln Met Ser Asn Arg Ala Ser
1               5

<210> SEQ ID NO 148
<211> LENGTH: 9
<212> TYPE: PRT
<213> ORGANISM: Artificial Sequence
<220> FEATURE:
<223> OTHER INFORMATION: Antibody sequence

<400> SEQUENCE: 148

Ala His Asn Leu Glu Leu Pro Trp Thr
1               5

<210> SEQ ID NO 149
<211> LENGTH: 449
<212> TYPE: PRT
<213> ORGANISM: Artificial Sequence
<220> FEATURE:
<223> OTHER INFORMATION: Antibody sequence

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
                20                  25                  30

Ile Ile Ala Trp Val Lys Gln Ala Pro Gly Gln Gly Leu Glu Trp Ile
            35                  40                  45

Gly Glu Ile Tyr Pro Gly Thr Gly Arg Thr Tyr Tyr Ser Glu Lys Phe
    50                  55                  60

Arg Gly Lys Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Arg Thr Ile Tyr Tyr Asp Tyr Asp Gly Asp Tyr Trp Gly Gln
            100                 105                 110

Gly Thr Leu Val Thr Val Ser Ser Ala Ser Thr Lys Gly Pro Ser Val
    115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
            290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 150
<211> LENGTH: 219
<212> TYPE: PRT
<213> ORGANISM: Artificial Sequence
<220> FEATURE:
<223> OTHER INFORMATION: Antibody sequence

<400> SEQUENCE: 150

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Trp Ile Asn Tyr Leu Tyr Trp Tyr Leu Gln Lys Pro Gly Gln Ser
            35                  40                  45

Pro Gln Leu Leu Ile Tyr Gln Met Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

```
Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 151
<211> LENGTH: 120
<212> TYPE: PRT
<213> ORGANISM: Artificial Sequence
<220> FEATURE:
<223> OTHER INFORMATION: Antibody sequence

<400> SEQUENCE: 151

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ile Ile Ala Trp Val Lys Gln Ala Pro Gly Gln Gly Leu Glu Trp Ile
        35                  40                  45

Gly Glu Ile Tyr Pro Gly Thr Gly Arg Thr Tyr Tyr Ser Glu Lys Phe
    50                  55                  60

Arg Gly Lys Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Arg Thr Ile Tyr Tyr Asp Tyr Asp Gly Asp Tyr Trp Gly Gln
            100                 105                 110

Gly Thr Leu Val Thr Val Ser Ser
        115                 120

<210> SEQ ID NO 152
<211> LENGTH: 5
<212> TYPE: PRT
<213> ORGANISM: Artificial Sequence
<220> FEATURE:
<223> OTHER INFORMATION: Antibody sequence

<400> SEQUENCE: 152

Asp Phe Ile Ile Ala
1               5

<210> SEQ ID NO 153
<211> LENGTH: 17
<212> TYPE: PRT
<213> ORGANISM: Artificial Sequence
<220> FEATURE:
<223> OTHER INFORMATION: Antibody sequence

<400> SEQUENCE: 153

Glu Ile Tyr Pro Gly Thr Gly Arg Thr Tyr Tyr Ser Glu Lys Phe Arg
1               5                   10                  15

Gly

<210> SEQ ID NO 154
<211> LENGTH: 11
<212> TYPE: PRT
<213> ORGANISM: Artificial Sequence
<220> FEATURE:
<223> OTHER INFORMATION: Antibody sequence

<400> SEQUENCE: 154

Arg Thr Ile Tyr Tyr Asp Tyr Asp Gly Asp Tyr
```

<210> SEQ ID NO 155
<211> LENGTH: 112
<212> TYPE: PRT
<213> ORGANISM: Artificial Sequence
<220> FEATURE:
<223> OTHER INFORMATION: Antibody sequence

<400> SEQUENCE: 155

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Trp Ile Asn Tyr Leu Tyr Trp Tyr Leu Gln Lys Pro Gly Gln Ser
        35                  40                  45

Pro Gln Leu Leu Ile Tyr Gln Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gln Gly Thr Lys Val Glu Ile Lys
            100                 105                 110

<210> SEQ ID NO 156
<211> LENGTH: 16
<212> TYPE: PRT
<213> ORGANISM: Artificial Sequence
<220> FEATURE:
<223> OTHER INFORMATION: Antibody sequence

<400> SEQUENCE: 156

Arg Ser Ser Gln Ser Leu Leu His Ser Asn Trp Ile Asn Tyr Leu Tyr
1               5                   10                  15

<210> SEQ ID NO 157
<211> LENGTH: 7
<212> TYPE: PRT
<213> ORGANISM: Artificial Sequence
<220> FEATURE:
<223> OTHER INFORMATION: Antibody sequence

<400> SEQUENCE: 157

Gln Gly Ser Asn Arg Ala Ser
1               5

<210> SEQ ID NO 158
<211> LENGTH: 9
<212> TYPE: PRT
<213> ORGANISM: Artificial Sequence
<220> FEATURE:
<223> OTHER INFORMATION: Antibody sequence

<400> SEQUENCE: 158

Ala His Asn Leu Glu Leu Pro Trp Thr
1               5

<210> SEQ ID NO 159
<211> LENGTH: 449
<212> TYPE: PRT
<213> ORGANISM: Artificial Sequence
<220> FEATURE:
<223> OTHER INFORMATION: Antibody sequence

<400> SEQUENCE: 159

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Phe
            20                  25                  30

Ile Ile Ala Trp Val Lys Gln Ala Pro Gly Gln Gly Leu Glu Trp Ile
        35                  40                  45

Gly Glu Ile Tyr Pro Gly Thr Gly Arg Thr Tyr Tyr Ser Glu Lys Phe
    50                  55                  60

Arg Gly Lys Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Arg Thr Ile Tyr Tyr Asp Tyr Asp Gly Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
```

```
                            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 160
<211> LENGTH: 219
<212> TYPE: PRT
<213> ORGANISM: Artificial Sequence
<220> FEATURE:
<223> OTHER INFORMATION: Antibody sequence

<400> SEQUENCE: 160

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Trp Ile Asn Tyr Leu Tyr Trp Tyr Leu Gln Lys Pro Gly Gln Ser
        35                  40                  45

Pro Gln Leu Leu Ile Tyr Gln Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala His Asn
                85                  90                  95

Leu Glu Leu Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 161
<211> LENGTH: 28
<212> TYPE: PRT
<213> ORGANISM: Artificial Sequence
<220> FEATURE:
<223> OTHER INFORMATION: c(RGDfK)

<400> SEQUENCE: 161

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25
```

```
<210> SEQ ID NO 162
<211> LENGTH: 20
<212> TYPE: PRT
<213> ORGANISM: Artificial Sequence
<220> FEATURE:
<223> OTHER INFORMATION: HER2-targeting peptide

<400> SEQUENCE: 162

Ala Thr Glu Pro Arg Lys Gln Tyr Ala Thr Pro Arg Val Phe Trp Thr
1               5                   10                  15

Asp Ala Pro Gly
            20

<210> SEQ ID NO 163
<211> LENGTH: 20
<212> TYPE: PRT
<213> ORGANISM: Artificial Sequence
<220> FEATURE:
<223> OTHER INFORMATION: HER2-targeting peptide

<400> SEQUENCE: 163

Leu Gln Trp Arg Arg Asp Asp Asn Val His Asn Phe Gly Val Trp Ala
1               5                   10                  15

Arg Tyr Arg Leu
            20

<210> SEQ ID NO 164
<211> LENGTH: 129
<212> TYPE: PRT
<213> ORGANISM: Homo sapiens

<400> SEQUENCE: 164

Met Ala Arg Gly Ser Leu Arg Arg Leu Leu Arg Leu Leu Val Leu Gly
1               5                   10                  15

Leu Trp Leu Ala Leu Leu Arg Ser Val Ala Gly Glu Gln Ala Pro Gly
                20                  25                  30

Thr Ala Pro Cys Ser Arg Gly Ser Ser Trp Ser Ala Asp Leu Asp Lys
            35                  40                  45

Cys Met Asp Cys Ala Ser Cys Arg Ala Arg Pro His Ser Asp Phe Cys
    50                  55                  60

Leu Gly Cys Ala Ala Ala Pro Pro Ala Pro Phe Arg Leu Leu Trp Pro
65                  70                  75                  80

Ile Leu Gly Gly Ala Leu Ser Leu Thr Phe Val Leu Gly Leu Leu Ser
                85                  90                  95

Gly Phe Leu Val Trp Arg Arg Cys Arg Arg Arg Glu Lys Phe Thr Thr
            100                 105                 110

Pro Ile Glu Glu Thr Gly Gly Glu Gly Cys Pro Ala Val Ala Leu Ile
        115                 120                 125

Gln

<210> SEQ ID NO 165
<211> LENGTH: 534
<212> TYPE: PRT
<213> ORGANISM: Homo sapiens

<400> SEQUENCE: 165

Met Leu Arg Arg Arg Gly Ser Pro Gly Met Gly Val His Val Gly Ala
1               5                   10                  15

Ala Leu Gly Ala Leu Trp Phe Cys Leu Thr Gly Ala Leu Glu Val Gln
                20                  25                  30
```

```
Val Pro Glu Asp Pro Val Val Ala Leu Val Gly Thr Asp Ala Thr Leu
             35                  40                  45

Cys Cys Ser Phe Ser Pro Glu Pro Gly Phe Ser Leu Ala Gln Leu Asn
 50                  55                  60

Leu Ile Trp Gln Leu Thr Asp Thr Lys Gln Leu Val His Ser Phe Ala
 65                  70                  75                  80

Glu Gly Gln Asp Gln Gly Ser Ala Tyr Ala Asn Arg Thr Ala Leu Phe
                 85                  90                  95

Pro Asp Leu Leu Ala Gln Gly Asn Ala Ser Leu Arg Leu Gln Arg Val
                100                 105                 110

Arg Val Ala Asp Glu Gly Ser Phe Thr Cys Phe Val Ser Ile Arg Asp
                115                 120                 125

Phe Gly Ser Ala Ala Val Ser Leu Gln Val Ala Ala Pro Tyr Ser Lys
130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
                180                 185                 190

Ser Gln Met Ala Asn Glu Gln Gly Leu Phe Asp Val His Ser Ile Leu
                195                 200                 205

Arg Val Val Leu Gly Ala Asn Gly Thr Tyr Ser Cys Leu Val Arg Asn
                210                 215                 220

Pro Val Leu Gln Gln Asp Ala His Ser Ser Val Thr Ile Thr Pro Gln
225                 230                 235                 240

Arg Ser Pro Thr Gly Ala Val Glu Val Gln Val Pro Glu Asp Pro Val
                245                 250                 255

Val Ala Leu Val Gly Thr Asp Ala Thr Leu Arg Cys Ser Phe Ser Pro
                260                 265                 270

Glu Pro Gly Phe Ser Leu Ala Gln Leu Asn Leu Ile Trp Gln Leu Thr
                275                 280                 285

Asp Thr Lys Gln Leu Val His Ser Phe Thr Glu Gly Arg Asp Gln Gly
290                 295                 300

Ser Ala Tyr Ala Asn Arg Thr Ala Leu Phe Pro Asp Leu Leu Ala Gln
305                 310                 315                 320

Gly Asn Ala Ser Leu Arg Leu Gln Arg Val Arg Val Ala Asp Glu Gly
                325                 330                 335

Ser Phe Thr Cys Phe Val Ser Ile Arg Asp Phe Gly Ser Ala Ala Val
                340                 345                 350

Ser Leu Gln Val Ala Ala Pro Tyr Ser Lys Pro Ser Met Thr Leu Glu
                355                 360                 365

Pro Asn Lys Asp Leu Arg Pro Gly Asp Thr Val Thr Ile Thr Cys Ser
370                 375                 380

Ser Tyr Arg Gly Tyr Pro Glu Ala Glu Val Phe Trp Gln Asp Gly Gln
385                 390                 395                 400

Gly Val Pro Leu Thr Gly Asn Val Thr Thr Ser Gln Met Ala Asn Glu
                405                 410                 415

Gln Gly Leu Phe Asp Val His Ser Val Leu Arg Val Val Leu Gly Ala
                420                 425                 430

Asn Gly Thr Tyr Ser Cys Leu Val Arg Asn Pro Val Leu Gln Gln Asp
                435                 440                 445

Ala His Gly Ser Val Thr Ile Thr Gly Gln Pro Met Thr Phe Pro Pro
```

-continued

```
                450                 455                 460
Glu Ala Leu Trp Val Thr Val Gly Leu Ser Val Cys Leu Ile Ala Leu
465                 470                 475                 480

Leu Val Ala Leu Ala Phe Val Cys Trp Arg Lys Ile Lys Gln Ser Cys
                485                 490                 495

Glu Glu Glu Asn Ala Gly Ala Glu Asp Gln Asp Gly Glu Gly Glu Gly
                500                 505                 510

Ser Lys Thr Ala Leu Gln Pro Leu Lys His Ser Asp Ser Lys Glu Asp
                515                 520                 525

Asp Gly Gln Glu Ile Ala
                530

<210> SEQ ID NO 166
<211> LENGTH: 1255
<212> TYPE: PRT
<213> ORGANISM: Homo sapiens

<400> SEQUENCE: 166

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285
```

-continued

```
Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
    450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
```

```
                705                 710                 715                 720
            Arg Lys Val Lys Val Leu Gly Ser Gly Ala Phe Gly Thr Val Tyr Lys
                            725                 730                 735
            Gly Ile Trp Ile Pro Asp Gly Glu Asn Val Lys Ile Pro Val Ala Ile
                            740                 745                 750
            Lys Val Leu Arg Glu Asn Thr Ser Pro Lys Ala Asn Lys Glu Ile Leu
                            755                 760                 765
            Asp Glu Ala Tyr Val Met Ala Gly Val Gly Ser Pro Tyr Val Ser Arg
                            770                 775                 780
            Leu Leu Gly Ile Cys Leu Thr Ser Thr Val Gln Leu Val Thr Gln Leu
            785                 790                 795                 800
            Met Pro Tyr Gly Cys Leu Leu Asp His Val Arg Glu Asn Arg Gly Arg
                            805                 810                 815
            Leu Gly Ser Gln Asp Leu Leu Asn Trp Cys Met Gln Ile Ala Lys Gly
                            820                 825                 830
            Met Ser Tyr Leu Glu Asp Val Arg Leu Val His Arg Asp Leu Ala Ala
                            835                 840                 845
            Arg Asn Val Leu Val Lys Ser Pro Asn His Val Lys Ile Thr Asp Phe
            850                 855                 860
            Gly Leu Ala Arg Leu Leu Asp Ile Asp Glu Thr Glu Tyr His Ala Asp
            865                 870                 875                 880
            Gly Gly Lys Val Pro Ile Lys Trp Met Ala Leu Glu Ser Ile Leu Arg
                            885                 890                 895
            Arg Arg Phe Thr His Gln Ser Asp Val Trp Ser Tyr Gly Val Thr Val
                            900                 905                 910
            Trp Glu Leu Met Thr Phe Gly Ala Lys Pro Tyr Asp Gly Ile Pro Ala
                            915                 920                 925
            Arg Glu Ile Pro Asp Leu Leu Glu Lys Gly Glu Arg Leu Pro Gln Pro
                            930                 935                 940
            Pro Ile Cys Thr Ile Asp Val Tyr Met Ile Met Val Lys Cys Trp Met
            945                 950                 955                 960
            Ile Asp Ser Glu Cys Arg Pro Arg Phe Arg Glu Leu Val Ser Glu Phe
                            965                 970                 975
            Ser Arg Met Ala Arg Asp Pro Gln Arg Phe Val Val Ile Gln Asn Glu
                            980                 985                 990
            Asp Leu Gly Pro Ala Ser Pro Leu Asp Ser Thr Phe Tyr Arg Ser Leu
                            995                 1000                1005
            Leu Glu Asp Asp Asp Met Gly Asp Leu Val Asp Ala Glu Glu Tyr
                1010                1015                1020
            Leu Val Pro Gln Gln Gly Phe Phe Cys Pro Asp Pro Ala Pro Gly
                1025                1030                1035
            Ala Gly Gly Met Val His His Arg His Arg Ser Ser Ser Thr Arg
                1040                1045                1050
            Ser Gly Gly Gly Asp Leu Thr Leu Gly Leu Glu Pro Ser Glu Glu
                1055                1060                1065
            Glu Ala Pro Arg Ser Pro Leu Ala Pro Ser Glu Gly Ala Gly Ser
                1070                1075                1080
            Asp Val Phe Asp Gly Asp Leu Gly Met Gly Ala Ala Lys Gly Leu
                1085                1090                1095
            Gln Ser Leu Pro Thr His Asp Pro Ser Pro Leu Gln Arg Tyr Ser
                1100                1105                1110
            Glu Asp Pro Thr Val Pro Leu Pro Ser Glu Thr Asp Gly Tyr Val
                1115                1120                1125
```

-continued

```
Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 167
<211> LENGTH: 1210
<212> TYPE: PRT
<213> ORGANISM: Homo sapiens

<400> SEQUENCE: 167

Met Arg Pro Ser Gly Thr Ala Gly Ala Ala Leu Leu Ala Leu Ala
1               5                   10                  15

Ala Leu Cys Pro Ala Ser Arg Ala Leu Glu Glu Lys Lys Val Cys Gln
        20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
                180                 185                 190

Ser Cys Pro Asn Gly Ser Cys Trp Gly Ala Gly Glu Asn Cys Gln
            195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
```

```
              225                 230                 235                 240
Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
                275                 280                 285

Ala Thr Cys Val Lys Lys Cys Pro Arg Asn Tyr Val Val Thr Asp His
            290                 295                 300

Gly Ser Cys Val Arg Ala Cys Gly Ala Asp Ser Tyr Glu Met Glu Glu
305                 310                 315                 320

Asp Gly Val Arg Lys Cys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
                355                 360                 365

Leu His Ile Leu Pro Val Ala Phe Arg Gly Asp Ser Phe Thr His Thr
            370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
                515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
            610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655
```

```
Leu Leu Val Val Ala Leu Gly Ile Gly Leu Phe Met Arg Arg His
            660                 665                 670

Ile Val Arg Lys Arg Thr Leu Arg Arg Leu Leu Gln Glu Arg Glu Leu
            675                 680                 685

Val Glu Pro Leu Thr Pro Ser Gly Glu Ala Pro Asn Gln Ala Leu Leu
        690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                 1005
```

-continued

| | | | | | | | | | | |
|---|---|---|---|---|---|---|---|---|---|---|
| Asp | Val 1010 | Val | Asp | Ala | Asp 1015 | Glu | Tyr | Leu | Ile | Pro Gln 1020 |
| Gln | Gly | Phe | | | | | | | | |
| Phe | Ser 1025 | Ser | Pro | Ser | Thr 1030 | Ser | Arg | Thr | Pro | Leu Leu 1035 |
| Ser | Ser | Leu | | | | | | | | |
| Ser | Ala 1040 | Thr | Ser | Asn | Asn 1045 | Ser | Thr | Val | Ala | Cys Ile 1050 |
| Asp | Arg | Asn | | | | | | | | |
| Gly | Leu 1055 | Gln | Ser | Cys | Pro 1060 | Ile | Lys | Glu | Asp | Ser Phe 1065 |
| Leu | Gln | Arg | | | | | | | | |
| Tyr | Ser 1070 | Ser | Asp | Pro | Thr 1075 | Gly | Ala | Leu | Thr | Glu Asp 1080 |
| Ser | Ile | Asp | | | | | | | | |
| Asp | Thr 1085 | Phe | Leu | Pro | Val 1090 | Pro | Glu | Tyr | Ile | Asn Gln 1095 |
| Ser | Val | Pro | | | | | | | | |
| Lys | Arg 1100 | Pro | Ala | Gly | Ser 1105 | Val | Gln | Asn | Pro | Val Tyr 1110 |
| His | Asn | Gln | | | | | | | | |
| Pro | Leu 1115 | Asn | Pro | Ala | Pro 1120 | Ser | Arg | Asp | Pro | His Tyr 1125 |
| Gln | Asp | Pro | | | | | | | | |
| His | Ser 1130 | Thr | Ala | Val | Gly 1135 | Asn | Pro | Glu | Tyr | Leu Asn 1140 |
| Thr | Val | Gln | | | | | | | | |
| Pro | Thr 1145 | Cys | Val | Asn | Ser 1150 | Thr | Phe | Asp | Ser | Pro Ala 1155 |
| His | Trp | Ala | | | | | | | | |
| Gln | Lys 1160 | Gly | Ser | His | Gln 1165 | Ile | Ser | Leu | Asp | Asn Pro 1170 |
| Asp | Tyr | Gln | | | | | | | | |
| Gln | Asp 1175 | Phe | Phe | Pro | Lys 1180 | Glu | Ala | Lys | Pro | Asn Gly 1185 |
| Ile | Phe | Lys | | | | | | | | |
| Gly | Ser 1190 | Thr | Ala | Glu | Asn 1195 | Ala | Glu | Tyr | Leu | Arg Val 1200 |
| Ala | Pro | Gln | | | | | | | | |
| Ser | Ser 1205 | Glu | Phe | Ile | Gly 1210 | Ala | | | | |

PRODRUGS OF CYTOTOXIC ACTIVE AGENTS HAVING ENZYMATICALLY CLEAVABLE GROUPS

CROSS REFERENCE TO RELATED APPLICATIONS

This application is a National Stage Entry Application under 35 U.S.C. § 371 of International Application No. PCT/EP2017/083305, filed internationally on Dec. 18, 2017, which claims the benefit of European Application No. 16205935.6, filed Dec. 21, 2016.

SUBMISSION OF SEQUENCE LISTING

The content of the following submission on ASCII text file is incorporated herein by reference in its entirety: a computer readable form (CRF) of the Sequence Listing (file name: 777052034400SEQLIST-SAN_FRANCISCO-4036284-V1.TXT, date recorded: Jun. 21, 2019, size: 177, 174 bytes).

INTRODUCTION AND STATE OF THE ART

The invention relates to novel prodrugs in which cytotoxic drugs, for example kinesin spindle protein inhibitors, are conjugated to groups which are selectively cleaved by tumour-associated proteases and hence release the drug, and to the use of these prodrugs or conjugates for treatment and/or prevention of diseases, and to the use of these prodrugs for production of medicaments for treatment and/or prevention of diseases, especially of hyperproliferative and/or angiogenic disorders, for example cancers. Such treatments can be effected as monotherapy or else in combination with other medicaments or further therapeutic measures.

Cancer cells frequently express particular proteases to a higher degree than normal cells. This has led to approaches for increasing the selectivity of cytotoxic drugs for cancer cells, in which the drugs are bonded to groups that are eliminated by such proteases, as a result of which the active ingredient is released.

Such a tumour-associated protease is legumain. Legumain is an asparaginyl endopeptidase (S. Ishii, Methods Enzymol. 1994, 244, 604; J. M. Chen et al. J. Biol. Chem. 1997, 272, 8090) and has been utilized for processing of prodrugs of small cytotoxic molecules, for example of doxorubicin and etoposide derivatives among others (W. Wu et al. Cancer Res. 2006, 66, 970; L. Stern et al; Bioconjugate Chem. 2009, 20, 500; K. M. Bajjuri et al. ChemMedChem 2011, 6, 54).

US 2015-0343083 A1 describes legumain-cleavable peptide-active ingredient conjugates of the formula R—Y—Z-Asn-linker-D in which linker is p-aminobenzylcarbamoyl or p-aminobenzylcarbonate, R is a residue selected from different chemical groups, D is a cytotoxic drug, Asn is the amino acid asparagine, Y is an amino acid selected from Ala, Thr, Ser, Leu, Arg, Pro, Val, Tyr and Phe, and Z is an amino acid selected from Ala, Thr, Asn and Pro, where these amino acids are always in the natural L configuration.

All the legumain-cleavable prodrugs described to date contain an oligopeptide sequence as legumain substrate.

GENERAL DESCRIPTION OF THE INVENTION

It is an object of the present invention to further improve the tumour selectivity of cytotoxic drugs. To achieve this object, the invention provides prodrugs of cytotoxic drug molecules. In this context, the active ingredient molecule is conjugated to a group cleavable by the enzyme legumain, with the active ingredient and the legumain-cleavable group joined either directly via a covalent bond or via a self-immolative linker. These prodrugs preferably contain a binder which, after binding to a receptor of a tumour cell, is internalized by the tumour cell and processed intracellularly (preferably lysosomally). This binder may either be bonded to the active ingredient molecule modified with the legumain-cleavable group, optionally via a linker, such that both groups (legumain-cleavable group and binder) have to be processed independently for formation of an active metabolite, or the binder may be bonded to the group cleavable by the enzyme legumain, optionally via a linker (such that, after cleavage of the legumain-cleavable group, the active ingredient is present separately from the binder or a derivative thereof). A preferred active ingredient molecule is a kinesin spindle protein inhibitor (KSP inhibitor). A preferred binder which is internalized after binding to a receptor on a tumour cell and is processed intracellularly (preferably lysosomally) is an antibody. Particular preference is given to antibody-active ingredient conjugates (ADCs), wherein antibody and active ingredient are joined to one another via a linker having a legumain-cleavable group. In addition, preference is given to conjugates of prodrugs with antibodies (APDCs), wherein the antibody is bonded to a prodrug of the antibody via a linker and wherein the action of the active ingredient is masked by a legumain-cleavable group. The legumain-cleavable group bonded to the active ingredient which is used in accordance with the invention has a structural motif reduced to the amino acid asparagine. This reduction, as a result of slowed cleavage by legumain, achieves an increase in stability in the lysosomes of healthy organs, but without impairing the high antitumour effect (see chapter C-1c below). As has been shown by representative comparisons with suitable reference examples containing a tripeptide as legumain-cleavable group (see chapter C-1a below), the ADCs and APDCs according to the invention with just one amino acid (asparagine) as enzymatic cleavage site in the linker have a high antitumour effect which is surprisingly barely inferior, if at all, to the analogues with conventional tripeptide substrates (three amino acids) in the linker (reference examples R1 and R6) (see chapter C-1a). The protease-cleavable linker sequence can thus be reduced to just one amino acid unit (one amino acid). Even for closely related conjugates with amino acids such as glutamine or leucine rather than asparagine (see model compound C RM-C below), it was not possible to show any cleavage by legumain in the enzymatic assay. Correspondingly, related ADCs to the examples 1 with glutamine rather than asparagine residues in the prodrug residue of the payload did not exhibit any cytotoxic effect. The same applies to analogous ADCs to example 6 that bear a leucine residue in place of asparagine in the linker; they also show virtually no cytotoxic effect, by contrast with the ADCs in example 6. While oligopeptide linkers can also be cleaved by various proteases, the ADCs according to the invention show a high preference for cleavage by a tumour-associated asparagine-cleaving protease such as legumain.

The inventive prodrugs have the following general formula (Ia):

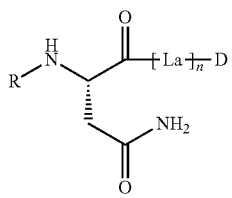

(Ia)

in which
La is a self-immolative linker,
n is 0 or 1
D is -$D_1$-($L_b$)$_o$-(LIG)$_p$,
$D_1$ is a cytotoxic agent,
LIG is a binder which, after binding to a receptor of a tumour cell, is preferably internalized by the tumour cell and processed intracellularly, preferably lysosomally,
Lb is a linker,
and p are each independently 0 or 1,
R is LIG-($L_c$)$_e$-,
LIG is a binder which, after binding to a receptor on a tumour cell, is preferably internalized by the tumour cell and processed intracellularly, preferably lysosomally,
Lc is a linker and
e is 0 or 1,
or
R is $Z_1$—(C=O)q-,
q is 0 or 1,
$Z_1$ is a $C_{1-10}$-alkyl, $C_{5-10}$-aryl, $C_{6-10}$-aryl-$C_{1-6}$-alkyl, $C_{3-10}$-heteroalkyl, $C_{1-10}$-alkyl-O—$C_{6-10}$-aryl, $C_{5-10}$-heterocycloalkyl, heteroaryl, heteroarylalkyl, $C_{5-10}$-heteroarylalkoxy, $C_{1-10}$-alkoxy, $C_{6-10}$-aryloxy, $C_{6-10}$-aryl-$C_{1-6}$-alkoxy, $C_{5-10}$-heteroalkoxy, $C_{1-10}$-alkyl-O—$C_{6-10}$-aryloxy-, $C_{5-10}$-heterocycloalkoxy group which may be mono- or polysubstituted identically or differently by —$NH_2$, —NH-alkyl, —N(alkyl)$_2$, —NH—C(=O)-alkyl, —N(alkyl)-C(=O)-alkyl, —S(=O)$_3$—H, —S(=O)$_2$—$NH_2$, —S(=O)$_2$—N(alkyl)$_2$, —COOH, —C(=O)—, —C(=O)$NH_2$, —C(=O)—N(alkyl)$_2$ or —OH, or is —H or a —($CH_2$)$_{0-1}$—O$_x$—($CH_2CH_2O$)$_v$—$R^1$ or —O$_x$—($CH_2CH_2O$)$_v$—$R^1$ group,
x is 0 or 1,
v is a number from 1 to 20, and
$R^1$ is —H, -alkyl, —$CH_2$—COOH, —$CH_2$—$CH_2$—COOH, or —$CH_2$—$CH_2$—$NH_2$.
In this context, $R^1$ when defined as alkyl is preferably $C_{1-12}$-alkyl.
Preferably, the binder (LIG) is an antibody or an antigen-binding fragment thereof. The antibody is preferably a human, humanized or chimeric monoclonal antibody or an antigen-binding fragment thereof, especially an anti-TWEAKR antibody, an anti-EGFR antibody, an anti-B7H3 antibody or an anti-HER2 antibody or an antigen-binding fragment thereof. Particular preference is given to the anti-TWEAKR antibodies TPP-7006, TPP-7007 and TPP-10337, the anti-B7H3 antibodies TPP-8382 and TPP-8567, the anti-EGFR-antibody cetuximab (TPP-981) and the anti-HER2-antibodies trastuzumab and TPP-1015, or an antigen-binding fragment of these.
The prodrugs according to the invention preferably contain a binder that can bind to a receptor of a tumour cell and, after binding to the receptor, is generally internalized by the tumour cell and processed intracellularly, preferably lysosomally.

There are preferably two possible embodiments here.

The binder can either be bonded to the group cleavable by the legumain enzyme, optionally via a linker, such that, after cleavage of the legumain-cleavable group, the active ingredient is present separately from the binder or a derivative thereof. The compounds of embodiment A thus preferably have the following general formula III':

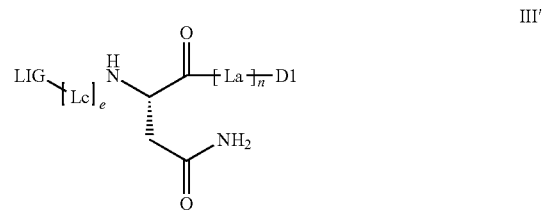

III' where n, e, LIG, La, $L_c$, and $D_1$ have the definitions given in the general formula (Ia).

In this case, -D in the general formula (Ia) represents -$D_1$ and —R in the general formula (Ia) represents LIG-($L_c$)$_e$- (embodiment A).

The present invention thus preferably relates to compounds of the general formula (Ia) in which
La is a self-immolative linker,
n is 0 or 1
D is -$D_1$-(Lb)$_O$-(LIG)$_p$,
and p are 0,
$D_1$ is a cytotoxic agent,
LIG is a binder which, after binding to a receptor of a tumour cell, is preferably internalized by the tumour cell and processed intracellularly, preferably lysosomally,
Lb is a linker,
R is LIG-(Lc)$_e$-,
LIG is a binder which, after binding to a receptor on a tumour cell, is preferably internalized by the tumour cell and processed intracellularly, preferably lysosomally,
Lc is a linker and
e is 0 or 1.
Or the binder may be bonded to the drug molecule, optionally via a linker, such that, after cleavage of the legumain-cleavable group, the drug is present together with the binder or a derivative thereof.

In this case, -D in the general formula (Ia) represents -$D_1$-($L_b$)$_o$-LIG and R— in the general formula (Ia) represents $Z_1$—(C(=O))q- (embodiment B).

The compounds of embodiment B thus preferably have the following general formula (IV'):

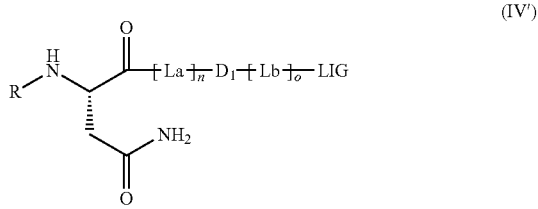

(IV')

where n, o, LIG, La, Lb and $D_1$ have the definitions given in the general formula (Ia) and R is $Z_1$—(C=O)q-, where q is 0 or 1 and $Z_1$ is a $C_{1-10}$-alkyl-, $C_{5-10}$-aryl-, $C_{6-10}$-aryl-$C_{1-6}$-alkyl-, $C_{3-10}$-heteroalkyl-, $C_{1-10}$-alkyl-O—$C_{6-10}$-aryl-, $C_{5-10}$-heterocycloalkyl-, heteroaryl-, $C_{5-10}$-heteroaryl-$C_{1-6}$-alkyl-, $C_{5-10}$-heteroaryl-alkoxy-, $C_{1-10}$-alkoxy-, $C_{6-10}$-aryloxy-, $C_{6-10}$-aryl-$C_{1-6}$-alkoxy-, $C_{5-10}$-heteroalkoxy-, $C_{1-10}$-alkyl-O—$C_{6-10}$-aryloxy-, $C_{5-10}$-heterocycloalkoxy group which may be mono- or polysubstituted identically or differently by —$NH_2$, —NH-alkyl, —N(alkyl)$_2$, —NH—C(=O)-alkyl, —N(alkyl)-C(=O)-alkyl, —S(=O)$_3$—H, —S(=O)$_2$—$NH_2$, —S(=O)$_2$—N(alkyl)$_2$, —COOH, —C(=O)—, —C(=O)$NH_2$, —C(=O)—N(alkyl)$_2$ or —OH, or is —H or a —(CH$_2$)$_o$-1-O$_x$—(CH$_2$CH$_2$O)v-$R^1$ or —O$_x$—(CH$_2$CH$_2$O)v-$R^1$ group, x is 0 or 1 v is a number from 1 to 20 and $R^1$ is —H, -alkyl, —CH$_2$—COOH, —CH$_2$—CH$_2$—COOH, or —CH$_2$—CH$_2$—$NH_2$.

The present invention thus preferably relates to compounds of the general formula (Ia) in which La is a self-immolative linker, n is 0 or 1

D is -$D_1$-(Lb)$_O$-(LIG)$_p$, 0 or 1 p is 1, $D_1$ is a cytotoxic agent,

LIG is a binder which, after binding to a receptor of a tumour cell, is preferably internalized by the tumour cell and processed intracellularly, preferably lysosomally, Lb is a linker, R is $Z_1$—(C=O)q-, q is 0 or 1, $Z_1$ is a $C_{1-10}$-alkyl, $C_{5-10}$-aryl, $C_{6-10}$-aryl-$C_{1-6}$-alkyl, $C_{3-10}$-heteroalkyl, $C_{1-10}$-alkyl-O—$C_{6-10}$-aryl, $C_{5-10}$-heterocycloalkyl, heteroaryl, $C_{5-10}$-heteroaryl-$C_{1-6}$-alkyl, $C_{5-10}$-heteroarylalkoxy, $C_{1-10}$-alkoxy, $C_{6-10}$-aryloxy, $C_{6-10}$-aryl-$C_{1-6}$-alkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted identically or differently by —$NH_2$, —NH-alkyl, —N(alkyl)$_2$, —NH—C(=O)-alkyl, —N(alkyl)-C(=O)-alkyl, —S(=O)$_3$—H, —S(=O)$_2$—$NH_2$, —S(=O)$_2$—N(alkyl)$_2$, —COOH, —C(=O)—, —C(=O)$NH_2$, —C(=O)—N(alkyl)$_2$ or —OH, or is —H or a —(CH$_2$)$_o$-1-O$_x$—(CH$_2$CH$_2$O)v-$R^1$ or —O$_x$—(CH$_2$CH$_2$O)$_V$—$R^1$ group, x is 0 or 1, v is a number from 1 to 20 and $R^1$ is —H, -alkyl, —CH$_2$—COOH, —CH$_2$—CH$_2$—COOH, or —CH$_2$—CH$_2$—$NH_2$.

DESCRIPTION OF THE FIGURES

FIGS. 2A-2Q show annotated sequences of preferred antibodies for binder-drug conjugates. What are shown are the protein sequences of the heavy and light chains of the IgGs, and the VH and VL regions of these antibodies. Below the sequences, important regions are annotated (VH and VL regions in IgGs, and the CDR regions (H-CDR1, H-CDR2, H-CDR3, L-CDR1, L-CDR2, L-CDR3)). SEQ ID NOs of annotated sequences are as follows: TPP-981 VH (PRT)—SEQ ID NO: 1, TPP-981 VL (PRT)—SEQ ID NO: 5, TPP-981 Heavy Chain (PRT)—SEQ ID NO: 9, TPP-981 Light Chain (PRT)—SEQ ID NO: 10, TPP-1015 VH (PRT)—SEQ ID NO: 11, TPP-1015 VL (PRT)—SEQ ID NO: 15, TPP-1015 Heavy Chain (PRT)—SEQ ID NO: 19, TPP-1015 Light Chain (PRT)—SEQ ID NO: 20, TPP-2090 VH (PRT)—SEQ ID NO: 21, TPP-2090 VL (PRT)—SEQ ID NO: 25, TPP-2090 Heavy Chain (PRT)—SEQ ID NO: 29, TPP-2090 Light Chain (PRT)—SEQ ID NO: 30, TPP-2658 VH (PRT)—SEQ ID NO: 31, TPP-2658 VL (PRT)—SEQ ID NO: 35, TPP-2658 Heavy Chain (PRT)—SEQ ID NO: 39, TPP-2658 Light Chain (PRT)—SEQ ID NO: 40, TPP-5442 VH (PRT)—SEQ ID NO: 41, TPP-5442 VL (PRT)—SEQ ID NO: 45, TPP-5442 Heavy Chain (PRT)—SEQ ID NO: 49, TPP-5442 Light Chain (PRT)—SEQ ID NO: 50, TPP-7006 VH (PRT)—SEQ ID NO: 51, TPP-7006 VL (PRT)—SEQ ID NO: 55, TPP-7006 Heavy Chain (PRT)—SEQ ID NO: 59, TPP-7006 Light Chain (PRT)—SEQ ID NO: 60, TPP-7007 VH (PRT)—SEQ ID NO: 61, TPP-7007 VL (PRT)—SEQ ID NO: 65, TPP-7007 Heavy Chain (PRT)—SEQ ID NO: 69, TPP-7007 Light Chain (PRT)—SEQ ID NO: 70, TPP-7510 VH (PRT)—SEQ ID NO: 71, TPP-7510 VL (PRT)—SEQ ID NO: 75, TPP-7510 Heavy Chain (PRT)—SEQ ID NO: 79, TPP-7510 Light Chain (PRT)—SEQ ID NO: 80, TPP-7511 VH (PRT)—SEQ ID NO: 81, TPP-7511 VL (PRT)—SEQ ID NO: 85, TPP-7511 Heavy Chain (PRT)—SEQ ID NO: 89, TPP-7511 Light Chain (PRT)—SEQ ID NO: 90, TPP-8382 VH (PRT)—SEQ ID NO: 91, TPP-8382 VL (PRT)—SEQ ID NO: 95, TPP-8382 Heavy Chain (PRT)—SEQ ID NO: 99, TPP-8382 Light Chain (PRT)—SEQ ID NO: 100, TPP-8567 VH (PRT)—SEQ ID NO: 101, TPP-8567 VL (PRT)—SEQ ID NO: 105, TPP-8567 Heavy Chain (PRT)—SEQ ID NO: 109, TPP-8567 Light Chain (PRT)—SEQ ID NO: 110, TPP-8825 VH (PRT)—SEQ ID NO: 111, TPP-8825 VL (PRT)—SEQ ID NO: 115, TPP-8825 Heavy Chain (PRT)—SEQ ID NO: 119, TPP-8825 Light Chain (PRT)—SEQ ID NO: 120, TPP-10334 VH (PRT)—SEQ ID NO: 121, TPP-10334 VL (PRT)—SEQ ID NO: 125, TPP-10334 Heavy Chain (PRT)—SEQ ID NO: 129, TPP-10334 Light Chain (PRT)—SEQ ID NO: 130, TPP-10335 VH (PRT)—SEQ ID NO: 131, TPP-10335 VL (PRT)—SEQ ID NO: 135, TPP-10335 Heavy Chain (PRT)—SEQ ID NO: 139, TPP-10335 Light Chain (PRT)—SEQ ID NO: 140, TPP-10336 VH (PRT)—SEQ ID NO: 141, TPP-10336 VL (PRT)—SEQ ID NO: 145, TPP-10336 Heavy Chain (PRT)—SEQ ID NO: 149, TPP-10336 Light Chain (PRT)—SEQ ID NO: 150, TPP-10337 VH (PRT)—SEQ ID NO: 151, TPP-10337 VL (PRT)—SEQ ID NO: 155, TPP-10337 Heavy Chain (PRT)—SEQ ID NO: 159, and TPP-10337 Light Chain (PRT)—SEQ ID NO: 160.

FIGS. 3A-3M show the sequence listing of sequences of the preferred antibodies for binder-drug conjugates and of sequences of the target proteins.

DETAILED DESCRIPTION OF THE INVENTION

Figure 1:
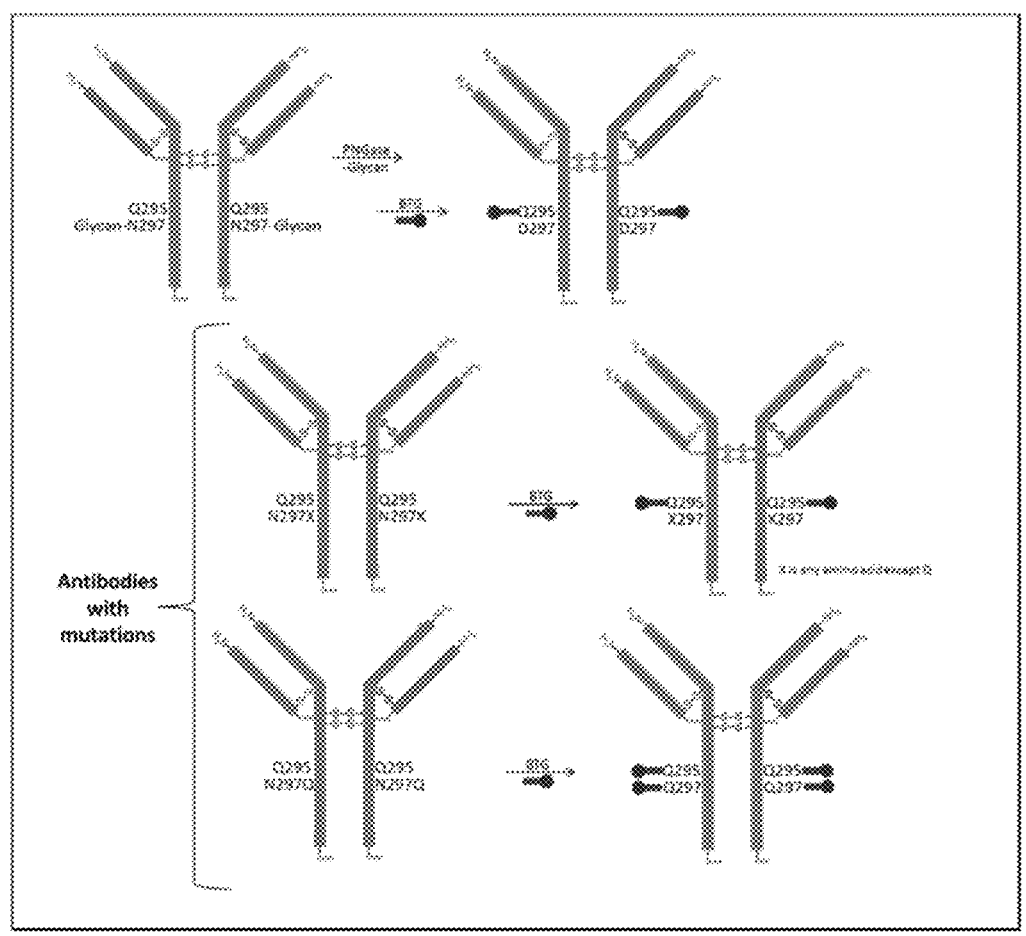
FIG. 1 shows the strategy of the transglutaminase-catalysed conjugation site-specific functionalization of aglycosylated antibodies.

First of all, there follows a description of legumain-cleavable groups usable in accordance with the invention and of the cytotoxic drugs D that are optionally joined to one another via a self-immolative linker. This is followed by a description of the binder LIG preferred in accordance with the invention, which, after binding to a receptor of a tumour cell, is internalized by the tumour cell and processed intracellularly (preferably lysosomally). The various elements of the compounds according to the invention can be used in any desired combination without restriction. In particular, the drugs D described in each case as preferred or particularly preferred can be used in combination with the binders LIG described in each case as preferred or particularly preferred, optionally in combination with the linkers described in each case as preferred or particularly preferred.

Legumain-Cleavable Group

The inventive compounds of the general formula (Ia) have a legumain-cleavable group of the formula (Ia')

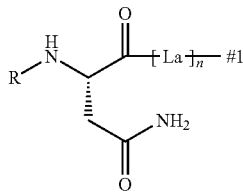

(Ia')

in which

La is a self-immolative linker, n is 0 or 1,

1 represents the bond to the cytotoxic drug (cytotoxic agent),

R is LIG-$(L_c)_e$-,

LIG is a binder which, after binding to a receptor of a tumour cell, is preferably internalized by the tumour cell and processed intracellularly, preferably lysosomally, Lc is a linker, and e is 0 or 1, or R is $Z_1$—(C=O)q-, q is 0 or 1, $Z_1$ is a $C_{1-10}$-alkyl, $C_{5-10}$-aryl, $C_{6-10}$-aryl-$C_{1-6}$-alkyl, $C_{3-10}$-heteroalkyl, $C_{1-10}$-alkyl-O—$C_{6-10}$-aryl, $C_{5-10}$-heterocycloalkyl, heteroaryl, $C_{5-10}$-heteroaryl-$C_{1-6}$-alkyl, $C_{5-10}$-heteroarylalkoxy, $C_{1-10}$-alkoxy, $C_{6-10}$-aryloxy, $C_{6-10}$-aryl-$C_{1-6}$-alkoxy, $C_{5-10}$-heteroalkoxy, $C_{1-10}$-alkyl-O—$C_{6-10}$-aryloxy, $C_{5-10}$-heterocycloalkoxy group which may be mono- or polysubstituted identically or differently by —$NH_2$, —NH-alkyl, —N(alkyl)$_2$, —NH—C(=O)-alkyl, —N(alkyl)-C(=O)-alkyl, —S(=O)$_3$—H, —S(=O)$_2$—$NH_2$, —S(=O)$_2$—N(alkyl)$_2$, —COOH, —C(=O)—, —C(=O)—$NH_2$, —C(=O)—N(alkyl)$_2$ or —OH, or is —H or a —$(CH_2)_o$-1-$O_x$—$(CH_2CH_2O)_v$—$R^1$ or —$O_x$—$(CH_2CH_2O)_v$—$R^1$ group, x is 0 or 1, v is a number from 1 to 20, and $R^1$ is —H, -alkyl, —$CH_2$—COOH, —$CH_2$—$CH_2$—COOH, or —$CH_2$—$CH_2$—$NH_2$.

In this context, $R^1$ when defined as alkyl is preferably $C_{1-12}$-alkyl.

When R is LIG-$(L_c)_e$-, the legumain-cleavable group of the formula Ia' is also referred to as legumain-cleavable linker (embodiment A).

When R is $Z_1$—(C(=O))q-, the legumain-cleavable group of the formula Ia' is also referred to as legumain-cleavable protecting group (embodiment B).

When the legumain-cleavable group of the formula Ia' refers to a legumain-cleavable protecting group, q is preferably 1.

$Z_1$ preferably represents a $C_{1-10}$-alkyl-, $C_{6-10}$-aryl-$C_{1-6}$-alkyl-, $C_{5-10}$-heteroaryl-$C_{1-6}$-alkyl-, $C_{6-10}$-aryl-$C_{1-6}$-alkoxy- or $C_{5-10}$-heteroarylalkoxy group which may be mono- or polysubstituted identically or differently by —$NH_2$, —NH-alkyl, —N(alkyl)$_2$, —NH—C(=O)-alkyl, —N(alkyl)-C(=O)-alkyl, —S(=O)$_3$—H, —S(=O)$_2$—$NH_2$, —S(=O)$_2$—N(alkyl)$_2$, —COOH, —C(=O)—, —C(=O)—$NH_2$, —C(=O)—N(alkyl)$_2$ or —OH.

$Z_1$ is more preferably a $C_{1-3}$-alkyl-, $C_{6-7}$-aryl-$C_{1-6}$-alkyl-, $C_{5-6}$-heteroaryl-$C_{1-3}$-alkyl-, or $C_{6-7}$-aryl-$C_{1-6}$-alkoxy group which may be mono- or polysubstituted identically or differently by —COOH, —C(=O)— or —OH.

Self-Immolative Linker $L_a$

In order to assure efficient release of the free drug, it is optionally also possible to incorporate what are called self-immolative linker elements ($L_a$) between the enzymatic cleavage site and drug (Anticancer Agents in Medicinal Chemistry, 2008, 8, 618-637). The drug can be released by various mechanisms, for example after initial enzymatic release of a nucleophilic group by subsequent elimination via an electronic cascade (Bioorg. Med. Chem., 1999, 7, 1597; J. Med. Chem., 2002, 45, 937; Bioorg. Med. Chem., 2002, 10, 71) or by cyclization of the corresponding linker element (Bioorg. Med. Chem., 2003, 11, 2277; Bioorg. Med. Chem., 2007, 15, 4973; Bioorg. Med. Chem. Lett., 2007, 17, 2241) or by a combination of the two (Angew. Chem. Inter. Ed., 2005, 44, 4378). Examples of such linker elements are shown in the figure:

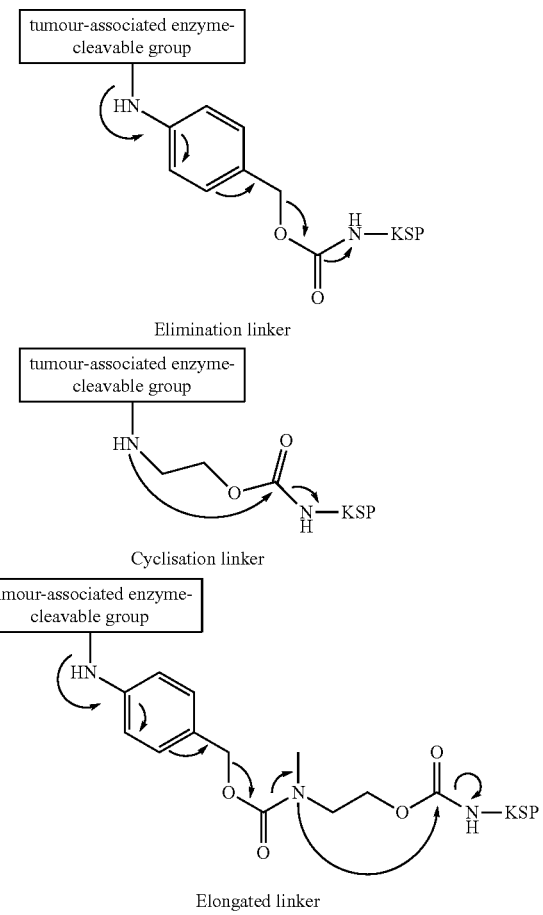

The self-immolative linker mentioned under La in the general formulae (Ia) and (Ia') here is, for example, one of the following groups:

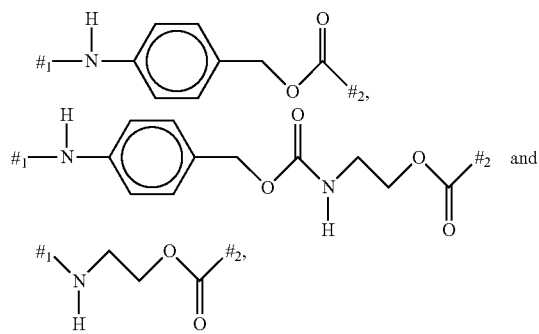
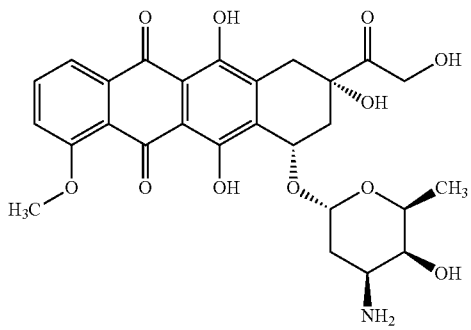

where #1 represents the bond to the carbonyl group and #2 the bond to the hydroxyl or amino group of $D_1$.

Cytotoxic Drugs

In the inventive compounds of the formula Ia, D is the -$D_1$-(Lb)o-(LIG)$_p$ group where
$D_1$ is a cytotoxic drug (cytotoxic agent),
LIG represents a binder which, after binding to a receptor of a tumour cell, is preferably internalized by the tumour cell and processed intracellularly and preferably lysosomally,
$L_b$ represents a linker and
and p are independently 0 or 1.

The cytotoxic drug used is preferably mitomycin, doxorubicin, aminopterin, actinomycin, bleomycin, 9-aminocamptothecin, n8-acetylspermidine, 1-(2-chloroethyl)-1,2-dimethanesulphonyl hydrazide, tallysomycin, cytarabin, etoposid, camptothecin, taxol, esperamicin, podophyllotoxin, anguidin, vincristin, vinblastin, morpholine-doxorubicin, n-(5,5-diacetoxypentyl)doxorubicin, duocarmycin, auristatin, monomethyl auristatin, dolastatin, tubulysine, maytansinoid, cryptophycin, amanitine, pyrrolobenzodiazepine derivatives, indolinobenzodiazepine, calicheamicin, daunorubicin, camptophecin DX8951 (exatecan) or a kinesin spindle protein inhibitor (KSP inhibitor), the drug being bonded via its hydroxyl or amino group to $L_a$ (when n=1) or the carbonyl group (when n=0) according to the general formula (Ia) A corresponding derivatization of these drugs may be based on known methods (see, for example, Synthesis, 1999, 1505 with regard to duocarmycin, Nat. Struct. Biol., 2002, 9, 337, Journal of Med. Chem., 2010, 53(3), 1043 with regard to camptothecin, ChemMedChem, 2011, 6(1), 54 with regard to auristatin, Mol. Cancer. Ther., 2005, 4, 751 with regard to doxorubicin, and J. Biol. Chem, 2008, 283, 9318 with regard to pyrrolobenzodiazepine derivatives (PBD derivatives); see also J. Med. Chem 2013, 56, 7564 and further references in the introduction, J. Med. Chem. 2001, 44, 1341, Oncology Reports 2011, 26, 629)).

In particular, drug classes already established as ADC payloads, as summarized in the review by A. Beck et al. (Nature Rev. Drug Discovery; 2017, 16, 315), can also be linked to antibodies via the linker chemistries described here. Preferably, the cleavable linkers in the described ADCs can be replaced by the linkers described here.

Particular preference is given to those cytotoxic drugs having a free hydroxyl or amino group that is essential to their efficacy, especially those having a free amino group that is essential to their efficacy. The coupling of the legumain-cleavable group to such a group can mask the efficacy of the cytotoxic drug. This group of drugs includes, for example, doxorubicin having the following formula:

By conjugation of the legumain-cleavable group to the free amino group of doxorubicin, the efficacy thereof can be masked.

Especially preferred cytotoxic drugs (cytotoxic agents) are kinesin spindle protein inhibitors, as disclosed, for example, in international patent application WO2015/096982.

Preferred cytotoxic drugs here are especially those kinesin spindle protein inhibitors of the following formula (II)

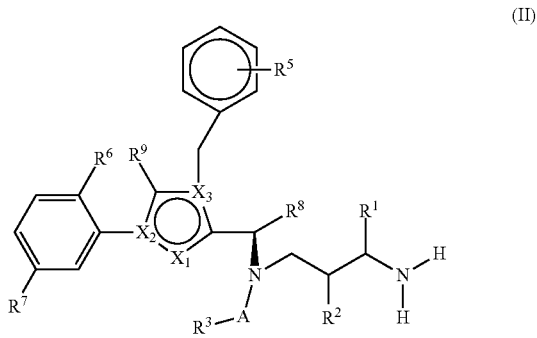

(II)

in which
$X_1$ is N,
$X_2$ is N and
$X_3$ is C,
 or
$X_1$ is N,
$X_2$ is C and
$X_3$ is N,
 or
$X_1$ is CH or CF,
$X_2$ is C and
$X_3$ is N,
 or
$X_1$ is NH,
$X_2$ is C and
$X_3$ is C,
 or
$X_1$ is CH,
$X_2$ is N and
$X_3$ is C.
A is —C(=O)—, —S(=O)—, —S(=O)$_2$—, or —S(=O)$_2$—NH—,
$R^1$ is —H, -L-#1, -MOD or —(CH$_2$)$_{0-3}$Z,
Z is —H, —NHY$^3$, —OY$^3$, —SY$^3$, halogen, —C(=O)—NY$^1$Y$^2$, or —C(=O)—OY$^3$, $Y^1$ and $Y^2$ are independently —H, —NH$_2$, —(CH$_2$CH$_2$O)$_{0-3}$—(CH$_2$)$_{0-3}$Z' or —CH(CH$_2$W)Z', $Y^3$ is —H or —(CH$_2$)$_{0-3}$Z', Z' is —H, —NH$_2$, —S(=O)$_3$H, —COOH, NH—C(=O)—CH$_2$—CH$_2$—CH(NH$_2$)COOH or —(C(=O)—NH—CHY$^4$)$_{1-3}$COOH, W is —H or —OH, $Y^4$ is linear or branched C$_{1-6}$ alkyl- optionally substituted by —NH—C(=O)—NH$_2$, or is aryl or benzyl optionally substituted by —NH$_2$, $R^2$ is —H, -L-#1, -MOD, —C(=O)—CHY$^4$—NHY$^5$ or —(CH$_2$)$_{0-3}$Z, Z is —H, halogen, —OY$^3$, —SY$^3$, —NHY$^3$, —C(=O)—NY$^1$Y$^2$, or —C(=O)—OY$^3$, $Y^1$ and $Y^2$ are independently —H, —NH$_2$, or —(CH$_2$)$_{0-3}$Z', $Y^3$ is —H or —(CH$_2$)$_{0-3}$Z', Z' is —H, —S(=O)$_3$H, —NH$_2$ or —COOH, $Y^4$ is linear or branched C$_{1-6}$ alkyl- optionally substituted by —NHC(=O)—NH$_2$, or is aryl or benzyl optionally substituted by —NH$_2$, $Y^5$ is —H or —C(=O)—CHY$^6$—NH$_2$, $Y^6$ is linear or branched C$_{1-6}$-alkyl, $R^3$ is -MOD, -L-#1, or an optionally substituted alkyl, cycloalkyl, aryl, heteroaryl, heteroalkyl, heterocycloalkyl group which may be substituted by one to three OH groups, one to three halogen atoms, one to three mono-, di- or trihalogenated alkyl groups, one to three —O-alkyl groups, one to three —SH groups, one to three —S-alkyl groups, one to three —O—C(=O)-alkyl groups, one to three —O—C(=O)—NH-alkyl groups, one to three —NH—C(=O)-alkyl groups, one to three —NH—C(=O)—NH-alkyl groups, one to three —S(=O)$_n$-alkyl groups, one to three —S(=O)$_2$—NH-alkyl groups, 1-3 —NH-alkyl groups, one to three —N(alkyl)$_2$ groups, one to three NH$_2$ groups or one to three —(CH$_2$)$_{0-3}$Z groups, n is 0, 1 or 2, Z is —H, halogen, —OY$^3$, —SY$^3$, —NHY$^3$, —C(=O)—NY$^1$Y$^2$ or —C(=O)—OY$^3$, $Y^1$ and $Y^2$ are independently —H, —NH$_2$, or —(CH$_2$)$_{0-3}$Z', $Y^3$ is —H, —(CH$_2$)$_{0-3}$—CH(NHC(=OCH$_3$)Z', —(CH$_2$)$_{0-3}$—CH(NH$_2$)Z' or —(CH$_2$)$_{0-3}$Z', Z' is —H, —S(=O)$_3$H, —NH$_2$ or —COOH, $R^5$ is —H, —NH$_2$, —NO$_2$, halogen, —CN, —CF$_3$, —OCF$_3$, —CH$_2$F, —CH$_2$F, —SH or —(CH$_2$)$_{0-3}$Z, Z is —H, —OY$^3$, —SY$^3$, halogen, —NHY$^3$, —C(=O)—NY$^1$Y$^2$, or —C(=O)—OY$^3$, $Y^1$ and $Y^2$ are independently —H, —NH$_2$, or —(CH$_2$)$_{0-3}$Z', $Y^3$ is —H or —(CH$_2$)$_{0-3}$Z', Z' is —H, —S(=O)$_3$H, —NH$_2$ or —COOH, $R^6$ and $R^7$ are independently —H, —CN, C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, hydroxyl, —NO$_2$, —NH$_2$, —COOH or halogen, $R^8$ is straight-chain or branched C$_{1-10}$-alkyl, fluoro-C$_{1-10}$-alkyl, C$_{2-10}$-alkenyl, fluoro-C$_{2-10}$-alkenyl, C$_{2-10}$-alkynyl or fluoro-C$_{2-10}$-alkynyl, or is C$_{4-10}$-cycloalkyl, fluoro-C$_{4-10}$-cycloalkyl or —(CH$_2$)$_{0-2}$—(HZ$^2$), HZ$^2$ is a 4- to 7-membered heterocycle having up to two heteroatoms selected from N, O and S, which may be substituted by —OH, —COOH, —NH$_2$ or -L-#1, $R^9$ is —H, —F, —CH$_3$, —CF$_3$, —CH$_2$F or —CHF$_2$, L-#1 is -(Lb)$_o$-(LIG)$_p$, LIG is a binder which, after binding to a receptor of a tumour cell, is internalized by the tumour cell and processed intracellularly and preferably lysosomally, Lb is a linker, and p are independently 0 or 1, MOD represents —(NR$^{10}$)n-(G1)o-G2-G3, $R^{10}$ is —H or C$_1$-C$_3$-alkyl, G1 is —NH—C(=O)—, —C(=O)—NH— or

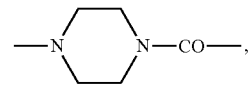

n is 0 or 1 is 0 or 1, and

G2 is a straight-chain or branched hydrocarbon chain which has 1 to 10 carbon atoms and may be interrupted once or more than once by —O—, —S—, —S(=O)—, —S(=O)$_2$—, —NRy-, —NRyC(=O)—, —C(=O)NRy-, —NRyNRy-, —S(=O)$_2$—NRyNRy-, —C(=O)—NRyNRy-, —C(=O)—, —CR$^x$=N—O—, and the straight-chain or branched hydrocarbon chain may be substituted by —NH—C(=O)—NH2, —COOH, —OH, —NH$_2$, sulphonamide, sulphone, sulphoxide, or sulphonic acid, $R^y$ is —H, phenyl, C$_1$-C$_{10}$-alkyl, C$_2$-C$_{10}$-alkenyl or C$_2$-C$_{10}$-alkynyl, each of which may be substituted by —NH—C(=O)—NH2, —COOH, —OH, —NH$_2$, sulphonamide, sulphone, sulphoxide, or sulphonic acid, Rx is —H, C$_1$-C$_3$-alkyl or phenyl, G3 is —H or —COOH, and MOD has at least one —COOH group, preferably two —COOH groups, and one amino group in -MOD may be acylated with the legumain-cleavable group of the formula (Ia'), and the salts, solvates and salts of the solvates thereof.

Preference is given here to those compounds in which $R^3$ is -L-#1, or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by one to three OH groups, one to three halogen atoms, one to three mono-, di- or trihalogenated alkyl groups, one to three —O-alkyl groups, one to three —SH groups, one to three —S-alkyl groups, one to three —O—C(=O)-alkyl groups, one to three —O—C(=O)—NH-alkyl groups, one to three —NH—C(=O)-alkyl groups, one to three —NH—C(=O)—NH-alkyl groups, one to three —S(=O)$_n$-alkyl groups, one to three —S(=O)$_2$—NH-alkyl groups, 1-3 —NH-alkyl groups, one to three —N(alkyl)$_2$ groups, one to three NH$_2$ groups or one to three —(CH$_2$)$_{0-3}$Z groups, n is 0, 1 or 2, Z is —H, halogen, —OY$^3$, —SY$^3$, —NHY$^3$, —C(=O)—NY$^1$Y$^2$ or —C(=O)—OY$^3$, $Y^1$ and $Y^2$ are independently —H, —NH$_2$, or —(CH$_2$)$_{0-3}$Z', $Y^3$ is —H, —(CH$_2$)$_{0-3}$—CH(NHC(=O)CH$_3$)Z', —(CH$_2$)$_{0-3}$—CH(NH$_2$)Z' or —(CH$_2$)$_{0-3}$Z' and Z' is —H, —S(=O)$_3$H, —NH$_2$ or —COOH.

Preference is given to those compounds of the general formula (II) in which $X_1$ is CH, $X_2$ is C and $X_3$ is N.

By conjugation of the legumain-cleavable group to the free amino group of the compounds of the formula II, the efficacy thereof can be masked.

These kinesin spindle protein inhibitors used in accordance with the invention have an amino group which is essential to the effect. By modification of this amino group with peptide derivatives or asparagine derivatives, the effect with respect to the kinesin spindle protein is blocked and hence the development of a cytotoxic effect is also inhibited. If this peptide residue, however, can be released by tumour-associated enzymes such as legumain, the effect can be re-established in a controlled manner in the tumour tissue.

Definitions

The term "substituted" means that one or more hydrogens on the designated atom or the designated group has/have been replaced by a selection from the group specified, with the proviso that the normal valency of the designated atom is not exceeded under the circumstances in question. Combinations of substituents and/or variables are permissible.

The term "optionally substituted" means that the number of substituents can be equal to or different from zero. Unless stated otherwise, optionally substituted groups may be substituted by as many optional substituents as can be accommodated by replacement of a hydrogen atom by a non-hydrogen substituent on any available carbon or nitrogen or sulphur atom. Normally, the number of optional substituents (if present) may be 1, 2, 3, 4 or 5, especially 1, 2 or 3.

As used here, the expression "mono- or poly-", for example in the definition of the substituents of the compounds of the general formulae of the present invention, means "1, 2, 3, 4 or 5, preferably 1, 2, 3 or 4, more preferably 1, 2 or 3, most preferably 1 or 2".

If radicals in the compounds according to the invention are substituted, the radicals may be mono- or polysubstituted, unless stated otherwise. Within the scope of protection of the present invention, the definitions of all radicals which occur more than once are independent of one another. Substitution by one, two or three identical or different substituents is preferred. Substitution by one substituent is particularly preferred.

Alkyl

Alkyl is a linear or branched saturated monovalent hydrocarbon radical having 1 to 10 carbon atoms ($C_1$-$C_{10}$-alkyl), generally 1 to 6 ($C_1$-$C_6$-alkyl), preferably 1 to 4 ($C_1$-$C_4$-alkyl) and more preferably 1 to 3 carbon atoms ($C_1$-$C_3$-alkyl).

Preferred examples include:
methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl, 1,2-dimethylbutyl.

Particular preference is given to a methyl, ethyl, propyl, isopropyl or tert-butyl radical.

Heteroalkyl

Heteroalkyl is a straight-chain and/or branched hydrocarbon chain which has 1 to 10 carbon atoms and may be interrupted once or more than once by one or more of the groups —O—, —S—,
—C(=O)—, —S(=O)—, —S(=O)$_2$—, —NRy-, —NRyC(=O)—, —C(=O)—NRy-, —NRyNRy-, —S(=O)$_2$—NRyNRy-,
—C(=O)—NRyNRy-, —CR$^x$=N—O—, and where the hydrocarbon chain including the side chains (branched hydrocarbon chain), if present, may be substituted by —NH—C(=O)—NH2, —COOH, —OH, —NH$_2$, NH—C(=NNH$_2$)—, sulphonamide, sulphone, sulphoxide, or sulphonic acid.

In this context, R$^y$ in each case is —H, phenyl, $C_1$-$C_{10}$-alkyl, $C_2$-$C_{10}$-alkenyl or $C_2$-$C_{10}$-alkynyl, which may in turn be substituted in each case by —NH—C(=O)—NH2, —COOH, —OH, —NH$_2$, —NH—C(=NNH$_2$)—, sulphonamide, sulphone, sulphoxide, or sulphonic acid.

In this context, R$^x$ is —H, $C_1$-$C_3$-alkyl or phenyl.

Alkenyl

Alkenyl is a straight-chain or branched monovalent hydrocarbon chain having one or two double bonds and 2, 3, 4, 5, 6, 7, 8, 9 or 10 carbon atoms ($C_2$-$C_{10}$-alkenyl), especially 2 or 3 carbon atoms ($C_2$-$C_3$-alkenyl), where, as will be apparent, when the alkenyl group contains more than one double bond, the double bonds may be isolated from one another or conjugated to one another. The alkenyl group is, for example, an ethenyl (or vinyl), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-Isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl, 1-(1,1-dimethylethyl)ethenyl, buta-1,3-dienyl, penta-1,4-dienyl or hexa-1,5-dienyl group. More particularly, the group is vinyl or allyl.

Alkynyl

Alkynyl is a straight-chain or branched monovalent hydrocarbon chain having one triple bond and having 2, 3, 4, 5, 6, 7, 8, 9 or 10 carbon atoms ($C_2$-$C_{10}$-alkynyl), especially 2 or 3 carbon atoms ($C_2$-$C_3$-alkynyl). The $C_2$-$C_6$-alkynyl group is, for example, an ethynyl, prop-1-ynyl, prop-2-ynyl (or propargyl), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl group. More particularly, the alkyl group is ethynyl, prop-1-ynyl or prop-2-ynyl.

Cycloalkyl

Cycloalkyl is a saturated monovalent mono- or bicyclic hydrocarbyl radical having 3-12 carbon atoms ($C_3$-$C_{12}$-cycloalkyl).

In this context, a monocyclic hydrocarbyl radical is a monovalent hydrocarbyl radical having generally 3 to 10 ($C_3$-$C_{10}$-cycloalkyl), preferably 3 to 8 ($C_3$-$C_8$-cycloalkyl) and more preferably 3 to 7 ($C_3$-$C_7$-cycloalkyl) carbon atoms.

Preferred examples of monocyclic hydrocarbyl radicals include:
cyclopropyl, cyclobutyl, cyclopentyl, cyclohexyl, cycloheptyl and cyclooctyl.

Particular preference is given to a cyclopropyl, cyclobutyl, cyclopentyl, cyclohexyl and cycloheptyl.

In this context, a bicyclic hydrocarbyl radical is a hydrocarbyl radical having generally 3 to 12 carbon atoms ($C_3$-$C_{12}$-cycloalkyl), which should be understood here to mean a fusion of two saturated ring systems which together share two directly adjacent atoms. Preferred examples of bicyclic hydrocarbyl radicals include: bicyclo[2.2.0]hexyl, bicyclo[3.3.0]octyl, bicyclo[4.4.0]decyl, bicyclo[5.4.0]undecyl, bicyclo[3.2.0]heptyl, bicyclo[4.2.0]octyl, bicyclo[5.2.0]nonyl, bicyclo[6.2.0]decyl, bicyclo[4.3.0]nonyl, bicyclo[5.3.0]decyl, bicyclo[6.3.0]undecyl and bicyclo[5.4.0]undecyl.

Heterocycloalkyl

Heterocycloalkyl is a nonaromatic mono- or bicyclic ring system having one, two, three or four heteroatoms which may be the same or different. The heteroatoms may be nitrogen atoms, oxygen atoms or sulphur atoms.

A monocyclic ring system according to the present invention may have 3 to 8, preferably 4 to 7 and more preferably 5 or 6 ring atoms.

Preferred examples of a heterocycloalkyl having 3 ring atoms include: aziridinyl.

Preferred examples of a heterocycloalkyl having 4 ring atoms include: azetidinyl, oxetanyl.

Preferred examples of a heterocycloalkyl having 5 ring atoms include:
pyrrolidinyl, imidazolidinyl, pyrazolidinyl, pyrrolinyl, dioxolanyl and tetrahydrofuranyl.

Preferred examples of a heterocycloalkyl having 6 ring atoms include:
piperidinyl, piperazinyl, morpholinyl, dioxanyl, tetrahydropyranyl and thiomorpholinyl.

Preferred examples of a heterocycloalkyl having 7 ring atoms include:
azepanyl, oxepanyl, 1,3-diazepanyl, 1,4-diazepanyl-.

Preferred examples of a heterocycloalkyl having 8 ring atoms include:
oxocanyl, azocanyl.

Among monocyclic heterocycloalkyl, preference is given to 4- to 7-membered saturated heterocyclyl radicals having up to two heteroatoms from the group of O, N and S. Particular preference is given to morpholinyl, piperidinyl, pyrrolidinyl and tetrahydrofuranyl.

A bicyclic ring system having one, two, three or four heteroatoms which may be the same or different may, according to the present invention, have 6 to 12 and preferably 6 to 10 ring atoms, where one, two, three or four carbon atoms may be exchanged for identical or different heteroatoms from the group of O, N and S.

Preferred examples include: azabicyclo[3.3.0]octyl, azabicyclo[4.3.0]nonyl, diazabicyclo[4.3.0]nonyl, oxazabicyclo[4.3.0]nonyl, thiazabicyclo[4.3.0]nonyl or azabicyclo[4.4.0]decyl, and radicals derived from further possible combinations as per the definition.

Particular preference is given to perhydrocyclopenta[c]pyrrolyl, perhydrofuro[3,2-c]pyridinyl, perhydropyrrolo[1,2-a]pyrazinyl, perhydropyrrolo[3,4-c]pyrrolyl and 3,4-methylenedioxyphenyl.

Heterocycloalkoxy

Heterocycloalkoxy is heterocycloalkyl bonded via an —O— group to the rest of the molecule.

Alkoxy

Alkoxy is a linear or branched saturated alkyl ether radical of the formula —O-alkyl having generally 1 to 6 ($C_1$-$C_6$-alkoxy), preferably 1 to 4 ($C_1$-$C_4$-alkoxy) and more preferably 1 to 3 ($C_1$-$C_3$-alkoxy) carbon atoms.

Preferred examples include:
methoxy, ethoxy, n-propoxy, isopropoxy, tert-butoxy, n-pentyloxy and n-hexyloxy.

Aryl

Aryl is a monovalent mono- or bicyclic aromatic ring system consisting of carbon atoms. Examples are naphthyl and phenyl; preference is given to phenyl or a phenyl radical.

$C_6$-$C_{10}$-Aralkyl or Arylalkyl $C_6$-$C_{10}$-Aralkyl or arylalkyl is understood to mean a linear or branched, saturated, monovalent hydrocarbon radical having 1 to 10 carbon atoms ($C_1$-$C_{10}$-alkyl), to which an aryl radical according to the above definition is bonded. These are understood to include, for example, a $C_{6\text{-}10}$-aryl-$C_{1\text{-}6}$-alkyl or benzyl group.

Heteroaryl

Heteroaryl is a monovalent monocyclic, bicyclic or tricyclic aromatic ring system which has 5, 6, 8, 9, 10, 11, 12, 13 or 14 ring atoms (a "5- to 14-membered heteroaryl" group), especially 5, 6, 9 or 10 ring atoms, and contains at least one ring heteroatom and optionally one, two or three further ring heteroatoms from the group of N, O and S, and is bonded via a ring carbon atom or optionally (when permitted by the valency) via a ring nitrogen atom.

The heteroaryl group may be a 5-membered heteroaryl group, for example thienyl, furyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, for example pyridinyl, pyridazinyl, pyrimidinyl, pyrazinyl or triazinyl; or a tricyclic heteroaryl group, for example carbazolyl, acridinyl or phenazinyl; or a 9-membered heteroaryl group, for example benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group, for example quinolinyl, quinazolinyl, isoquinolinyl, cinnolinyl, phthalazinyl, quinoxalinyl or pteridinyl.

In general, and unless stated otherwise, the heteroaryl radicals include all possible isomeric forms, for example tautomers and positional isomers in relation to the attachment point to the rest of the molecule. Thus, as an illustrative, non-exclusive example, the term pyridinyl includes pyridin-2-yl, pyridin-3-yl and pyridin-4-yl; or the term thienyl includes thien-2-yl and thien-3-yl.

$C_5$-$C_{10}$-Heteroaryl $C_{5\text{-}10}$-Heteroaryl in the context of the invention is a mono- or bicyclic aromatic ring system having one, two, three or four heteroatoms which may be the same or different. The heteroatoms that can occur are: N, O, S, S(=O) and/or S(=O)$_2$. The bonding valence may be at any aromatic carbon atom or at a nitrogen atom.

A monocyclic heteroaryl radical according to the present invention has 5 or 6 ring atoms. Preference is given to heteroaryl radicals having one or two heteroatoms. Particular preference is given here to one or two nitrogen atoms.

Heteroaryl radicals having 5 ring atoms include, for example, the following rings: thienyl, thiazolyl, furyl, pyrrolyl, oxazolyl, imidazolyl, pyrazolyl, isoxazolyl, isothiazolyl, oxadiazolyl, triazolyl, tetrazolyl and thiadiazolyl.

Heteroaryl radicals having 6 ring atoms include, for example, the following rings: pyridinyl, pyridazinyl, pyrimidinyl, pyrazinyl and triazinyl.

A bicyclic heteroaryl radical in accordance with the present invention has 9 or 10 ring atoms.

Heteroaryl radicals having 9 ring atoms include, for example, the following rings: phthalidyl, thiophthalidyl, indolyl, isoindolyl, indazolyl, benzothiazolyl, benzofuryl, benzothienyl, benzimidazolyl, benzoxazolyl, azocinyl, indolizinyl, purinyl, indolinyl.

Heteroaryl radicals having 10 ring atoms include, for example, the following rings: isoquinolinyl, quinolinyl, quinolizinyl, quinazolinyl, quinoxalinyl, cinnolinyl, phthalazinyl, 1,7- and 1,8-naphthyridinyl, pteridinyl, chromanyl.

Heteroarylalkyl

Heteroarylalkyl is understood to mean a linear or branched, saturated monovalent hydrocarbyl radical having 1 to 10 carbon atoms ($C_1$-$C_{10}$-alkyl), to which a heteroaryl radical according to the above definition is bonded. This is understood to include, for example, a $C_{5-10}$-heteroaryl-$C_{1-6}$-alkyl group.

Aralkoxy or Arylalkoxy

Aralkoxy or arylalkoxy is understood to mean a linear or branched, saturated monovalent hydrocarbyl radical having 1 to 10 carbon atoms ($C_1$-$C_{10}$-alkyl), to which an aryl radical according to the above definition is bonded. This is understood to include, for example, a $C_{6-10}$-aryl-$C_{1-6}$-alkoxy group.

Aryloxy

Aryloxy is an aryl radical of the formula aryl-O—.

Preferred examples include: phenoxy and naphthyloxy.

Heteroalkoxy

Heteroalkoxy is a straight-chain and/or branched hydrocarbyl chain which has 1 to 10 carbon atoms and is bonded via —O— to the rest of the molecule and may additionally be interrupted once or more than once by one or more of the groups —O—, —S—, —C(=O)—, —S(=O)—, —S(=O)$_2$—, —NR$^y$—,
—NR$^y$C(=O)—, —C(=O)—NR$^y$—, —NR$^y$NR$^y$—, —S(=O)$_2$—NR$^y$NR$^y$—, —C(=O)—NR$^y$NR$^y$—, —CR$^x$=N—O—, and where the hydrocarbon chain, including the side chains (branched hydrocarbon chain), if present, may be substituted by —NH—C(=O)—NH2, —COOH, —OH, —NH$_2$, —NH—C(=NNH$_2$)—, sulphonamide, sulphone, sulphoxide, or sulphonic acid.

In this context, R$^y$ in each case is —H, phenyl, $C_1$-$C_{10}$-alkyl, $C_2$-$C_{10}$-alkenyl or $C_2$-$C_{10}$-alkynyl, which may in turn be substituted in each case by —NH—C(=O)—NH$_2$, —COOH, —OH, —NH$_2$, —NH—C(=NNH$_2$)—, sulphonamide, sulphone, sulphoxide, or sulphonic acid.

In this context, R$^x$ is —H, $C_1$-$C_3$-alkyl or phenyl.

Halogen or halogen atom in the context of the invention is fluorine (—F), chlorine (—Cl), bromine (—Br), or iodine (—I).

Preference is given to fluorine (—F), chlorine (—Cl) and bromine (—Br).

The kinesin spindle protein inhibitors (cytotoxic agent) according to the invention preferably have the following formula (IIa):

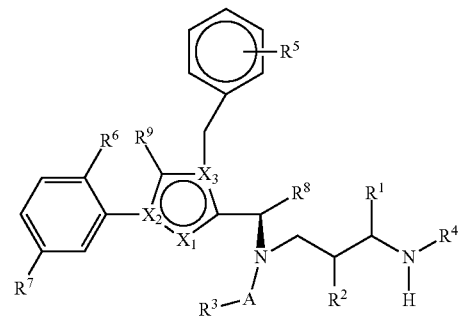

(IIa)

in which
$X_1$ is N,
$X_2$ is N and
$X_3$ is C,
or
$X_1$ is N,
$X_2$ is C and
$X_3$ is N,
or
X is CH or CF,
$X_2$ is C and
$X_3$ is N,
or
$X_1$ is NH,
$X_2$ is C and
$X_3$ is C,
or
$X_1$ is CH,
$X_2$ is N and
$X_3$ is C.
A is —C(=O)—, —S(=O)—, —S(=O)$_2$—, or —S(=O)$_2$—NH—,
$R^1$ is —H, -L-#1, -MOD or —(CH$_2$)$_{0-3}$Z,
Z is —H, —NHY$^3$, —OY$^3$, —SY$^3$, halogen, —C(=O)—NY$^1$Y$^2$, or —C(=O)—OY$^3$,
$Y^1$ and $Y^2$ are independently —H, —NH$_2$—(CH$_2$CH$_2$O)$_{0-3}$—(CH$_2$)$_{0-3}$Z' or —CH(CH$_2$W)Z',
$Y^3$ is —H or —(CH$_2$)$_{0-3}$Z',
Z' is —H, —NH$_2$, —S(=O)$_3$H, —COOH, —NH—C(=O)—CH$_2$—CH$_2$—CH(NH$_2$)COOH or —(C(=O)—NH—CHY$^4$)$_{1-3}$COOH,
W is —H or —OH,
$Y^4$ is linear or branched $C_{1-6}$ alkyl optionally substituted by —NH—C(=O)—NH$_2$, or is aryl or benzyl optionally substituted by —NH$_2$,
$R^2$ is —H, -L-#1, -MOD, —C(=O)—CHY$^4$—NHY$^5$ or —(CH$_2$)$_{0-3}$Z,
Z is —H, halogen, —OY$^3$, —SY$^3$, —NHY$^3$, —C(=O)—NY$^1$Y$^2$, or —C(=O)—OY$^3$,
$Y^1$ and $Y^2$ are independently —H, —NH$_2$, or —(CH$_2$)$_{0-3}$Z',
$Y^3$ is —H or —(CH$_2$)$_{0-3}$Z',
Z' is —H, —S(=O)$_3$H, —NH$_2$ or —COOH,
$Y^4$ is linear or branched $C_{1-6}$ alkyl optionally substituted by —NH—C(=O)—NH$_2$, or is aryl or benzyl optionally substituted by —NH$_2$,
$Y^5$ is —H or —C(=O)—CHY$^6$—NH$_2$,
$Y^6$ is linear or branched $C_{1-6}$-alkyl,
$R^3$ is -MOD, -L-#1, or an optionally substituted alkyl, cycloalkyl, aryl, heteroaryl, heteroalkyl, heterocycloalkyl group which may be substituted by one to three OH groups, one to three halogen atoms, one to three mono-, di- or trihalogenated alkyl groups, one to three —O-alkyl groups, one to three —SH groups, one to three —S-alkyl groups, one to three —O—C(=O)-alkyl groups, one to three —O—C(=O)—NH-alkyl groups, one to three —NH—C(=O)-alkyl groups, one to three —NH—C(=O)—NH-alkyl groups, one to three —S(=O)$_n$-alkyl groups, one to three —S(=O)$_2$—NH-alkyl groups, 1-3 —NH-alkyl groups, one to three —N(alkyl)$_2$ groups, one to three NH$_2$ groups or one to three —(CH$_2$)$_{0-3}$Z groups, n is 0, 1 or 2, Z is —H, halogen, —OY$^3$, —SY$^3$, —NHY$^3$, —C(=O)—NY$^1$Y$^2$ or —C(=O)—OY$^3$, Y$^1$ and Y$^2$ are independently —H, —NH$_2$, or —(CH$_2$)$_{0-3}$Z', Y$^3$ is —H, —(CH$_2$)$_{0-3}$—CH(NHC(=O)CH$_3$)Z', —(CH$_2$)$_{0-3}$—CH(NH$_2$)Z' or —(CH$_2$)$_{0-3}$Z', Z' is —H, —S(=O)$_3$H, —NH$_2$ or —C(=O)—OH, R$^4$ is the legumain-cleavable group of the formula Ia', R$^5$ is —H, —NH$_2$, —NO$_2$, halogen, —CN, CF$_3$, —OCF$_3$, —CH$_2$F, —CH$_2$F, —SH or —(CH$_2$)$_{0-3}$Z, Z is —H, —OY$^3$, —SY$^3$, halogen, —NHY$^3$, —C(=O)—NY$^1$Y$^2$, or —C(=O)—OY$^3$, Y$^1$ and Y$^2$ are independently —H, —NH$_2$, or —(CH$_2$)$_{0-3}$Z', Y$^3$ is —H or —(CH$_2$)$_{0-3}$Z', Z' is —H, —S(=O)$_3$H, —NH$_2$ or —COOH, R$^6$ and R$^7$ are independently —H, —CN, C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, hydroxyl, —NO$_2$, —NH$_2$, —COOH or halogen, R$^8$ is straight-chain or branched C$_{1-10}$-alkyl, fluoro-C$_{1-10}$-alkyl, C$_{2-10}$-alkenyl, fluoro-C$_{2-10}$-alkenyl, C$_{2-10}$-alkynyl or fluoro-C$_{2-10}$-alkynyl, or is C$_{4-10}$-cycloalkyl, fluoro-C$_{4-10}$-cycloalkyl or —(CH$_2$)$_{0-2}$—(HZ$^2$), HZ$^2$ is a 4- to 7-membered heterocycle having up to two heteroatoms selected from N, O and S, which may be substituted by —OH, —COOH, —NH$_2$ or -L-#1, R$^9$ is —H, —F, —CH$_3$, —CF$_3$, —CH$_2$F or —CHF$_2$, L-#1 is -(Lb)o-(LIG)$_p$, LIG is a binder which, after binding to a receptor of a tumour cell, is internalized by the tumour cell and processed intracellularly and preferably lysosomally, L$_b$ is a linker, and p are independently 0 or 1, MOD represents —(NR$^{10}$)n-(G1)o-G2-G3, R$^{10}$ is —H or C$_1$-C$_3$-alkyl, G1 is —NH—C(=O)—, —C(=O)—NH— or

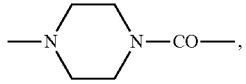

n is 0 or 1;

o is 0 or 1 and

G2 is a straight-chain or branched hydrocarbon chain which has 1 to 10 carbon atoms and may be interrupted once or more than once by —O—, —S—, —S(=O)—, —S(=O)$_2$—, —NRy-, —NRyC(=O)—, —C(=O)NRy-, —NRyNRy-, —S(=O)$_2$—NRyNRy-, —C(=O)—NRyNRy-, —C(=O)—, —CR$^x$=N—O and the straight-chain or branched hydrocarbon chain may be substituted by —NH—C(=O)—NH2, —COOH, —OH, —NH$_2$, sulphonamide, sulphone, sulphoxide, or sulphonic acid, R$^y$ is —H, phenyl, C1-C10-alkyl, C2-C10-alkenyl or C2-C10-alkynyl, each of which may be substituted by —NH—C(=O)—NH2, —COOH, —OH, —NH$_2$, sulphonamide, sulphone, sulphoxide, or sulphonic acid, Rx is —H, C1-C3-alkyl or phenyl, G3 is —H or —COOH and MOD has at least one —COOH group, preferably two —COOH groups, and one amino group in -MOD may be acylated with the legumain-cleavable group of the formula (Ia'), and the salts, solvates and salts of the solvates thereof.

Preference is given here to those compounds in which

R$^3$ is -L-#1 or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by one to three OH groups, one to three halogen atoms, one to three mono-, di- or trihalogenated alkyl groups, one to three —O-alkyl groups, one to three —SH groups, one to three —S-alkyl groups, one to three —O—C(=O)-alkyl groups, one to three —O—C(=O)—NH-alkyl groups, one to three —NH—C(=O)-alkyl groups, one to three —NH—C(=O)—NH-alkyl groups, one to three —S(=O)$_n$-alkyl groups, one to three —S(=O)$_2$—NH-alkyl groups, 1-3 —NH-alkyl groups, one to three —N(alkyl)$_2$ groups, one to three NH$_2$ groups or one to three —(CH$_2$)$_{0-3}$Z groups, where n and Z have the definitions given above.

The —(C(=O)—NH—CHY$^4$)$_{1-3}$—COOH radical means that one —C(=O)—NH—CHY$^4$—COOH radical is present, or two —(C(=O)—NH—CHY$^4$) radicals may be joined to one another, according to

C(=O)—NH—CHY$^4$—C(=O)—NH—CHY$^4$—COOH, or three radicals may be joined to one another, according to

C(=O)—NH—CHY$^4$—C(=O)—NH—CHY$^4$—C(=O)—NH—CHY$^4$—COOH.

Particular preference is given to the compounds of the general formula (IIa) in which X$^1$ is N, X$_2$ is N and X$_3$ is C, or X$_1$ is CH or CF, X$_2$ is C and X$_3$ is N, or X$_1$ is NH, X$_2$ is C and X$_3$ is C, or X$_1$ is H, X$_2$ is N and X$_3$ is C.

Especially preferred are those compounds of the general formula (IIa) in which

X$_1$ is N,

X$_2$ is N and

X$_3$ is C, or

X$_1$ is CH,

X$_2$ is C and

X$_3$ is N.

Very particular preference is given to those compounds of the general formula (IIa) in which $X_1$ is CH,
$X_2$ is C and
$X_3$ is N.

Preference is given to those compounds of the general formula (IIa) in which A is —C(=O)—.

Additionally preferred are those compounds of the general formula (IIa) in which $R^1$ is -L-#1, -MOD, —H, —COOH, —C(=O)—NH—NH$_2$, —(CH$_2$)$_{1-3}$NH$_2$, —C(=O)—NZ"(CH$_2$)$_{1-3}$ NH$_2$ and —C(=O)—NZ"CH$_2$COOH and Z" is —H or —NH$_2$.

If, in the general formula (IIa), $R^4$ is -L-#$_1$, $R^1$ is preferably -MOD.

More particularly, in the general formula (IIa), R4 is -L-#1 and $R^1$ is -MOD if $R^3$ is not -MOD.

In the general formula (IIa), $R^2$ is preferably —H.

In the general formula (IIa), $R^3$ is preferably
L-#1 or -MOD, or is $C_{1-10}$-alkyl which may optionally be substituted by —OH, —O-alkyl, —SH, —S-alkyl, —O—C(=O)-alkyl, —O—C(=O)—NH-alkyl, —NH—C(=O)-alkyl, —NH—C(=O)—NH-alkyl, —S(=O)$_n$-alkyl, —S(=O)$_2$—NH-alkyl, —NH-alkyl, —N(alkyl)$_2$, or —NH$_2$.

Alkyl here is preferably $C_{1-3}$alkyl-.

In the general formula (IIa), $R^5$ is preferably —H or —F.

In the general formula (IIa), $R^6$ and $R^7$ are preferably independently —H, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxyl or halogen.

In the general formula (IIa), $R^8$ is preferably a branched $C_{1-5}$-alkyl group, especially a —C(CH$_3$)$_2$—(CH$_2$)$_{0-2}$—R$^y$ group, where R$^y$ is —H, —OH, —C(=O)$_2$H, or —NH$_2$.

More preferably, $R^8$ is the —C(CH$_3$)$_2$—(CH$_2$)—R$^y$ group where R$^y$ is —H.

In the general formula (IIa), $R^9$ is preferably —H or —F.

In the general formula (IIa), -MOD is preferably the group QOC—(CHX)x-AM-CH$_2$—CH$_2$—NH—C(=O)—, where
x is a number from 2 to 6,
Q is —OH or —NH$_2$
W in the —(CHX)$_x$— groups is independently —H, —NH$_2$, COOH or —CONH$_2$, and
AM is —C(=O)—NH— or —NH—C(=O)—.

In the general formula (IIa), -MOD is more preferably the group
QOC—CH$_2$—CH$_2$—CH(COQ)-NH—C(=O)—CH$_2$—CH$_2$—NH—C(=O)—,
HOOC—CH(NH$_2$)—CH$_2$—CH$_2$—C(=O)—NH—CH$_2$—CH$_2$—NH—C(=O)—
and
HOOC—CH(NH$_2$)—(CH$_2$)$_4$—NH—C(=O)—CH$_2$—CH$_2$—NH—C(=O)—,
where Q is —OH or —NH$_2$.

Preference is given to those compounds of the general formula (IIa) in which
$X_1$ is CH,
$X_2$ is C and
$X_3$ is N,
A is —C(=O)—,
$R^1$ is -L-#1, —H, or -MOD
L-#1 is -(L$_b$)$_o$-(LIG)$_p$,
LIG is a binder which, after binding to a receptor of a tumour cell, is internalized by the tumour cell and processed intracellularly, preferably lysosomally,
Lb is a linker,
and p are independently 0 or 1,
MOD is the group —(NR$^{10}$)$_n$-(G1)$_o$-G2-G3, $R^{10}$ is —H or $C_1$-$C_3$-alkyl-,
n is 0 or 1,
G1 is —NH—C—(=O)— or —C(=O)—NH—,
o is 0 or 1 and
G2 is a straight-chain or branched hydrocarbyl chain which has 1 to 100 carbon atoms and may be interrupted once or more than once, identically or differently, by —O—, —S—, —S(=O)—, —S(=O)$_2$—, —NR$^y$C(=O)—, —C(=O)NR$^y$—, —NR$^y$NR$^y$—, —S(=O)$_2$—NR$^y$NR$^y$—, —C(=O)—NR$^y$NR$^y$—, —C(=O)—, —CR$^x$=N—O—, and the straight-chain or branched hydrocarbyl chain may be mono- or polysubstituted identically or differently by —NH—C(=O)—NH$_2$, —C(=O)—NH$_2$, —COOH, —OH, —NH$_2$, sulphonamide, sulphone, sulphoxide or sulphonic acid, R$^y$ is —H, phenyl-, $C_1$-$C_{10}$-alkyl-, $C_2$-$C_{10}$-alkenyl- or $C_2$-$C_{10}$-alkynyl-, each of which may be substituted by —NH—C(=O)—NH$_2$, —COOH, —OH, —NH$_2$, sulphonamide, sulphone, sulphoxide or sulphonic acid, Rx is —H, $C_1$-$C_3$-alkyl- or phenyl-,
G3 is —H or —COOH
$R^2$ is —H,
$R^3$ is -MOD, -L-#1, or an optionally substituted alkyl, cycloalkyl, aryl, heteroaryl, heteroalkyl, heterocycloalkyl group which may be substituted by one to three OH groups, one to three halogen atoms, one to three mono-, di- or trihalogenated alkyl groups, one to three —O-alkyl groups, one to three —SH— groups, one to three —S-alkyl groups, one to three —O—C(=O)-alkyl-groups, one to three —O—C(=O)—NH-alkyl groups, one to three —NH—C(=O)-alkyl groups, one to three —NH—C(=O)—NH-alkyl groups, one to three —S(=O)$_n$-alkyl groups, one to three —S(=O)$_2$—NH-alkyl groups, 1-3 —NH-alkyl groups, one to three —N(alkyl)$_2$ groups, one to three NH$_2$ groups or one to three —(CH$_2$)$_{0-3}$Z groups,
n is 0, 1 or 2,
Z is —H, halogen, —OY$^3$, —SY$^3$, —NHY$^3$, —C(=O)—NY$^1$Y$^2$ or —C(=O)—OY$^3$,
Y$^1$ and Y$^2$ are independently —H, —NH$_2$, or —(CH$_2$)$_{0-3}$Z',
Y$^3$ is —H, —(CH$_2$)$_{0-3}$—CH(NHC(=O)CH$_3$)Z', —(CH$_2$)$_{0-3}$—CH(NH$_2$)Z' or —(CH$_2$)$_{0-3}$Z',
Z' is —H, —S(=O)$_3$H, —NH$_2$ or —C(=O)—OH,
$R^4$ is the legumain-cleavable group of the formula (Ia'),
$R^5$ is —H,
$R^6$ and $R^7$ are fluorine,
$R^8$ is t-butyl,
$R^9$ is —H,
L-#1 is -(L$_b$)$_o$-(LIG)$_p$,
LIG is a binder which, after binding to a receptor of a tumour cell, is internalized by the tumour cell and processed intracellularly, preferably lysosomally,
Lb is a linker,
and p are independently 0 or 1,
and the salts, solvates and salts of the solvates thereof.

Particular preference is given here to $C_{1-3}$-alkyl.

Preference is further given to those compounds of the general formula (IIa) in which
$X_1$ is CH,
$X_2$ is C and
$X_3$ is N,
A is —C(=O)—,
$R^1$ is -L-#1, —H, or -MOD
L-#1 is -(L$_b$)$_o$-(LIG)$_p$, LIG is a binder which, after binding to a receptor of a tumour cell, is internalized by the tumour cell and processed intracellularly, preferably lysosomally,
Lb is a linker,
and p are independently 0 or 1,
-MOD is the group —(NR$^{10}$)n-(G1)O-G2-G3,
R$^{10}$ is —H or C$_1$-C$_3$-alkyl-,
n 0,
G1 is —C(=O)—NH—,
is 1 and
G2 is a straight-chain or branched hydrocarbyl chain which has 1 to 100 carbon atoms and may be interrupted once or more than once, identically or differently, by —O—, —S—, —NR$^y$— or —C(=O)—, and the straight-chain or branched hydrocarbyl chain may be mono- or polysubstituted by —C(=O)—NH$_2$, —COOH,
R$^y$ is —H or C$_1$-C$_{10}$-alkyl- which may be substituted by —NH—C(=O)—NH$_2$, —COOH, —OH, —NH$_2$,
G3 is -COOH
R$^2$ is —H,
R$^3$ is -L-#1,
R$^4$ is the legumain-cleavable group of the formula (Ia'),
R$^5$ is —H,
R$^6$ and R$^7$ are fluorine,
R$^8$ is t-butyl,
R$^9$ is —H,
L-#1 is -(Lb)$_O$-(LIG)$_p$,
LIG is a binder which, after binding to a receptor of a tumour cell, is internalized by the tumour cell and processed intracellularly, preferably lysosomally,
Lb is a linker,
and p are independently 0 or 1,
and the salts, solvates and salts of the solvates thereof.
Also preferred are compounds of the general formula (IIa')

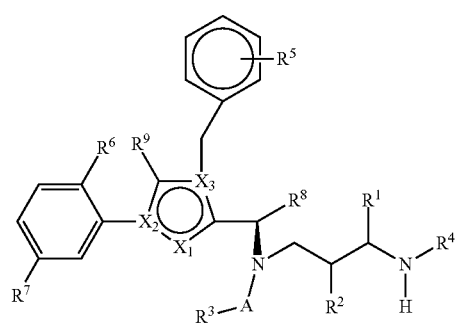

(IIa')

in which
X$_1$ is N,
X$_2$ is N and
X$_3$ is C,
or
X$_1$ is N,
X$_2$ is C and
X$_3$ is N,
or
X$_1$ is CH or CF,
X$_2$ is C and
X$_3$ is N,
or
X$_1$ is NH,
X$_2$ is C and
X$_3$ is C,
or
X$_1$ is CH,
X$_2$ is N and
X$_3$ is C.
A is the group *—C(=O)—(CH$_2$)$_x$—S—CH$_2$—CH(COOH)—NH—**,
x is 1 or 2,
* is the bond to the drug molecule,
** is the bond to the legumain-cleavable group of the formula (Ia'),
R$^1$ is -MOD,
MOD is the group —(NR$^{10}$)$_n$-(G1)$_o$-G2-G3,
R$^{10}$ is —H or C$_1$-C$_3$-alkyl-,
n is 0,
G1 is —C(=O)—NH—,
o is 1,
G2 is a straight-chain or branched hydrocarbyl chain which has 1 to 100 carbon atoms and may be interrupted once or more than once, identically or differently, by —O—, —S—, —S(=O)—, —S(=O)$_2$—, —NR$^y$C(=O)—, —C(=O)NR$^y$—, —NR$^y$NR$^y$—, —S(=O)$_2$—NR$^y$NR$^y$—, —C(=O)—NR$^y$NR$^y$—, —C(=O)—, —CR$^x$=N—O—, and the straight-chain or branched hydrocarbyl chain may be mono- or polysubstituted identically or differently by —NH—C(=O)—NH$_2$, —C(=O)—NH$_2$, —COOH, —OH, —NH$_2$, sulphonamide, sulphone, sulphoxide or sulphonic acid,
R$^y$ is —H, phenyl-, C$_1$-C$_{10}$-alkyl-, C$_2$-C$_{10}$-alkenyl- or C$_2$-C$_{10}$-alkynyl-, each of which may be substituted by —NH—C(=O)—NH$_2$, —COOH, —OH, —NH$_2$, sulphonamide, sulphone, sulphoxide or sulphonic acid,
Rx is —H, C$_1$-C$_3$-alkyl- or phenyl-,
G3 is —H or —COOH
R$^2$ is —H,
R$^3$ is the legumain-cleavable group of the formula (Ia'),
R$^4$ is-H,
R$^5$ is —H, —NH$_2$, —NO$_2$, halogen, —CN, CF$_3$, —OCF$_3$, —CH$_2$F, —CH$_2$F, —SH or —(CH$_2$)$_{0-3}$Z,
Z is —H, —OY$^3$, —SY$^3$, halogen, —NHY$^3$, —C(=O)—NY$^1$Y$^2$, or —C(=O)—OY$^3$,
Y$^1$ and Y$^2$ are independently —H, —NH$_2$, or —(CH$_2$)$_{0-3}$Z',
Y$^3$ is —H or —(CH$_2$)$_{0-3}$Z',
Z' is —H, —S(=O)$_3$H, —NH$_2$ or —COOH,
R$^6$ and R$^7$ are independently —H, —CN, C$_{1-10}$-alkyl, fluoro-C$_{1-10}$-alkyl, C$_{2-10}$-alkenyl-, fluoro-C$_{2-10}$-alkenyl-, C$_{2-10}$-alkynyl-, fluoro-C$_{2-10}$-alkynyl-, hydroxyl-, —NO$_2$, —NH$_2$, —COOH or halogen,
R$^8$ is straight-chain or branched C$_{1-10}$-alkyl, fluoro-C$_{1-10}$-alkyl, C$_{2-10}$-alkenyl-, fluoro-C$_{2-10}$-alkenyl-, C$_{2-10}$-alkynyl- or fluoro-C$_{2-10}$-alkynyl-, or is C$_4$-1$_0$-cycloalkyl- or fluoro-C$_4$-1$_0$-cycloalkyl-,
R$^9$ is —H, —F, —CH$_3$, —CF$_3$, —CH$_2$F or —CHF$_2$,
and the salts, solvates and salts of the solvates thereof.
Among these, particular preference is given to those compounds of the general formula (IIa') in which
X$_1$ is CH,
X$_2$ is C and
X$_3$ is N,
A is the group *—C(=O)—(CH$_2$)x-S—CH$_2$—CH(COOH)—NH—**,
x is 1 or 2,
* is the bond to the drug molecule,

** is the bond to the legumain-cleavable group of the formula (Ia'),
$R^1$ is -MOD,
MOD is the group —$(NR^{10})_n$-$(G1)_o$-G2-G3,
$R^{10}$ is —H or $C_1$-$C_3$-alkyl-,
n is 0,
G1 is —C(=O)—NH—,
o is 1,
G2 is a straight-chain or branched hydrocarbyl chain which has 1 to 100 carbon atoms and may be interrupted once or more than once, identically or differently, by —O—, —S—, —S(=O)—, —S(=O)$_2$—, —$NR^yC$(=O)—, —C(=O)$NR^y$—, —$NR^yNR^y$—, —S(=O)$_2$—$NR^yNR^y$—, —C(=O)—$NR^yNR^y$—, —C(=O)—, —$CR^x$=N—O—, and the straight-chain or branched hydrocarbyl chain may be mono- or poly-substituted identically or differently by —NH—C(=O)—NH$_2$, —C(=O)—NH$_2$, —COOH, —OH, —NH$_2$, sulphonamide, sulphone, sulphoxide or sulphonic acid,
$R^y$ is —H, phenyl-, $C_1$-$C_{10}$-alkyl-, $C_2$-$C_{10}$-alkenyl- or $C_2$-$C_{10}$-alkynyl-, each of which may be substituted by —NH—C(=O)—NH$_2$, —COOH, —OH, —NH$_2$, sulphonamide, sulphone, sulphoxide or sulphonic acid,
Rx is —H, $C_1$-$C_3$-alkyl- or phenyl-,
G3 is —H or —COOH
$R^2$ is —H,
$R^3$ is the legumain-cleavable group of the formula (Ia),
$R^4$ is —H,
$R^5$ is —H,
$R^6$ and $R^7$ are fluorine,
$R^8$ is t-butyl and
$R^9$ is —H,
and the salts, solvates and salts of the solvates thereof.

Preference is further given to those compounds of the general formula (IIa″)

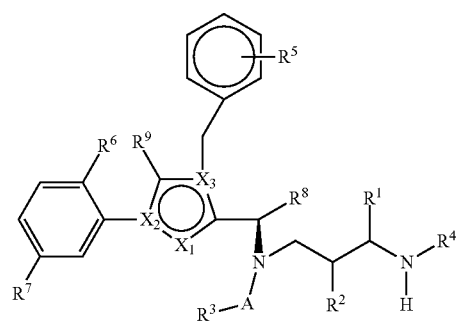

(IIa″)

in which
$X_1$ is N,
$X_2$ is N and
$X_3$ is C,
or
$X_1$ is N,
$X_2$ is C and
$X_3$ is N,
or
X is CH or CF,
$X_2$ is C and
$X_3$ is N,
or
$X_1$ is NH,
$X_2$ is C and
$X_3$ is C,
or
$X_1$ is CH,
$X_2$ is N and
$X_3$ is C.
A is —C(=O)—, —S(=O), —S(=O)$_2$—, or —S(=O)$_2$—NH—,
$R^1$ is the group *-$(G1)_o$-G2-NH— **,
* is the bonding site to the drug molecule (cytotoxic agent),
** is the bond to the legumain-cleavable group of the formula Ia',
G1 is —C(=O)—NH—,
o is 1,
G2 is a straight-chain or branched hydrocarbyl chain which has 1 to 100 carbon atoms and may be interrupted once or more than once, identically or differently, by —O—, —S—, —S(=O)—, —S(=O)$_2$—, —$NR^yC$(=O)—, —C(=O)$NR^y$—, —$NR^yNR^y$—, —S(=O)$_2$—$NR^yNR^y$—, —C(=O)—$NR^yNR^y$—, —C(=O)—, —$CR^x$=N—O—, and the straight-chain or branched hydrocarbyl chain may be mono- or poly-substituted identically or differently by —NH—C(=O)—NH$_2$, —C(=O)—NH$_2$, —COOH, —OH, —NH$_2$, sulphonamide, sulphone, sulphoxide or sulphonic acid,
$R^y$ is —H, phenyl-, $C_1$-$C_{10}$-alkyl-, $C_2$-$C_{10}$-alkenyl- or $C_2$-$C_{10}$-alkynyl-, each of which may be substituted by —NH—C(=O)—NH$_2$, —COOH, —OH, —NH$_2$, sulphonamide, sulphone, sulphoxide or sulphonic acid,
Rx is —H, $C_1$-$C_3$-alkyl- or phenyl-,
$R^2$ is —H,
$R^3$ is an optionally substituted alkyl, cycloalkyl, aryl, heteroaryl, heteroalkyl, heterocycloalkyl group which may be substituted by one to three OH groups, one to three halogen atoms, one to three mono-, di- or trihalogenated alkyl groups, one to three —O-alkyl groups, one to three —SH— groups, one to three —S-alkyl groups, one to three —O—C(=O)-alkyl- groups, one to three —O—C(=O)—NH-alkyl groups, one to three —NH—C(=O)-alkyl groups, one to three —NH—C(=O)—NH-alkyl groups, one to three —S(=O)$_n$-alkyl groups, one to three —S(=O)$_2$—NH-alkyl groups, 1-3 —NH-alkyl groups, one to three —N(alkyl)$_2$ groups, one to three $NH_2$ groups or one to three —$(CH_2)_{0-3}$Z groups,
n is 0, 1 or 2,
Z is —H, halogen, —$OY^3$, —$SY^3$, —$NHY^3$, —C(=O)—$NY^1Y^2$ or —C(=O)—$OY^3$,
$Y^1$ and $Y^2$ are independently —H, —NH$_2$, or —$(CH_2)_{0-3}$Z',
$Y^3$ is —H, —$(CH_2)_{0-3}$—CH(NHC(=O)CH$_3$)Z', —$(CH_2)_{0-3}$—CH(NH$_2$)Z' or —$(CH_2)_{0-3}$Z',
Z' is —H, —S(=O)$_3$H, —NH$_2$ or —COOH,
$R^4$ is —H,
$R^5$ is —H, —NH$_2$, —NO$_2$, halogen, —CN, CF$_3$, —OCF$_3$, —CH$_2$F, —CH$_2$F, —SH or —$(CH_2)_{0-3}$Z,
Z is —H, —$OY^3$, —$SY^3$, halogen, —$NHY^3$, —C(=O)—$NY^1Y^2$, or —C(=O)—$OY^3$,
$Y^1$ and $Y^2$ are independently —H, —NH$_2$, or —$(CH_2)_{0-3}$Z',
$Y^3$ is —H or —$(CH_2)_{0-3}$Z',
Z' is —H, —S(=O)$_3$H, —NH$_2$ or —COOH,
$R^6$ and $R^7$ are independently —H, —CN, $C_{1-10}$-alkyl, fluoro-$C_{1-10}$-alkyl, $C_{2-10}$-alkenyl-, fluoro-$C_{2-10}$-alkenyl-, $C_{2-10}$-alkynyl-, fluoro-$C_{2-10}$-alkynyl-, hydroxyl-, —$NO_2$, —$NH_2$, —COOH or halogen, $R^8$ is straight-chain or branched $C_{1-10}$-alkyl, fluoro-$C_{1-10}$-alkyl, $C_{2-10}$-alkenyl, fluoro-$C_{2-10}$-alkenyl-, $C_{2-10}$-alkynyl- or fluoro-$C_{2-10}$-alkynyl-, or is $C_{4-10}$-cycloalkyl- or fluoro-$C_{4-10}$-cycloalkyl-, $R^9$ is —H, —F, —$CH_3$, —$CF_3$, —$CH_2F$ or —$CHF_2$, and the salts, solvates and salts of the solvates thereof.

Among these, particular preference is given to those compounds of the general formula (II″) in which $X_1$ is CH, $X_2$ is C and $X_3$ is N, A is —C(=O)—, $R^1$ is the group *-(G1)$_o$-G2-NH—**,

* is the bonding site to the drug molecule (cytotoxic agent),

** is the bond to the legumain-cleavable group of the formula (Ia′),

G1 is —C(=O)—NH—, o is 1,

G2 is a straight-chain or branched hydrocarbyl chain which has 1 to 100 carbon atoms and may be interrupted once or more than once, identically or differently, by —O—, —S—, —S(=O)—, —S(=O)$_2$—, —$NR^y$C(=O)—, —C(=O)$NR^y$—, —$NR^y NR^y$—, —S(=O)$_2$—$NR^y NR^y$—, —C(=O)—$NR^y NR^y$—, —C(=O)—, —$CR^x$=N—O—, and the straight-chain or branched hydrocarbyl chain may be mono- or polysubstituted identically or differently by —NH—C(=O)—$NH_2$, —C(=O)—$NH_2$, —COOH, —OH, —$NH_2$, sulphonamide, sulphone, sulphoxide or sulphonic acid, $R^y$ is —H, phenyl-, $C_1$-$C_{10}$-alkyl-, $C_2$-$C_{10}$-alkenyl- or $C_2$-$C_{10}$-alkynyl-, each of which may be substituted by —NH—C(=O)—$NH_2$, —COOH, —OH, —$NH_2$, sulphonamide, sulphone, sulphoxide or sulphonic acid, Rx is —H, $C_1$-$C_3$-alkyl- or phenyl-, $R^2$ is —H, $R^3$ is —$CH_2$—OH, $R^4$ is —H, $R^5$ is —H, $R^6$ and $R^7$ are fluorine, $R^8$ is t-butyl and $R^9$ is —H, and the salts, solvates and salts of the solvates thereof.

Additionally preferred are the compounds of the general formula (IIa) in which $R^1$ is —H, -L-#1, —COOH, QOC—$CH_2$—$CH_2$—CH(COQ)-NH—C(=O)—$CH_2$—$CH_2$—NH—C(=O)—; HOOC—CH($NH_2$)—$CH_2$—$CH_2$—C(=O)—NH—$CH_2$—$CH_2$—NH—C(=O)— or HOOC—CH($NH_2$)—($CH_2$)$_4$—NH—C(=O)—$CH_2$—$CH_2$—NH—C(=O)—, $R^2$ is —H, A is —C(=O)—, Q is —OH or —$NH_2$ $R^3$ is —($CH_2$)OH, —CH($CH_3$)OH, —$CH_2$—S—$CH_2$CH—(COOH)—NH—C(=O)—$CH_3$, —CH($CH_3$)OCH$_3$, a phenyl group which may be substituted by one to three halogen atoms, one to three amino groups, one to three alkyl groups or one to three haloalkyl groups, HOOC—CH2-CH2-CH(COOH)—NH—C(=O)—CH2-CH2-NH—C(=O)—; HOOC—CH(NH2)-CH2-CH2-C(=O)—NH—CH2-CH2-NH—C(=O)—; HOOC—CH(NH2)-(CH2)4-NH—C(=O)—CH2-CH2-NH—C(=O)— or —$CH_2$—Sr—($CH_2$)$_{0-4}$—CHY$^5$—COOH, x is 0 or 1, $Y^5$ is —H or —NHY$^6$, $Y^6$ is —H, —C(=O)—$CH_3$ or -L-#1, $R^5$ is —H, $R^6$ and $R^7$ are independently —H, $C_{1-3}$-alkyl or halogen, $R^8$ is $C_{1-4}$-alkyl and $R^9$ is —H.

Preference is given here especially to those compounds in which $R^6$ and $R^7$ are independently hydrogen or fluorine and $R^8$ is tert-butyl.

Additionally preferred are those compounds in which $R^1$ is —H, —COOH, QOC—$CH_2$—$CH_2$—CH(COQ)-NH—C(=O)—$CH_2$—$CH_2$—NH—C(=O)—, HOOC—CH($NH_2$)—$CH_2$—$CH_2$—C(=O)—NH—$CH_2$—$CH_2$—NH—C(=O)— or HOOC—CH($NH_2$)—($CH_2$)$_4$—NH—C(=O)—$CH_2$—$CH_2$—NH—C(=O)—, $R^2$ is —H, A is —C(=O)—, $R^3$ is —($CH_2$)OH, —CH($CH_3$)OH, —$CH_2$—S—$CH_2$CH(COOH)NH—C(=O)—$CH_3$, —CH($CH_3$)OCH$_3$, HOOC—CH2-CH2-CH(COOH)—NH—C(=O)—CH2-CH2-NH—C(=O)—, HOOC—CH(NH2)-CH2-CH2-C(=O)—NH—CH2-CH2-NH—C(=O)—, HOOC—CH(NH2)-(CH2)4-NH—C(=O)—CH2-CH2-NH—C(=O)—, —$CH_2$—Sr—($CH_2$)$_{0-4}$—CHY$^5$—COOH or a phenyl group which may be substituted by 1-3 halogen atoms, one to three amino groups, one to three alkyl groups or one to three haloalkyl groups, x is 0 or 1, $Y^5$ is —H or —NHY$^6$, $Y^6$ is —H, —C(=O)—$CH_3$ or -L-#1, $R^5$ is —H, $R^6$ and $R^7$ are independently —H, $C_{1-3}$-alkyl or halogen, $R^8$ is $C_{1-4}$-alkyl and $R^9$ is —H, where one of the substituents $R^1$ and $R^3$ is -L-#1.

Preference is given here especially to those compounds in which $R^6$ and $R^7$ are —F and $R^8$ is tert-butyl.

Additionally preferred are compounds of the general formula (IIb)

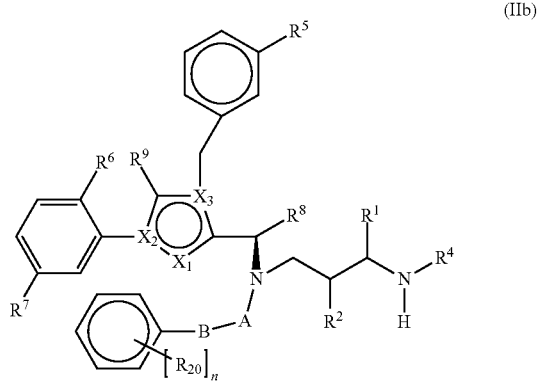

in which
- $X_1$, $X_2$, $X_3$, $R^1$,
- $R^2$, $R^4$, $R^5$, $R^6$,
- $R^7$, $R^8$ and $R^9$ have the definitions given in the general formula (IIa) and
- A is —C(=O)—,
- B is a single bond, —O—CH$_2$— or —CH$_2$—O—,
- $R^{20}$ is —NH$_2$, —F, —CF$_3$, or —CH$_3$ and
- n is 0, 1 or 2.

Preference is given here to those compounds of the general formula (IIb) in which
- $X_1$ is CH,
- $X_2$ is C and
- $X_3$ is N.

Preference is also given to those compounds of the general formula (IIc)

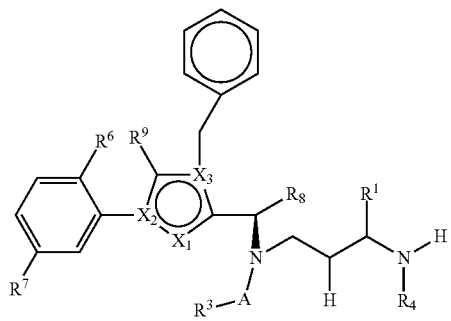

(IIc)

in which
- $X_1$, $X_2$, $X_3$ A, $R^1$, $R^3$, $R^4$, $R^6$, $R^7$, $R^8$ and $R^9$ have the definitions given in the general formula (IIa).

Preference is given here to those compounds of the general formula (IIc) in which
- $X_1$ is CH,
- $X_2$ is C,
- $X_3$ is N,
- A is —C(=O)— and
- $R^3$ is —CH$_2$OH, —CH$_2$OCH$_3$, —CH(CH$_3$)OH or —CH(CH$_3$)OCH$_3$.

Preference is further also given to those compounds of the general formula (IId)

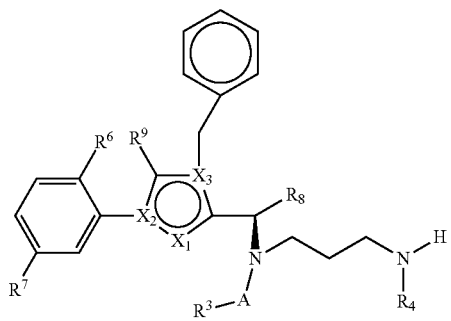

(IId)

in which
- $X_1$, $X_2$, $X_3$, A, $R^3$, $R^4$, $R^6$, $R^7$, $R^8$ and $R^9$ have the definitions given in the general formula (IIa).

Preference is given here to those compounds of the general formula (IId) in which
- $X_1$ is CH,
- $X_2$ is C,
- $X_3$ is N,
- A is —C(=O)—,
- $R^3$ is —CH$_2$—Sr—(CH$_2$)$_{0-4}$—CHY$^5$—COOH,
- x is 0 or 1,
- $Y^5$ is —H or —NHY$^6$ and
- $Y^6$ is —H or —C(=O)CH$_3$.

Additionally preferred are those compounds of the general formulae (IIa), (IIb), (IIc) and (IId) in which
- Z is —Cl or —Br;
- $R^1$ is —(CH$_2$)$_{0-3}$Z,
- Z is —C(=O)—NY$^1$Y$^2$,
- $Y^1$ is —H, —NH$_2$, or —(CH$_2$CH$_2$O)$_{0-3}$—(CH$_2$)$_{0-3}$Z';
- $Y^2$ is —(CH$_2$CH$_2$O)$_{0-3}$—(CH$_2$)$_{0-3}$Z' and
- Z' is —C(=O)—OH;
- $Y^1$ is —H,
- $Y^2$ is —(CH$_2$CH$_2$O)$_3$—CH$_2$CH$_2$Z' and
- Z' is —C(=O)—OH;
- $Y^1$ is —H,
- $Y^2$ is —CH$_2$CH$_2$Z',
- Z' is —(C(=O)NHCHY$^4$)$_2$—COOH and
- $Y^4$ has the definition given in the general formula (IIa);
- $Y^1$ is —H,
- $Y^2$ is —CH$_2$CH$_2$Z',
- Z' is —(C(=O)—NHCHY$^4$)$_2$—COOH and
- $Y^4$ is i-propyl or —(CH$_2$)$_3$—NH—C(=O)—NH$_2$;
- $Y^1$ is —H,
- $Y^2$ is —CH$_2$CH$_2$Z',
- Z' is —(C(=O)—NHCHY$^4$)$_2$—COOH and
- $Y^4$ is —CH$_3$ or —(CH$_2$)$_3$—NH—C(=O)—NH$_2$;
- $Y^4$ is linear or branched C$_{1-6}$ alkyl optionally substituted by —NH—C(=O)—NH$_2$;
- $Y^4$ is i-propyl or —CH$_3$;
- $Y^1$ is —H,
- $Y^2$ is —CH$_2$CH$_2$Z',
- Z' is —C(=O)—NHCHY$^4$—COOH and
- $Y^4$ is optionally —NH$_2$-substituted aryl or benzyl;
- $Y^4$ is aminobenzyl;
- $R^2$ is —(CH$_2$)$_{0-3}$Z,
- Z is —SY$^3$ and
- $Y^3$ has the definition given above;
- $R^4$ is —C(=O)—CHY$^4$—NHY$^5$,
- $Y^4$ has the definition given above and
- $Y^5$ is —H;
- $R^4$ is —C(=O)—CHY$^4$—NHY$^5$,
- $Y^5$ is —C(=O)—CHY$^6$—NH$_2$ and
- $Y^4$ and $Y^6$ have the definitions given above;
- $Y^4$ is linear or branched C$_{1-6}$ alkyl which may optionally be substituted by —NH—C(=O)—NH$_2$.

Additionally preferred are those compounds of the general formula (IIa) in which $R^1$, $R^2$ or $R^3$ is -MOD.

Particular preference is given to those compounds in which $R^3$ is -MOD and $R^1$ is -L-#1, where
- MOD is —(NR$^{10}$)$_n$-(G1)$_o$-G2-G3,
- $R^{10}$ is —H or C$_1$-C$_3$-alkyl;
- G1 is —NH—C(=O)—, —C(=O)—NH— or

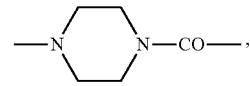

- n is 0 or 1,
- is 0 or 1,

G2 is a straight-chain or branched hydrocarbon chain which has 1 to 20 carbon atoms and may be interrupted once or more than once, identically or differently, by —O—, —S—, —S(=O)—, —S(=O)$_2$—, —NR$^y$—, —NR$^y$C(=O)—, —C(=O)—NR$^y$, —NR$^y$NR$^y$—, —S(=O)$_2$—NR$^y$NR$^y$—, —C(=O)—NR$^y$NR$^y$—, —C(=O)—, —CR$^x$=N—O—, where the straight-chain or branched hydrocarbon chain may be substituted by NH—C(=O)—NH$_2$, —COOH, —OH, —NH$_2$, sulphonamide, sulphone, sulphoxide, or sulphonic acid, R$^y$ is —H, phenyl, C$_1$-C$_{10}$-alkyl, C$_2$-C$_{10}$-alkenyl or C$_2$-C$_{10}$-alkynyl, each of which may be substituted by —NH—C(=O)—NH2, —COOH, —OH, —NH$_2$, sulphonamide, sulphone, sulphoxide, or sulphonic acid, Rx is —H, C$_1$-C$_3$-alkyl or phenyl, G3 is —H or —COOH and where the -MOD group preferably has at least one —COOH group or preferably two —COOH groups, and one amino group in -MOD may be acylated with the legumain-cleavable group of the formula (Ia').

More preferably, the group -MOD has at least one —COOH group, for example in a betaine group.

Preferably, this —COOH group is in a terminal position.

Additionally more preferably, the -MOD group is the group

—CH$_2$—Sr—(CH$_2$)$_{0-4}$—CHY$^5$—COOH in which x is 0 or 1,

Y$^5$ is —H or —NHY$^6$ and

Y$^6$ is —H or —C(=O)CH$_3$.

Additionally preferred are the compounds of the general formulae (IIa), (IIb), (IIc) and (IId) in which X$_1$ is N,
X$_2$ is N and
X$_3$ is C,
or
X$_1$ is N,
X$_2$ is C and
X$_3$ is N,
or
X is CH or CF,
X$_2$ is C and
X$_3$ is N,
or
X$_1$ is NH,
X$_2$ is C and
X$_3$ is C,
or
X is CH or CF,
X$_2$ is N and
X$_3$ is C,
R$^1$ is —H, -L-#1, -MOD or —(CH$_2$)$_{0-3}$Z,
Z is —H, —NHY$^3$, —OY$^3$, —SY$^3$, halogen, —C(=O)—NY$^1$Y$^2$ or —C(=O)—OY$^3$,
Y$^1$ and Y$^2$ are independently —H, —NH$_2$, —(CH$_2$CH$_2$O)$_{0-3}$—(CH$_2$)$_{0-3}$Z' or —CH(CH$_2$W)Z',
Y$^3$ is —H or —(CH$_2$)$_{0-3}$Z',
Z' is —H, —NH$_2$, —S(=O)$_3$H, —COOH, —NH—C(=O)—CH$_2$—CH$_2$—CH(NH$_2$)—COOH or —(C(=O)—NH—CHY$^4$)$_{1-3}$COOH,
W is —H or —OH,
Y$^4$ is linear or branched C$_{1-6}$ alkyl optionally substituted by —NHC(=O)—NH$_2$, or is aryl or benzyl optionally substituted by —NH$_2$,
R$^2$ is —H, —C(=O)—CHY$^4$—NHY$^5$ or —(CH$_2$)$_{0-3}$Z, Z is —H, halogen, —OY$^3$, —SY$^3$, —NHY$^3$, —C(=O)—NY$^1$Y$^2$, or —C(=O)—OY$^3$,
Y$^1$ and Y$^2$ are independently —H, —NH$_2$, or —(CH$_2$)$_{0-3}$Z',
Y$^3$ is —H or —(CH$_2$)$_{0-3}$Z',
Z' is —H, —S(=O)$_3$H, —NH$_2$ or —COOH;
Y$^4$ is linear or branched C$_{1-6}$ alkyl optionally substituted by —NH—C(=O)—NH$_2$ or is aryl or benzyl optionally substituted by —NH$_2$,
Y$^5$ is —H or —C(=O)—CHY$^6$—NH$_2$,
Y$^6$ is linear or branched C$_{1-6}$-alkyl,
A is —C(=O)—, —S(=O)—, —S(=O)$_2$— or —S(=O)$_2$—NH—,
R$^3$ is -L-#1, -MOD, or an alkyl, cycloalkyl, aryl, heteroaryl, heteroalkyl, heterocycloalkyl group which may optionally be substituted by one to three OH groups, one to three halogen atoms, one to three mono-, di- or trihalogenated alkyl groups, one to three —O-alkyl groups, one to three —SH groups, one to three —S-alkyl groups, one to three —O—C(=O)-alkyl groups, one to three —O—C(=O)—NH-alkyl groups, one to three —NH—C(=O)-alkyl groups, one to three —NH—C(=O)—NH-alkyl groups, one to three —S(=O)$_n$-alkyl groups, one to three —S(=O)$_2$—NH-alkyl groups, one to three —NH-alkyl groups, one to three —N(alkyl)$_2$ groups, one to three —NH((CH$_2$CH$_2$O)$_{1-20}$H)— groups, one to three NH$_2$ groups or one to three —(CH$_2$)$_{0-3}$Z— groups,
Z is —H, halogen, —OY$^3$, —SY$^3$, —NHY$^3$, —C(=O)—NY$^1$Y$^2$ or —C(=O)—OY$^3$,
Y$^1$ and Y$^2$ are independently —H, —NH$_2$, or —(CH$_2$)$_{0-3}$Z',
Y$^3$ is —H, —(CH$_2$)$_{0-3}$—CH(NH—C(=O)CH$_3$)Z', —(CH$_2$)$_{0-3}$—CH(NH$_2$)Z' or —(CH$_2$)$_{0-3}$Z',
Z' is —H, —S(=O)$_3$H, —NH$_2$ or —COOH,
R$^5$ is —H, -MOD, —NH$_2$, —NO$_2$, halogen, —CN, —CF$_3$, —OCF$_3$, —CH$_2$F, —CH$_2$F, —SH or —(CH$_2$)$_{0-3}$Z,
Z is —H, —OY$^3$, —SY$^3$, halogen, —NHY$^3$, —C(=O)—NY$^1$Y$^2$, or —C(=O)—OY$^3$,
Y$^1$ and Y$^2$ are independently —H, —NH$_2$, or —(CH$_2$)$_{0-3}$Z',
Y$^3$ is —H or —(CH$_2$)$_{0-3}$Z' and
Z' is —H, —S(=O)$_3$H, —NH$_2$ or —C(=O)—OH,
R$^6$ and R$^7$ are independently —H, —CN, C$_{1-10}$-alkyl, fluoro-C$_{1-10}$-alkyl, C$_{2-10}$-alkenyl, fluoro-C$_{2-10}$-alkenyl, C$_{2-10}$-alkynyl, fluoro-C$_{2-10}$-alkynyl, hydroxyl, —NO$_2$, —NH$_2$, —COOH or halogen,
R$^8$ is straight-chain or branched C$_{1-10}$-alkyl, fluoro-C$_{1-10}$-alkyl, C$_{2-10}$-alkenyl, fluoro-C$_{2-10}$-alkenyl, C$_{2-10}$-alkynyl or fluoro-C$_{2-10}$-alkynyl, or is C$_{4-10}$-cycloalkyl or fluoro-C$_{4-10}$-cycloalkyl,
R$^9$ is —H, —F, —CH$_3$, —CF$_3$, —CH$_2$F or —CHF$_2$,
MOD is the —(NR$^{10}$)$_n$-(G1)$_o$-G2-G3 group,
R$^{10}$ is —H or C$_1$-C$_3$-alkyl,
G1 is —NH—C(=O)—, —C(=O)—NH— or

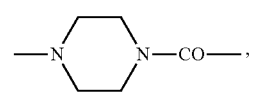

n is 0 or 1,
is 0 or 1,
G2 is a straight-chain or branched hydrocarbon chain which has 1 to 10 carbon atoms and may be interrupted once or more than once by —O—, —S—, —S(=O)—, —S(=O)$_2$—, —NR$^y$—, —NR$^y$C(=O)—, —C(=O)—NR$^y$—, —NR$^y$NR$^y$—, —S(=O)$_2$—NR$^y$NR$^y$—, —C(=O)—NR$^y$NR$^y$—, where the straight-chain or branched hydrocarbon chain may be substituted by —NH—C(=O)—NH$_2$, —COOH, —OH, —NH$_2$, sulphonamide, sulphone, sulphoxide, or sulphonic acid, R$^y$ is —H, —C(=O)—, —CR$^x$=N—O— or is optionally NH—C(=O)—NH$_2$—, —COOH—, —OH—, —NH$_2$—, sulphonamide-, sulphone-, sulphoxide- or sulphonic acid-substituted phenyl, C$_1$-C$_{10}$-alkyl, C$_2$-C$_{10}$-alkenyl or C$_2$-C$_{10}$-alkynyl, R$^x$ is —H, C$_1$-C$_3$-alkyl or phenyl, G3 is —H or —COOH and where the -MOD group preferably has at least one —COOH group and where R$^1$ and R$^3$ are not both -L-#1, and the salts, solvates and salts of the solvates thereof.

Particular preference is given here to the compounds of the general formulae (IIa), (IIb), (IIc) and (IId) in which X$_1$ is CH,
X$_2$ is C and
X$_3$ is N.

Additionally particularly preferred here are the compounds of the general formulae (IIa), (IIb), (IIc) and (IId) in which R$^3$ is a C$_{1-10}$-alkyl, C$_{6-10}$-aryl, C$_{6-10}$-aralkyl, C$_{5-10}$-heteroalkyl, C$_{1-10}$-alkyl-O—C$_{6-10}$-aryl or C$_{5-10}$-heterocycloalkyl group which may optionally be substituted by one to three OH groups, one to three halogen atoms, one to three mono-, di- or trihalogenated alkyl groups, one to three —O-alkyl groups, one to three —SH groups, one to three —S-alkyl groups, one to three —O—C(=O)-alkyl groups, one to three —O—C(=O)—NH-alkyl groups, one to three —NH—C(=O)-alkyl groups, one to three —NH—C(=O)—NH-alkyl groups, one to three —S(=O)$_n$-alkyl groups, one to three —S(=O)$_2$—NH-alkyl groups, one to three —NH-alkyl groups, one to three —N(alkyl)$_2$ groups, one to three —NH((CH$_2$CH$_2$O)$_{1-20}$H) groups, one to three NH$_2$ groups or one to three —(CH$_2$)$_{0-3}$Z groups, and Z is —H, halogen, —OY$^3$, —SY$^3$, —NHY$^3$, —C(=O)—NY$^1$Y$^2$ or —C(=O)—OY$^3$, Y$^1$ and Y$^2$ are independently —H, —NH$_2$, or —(CH$_2$)$_{0-3}$Z', Y$^3$ is —H, —(CH$_2$)$_{0-3}$—CH(NH—C(=O)CH$_3$)Z', —(CH$_2$)$_{0-3}$—CH(NH$_2$)Z' or —(CH$_2$)$_{0-3}$Z' and Z' is —H, —S(=O)$_3$H, —NH$_2$ or —COOH.

Additionally preferred compounds of the general formulae (IIa), (IIb), (IIc) and (IId) are those in which X$_1$ is N,
X$_2$ is N and
X$_3$ is C,
or
X$_1$ is N,
X$_2$ is C and
X$_3$ is N,
or
X is CH or CF,
X$_2$ is C and
X$_3$ is N,
or
X$_1$ is NH,
X$_2$ is C and
X$_3$ is C,
or
X is CH or CF,
X$_2$ is N and
X$_3$ is C,
R$^1$ is —H, -L-#1, -MOD or —(CH$_2$)$_{0-3}$Z,
Z is —H, —NHY$^3$, —OY$^3$, —SY$^3$, halogen, —C(=O)—NY$^1$Y$^2$ or —C(=O)—OY$^3$,
Y$^1$ and Y$^2$ are independently —H, —NH$_2$, —(CH$_2$CH$_2$O)$_{0-3}$—(CH$_2$)$_{0-3}$Z' or —CH(CH$_2$W)Z',
Y$^3$ is —H or —(CH$_2$)$_{0-3}$Z',
Z' is —H, —NH$_2$, —S(=O)$_3$H, —COOH, —NH—C(=O)—CH$_2$—CH$_2$—CH(NH$_2$)—COOH or —(C(=O)—NH—CHY$^4$)$_{1-3}$COOH,
W is —H or —OH,
Y$^4$ is linear or branched, optionally —NH—C(=O)—NH$_2$-substituted C$_{1-6}$ alkyl or optionally —NH$_2$-substituted aryl or benzyl,
R$^2$ is —H, —C(=O)—CHY$^4$—NHY$^5$ or —(CH$_2$)$_{0-3}$Z,
Z is —H, halogen, —OY$^3$, —SY$^3$, —NHY$^3$, —C(=O)—NY$^1$Y$^2$ or —C(=O)—OY$^3$,
Y$^1$ and Y$^2$ are independently —H, —NH$_2$, or —(CH$_2$)$_{0-3}$Z',
Y$^3$ is —H or —(CH$_2$)$_{0-3}$Z',
Z' is —H, —S(=O)$_3$H, —NH$_2$ or —COOH,
Y$^4$ is linear or branched, optionally —NH—C(=O)—NH$_2$-substituted C$_{1-6}$ alkyl or optionally —NH$_2$-substituted aryl or benzyl,
Y$^5$ is —H or —C(=O)—CHY$^6$—NH$_2$,
Y$^6$ is linear or branched C$_{1-6}$-alkyl,
A is —C(=O)—, —S(=O)—, —S(=O)$_2$— or —S(=O)$_2$—NH—,
R$^3$ is -L-#1, -MOD or an alkyl, cycloalkyl, aryl, heteroaryl, heteroalkyl, heterocycloalkyl group which may optionally be substituted by one to three OH groups, one to three halogen atoms, one to three mono-, di- or trihalogenated alkyl groups, one to three —O-alkyl groups, one to three —SH groups, one to three —S-alkyl groups, one to three —O—C(=O)-alkyl groups, one to three —O—C(=O)—NH-alkyl groups, one to three —NH—C(=O)-alkyl groups, one to three —NH—C(=O)—NH-alkyl groups, one to three —S(=O)$_n$-alkyl groups, one to three —S(=O)$_2$—NH-alkyl groups, one to three —NH-alkyl groups, one to three —N(alkyl)$_2$ groups, one to three —NH((CH$_2$CH$_2$O)$_{1-20}$H)— groups, one to three NH$_2$ groups or one to three —(CH$_2$)$_{0-3}$Z— groups,
Z is —H, halogen, —OY$^3$, —SY$^3$, —NHY$^3$, —C(=O)—NY$^1$Y$^2$ or —C(=O)—OY$^3$,
Y$^1$ and Y$^2$ are independently —H, —NH$_2$, or —(CH$_2$)$_{0-3}$Z',
Y$^3$ is —H, —(CH$_2$)$_{0-3}$—CH(NH—C(=O)CH$_3$)Z', —(CH$_2$)$_{0-3}$—CH(NH$_2$)Z' or —(CH$_2$)$_{0-3}$Z', Z' is —H, —S(=O)$_3$H, —NH$_2$ or —COOH,
R$^5$ is —H, -MOD, —NH$_2$, —NO$_2$, halogen, —CN, —CF$_3$, —OCF$_3$, —CH$_2$F, —CH$_2$F, SH or —(CH$_2$)$_{0-3}$Z,
Z is —H, —OY$^3$, —SY$^3$, halogen, —NHY$^3$, —C(=O)—NY$^1$Y$^2$, or —C(=O)—OY$^3$,
Y$^1$ and Y$^2$ are independently —H, —NH$_2$, or —(CH$_2$)$_{0-3}$Z',
Y$^3$ is —H or —(CH$_2$)$_{0-3}$Z',
Z' is —H, —S(=O)$_3$H, —NH$_2$ or —COOH,
R$^6$ and R$^7$ are independently —H or halogen,
R$^8$ is straight-chain or branched C$_{1-10}$-alkyl or fluoro-C$_{1-10}$-alkyl,
R$^9$ is —H, —F, —CH$_3$, —CF$_3$, —CH$_2$F or —CHF$_2$,
L-#1 is the -(L$_b$)$_o$-(LIG)$_p$ group, LIG is a binder which, after binding to a receptor of a tumour cell, is internalized by the tumour cell and processed intracellularly, preferably lysosomally,
Lb is a linker,
and p are each independently 0 or 1,
MOD is —CH$_2$—Sr—(CH$_2$)$_{0-4}$—CHY$^5$—COOH,
x is 0 or 1,
Y$^5$ is —H or —NHY$^6$,
Y$^6$ is —H or —C(=O)CH$_3$ and
where R$^1$ and R$^3$ are not both -L-#1,
and the salts, solvates and salts of the solvates thereof.

Preference is given here to those compounds of the general formulae (IIa), (IIb), (IIc) and (IId) in which
X$_1$ is CH,
X$_2$ is C and
X$_3$ is N.

Additionally preferred here are those compounds of the general formulae (IIa), (IIb), (IIc) and (IId) in which
R$^3$ is a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by one to three OH groups, one to three halogen atoms, one to three mono-, di- or trihalogenated alkyl groups, one to three —O-alkyl groups, one to three —SH groups, one to three —S-alkyl groups, one to three —O—C(=O)-alkyl groups, one to three —O—C(=O)—NH-alkyl groups, one to three —NH—C(=O)-alkyl groups, one to three —NH—C(=O)—NH-alkyl groups, one to three —S(=O)-alkyl groups, one to three —S(=O)$_2$—NH-alkyl groups, 1-3 —NH-alkyl groups, one to three —N(alkyl)$_2$ groups, one to three NH$_2$ groups or one to three —(CH$_2$)$_{0-3}$Z groups,
Z is —H, halogen, —OY$^3$, —SY$^3$, —NHY$^3$, —C(=O)—NY$^1$Y$^2$ or —C(=O)—OY$^3$,
Y$^1$ and Y$^2$ are independently —H, —NH$_2$, or —(CH$_2$)$_{0-3}$Z',
Y$^3$ is —H, —(CH$_2$)$_{0-3}$—CH(NH—C(=O)CH$_3$)Z', —(CH$_2$)$_{0-3}$—CH(NH$_2$)Z' or —(CH$_2$)$_{0-3}$Z' and Z' is —H, —S(=O)$_3$H, —NH$_2$ or —COOH.

If the term "alkyl" is otherwise undefined, alkyl is preferably C$_1$-C$_{10}$-alkyl.

If the term "halogen" is otherwise undefined, halogen is fluorine (—F), chlorine (—Cl) and bromine (—Br).

Particular preference is given to the following compounds of the general formulae (V), (VI) and (VII) in which R$^1$, R$^2$, R$^3$, R$^4$ and R$^5$ have the definitions given in the general formula (IIa):

Formula (V)

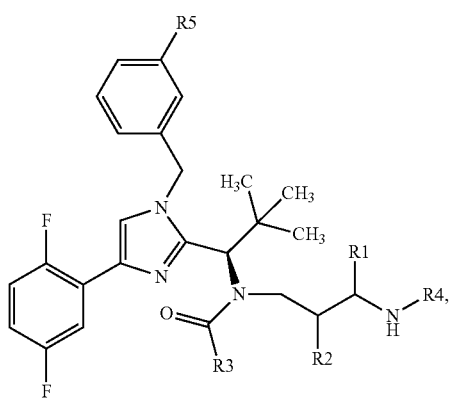

-continued

Formula (VI)

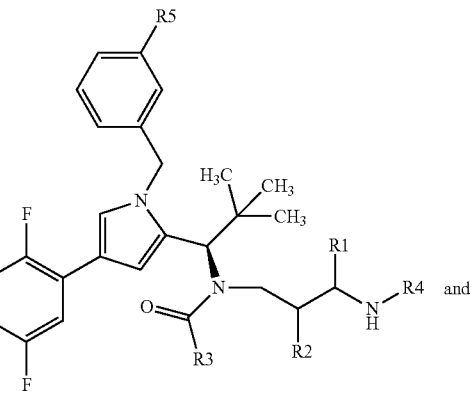

Formula (VII)

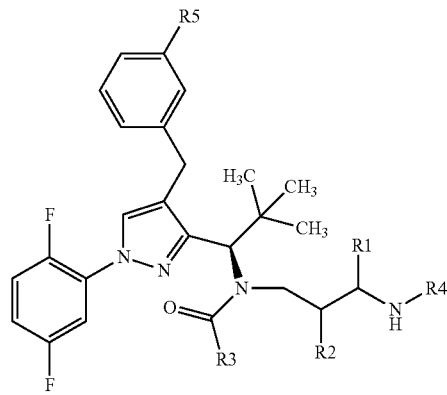

Particular preference is given to the compounds of the general formulae (V), (VI) and (VII) in which
R$^1$, R$^2$ and R$^5$ are —H and R$^4$ has the definitions given in the general formula (IIa).

Especial preference is given here to the compounds of the general formula (VI).

Binder which Binds to a Receptor of a Tumour Cell

In the broadest sense, the term "binder" is understood to mean a molecule which binds to a target molecule present at a certain target cell population to be addressed by the binder-drug conjugate. The term binder is to be understood in its broadest meaning and also comprises, for example, lectins, proteins capable of binding to certain sugar chains, and phospholipid-binding proteins. Such binders include, for example, high molecular weight proteins (binding proteins), polypeptides or peptides (binding peptides), non-peptidic (e.g. aptamers (U.S. Pat. No. 5,270,163) review by Keefe A D., et al., Nat. Rev. Drug Discov. 2010; 9:537-550), or vitamins) and all other cell-binding molecules or substances. Binding proteins are, for example, antibodies and antibody fragments or antibody mimetics, for example affibodies, adnectins, anticalins, DARPins, avimers, nanobodies (review by Gebauer M. et al., Curr. Opinion in Chem. Biol. 2009; 13:245-255; Nuttall S. D. et al., Curr. Opinion in Pharmacology 2008; 8:608-617). Binding peptides are, for example, ligands of a ligand/receptor pair such as, for example, VEGF of the ligand/receptor pair VEGF/KDR, such as transferrin of the ligand/receptor pair transferrin/transferrin receptor or cytokine/cytokine receptor, such as TNFalpha of the ligand/receptor pair TNFalpha/TNFalpha receptor.

The prodrugs according to the invention preferably contain a binder which can bind to a receptor of a tumour cell and is generally, after binding to the receptor, internalized by the tumour cell and processed intracellularly, preferably lysosomally. One way in which this binder can be joined is by the group cleavable by the enzyme legumain, optionally via a linker, such that, after cleavage of the legumain-cleavable group, the active ingredient is present separately from the binder or a derivative thereof. In this case, -D in the general formula (Ia) represents -D$_1$ and —R in the general formula (Ia) represents (L$_c$)$_r$-LIG (embodiment A). In addition, the binder can be joined to the drug molecule, optionally via a linker, such that, after cleavage of the legumain-cleavable group, the active ingredient is present together with the binder or a derivative thereof. In this case, -D in the general formula (Ia) represents -D$_1$-(L$_b$)$_o$-LIG and R— in the general formula (Ia) represents Z$_1$—(C(═O))q- (embodiment B).

The compounds of embodiment A preferably have the following general formula (III'):

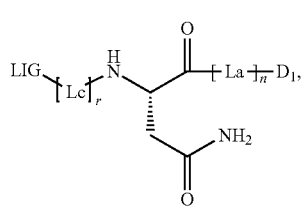

(III')

where n, r, LIG, La, Lc, and D$_1$ have the definitions given in the general formula (Ia).

The compounds of embodiment B preferably have the following general formula (IV'):

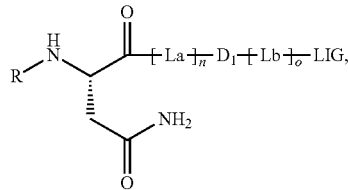

(IV')

where n, o, R, LIG, La, Lb and D$_1$ have the definitions given in the general formula (Ia).

The binder LIG is generally a peptide, protein or a derivative thereof. Corresponding peptides are known from the literature (a review is given by D. Bohme and A. Beck-Sickinger, J. Pept. Sci. 2015-21.186; see also B. Forner et al., Specialty Chemicals Magazine, May 2012; V. Ahrens et al., Future Med. Chem. 2012, 4, 1567; W. Tai et al., Mol. Pharmaceutics 2011, 8, 901; R. Soudy et al., J. Med. Chem. 2013, 56, 7564 and further references in the introduction by R. Soudy et al., M. Langer et al., J. Med. Chem. 2001, 44, 1341; C. Gruendker et al., Oncology Reports 2011, 26, 629). The peptide or derivative thereof is preferably selected from octreotide, GnRH-III, [D-Tyr$^6$, β-Ala$^{11}$, Phe$^{13}$, Nle$^{14}$]BN(6-14), NT(8-13), c(RGDfK), HSDAVFTDNYTRLRKQMAVKKYLNSILN-NH$_2$ (SEQ ID NO: 161), NAPamide, [Phe$^7$, Pro$^{34}$]NPY, HER2-targeting peptide, ATEPRKQYATPRVFWTDAPG (SEQ ID NO: 162) or LQWRRDDNVHNFGVWARYRL (SEQ ID NO: 163) [the peptide sequences are stated here in the standard 1-letter code for amino acids]. It is possible to ascertain further peptide sequences with the aid of a screening method, as described in Umlauf et al, Bioconj. Chem. 2014, Oct. 15; 25(10): 1829-37.

In the case of embodiment A, the peptide can be bonded directly (for example by its C terminus) to the N terminus of the legumain-cleavable group by a peptide bond. It is also possible for the peptide to be bonded to the N terminus of the legumain-cleavable group via a linker L$_c$, in which case the linker is preferably bonded to the C or N terminus of the peptide or to a lysine or cysteine side chain of the peptide.

In the case of embodiment B, the peptide can be bonded directly to the drug molecule. However, it is preferable for the peptide to be bonded to the drug molecule via a linker Lb, in which case the linker is preferably bonded to the C or N terminus of the peptide or to a lysine or cysteine side chain of the peptide. The binding of Lb or of the peptide is generally effected by substitution of a hydrogen atom in the drug molecule.

For instance, in the case of the compounds of the general formulae (IIa), (IIb), (IIc), (IId), (V), (VI) or (VII), it is possible to obtain conjugates by substitution of a hydrogen atom in R$^1$, R$^2$, R$^3$, R$^5$ or R$^8$, in a manner known to the person of average skill in the art, where one of the substituents R$^1$, R$^2$, R$^3$, R$^5$ or R$^8$ represents -(Lb)$_o$-LIG. A particularly preferred binder LIG is an antibody or an antigen-binding fragment or derivative thereof, which binds to an extracellular target molecule of a tumour cell. More preferably, LIG is an antibody or a fragment thereof to which one or more cytotoxic drug molecules are bound. In the case of embodiment A, the compounds according to the invention are thus antibody-drug conjugates (ADCs) of the following general formula (IIIa'):

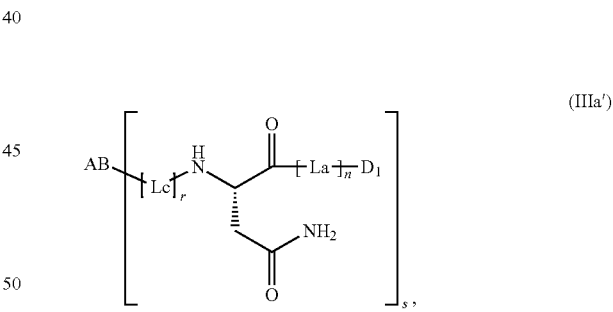

(IIIa')

where n, r, La, Lc and D$_1$ have the definitions given in the general formula (Ia), AB represents an antibody, and s represents a number from 1 to 20, preferably 2 to 8, more preferably 2 to 6, for example 4.

In this context, D$_1$ is preferably a compound of the general formula (IIa), (IIb), (IIc), (IId), (V), (VI) or (VII), where one substituent selected from R$^1$, R$^2$, R$^3$, R$^4$, R$^8$ does not have the definition given above under the general formulae (IIa), (IIb), (IIc), (IId), (V), (VI) and (VII), but represents a bond to La, i.e. the self-immolative linker, or a bond to a carbonyl group.

In the case of embodiment B, the compounds according to the invention are antibody-prodrug conjugates (APDCs) of the following general formulae (Iva'):

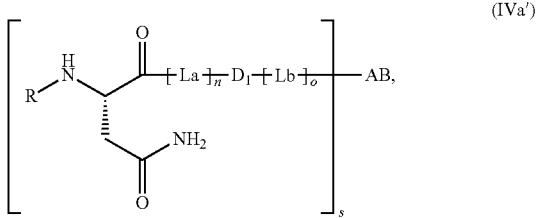

in which n, o, R, La and Lb have the definitions given in the general formula (Ia) and AB represents an antibody, and s represents a number from 1 to 20, preferably 2 to 8, more preferably 2 to 6, for example 4. In this context, $D_1$ is preferably a compound of the general formulae (IIa), (IIb), (IIc), (IId), (V), (VI) or (VII), where one substituent $R^4$ does not have the definition given above under the general formulae (IIa), (IIb), (IIc), (IId), (V), (VI) or (VII), but represents the bond to La or a carbonyl group.

The antibody (for example AB in the above general formulae (IIIa) and (IVa) is preferably a human, humanized or chimeric monoclonal antibody or antigen-binding fragment thereof, especially an anti-TWEAKR antibody, an anti-EGFR antibody, an anti-B7H3 antibody or an anti-HER2 antibody or an antigen-binding fragment of these. Particular preference is given to the anti-TWEAKR antibodies TPP-7006, TPP-7007 and TPP-10337, the anti-B7H3 antibodies TPP-8382 and TPP-8567, the anti-EGFR-antibody cetuximab (TPP-981) and the anti-HER2-antibodies trastuzumab and TPP-1015, or an antigen-binding fragment of these.

The literature also discloses various options of covalent coupling (conjugation) of organic molecules to antibodies. Preference according to the invention is given to conjugation to the antibody via one or more sulphur atoms of cysteine residues of the antibody and/or via one or more NH groups of lysine residues of the antibody. However, it is also possible to bind the organic molecule to the antibody via free carboxyl groups or via sugar residues of the antibody.

The antibody binds to an extracellular target molecule of the tumour cell. A "target molecule" in the broadest sense is understood to mean a molecule which is present in the target cell population and which may be a protein (for example a receptor of a growth factor) or a non-peptidic molecule (for example a sugar or phospholipid). It is preferably a receptor or an antigen.

The term "extracellular" target molecule describes a target molecule, bound to the cell, which is on the outside of a cell, or the part of a target molecule which is on the outside of a cell, i.e. an antibody can bind to its extracellular target molecule in an intact cell. An extracellular target molecule may be anchored in the cell membrane or be a component of the cell membrane. The person skilled in the art is aware of methods for identifying extracellular target molecules. For proteins, this may be by determining the transmembrane domain(s) and the orientation of the protein in the membrane. These data are usually deposited in protein databases (e.g. SwissProt).

The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

The term "binder" according to the present invention is understood to mean a binder peptide, a derivative of a binder peptide, a binder protein or a derivative of a binder protein. The binder is linked to the linker via a bond. The binder can be linked by means of a heteroatom of the binder. Inventive heteroatoms of the binder which can be used for linkage are:
  sulphur, via a sulphhydryl group of the binder,
  oxygen, via a carboxylic group or hydroxyl group of the binder, and
  nitrogen, via a primary or secondary amine group.

More particularly, according to the present invention, the term "binder" is understood to mean an antibody.

The above-listed heteroatoms may be present in the natural antibody or are introduced by chemical methods or methods of molecular biology. According to the invention, the attachment of the antibody to the organic radical in formula (I) has only a minor effect on the binding activity of the antibody with respect to the target molecule.

In a preferred embodiment, the linkage has no effect on the binding activity of the binder with respect to the target molecule.

In accordance with the present invention, the term "antibody" is to be understood in its broadest meaning and comprises immunoglobulin molecules, for example intact or modified monoclonal antibodies, polyclonal antibodies or multispecific antibodies (e.g. bispecific antibodies). An immunoglobulin molecule preferably comprises a molecule having four polypeptide chains, two heavy chains (H chains) and two light chains (L chains) which are typically linked by disulphide bridges. Each heavy chain comprises a variable domain of the heavy chain (abbreviated VH) and a constant domain of the heavy chain. The constant domain of the heavy chain may, for example, comprise three domains CH1, CH2 and CH3. Each light chain comprises a variable domain (abbreviated VL) and a constant domain. The constant domain of the light chain comprises a domain (abbreviated CL). The VH and VL domains may be subdivided further into regions having hypervariability, also referred to as complementarity determining regions (abbreviated CDR) and regions having low sequence variability (framework region, abbreviated FR). Typically, each VH and VL region is composed of three CDRs and up to four FRs. For example from the amino terminus to the carboxy terminus in the following order: FR1, CDR1, FR2, CDR2, FR3, CDR3, FR4. An antibody may be obtained from any suitable species, e.g. rabbit, llama, camel, mouse or rat. In one embodiment, the antibody is of human or murine origin. An antibody may, for example, be human, humanized or chimeric.

The term "monoclonal" antibody refers to antibodies obtained from a population of substantially homogeneous antibodies, i.e. individual antibodies of the population are identical except for naturally occurring mutations, of which there may be a small number. Monoclonal antibodies recognize a single antigenic binding site with high specificity. The term monoclonal antibody does not refer to a particular preparation process.

The term "intact" antibody refers to antibodies comprising both an antigen-binding domain and the constant domain of the light and heavy chain. The constant domain may be a naturally occurring domain or a variant thereof having a number of modified amino acid positions.

The term "modified intact" antibody refers to intact antibodies fused via their amino terminus or carboxy terminus by means of a covalent bond (e.g. a peptide bond) with a further polypeptide or protein not originating from an antibody. Furthermore, antibodies may be modified such that, at defined positions, reactive cysteines are introduced to facilitate coupling to a toxophore (see Junutula et al. Nat Biotechnol. 2008, 26(8)925-32).

The term "human" antibody refers to antibodies which can be obtained from a human or which are synthetic human antibodies. A "synthetic" human antibody is an antibody which is partially or entirely obtainable in silico from synthetic sequences based on the analysis of human antibody sequences. A human antibody can be encoded, for example, by a nucleic acid isolated from a library of antibody sequences of human origin. An example of such an antibody can be found in Söderlind et al., Nature Biotech. 2000, 18:853-856.

The term "humanized" or "chimeric" antibody describes antibodies consisting of a non-human and a human portion of the sequence. In these antibodies, part of the sequences of the human immunoglobulin (recipient) is replaced by sequence portions of a non-human immunoglobulin (donor). In many cases, the donor is a murine immunoglobulin. In the case of humanized antibodies, amino acids of the CDR of the recipient are replaced by amino acids of the donor. Sometimes, amino acids of the framework, too, are replaced by corresponding amino acids of the donor. In some cases the humanized antibody contains amino acids present neither in the recipient nor in the donor, which were introduced during the optimization of the antibody. In the case of chimeric antibodies, the variable domains of the donor immunoglobulin are fused with the constant regions of a human antibody.

The term complementarity determining region (CDR) as used herein refers to those amino acids of a variable antibody domain which are required for binding to the antigen. Typically, each variable region has three CDR regions referred to as CDR1, CDR2 and CDR3. Each CDR region may embrace amino acids according to the definition of Kabat and/or amino acids of a hypervariable loop defined according to Chotia. The definition according to Kabat comprises, for example, the region from about amino acid position 24-34 (CDR1), 50-56 (CDR2) and 89-97 (CDR3) of the variable light chain and 31-35 (CDR1), 50-65 (CDR2) and 95-102 (CDR3) of the variable heavy chain (Kabat et al., Sequences of Proteins of Immunological Interest, 5th Ed. Public Health Service, National Institutes of Health, Bethesda, MD. (1991)). The definition according to Chotia comprises, for example, the region from about amino acid position 26-32 (CDR1), 50-52 (CDR2) and 91-96 (CDR3) of the variable light chain and 26-32 (CDR1), 53-55 (CDR2) and 96-101 (CDR3) of the variable heavy chain (Chothia and Lesk; J Mol Biol 196 901-917 (1987)). In some cases, a CDR may comprise amino acids from a CDR region defined according to Kabat and Chotia.

Depending on the amino acid sequence of the constant domain of the heavy chain, antibodies may be categorized into different classes. There are five main classes of intact antibodies: IgA, IgD, IgE, IgG and IgM, and several of these can be divided into further subclasses. (Isotypes), e.g. IgG1, IgG2, IgG3, IgG4, IgA1 and IgA2. The constant domains of the heavy chain, which correspond to the different classes, are referred to as [alpha/α], [delta/δ], [epsilon/ε], [gamma/γ] and [my/μ]. Both the three-dimensional structure and the subunit structure of antibodies are known.

The term "functional fragment" or "antigen-binding antibody fragment" of an antibody/immunoglobulin is defined as a fragment of an antibody/immunoglobulin (e.g. the variable domains of an IgG) which still comprise the antigen binding domains of the antibody/immunoglobulin. The "antigen binding domain" of an antibody typically comprises one or more hypervariable regions of an antibody, for example the CDR, CDR2 and/or CDR3 region. However, the "framework" or "skeleton" region of an antibody may also play a role during binding of the antibody to the antigen. The framework region forms the skeleton of the CDRs. Preferably, the antigen binding domain comprises at least amino acids 4 to 103 of the variable light chain and amino acids 5 to 109 of the variable heavy chain, more preferably amino acids 3 to 107 of the variable light chain and 4 to 111 of the variable heavy chain, especially preferably the complete variable light and heavy chains, i.e. amino acids 1-109 of the VL and 1 to 113 of the VH (numbering according to WO97/08320).

"Functional fragments" or "antigen-binding antibody fragments" of the invention encompass, non-conclusively, Fab, Fab', F(ab')$_2$ and Fv fragments, diabodies, Single Domain Antibodies (DAbs), linear antibodies, individual chains of antibodies (single-chain Fv, abbreviated to scFv); and multispecific antibodies, such as bi and tri-specific antibodies, for example, formed from antibody fragments C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag. Antibodies other than "multispecific" or "multifunctional" antibodies are those having identical binding sites. Multispecific antibodies may be specific for different epitopes of an antigen or may be specific for epitopes of more than one antigen (see, for example, WO 93/17715; WO 92/08802; WO 91/00360; WO 92/05793; Tutt, et al., 1991, J. Immunol. 14760 69; U.S. Pat. Nos. 4,474,893; 4,714,681; 4,925,648; 5,573,920; 5,601,819; or Kostelny et al., 1992, J. Immunol. 148 1547 1553). An F(ab')$_2$ or Fab molecule may be constructed such that the number of intermolecular disulphide interactions occurring between the Ch1 and the CL domains can be reduced or else completely prevented.

"Epitopes" refer to protein determinants capable of binding specifically to an immunoglobulin or T cell receptors. Epitopic determinants usually consist of chemically active surface groups of molecules such as amino acids or sugar side chains or combinations thereof, and usually have specific 3-dimensional structural properties and also specific charge properties.

"Functional fragments" or "antigen-binding antibody fragments" may be fused with another polypeptide or protein, not originating from an antibody, via the amino terminus or carboxyl terminus thereof, by means of a covalent bond (e.g. a peptide linkage). Furthermore, antibodies and antigen-binding fragments may be modified by introducing reactive cysteines at defined locations, in order to facilitate coupling to a toxophore (see Junutula et al. Nat Biotechnol. 2008 August; 26(8)925-32).

Polyclonal antibodies can be prepared by methods known to a person of ordinary skill in the art. Monoclonal antibodies may be prepared by methods known to a person of ordinary skill in the art (Kohler and Milstein, Nature, 256, 495-497, 1975). Human and humanized monoclonal antibodies may be prepared by methods known to a person of ordinary skill in the art (Olsson et al., Meth Enzymol. 92, 3-16 or Cabilly et al U.S. Pat. No. 4,816,567 or Boss et al U.S. Pat. No. 4,816,397).

A person of ordinary skill in the art is aware of diverse methods for preparing human antibodies and fragments thereof, such as, for example, by means of transgenic mice (N Lonberg and D Huszar, Int Rev Immunol. 1995; 13(1) 65-93) or phage display technologies (Clackson et al., Nature. 1991 Aug. 15; 352(6336)624-8). Antibodies of the invention may be obtained from recombinant antibody libraries consisting for example of the amino acid sequences of a multiplicity of antibodies compiled from a large number of healthy volunteers. Antibodies may also be produced by means of known recombinant DNA technologies. The nucleic acid sequence of an antibody can be obtained by routine sequencing or is available from publically accessible databases.

An "isolated" antibody or binder has been purified to remove other constituents of the cell. Contaminating constituents of a cell which may interfere with a diagnostic or therapeutic use are, for example, enzymes, hormones, or other peptidic or non-peptidic constituents of a cell. A preferred antibody or binder is one which has been purified to an extent of more than 95% by weight, relative to the antibody or binder (determined for example by Lowry method, UV-Vis spectroscopy or by SDS capillary gel electrophoresis). Moreover an antibody which has been purified to such an extent that it is possible to determine at least 15 amino acids of the amino terminus or of an internal amino acid sequence, or which has been purified to homogeneity, the homogeneity being determined by SDS-PAGE under reducing or non-reducing conditions (detection may be determined by means of Coomassie Blau staining or preferably by silver coloration). However, an antibody is normally prepared by one or more purification steps.

The term "specific binding" or "binds specifically" refers to an antibody or binder which binds to a predetermined antigen/target molecule. Specific binding of an antibody or binder typically describes an antibody or binder having an affinity of at least $10^{-7}$ M (as Kd value; i.e. preferably those with Kd values smaller than $10^{-7}$ M), with the antibody or binder having an at least two times higher affinity for the predetermined antigen/target molecule than for a non-specific antigen/target molecule (e.g. bovine serum albumin, or casein) which is not the predetermined antigen/target molecule or a closely related antigen/target molecule. Specific binding of an antibody or binder does not mean that the antibody or binder cannot bind to multiple antigens/target molecules (e.g. orthologues from different species). The antibodies preferably have an affinity of at least $10^{-7}$ M (as Kd value; in other words preferably those with smaller Kd values than $10^{-7}$ M), preferably of at least $10^{-8}$ M, more preferably in the range from $10^{-9}$ M to $10^{-1}$ M. The Kd values may be determined, for example, by means of surface plasmon resonance spectroscopy.

The antibody-drug conjugates of the invention likewise exhibit affinities in these ranges. The affinity is preferably not substantially affected by the conjugation of the drugs (in general, the affinity is reduced by less than one order of magnitude, in other words, for example, at most from $10^{-8}$ M to $10^{-7}$ M).

The antibodies used in accordance with the invention are also notable preferably for a high selectivity. A high selectivity exists when the antibody of the invention exhibits an affinity for the target protein which is better by a factor of at least 2, preferably by a factor of 5 or more preferably by a factor of 10, than for an independent other antigen, e.g. human serum albumin (the affinity may be determined, for example, by means of surface plasmon resonance spectroscopy).

Furthermore, the antibodies of the invention that are used are preferably cross-reactive. In order to be able to facilitate and better interpret preclinical studies, for example toxicological or activity studies (e.g. in xenograft mice), it is advantageous if the antibody used in accordance with the invention not only binds the human target protein but also binds the species target protein in the species used for the studies. In one embodiment the antibody used in accordance with the invention, in addition to the human target protein, is cross-reactive to the target protein of at least one further species. For toxicological and activity studies it is preferred to use species of the families of rodents, dogs and non-human primates. Preferred rodent species are mouse and rat. Preferred non-human primates are rhesus monkeys, chimpanzees and long-tailed macaques.

In one embodiment, the antibody used in accordance with the invention, in addition to the human target protein, is cross-reactive to the target protein of at least one further species selected from the group of species consisting of mouse, rat and long-tailed macaque (*Macaca fascicularis*). Especially preferred are antibodies used in accordance with the invention which in addition to the human target protein are at least cross-reactive to the mouse target protein. Preference is given to cross-reactive antibodies whose affinity for the target protein of the further non-human species differs by a factor of not more than 50, more particularly by a factor of not more than ten, from the affinity for the human target protein.

Antibodies Directed Against a Cancer Target Molecule

The target molecule towards which the binder, for example an antibody or an antigen-binding fragment thereof, is directed is preferably a cancer target molecule. The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

Antibodies which are specific against an antigen, for example cancer cell antigen, can be prepared by a person of ordinary skill in the art by means of methods with which he or she is familiar (such as recombinant expression, for example) or may be acquired commercially (as for example from Merck KGaA, Germany). Examples of known commercially available antibodies in cancer therapy are Erbitux® (cetuximab, Merck KGaA), Avastin® (bevacizumab, Roche) and Herceptin® (trastuzumab, Genentech). Trastuzumab is a recombinant humanized monoclonal antibody of the IgG1kappa type which in a cell-based assay (Kd=5 nM) binds the extracellular domains of the human epidermal growth receptor with high affinity. The antibody is produced recombinantly in CHO cells.

In a preferred embodiment, the target molecule is a selective cancer target molecule.

In a particularly preferred embodiment, the target molecule is a protein.

In one embodiment, the target molecule is an extracellular target molecule. In a preferred embodiment, the extracellular target molecule is a protein.

Cancer target molecules are known to those skilled in the art. Examples of these are listed below.

Examples of cancer target molecules are:
(1) EGFR (EGF receptor, NCBI Reference Sequence NP_005219.2, NCBI Gene ID: 1956)
(2) mesothelin (SwissProt Reference Q13421-3), mesothelin being encoded by amino acids 296-598. Amino acids 37-286 code for megakaryocyte-potentiating factor. Mesothelin is anchored in the cell membrane by a GPI anchor and is localized extracellularly.
(3) Carboanhydrase IX (CA9, SwissProt Reference Q16790), NCBI Gene ID: 768) (4) C4.4a (NCBI Reference Sequence NP_055215.2; synonym LYPD3, NCBI Gene ID: 27076)
(5) CD52 (NCBI Reference Sequence NP_001794.2)
(6) HER2 (ERBB2; NCBI Reference Sequence NP_004439.2; NCBI Gene ID: 2064)
(7) CD20 (NCBI Reference Sequence NP_068769.2)
(8) the lymphocyte activation antigen CD30 (SwissProt ID P28908)
(9) the lymphocyte adhesion molecule CD22 (SwissProt ID P20273; NCBI Gene ID: 933)
(10) the myloid cell surface antigen CD33 (SwissProt ID P20138; NCBI Gene ID: 945)
(11) the transmembrane glycoprotein NMB (GPNMB, SwissProt ID Q14956, NCBI Gene ID: 10457)
(12) the adhesion molecule CD56 (SwissProt ID P13591)
(13) the surface molecule CD70 (SwissProt ID P32970, NCBI Gene ID: 970)
(14) the surface molecule CD74 (SwissProt ID P04233, NCBI Gene ID: 972)
(15) the B-lymphocyte antigen CD19 (SwissProt ID P15391, NCBI Gene ID: 930)
(16) the surface protein Mucin-1 (MUC1, SwissProt ID P15941, NCBI Gene ID: 4582)
(17) the surface protein CD138 (SwissProt ID P18827)
(18) the integrin alphaV (NCBI Reference Sequence: NP_002201.1, NCBI Gene ID: 3685)
(19) the teratocarcinoma-derived growth factor 1 protein TDGF1 (NCBI Reference Sequence: NP_003203.1, NCBI Gene ID: 6997)
(20) the prostate-specific membrane antigen PSMA (Swiss Prot ID: Q04609; NCBI Gene ID: 2346)
(21) the tyrosine protein kinase EPHA2 (Swiss Prot ID: P29317, NCBI Gene ID: 1969)
(22) the surface protein SLC44A4 (NCBI Reference Sequence: NP_001171515.1, NCBI Gene ID: 80736)
(23) the surface protein BMPR1B (SwissProt: 000238)
(24) the transport protein SLC7A5 (SwissProt: Q01650)
(25) the epithelial prostate antigen STEAP1 (SwissProt: Q9UHE8, Gene ID: 26872)
(26) the ovarian carcinoma antigen MUC16 (SwissProt: Q8WXI7, Gene ID: 94025)
(27) the transport protein SLC34A2 (SwissProt: 095436, Gene ID: 10568)
(28) the surface protein SEMA5b (SwissProt: Q9P283)
(29) the surface protein LYPD1 (SwissProt: Q8N2G4)
(30) the endothelin receptor type B EDNRB (SwissProt: P24530, NCBI Gene ID: 1910)
(31) the ring finger protein RNF43 (SwissProt: Q68DV7)
(32) the prostate carcinoma-associated protein STEAP2 (SwissProt: Q8NFT2)
(33) the cation channel TRPM4 (SwissProt: Q8TD43)
(34) the complement receptor CD21 (SwissProt: P20023)
(35) the B-cell antigen receptor complex-associated protein CD79b (SwissProt: P40259, NCBI Gene ID: 974)
(36) the cell adhesion antigen CEACAM6 (SwissProt: P40199)
(37) the dipeptidase DPEP1 (SwissProt: P16444)
(38) the interleukin receptor IL20Ralpha (SwissProt: Q9UHF4, NCBI Gene ID: 3559)
(39) the proteoglycan BCAN (SwissProt: Q96GW7)
(40) the ephrin receptor EPHB2 (SwissProt: P29323)
(41) the prostate stem cell-associated protein PSCA (NCBI Reference Sequence: NP_005663.2)
(42) the surface protein LHFPL3 (SwissProt: Q86UP9)
(43) the receptor protein TNFRSF13C (SwissProt: Q96RJ3)
(44) the B-cell antigen receptor complex-associated protein CD79a (SwissProt: P11912)
(45) the receptor protein CXCR5 (CD185; SwissProt: P32302; NCBI Gene ID 643, NCBI Reference Sequence: NP_001707.1)
(46) the ion channel P2x5 (SwissProt: Q93086)
(47) the lymphocyte antigen CD180 (SwissProt: Q99467)
(48) the receptor protein FCRL1 (SwissProt: Q96LA6)
(49) the receptor protein FCRL5 (SwissProt: Q96RD9)
(50) the MHC class II molecule Ia antigen HLA-DOB (NCBI Reference Sequence: NP_002111.1)
(51) the T-cell protein VTCN1 (SwissProt: Q7Z7D3)
(52) TWEAKR (FN14, TNFRSF12A, NCBI Reference Sequence: NP_057723.1, NCBI Gene ID: 51330)
(53) the lymphocyte antigen CD37 (Swiss Prot: P11049, NCBI Gene ID: 951)
(54) the FGF receptor 2; FGFR2 (NCBI Gene ID: 2263; Official Symbol: FGFR2). FGFR2 receptor occurs in different splice variants (alpha, beta, IIIb, IIIc). All splice variants can act as target molecule.
(55) the transmembrane glycoprotein B7H3 (CD276; NCBI Gene ID: 80381 NCBI Reference Sequence: NP_001019907.1, Swiss Prot: Q5ZPR3-1)
(56) the B cell receptor BAFFR (CD268; NCBI Gene ID:115650)
(57) the receptor protein ROR 1 (NCBI Gene ID: 4919)
(58) the surface receptor CD123 (IL3RA; NCBI Gene ID: 3563; NCBI Reference Sequence: NP_002174.1; Swiss-Prot: P26951)
(59) the receptor protein syncytin (NCBI Gene ID 30816)
(60) aspartate beta-hydroxylase (ASPH; NCBI Gene ID 444)
(61) the cell surface glycoprotein CD44 (NCBI Gene ID: 960)
(62) CDH15 (Cadherin 15, NCBI Gene ID: 1013)
(63) the cell surface glycoprotein CEACAM5 (NCBI Gene ID: 1048)
(64) the cell adhesion molecule L1-like (CHL1, NCBI Gene ID: 10752)
(65) the receptor tyrosine kinase c-Met (NCBI Gene ID: 4233)
(66) the notch ligand DLL3 (NCBI Gene ID: 10683)
(67) the ephrin A4 (EFNA4, NCBI Gene ID: 1945)
(68) ectonucleotide pyrophosphatase/phosphodiesterase 3 (ENPP3, NCBI Gene ID: 5169)
(69) coagulation factor III (F3, NCBI Gene ID: 2152)
(70) FGF receptor 3 (FGFR3, NCBI Gene ID: 2261)
(71) the folate hydrolase FOLH1 (NCBI Gene ID: 2346)
(72) the folate receptor 1 (FOLR1; NCBI Gene ID: 2348)
(73) the guanylate cyclase 2C (GUCY2C, NCBI Gene ID: 2984)
(74) the KIT proto-oncogen receptor tyrosine kinase (NCBI Gene ID: 3815)
(75) lysosomal-associated membrane protein 1 (LAMP1, NCBI Gene ID: 3916)
(76) lymphocyte antigen 6 complex, locus E (LY6E, NCBI Gene ID: 4061)
(77) the protein NOTCH3 (NCBI Gene ID: 4854)

(78) protein tyrosine kinase 7 (PTK7, NCBI Gene ID: 5754)
(79) nectin cell adhesion molecule 4 (PVRL4, NECTIN4, NCBI Gene ID: 81607)
(80) the transmembrane protein syndecan 1 (SDC1, NCBI Gene ID: 6382)
(81) SLAM family member 7 (SLAMF7, NCBI Gene ID: 57823)
(82) the transport protein SLC39A6 (NCBI Gene ID: 25800)
(83) SLIT- and NTRK-like family member 6 (SLITRK6, NCBI Gene ID: 84189)
(84) the cell surface receptor TACSTD2 (NCBI Gene ID: 4070)
(85) the receptor protein TNFRSF8 (NCBI Gene ID: 943)
(86) the receptor protein TNFSF13B (NCBI Gene ID: 10673)
(87) the glycoprotein TPBG (NCBI Gene ID: 7162)
(88) the cell surface receptor TROP2 (TACSTD2, NCBI Gene ID: 4070)
(89) the galanin-like G protein-coupled receptor KISS1R (GPR54, NCBI Gene ID: 84634)
(90) the transport protein SLAMF6 (NCBI Gene ID: 114836)

In a preferred subject of the invention, the cancer target molecule is selected from the group consisting of the cancer target molecules (1)-(90), especially TWEAKR, B7H3, EGFR and HER2.

In a further particularly preferred subject of the invention, the binder binds to an extracellular cancer target molecule which is selected from the group consisting of the cancer target molecules (1)-(90), especially TWEAKR, B7H3, EGFR and HER2.

In a further particularly preferred subject of the invention, the binder binds specifically to an extracellular cancer target molecule which is selected from the group consisting of the cancer target molecules (1)-(90), especially TWEAKR, B7H3, EGFR and HER2. In a preferred embodiment, the binder, after binding to its extracellular target molecule on the target cell, is internalized by the target cell through the binding. This causes the binder-drug conjugate, which may be an immunoconjugate or an ADC, to be taken up by the target cell. The binder is then processed, preferably intracellularly, with preference lysosomally.

In one embodiment the binder is a binding protein. In a preferred embodiment the binder is an antibody, an antigen-binding antibody fragment, a multispecific antibody or an antibody mimetic.

Preferred antibody mimetics are affibodies, adnectins, anticalins, DARPins, avimers, or nanobodies. Preferred multispecific antibodies are bispecific and trispecific antibodies.

In a preferred embodiment the binder is an antibody or an antigen-binding antibody fragment, more preferably an isolated antibody or an isolated antigen-binding antibody fragment.

Preferred antigen-binding antibody fragments are Fab, Fab', F(ab')2 and Fv fragments, diabodies, DAbs, linear antibodies and scFv. Particularly preferred are Fab, diabodies and scFv.

In a particularly preferred embodiment the binder is an antibody. Particularly preferred are monoclonal antibodies or antigen-binding antibody fragments thereof. Further particularly preferred are human, humanized or chimeric antibodies or antigen-binding antibody fragments thereof.

Antibodies or antigen-binding antibody fragments which bind cancer target molecules may be prepared by a person of ordinary skill in the art using known processes, such as, for example, chemical synthesis or recombinant expression. Binders for cancer target molecules may be acquired commercially or may be prepared by a person of ordinary skill in the art using known processes, such as, for example, chemical synthesis or recombinant expression. Further processes for preparing antibodies or antigen-binding antibody fragments are described in WO 2007/070538 (see page 22 "Antibodies"). The person skilled in the art knows how processes such as phage display libraries (e.g. Morphosys HuCAL Gold) can be compiled and used for discovering antibodies or antigen-binding antibody fragments (see WO 2007/070538, page 24 ff and AK Example 1 on page 70, AK Example 2 on page 72). Further processes for preparing antibodies that use DNA libraries from B cells are described for example on page 26 (WO 2007/070538). Processes for humanizing antibodies are described on page 30-32 of WO2007070538 and in detail in Queen, et al., Pros. Natl. Acad. Sci. USA 8610029-10033, 1989 or in WO 90/0786. Furthermore, processes for recombinant expression of proteins in general and of antibodies in particular are known to the person skilled in the art (see, for example, in Berger and Kimmel (Guide to Molecular Cloning Techniques, Methods in Enzymology, Vol. 152, Academic Press, Inc.); Sambrook, et al., (Molecular Cloning A Laboratory Manual, (Second Edition, Cold Spring Harbor Laboratory Press; Cold Spring Harbor, N.Y.; 1989) Vol. 1-3); Current Protocols in Molecular Biology, (F. M. Ausabel et al. [Eds.], Current Protocols, Green Publishing Associates, Inc./John Wiley & Sons, Inc.); Harlow et al., (Monoclonal Antibodies A Laboratory Manual, Cold Spring Harbor Laboratory Press (19881, Paul [Ed.]); Fundamental Immunology, (Lippincott Williams & Wilkins (1998)); and Harlow, et al., (Using Antibodies A Laboratory Manual, Cold Spring Harbor Laboratory Press (1998)). The person skilled in the art knows the corresponding vectors, promoters and signal peptides which are necessary for the expression of a protein/antibody. Commonplace processes are also described in WO 2007/070538 on pages 41-45. Processes for preparing an IgG1 antibody are described for example in WO 2007/070538 in Example 6 on page 74 ff. Processes which allow the determination of the internalization of an antibody after binding to its antigen are known to the skilled person and are described for example in WO 2007/070538 on page 80. The person skilled in the art is able to use the processes described in WO 2007/070538 that have been used for preparing carboanhydrase IX (Mn) antibodies in analogy for the preparation of antibodies with different target molecule specificity.

Bacterial Expression

The person skilled in the art is aware of the way in which antibodies, antigen-binding fragments thereof or variants thereof can be produced with the aid of bacterial expression. Suitable expression vectors for bacterial expression of desired proteins are constructed by insertion of a DNA sequence which encodes the desired protein within the functional reading frame together with suitable translation initiation and translation termination signals and with a functional promoter. The vector comprises one or more phenotypically selectable markers and a replication origin in order to enable the retention of the vector and, if desired, the amplification thereof within the host. Suitable prokaryotic hosts for transformation include but are not limited to *E. coli, Bacillus subtilis, Salmonella typhimurium* and various species from the genus *Pseudomonas, Streptomyces,* and *Staphylococcus*. Bacterial vectors may be based, for example, on bacteriophages, plasmids, or phagemids. These vectors may contain selectable markers and a bacterial replication origin, which are derived from commercially available plasmids. Many commercially available plasmids typically contain elements of the well-known cloning vector pBR322 (ATCC 37017). In bacterial systems, a number of advantageous expression vectors can be selected on the basis of the intended use of the protein to be expressed.

After transformation of a suitable host strain and growth of the host strain to an appropriate cell density, the selected promoter is de-reprimed/induced by suitable means (for example a change in temperature or chemical induction), and the cells are cultivated for an additional period. The cells are typically harvested by centrifugation and if necessary digested in a physical manner or by chemical means, and the resulting raw extract is retained for further purification.

Therefore, a further embodiment of the present invention is an expression vector comprising a nucleic acid which encodes a novel antibody of the present invention.

Antibodies of the present invention or antigen-binding fragments thereof include naturally purified products, products which originate from chemical syntheses, and products which are produced by recombinant technologies in prokaryotic hosts, for example *E. coli, Bacillus subtilis, Salmonella typhimurium* and various species from the genus *Pseudomonas, Streptomyces,* and *Staphylococcus*, preferably *E. coli*.

Mammalian Cell Expression

The person skilled in the art is aware of the way in which antibodies, antigen-binding fragments thereof or variants thereof can be produced with the aid of mammalian cell expression.

Preferred regulatory sequences for expression in mammalian cell hosts include viral elements which lead to high expression in mammalian cells, such as promoters and/or expression amplifiers derived from cytomegalovirus (CMV) (such as the CMV promoter/enhancer), simian virus 40 (SV40) (such as the SV40 promoter/enhancer), from adenovirus, (for example the adenovirus major late promoter (AdMLP)) and from polyoma. The expression of the antibodies may be constitutive or regulated (for example induced by addition or removal of small molecule inductors such as tetracycline in combination with the Tet system).

For further description of viral regulatory elements and sequences thereof, reference is made, for example, to U.S. Pat. No. 5,168,062 by Stinski, U.S. Pat. No. 4,510,245 by Bell et al. and U.S. Pat. No. 4,968,615 by Schaffner et al. The recombinant expression vectors may likewise include a replication origin and selectable markers (see, for example, U.S. Pat. Nos. 4,399,216, 4,634,665 and 5,179,017). Suitable selectable markers include genes which impart resistance to substances such as G418, puromycin, hygromycin, blasticidin, zeocin/bleomycin, or methotrexate, or selectable markers which lead to auxotrophy of a host cell, such as glutamine synthetase (Bebbington et al., Biotechnology (N Y). 1992 February; 10(2):169-75), when the vector has been introduced into the cell.

For example, the dihydrofolate reductase (DHFR) gene imparts resistance to methotrexate, the neo gene imparts resistance to G418, the bsd gene from *Aspergillus terreus* imparts resistance to blasticidin, puromycin N-acetyltransferase imparts resistance to puromycin, the Sh ble gene product imparts resistance to zeocin, and resistance to hygromycin is imparted by the *E. coli* hygromycin resistance gene (hyg or hph). Selectable markers such as DHFR or glutamine synthetase are also helpful for amplification techniques in conjunction with MTX and MSX.

The transfection of an expression vector into a host cell can be executed with the aid of standard techniques, including by electroporation, nucleofection, calcium phosphate precipitation, lipofection, polycation-based transfection such as polyethyleneimine (PEI)-based transfection and DEAE-dextran transfection.

Suitable mammalian host cells for the expression of antibodies, antigen-binding fragments thereof, or variants thereof include Chinese hamster ovary (CHO) cells such as CHO-K1, CHO-S, CHO-K1SV [including DHFR-CHO cells, described in Urlaub and Chasin, (1980) Proc. Natl. Acad. Sci. USA 77:4216-4220 and Urlaub et al., Cell. 1983 June; 33(2):405-12, used with a DHFR-selectable marker, as described in R. J. Kaufman and P. A. Sharp (1982) Mol. Biol. 159:601-621, and other knockout cells, as detailed in Fan et al., Biotechnol Bioeng. 2012 April; 109(4):1007-15), NS0 myeloma cells, COS cells, HEK293 cells, HKB11 cells, BHK21 cells, CAP cells, EB66 cells, and SP2 cells.

The expression of antibodies, antigen-binding fragments thereof, or variants thereof can also be effected in a transient or semi-stable manner in expression systems such as HEK293, HEK293T, HEK293-EBNA, HEK293E, HEK293-6E, HEK293 Freestyle, HKB11, Expi293F, 293EBNALT75, CHO Freestyle, CHO-S, CHO-K1, CHO-K1SV, CHOEBNALT85, CHOS-XE, CHO-3E7 or CAP-T cells (for example like Durocher et al., Nucleic Acids Res. 2002 Jan. 15; 30(2):E9) In some embodiments, the expression vector is constructed in such a way that the protein to be expressed is secreted into the cell culture medium in which the host cells are growing. The antibodies, the antigen-binding fragments thereof, or the variants thereof can be obtained from the cell culture medium with the aid of protein purification methods known to those skilled in the art.

Purification

The antibodies, the antigen-binding fragments thereof, or the variants thereof can be obtained and purified from recombinant cell cultures with the aid of well-known methods, examples of which include ammonium sulphate or ethanol precipitation, acid extraction, protein A chromatography, protein G chromatography, anion or cation exchange chromatography, phosphocellulose chromatography, hydrophobic interaction chromatography (HIC), affinity chromatography, hydroxyapatite chromatography and lectin chromatography. High-performance liquid chromatography ("HPLC") can likewise be employed for purification. See, for example, Colligan, Current Protocols in Immunology, or Current Protocols in Protein Science, John Wiley & Sons, NY, N.Y., (1997-2001), e.g., Chapters 1, 4, 6, 8, 9, 10.

Antibodies of the present invention or antigen-binding fragments thereof, or variants thereof include naturally purified products, products from chemical synthesis methods and products which are produced with the aid of recombinant techniques in prokaryotic or eukaryotic host cells. Eukaryotic hosts include, for example, yeast cells, higher plant cells, insect cells and mammalian cells. Depending on the host cell chosen for the recombinant expression, the protein expressed may be in glycosylated or non-glycosylated form.

In a preferred embodiment, the antibody is purified (1) to an extent of more than 95% by weight, measured, for example, by the Lowry method, by UV-vis spectroscopy or by SDS capillary gel electrophoresis (for example with a Caliper LabChip GXII, GX 90 or Biorad Bioanalyzer instrument), and in more preferred embodiments more than 99% by weight, (2) to a degree suitable for determination of at least 15 residues of the N-terminal or internal amino acid sequence, or (3) to homogeneity determined by SDS-PAGE under reducing or non-reducing conditions with the aid of Coomassie blue or preferably silver staining.

Usually, an isolated antibody is obtained with the aid of at least one protein purification step.

Preferred is the antigen-binding fragment according to any of the preceding embodiments or the antigen-binding fragment of an antibody according to any of the preceding embodiments which is an scFv, Fab, Fab fragment or a F(ab)2 fragment.

Preferred is the antibody or the antigen-binding fragment according to any of the preceding embodiments which is a monoclonal antibody or an antigen-binding fragment thereof.

Preferred is the antibody or the antigen-binding fragment according to any of the preceding embodiments which is a human, humanized or chimeric antibody or an antigen-binding fragment.

Anti-TWEAKR Antibodies

According to the invention, it is possible to use anti-TWEAKR antibodies.

The expression "anti-TWEAKR antibody" or "an antibody which binds specifically to TWEAKR" relates to an antibody which binds the cancer target molecule TWEAKR (NCBI Reference Sequence: NP_057723.1, SEQ ID NO: 164), preferably having affinity sufficient for a diagnostic and/or therapeutic application. In particular embodiments, the antibody binds TWEAKR with a dissociation constant ($K_D$) of ≤1 µM, ≤100 nM, ≤10 nM, ≤1 nM, ≤0.1 nM, ≤0.01 nM, or ≤0.001 nM.

Examples of antibodies which bind to TWEAKR are disclosed, for example, in WO2009/020933(A2), WO2009/140177 (A2), WO 2014/198817 (A1) and WO 2015/189143 (A1). These antibodies and antigen-binding fragments can be used in the context of this invention.

ITEM-4 is an anti-TWEAKR antibody which was described by Nakayama et al. (Nakayama, et al., 2003, Biochem Biophy Res Comm, 306:819-825). Humanized variants of this antibody based on CDR grafting are described by Zhou et al. (Zhou et al., 2013, J Invest Dermatol. 133(4):1052-62) and in WO 2009/020933. Humanized variants of ITEM-4 are TPP-7006, TPP-7007, TPP-10334, TPP-10335, TPP-10336 and TPP-10337. These antibodies and antigen-binding fragments can be used in the context of this invention.

Preference is given in the context of this invention to the anti-TWEAKR antibodies TPP-2090, TPP-2658, TPP-5442, TPP-8825, TPP-7006, TPP-7007, TPP-10334, TPP-10335, TPP-10336 and TPP-10337. More preferred are the anti-TWEAKR antibodies TPP-7006, TPP-7007, TPP-10334, TPP-10335, TPP-10336 and TPP-10337. Particular preference is given to the anti-TWEAKR antibodies TPP-7006, TPP-7007 and TPP-10337.

Anti-B7H3 Antibodies

According to the invention, it is possible to use anti-B7H3 antibodies.

The expression "anti-B7H3 antibody" or "an antibody which binds specifically to B7H3" relates to an antibody which binds the cancer target molecule B7H3 (NCBI Reference Sequence: NP_001019907.1, SEQ ID NO: 165), preferably having affinity sufficient for a diagnostic and/or therapeutic application. In particular embodiments, the antibody binds B7H3 with a dissociation constant ($K_D$) of ≤1 µM, ≤100 nM, ≤10 nM, ≤1 nM, ≤0.1 nM, ≤0.01 nM, or ≤0.001 nM.

Examples of antibodies and antigen-binding fragments which bind to B7H3 are known to those skilled in the art and are described, for example, in WO201109400, EP1773884 and WO2014061277. EP2121008 describes the anti-B7H3 antibody 8H9 and the CDR sequences thereof.

These antibodies and antigen-binding fragments can be used in the context of this invention.

A preferred embodiment of the anti-B7H3 antibodies was obtained by screening an antibody phage display library for cells that express recombinant mouse B7H3 (mouse CD276; Gene ID: 102657) and human B7H3 (human CD276; Gene ID: 80381). The antibodies obtained were transformed to the human IgG1 format. The anti-B7H3 antibody TPP-8382 is a preferred example.

Preference is given in the context of this invention to the anti-B7H3 antibodies TPP-8382 and TPP-8567.

Anti-HER2 Antibodies:

According to the invention, it is possible to use anti-HER2 antibodies.

The expression "anti-HER2 antibody" or "an antibody which binds specifically to HER2" relates to an antibody which binds the cancer target molecule HER2 (NCBI Reference Sequence: NP_004439.2, SEQ ID NO: 166), preferably having affinity sufficient for a diagnostic and/or therapeutic application. In particular embodiments, the antibody binds HER2 with a dissociation constant ($K_D$) of ≤1 µM, ≤100 nM, ≤10 nM, ≤1 nM, ≤0.1 nM, ≤0.01 nM or ≤0.001 nM.

An example of an antibody that binds to the cancer target molecule HER2 is trastuzumab (Genentech). Trastuzumab is a humanized antibody used inter alia for the treatment of breast cancer. In a particularly preferred embodiment, the anti-HER2 antibody is TPP-1015 (trastuzumab analogue).

Further examples of antibodies that bind to HER2 are, in addition to trastuzumab (INN 7637, CAS No: RN: 180288-69-1) and pertuzumab (CAS No: 380610-27-5), also antibodies as disclosed in WO 2009/123894-A2, WO 200/8140603-A2, or in WO 2011/044368-A2. An example of an anti-HER2 conjugate is trastuzumab-emtansine (INN-No. 9295). These antibodies and antigen-binding fragments can be used in the context of this invention.

Particular preference is given in the context of this invention to the anti-HER2 antibodies trastuzumab and TPP-1015.

Anti-EGFR Antibodies

According to the invention, it is possible to use anti-EGFR antibodies.

The expression "anti-EGFR antibody" or "an antibody which binds specifically to EGFR" relates to an antibody which binds the cancer target molecule EGFR (NCBI Reference Sequence: NP_005219.2, SEQ ID NO: 167), preferably having affinity sufficient for a diagnostic and/or therapeutic application. In particular embodiments, the antibody binds EGFR with a dissociation constant ($K_D$) of ≤1 µM, ≤100 nM, ≤10 nM, ≤1 nM, ≤0.1 nM, ≤0.01 nM, or ≤0.001 nM.

In a preferred embodiment, the anti-EGFR antibodies are selected from the group consisting of TPP-981 (Cetuximab), panitumumab, nimotuzumab. In a particularly preferred embodiment, the anti-EGFR antibody is TPP-981 (cetuximab).

Further embodiments of EGFR antibodies are as follows:
zalutumumab/2F8/HuMax-EGFr, from Genmab A/S (WO 02/100348, WO 2004/056847, INN number 8605)
necitumumab/11F8, ImClone/IMC-11F8, from ImClone Systems Inc. [Eli Lilly & Co] (WO 2005/090407 (EP 01735348-A1, US 2007/0264253-A1, U.S. Pat. No. 7,598,350, WO 2005/090407-A1), INN number 9083)
matuzumab/anti-EGFR MAb, Merck KGaA/anti-EGFR MAb, Takeda/EMD 72000/EMD-6200/EMD-72000 and EMD-55900/MAb 425/monoclonal antibody 425, from Merck KGaA/Takeda (WO 92/15683, INN number 8103 (Matuzumab))

RG-7160/GA-201/GA201/R-7160/R7160/RG7160/RO-4858696/RO-5083945/R04858696/R05083945, from Glycart Biotechnology AG (Roche Holding AG) (WO 2010/112413-A1, WO 2010/115554)

GT-MAB 5.2-GEX/CetuGEX, from Glycotope GmbH (WO 2008/028686-A2 (EP 01900750-A1, EP 01911766-A1, EP 02073842-A2, US 2010/0028947-A1)

ISU-101, from Isu Abxis Inc (ISU Chemical Co Ltd)/Scancell (WO 2008/004834-A1)

ABT-806/mAb-806/ch-806/anti-EGFR monoclonal antibody 806, from Ludwig Institute for Cancer Research/Abbott/Life Science Pharmaceuticals (WO 02/092771, WO 2005/081854 and WO 2009/023265)

SYM-004 (consists of two chimeric IgG1 antibodies (992 and 1024)), from Symphogen A/S (WO 2010/022736-A2)

MR1-1/MR1-1KDEL, from IVAX Corp (Teva Pharmaceutical Industries Ltd) (Duke University), (patent: WO2001/062931-A2)

Antibody against the deletion mutant, EGFRvIII, from Amgen/Abgenix (WO 2005/010151, U.S. Pat. No. 7,628,986)

SC-100, from Scancell Ltd (WO 01/088138-A1)

MDX-447/EMD 82633/BAB-447/H 447/MAb, EGFR, Medarex/Merck KgaA, from Bristol-Myers Squibb (US)/Merck KGaA (DE)/Takeda (JP), (WO 91/05871, WO 92/15683)

anti-EGFR-Mab, from Xencor (WO 2005/056606)

DXL-1218/anti-EGFR monoclonal antibody (cancer), InNexus, from InNexus Biotechnology Inc, Pharmaprojects PH048638

Anti-Carboanhydrase IX Antibodies

Examples of antibodies which bind the cancer target molecule carboanhydrase IX are described in WO 2007/070538-A2 (e.g. Claims 1-16).

Anti-CD123 Antibodies

The expression "anti-CD123 antibody" or "an antibody which binds specifically to CD123" relates to an antibody which binds the cancer target molecule CD123 (NCBI Reference Sequence: NP_002174.1; Swiss-Prot: P26951), preferably having affinity sufficient for a diagnostic and/or therapeutic application. In particular embodiments, the antibody binds CD123 with a dissociation constant ($K_D$) of ≤1 µM, ≤100 nM, ≤10 nM, ≤1 nM, ≤0.1 nM, ≤0.01 nM, or ≤0.001 nM.

Sun et al. (Sun et al., 1996, Blood 87(1)83-92) describe the generation and properties of the monoclonal antibody 7G3, which binds the N-terminal domain of IL-3Ra, CD123. U.S. Pat. No. 6,177,078 (Lopez) relates to the anti-CD123 antibody 7G3. A chimeric variant of this antibody (CSL360) is described in WO 2009/070844, and a humanized version (CSL362) in WO 2012/021934. The sequence of the 7G3 antibody is disclosed in EP2426148. This sequence constitutes the starting point for humanized antibodies which are obtained by CDR grafting.

An antibody which, after cell surface antigen binding, is internalized particularly well is the anti-CD123 antibody 12F1 disclosed by Kuo et al. (Kuo et al., 2009, Bioconjug Chem. 20(10):1975-82). The antibody 12F1 binds with higher affinity to CD123 than the antibody 7G3 and, after cell surface antigen binding, is internalized markedly faster than 7G3. Bispecific scFv immunofusion proteins based on 12F1 are disclosed in WO 2013/173820. Antibody TPP-6013 is a chimeric variant of 12F1.

Humanized variants of these murine antibodies were generated on the basis of CDR grafting in germline sequences and optimization.

Anti-CXCR5 Antibodies

The expression "anti-CXCR5 antibody" or "an antibody which binds specifically to CXCR5" relates to an antibody which binds the cancer target molecule CXCR5 (NCBI Reference Sequence: NP_001707.1), preferably having affinity sufficient for a diagnostic and/or therapeutic application. In particular embodiments, the antibody binds CXCR5 with a dissociation constant ($K_D$) of ≤1 µM, ≤100 nM, ≤10 nM, ≤1 nM, ≤0.1 nM, ≤0.01 nM, or ≤0.001 nM.

Examples of antibodies and antigen-binding fragments which bind to CXCR5 are known to those skilled in the art and are described, for example, in EP2195023.

The hybridoma cells for the rat antibody RF8B2 (ACC2153) were purchased from DSMZ and the sequence of the antibody was identified by standard methods. This sequence constitutes the starting point for the humanized antibodies which are obtained by CDR grafting.

Humanized variants of this antibody are generated on the basis of CDR grafting in germline sequences.

Anti-C4.4a Antibodies:

Examples of C4.4a antibodies and antigen-binding fragments are described in WO 2012/143499 A2. The sequences of the antibodies are given in Table 1 of WO 2012/143499 A2, where each row shows the respective CDR amino acid sequences of the variable light chain or the variable heavy chain of the antibody listed in column 1.

Anti-CD20 Antibodies:

An example of an antibody that binds the cancer target molecule CD20 is rituximab (Genentech). Rituximab (CAS Number: 174722-31-7) is a chimeric antibody used for the treatment of non-Hodgkin's lymphoma. These antibodies and antigen-binding fragments thereof can be used in the context of this invention.

Anti-CD52 Antibodies:

An example of an antibody that binds the cancer target molecule CD52 is alemtuzumab (Genzyme). Alemtuzumab (CAS Number: 216503-57-0) is a humanized antibody used for the treatment of chronic lymphocytic leukaemia. These antibodies and antigen-binding fragments thereof can be used in the context of this invention.

Anti-Mesothelin Antibodies:

Examples of anti-mesothelin antibodies are described, for example, in WO2009/068204. All antibodies and antigen-binding fragments disclosed in WO2009/068204 can be used in the context of the invention disclosed herein. More preferably, the antibody disclosed in WO2009/068204 is MF-T.

Anti-CD30 Antibodies

Examples of antibodies which bind the cancer target molecule CD30 and can be used for treatment of cancer, for example Hodgkin's lymphoma, are brentuximab, iratumumab and antibodies disclosed in WO 2008/092117, WO 2008/036688 or WO 2006/089232. An example of an anti-CD30 conjugate is brentuximab vedotin (INN No. 9144). These antibodies and antigen-binding fragments thereof can be used in the context of this invention.

Anti-CD22 Antibodies

Examples of antibodies which bind the cancer target molecule CD22 and can be used for treatment of cancer, for example lymphoma, are inotuzumab and epratuzumab. Examples of anti-CD22 conjugates are inotuzumab ozagamycin (INN No. 8574) or anti-CD22-MMAE and anti- CD22-MC-MMAE (CAS RN: 139504-50-0 and 474645-27-7, respectively). These antibodies and antigen-binding fragments thereof can be used in the context of this invention.

Anti-CD33 Antibodies

Examples of antibodies which bind the cancer target molecule CD33 and can be used for treatment of cancer, for example leukaemia, are gemtuzumab and lintuzumab (INN 7580). An example of an anti-CD33 conjugate is gemtuzumab-ozagamycin. These antibodies and antigen-binding fragments can be used in the context of this invention.

Anti-NMB Antibodies

An example of an antibody which binds the cancer target molecule NMB and can be used for treatment of cancer, for example melanoma or breast cancer, is glembatumumab (INN 9199). An example of an anti-NMB conjugate is glembatumumab vedotin (CAS RN: 474645-27-7). These antibodies and antigen-binding fragments thereof can be used in the context of this invention.

Anti-CD56 Antibodies

An example of an antibody which binds the cancer target molecule CD56 and can be used for treatment of cancer, for example multiple myeloma, small-cell lung carcinoma, MCC or ovarial carcinoma is lorvotuzumab. An example of an anti-CD57 conjugate is lorvotuzumab mertansine (CAS RN: 139504-50-0). These antibodies and antigen-binding fragments can be used in the context of this invention.

Anti-CD70 Antibodies

Examples of antibodies which bind the cancer target molecule CD70 and can be used for treatment of cancer, for example non-Hodgkin's lymphoma or renal cell cancer, are disclosed in WO 2007/038637-A2 and WO 2008/070593-A2. An example of an anti-CD70 conjugate is SGN-75 (CD70 MMAF). These antibodies and antigen-binding fragments can be used in the context of this invention.

Anti-CD74 Antibodies

An example of an antibody which binds the cancer target molecule CD74 and can be used for treatment of cancer, for example multiple myeloma, is milatuzumab. An example of an anti-CD74 conjugate is milatuzumab-doxorubicin (CAS RN: 23214-92-8). These antibodies and antigen-binding fragments can be used in the context of this invention.

Anti-CD19 Antibodies

An example of an antibody which binds the cancer target molecule CD19 and can be used for treatment of cancer, for example non-Hodgkin's lymphoma, is disclosed in WO 2008/031056-A2. Further antibodies and examples of an anti-CD19 conjugate (SAR3419) are disclosed in WO 2008/047242-A2. These antibodies and antigen-binding fragments thereof can be used in the context of this invention.

Anti-mucin Antibodies

Examples of antibodies which bind the cancer target molecule mucin-1 and can be used for treatment of cancer, for example non-Hodgkin's lymphoma, are clivatuzumab and the antibodies disclosed in WO 2003/106495-A2, WO 2008/028686-A2. Examples of anti-mucin conjugates are disclosed in WO 2005/009369-A2. These antibodies and antigen-binding fragments thereof can be used in the context of this invention.

Anti-CD138 Antibodies

Examples of antibodies which bind the cancer target molecule CD138 and conjugates thereof, which can be used for treatment of cancer, for example multiple myeloma, are disclosed in WO 2009/080829-A1, WO 2009/080830-A1. These antibodies and antigen-binding fragments thereof can be used in the context of this invention.

Anti-integrin-alphaV Antibodies

Examples of antibodies which bind the cancer target molecule integrin alphaV and can be used for treatment of cancer, for example melanoma, sarcoma or carcinoma, are intetumumab (CAS RN: 725735-28-4), abciximab (CAS RN: 143653-53-6), etaracizumab (CAS RN: 892553-42-3) and the antibodies disclosed in U.S. Pat. No. 7,465,449, EP 719859-A1, WO 2002/012501-A1 and WO2006/062779-A2. Examples of anti-integrin AlphaV conjugates are intetumumab-DM4 and other ADCs disclosed in WO 2007/024536-A2. These antibodies and antigen-binding fragments thereof can be used in the context of this invention.

Anti-TDGF1 Antibodies

Examples of antibodies which bind the cancer target molecule TDGF1 and can be used for treatment of cancer are the antibodies disclosed in WO 02/077033-A1, U.S. Pat. No. 7,318,924, WO 2003/083041-A2 and WO 2002/088170-A2. Examples of anti-TDGF1 conjugates are disclosed in WO 2002/088170-A2. These antibodies and antigen-binding fragments thereof can be used in the context of this invention.

Anti-PSMA Antibodies

Examples of antibodies which bind the cancer target molecule PSMA and can be used for treatment of cancer, for example prostate carcinoma, are the antibodies disclosed in WO 97/35616-A1, WO 99/47554-A1, WO 01/009192-A1 and WO2003/034903. Examples of anti-PSMA conjugates are disclosed in WO 2009/026274-A1 and WO 2007/002222. These antibodies and antigen-binding fragments can be used in the context of this invention.

Anti-EPHA2 Antibodies

Examples of antibodies which bind the cancer target molecule EPHA2 and can be used for preparation of a conjugate and for treatment of cancer are disclosed in WO 2004/091375-A2. These antibodies and antigen-binding fragments can be used in the context of this invention.

Anti-SLC44A4 Antibodies

Examples of antibodies which bind the cancer target molecule SLC44A4 and can be used for preparation of a conjugate and for treatment of cancer, for example pancreas or prostate carcinoma, are disclosed in WO2009/033094-A2 and US2009/0175796-A1. These antibodies and antigen-binding fragments thereof can be used in the context of this invention.

Anti-HLA-DOB Antibodies

An example of an antibody that binds the cancer target molecule HLA-DOB is the antibody Lym-1 (CAS RN: 301344-99-0) which can be used for treatment of cancer, for example non-Hodgkin's lymphoma. Examples of anti-HLA-DOB conjugates are disclosed, for example, in WO 2005/081711-A2. These antibodies and antigen-binding fragments thereof can be used in the context of this invention.

Anti-VTCN1 Antibodies

Examples of antibodies which bind the cancer target molecule VTCN1 and can be used for preparation of a conjugate and for treatment of cancer, for example ovarial carcinoma, pancreas, lung or breast cancer, are disclosed in WO 2006/074418-A2. These antibodies and antigen-binding fragments thereof can be used in the context of this invention.

Anti-FGFR2 Antibodies

Examples of anti-FGFR2 antibodies and antigen-binding fragments are described in WO2013076186. The sequences of the antibodies are shown in Table 9 and Table 10 of WO2013076186. Preference is given to antibodies, antigen-binding fragments and variants of the antibodies which derive from the antibodies referred to as M048-D01 and M047-D08.

Preferred Antibodies and Antigen-Binding Antibody Fragments for Binder-Drug Conjugates According to the Invention In this application, in the context of the binder-drug conjugate, reference is made to the following preferred antibodies as shown in the following table: TPP-2090, TPP-2658, TPP-5442, TPP-8825, TPP-7006, TPP-7007, TPP-10334, TPP-10335, TPP-10336, TPP-10337, TPP-1015, TPP-7510, TPP-7511, TPP-8382 and TPP-8567.

SEQ ID NO: 12, the variable CDR2 sequence of the heavy chain (H-CDR2), as shown by SEQ ID NO: 13 and the variable CDR3 sequence of the heavy chain (H-CDR3), as shown by SEQ ID NO: 14, and a variable region of the light chain (VL) comprising the variable CDR1 sequence of the light chain (L-CDR1), as shown by SEQ ID NO: 16, the variable CDR2 sequence of the light chain (L-CDR2), as shown by SEQ ID NO: 17 and the variable CDR3 sequence of the light chain (L-CDR3), as shown by SEQ ID NO: 18.

TPP-2090 is an anti-TWEAKR antibody comprising a variable region of the heavy chain (VH) comprising the variable CDR1 sequence of the heavy chain (H-CDR1), as

TABLE

Protein sequences of the antibodies:

| Antibody TPP-XXX | Antigen | SEQ ID NO: VH | SEQ ID NO: H-CDR1 | SEQ ID NO: H-CDR2 | SEQ ID NO: H-CDR3 | SEQ ID NO: VL | SEQ ID NO: L-CDR1 | SEQ ID NO: L-CDR2 | SEQ ID NO: L-CDR3 | SEQ ID NO: IgG heavy chain | SEQ ID NO: IgG light chain |
|---|---|---|---|---|---|---|---|---|---|---|---|
| TPP-981 | EGFR | 1 | 2 | 3 | 4 | 5 | 6 | 7 | 8 | 9 | 10 |
| TPP-1015 | HER2 | 11 | 12 | 13 | 14 | 15 | 16 | 17 | 18 | 19 | 20 |
| TPP-2090 | TWEAKR | 21 | 22 | 23 | 24 | 25 | 26 | 27 | 28 | 29 | 30 |
| TPP-2658 | TWEAKR | 31 | 32 | 33 | 34 | 35 | 36 | 37 | 38 | 39 | 40 |
| TPP-5442 | TWEAKR | 41 | 42 | 43 | 44 | 45 | 46 | 47 | 48 | 49 | 50 |
| TPP-7006 | TWEAKR | 51 | 52 | 53 | 54 | 55 | 56 | 57 | 58 | 59 | 60 |
| TPP-7007 | TWEAKR | 61 | 62 | 63 | 64 | 65 | 66 | 67 | 68 | 69 | 70 |
| TPP-7510 | HER2 | 71 | 72 | 73 | 74 | 75 | 76 | 77 | 78 | 79 | 80 |
| TPP-7511 | HER2 | 81 | 82 | 83 | 84 | 85 | 86 | 87 | 88 | 89 | 90 |
| TPP-8382 | B7H3 | 91 | 92 | 93 | 94 | 95 | 96 | 97 | 98 | 99 | 100 |
| TPP-8567 | B7H3 | 101 | 102 | 103 | 104 | 105 | 106 | 107 | 108 | 109 | 110 |
| TPP-8825 | TWEAKR | 111 | 112 | 113 | 114 | 115 | 116 | 117 | 118 | 119 | 120 |
| TPP-10334 | TWEAKR | 121 | 122 | 123 | 124 | 125 | 126 | 127 | 128 | 129 | 130 |
| TPP-10335 | TWEAKR | 131 | 132 | 133 | 134 | 135 | 136 | 137 | 138 | 139 | 140 |
| TPP-10336 | TWEAKR | 141 | 142 | 143 | 144 | 145 | 146 | 147 | 148 | 149 | 150 |
| TPP-10337 | TWEAKR | 151 | 152 | 153 | 154 | 155 | 156 | 157 | 158 | 159 | 160 |

TPP-2090, TPP-2658, TPP-5442, TPP-8825, TPP-7006, TPP-7007, TPP-10334, TPP-10335, TPP-10336, TPP-10337, TPP-1015, TPP-7510, TPP-7511, TPP-8382 and TPP-8567 are antibodies comprising one or more of the CDR sequences specified in the above table (H-CDR1, H-CDR2, H-CDR3, L-CDR1, L-CDR2, L-CDR3) in the variable region of the heavy chain (VH) or the variable region of the light chain (VL). Preferably, the antibodies comprise the specified variable region of the heavy chain (VH) and/or the variable region of the light chain (VL). Preferably, the antibodies comprise the specified region of the heavy chain (IgG heavy chain) and/or the specified region of the light chain (IgG light chain).

TPP-981 is an anti-EGFR antibody comprising a variable region of the heavy chain (VH) comprising the variable CDR1 sequence of the heavy chain (H-CDR1), as shown by SEQ ID NO: 2, the variable CDR2 sequence of the heavy chain (H-CDR2), as shown by SEQ ID NO: 3 and the variable CDR3 sequence of the heavy chain (H-CDR3), as shown by SEQ ID NO: 4, and a variable region of the light chain (VL) comprising the variable CDR1 sequence of the light chain (L-CDR1), as shown by SEQ ID NO: 6, the variable CDR2 sequence of the light chain (L-CDR2), as shown by SEQ ID NO: 7 and the variable CDR3 sequence of the light chain (L-CDR3), as shown by SEQ ID NO: 8.

TPP-1015 is an anti-HER2 antibody comprising a variable region of the heavy chain (VH) comprising the variable CDR1 sequence of the heavy chain (H-CDR1), as shown by shown by SEQ ID NO: 22, the variable CDR2 sequence of the heavy chain (H-CDR2), as shown by SEQ ID NO: 23 and the variable CDR3 sequence of the heavy chain (H-CDR3), as shown by SEQ ID NO: 24, and a variable region of the light chain (VL) comprising the variable CDR1 sequence of the light chain (L-CDR1), as shown by SEQ ID NO: 26, the variable CDR2 sequence of the light chain (L-CDR2), as shown by SEQ ID NO: 27 and the variable CDR3 sequence of the light chain (L-CDR3), as shown by SEQ ID NO: 28.

TPP-2658 is an anti-TWEAKR antibody comprising a variable region of the heavy chain (VH) comprising the variable CDR1 sequence of the heavy chain (H-CDR1), as shown by SEQ ID NO: 32, the variable CDR2 sequence of the heavy chain (H-CDR2), as shown by SEQ ID NO: 33 and the variable CDR3 sequence of the heavy chain (H-CDR3), as shown by SEQ ID NO: 34, and a variable region of the light chain (VL) comprising the variable CDR1 sequence of the light chain (L-CDR1), as shown by SEQ ID NO: 36, the variable CDR2 sequence of the light chain (L-CDR2), as shown by SEQ ID NO: 37 and the variable CDR3 sequence of the light chain (L-CDR3), as shown by SEQ ID NO: 38.

TPP-5442 is an anti-TWEAKR antibody comprising a variable region of the heavy chain (VH) comprising the variable CDR1 sequence of the heavy chain (H-CDR1), as shown by SEQ ID NO: 42, the variable CDR2 sequence of the heavy chain (H-CDR2), as shown by SEQ ID NO: 43 and the variable CDR3 sequence of the heavy chain (H-CDR3), as shown by SEQ ID NO: 44, and a variable region of the light chain (VL) comprising the variable CDR1 sequence of the light chain (L-CDR1), as shown by SEQ ID NO: 46, the variable CDR2 sequence of the light chain (L-CDR2), as shown by SEQ ID NO: 47 and the variable CDR3 sequence of the light chain (L-CDR3), as shown by SEQ ID NO: 48.

TPP-7006 is an anti-TWEAKR antibody comprising a variable region of the heavy chain (VH) comprising the variable CDR1 sequence of the heavy chain (H-CDR1), as shown by SEQ ID NO: 52, the variable CDR2 sequence of the heavy chain (H-CDR2), as shown by SEQ ID NO: 53 and the variable CDR3 sequence of the heavy chain (H-CDR3), as shown by SEQ ID NO: 54, and a variable region of the light chain (VL) comprising the variable CDR1 sequence of the light chain (L-CDR1), as shown by SEQ ID NO: 56, the variable CDR2 sequence of the light chain (L-CDR2), as shown by SEQ ID NO: 57 and the variable CDR3 sequence of the light chain (L-CDR3), as shown by SEQ ID NO: 58.

TPP-7007 is an anti-TWEAKR antibody comprising a variable region of the heavy chain (VH) comprising the variable CDR1 sequence of the heavy chain (H-CDR1), as shown by SEQ ID NO: 62, the variable CDR2 sequence of the heavy chain (H-CDR2), as shown by SEQ ID NO: 63 and the variable CDR3 sequence of the heavy chain (H-CDR3), as shown by SEQ ID NO: 64, and a variable region of the light chain (VL) comprising the variable CDR1 sequence of the light chain (L-CDR1), as shown by SEQ ID NO: 66, the variable CDR2 sequence of the light chain (L-CDR2), as shown by SEQ ID NO: 67 and the variable CDR3 sequence of the light chain (L-CDR3), as shown by SEQ ID NO: 68.

TPP-7510 is an anti-HER2 antibody comprising a variable region of the heavy chain (VH) comprising the variable CDR1 sequence of the heavy chain (H-CDR1), as shown by SEQ ID NO: 72, the variable CDR2 sequence of the heavy chain (H-CDR2), as shown by SEQ ID NO: 73 and the variable CDR3 sequence of the heavy chain (H-CDR3), as shown by SEQ ID NO: 74, and a variable region of the light chain (VL) comprising the variable CDR1 sequence of the light chain (L-CDR1), as shown by SEQ ID NO: 76, the variable CDR2 sequence of the light chain (L-CDR2), as shown by SEQ ID NO: 77 and the variable CDR3 sequence of the light chain (L-CDR3), as shown by SEQ ID NO: 78.

TPP-7511 is an anti-HER2 antibody comprising a variable region of the heavy chain (VH) comprising the variable CDR1 sequence of the heavy chain (H-CDR1), as shown by SEQ ID NO: 82, the variable CDR2 sequence of the heavy chain (H-CDR2), as shown by SEQ ID NO: 83 and the variable CDR3 sequence of the heavy chain (H-CDR3), as shown by SEQ ID NO: 84, and a variable region of the light chain (VL) comprising the variable CDR1 sequence of the light chain (L-CDR1), as shown by SEQ ID NO: 86, the variable CDR2 sequence of the light chain (L-CDR2), as shown by SEQ ID NO: 87 and the variable CDR3 sequence of the light chain (L-CDR3), as shown by SEQ ID NO: 88.

TPP-8382 is an anti-B7H3 antibody comprising a variable region of the heavy chain (VH) comprising the variable CDR1 sequence of the heavy chain (H-CDR1), as shown by SEQ ID NO: 92, the variable CDR2 sequence of the heavy chain (H-CDR2), as shown by SEQ ID NO: 93 and the variable CDR3 sequence of the heavy chain (H-CDR3), as shown by SEQ ID NO: 94, and a variable region of the light chain (VL) comprising the variable CDR1 sequence of the light chain (L-CDR1), as shown by SEQ ID NO: 96, the variable CDR2 sequence of the light chain (L-CDR2), as shown by SEQ ID NO: 97 and the variable CDR3 sequence of the light chain (L-CDR3), as shown by SEQ ID NO: 98.

TPP-8567 is an anti-B7H3 antibody comprising a variable region of the heavy chain (VH) comprising the variable CDR1 sequence of the heavy chain (H-CDR1), as shown by SEQ ID NO: 102, the variable CDR2 sequence of the heavy chain (H-CDR2), as shown by SEQ ID NO: 103 and the variable CDR3 sequence of the heavy chain (H-CDR3), as shown by SEQ ID NO: 104, and a variable region of the light chain (VL) comprising the variable CDR1 sequence of the light chain (L-CDR1), as shown by SEQ ID NO: 106, the variable CDR2 sequence of the light chain (L-CDR2), as shown by SEQ ID NO: 107 and the variable CDR3 sequence of the light chain (L-CDR3), as shown by SEQ ID NO: 108.

TPP-8825 is an anti-TWEAKR antibody comprising a variable region of the heavy chain (VH) comprising the variable CDR1 sequence of the heavy chain (H-CDR1), as shown by SEQ ID NO: 112, the variable CDR2 sequence of the heavy chain (H-CDR2), as shown by SEQ ID NO: 113 and the variable CDR3 sequence of the heavy chain (H-CDR3), as shown by SEQ ID NO: 114, and a variable region of the light chain (VL) comprising the variable CDR1 sequence of the light chain (L-CDR1), as shown by SEQ ID NO: 116, the variable CDR2 sequence of the light chain (L-CDR2), as shown by SEQ ID NO: 117 and the variable CDR3 sequence of the light chain (L-CDR3), as shown by SEQ ID NO: 118.

TPP-10334 is an anti-TWEAKR antibody comprising a variable region of the heavy chain (VH) comprising the variable CDR1 sequence of the heavy chain (H-CDR1), as shown by SEQ ID NO: 122, the variable CDR2 sequence of the heavy chain (H-CDR2), as shown by SEQ ID NO: 123 and the variable CDR3 sequence of the heavy chain (H-CDR3), as shown by SEQ ID NO: 124, and a variable region of the light chain (VL) comprising the variable CDR1 sequence of the light chain (L-CDR1), as shown by SEQ ID NO: 126, the variable CDR2 sequence of the light chain (L-CDR2), as shown by SEQ ID NO: 127 and the variable CDR3 sequence of the light chain (L-CDR3), as shown by SEQ ID NO: 128.

TPP-10335 is an anti-TWEAKR antibody comprising a variable region of the heavy chain (VH) comprising the variable CDR1 sequence of the heavy chain (H-CDR1), as shown by SEQ ID NO: 132, the variable CDR2 sequence of the heavy chain (H-CDR2), as shown by SEQ ID NO: 133 and the variable CDR3 sequence of the heavy chain (H-CDR3), as shown by SEQ ID NO: 134, and a variable region of the light chain (VL) comprising the variable CDR1 sequence of the light chain (L-CDR1), as shown by SEQ ID NO: 136, the variable CDR2 sequence of the light chain (L-CDR2), as shown by SEQ ID NO: 137 and the variable CDR3 sequence of the light chain (L-CDR3), as shown by SEQ ID NO: 138.

TPP-10336 is an anti-TWEAKR antibody comprising a variable region of the heavy chain (VH) comprising the variable CDR1 sequence of the heavy chain (H-CDR1), as shown by SEQ ID NO: 142, the variable CDR2 sequence of the heavy chain (H-CDR2), as shown by SEQ ID NO: 143 and the variable CDR3 sequence of the heavy chain (H-CDR3), as shown by SEQ ID NO: 144, and a variable region of the light chain (VL) comprising the variable CDR1 sequence of the light chain (L-CDR1), as shown by SEQ ID NO: 146, the variable CDR2 sequence of the light chain (L-CDR2), as shown by SEQ ID NO: 147 and the variable CDR3 sequence of the light chain (L-CDR3), as shown by SEQ ID NO: 148.

TPP-10337 is an anti-TWEAKR antibody comprising a variable region of the heavy chain (VH) comprising the variable CDR1 sequence of the heavy chain (H-CDR1), as shown by SEQ ID NO: 152, the variable CDR2 sequence of the heavy chain (H-CDR2), as shown by SEQ ID NO: 153 and the variable CDR3 sequence of the heavy chain (H-CDR3), as shown by SEQ ID NO: 154, and a variable region of the light chain (VL) comprising the variable CDR1 sequence of the light chain (L-CDR1), as shown by SEQ ID NO: 156, the variable CDR2 sequence of the light chain (L-CDR2), as shown by SEQ ID NO: 157 and the variable CDR3 sequence of the light chain (L-CDR3), as shown by SEQ ID NO: 158.

TPP-981 is an anti-EGFR antibody comprising preferably a variable region of the heavy chain (VH) as shown by SEQ ID NO: 1 and a variable region of the light chain (VL) as shown by SEQ ID NO: 5.

TPP-1015 is an anti-HER2 antibody comprising preferably a variable region of the heavy chain (VH) as shown by SEQ ID NO: 11 and a variable region of the light chain (VL) as shown by SEQ ID NO: 15.

TPP-2090 is an anti-TWEAKR antibody comprising preferably a variable region of the heavy chain (VH) as shown by SEQ ID NO: 21 and a variable region of the light chain (VL) as shown by SEQ ID NO: 25.

TPP-2658 is an anti-TWEAKR antibody comprising preferably a variable region of the heavy chain (VH) as shown by SEQ ID NO: 31 and a variable region of the light chain (VL) as shown by SEQ ID NO: 35.

TPP-5442 is an anti-TWEAKR antibody comprising preferably a variable region of the heavy chain (VH) as shown by SEQ ID NO: 41 and a variable region of the light chain (VL) as shown by SEQ ID NO: 45.

TPP-7006 is an anti-TWEAKR antibody comprising preferably a variable region of the heavy chain (VH) as shown by SEQ ID NO: 51 and a variable region of the light chain (VL) as shown by SEQ ID NO: 55.

TPP-7007 is an anti-TWEAKR antibody comprising preferably a variable region of the heavy chain (VH) as shown by SEQ ID NO: 61 and a variable region of the light chain (VL) as shown by SEQ ID NO: 65.

TPP-7510 is an anti-HER2 antibody comprising preferably a variable region of the heavy chain (VH) as shown by SEQ ID NO: 71 and a variable region of the light chain (VL) as shown by SEQ ID NO: 75.

TPP-7511 is an anti-HER2 antibody comprising preferably a variable region of the heavy chain (VH) as shown by SEQ ID NO: 81 and a variable region of the light chain (VL) as shown by SEQ ID NO: 85.

TPP-8382 is an anti-B7H3 antibody comprising preferably a variable region of the heavy chain (VH) as shown by SEQ ID NO: 91 and a variable region of the light chain (VL) as shown by SEQ ID NO: 95.

TPP-8567 is an anti-B7H3 antibody comprising preferably a variable region of the heavy chain (VH) as shown by SEQ ID NO: 101 and a variable region of the light chain (VL) as shown by SEQ ID NO: 105.

TPP-8825 is an anti-TWEAKR antibody comprising preferably a variable region of the heavy chain (VH) as shown by SEQ ID NO: 111 and a variable region of the light chain (VL) as shown by SEQ ID NO: 115.

TPP-10334 is an anti-TWEAKR antibody comprising preferably a variable region of the heavy chain (VH) as shown by SEQ ID NO: 121 and a variable region of the light chain (VL) as shown by SEQ ID NO: 125.

TPP-10335 is an anti-TWEAKR antibody comprising preferably a variable region of the heavy chain (VH) as shown by SEQ ID NO: 131 and a variable region of the light chain (VL) as shown by SEQ ID NO: 135.

TPP-10336 is an anti-TWEAKR antibody comprising preferably a variable region of the heavy chain (VH) as shown by SEQ ID NO: 141 and a variable region of the light chain (VL) as shown by SEQ ID NO: 145.

TPP-10337 is an anti-TWEAKR antibody comprising preferably a variable region of the heavy chain (VH) as shown by SEQ ID NO: 151 and a variable region of the light chain (VL) as shown by SEQ ID NO: 155.

TPP-981 is an anti-EGFR antibody comprising preferably a region of the heavy chain as shown by SEQ ID NO: 9 and a region of the light chain as shown by SEQ ID NO: 10.

TPP-1015 is an anti-HER2 antibody comprising preferably a region of the heavy chain as shown by SEQ ID NO: 19 and a region of the light chain as shown by SEQ ID NO: 20.

TPP-2090 is an anti-TWEAKR antibody comprising preferably a region of the heavy chain as shown by SEQ ID NO: 29 and a region of the light chain as shown by SEQ ID NO: 30.

TPP-2658 is an anti-TWEAKR antibody comprising preferably a region of the heavy chain as shown by SEQ ID NO: 39 and a region of the light chain as shown by SEQ ID NO: 40.

TPP-5442 is an anti-TWEAKR antibody comprising preferably a region of the heavy chain as shown by SEQ ID NO: 49 and a region of the light chain as shown by SEQ ID NO: 50.

TPP-7006 is an anti-TWEAKR antibody comprising preferably a region of the heavy chain as shown by SEQ ID NO: 59 and a region of the light chain as shown by SEQ ID NO: 60.

TPP-7007 is an anti-TWEAKR antibody comprising preferably a region of the heavy chain as shown by SEQ ID NO: 69 and a region of the light chain as shown by SEQ ID NO: 70.

TPP-7510 is an anti-HER2 antibody comprising preferably a region of the heavy chain as shown by SEQ ID NO: 79 and a region of the light chain as shown by SEQ ID NO: 80.

TPP-7511 is an anti-HER2 antibody comprising preferably a region of the heavy chain as shown by SEQ ID NO: 89 and a region of the light chain as shown by SEQ ID NO: 90.

TPP-8382 is an anti-B7H3 antibody comprising preferably a region of the heavy chain as shown by SEQ ID NO: 99 and a region of the light chain as shown by SEQ ID NO: 100.

TPP-8567 is an anti-B7H3 antibody comprising preferably a region of the heavy chain as shown by SEQ ID NO: 109 and a region of the light chain as shown by SEQ ID NO: 110.

TPP-8825 is an anti-TWEAKR antibody comprising preferably a region of the heavy chain as shown by SEQ ID NO: 119 and a region of the light chain as shown by SEQ ID NO: 120.

TPP-10334 is an anti-TWEAKR antibody comprising preferably a region of the heavy chain as shown by SEQ ID NO: 129 and a region of the light chain as shown by SEQ ID NO: 130.

TPP-10335 is an anti-TWEAKR antibody comprising preferably a region of the heavy chain as shown by SEQ ID NO: 139 and a region of the light chain as shown by SEQ ID NO: 140.

TPP-10336 is an anti-TWEAKR antibody comprising preferably a region of the heavy chain as shown by SEQ ID NO: 149 and a region of the light chain as shown by SEQ ID NO: 150.

TPP-10337 is an anti-TWEAKR antibody comprising preferably a region of the heavy chain as shown by SEQ ID NO: 159 and a region of the light chain as shown by SEQ ID NO: 160.

Linkers for the LIG Binder ($L_b$ and $L_c$)

The literature discloses various options for covalent coupling (conjugation) of organic molecules to peptides or proteins such as antibodies (see, for example, K. Lang and J. W. Chin. *Chem. Rev.* 2014, 114, 4764-4806, M. Rashidian et al. *Bioconjugate Chem.* 2013, 24, 1277-1294). Preference is given in accordance with the invention to conjugation of the organic radical to an antibody via one or more sulphur atoms of cysteine residues of the antibody which are either already present as free thiols or are generated by reduction of disulphide bridges, and/or via one or more NH groups of lysine residues of the antibody. However, it is also possible to bind the KSP inhibitor or prodrug to the antibody via tyrosine residues, via glutamine residues, via residues of unnatural amino acids, via free carboxyl groups or via sugar residues of the antibody.

It is also possible in accordance with the invention to conjugate the drug molecules to specific conjugation sites of the binder, which improves product homogeneity. The literature describes various methods of conjugation site-specific conjugation (Agarwal et al., *Bioconjug. Chem.* 26, 176-192 (2015); Cal et al., *Angew. Chem. Int. Ed. Engl.* 53, 10585-10587 (2014); Behrens et al., *MAbs* 6, 46-53 (2014); Panowski et al., *MAbs* 6, 34-(2014)). These methods also include, in particular, enzymatic conjugation methods which use, for example, transglutaminases (TGases), glycosyltransferases or the formylglycine-generating enzyme ((Sochaj et al., *Biotechnology Advances* 33, 775-784, (2015)).

According to the invention, it is possible to provide conjugation site-specific binder conjugates of the kinesin spindle protein inhibitor, in which the kinesin spindle protein inhibitors are conjugated to glutamine side chains of the binders.

When the binder is an antibody, it contains an acceptor glutamine, preferably in the constant region. Such acceptor glutamines can be introduced via mutation of suitable positions to glutamine (for example the mutation N297Q of the heavy chain, Kabat EU numbering) or via generation of deglycosylated or aglycosylated antibodies (for example via enzymatic deglycosylation by means of PNGaseF or via mutation N297X of the heavy chain, Kabat EU numbering (X here may be any amino acid except N)). In the latter case of a deglycosylated or aglycosylated antibody, the glutamine residue Q295 (Kabat EU numbering) of the heavy chain becomes an acceptor glutamine. Particular preference is given to an antibody containing the N297A or N297Q mutation (Kabat EU numbering). Therefore, all the antibodies described in this invention likewise include aglycosylated variants of these antibodies, which are produced either via deglycosylation by means of PNGaseF or by mutation of N297 (Kabat EU numbering) (Kabat numbering system of antibodies, see Kabat et al., Sequences of Proteins of Immunological Interest, 5th Ed. Public Health Service, National Institutes of Health, Bethesda, MD. (1991)) of the heavy chain to any other amino acid except N. In addition, all the antibodies described here likewise contain variants of the antibodies described which, by virtue of engineering, contain one or more acceptor glutamine residues for transglutaminase-catalysed reactions.

One method for such conjugation site specific-conjugations is approaches described in the literature which are concerned with conjugation site-specific conjugation of binders by means of transglutaminase. Transglutaminases (TGases) which also include bacterial transglutaminase (BTG) (EC 2.3.2.13) are a family of enzymes which catalyse the formation of a covalent bond between the γ-carbonyl-amide group of glutamines and the primary amine group of lysines. Since such transglutaminases also accept substrates other than lysine as amine donor, they have been used in order to modify proteins including antibodies at suitable acceptor glutamines (Jeger et al., *Angewandte Chemie Int. Ed. Eng* 49, 9995-9997 (2010); Josten et al., *J. Immunol. Methods* 240, 47-54 (2000); Mindt et al., *Bioconjugate Chem.* 19, 271-278 (2008); Dennler et al., in Antibody Drug Conjuagtes (Ducry, L., Ed.), pp 205-215, Humana Press. (2013)). On the one hand, transglutaminases have been used for the conjugation of drugs to antibodies containing artificial glutamine tags which are acceptor glutamine residues which have been introduced into the antibody by genetic engineering (Strop et al., *Chem. Biol.* 20, 161-167 (2013)). On the other hand, it has been stated that the conserved glutamine residue Q295 (Kabat EU numbering) of the constant region of the heavy chain of antibodies is the only γ-carbonyl-amide donor for the bacterial transglutaminase (EC 2.3.2.13) in the backbone of aglycosylated IgG1 molecules, and is thus an acceptor glutamine, whereas no acceptor glutamine is present in the backbone of IgG1 when the antibody has been glycosylated at position N297 (Kabat EU numbering) of the heavy chain (Jeger et al., *Angewandte Chemie Int. Ed. Eng* 49, 9995-9997 (2010)). In summary, bacterial transglutaminase can be used for the conjugation of an amine-donor substrate, for example a drug-linker construct, at an acceptor glutamine residue of an antibody. Such acceptor glutamines can be introduced by engineering of the antibody by mutations or by the generation of aglycosylated antibodies. Such aglycosylated antibodies can be introduced by deglycosylation using N-glycosidase F (PNGase F) or by mutation of N297 of the glycosylation site of the heavy chain (Kabat EU numbering) to any other amino acid except N. The enzymatic conjugation of such aglycosylated antibodies using bacterial transglutaminase has been described for aglycosylated antibody variants containing the mutations N297D, N297Q (Jeger et al., *Angewandte Chemie Int. Ed. Eng* 49, 9995-9997 (2010)) or N297S (see patent applications WO2013092998A1 and WO2013092983A2). The enzymatic conjugation of such aglycosylated antibodies by means of transglutaminase generally affords ADCs having a DAR of 2, in which both heavy chains are specifically functionalized at position Q295 (Kabat EU numbering). Only mutation N297Q of the heavy chain affords an additional conjugation site per heavy chain. The conjugation of such variants leads to ADCs having a DAR of 4, in which both heavy chains are specifically functionalized at positions Q295 and Q297. Antibody variants in which the heavy chains bear the mutations Q295N and N297Q have only one acceptor glutamine residue at position Q297 (Kabat numbering) per heavy chain (Simone Jeger, Site specific conjugation of tumour targeting antibodies using transglutaminase, Thesis at ETH Zurich (2009)). There exist several examples in the literature which describe the conjugation site-specific conjugation of aglycosylated antibodies using bacterial transglutaminase (for example Dennler et al., *Bioconjugate Chemistry* 19, 569-578 (2014); Lhospice et al., Molecular Pharmaceutics 12, 1863-1871 (2015)). The strategy of transglutaminase-catalysed conjugation site-specific functionalization of aglycosylated antibodies is summarized in FIG. 1.

Coupling—both in a conjugation site-specific and in a conjugation site-nonspecific manner—is accomplished using what are called linkers. Linkers can be categorized into the group of the linkers which can be cleaved in vivo and the group of the linkers which are stable in vivo (see L. Ducry and B. Stump, Bioconjugate Chem. 21, 5-13 (2010)). The linkers which can be cleaved in vivo have a group which can be cleaved in vivo, where, in turn, a distinction may be made between groups which are chemically cleavable in vivo and groups which are enzymatically cleavable in vivo. "Chemically cleavable in vivo" and "enzymatically cleavable in vivo" means that the linkers or groups are stable in circulation and are cleaved only at or in the target cell by the chemically or enzymatically different environment therein (lower pH; elevated glutathione concentration; presence of lysosomal enzymes such as cathepsin or plasmin, or glyosidases such as, for example, β-glucuronidases), thus releasing the low-molecular weight KSP inhibitor or a derivative thereof. Groups which can be cleaved chemically in vivo are in particular disulphide, hydrazone, acetal and aminal; groups which can be cleaved enzymatically in vivo are in particular the 2-8-oligopeptide group, especially a dipeptide group or glycoside. Peptide cleaving sites are disclosed in Bioconjugate Chem. 2002, 13, 855-869 and Bioorganic & Medicinal Chemistry Letters 8 (1998) 3341-3346 and also Bioconjugate Chem. 1998, 9, 618-626. These include, for example, alanine-alanine-asparagine, valine-alanine, valine-lysine, valine-citrulline, alanine-lysine and phenylalanine-lysine (optionally with additional amide group).

In order to assure efficient release of the free drug, it is optionally also possible to incorporate what are called self-immolative linker elements (SIG) between the enzymatic cleavage site and drug (Anticancer Agents in Medicinal Chemistry, 2008, 8, 618-637). The drug can be released by various mechanisms, for example after initial enzymatic release of a nucleophilic group by subsequent elimination via an electronic cascade (Bioorg. Med. Chem., 1999, 7, 1597; J. Med. Chem., 2002, 45, 937; Bioorg. Med. Chem., 2002, 10, 71) or by cyclization of the corresponding linker element (Bioorg. Med. Chem., 2003, 11, 2277; Bioorg. Med. Chem., 2007, 15, 4973; Bioorg. Med. Chem. Lett., 2007, 17, 2241) or by a combination of the two (Angew. Chem. Inter. Ed., 2005, 44, 4378). Examples of such linker elements are shown in the figure:

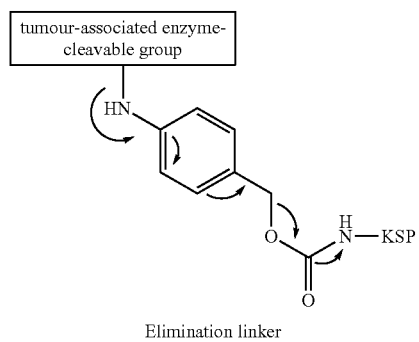

Elimination linker

Cyclisation linker

Elongated linker

Examples of successive enzymatic steps for drug release, for example by means of histone deacetylase and cathepsin L, are described in Nat. Commun., 2013, 4, 2735 and are illustrated in FIGS. 2A-2Q.

Linkers which are stable in vivo are distinguished by a high stability (less than 5% metabolites after 24 hours in plasma) and do not have the chemically or enzymatically in vivo cleavable groups mentioned above.

The linker -$L_b$- or -$L_c$- preferably has one of the following base structures (i) and (ii):

$$—(C=O)_m\text{-}(L1)_n\text{-}(L2)_n\text{-} \qquad (i)$$

$$—(C=O)_m\text{-L1-SG-L2-} \qquad (ii)$$

where m and n are 0 or 1

SG is a (chemically or enzymatically) in vivo cleavable group (in particular disulphide, hydrazone, acetal and aminal; or a 2-8-oligopeptide group which can be cleaved by legumain, cathepsin or plasmin), L1 represents in vivo stable organic groups, and L2 represents a coupling group to the binder or a single bond.

Here, coupling is preferably to a cysteine residue or a lysine residue of the antibody. Alternatively, coupling can be to a tyrosine residue, glutamine residue or to an unnatural amino acid of the antibody. The unnatural amino acids may contain, for example, aldehyde or keto groups (such as, for example, formylglycine) or azide or alkyne groups (see Lan & Chin, Cellular Incorporation of Unnatural Amino Acids and Bioorthogonal Labeling of Proteins, Chem. Rev. 2014, 114, 4764-4806).

Particular preference according to the invention is given to the basic linker structure (i). Via metabolization, the administration of a conjugate according to the invention of embodiment B having a basic linker structure (i) and coupling of the linker to a cysteine or lysine residue of the antibody leads to cysteine or lysine derivatives of the following formulae:

$$—L_1—L_2—NH—(CH_2)_4—\overset{\displaystyle COOH}{\underset{\displaystyle}{CH}}—NH_2;$$

-continued

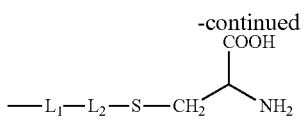

where L1 is in each case joined to the cytotoxic drug, for example the low molecular weight KSP inhibitor, for example a compound of the formula (IIa), (IIb), (IIc), (IId), (V), (VI) or (VII).

Administration of a conjugate according to the invention with a linker base structure (i) in embodiment A, after metabolism, leads to a KSP inhibitor that preferably has the structure of a compound of the general formula (IIa), (IIa'), (IIa''), (IIb), (IIc), (IId), (V), (VI) or (VII).

Preference is also given in accordance with the invention to the linker base structures (ii), especially in the case of binding to position R1 in a compound of the formula (IIa), (IIb), (IIc), (IId), or (V), especially when L1 has one of the following structures:

(a) —NH—$(CH_2)_{0-4}$—$(CHCH_3)_{0-4}$—$CHY^5$—$C(=O)$—$Y^7$ in which
$Y^5$ is —H or —$NHY^6$,
$Y^6$ is —H or —$C(=O)$—$CH_3$ and
$Y^7$ is a single bond or —NH—$(CH_2)_{0-4}$—$CHNH_2$—$C(=O)$—,
such that, after cleavage of embodiment B, the corresponding structure —NH—$(CH_2)_{0-4}$—$(CHCH_3)_{0-4}$—$CHY^5$—COOH or —NH—$(CH_2)_{0-4}$—$(CHCH_3)_{0-4}$—$CHY^5$—$C(=O)$—NH—$(CH_2)_{0-4}$—$CHNH_2$—COOH is obtained.

(b) —$CH_2$—$S_x$—$(CH_2)_{0-4}$—$CHY^5$—$C(=O)$— in which
x is 0 or 1,
$Y^5$ is —H or —$NHY^6$ and
$Y^6$ is —H or —$C(=O)$—$CH_3$,
such that, after cleavage of embodiment B, the corresponding structure —$CH_2$—$S_x$—$(CH_2)_{0-4}$—$CHY^5$—COOH
is obtained.

Administration of a conjugate according to the invention with a linker base structure (ii) in embodiment A, after metabolism, leads to a KSP inhibitor having the structure of the general formula (II).

When the linker is joined to a cysteine side chain or a cysteine residue, L2 preferably derives from a group which reacts with the sulphhydryl group of the cysteine. These include haloacetyls, maleimides, aziridines, acryloyls, arylating compounds, vinylsulphones, pyridyl disulphides, TNB thiols and disulphide-reducing agents. These groups generally react in an electrophilic manner with the sulphhydryl bond, forming a sulphide (e.g. thioether) or disulphide bridge. Preference is given to stable sulphide bridges.

L2 preferably has the following structures:

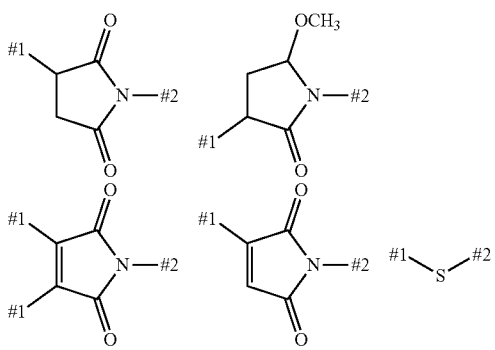

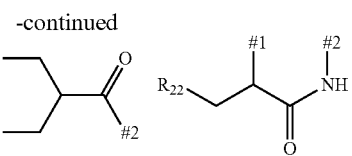

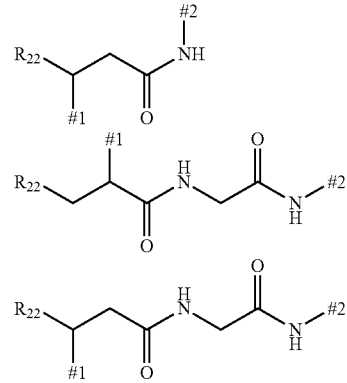

in which
$\#^1$ is the linkage site to the sulphur atom of the antibody,
$\#^2$ is the linkage site to the L1 group, and
$R_{22}$ is —COOH, —$C(=O)$—OR, —$C(=O)R$, —$C(=O)$—NHR or —$C(=O)N(R)_2$ and
R is $C_{1-3}$-alkyl.
It is preferable here when $R_{22}$ is —COOH.

Particular preference is given to the compounds of the present invention in which L2 has the following formulae A3 and A4:

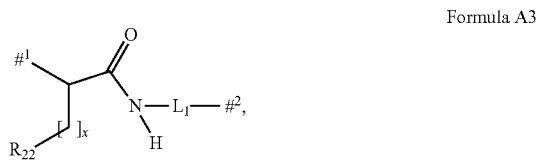

Formula A3

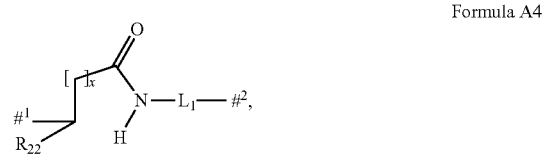

Formula A4 in which
$\#^1$ is the linkage site to the sulphur atom of the antibody,
$\#^2$ is the linkage site to the drug molecule,
x is 1 or 2 and
$R^{22}$ is —COOH, —$C(=O)$—OR, —$C(=O)$—R, —$C(=O)$—$NR_2$, —$C(=O)$—NHR or —$C(=O)$—$NH_2$ and
R is $C_{1-3}$-alkyl.
Preferably in this context, $R^{22}$ is —COOH and, in particular, in this context, $R^{22}$ is —COOH if x is 1.

In the compounds according to the invention, the linker $L_b$ or Lc may be bonded to a cysteine side chain or a cysteine residue in the binder and in that case has the following formulae:

—$(C=O)_m$-(L1)$_n$-(L2)$_n$-     (i)

and

—$(C=O)_m$-L1-SG-L2     (ii)

in which m and n are independently 0 or 1,

SG is a group cleavable chemically or enzymatically in vivo (especially disulphide, hydrazone, acetal and aminal; or a legumain-, cathepsin- or plasmin-cleavable 2-8-oligopeptide group), L2 is a single bond or is the group

[structures shown]

where

¹ indicates the bonding site to the sulphur atom in the binder,

² indicates the bonding site to the L1 group,

L1 is —(NR¹⁰)$_n$-(G1)$_o$-G2-,

R¹⁰ is —H or $C_1$-$C_3$-alkyl,

G1 is —NH—C(=O)—, —C(=O)—NH— or —(CH$_2$)$_{0-3}$—C(=O)—NH—, n is 0 or 1, is 0 or 1,

G2 is a bond or a straight-chain or branched hydrocarbyl chain which has 1 to 100 carbon atoms and may be interrupted once or more than once, identically or differently, by —O—, —S—, —S(=O)—, —S(=O)$_2$, —NH—, —C(=O)—, —CH(COOH)—, —CH(CH$_2$—C(=O)—NH$_2$), —NMe-, —NHNH—, —S(=O)$_2$—NHNH—, —NH C(=O)—, —C(=O)—NH—, —C(=O)—NHNH—, a 5- to 10-membered, aromatic or nonaromatic heterocycle having up to 4 heteroatoms selected from N, O and S, —S(=O)— or —S(=O)$_2$—, and where the side chains in the branched carbon chain, if present, may be substituted by —NH—C(=O)—NH$_2$, —COOH, —OH, —NH$_2$, —NH—CNNH$_2$, sulphonamide, sulphone, sulphoxide or sulphonic acid, or represents one of the following groups

[structures shown]

where

Rx is —H, $C_1$-$C_3$-alkyl or phenyl.

Preferably, the present invention relates to compounds in which the linker Lb or Lc is bonded to a cysteine side chain or a cysteine residue of the binder and has the following formula:

§ —(C=O)$_m$-L1-(L2)$_n$- § § in which m is 0 or 1, n is 0 or 1,

§ is the bond to the drug molecule or the legumain-cleavable group of the formula (Ia') and § § is the bond to the binder, L2 is the group

[structures shown]

or is a bond, where

¹ indicates the bonding site to the sulphur atom of the binder,

² indicates the bonding site to the L1 group,

L1 is —(NR¹⁰)$_n$-(G1)$_o$-G2-,

R¹⁰ is —H or $C_1$-$C_3$-alkyl,

G1 is —NH—C(=O)—, —C(=O)—NH— or —(CH$_2$)$_{0-3}$—C(=O)—NH—, n is 0 or 1, is 0 or 1,

G2 is a bond or a straight-chain or branched hydrocarbyl chain which has 1 to 100 carbon atoms and may be interrupted once or more than once, identically or differently, by —O—, —S—, —S(=O)—, —S(=O)$_2$, —NH—, —C(=O)—, —CH(COOH)—, —CH(CH$_2$—C(=O)—NH$_2$), —NMe-, —NHNH—, —S(=O)$_2$—NHNH—, —NH—C(=O)—, —C(=O)—NH—, —C(=O)—NHNH—, a 5- to 10-membered, aromatic or nonaromatic heterocycle having up to 4 heteroatoms selected from N, O and S, —S(=O)— or —S(=O)$_2$—, and where the side chains in the branched carbon chain, if present, may be substituted by —NH—C(=O)—NH$_2$, —COOH, —OH, —NH$_2$, —NH—CNNH$_2$, sulphonamide, sulphone, sulphoxide or sulphonic acid, or represents one of the following groups

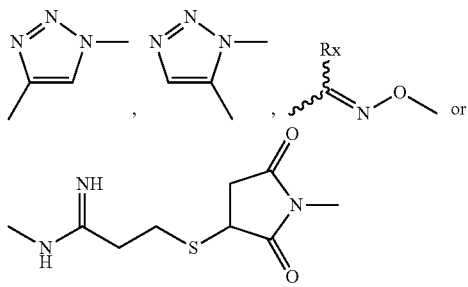

where
Rx is —H, C$_1$-C$_3$-alkyl or phenyl.

In the compounds according to the invention, the linker L$_b$ or Lc may also be bonded to a lysine side chain or a lysine residue of the binder and in that case has the general base structures (i) and (ii)

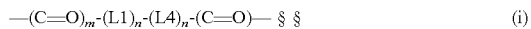   (i)

and

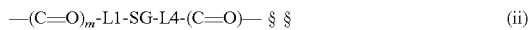   (ii)

in which
m and n are independently 0 or 1,
SG is a group cleavable chemically or enzymatically in vivo (especially disulphide, hydrazone, acetal and aminal; or a legumain-, cathepsin- or plasmin-cleavable 2-8-oligopeptide group),
L1 is —(NR$^{10}$)$_n$-(G1)$_o$-G2-,
R$^{10}$ is —H or C$_1$-C$_3$-alkyl,
G1 is —NH—C(=O)—, —C(=O)—NH— or —(CH$_2$)$_{0-3}$—C(=O)—NH—,
n is 0 or 1,
is 0 or 1,
G2 is a bond or a straight-chain or branched hydrocarbyl chain which has 1 to 100 carbon atoms and may be interrupted once or more than once, identically or differently, by —O—, —S—, —S(=O)—, —S(=O)$_2$, —NH—, —C(=O)—, —CH(COOH)—, —CH(CH$_2$—C(=O)—NH$_2$), —NMe-, —S(=O)$_2$—NHNH—, —NH—C(=O)—, —C(=O)—NH—, —C(=O)—NHNH—, a 5- to 10-membered, aromatic or nonaromatic heterocycle having up to 4 heteroatoms selected from N, O and S, —S(=O)— or —S(=O)$_2$—, and where the side chains in the branched carbon chain, if present, may be substituted by —NH—C(=O)—NH$_2$, —COOH, —OH, —NH— CNNH$_2$, sulphonamide, sulphone, sulphoxide or sulphonic acid, or represents one of the following groups

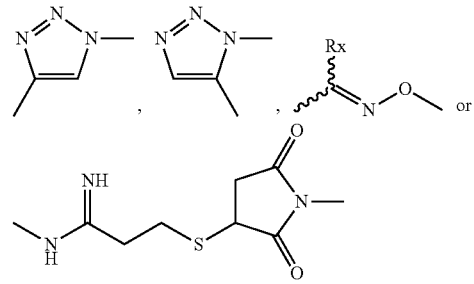

where
Rx is —H, C$_1$-C$_3$-alkyl or phenyl,
L4 is a single bond or a group

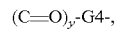

y is 0 or 1 and
G4 is a straight-chain or branched hydrocarbyl chain which has 1 to 100 carbon atoms and may be interrupted once or more than once, identically or differently, by —O—, —S—, —S(=O)—, —S(=O)$_2$, —NH—, —C(=O)—, —NH—C(=O)—, —C(=O)—NH—, —NMe-, —S(=O)$_2$—NHNH—, —C(=O)—NHNH—, —CH(COOH)— and a 5- to 10-membered, aromatic or nonaromatic heterocycle having up to 4 heteroatoms selected from N, O and S, S(=O)— or S(=O)$_2$, where the side chains in the branched carbon chain, if present, may be substituted by —NH—C(=O)—NH$_2$, —COOH, —OH, —NH— CN—NH$_2$, sulphonamide, sulphone, sulphoxide or sulphonic acid, § § is the bonding site to the nitrogen atom of a lysine residue in the binder.

Preferably, the present invention relates to compounds in which the linker L$_b$ or Lc may also be bonded to a lysine side chain or a lysine residue of the binder and in that case has the following formula

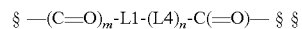

in which
m is 0 or 1,
n is 0 or 1,
§ is the bond to the drug molecule or the legumain-cleavable group of the formula (Ia') and
§ § represents the bond to a nitrogen atom in the binder,
L1 is —(NR$^{10}$)$_n$-(G1)$_o$-G2-,
R$^{10}$ is —H or C$_1$-C$_3$-alkyl,
G1 is —NH—C(=O)—, —C(=O)—NH— or —(CH$_2$)$_{0-3}$—C(=O)—NH—,
n is 0 or 1,
is 0 or 1,
G2 is a bond or a straight-chain or branched hydrocarbyl chain which has 1 to 100 carbon atoms and may be interrupted once or more than once, identically or differently, by —O—, —S—, —S(=O)—, —S(=O)$_2$, —NH—, —C(=O)—, —CH(COOH)—, —CH(CH$_2$—C(=O)—NH$_2$), —NMe-, —S(=O)$_2$— NHNH—, —NH—C(=O)—, —C(=O)—NH—, —C(=O)—NHNH—, a 5- to 10-membered, aromatic or nonaromatic heterocycle having up to 4 heteroatoms selected from N, O and S, —S(=O)— or —S(=O)$_2$—, and where the side chains in the branched carbon chain, if present, may be substituted by —NH—C(=O)—NH$_2$, —COOH, —OH, —NH—CNNH$_2$, sulphonamide, sulphone, sulphoxide or sulphonic acid, or represents one of the following groups

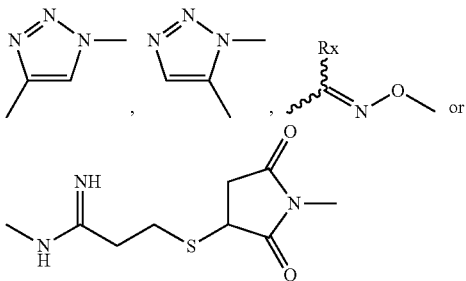

where
Rx is —H, C$_1$-C$_3$-alkyl or phenyl,
L4 is a single bond or a group (C=O)$_y$-G4-, y is 0 or 1 and
G4 is a straight-chain or branched hydrocarbyl chain which has 1 to 100 carbon atoms and may be interrupted once or more than once, identically or differently, by —O—, —S—, —S(=O)—, —S(=O)$_2$, —NH—, —C(=O)—, —NH—C(=O)—, —C(=O)—NH—, —NMe-, —S(=O)$_2$—NHNH—, —C(=O)—NHNH—, —CH(COOH)—, and a 5- to 10-membered, aromatic or nonaromatic heterocycle having up to 4 heteroatoms selected from N, O and S, S(=O)— or S(=O)$_2$, and where the side chains in the branched carbon chain, if present, may be substituted by —NH—C(=O)—NH$_2$, —COOH, —OH, —NH—CN—NH$_2$, sulphonamide, sulphone, sulphoxide or sulphonic acid.

More preferably, the linker L2 has one or both of the following formulae

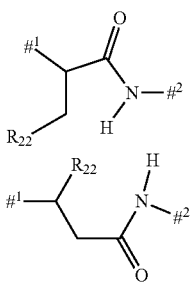

where
$^1$ is the bonding site to the sulphur atom in the binder,
$^2$ is the bonding site to the L1 group,
R$^{22}$ is —COOH and
the bonds to the sulphur atom in the binder are in one of these two formulae to an extent of more than 80% (based on the total number of bonds of the linker to the binder).

In a conjugate according to the invention or in a mixture of the conjugates according to the invention, the bonds to a cysteine residue of the antibody are present to an extent of preferably more than 80%, more preferably more than 90% (based in each case on the total number of bonds of the linker to the antibody), more preferably as one of the two structures of the formula A3 or A4. Here, the structures of the formula A3 or A4 are generally present together, preferably in a ratio of from 60:40 to 40:60, based on the number of bonds to the antibody. The remaining bonds are then present as the structure

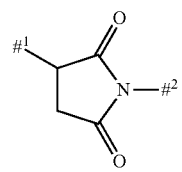

in which
$^1$ is the linkage site to the sulphur atom of the antibody and
$^2$ is the linkage site to L1 to the drug molecule,
L4 preferably has the following structures:

$^1$—C(=O)—(CH$_2$)$_{2\text{-}20}$—C(=O)—#$^2$ where the chain may be interrupted by 1-4 oxygen atoms and
$^1$ is the bonding site to the nitrogen atom in a lysine in the antibody and
$^2$ is the bonding site to L1 with the drug molecule.

According to the invention, L1 is preferably represented by the formula

$^1$—(NR$^{10}$)$_n$-(G1)$_o$-G2$_{w'}$-#$^2$ in which
$^1$ is the linkage site to the sulphur atom of the antibody and
$^2$ is the linkage site to the drug molecule or to the legumain-cleavable group,
R$^{10}$ is —H, —NH$_2$ or C$_1$-C$_3$-alkyl,
n is 0 or 1,
o is 0 or 1,
w' is 0 or 1
G1 is —NH—C(=O)—, —C(=O)—NH— or

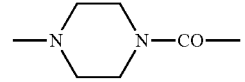

and
G2 is a straight-chain or branched hydrocarbyl chain having 1 to 100 carbon atoms consisting of arylene groups and/or straight-chain and/or branched and/or cyclic alkylene groups, which may be interrupted once or more than once by one or more of the groups —O—, —S—, —S(=O)—, —S(=O)$_2$, —NR$^y$—, CH(COOH)—, —CH(CH$_2$—C(=O)—NH$_2$, —NR$^y$C(=O)—, —C(NH)NR$^y$—, —C(=O)—NR$^y$—, —NR$^y$NR$^y$—, —S(=O)$_2$—NR$^y$NR$^y$—, —C(=O)—NR$^y$NR$^y$—, —C(=O)—, —CR$^x$=N—O— and/or a 3- to 10-membered, aromatic or nonaromatic heterocycle having up to 4 heteroatoms selected from N, O and S, —S(=O)— or —S(=O)$_2$—, and where the straight-chain or branched hydrocarbon chain may additionally be substituted by —NH—C(=O)—NH$_2$, —COOH, —OH, sulphonamide, sulphone, sulphoxide, or sulphonic acid,
R$^y$ is —H, phenyl, C$_1$-C$_{10}$-alkyl, C$_2$-C$_{10}$-alkenyl or C$_2$-C$_{10}$-alkynyl, each of which may be substituted by —NH—C(=O)—NH$_2$, —COOH, —OH, —NH$_2$, sulphonamide, sulphone, sulphoxide, or sulphonic acid, and Rx is —H, C$_1$-C$_3$-alkyl or phenyl.

In this context, G1 is preferably

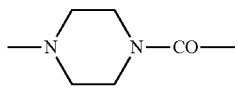

and R$^{10}$ is preferably not —NH$_2$ if G1 is —NH—C(=O)— or

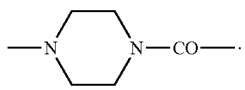

Preferably, G2 is a straight-chain or branched hydrocarbyl chain having 1 to 100 carbon atoms composed of arylene groups and/or straight-chain and/or branched and/or cyclic alkylene groups, which may be interrupted once or more than once by one or more of the groups —O—, —S—, —S(=O)—, —S(=O)$_2$—, —NH—, —C(=O)—, —NH—C(=O)—, —C(=O)—NH—, —NMe-, —NHNH—, —S(=O)$_2$—NHNH—, —C(=O)—NHNH— and a 5- to 10-membered aromatic or nonaromatic heterocycle having up to 4 heteroatoms selected from N, O and S, or —S(=O)—.

More preferably, G1 is

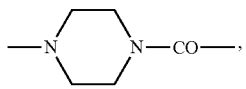

and the straight-chain or branched hydrocarbon chain may additionally be substituted by —NH—C(=O)—NH$_2$.

G2 is further preferably a straight-chain or branched hydrocarbyl chain having 1 to 100 carbon atoms composed of arylene groups and/or straight-chain and/or branched and/or cyclic alkylene groups, which may be interrupted once or more than once by one or more of the groups —O—, —S—, —S(=O)—, —S(=O)$_2$—, —NH—, —C(=O)—, —NH—C(=O)—, —C(=O)—NH—, —CH(COOH)—, —CH(CH$_2$—C(=O)—NH$_2$), —NMe-, —NHNH— —S(=O)$_2$— NHNH—, —C(=O)—NHNH—, —CR$^x$=N—O— and/or a 3- to 10-membered, aromatic or nonaromatic heterocycle having up to 4 heteroatoms selected from N, O and S, —S(=O)— or —S(=O)$_2$—, where the straight-chain or branched hydrocarbon chain may additionally be substituted by —NH—C(=O)—NH$_2$, —COOH, —OH, —NH$_2$, sulphonamide, sulphone, sulphoxide, or sulphonic acid and Rx is —H, C$_1$-C$_3$-alkyl or phenyl.

In this context, G2 is preferably

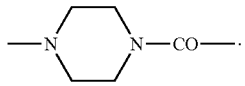

Preferably, G2 represents the interrupting groups of the structures

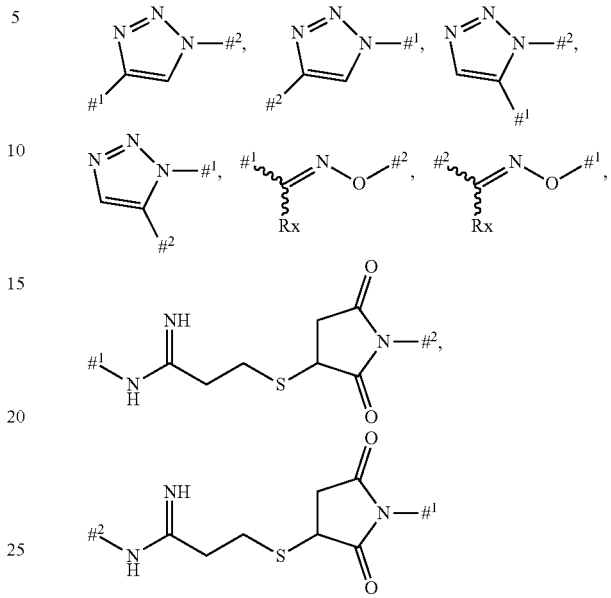

in which

Rx is —H, C$_1$-C$_3$-alkyl or phenyl,

$^1$ is the bond to the KSP inhibitor or prodrug and

$^2$ is the bond to the coupling group to the antibody (e.g. L2).

A straight-chain or branched hydrocarbon chain of arylene groups and/or straight-chain and/or branched and/or cyclic alkylene groups generally comprises a α,ω-divalent alkyl radical having the respective number of carbon atoms stated. Preferred examples include: methylene, ethane-1,2-diyl (1,2-ethylene), propane-1,3-diyl (1,3-propylene), butane-1,4-diyl (1,4-butylene), pentane-1,5-diyl (1,5-pentylene), hexane-1,6-diyl (1,6-hexylene), heptane-1,7-diyl (1,7-hexylene), octane-1,8-diyl (1,8-octylene), nonane-1,9-diyl (1,9-nonylene), decane-1,10-diyl (1,10-decylene).

A branched hydrocarbon chain means that one or more hydrogen atoms in the straight hydrocarbon chain or the straight alkylene groups are substituted by C$_{1-10}$-alkyl groups, thus forming branched hydrocarbon or side chains (branched hydrocarbon chain).

The hydrocarbon chain may additionally contain cyclic alkylene groups (cycloalkanediyl), for example 1,4-cyclohexanediyl or 1,3-cyclopentanediyl. These cyclic groups may be unsaturated. In particular, aromatic groups (arylene groups), for example phenylene, may be present in the hydrocarbon chain. It is also possible in turn for one or more hydrogen atoms in the cyclic alkylene groups and the arylene groups to be optionally substituted by C$_{1-10}$-alkyl groups. In this way, an optionally branched hydrocarbon chain is formed. This hydrocarbon chain has a total of 0 to 100 carbon atoms, preferably 1 to 50, particularly preferably 2 to 25 carbon atoms.

The branched hydrocarbon or side chains (branched hydrocarbon chain) may be substituted by —NH—C(=O)—NH2, —COOH, —OH, —NH$_2$, sulphonamide, sulphone, sulphoxide, or sulphonic acid.

The hydrocarbon chains may be interrupted once or more than once by one or more of the groups —O—, —S—, —S(=O)—, —S(=O)₂—, —NH—, —C(=O)—, —NH—C(=O)—, —C(=O)—NH—, —CH(COOH)—, —CH(CH₂—C(=O)—NH₂), —NMe-, —NHNH—, —S(=O)₂—NHNH—, —C(=O)—NHNH— and a 5- to 10-membered aromatic or nonaromatic heterocycle having up to 4 heteroatoms selected from =N—, —O— and —S—, —S(=O)— or —S(=O)₂—.
Preference is given here to a group
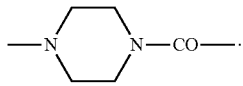
Further interrupting groups in G2 are preferably
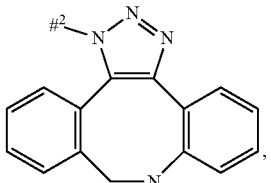,
,
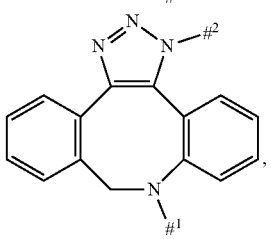,
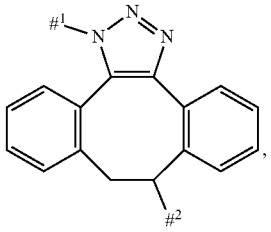,
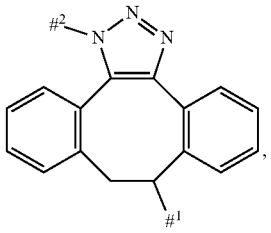,
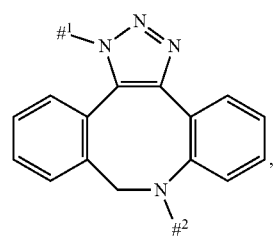,
-continued
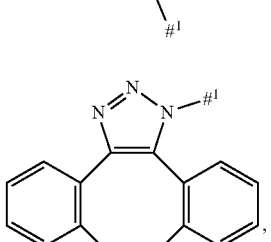,
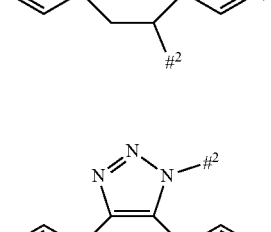,
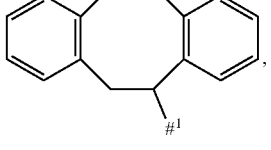, -continued

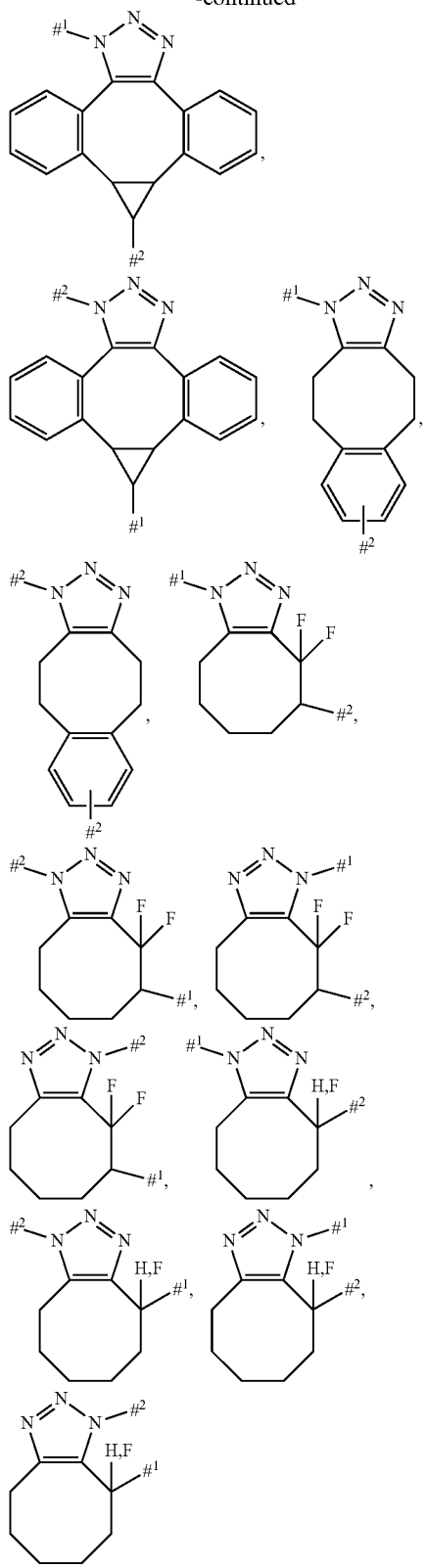

More preferably, and with reference to the above definitions, L1 corresponds to the following simplified formula:

—NR$^{11}$B— in which
R$^{11}$ is —H or —NH$_2$,
B is the —[(CH$_2$)$_x$—(X$^4$)$_y$]w-(CH$_2$)$_z$— group,
w is 0 to 20,
x is 0 to 5,
y is 0 or 1,
z is 0 to 5 and
X$^4$ is —O—, —C(=O)—NH—, —NH—C(=O)— or

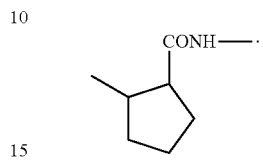

Preferably, the linker L has the formula

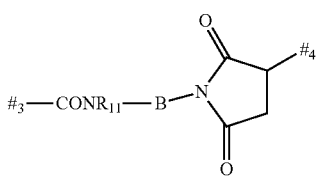

in which
3 is the bond to the drug molecule or prodrug,
4 is the bond to the binder peptide or protein,
R$^{11}$ is —H or —NH$_2$,
B is the —[(CH$_2$)$_x$—(X$^4$)$_y$]w-(CH$_2$)$_z$— group,
w is 0 to 20,
x is 0 to 5,
y is 0 or 1,
z is 1 to 5 and
X$_4$ is —O—, —C(=O)—NH—, —NH—C(=O)— or

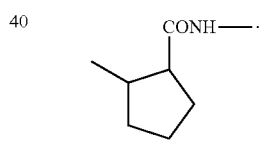

The abovementioned linkers are especially preferred in conjugates of the formula (IIa) in which the linker couples to R$^1$ by substitution of a hydrogen atom, i.e. R$^1$ is -L-#1 where #1 is the bond to the antibody.

In a conjugate according to the invention or in a mixture of the conjugates according to the invention, the bonds to a cysteine residue of the antibody are present to an extent of preferably more than 80%, more preferably more than 90% (based in each case on the total number of bonds of the linker to the antibody).

Particular preference is given here to the two structures of the general formulae (A5) and (A6)

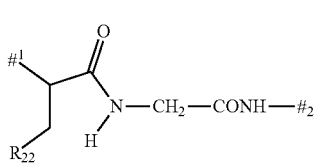

(A5)

and

-continued (A6)

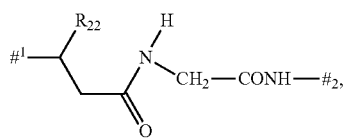

in which
¹ is the linkage site to the sulphur atom of the antibody,
² is the linkage site to the L¹ group,
$R^{22}$ is —COOH, —C(=O)—OR, —C(=O)—R, —C(=O)—NH$_2$, —C(=O)—NR$_2$ or —C(=O)—NHR and
R is $C_{1-3}$-alkyl.
More preferably, $R^{22}$ is —COOH.
The structures of the general formulae A5 or A6 are generally present here together, preferably in a ratio of from 60:40 to 40:60, based on the number of bonds to the antibody. The remaining bonds are then present in the structure

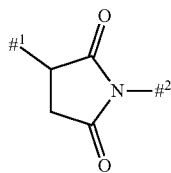

in which
1 and #2 have the definitions given above.
Preferred groups L1 in the above formula § —(C(=O))$_m$-(L1)$_n$-L2- § § are those listed in the table which follows, where r is a number from 0 to 20, preferably from 0 to 15, especially preferably from 0 to 10:

| L1 |
|---|

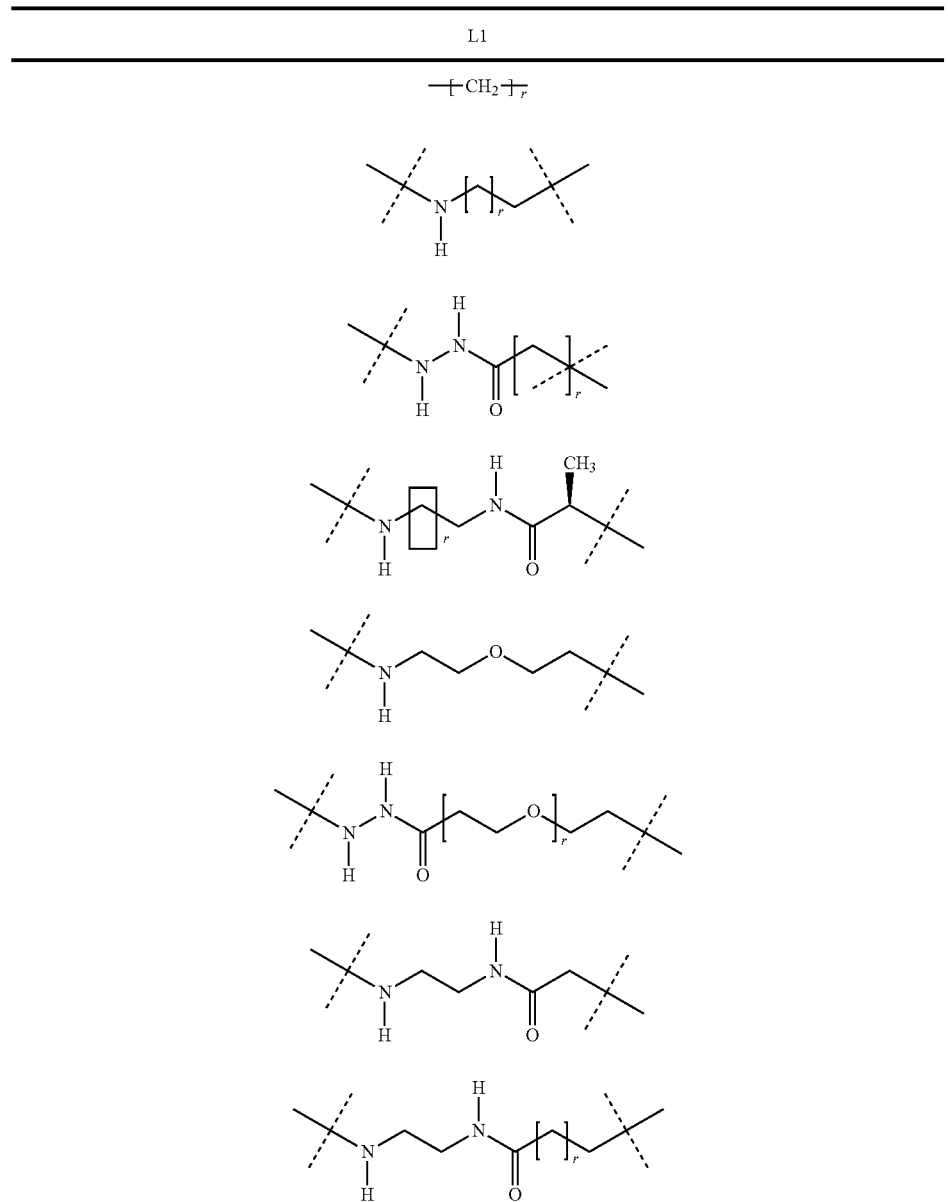

| L1 |
|---|
| 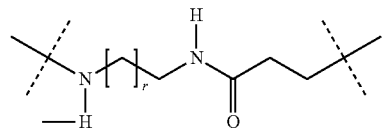 |
| 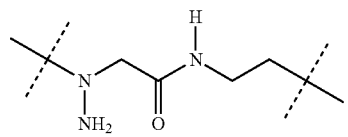 |
| 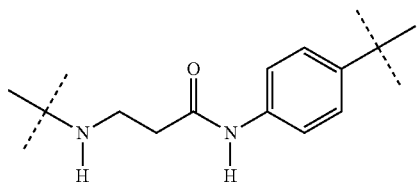 |
| 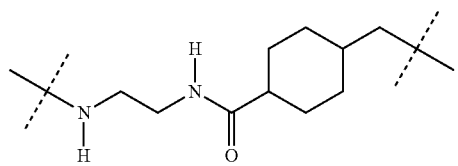 |
| 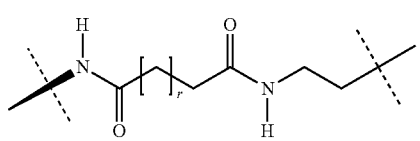 |
| 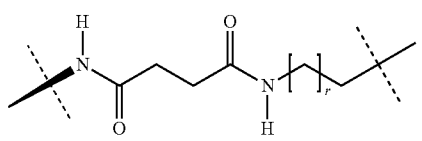 |
| 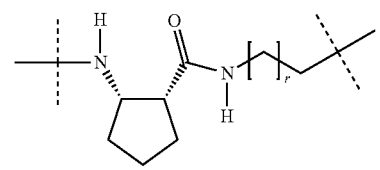 |
| 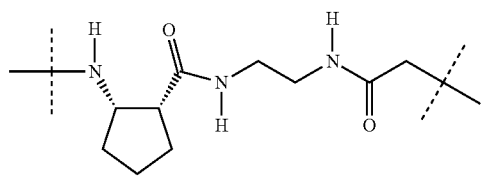 |
| 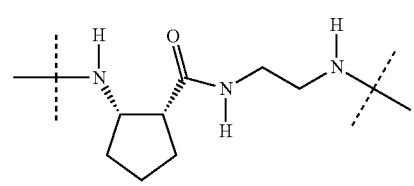 |

| L1 |
|---|
| 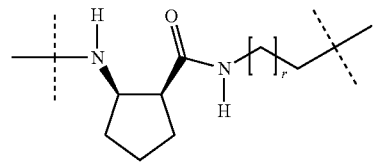 |
| 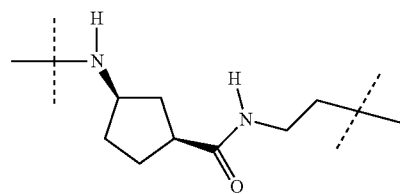 |
| 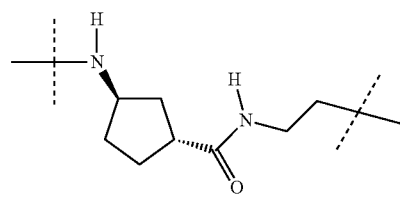 |
| 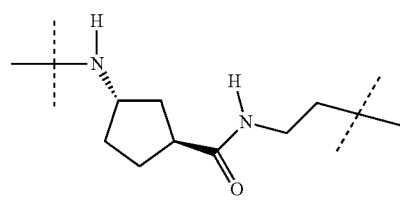 |
| 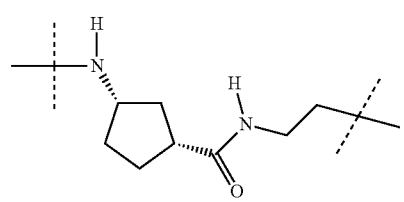 |
| 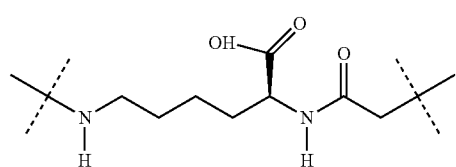 |
| 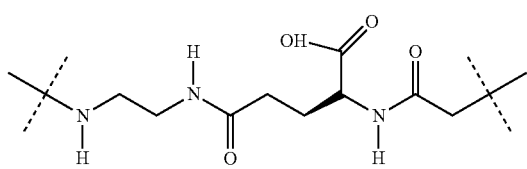 |
| 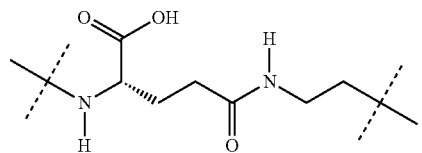 |

| L1 |
|---|
| 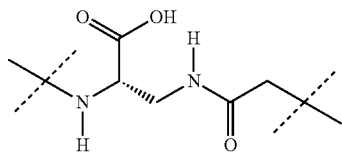 |
| 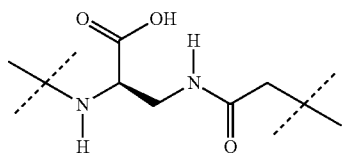 |
| 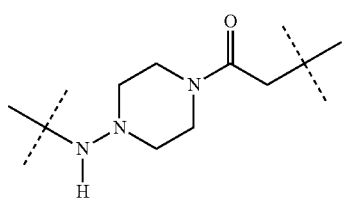 |
| 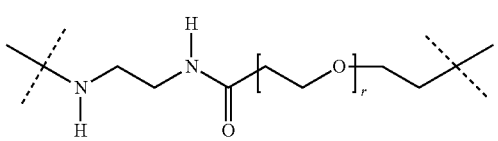 |
| 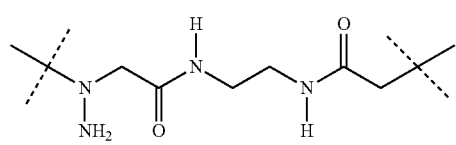 |
| 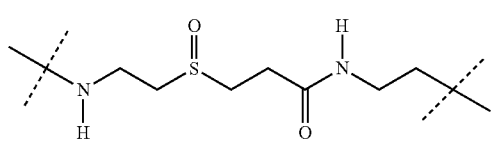 |
| 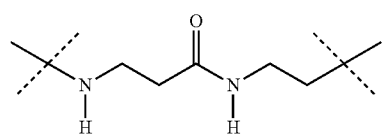 |
| 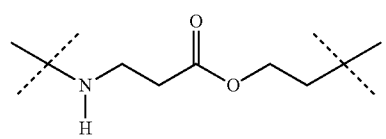 |
| 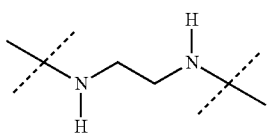 |
| 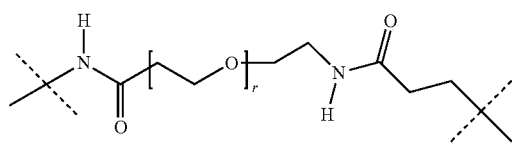 |

| L1 |
|---|
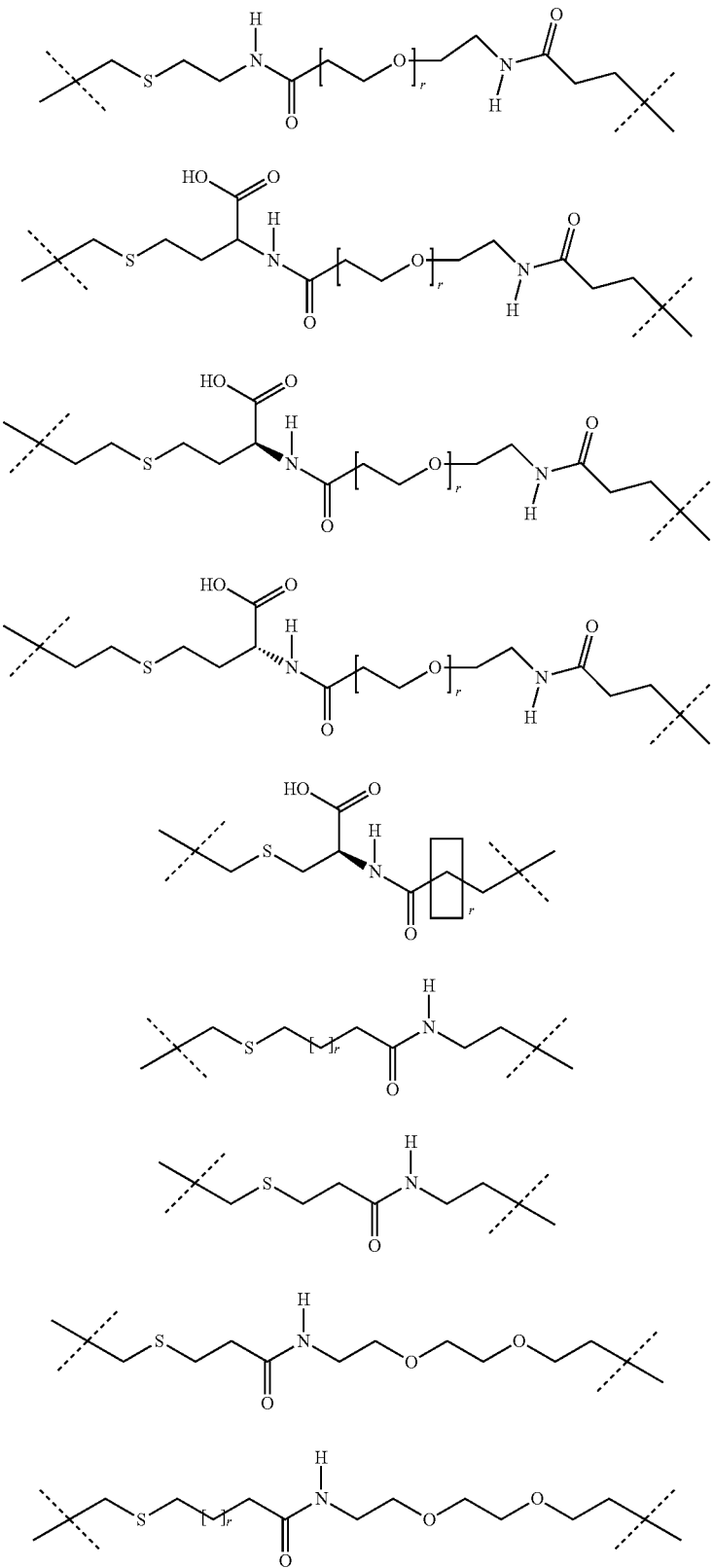

| L1 |
|---|
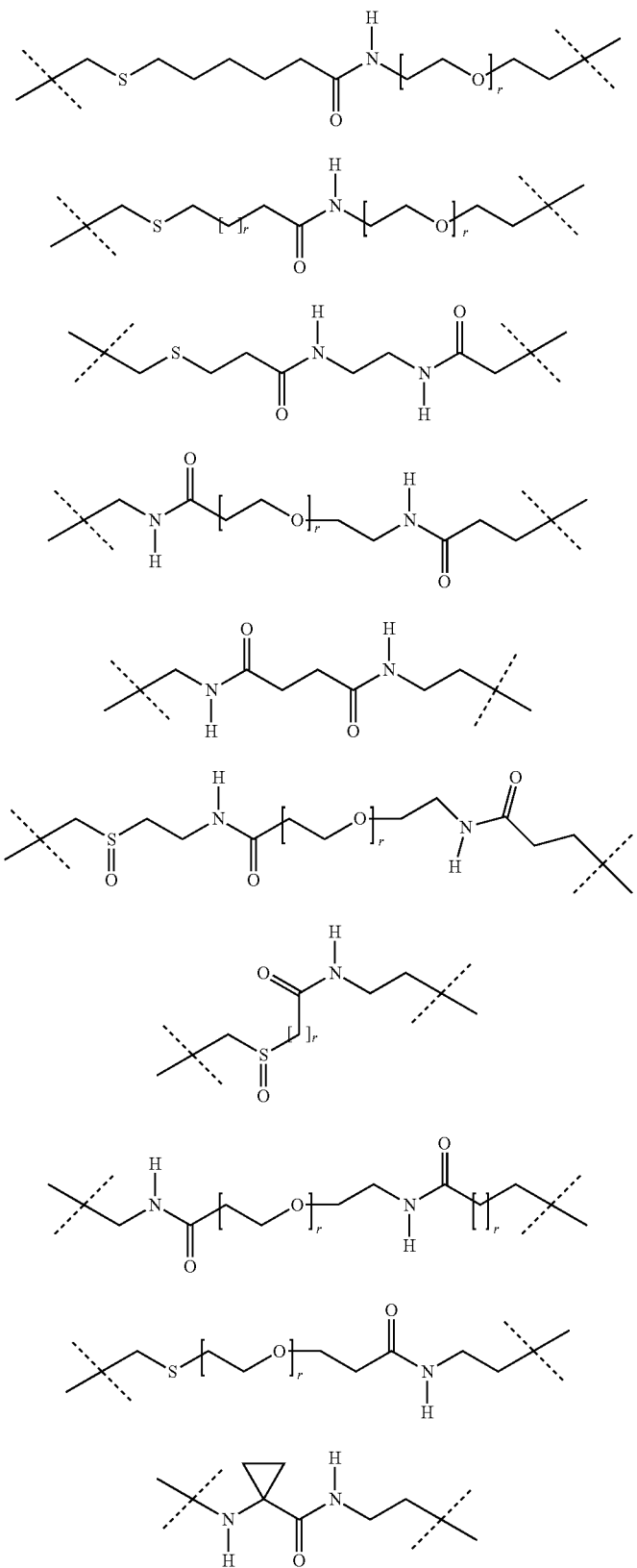

-continued
| L1 |
|---|
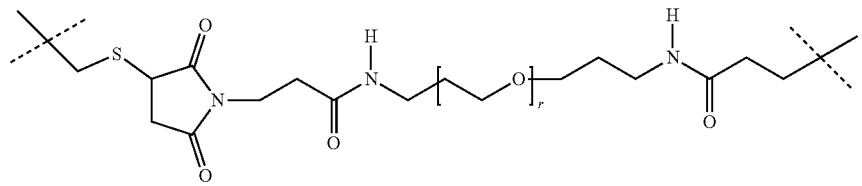
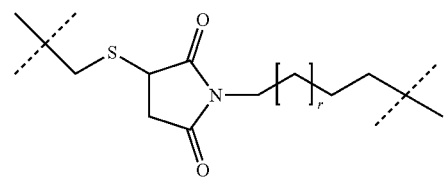
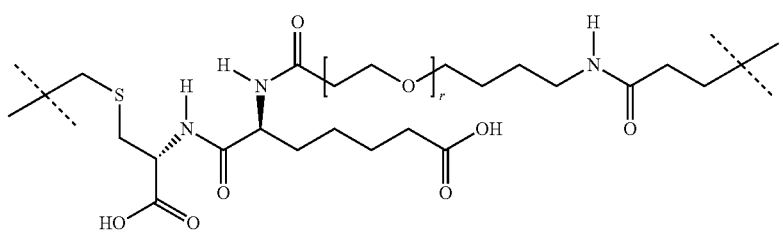
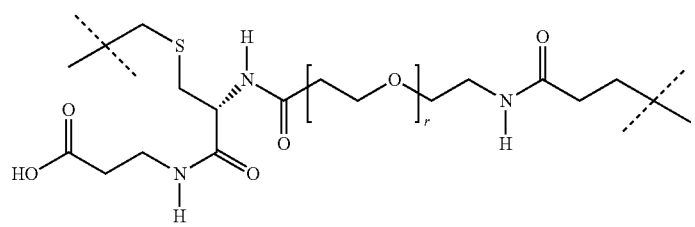
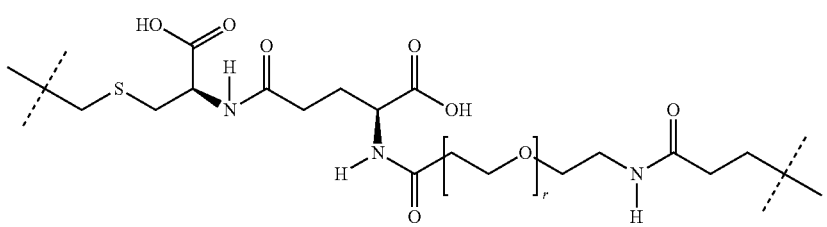
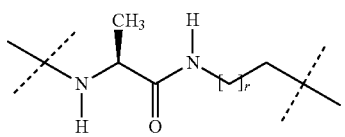
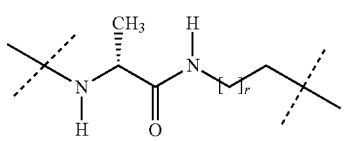
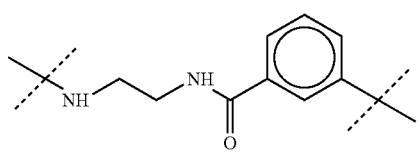

-continued
L1
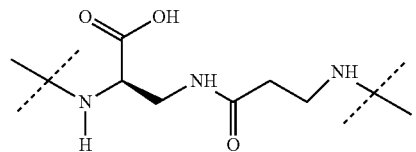
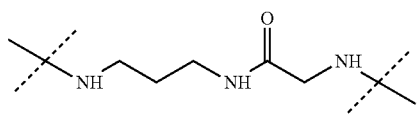
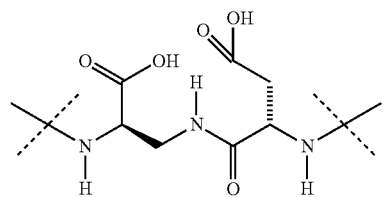
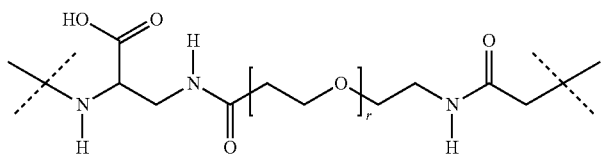
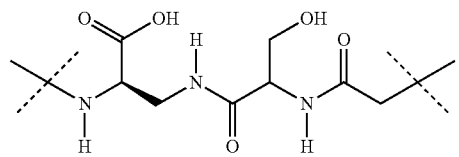
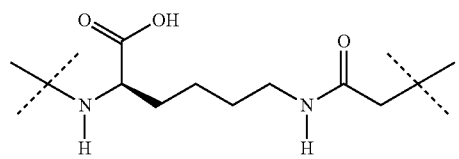
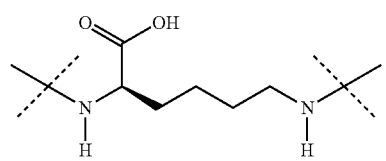
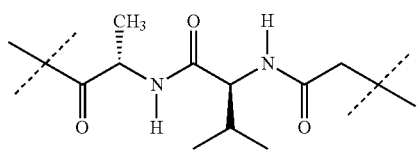
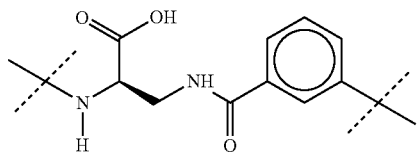

-continued
| L1 |
|---|
| 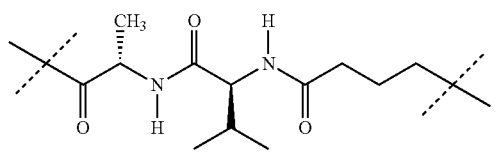 |
| 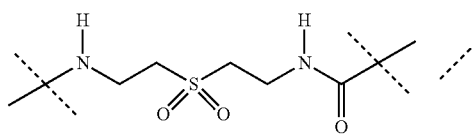 |
| 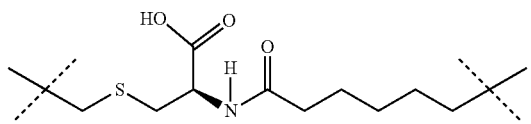 |
| 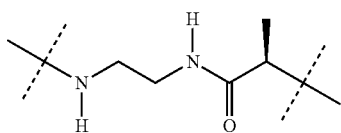 |
| 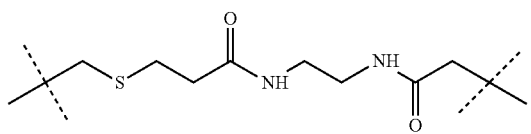 |
| 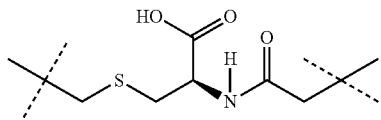 |
| 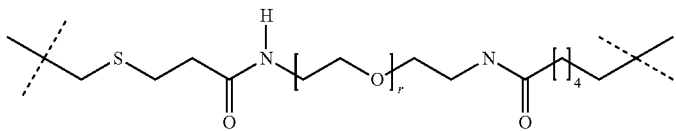 |
| 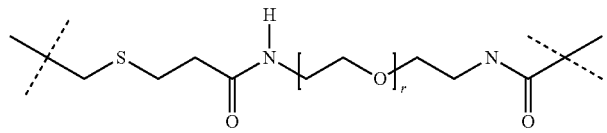 |
| 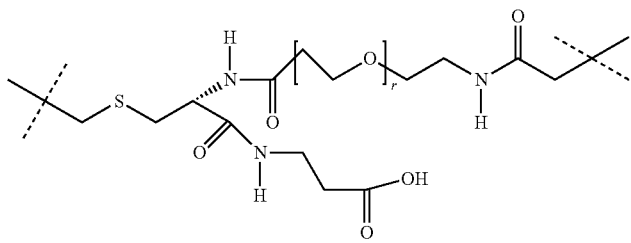 |
| 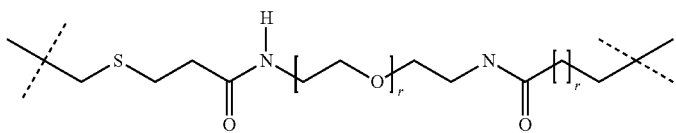 |

| L1 |
|---|
| 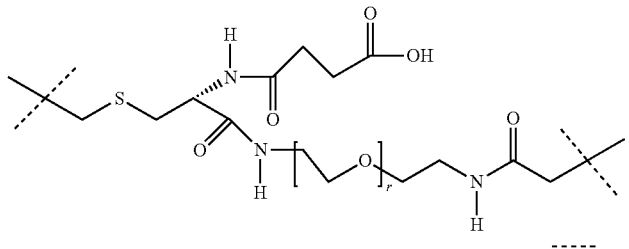 |
| 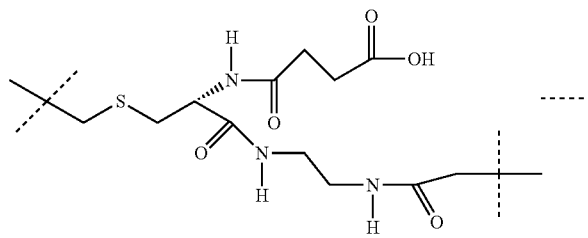 |
| 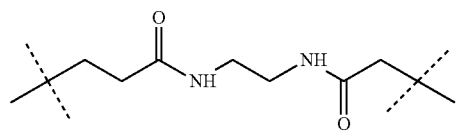 |
| 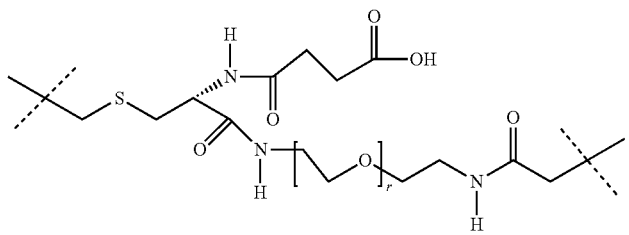 |
| 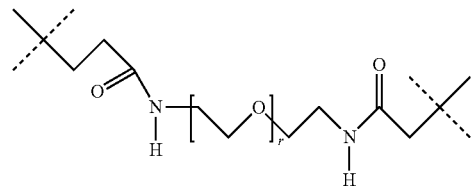 |
| 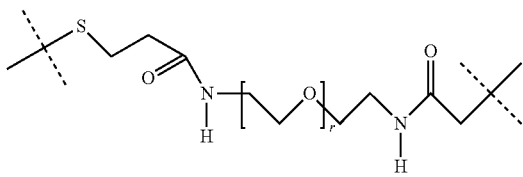 |
| 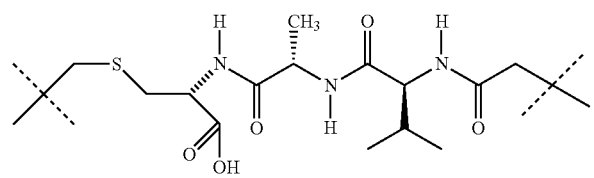 |

| L1 |
|---|
| 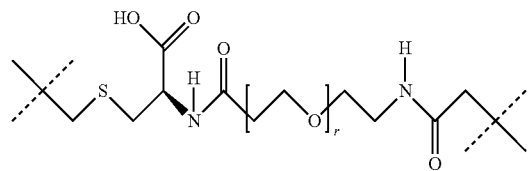 |
| 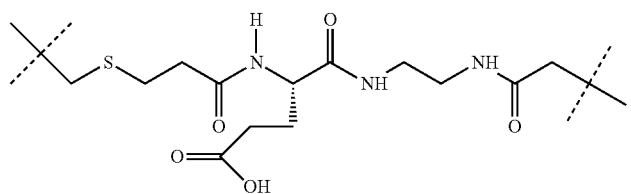 |
| 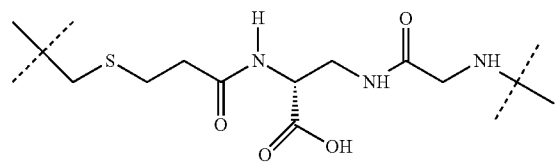 |
| 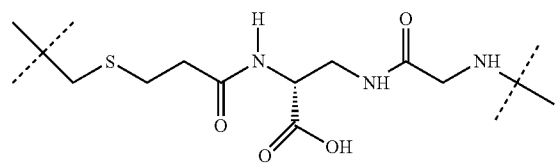 |
| 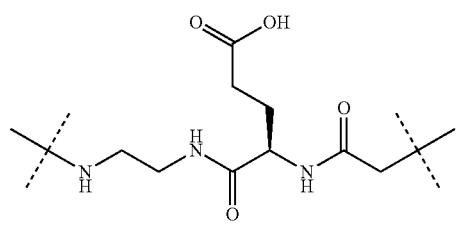 |
| 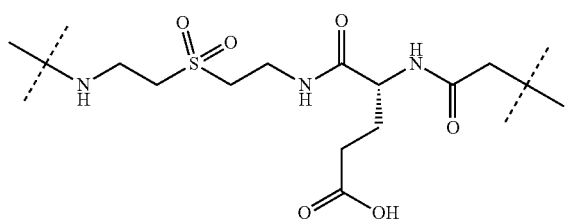 |
| 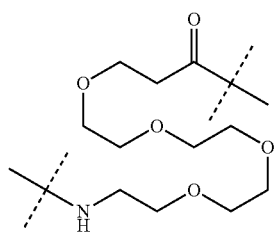 |

| L1 |
|---|
| 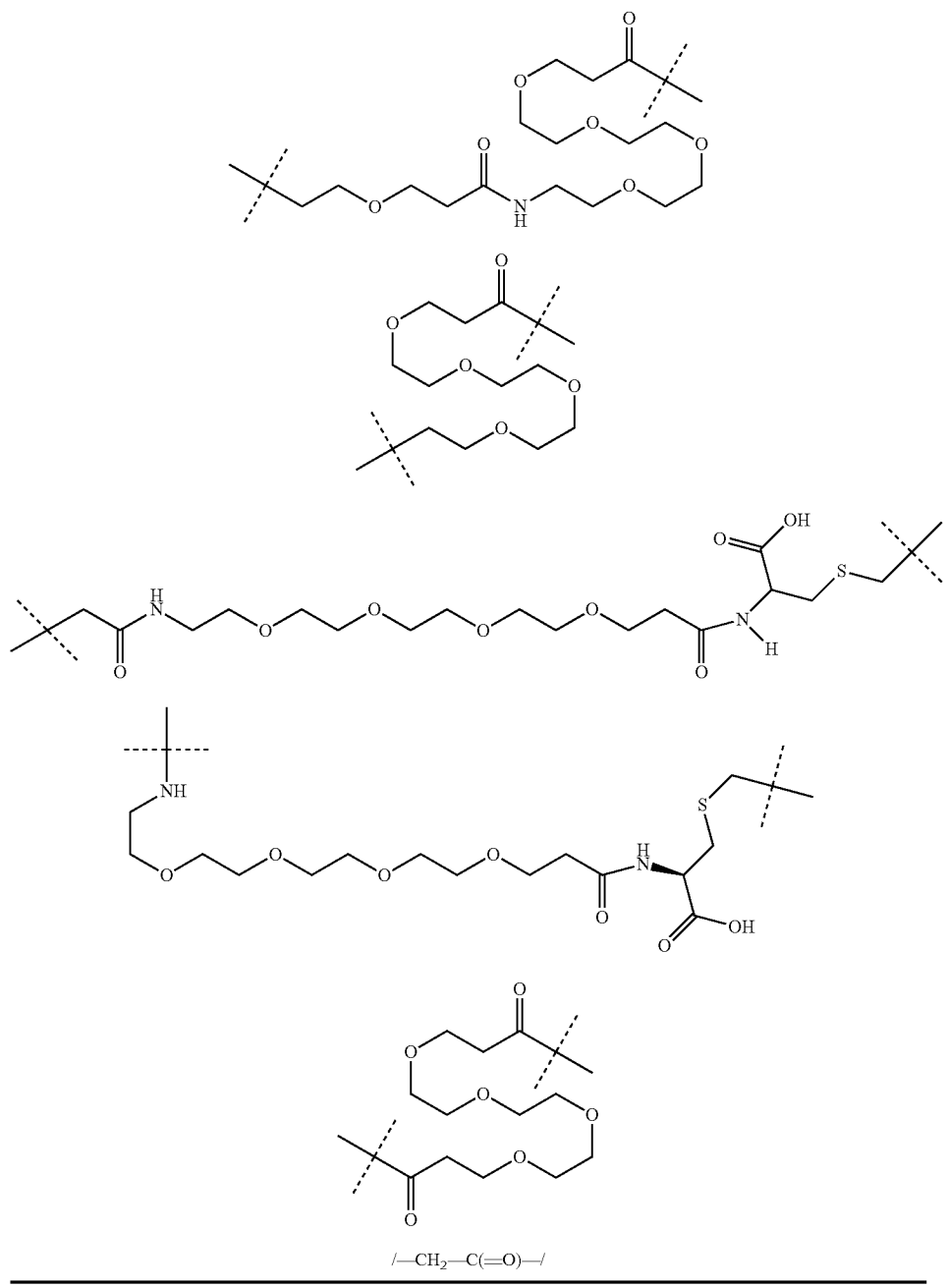 |
|  /—CH$_2$—C(=O)—/ |

More preferably, AK1 is an antibody or an antigen-binding fragment thereof. The antibody is preferably a human, humanized or chimeric monoclonal antibody or an antigen-binding fragment thereof, especially an anti-TWEAKR antibody, an anti-EGFR antibody, an anti-B7H3 antibody or an anti-HER2 antibody or an antigen-binding fragment thereof. Particular preference is given to the anti-TWEAKR antibodies TPP-7006, TPP-7007 and TPP-10337, the anti-B7H3 antibodies TPP-8382 and TPP-8567, the anti-EGFR-antibody cetuximab (TPP-981) and the anti-HER2-antibodies trastuzumab and TPP-1015, or an antigen-binding fragment of these.

Additionally preferred is the base structure (ii) of the linkers $$—(C=O)_m\text{-}(L1)_n\text{-}SG\text{-}L2, \quad (ii)$$

where SG represents a group cleavable by protease, for example cathepsin, and m, n, SG, L1 and L2 have the definitions given above. Particular preference is given to the following groups:

Val-Ala-C(=O)—NH— (resulting in cleavage of the amide bond at the C-terminal amide of alanine)

NH-Val-Lys-C(=O)—NH— (cleavage of the amide bond at the C-terminal amide of lysine)

NH-Val-Cit-C(=O)—NH— (cleavage of the amide bond at the C-terminal amide of citrulline)
NH-Phe-Lys-C(=O)—NH— (cleavage of the amide bond at the C-terminal amide of lysine)
NH-Ala-Lys-C(=O)—NH— (cleavage of the amide bond at the C-terminal amide of lysine)
NH-Ala-Cit-C(=O)—NH— (cleavage of the amide bond at the C-terminal amide of citrulline)

In this context, SG is preferably:

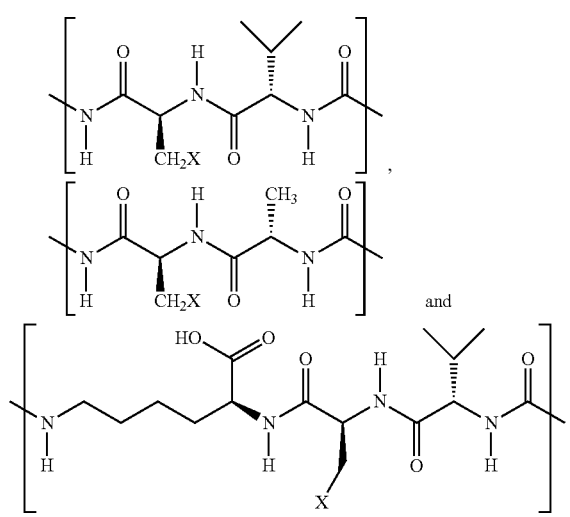

in which
X is —H or a $C_{1-10}$-alkyl group which may optionally be substituted by —NH—C(=O)—NH$_2$, —COOH, —OH, —NH$_2$, or sulphonic acid.

In the case of transglutaminase-catalysed conjugation, the literature discloses various options for the covalent coupling (conjugation) of organic molecules to binders, for example antibodies, in a conjugation site-specific manner (see, for example Sochaj et al., *Biotechnology Advances*, 33, 775-784, (2015), Panowski et al., *MAbs* 6, 34-45 (2014)). Preference is given in accordance with the invention to the conjugation of the KSP inhibitors or prodrugs to an antibody via acceptor glutamine residues of the antibody using transglutaminase. Such acceptor glutamine residues can be generated by engineering of the antibody or by mutations which create aglycosylated antibodies. The number of these acceptor glutamines in the antibody is preferably 2 or 4. Suitable linkers are used for the coupling (conjugation). Suitable linker structures are those which possess a free amine donor functionality which constitutes a suitable substrate for the transglutaminase. The linker can be joined to the antibody in various ways.

Preferably, in the case of transglutaminase-catalysed conjugation, the linker has one of the base structures (i) and (ii) already mentioned above

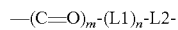 (i)

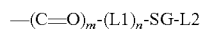 (ii)

in which
L1, SG, SG1 and m have the definitions given above,
L2 preferably, however, represents one of the following groups:

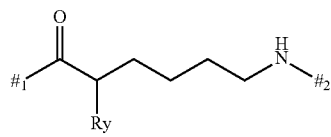

in which
Ry is —H, —NH—C(=O)-alkyl,
$\#^1$ is the linkage point to $L^1$ and
$\#^2$ is the linkage point to the glutamine residue of the binder.

Preferably in this context, Ry is —H or —NH—C(=O)—CH$_3$.

Examples of corresponding conjugates have the following structures, where MOD and L1 have the definitions given above, AK$_3$ is a binder which is preferably an antibody, and n is preferably 2 or 4.

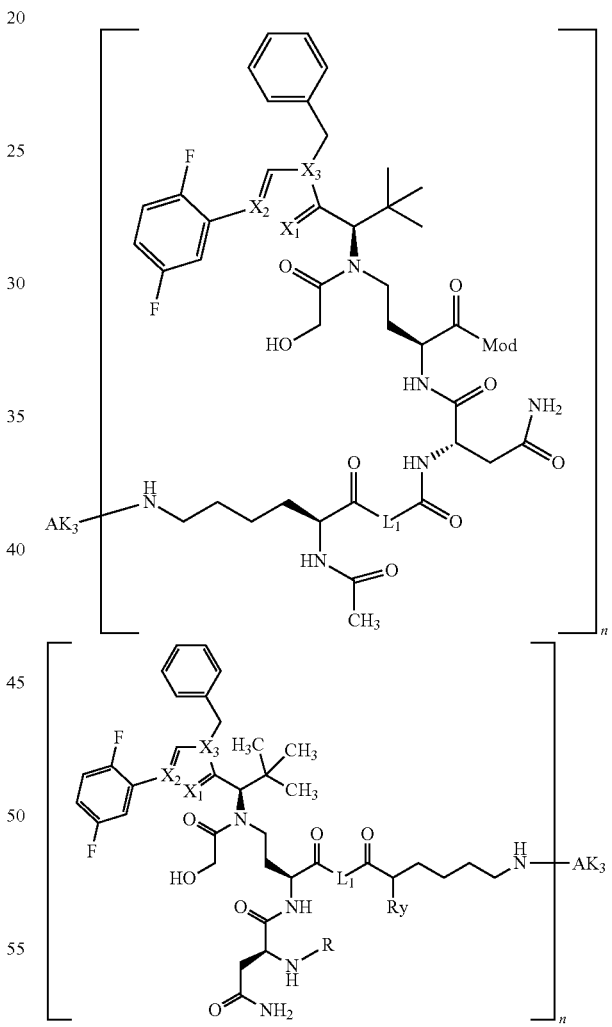

Particularly Preferred KSP Inhibitor Conjugates

Particular preference is given in accordance with the invention to the following KSP-inhibitor conjugates in which AK (AK$_1$; AK$_2$; AK$_3$) is a binder, preferably an antibody or an antigen-binding fragment, and n is a number from 1 to 50, preferably 1 to 20, more preferably 2 to 8 and especially 2 to 6.

AK₁ is preferably an antibody bonded to the KSP inhibitor via a cysteine residue.

AK₂ is preferably an antibody bonded to the KSP inhibitor via a lysine residue.

AK₃ is preferably an antibody bonded to the KSP inhibitor via a glutamine residue.

The binders or antibodies used here are preferably the binders and antibodies described as preferred in the description.

Especially preferred are the anti-TWEAKR antibodies TPP-7006, TPP-7007 and TPP-10337, the anti-B7H3 antibodies TPP-8382 and TPP-8567, the anti-EGFR-antibody cetuximab (TPP-981) and the anti-HER2-antibodies trastuzumab and TPP-1015, or an antigen-binding fragment of these.

Particularly preferred conjugates are:

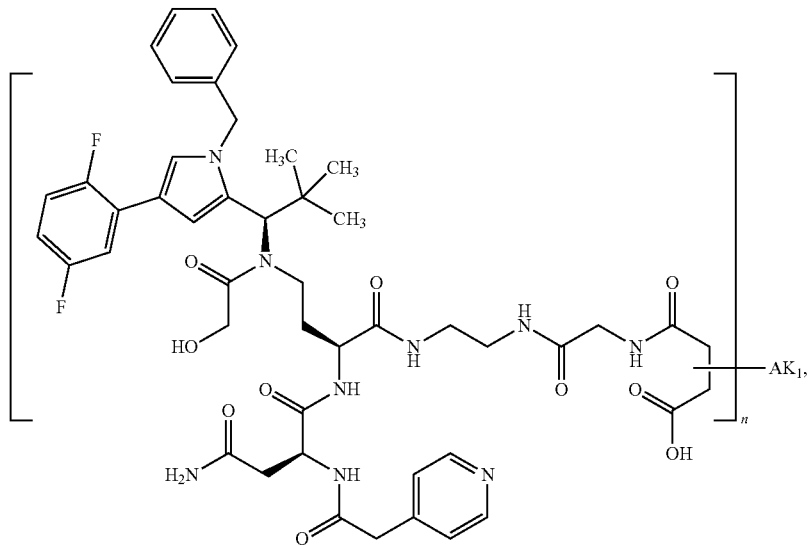

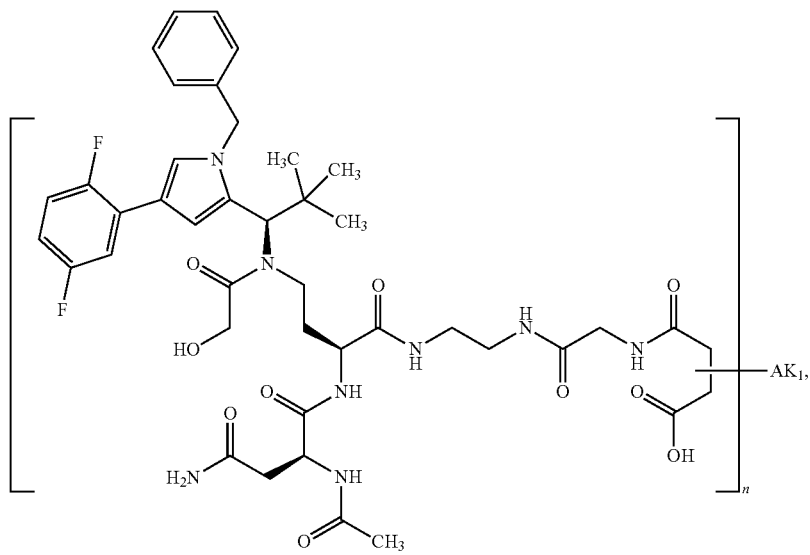

-continued
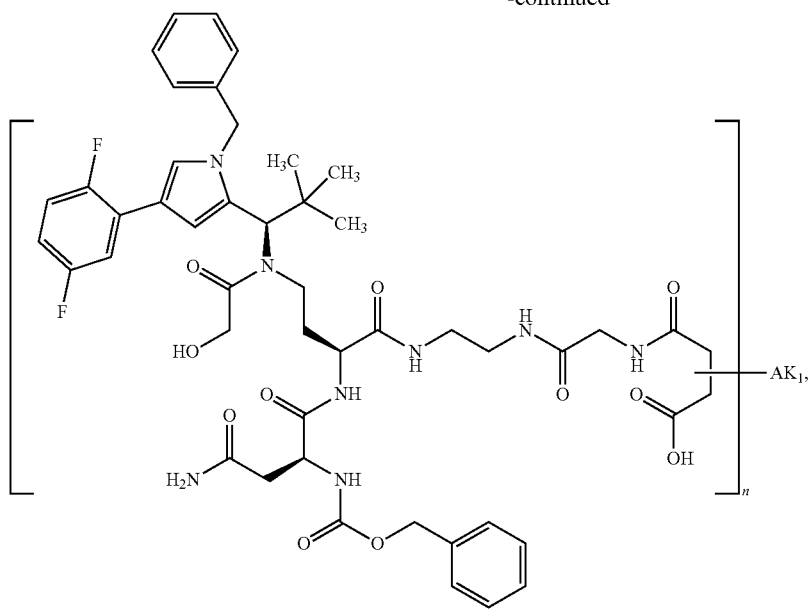
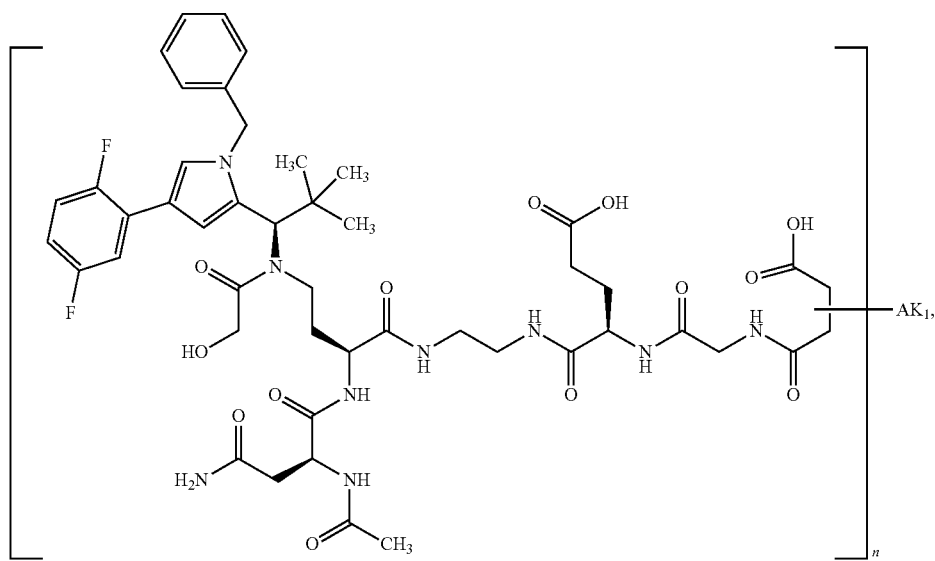
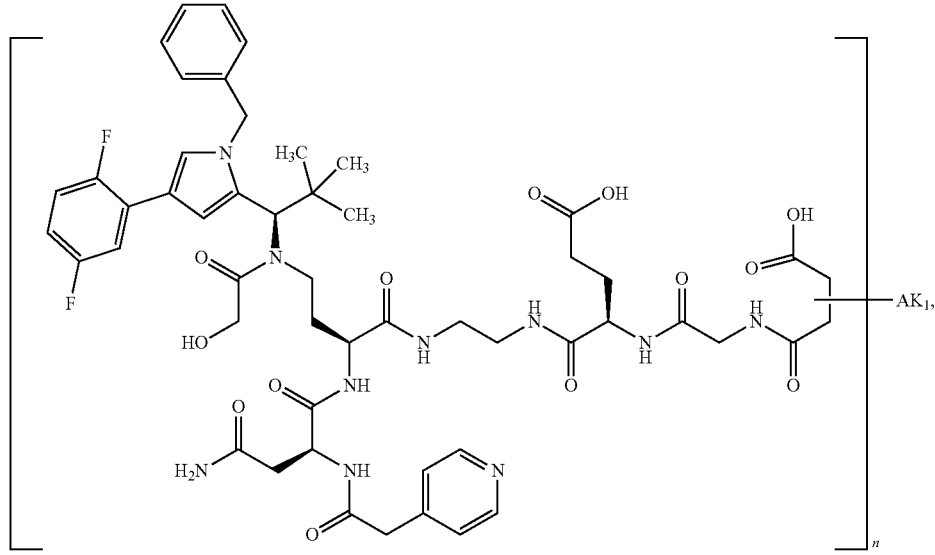

-continued
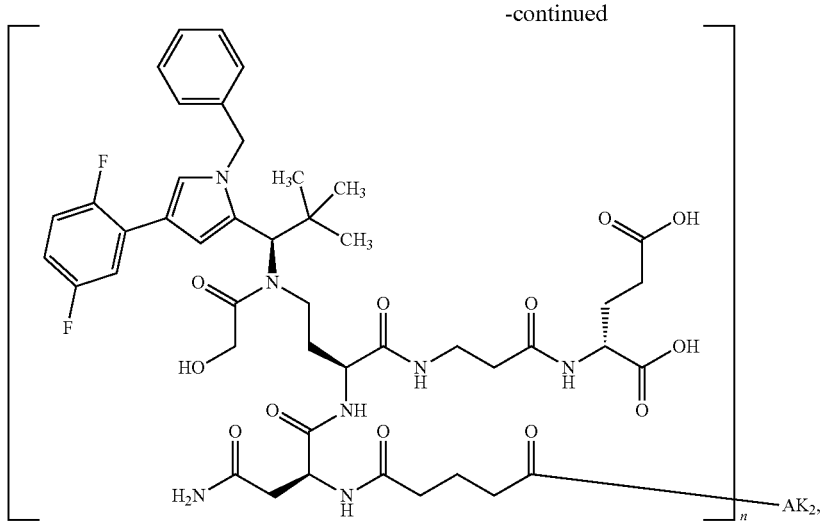
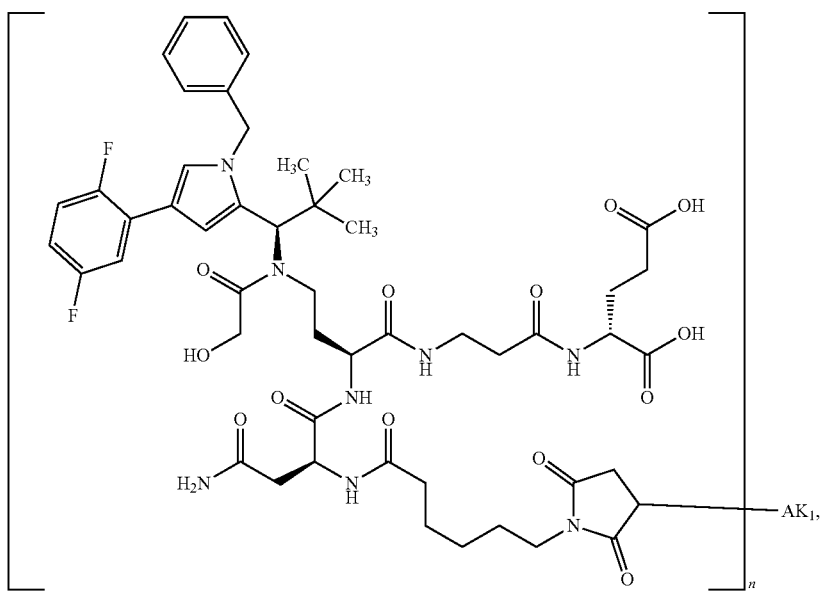
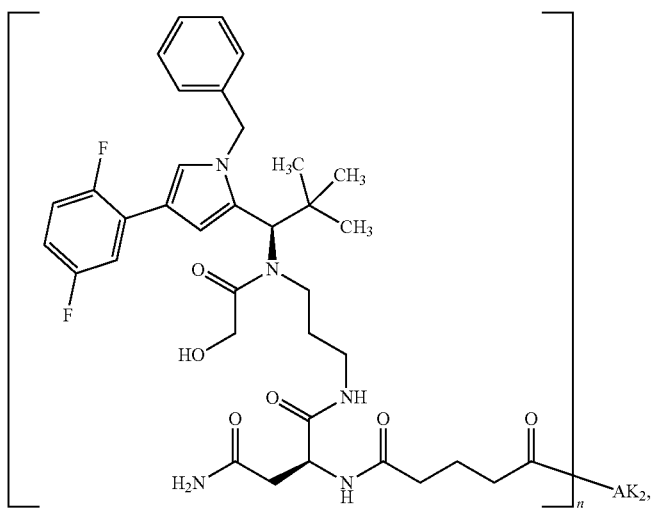

-continued
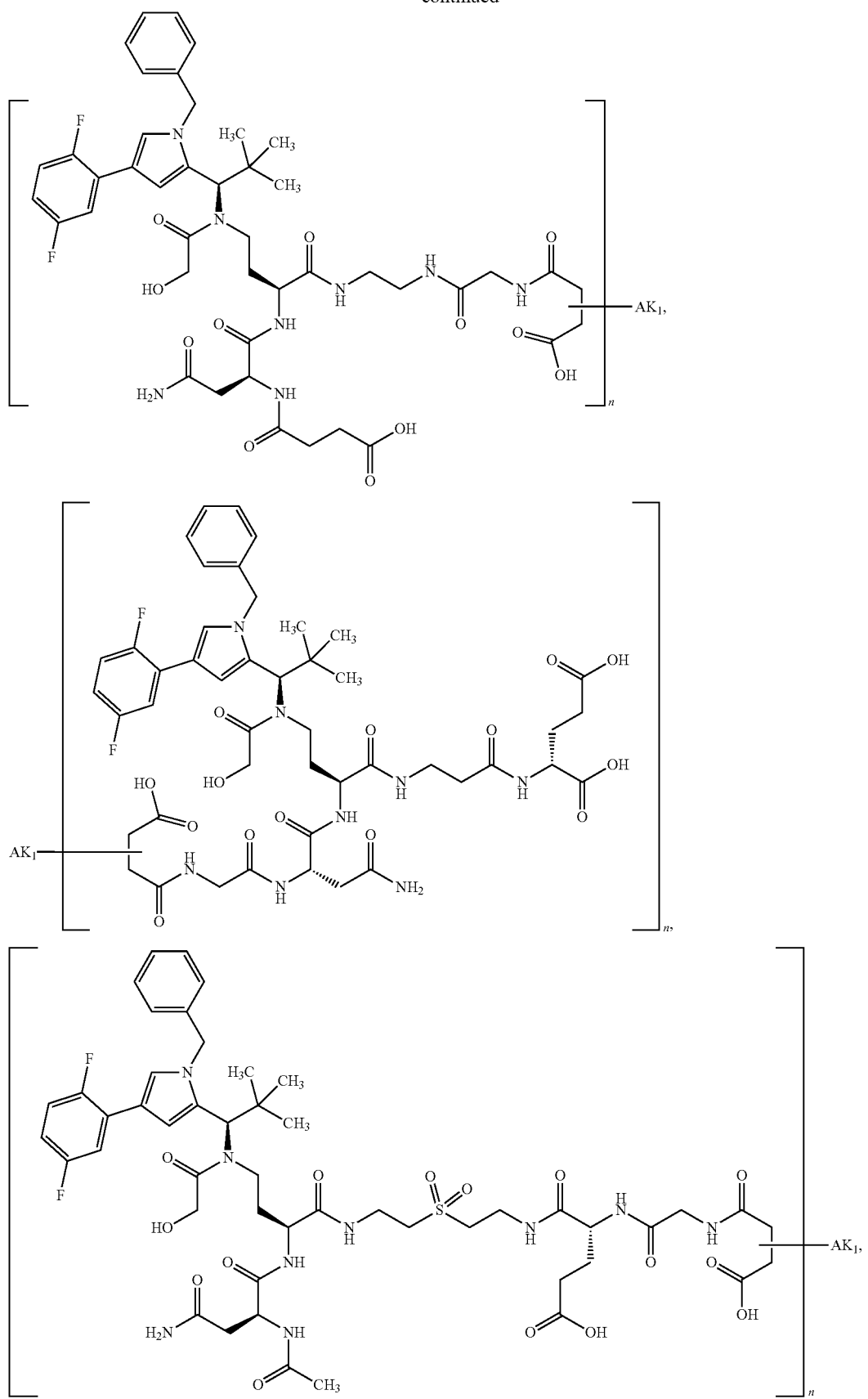

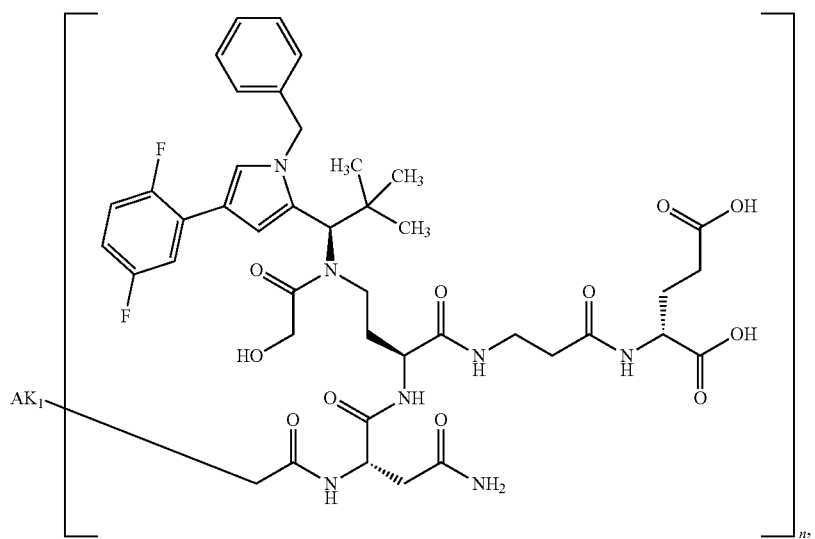
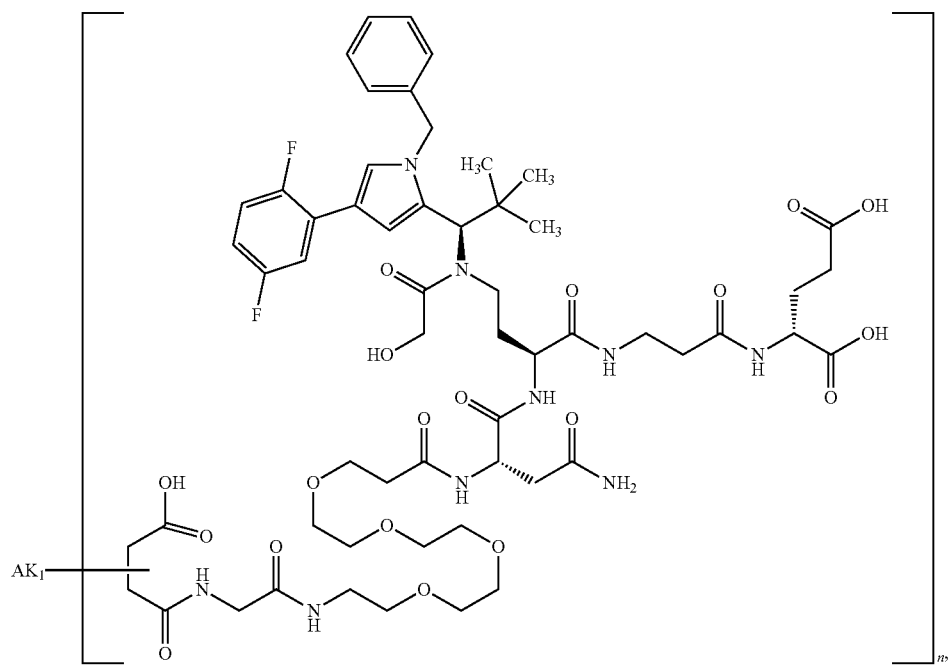

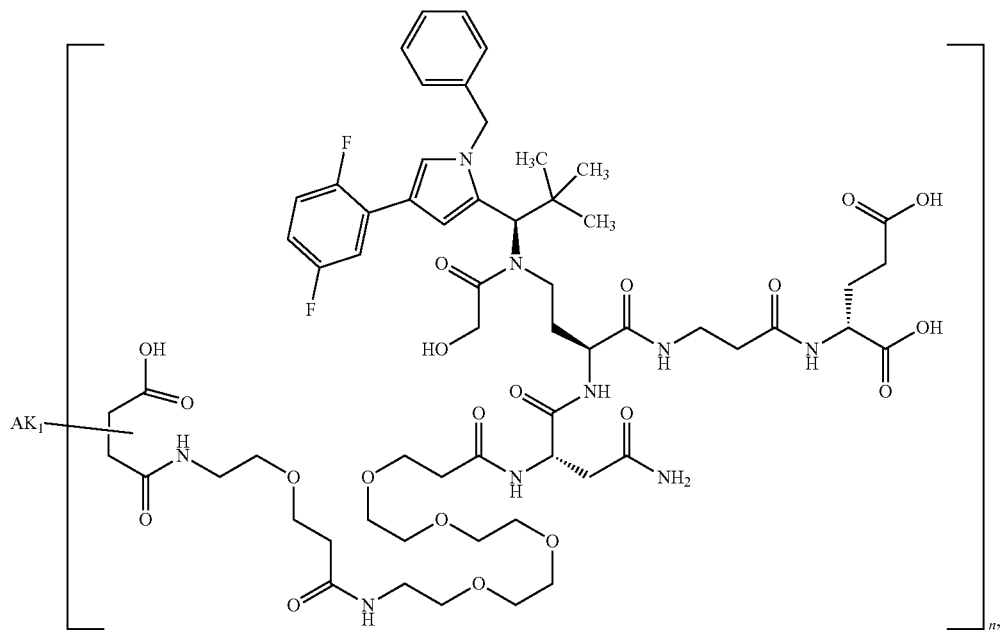
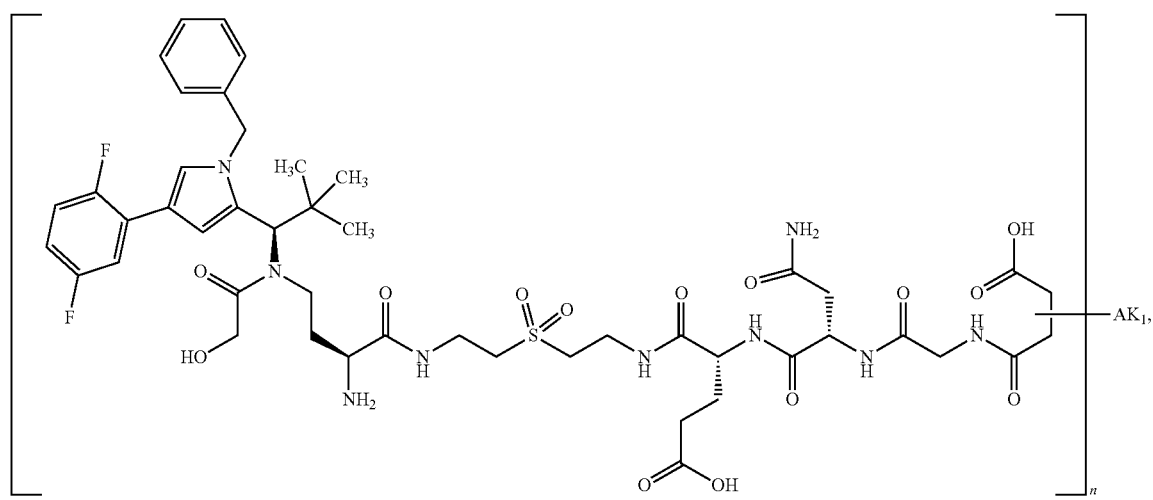

119
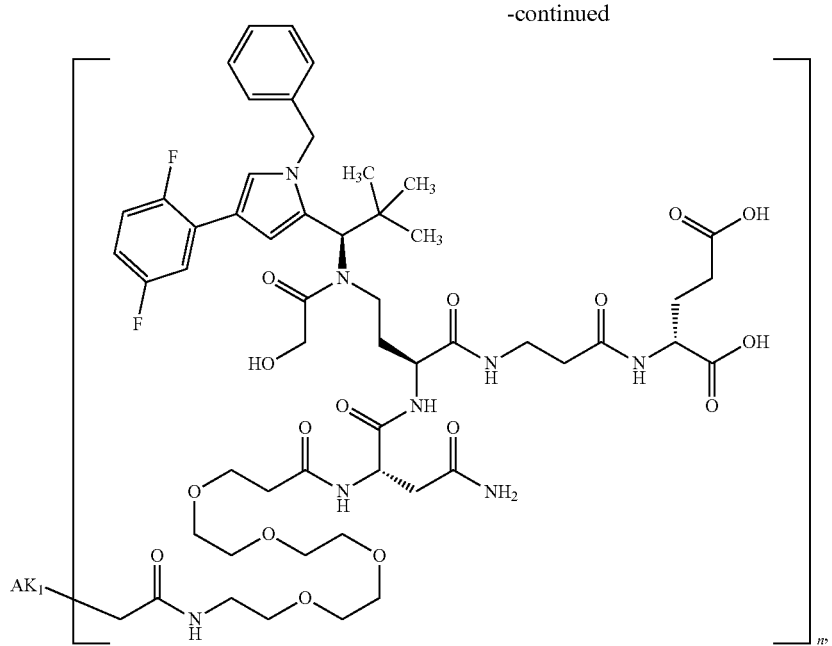
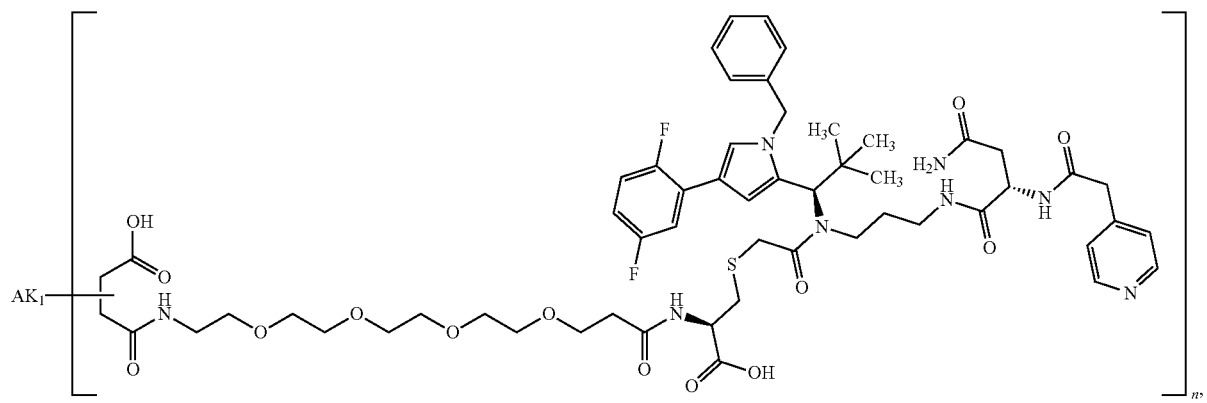
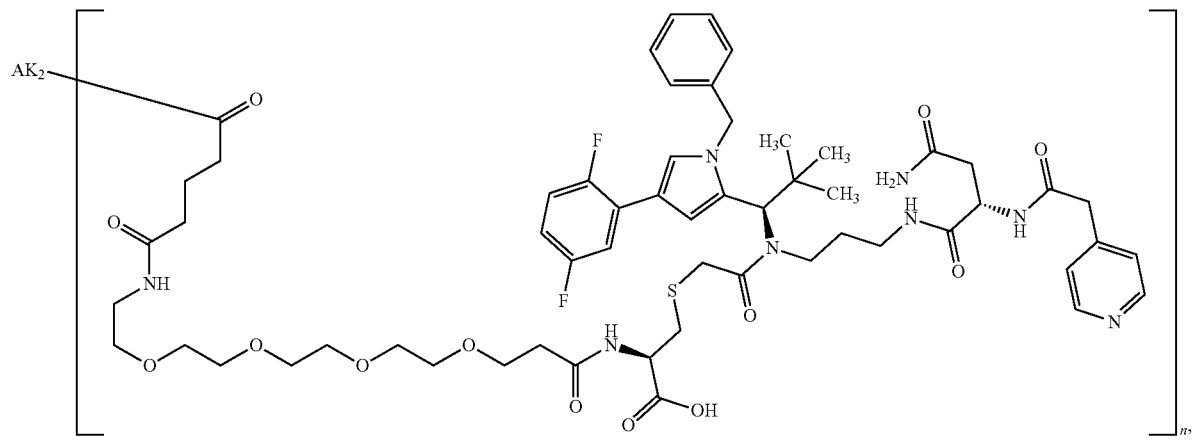

-continued
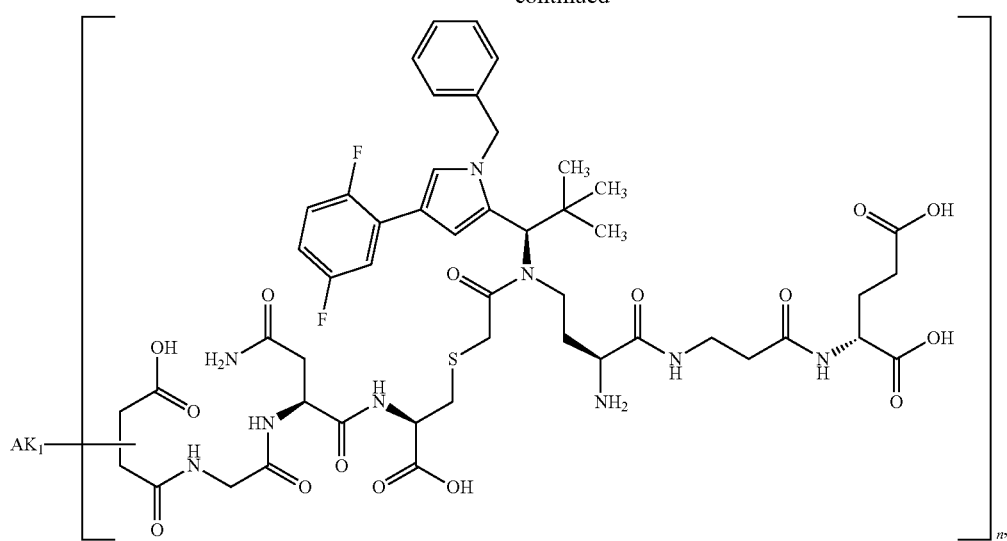
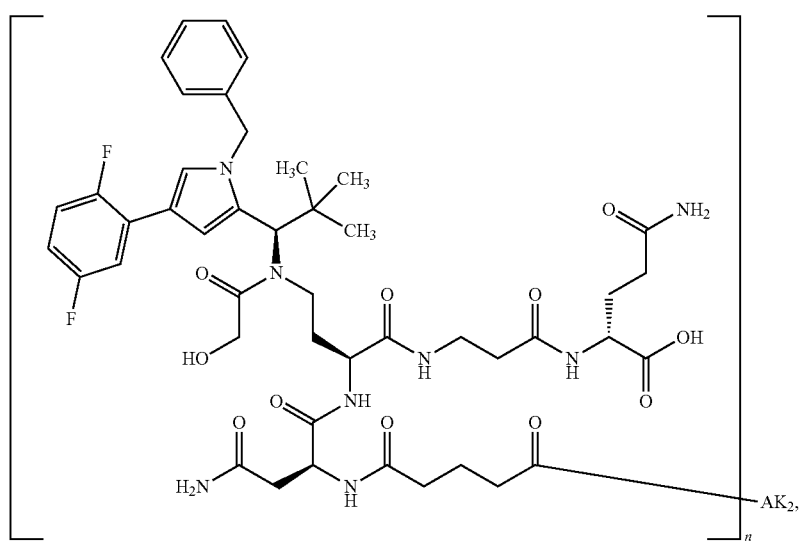
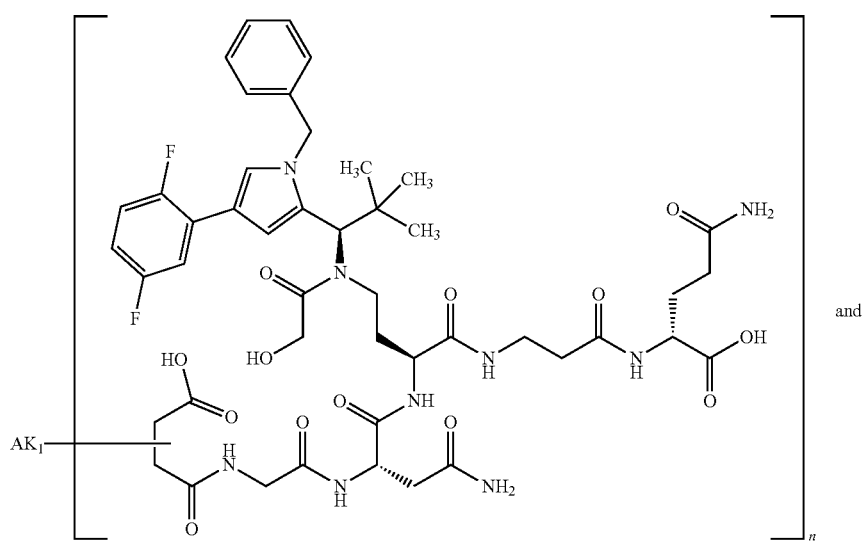
and

-continued

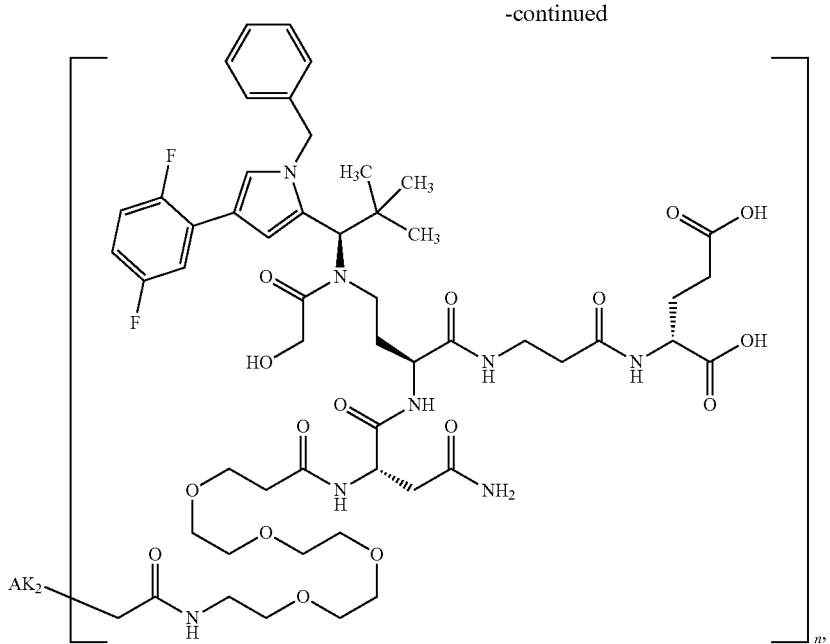

in which

AK$_1$ and AK$_2$ are an antibody or an antigen-binding antibody fragment, and n is a number from 1 to 50, preferably 1 to 20, more preferably 2 to 8 and especially 2 to 6.

KSP Inhibitor-Linker Intermediates or Prodrug-Linker Intermediates and Preparation of the Conjugates The conjugates according to the invention are prepared by initially providing the low-molecular weight KSP inhibitor or the prodrug thereof with a linker. The intermediate obtained in this manner is then reacted with the binder (preferably antibody).

Preferably, for coupling to a cysteine residue, one of the compounds below is reacted with the cysteine-containing binder such as an antibody, which is optionally partially reduced for this purpose:

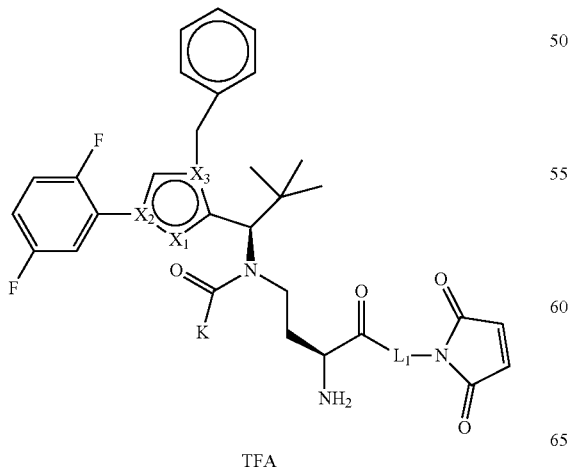

TFA

-continued

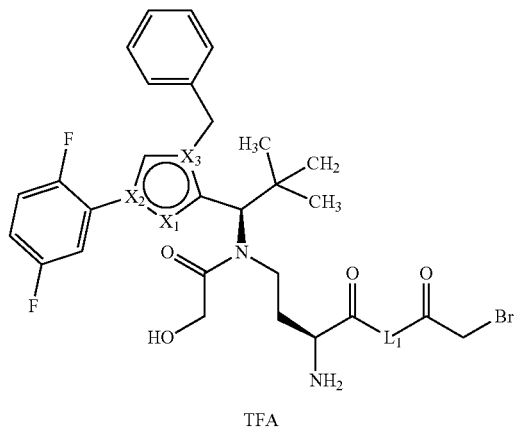

TFA

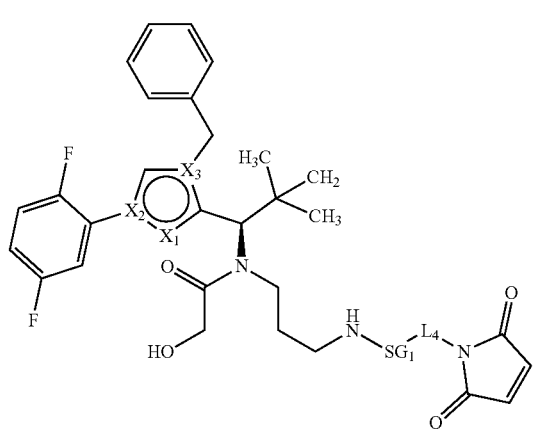

125
-continued
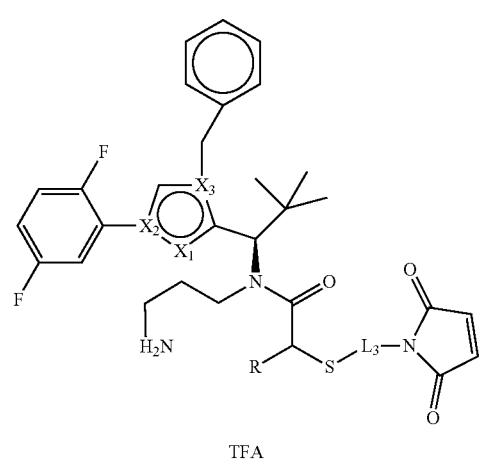
TFA
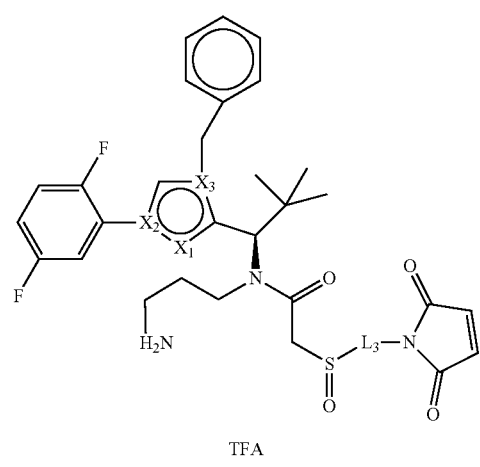
TFA
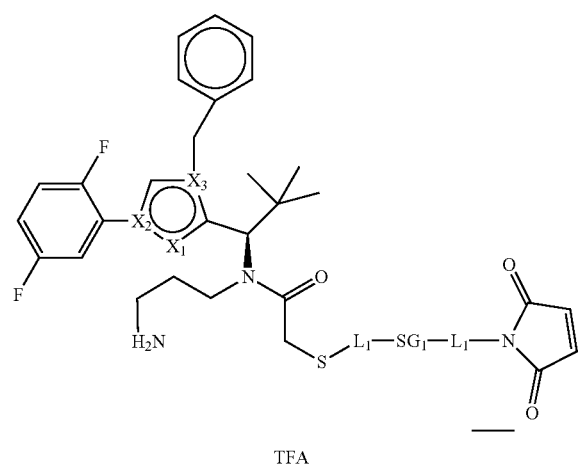
TFA
126
-continued
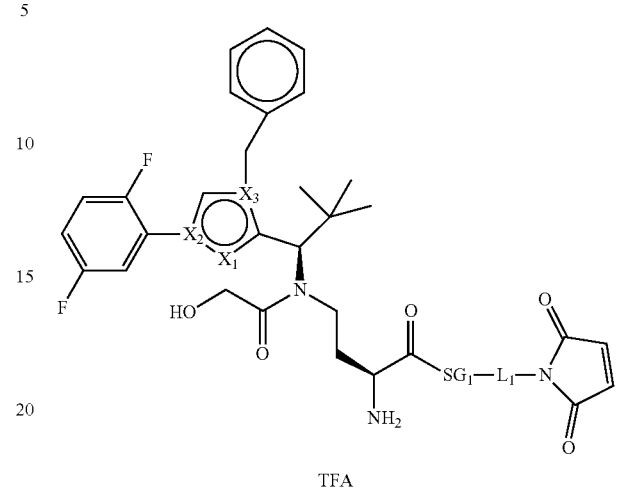
TFA
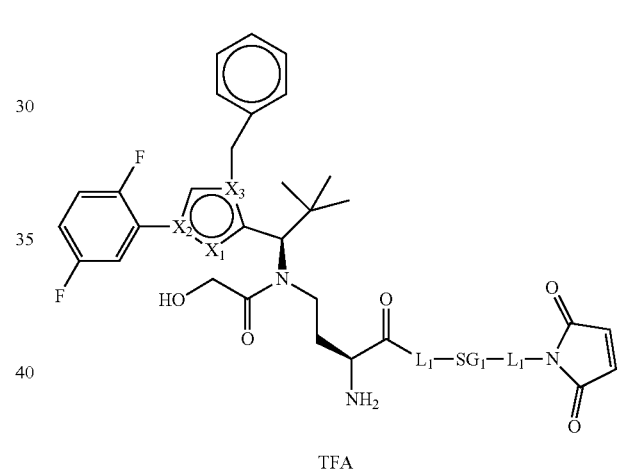
TFA
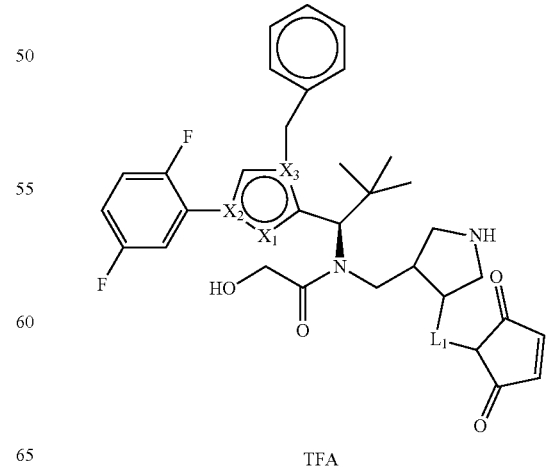
TFA -continued

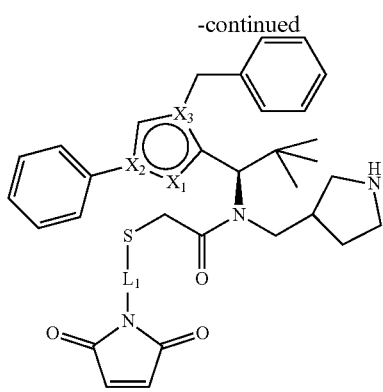

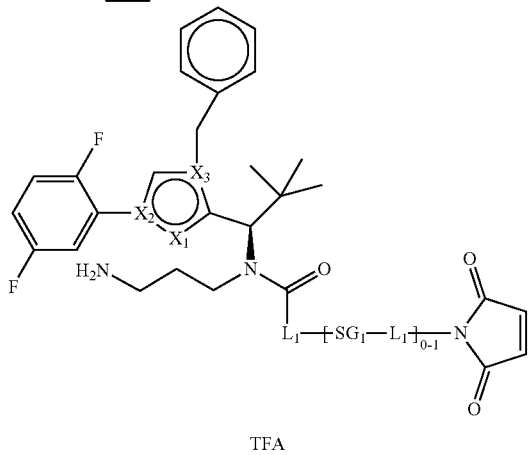

TFA in which
X$_1$ is CH,
X$_2$ is C,
X$_3$ is N,
R is —H or —COOH,
K is linear or branched, optionally C$_1$-C$_6$ alkoxy- or —OH-substituted C$_1$-C$_6$ alkyl and
SG$_1$, L$_1$, L$_2$, L$_3$
and L4 have the definitions given above.

In the above-described formulae, and also in the reaction schemes and structural formulae which follow, the hydrogen atom in position R$^4$ according to formula IIa, i.e. in the —NH2 group, may be replaced by the legumain-cleavable group of the formula Ia used in accordance with the invention.

In each of the above compounds and in the compounds below, the tert-butyl group may be replaced by cyclohexyl.

The compound can be used, for example, in the form of its trifluoroacetic acid salt. For reaction with the binder, for example with the antibody, the compound is preferably used in a 2- to 12-fold molar excess with respect to the binder.

Preferably, for coupling to a lysine residue, one of the compounds below is reacted with the lysine-containing binder such as an antibody:

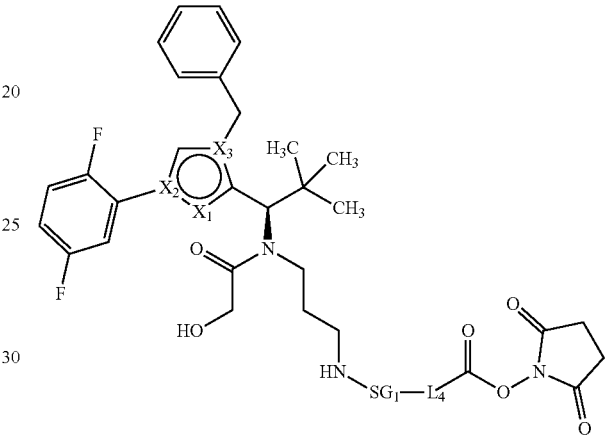

In the formula,
X$_1$ is CH,
X$_2$ is C,
X$_3$ is N and
L$_4$ has the same definition as L$_1$, where L$_1$ has the same definition as described above.

For an intermediate that couples to a cysteine residue, the reactions can be illustrated as follows:

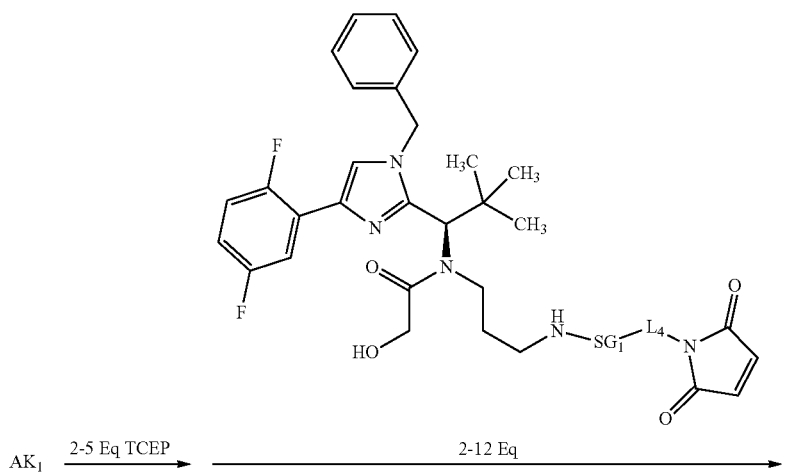

AK$_1$ $\xrightarrow{\text{2-5 Eq TCEP}}$ $\xrightarrow{\text{2-12 Eq}}$

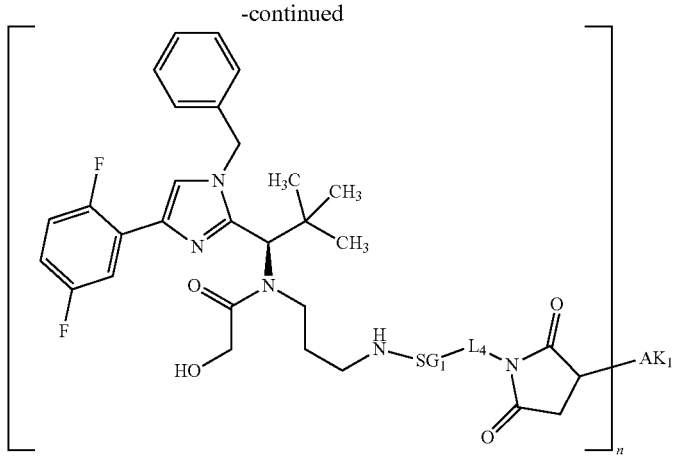
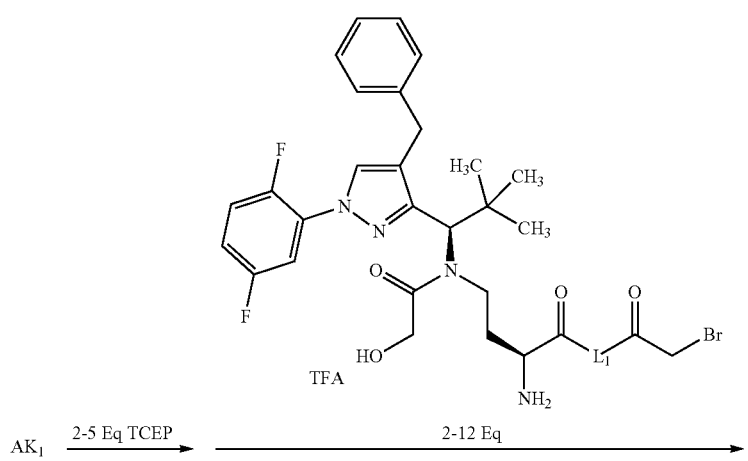
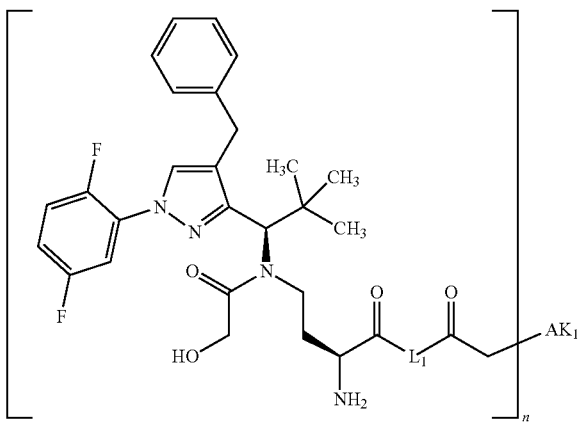
The other intermediates and other antibodies can be reacted correspondingly.
For an intermediate that couples to a lysine residue, the reaction can be illustrated as follows:

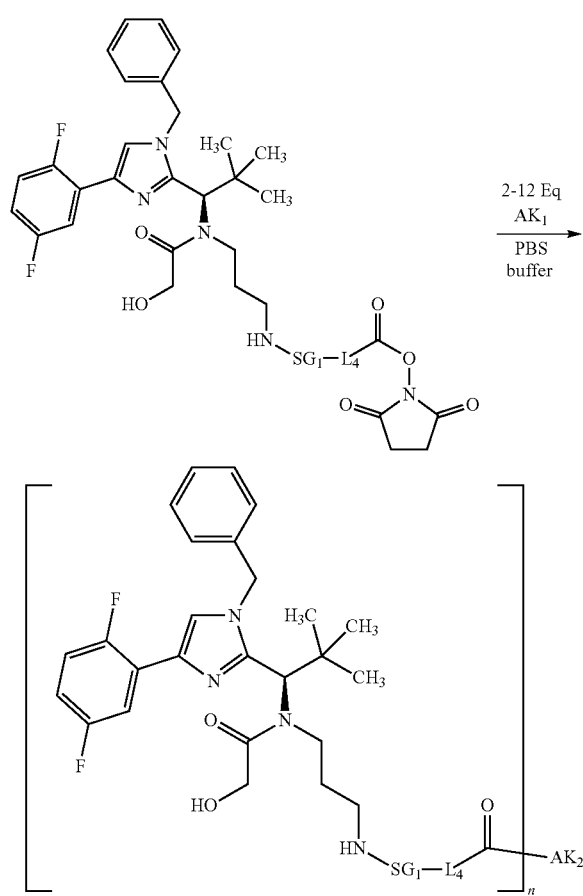

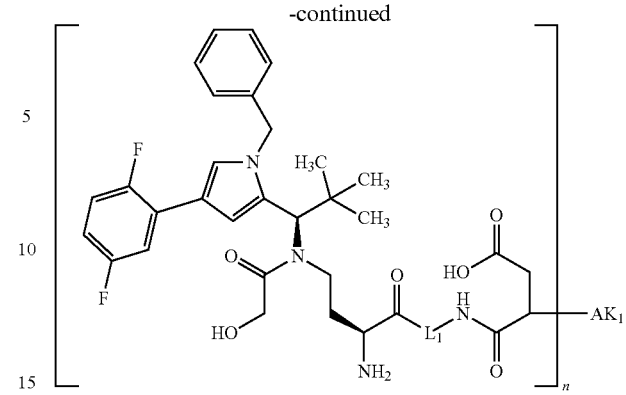

In accordance with the invention, this gives the following conjugates:

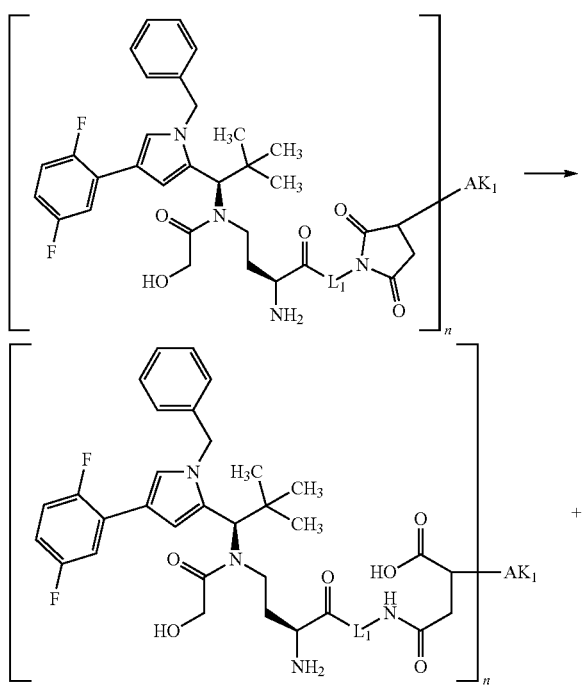

This reaction (ring opening) can be effected at pH 7.5 to 9, preferably at pH 8, at a temperature of 25° C. to 37° C., for example by stirring. The preferred stirring time is 8 to 30 hours.

In the above formulae, X1 represents CH, X2 represents C and X3 represents N, SG1 and L1 have the same definition as described above, and L2, L3 and L4 have the same definition as L1; and R and K have the same definition as described above.

AK1 is an anti-TWEAKR antibody coupled via a cysteine residue, an anti-EGFR antibody, an anti-B7H3 antibody or an anti-HER2 antibody or an antigen-binding fragment of these, and AK2 is an anti-TWEAKR antibody coupled via a lysine residue, an anti-EGFR antibody, an anti-B7H3 antibody or an anti-HER2 antibody or an antigen-binding fragment of these. More preferably, AK1 and AK2 are the anti-TWEAKR antibodies TPP-7006, TPP-7007 and TPP-10337, the anti-B7H3 antibodies TPP-8382 and TPP-8567, the anti-EGFR-antibody cetuximab (TPP-981) and the anti-HER2-antibodies trastuzumab and TPP-1015, or an antigen-binding fragment of these.

Further Definitions

The expression "transglutaminase", also used interchangeably as "TGase" or "TG", is understood to mean an enzyme having the ability to join proteins via an acyl transfer reaction between the γ-carboxamide group of peptide-bound glutamine and the ε-amino group of lysine or a structurally related primary amine, for example an aminopentyl group or, for example, a peptide-bound lysine, which results in an 8-(γ-glutamyl)-lysine isopeptide bond. TGases include bacterial transglutaminase (BTG), for example the enzyme having EC reference number 2.3.2.13 (protein-glutamine γ-glutamyltransferase).

The expression "acceptor glutamine" means, when referring to an amino acid residue of an antibody, a glutamine residue which, under suitable conditions, is recognized by a transglutaminase and can be joined therewith under transglutaminase catalysis by a reaction between this specific glutamine and a lysine or a structurally related primary amine, for example an aminopentyl group. The acceptor glutamine may be a surface-exposed glutamine.

"Amino acid modification" or "mutation" here means an amino acid substitution, insertion and/or deletion in a polypeptide sequence. The preferred amino acid modification here is a substitution. "Amino acid substitution" or "substitution" here means an exchange of an amino acid at a given position in a protein sequence for another amino acid. For example, the substitution Y50W describes a variant of a parent polypeptide in which the tyrosine at position 50 has been exchanged for a tryptophan. A "variant" of a polypeptide describes a polypeptide having an amino acid sequence substantially identical to a reference polypeptide, typically a native or "parent" polypeptide. The polypeptide variant may have one or more amino acid exchanges, deletions and/or insertions at particular positions in the native amino acid sequence.

The expression "conjugation site-specific conjugate" describes a conjugate of a binder, preferably an antibody, and a residue, preferably a linker-drug residue, where the binder is functionalized at one or more defined positions, preferably glutamine residues. Transglutaminases (TGases), including bacterial transglutaminase (BTG) (EC 2.3.2.13), show strong specificity in the recognition of glutamine-protein substrates and can catalyse "conjugation site-specific conjugation".

The expression "homogeneous conjugate" or "homogeneous ADC" describes a mixture of conjugation site-specific conjugates wherein at least 60%, 70%, 80% or 90% of the binders have the same number of conjugated residues per binder. In the case of an antibody, this number should be an even number, preferably 2 or 4.

Isotopes, Salts, Solvates, Isotopic Variants The present invention also encompasses all suitable isotopic variants of the compounds according to the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I, and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labelled with $^3$H or $^{14}$C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by the processes known to those skilled in the art, for example by the methods described further down and the procedures described in the working examples, by using corresponding isotopic modifications of the respective reagents and/or starting compounds.

Preferred salts in the context of the present invention are physiologically acceptable salts of the compounds according to the invention. Also encompassed are salts which are not themselves suitable for pharmaceutical applications but can be used, for example, for isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylpiperidine, N-methylmorpholine, arginine, lysine and 1,2-ethylenediamine.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The present invention additionally also encompasses prodrugs of the compounds according to the invention. The term "prodrugs" in this context refers to compounds which may themselves be biologically active or inactive but are reacted (for example metabolically or hydrolytically) to give compounds according to the invention during their residence time in the body.

PARTICULAR EMBODIMENTS

The following embodiments are particularly preferred:

Embodiment A'

An APDC of the formulae IVa' or IVa" or IVa''', where $D_1$ in the formulae IVa' or IVa" or IVa''' is a compound of the formula (IIe)

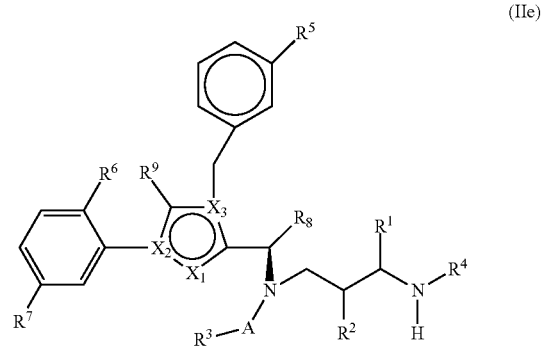

(IIe)

in which
  $X_1$ is N,
  $X_2$ is N and
  $X_3$ is C
    or
  $X_1$ is CH,
  $X_2$ is C and
  $X_3$ is N or
X₁ is NH,
X₂ is C and
X₃ is C
or
X₁ is CH,
X₂ is N and
X₃ is C,
A is —C(=O)—,
R¹ is -L-#1, —H, —COOH, —C(=O)—NHNH₂, —(CH₂)₁₋₃NH₂, —C(=O)—NZ"(CH₂)₁₋₃NH₂ and —C(=O)—NZ"CH₂—C(=O)—OH,
Z" is —H or —NH₂,
R² is —H,
R⁴ is a group of the formula (Ia)
R³ is -L-#1 or a C₁₋₁₀-alkyl group which may optionally be substituted by —OH, —O-alkyl, —SH, —S-alkyl, —O—C(=O)-alkyl, —O—C(=O)—NH-alkyl, —NH—C(=O)-alkyl, —NH—C(=O)—NH-alkyl, —S(=O)ₙ-alkyl, —S(=O)₂—NH-alkyl, —NH-alkyl, —N(alkyl)₂, or —NH₂,
R⁵ is —H or —F,
R⁶ and R⁷ are independently —H, C₁₋₃-alkyl, fluoro-C₁₋₃-alkyl, C₂₋₄-alkenyl, fluoro-C₂₋₄-alkenyl, C₂₋₄-alkynyl, fluoro-C₂₋₄-alkynyl, hydroxyl or halogen,
R⁸ is a branched C₁₋₅-alkyl group or cyclohexyl group,
R⁹ is —H or —F,
L-#1 is the linker group

§ —(C(=O))ₘ-(L1)ₙ-L2- § § in which
m and n are independently 0 or 1,
§ represents the bond to the KSP inhibitor,
§ § represents the bond to the antibody,
L2 is one of the groups

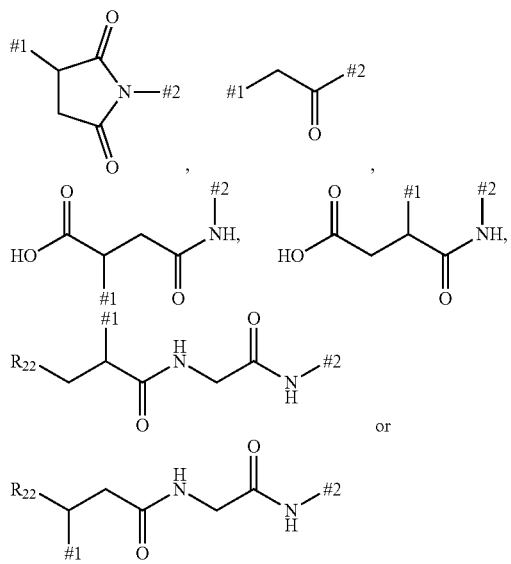

¹ is the linkage site to the sulphur atom of the antibody,
² is the linkage site to the L1 group,
L1 is the group

¹—(NR¹⁰)ₙ-(G1)ₒ-G2-#² in which
R¹⁰ is —H, —NH₂ or C₁₋₃-alkyl,
G1 is —NHC(=O)— or

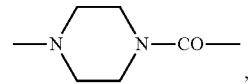, n is 0 or 1,
o is 0 or 1 and
G2 is a straight-chain or branched hydrocarbon chain having 1 to 100 carbon atoms, composed of arylene groups and/or straight-chain and/or branched and/or cyclic alkylene groups, which may be interrupted once or more than once, identically or differently, by —O—, —S—, —S(=O)—, —S(=O)₂—, —NH—, —C(=O)—, —NH—C(=O)—, —C(=O)—NH—, —NMe-, —NHNH—, —S(=O)₂—NHNH—, —C(=O)—NHNH— and a 3- to 10-membered aromatic or nonaromatic heterocycle having up to 4 heteroatoms selected from =N—, —O— and —S—, or —S(=O)—, where the straight-chain or branched hydrocarbon chain may be substituted by —NH—C(=O)—NH₂, —COOH, —OH, —NH₂, sulphonamide, sulphone, sulphoxide, or sulphonic acid,
¹ is the bond to the KSP inhibitor,
² is the bond to L2 to the antibody,
where one of the substituents R¹ and R³ is the linker group -L-#1, and the salts, solvates and salts of the solvates thereof, and where the antibodies mentioned in the formulae IVa' or IVa" or IVa'" are human, humanized or chimeric monoclonal antibodies or an antigen-binding fragment thereof, and n in the formulae IVa' or IVa" or IVa' is a number from 1 to 10.

Preferably, the antibody here is an anti-TWEAKR antibody, an anti-EGFR antibody, an anti-B7H3 antibody or an anti-HER2 antibody or an antigen-binding fragment of these.

Particular preference is given to the anti-TWEAKR antibodies TPP-7006, TPP-7007 and TPP-10337, the anti-B7H3 antibodies TPP-8382 and TPP-8567, the anti-EGFR-antibody cetuximab (TPP-981) and the anti-HER2-antibodies trastuzumab and TPP-1015, or an antigen-binding fragment of these.

Preference is given here to those compounds of the formula (IIe) in which R₃ is defined as alkyl, preferably as C₁₋₃ alkyl.

In this context, G2 is preferably

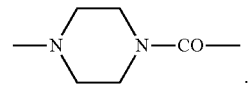.

Alternatively, the linker -L-#1 may be bonded to a lysine side chain or a lysine residue. In that case, it preferably has the following formula:

- § —(SG)ₓ-L4-C(=O)— § § in which
§ represents the bond to the KSP inhibitor,
§ § represents the bond to the antibody,
x is 0 or 1,
SG is a cleavable group,
L4 is a single bond or a group

—(C(=O))ᵧ-G4- y is 0 or 1 and

G4 is a straight-chain or branched hydrocarbon chain having 1 to 100 carbon atoms, composed of arylene groups and/or straight-chain and/or branched and/or cyclic alkylene groups, which may be interrupted once or more than once, identically or differently, by —O—, —S—, —S(=O)—, —S(=O)$_2$—, —NH—, —C(=O)—, —NH—C(=O)—, —C(=O)—NH—, —NMe-, —NHNH—, —S(=O)$_2$—NHNH—, —C(=O)—NHNH— and a 5- to 10-membered aromatic or nonaromatic heterocycle having up to 4 heteroatoms selected from =N—, —O— and —S—, —S(=O)— or —S(=O)$_2$—, where the straight-chain or branched hydrocarbon chain may be substituted by —NH—C(=O)—NH$_2$, —COOH, —OH, sulphonamide, sulphone, sulphoxide or sulphonic acid.

In this context, SG is preferably a 2-8 oligopeptide, more preferably a dipeptide.

Preferably, the straight-chain or branched hydrocarbon chain of G4 may be interrupted by

—N⌒N—CO—
  ⌣

Embodiment B'

An APDC of the formulae IVa' or IVa" or IVa'", where D$_1$ in the formulae IVa' or IVa" or IVa'" is a compound of the formula (IIf)

(IIf)

in which
X$_1$ is N,
X$_2$ is N and
X$_3$ is C,
or
X$_1$ is CH,
X$_2$ is C and
X$_3$ is N,
or
X$_1$ is NH,
X$_2$ is C and
X$_3$ is C,
or
X$_1$ is CH,
X$_2$ is N and
X$_3$ is C,
A is —C(=O)—, R$^1$ is -L-#1, —H, —COOH, —C(=O)—NHNH$_2$, —(CH$_2$)$_{1-3}$NH$_2$, —C(=O)—NZ"(CH$_2$)$_{1-3}$NH$_2$ and —C(=O)—NZ"CH$_2$C(=O)—OH, Z" is —H or —NH$_2$,
R$^2$ is —H,
R$^4$ is a group of the formula (Ia),
R$^3$ is -L-#1 or a C$_{1-10}$-alkyl group which may optionally be substituted by —OH, —O-alkyl, —SH, —S-alkyl, —O—C(=O)-alkyl, —O—C(=O)—NH-alkyl, —NH—C(=O)-alkyl, —NH—C(=O)—NH-alkyl, —S(=O)$_n$-alkyl, —S(=O)$_2$—NH-alkyl, —NH-alkyl, —N(alkyl)$_2$ and —NH$_2$, R$^5$ is —H or —F,
R$^6$ and R$^7$ are independently —H, C$_{1-3}$-alkyl, fluoro-C$_{1-3}$-alkyl, C$_{2-4}$-alkenyl, fluoro-C$_{2-4}$-alkenyl, C$_{2-4}$-alkynyl, fluoro-C$_{2-4}$-alkynyl, hydroxyl or halogen,
R$^8$ is a branched C$_{1-5}$-alkyl group,
R$^9$ is —H or —F,
L-#1 is the group §—(C(=O))$_m$-(L1)$_n$-L2- § § in which
m is 0 or 1;
§ represents the bond to the KSP inhibitor,
§ § represents the bond to the antibody,
L2 is the group

$^1$ is the linkage site to the sulphur atom of the antibody,
$^2$ is the linkage site to the L1 group,
L1 is the group

$^1$—(NR$^{10}$)$_n$-(G1)$_o$-G2-#$^2$ in which
R$^{10}$ is —H, —NH$_2$ or C$_{1-3}$-alkyl,
G1 is —NH—C(=O)— or

—N⌒N—CO—
  ⌣ n is 0 or 1,
is 0 or 1,

G2 is a straight-chain or branched hydrocarbon chain having 1 to 100 carbon atoms, composed of arylene groups and/or straight-chain and/or branched and/or cyclic alkylene groups, which may be interrupted once or more than once, identically or differently, by —O—, —S—, —S(=O)—, —S(=O)$_2$—, —NH—, —C(=O)—, —NH—C(=O)—, —C(=O)—NH—, —NMe-, —NHNH—, —S(=O)$_2$—NHNH—, —C(=O)—NHNH— and a 3- to 10-membered, aromatic or nonaromatic heterocycle having up to 4 heteroatoms, selected from =N—, —O— and —S—, or —S(=O)—, where the straight-chain or branched hydrocarbon chain may be substituted by —NH—C(=O)—NH2, —COOH, —OH, —NH$_2$, sulphonamide, sulphone, sulphoxide, or sulphonic acid,

1 is the bond to the KSP inhibitor,
2 is the bond to L2 to the antibody, where one of the substituents $R^1$ and $R^3$ is the linker group -L-#1, and the salts, solvates and salts of the solvates thereof, and where the antibodies mentioned in the formulae IVa' or IVa" or IVa''' are human, humanized or chimeric monoclonal antibodies or an antigen-binding fragment thereof, and n in the formulae IVa' or IVa" or IVa' is a number from 1 to 10.

Preferably, the antibody here is an anti-TWEAKR antibody, an anti-EGFR antibody, an anti-B7H3 antibody or an anti-HER2 antibody or an antigen-binding fragment of these.

Particular preference is given to the anti-TWEAKR antibodies TPP-7006, TPP-7007 and TPP-10337, the anti-B7H3 antibodies TPP-8382 and TPP-8567, the anti-EGFR-antibody cetuximab (TPP-981) and the anti-HER2-antibodies trastuzumab and TPP-1015, or an antigen-binding fragment of these.

Preference is given here to those compounds of the formula (IIf) in which $R_3$ is defined as alkyl, preferably as $C_{1-3}$ alkyl.

In this context, G2 is preferably

—N⌒N—CO—.

Alternatively, the linker -L-#1 may be bonded to a lysine side chain or a lysine residue. In that case, it preferably has the following formula:

- § —(SG)r-L4-C(=O)— § § in which
§ represents the bond to the KSP inhibitor,
§ § represents the bond to the antibody,
x is 0 or 1,
SG is a cleavable group,
L4 is a single bond or a group —(C=O)$_y$-G4- y is 0 or 1 and
G4 is a straight-chain or branched hydrocarbon chain having 1 to 100 carbon atoms, composed of arylene groups and/or straight-chain and/or branched and/or cyclic alkylene groups, which may be interrupted once or more than once, identically or differently, by —O—, —S—, —S(=O)—, —S(=O)$_2$—, —NH—, —C(=O)—, —NH—C(=O)—, —C(=O)—NH—, —NMe-, —S(=O)$_2$—NHNH—, —C(=O)—NHNH— and a 5- to 10-membered, aromatic or non-aromatic heterocycle having up to 4 heteroatoms, selected from =N—, —O— and —S—, —S(=O)— or —S(=O)$_2$—, where the straight-chain or branched hydrocarbon chain may be substituted by —NH—C(=O)—NH$_2$, —COOH, —OH, sulphonamide, sulphone, sulphoxide, or sulphonic acid.

In this context, SG is preferably a 2-8 oligopeptide, more preferably a dipeptide.

Preferably, the straight-chain or branched hydrocarbon chain of G4 may be interrupted by

—N⌒N—CO—.

Embodiment C'

An APDC of the formula IVa' or IVa" or IVa''', where $D_1$ in the formulae IVa' or IVa" or IVa''' is a compound of the formula (IIg)

(IIg)

in which
$X_1$ is N,
$X_2$ is N and
$X_3$ is C
or
$X_1$ is CH,
$X_2$ is C and
$X_3$ is N
or
$X_1$ is NH,
$X_2$ is C and
$X_3$ is C
or
$X_1$ is CH,
$X_2$ is N and
$X_3$ is C,
A is —C(=O)—,
$R^1$ is -L-#1,
$R^2$ is —H,
$R^4$ is a group of the formula (Ia),
$R^3$ is a $C_{1-10}$-alkyl group which may optionally be substituted by —OH, —O-alkyl, —SH, —S-alkyl, —O—C(=O)-alkyl, —O—C(=O)—NH-alkyl, —NH—C(=O)-alkyl, —NH—C(=O)—NH-alkyl, —S(=O)$_n$-alkyl, —S(=O)$_2$—NH-alkyl, —NH-alkyl, —N(alkyl)$_2$ or —NH$_2$, or is -MOD, MOD is the group

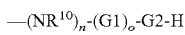

R[10] is —H or $C_1$-$C_3$-alkyl;
G1 is —NH—C(=O)—, —C(=O)—NH— or

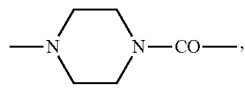

n is 0 or 1,
is 0 or 1,
G2 is a straight-chain and/or branched hydrocarbon chain which has 1 to 10 carbon atoms and may be interrupted once or more than once, identically or differently, by —O—, —S—, —SO—, —S(=O)$_2$—, —NR$^y$—, —NR$^y$C(=O)—, —C(=O)NR$^y$—, —NR$^y$NR$^y$—, —S(=O)$_2$—NR$^y$NR$^y$—, —C(=O)—NR$^y$NR$^y$—C(=O)— or —CR$^x$=N—O—, where the straight-chain or branched hydrocarbon chain may be substituted by —NH—C(=O)—NH2, —COOH, —OH, —NH$_2$, sulphonamide, sulphone, sulphoxide, or sulphonic acid,
Rx is —H, $C_1$-$C_3$-alkyl or phenyl, R$^y$ is —H, phenyl, $C_1$-$C_{10}$-alkyl, $C_2$-$C_{10}$-alkenyl or $C_2$-$C_{10}$-alkynyl, each of which may be substituted by —NH—C(=O)—NH$_2$, —COOH, —OH, —NH$_2$, sulphonamide, sulphone, sulphoxide, or sulphonic acid,
R$^5$ is —H or —F,
R$^6$ and R$^7$ are independently —H, $C_{1-3}$-alkyl, fluoro-$C_{1-3}$-alkyl, $C_{2-4}$-alkenyl, fluoro-$C_{2-4}$-alkenyl, $C_{2-4}$-alkynyl, fluoro-$C_{2-4}$-alkynyl, hydroxyl or halogen,
R$^8$ is a branched $C_{1-5}$-alkyl group,
R$^9$ is —H or —F,
L-#1 is the linker group

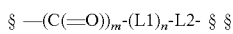

in which
m, n are independently 0 or 1,
§ represents the bond to the KSP inhibitor,
§ § represents the bond to the antibody,
L2 is one of the groups

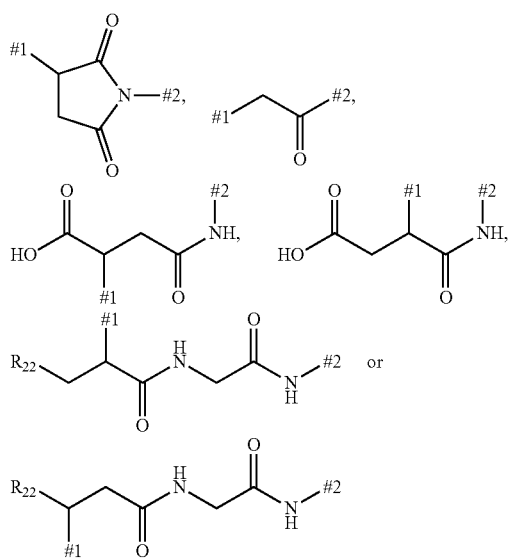

[1] is the linkage site to the sulphur atom of the antibody,
[2] is the linkage site to the L1 group,
L1 is the group

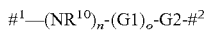

in which
R[10] is —H, —NH$_2$ or $C_{1-3}$-alkyl,
G1 is —NHC(=O)— or

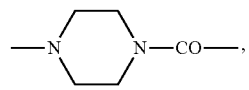

n is 0 or 1,
o is 0 or 1 and
G2 is a straight-chain or branched hydrocarbon chain having 1 to 100 carbon atoms, composed of arylene groups and/or straight-chain and/or branched and/or cyclic alkylene groups, which may be interrupted once or more than once, identically or differently, by —O—, —S—, —S(=O)—, —S(=O)$_2$—, —NH—, —C(=O)—, —NH—C(=O)—, —C(=O)—NH—, —NMe-, —NHNH—, —S(=O)$_2$—NHNH—, —C(=O)—NHNH— and a 3- to 10-membered aromatic or nonaromatic heterocycle having up to 4 heteroatoms selected from =N—, —O— and —S—, or —S(=O)—, where the straight-chain or branched hydrocarbon chain may be substituted by —NH—C(=O)—NH$_2$, —COOH, —OH, —NH$_2$, sulphonamide, sulphone, sulphoxide, or sulphonic acid,
1 is the bond to the KSP inhibitor,
2 is the bond to L2 to the antibody,
and the salts, solvates and salts of the solvates thereof, and where the antibodies mentioned in the formulae IVa' or IVa" or IVa'" are human, humanized or chimeric monoclonal antibodies or an antigen-binding fragment thereof, and n in the formulae IVa' or IVa" or IVa'" is a number from 1 to 10.

Preferably, the antibody here is an anti-TWEAKR antibody, an anti-EGFR antibody, an anti-B7H3 antibody or an anti-HER2 antibody or an antigen-binding fragment of these.

Particular preference is given to the anti-TWEAKR antibodies TPP-7006, TPP-7007 and TPP-10337, the anti-B7H3 antibodies TPP-8382 and TPP-8567, the anti-EGFR-antibody cetuximab (TPP-981) and the anti-HER2-antibodies trastuzumab and TPP-1015, or an antigen-binding fragment of these.

Preference is given here to those compounds of the formula (IIg) in which R$^3$ is defined as alkyl, preferably as $C_{1-3}$ alkyl.

In this case, -MOD preferably has at least one COOH— group.

Embodiment D'

An APDC of the formulae IVa' or IVa" or IVa'", where D$_1$ in the formulae IVa' or IVa" or IVa'" is a compound of the formula (IIh)

(IIh)

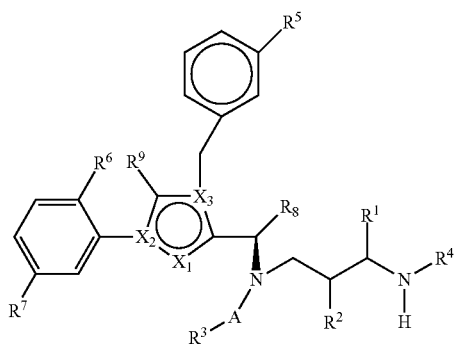

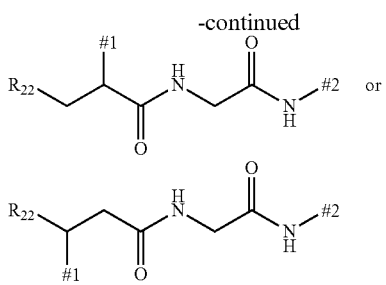

in which
X$_1$ is N,
X$_2$ is N and
X$_3$ is C
or
X$_1$ is CH,
X$_2$ is C and
X$_3$ is N
or
X$_1$ is NH,
X$_2$ is C and
X$_3$ is C
or
X$_1$ is CH,
X$_2$ is N and
X$_3$ is C,
A is —C(=O)—,
R$^1$ is —H or —COOH,
R$^2$ is —H,
R$^4$ is a group of the formula Ia,
R$^3$ is -L-#1,
R$^5$ is —H or —F,
R$^6$ and R$^7$ are independently —H, C$_{1-3}$-alkyl, fluoro-C$_{1-3}$-alkyl, C$_{2-4}$-alkenyl, fluoro-C$_{2-4}$-alkenyl, C$_{2-4}$-alkynyl, fluoro-C$_{2-4}$-alkynyl, hydroxyl or halogen,
R$^8$ is a branched C$_{1-5}$-alkyl group,
R$^9$ is —H or —F,
L-#1 is the linker group § —(C(=O))$_m$-(L1)$_n$-L2- § § in which
m, n are independently 0 or 1,
§ represents the bond to the KSP inhibitor,
§ § represents the bond to the antibody,
L2 is one of the groups

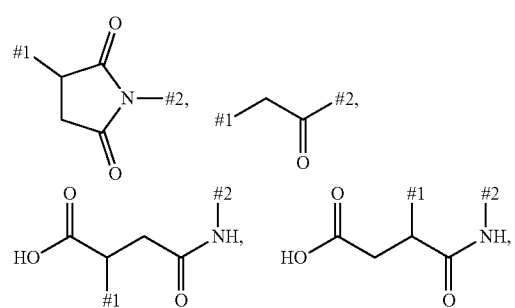

$^1$ is the linkage site to the sulphur atom of the antibody,
$^2$ is the linkage site to the L1 group,
L1 is the group

$^1$—(NR$^{10}$)$_n$-(G1)$_o$-G2-#$^2$ in which
R$^{10}$ is —H, —NH$_2$ or C$_{1-3}$-alkyl,
G1 is —NHC(=O)— or

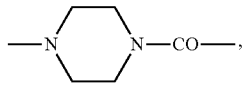

n is 0 or 1,
o is 0 or 1 and
G2 is a straight-chain or branched hydrocarbon chain having 1 to 100 carbon atoms, composed of arylene groups and/or straight-chain and/or branched and/or cyclic alkylene groups, which may be interrupted once or more than once, identically or differently, by —O—, —S—, —S(=O)—, —S(=O)$_2$—, —NH—, —C(=O)—, —NH—C(=O)—, —C(=O)—NH—, —NMe-, —NHNH—, —S(=O)$_2$—NHNH—, —C(=O)—NHNH— and a 3- to 10-membered aromatic or nonaromatic heterocycle having up to 4 heteroatoms selected from =N—, —O— and —S—, or —S(=O)—, where the straight-chain or branched hydrocarbon chain may be substituted by —NH—C(=O)—NH$_2$, —COOH, —OH, —NH$_2$, sulphonamide, sulphone, sulphoxide, or sulphonic acid,
1 is the bond to the KSP inhibitor,
2 is the bond to L2 to the antibody, and the salts, solvates and salts of the solvates thereof, and where the antibodies mentioned in the formulae IVa' or IVa" or IVa' are human, humanized or chimeric monoclonal antibodies or an antigen-binding fragment thereof, and n in the formulae IVa' or IVa" or IVa''' is a number from 1 to 10.

Preferably, the antibody here is an anti-TWEAKR antibody, an anti-EGFR antibody, an anti-B7H3 antibody or an anti-HER2 antibody or an antigen-binding fragment of these.

Particular preference is given to the anti-TWEAKR antibodies TPP-7006, TPP-7007 and TPP-10337, the anti-B7H3 antibodies TPP-8382 and TPP-8567, the anti-EGFR-antibody cetuximab (TPP-981) and the anti-HER2-antibodies trastuzumab and TPP-1015, or an antigen-binding fragment of these.

In this context, G2 is preferably

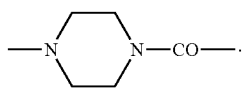

Embodiment E'

An APDC of the formulae IVa' or IVa'' or IVa''', where $D_1$ in the formulae IVa' or IVa'' or IVa''' is a compound of the formula (IIi)

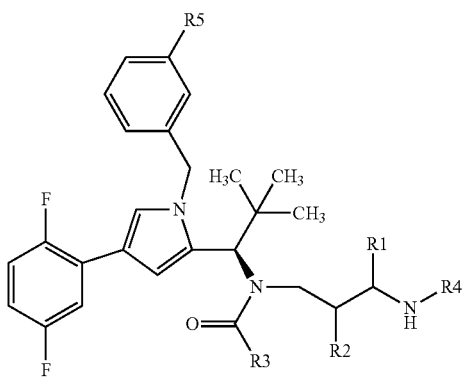

(IIi)

in which
$R^1$ is -L-#1,
L-#1 is the linker group

§ —(C(=O))$_m$-(L1)$_n$-L2- § § in which
m, n are independently 0 or 1,
§ represents the bond to the KSP inhibitor,
§ § represents the bond to the antibody,
L2 is the group

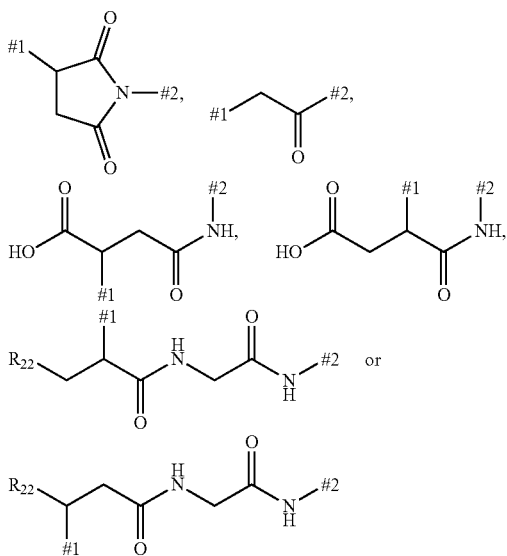

$R^{22}$ is —COOH, —C(=O)—O—C$_{1-3}$-alkyl, —C(=O)—C$_{1-3}$-alkyl, —C(=O)—NH—C$_{1-3}$-alkyl or —C(=O)—NH2,
1 is the linkage site to the sulphur atom of the antibody,
2 is the bond to L1,
L1 is the group

$^1$—(NR$^{10}$)$_n$-(G1)$_o$-G2-#$^2$ in which
$R^{10}$ is —H,
G1 is —NHC(=O)— or

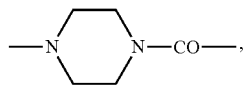

n is 0 or 1,
is 0 or 1,
G2 is C$_{1-3}$-alkyl,
1 is the bond to the KSP inhibitor,
2 is the bond to L2 to the antibody,
$R^2$ and $R^5$ are —H,
$R^3$ is —CH$_2$OH and
$R^4$ is a group of the formula (Ia),
and the salts, solvates and salts of the solvates thereof, and where the antibodies mentioned in the formulae IVa' or IVa'' or IVa''' are human, humanized or chimeric monoclonal antibodies or an antigen-binding fragment thereof, and n in the formulae IVa' or IVa'' or IVa''' is a number from 1 to 10.

Preference is given to those compounds of the formula (IIi) in which $R^{22}$ is —COOH.

In a conjugate according to the invention or in a mixture of the conjugates according to the invention, the bonds to a cysteine residue of the antibody, based in each case on the total number of bonds of the linker to the antibody, are preferably present to an extent of more than 80%, more preferably to an extent of more than 90%.

Particular preference is given here in accordance with the invention to conjugates having, as L2, the group

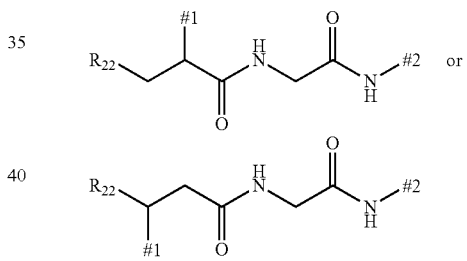

in which $R^{22}$ has the definitions given above.

In general, conjugates having both kinds of L2 group are present, preferably in a ratio of from 60:40 to 40:60, based on the number of bonds to the antibody.

The remaining bonds are then present with the structure

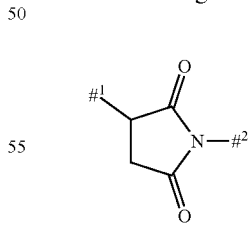

in which #1 and #2 have the definitions given above.

Preferably, the antibody here is an anti-TWEAKR antibody, an anti-EGFR antibody, an anti-B7H3 antibody or an anti-HER2 antibody or an antigen-binding fragment of these.

Particular preference is given to the anti-TWEAKR antibodies TPP-7006, TPP-7007 and TPP-10337, the anti-B7H3 antibodies TPP-8382 and TPP-8567, the anti-EGFR-antibody cetuximab (TPP-981) and the anti-HER2-antibodies trastuzumab and TPP-1015, or an antigen-binding fragment of these.

Therapeutic Uses

The hyper-proliferative diseases, for the treatment of which the compounds according to the invention may be employed, include in particular the group of cancer and tumour diseases. In the context of the present invention, these are understood to mean especially the following diseases, but without any limitation thereto: mammary carcinomas and mammary tumours (mammary carcinomas including ductal and lobular forms, also in situ), tumours of the respiratory tract (small-cell and non-small cell carcinoma, bronchial carcinoma), cerebral tumours (e.g. of the brain stem and of the hypothalamus, astrocytoma, ependymoma, glioblastoma, glioma, medulloblastoma, meningioma and neuro-ectodermal and pineal tumours), tumours of the digestive organs (carcinomas of the oesophagus, stomach, gall bladder, small intestine, large intestine, rectum and anal carcinomas), liver tumours (inter alia hepatocellular carcinoma, cholangiocarcinoma and mixed hepatocellular cholangiocarcinoma), tumours of the head and neck region (larynx, hypopharynx, nasopharynx, oropharynx, lips and oral cavity carcinomas, oral melanomas), skin tumours (basaliomas, spinaliomas, squamous cell carcinomas, Kaposi's sarcoma, malignant melanoma, non-melanomatous skin cancer, Merkel cell skin cancer, mast cell tumours), tumours of soft tissue (inter alia soft tissue sarcomas, osteosarcomas, malignant fibrous histiocytomas, chondrosarcomas, fibrosarcomas, hemangiosarcomas, leiomyosarcomas, liposarcomas, lymphosarcomas and rhabdomyosarcomas), tumours of the eyes (inter alia intraocular melanoma and retinoblastoma), tumours of the endocrine and exocrine glands (e.g. of the thyroid and parathyroid glands, pancreas and salivary gland carcinomas, adenocarcinomas), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testes in men). These also include proliferative diseases of the blood, the lymph system and the spinal cord, in solid form and as circulating cells, such as leukaemias, lymphomas and myeloproliferative diseases, for example acute myeloid, acute lymphoblastic, chronic lymphocytic, chronic myelogenous and hairy cell leukaemia, and AIDS-correlated lymphomas, Hodgkin's lymphomas, non-Hodgkin's lymphomas, cutaneous T cell lymphomas, Burkitt's lymphomas and lymphomas in the central nervous system.

These well-characterized diseases in humans can also occur with a comparable aetiology in other mammals and can likewise be treated there with the compounds of the present invention.

The treatment of the cancer diseases mentioned above with the compounds according to the invention comprises both a treatment of the solid tumours and a treatment of metastasizing or circulating forms thereof.

In the context of this invention, the term "treatment" or "treat" is used in the conventional sense and means attending to, caring for and nursing a patient with the aim of combating, reducing, attenuating or alleviating a disease or health abnormality, and improving the living conditions impaired by this disease, as, for example, in the event of a cancer.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides for the use of the compounds of the invention in a method for treatment and/or prevention of disorders, especially of the aforementioned disorders.

The present invention further provides a process for treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further drugs, especially for treatment and/or prevention of the aforementioned disorders.

For example, the compounds of the present invention can be combined with known anti-hyper-proliferative, cytostatic, cytotoxic or immunotherapeutic substances for the treatment of cancer diseases. Examples of suitable combination drugs include: 131I-chTNT, abarelix, abiraterone, aclarubicin, adalimumab, ado-trastuzumab emtansin, afatinib, aflibercept, aldesleukin, alemtuzumab, alendronic acid, alitretinoin, altretamine, amifostine, aminoglutethimide, hexyl 5-aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, atezolizumab, avelumab, axitinib, azacitidine, belotecan, bendamustine, besilesomab, belinostat, bevacizumab, bexaroten, bicalutamide, bisantrene, bleomycin, blinatumomab, bortezomib, buserelin, bosutinib, brentuximab vedotin, busulfan, cabazitaxel, cabozantinib, calcitonin, calcium folinate, calcium levofolinate, capecitabine, capromab, carbamazepine, carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, dabrafenib, darolutamide, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, durvalumab, edrecolomab, elliptinium acetate, endostatin, enocitabine, enzalutamide, epacadostat, epirubicin, epitiostanol, epoetin-alfa, epoetin-beta, epoetin-zeta, eptaplatin, eribulin, erlotinib, esomeprazole, estramustine, etoposide, ethinylestradiol, everolimus, exemestane, fadrozole, fentanyl, fluoxymesterone, floxuridine, fludarabine, fluoruracil, flutamide, folic acid, formestan, fosaprepitant, fotemustine, fulvestrant, gadobutrol, gadoteridol, gadoteric acid meglumine salt, gadoversetamide, gadoxetic acid disodium salt (Gd-EOB-DTPA disodium salt), gallium nitrate, ganirelix, gefitinib, gemcitabine, gemtuzumab, glucarpidase, glutoxim, goserelin, granisetron, granulocyte colony stimulating factor (G-CSF), granulocyte macrophage colony stimulating factor (GM-CSF), histamine dihydrochloride, histrelin, hydroxycarbamide, I-125 seeds, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon-gamma, iobitridol, iobenguane (123I), iomeprol, ipilimumab, irinotecan, itraconazole, ixabepilone, ixazomib, Ianreotide, Iansoprazole, lapatinib, lasocholine, lenalidomide, lenvatinib, lenograstim, lentinan, letrozole, leuprorelin, levamisole, levonorgestrel, levothyroxin-sodium, lipegfilgrastim, lisurid, lobaplatin, lomustin, Ionidamin, masoprocol, medroxyprogesterone, megestrol, melarsoprol, melphalan, mepitiostane, mercaptopurine, mesna, methadone, methotrexate, methoxsalen, methyl aminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumab, nivolumab pentetreotide, nilotinib, nilutamide, nimorazole, nimotuzumab, nimustine, nintedanib, nitracrin, nivolumab, obinutuzumab, octreotide, ofatumumab, olaparib, olaratumab, omacetaxin mepesuccinate, omeprazole, ondansetron, orgotein, orilotimod, osimertinib, oxaliplatin, oxycodone, oxymetholone, ozogamicin, p53 gene therapy, paclitaxel, palbociclib, palifermin, palladium-103 seed, palonosetron, pamidronic acid, panitumumab, panobinostat, pantoprazole, pazopanib, pegaspargase, pembrolizumab, peg interferon alfa-2b, pembrolizumab, pemetrexed, pentostatin, peplomycin, perflubutane, perfosfamide, pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer-sodium, pralatrexate, prednimustine, prednisone, procarbazine, procodazole, propranolol, quinagolide, rabeprazole, racotumomab, radium-223 chloride, radotinib, raloxifen, raltitrexed, ramosetron, ramucirumab, ranimustine, rasburicase, razoxane, refametinib, regorafenib, risedronic acid, rhenium-186 etidronate, rituximab, rogaratinib, rolapitant, romidepsin, romurtide, roniciclib, samarium (153Sm) lexidronam, satumomab, secretin, siltuximab, sipuleucel-t, sizofiran, sobuzoxane, sodium glycididazole, sonidegib, sorafenib, stanozolol, streptozocin, sunitinib, talaporfin, talimogen laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, treosulfan, tretinoin, trifluridine+tipiracil, trametinib, trilostane, triptorelin, trofosfamide, thrombopoietin, ubenimex, valrubicin, vandetanib, vapreotide, valatinib, vemurafenib, vinblastine, vincristine, vindesine, vinflunine, vinorelbine, vismodegib, vorinostat, yttrium-90 glass microbeads, zinostatin, zinostatin-stimalamer, zoledronic acid, zorubicin.

In addition, the antibodies may be selected from the class of the MPS1 inhibitors or antibodies against the targets OX-40, CD137/4-1BB, DR3, IDO1/IDO2, LAG-3 and CD40.

This invention further provides for the combination of a binder-drug conjugate (ADC) according to the invention with a cancer immunotherapy for use in the treatment of cancer and tumours. The intrinsic mechanism of action of cytotoxic binder-drug conjugates includes the direct triggering of cell death of the tumour cells and hence the release of tumour antigens that can stimulate an immune response. In addition, there are pointers that the KSP inhibitor toxophore class induces markers of what is called immunogenic cell death (ICD) in vitro. Thus, the combination of the binder-drug conjugates (ADCs) of the present invention with one or more therapeutic approaches for cancer immunotherapy or with one or more drugs, preferably antibodies, directed against a molecular target from cancer immunotherapy constitutes a preferred method for treatment of cancer and tumours. i) Examples of therapeutic approaches for cancer immunotherapy include immunomodulatory monoclonal antibodies and low molecular weight substances directed against targets from cancer immunotherapy, vaccines, CAR T cells, bi-specific T cell-recruiting antibodies, oncolytic viruses, cell-based vaccination approaches. ii) Examples of selected targets from cancer immunotherapy suitable for immunomodulatory monoclonal antibodies include CTLA-4, PD-1/PDL-1, OX-40, CD137, DR3, IDO1, IDO2, TDO2, LAG-3, TIM-3, CD40, ICOS/ICOSL, TIGIT; GITR/GITRL, VISTA, CD70, CD27, HVEM/BTLA, CEACAM1, CEACAM6, ILDR2, CD73, CD47, B7H3, TLRs. The combination of a binder-drug conjugate (ADC) according to the invention with cancer immunotherapy could therefore firstly make tumours having weakly immunogenic properties more immunogenic and enhance the effectiveness of cancer immunotherapy and also display a long-lasting therapeutic effect.

In addition, the compounds according to the invention can also be used in combination with radiotherapy and/or surgical intervention.

Generally, the following aims can be pursued with the combination of compounds of the present invention with other cytostatically, cytotoxically or immunotherapeutically active agents:

improved efficacy in slowing the growth of a tumour, in reducing its size or even in completely eliminating it, compared with treatment with an individual active ingredient;

the possibility of using the chemotherapeutics used in a lower dosage than in the case of monotherapy;

the possibility of a more tolerable therapy with fewer side effects compared with individual administration;

the possibility of treatment of a broader spectrum of neoplastic disorders;

the achievement of a higher rate of response to the therapy;

a longer survival time of the patient compared with present-day standard therapy.

In addition, the compounds according to the invention can also be used in combination with radiotherapy and/or surgical intervention.

The present invention further provides medicaments which comprise at least one compound of the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example parenterally, possibly inhalatively or as implants or stents.

The compounds according to the invention can act systemically and/or locally. For this purpose, they can be administered in a suitable manner, for example by the oral, parenteral, pulmonal, nasal, sublingual, lingual, buccal, rectal, vaginal, dermal, transdermal, conjunctival or otic route, or as an implant or stent.

The compounds according to the invention can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay, which control the release of the compound according to the invention), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can bypass an absorption step (for example intravenously, intraarterially, intracardially, intraspinally or intralumbally) or include an absorption (for example intramuscularly, subcutaneously, intracutaneously, percutaneously or intraperitoneally). Administration forms suitable for parenteral administration include preparations for injection and infusion in the form of solutions, suspensions, emulsions, lyophilizates or sterile powders.

Suitable administration forms for the other administration routes are, for example, pharmaceutical forms for inhalation (including powder inhalers, nebulizers), nasal drops, solutions or sprays; tablets for lingual, sublingual or buccal administration, films/wafers or capsules, suppositories, eye drops, eye ointments, eyewashes, ocular inserts, ear drops, sprays, powders, washes or tampons, vaginal capsules, aqueous suspensions (lotions, shaking mixtures), lipophilic suspensions, emulsions, microemulsions, ointments, creams, transdermal therapeutic systems (for example patches), milk, pastes, foams, dusting powders, implants or stents.

Preference is given to parenteral administration, especially intravenous administration.

The compounds according to the invention can be converted to the administration forms mentioned. This can be accomplished in a manner known per se by mixing with pharmaceutically suitable excipients. These excipients include fillers and carriers (for example cellulose, microcrystalline cellulose, for example Avicel®, lactose, mannitol, starch, calcium phosphates, for example Di-Cafos®), ointment bases (for example vaseline, paraffins, triglycerides, waxes, wool wax, wool wax alcohols, lanolin, hydrophilic ointment, polyethylene glycols), suppository bases (for example polyethylene glycols, cocoa butter, hard fat), solvents (e.g. water, ethanol, isopropanol, glycerol, propylene glycol, mid-chain triglycerides of fatty oils, liquid polyethylene glycols, paraffins), surfactants, emulsifiers, dispersants or wetting agents (for example sodium dodecylsulphate, lecithin, phospholipids, fatty alcohols, for example Lanette®, sorbitan fatty acid esters, for example Span®, polyoxyethylene sorbitan fatty acid esters, for example Tween®, polyoxyethylene fatty acid glycerides, for example Cremophor®, polyoxyethylene fatty acid esters, polyoxyethylene fatty alcohol ethers, glycerol fatty acid esters, poloxamers, for example Pluronic®), buffer substances, and also acids and bases (for example phosphates, carbonates, citric acid, acetic acid, hydrochloric acid, sodium hydroxide, ammonium carbonate, trometamol, triethanolamine), isotonizing agents (for example glucose, sodium chloride), adsorbents (for example finely divided silicas), viscosity-increasing agents, gel formers, thickeners or binders (for example polyvinylpyrrolidone, methyl cellulose, hydroxypropyl methyl cellulose, hydroxypropyl cellulose, carboxymethyl cellulose-sodium, starch, carbomers, polyacrylic acids, for example Carbopol®, alginates, gelatins), disintegrants (for example modified starch, carboxymethyl cellulose-sodium, sodium starch glycolate, for example Explotab®, crosslinked polyvinylpyrrolidone, croscarmellose-sodium, for example AcDiSol®), flow regulators, lubricants, glidants and mould release agents (for example magnesium stearate, stearic acid, talc, finely divided silicas, for example Aerosil®), coating agents (for example sugar, shellac) and film formers for films or diffusion membranes with fast or modified dissolution (for example by polyvinylpyrrolidones, for example Kollidon®, polyvinyl alcohol, hydroxypropyl methyl cellulose, hydroxypropyl cellulose, ethyl cellulose, hydroxypropyl methyl cellulose phthalate, cellulose acetate, cellulose acetate phthtalate, polyacrylates, polymethacrylates, for example Eudragit®), capsule materials (e.g. gelatins, hydroxypropyl methyl cellulose), synthetic polymers (for example polylactides, polyglycolides, polyacrylates, polymethacrylates, for example Eudragit®, polyvinylpyrrolidones, for example Kollidon®, polyvinyl alcohols, polyvinyl acetate, polyethylene oxides, polyethylene glycols and the copolymers and block copolymers thereof), plasticizers (for example polyethylene glycols, propylene glycol, glycerol, triacetin, triacetyl citrate, dibutyl phthalate), penetration enhancers, stabilizers (e.g. antioxidants, for example ascorbic acid, ascorbyl palmitate, sodium ascorbate, butylhydroxyanisole, butylhydroxytoluene, propyl gallate), preservatives (for example parabens, sorbic acid, thiomersal, benzalkonium chloride, chlorhexidine acetate, sodium benzoate), dyes (e.g. inorganic pigments, for example iron oxides, titanium dioxide), aromas, sweeteners, flavour and/or odour correctors.

The present invention further provides pharmaceutical compositions comprising at least one compound according to the invention, typically together with one or more pharmaceutically suitable excipients, and the use thereof for the aforementioned purposes.

In general, it has been found to be advantageous in the case of parenteral administration to administer amounts of about 0.1 to 20 mg/kg, preferably about 0.3 to 7 mg/kg, of body weight to achieve effective results.

It may nevertheless be necessary in some cases to deviate from the stated amounts, specifically as a function of body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The compounds according to the invention may also take the form of isotopic variants.

The invention therefore encompasses one or more isotopic variants of the compounds according to the invention, especially deuterium-containing compounds.

The term "isotopic variant" of a compound or reagent is defined as a compound with an unnatural fraction of one or more isotopes from which such a compound is constituted.

The term "isotopic variant of the compounds according to the invention" is defined as a compound according to the invention with an unnatural fraction of one or more isotopes from which such a compound is constituted.

The expression "unnatural fraction" is understood to mean a fraction of such an isotope higher than its natural frequency. The natural frequencies of isotopes to be employed in this connection can be found in "Isotopic Compositions of the Elements 1997", Pure Appl. Chem., 70(1), 217-235, 1998.

Examples of such isotopes are stable and radioactive isotopes of hydrogen, carbon, nitrogen, oxygen, phosphorus, sulphur, fluorine, chlorine, bromine and iodine, such as $^2$H (deuterium), $^3$H (tritium), $^{11}$C, $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{125}$I, $^{129}$I and $^{131}$I.

With regard to the treatment and/or prophylaxis of the disorders specified here, the isotopic variant(s) of the compounds according to the invention preferably contain deuterium ("deuterium-containing compounds according to the invention"). Isotopic variants of the compounds according to the invention into which one or more radioactive isotopes such as $^3$H or $^{14}$C have been incorporated are beneficial, for example, in medicament and/or substrate tissue distribution studies. Because of their easy incorporability and detectability, these isotopes are particularly preferred. It is possible to incorporate positron-emitting isotopes such as $^{18}$F or $^{11}$C into a compound according to the invention. These isotopic variants of the compounds according to the invention are suitable for use in in vivo imaging applications. Deuterium-containing and $^{13}$C-containing compounds according to the invention can be used within preclinical or clinical studies in mass spectrometry analyses.

Isotopic variants of the compounds according to the invention can generally be prepared by processes known to those skilled in the art as described in the schemes and/or examples described here, by replacing a reagent with an isotopic variant of the reagent, preferably a deuterium-containing reagent. According to the desired deuteration sites, in some cases, deuterium from $D_2O$ can either be incorporated directly into the compounds or into reagents which can be used for the synthesis of such compounds. Another useful reagent for incorporation of deuterium into molecules is deuterium gas. A rapid route to the incorporation of deuterium is the catalytic deuteration of olefinic bonds and acetylenic bonds. For direct exchange of hydrogen for deuterium in hydrocarbons containing functional groups, it is also possible to use metal catalysts (i.e. Pd, Pt and Rh) in the presence of deuterium gas. Various deuterated reagents and synthesis units are commercially available from companies like, for example, C/D/N Isotopes, Quebec, Canada; Cambridge Isotope Laboratories Inc., Andover, MA, USA; and CombiPhos Catalysts, Inc., Princeton, NJ, USA.

The term "deuterium-containing compound" is defined as a compound according to the invention in which one or more hydrogen atoms have been replaced by one or more deuterium atoms and in which the frequency of deuterium in every deuterated position in the compound of the general formula (I) is higher than the natural frequency of deuterium, which is about 0.015%. More particularly, in a deuterium-containing compound according to the invention, the frequency of deuterium in every deuterated position in the compound of the general formula (I) is higher than 10%, 20%, 30%, 40%, 50%, 60%, 70% or 80%, preferably higher than 90%, 95%, 96% or 97%, even further preferably higher than 98% or 99%, in this position or these positions. It will be apparent that the frequency of deuterium in every deuterated position is independent of the frequency of deuterium in other deuterated positions.

Through the selective incorporation of one or more deuterium atoms into a compound according to the invention, it is possible to alter the physicochemical properties (for example acidity [C. L. Perrin, et al., J. Am. Chem. Soc., 2007, 129, 4490], basicity [C. L. Perrin et al., J. Am. Chem. Soc., 2005, 127, 9641], lipophilicity [B. Testa et al., Int. J. Pharm., 1984, 19(3), 271]) and/or the metabolic profile of the molecule and cause changes in the ratio of parent compound to metabolites or the amounts of metabolites formed. Such changes may lead to particular therapeutic benefits and therefore be preferable under particular circumstances. Reduced rates of metabolism and metabolic switching, where the ratio of metabolites is changed, have been reported (A. E. Mutlib et al., Toxicol. Appl. Pharmacol., 2000, 169, 102). These changes in the exposure to parent drug and metabolites can have important consequences with respect to the pharmacodynamics, tolerability and efficacy of a deuterium-containing compound according to the invention. In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. Examples of this deuterium effect are ML-337 (C. J. Wenthur et al., J. Med. Chem., 2013, 56, 5208) and odanacatib (K. Kassahun et al., WO2012/112363). Still other cases have been reported in which reduced rates of metabolism result in an increase in exposure of the drug without changing the rate of systemic clearance (e.g. Rofecoxib: F. Schneider et al., Arzneim. Forsch. Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

Compounds according to the invention may have two or more potential attack sites for metabolization. To optimize the above-described effects on physicochemical properties and metabolic profile, deuterium-containing compounds according to the invention having a certain pattern of one or more deuterium-hydrogen exchange(s) can be selected. More particularly, the deuterium atom(s) of deuterium-containing compound(s) according to the invention is/are bonded to a carbon atom and/or is/are at those positions in the compounds according to the invention that are attack sites for metabolizing enzymes, for example cytochrome $P_{450}$.

EXAMPLES

The examples which follow illustrate the executability of the present invention, the invention is not restricted solely to these examples.

Unless stated otherwise, the percentages in the tests and examples which follow are percentages by weight; parts are parts by weight. Solvent ratios, dilution ratios and concentration data for the liquid/liquid solutions are based in each case on volume.

Synthesis Routes:

By way of example for the working examples, the schemes which follow show illustrative synthesis routes.

In these schemes, according to formula IIa, the $R^4$ substituent on the amino group —$NHR^4$ may be substituted by the $Z_1$—(C=O)—NH—CH(CH$_2$C(=O)NH$_2$)—C(=O) group.

In this context, $Z_1$ is a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, $C_{5-10}$-heteroarylalkoxy, $C_{1-10}$-alkoxy, $C_{6-10}$-aryloxy, $C_{6-10}$-aryl-$C_{1-10}$-alkyloxy or $C_{6-10}$-aralkoxy, $C_{5-10}$-heteroalkoxy, $C_{1-10}$-alkyl-O—$C_{6-10}$-aryloxy- or $C_{5-10}$-heterocycloalkoxy group which may be mono- or polysubstituted by —NH$_2$, —C(=O)—, —NH-alkyl, —N(alkyl)$_2$, —NH—C(=O)-alkyl, —N(alkyl)-C(=O)-alkyl, —S(=O)$_3$—H, —S(=O)$_2$—NH$_2$, —S(=O)$_2$—N(alkyl)$_2$, —COOH, —C(=O)NH$_2$, —C(=O)—N(alkyl)$_2$ or —OH, or is —H or a —(CH$_2$)$_o$-1-O$_x$—(CH$_2$CH$_2$O)v-$R^1$ group, x is 0 or 1, v is a number from 1 to 20 and $R^1$ has the definitions given in the formula (II).

Scheme 1: Synthesis of cysteine-linked ADCs

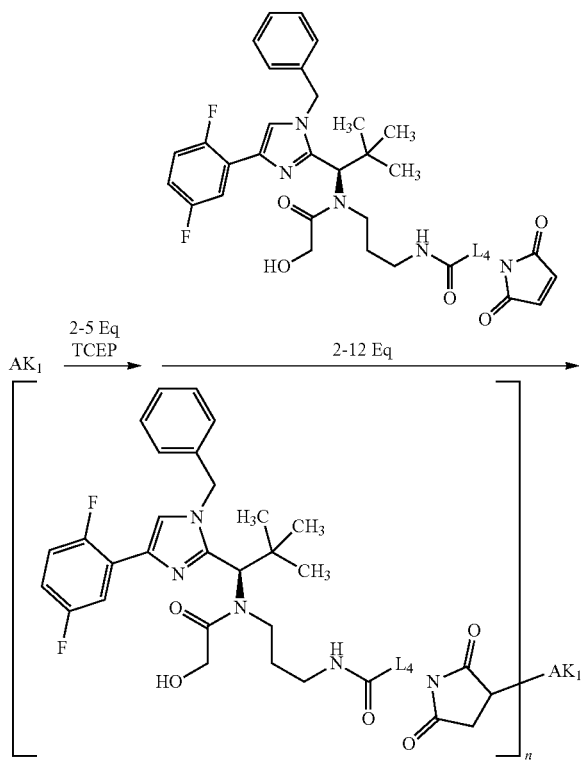

Scheme 2: Synthesis of cysteine-linked ADCs

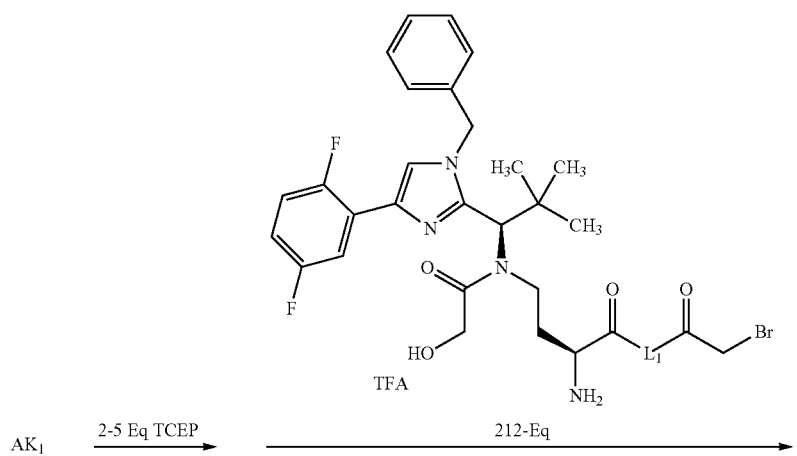

-continued
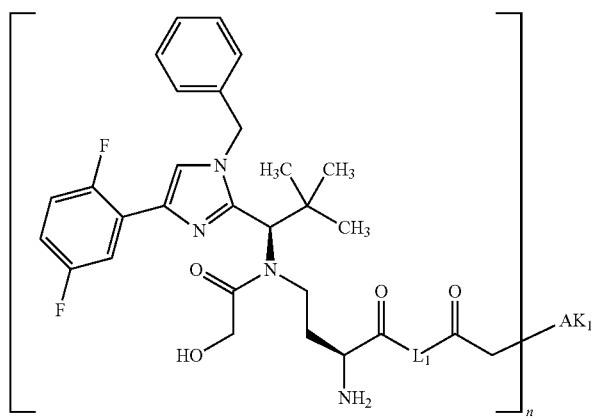
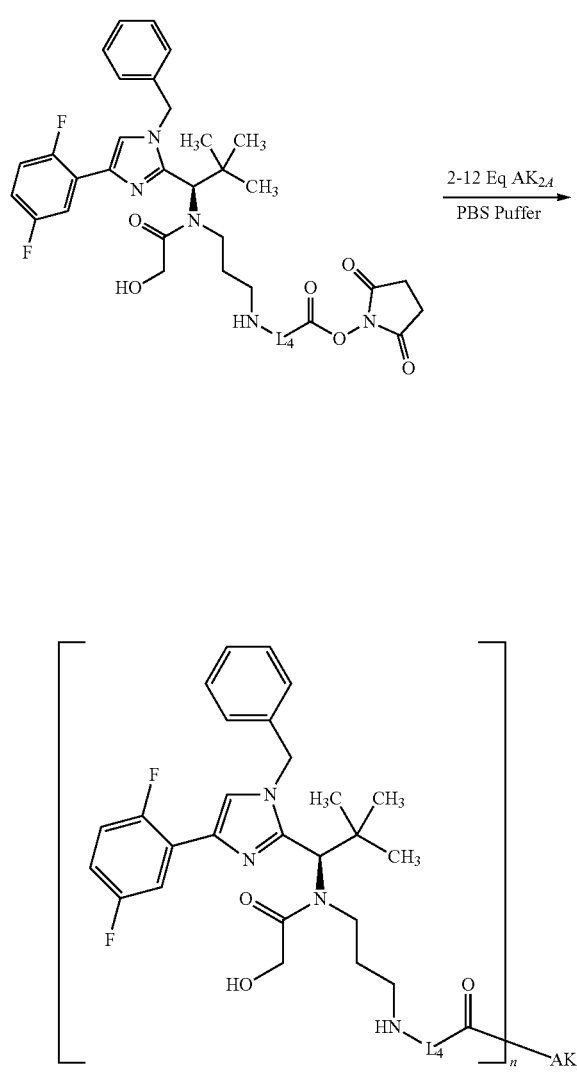
Scheme 3: Synthesis of lysine-linked ADCs
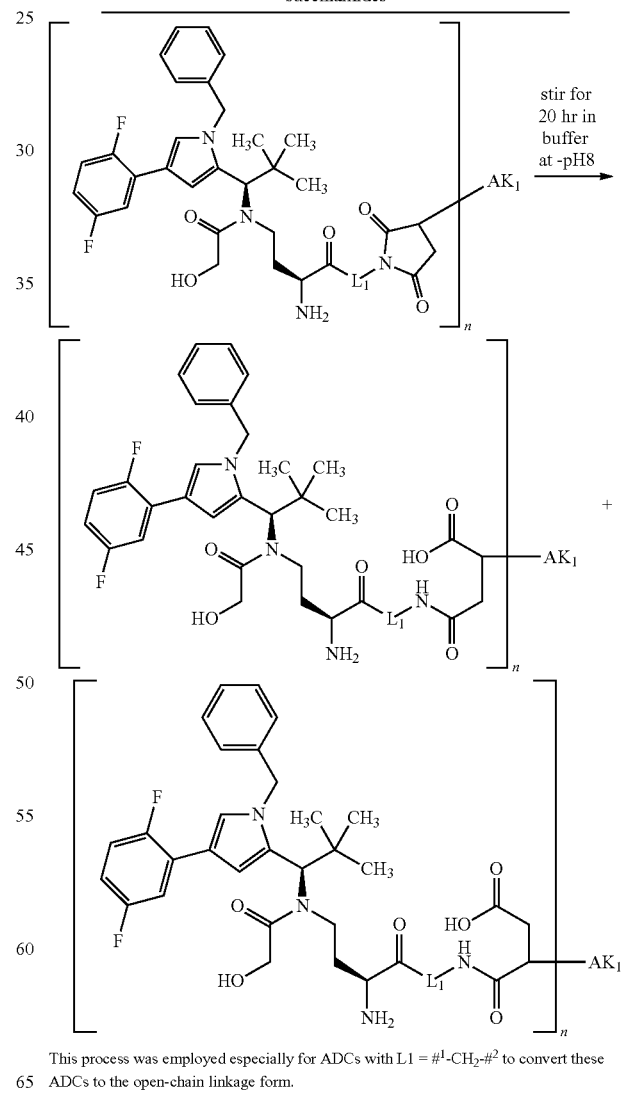
Scheme 4: Synthesis of cysteine-linked ADCs via hydrolysed succinamides
This process was employed especially for ADCs with L1 = #¹-CH₂-#² to convert these ADCs to the open-chain linkage form.

Scheme 5: Synthesis of ADC precursor molecules
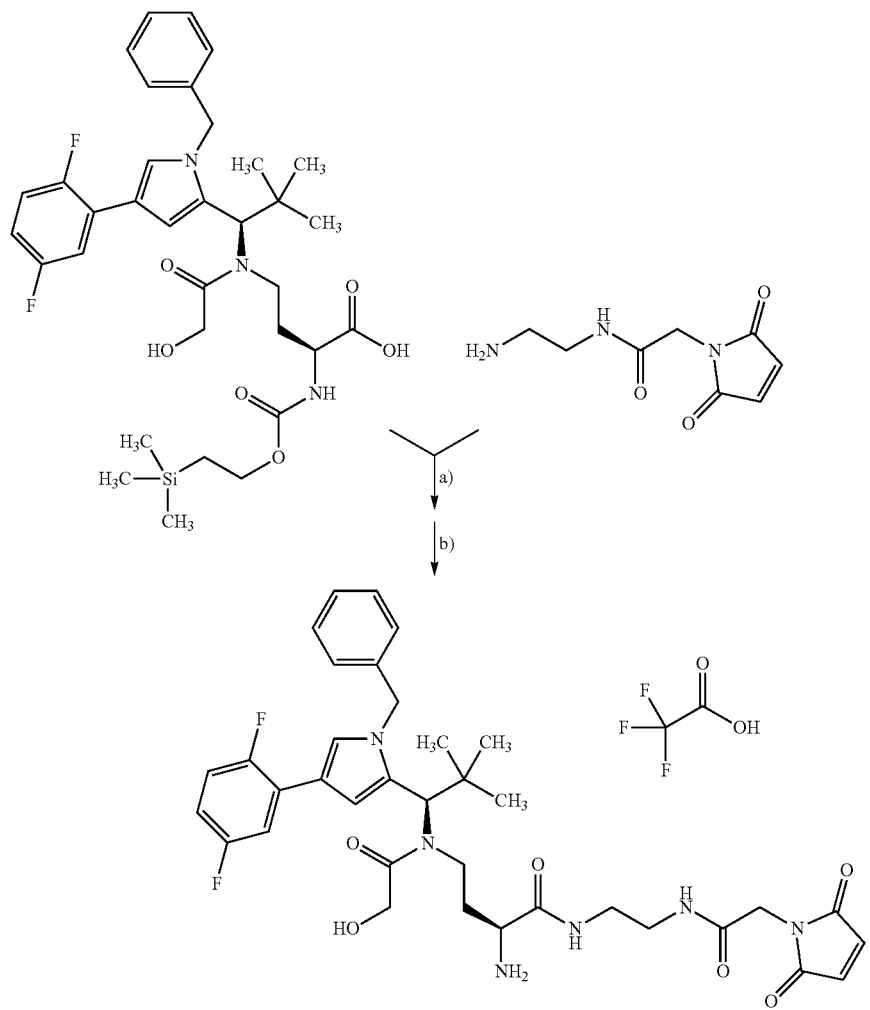
[a]: HATU, DMF, diisopropylethylamine, RT; b) zinc chloride, trifluoroethanol, 50° C., EDTA.]
Scheme 6: General method for synthesis of intermediates and ADC precursors
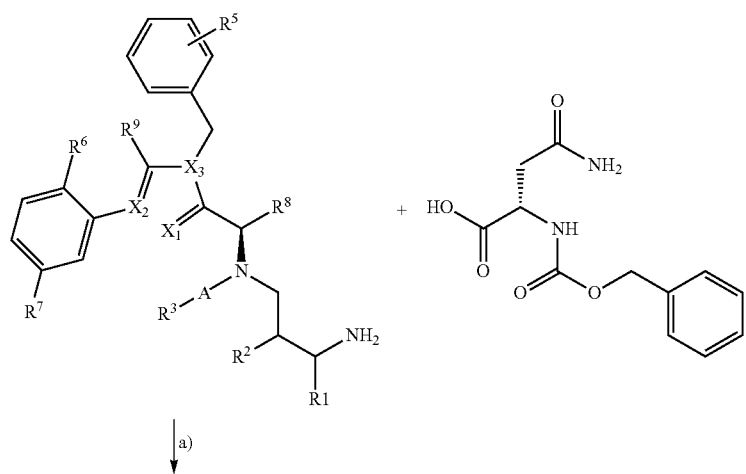

-continued
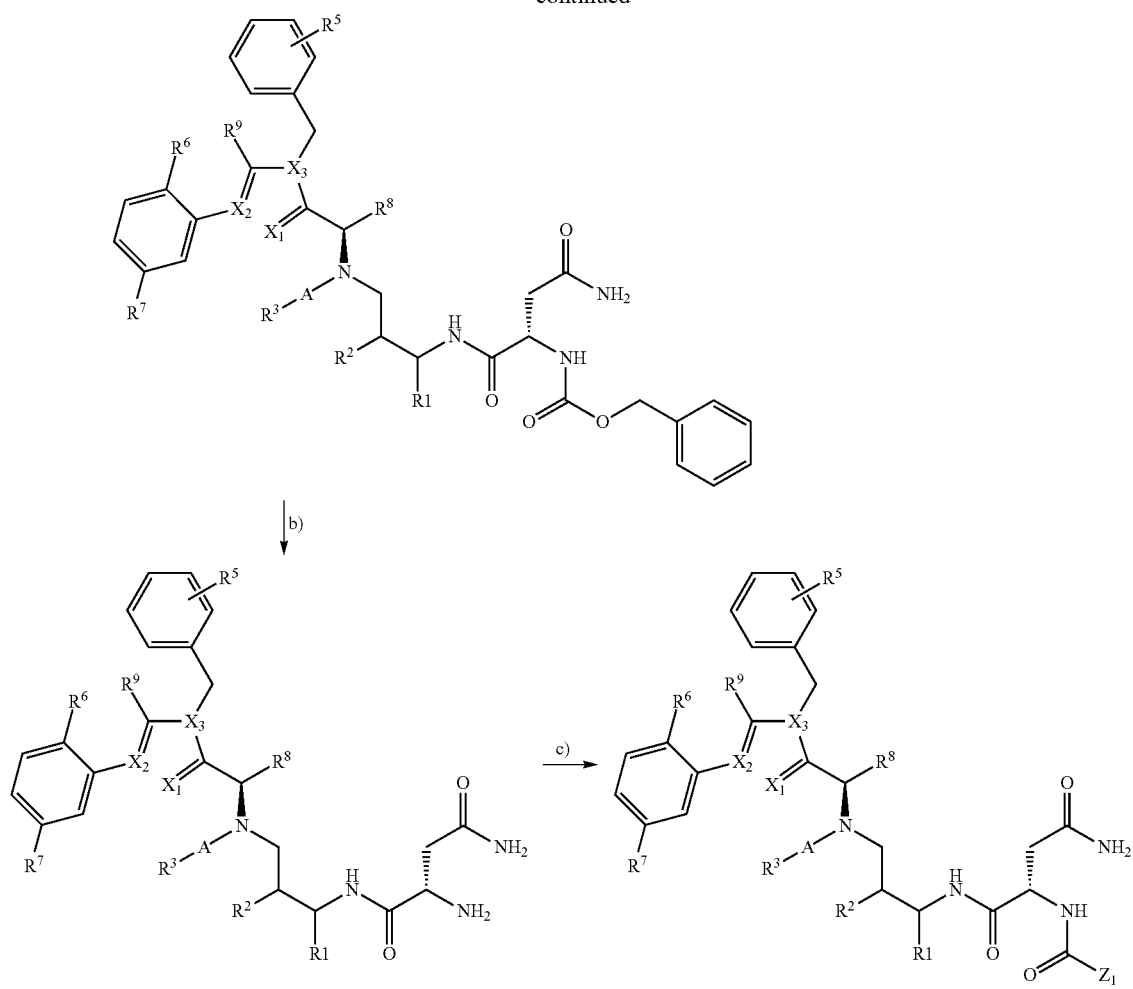
[a]: HATU, DMF, N,N-diisopropylethylamine, RT or EDCl, HOBT, N,N-diisopropylethylamine, DMF, RT b) $H_2$, 10% Pd—C, MeOH, RT; c) $Z_1$—COOH, EDCl, HOBT, N,N-diisopropylethylamine, DMF, RT or $Z_1$—COOH, HATU, N,N-diisopropylethylamine, DMF, RT or $Z^1$—COOSu, N,N-diisopropylethylamine, DMF, RT]
Scheme 7: Synthesis of ADC precursor molecules having legumain-cleavable linkers
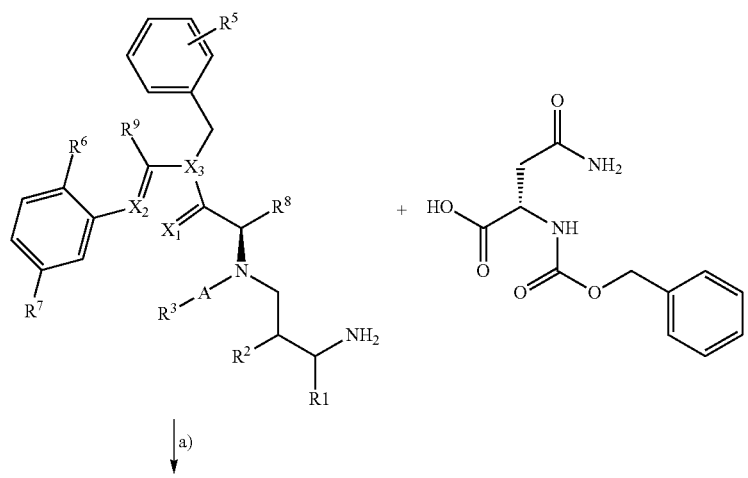

-continued
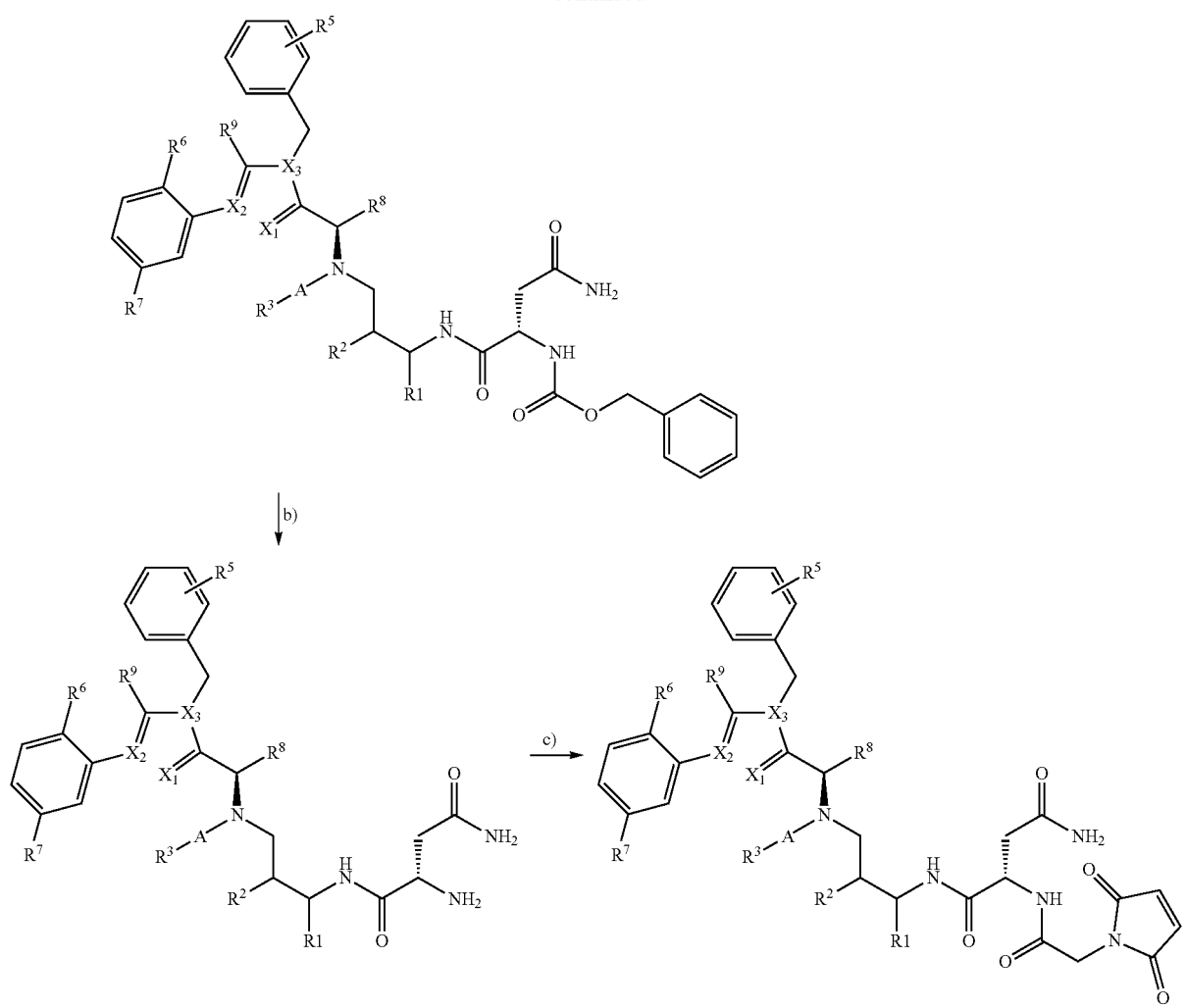
[a]: HATU, DMF, N,N-diisopropylethylamine, RT or EDCl, HOBT, N,N-diisopropylethylamine, DMF, RT b) H₂, 10% Pd—C, MeOH, RT; c) 1,1'-[(1,5-dioxopentane-1,5-diyl)bis(oxy)]dipyrrolidine-2,5-dione, N,N-diisopropylethylamine, DMF, RT]
Scheme 8: Synthesis of ADC precursor molecules having legumain-cleavable linkers
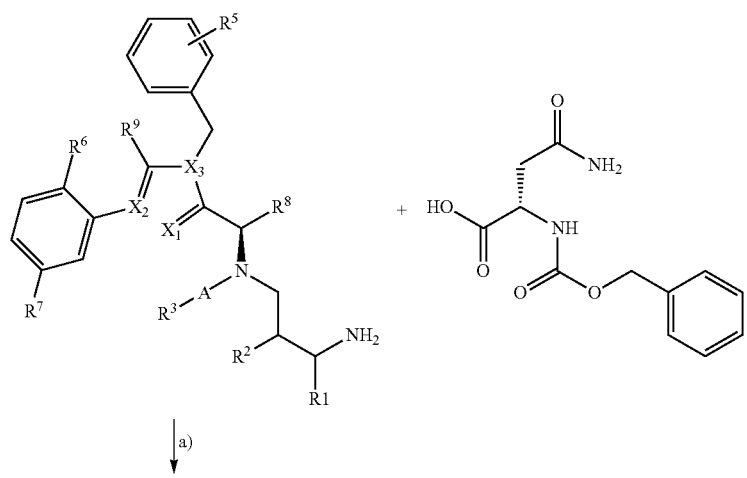

-continued
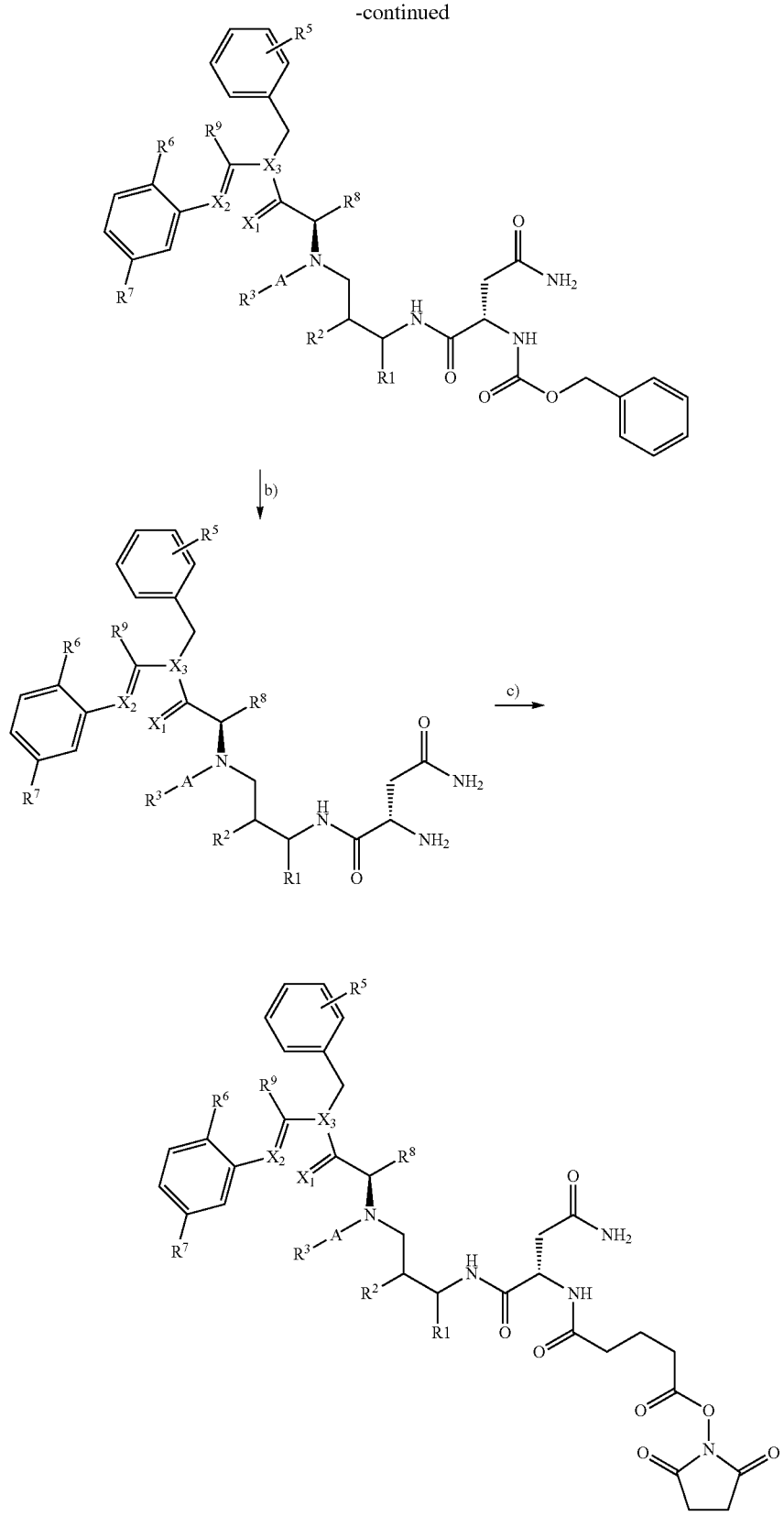
[a]: HATU, DMF, N,N-diisopropylethylamine, RT or EDCl, HOBT, N,N-diisopropylethylamine, DMF, RT b) H₂, 10% Pd—C, MeOH, RT; c) 1,1'-[(1,5-dioxopentane-1,5-diyl)bis(oxy)]dipyrrolidine-2,5-dione, N,N-diisopropylethylamine, DMF, RT]

In addition, other intermediates according to Schemes 6, 7 and 8 can be converted to legumain-cleavable ADC and APDC precursors.

As an alternative to the benzyloxycarbonyl group shown in Schemes 6-8, it is possible to use other protecting groups established in peptide chemistry and detach them by corresponding methods that are likewise known. The selection of the protecting group strategy is made according to requirements known to those skilled in the art relating to compatibility with other structural elements that occur in the molecule. If they are still present, further protecting groups in the molecule may be removed in a last step. The syntheses may also optionally be rearranged in terms of their sequence.

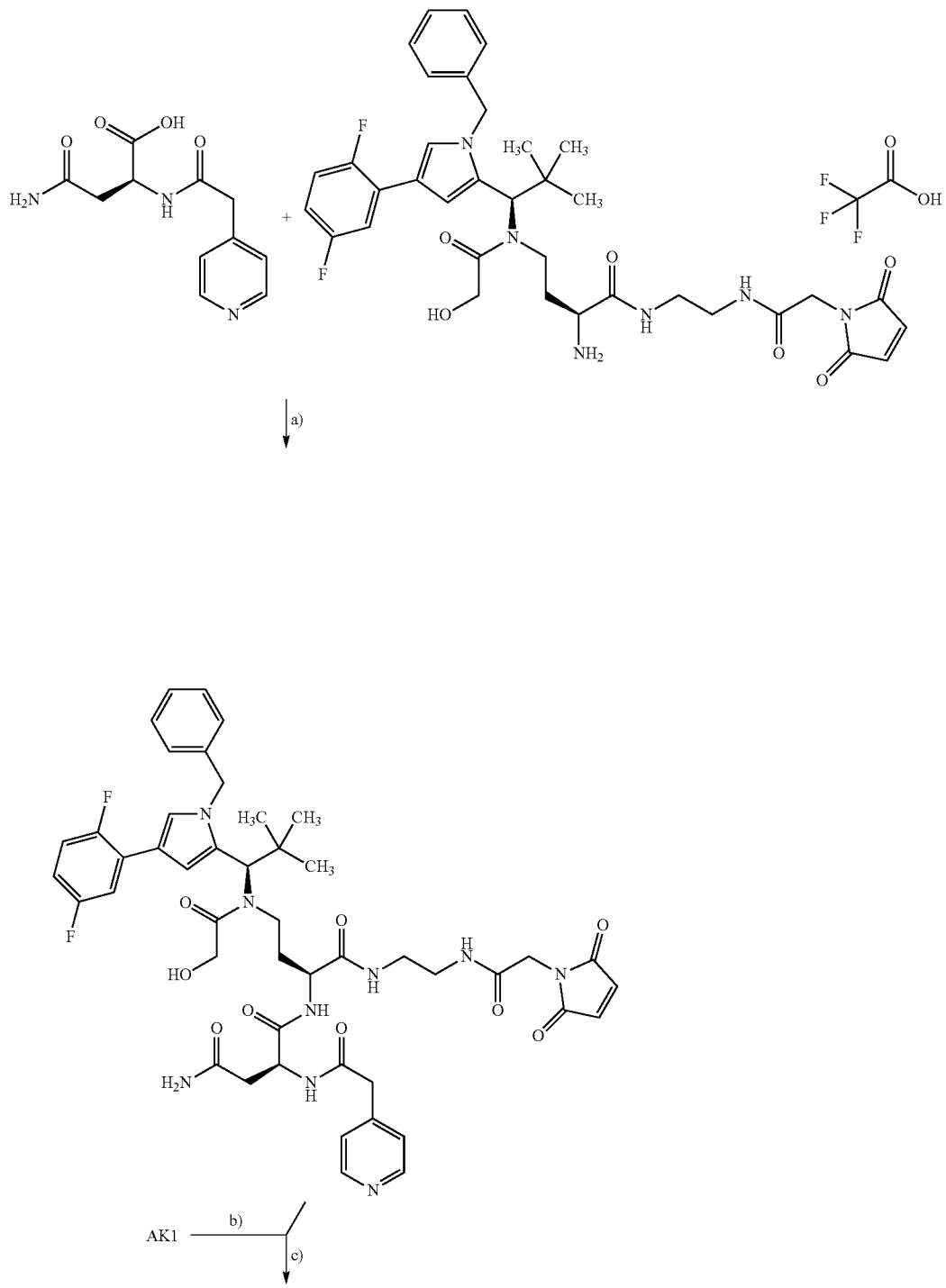

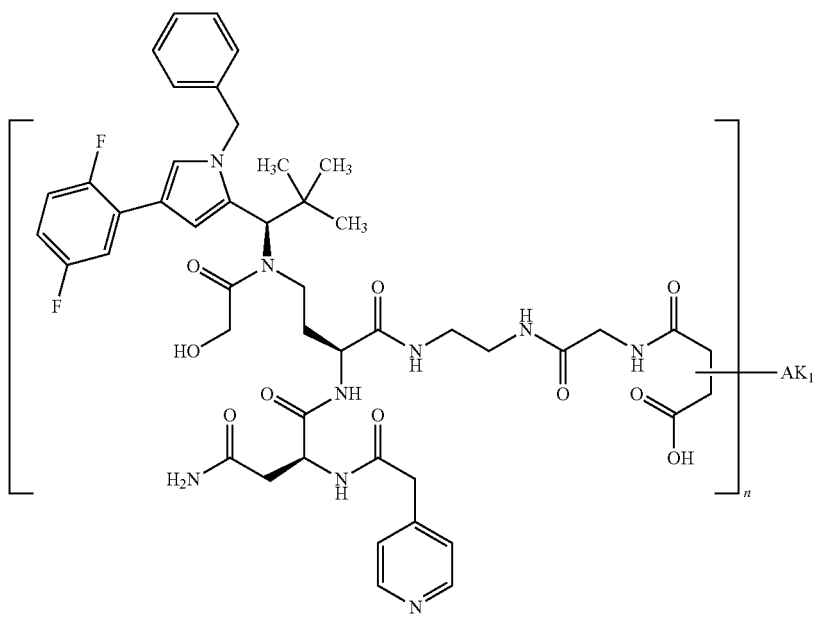

[a): HATU, DMF, N,N-diisopropylethylamine, RT; b) 2-5 eq TCEP, PBS pH7.2, stirring at RT for 30 min; c) stirring at RT under argon for 90 min, then rebuffering to pH 8 by means of PD 10 columns (Sephadex® G-25, GE Healthcare) and stirring under argon at RT overnight and subsequent concentration by means of ultracentrifugation and setting of the concentration desired with PBS at pH 7.2)]

Scheme 10: Synthesis of lysine-bonded ADCs with legumain-cleavable linker

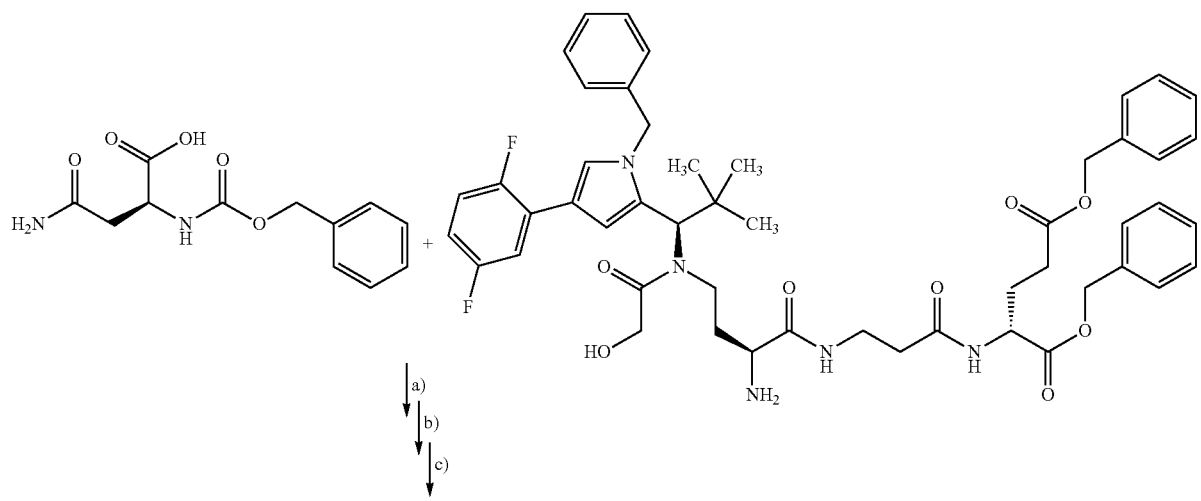

-continued

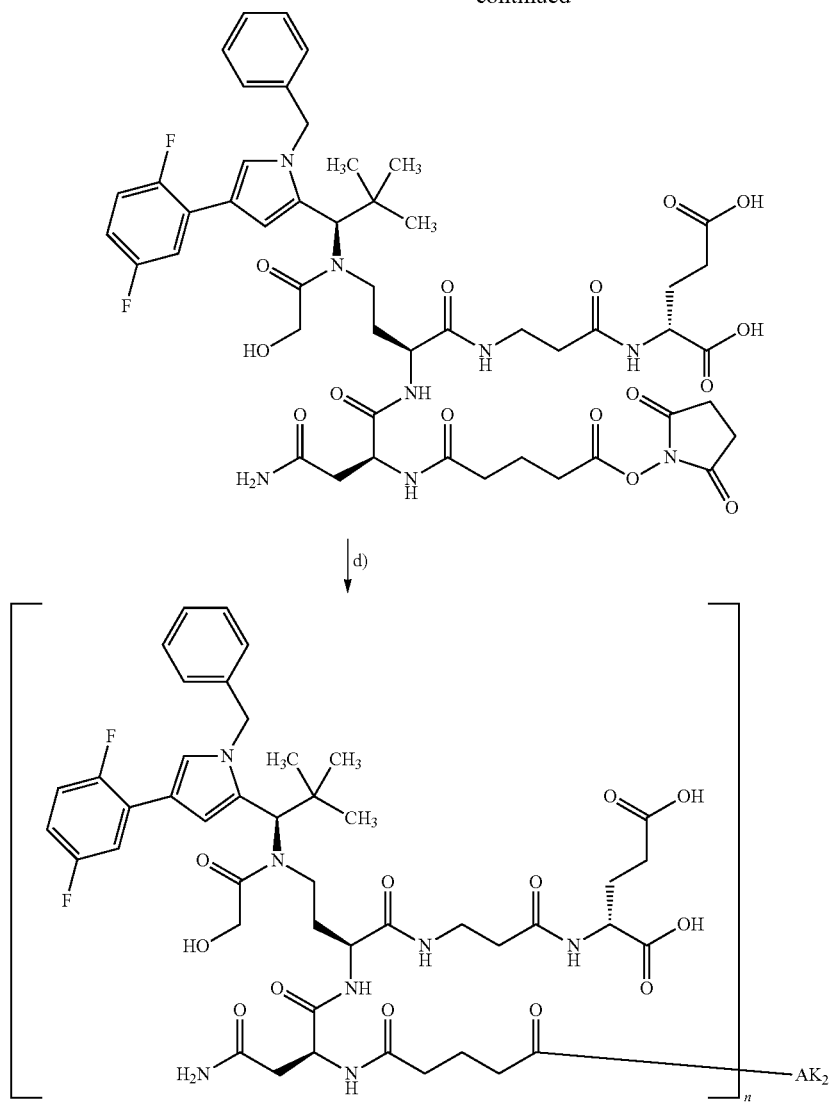

[a]: HATU, DMF, N,N-diisopropylethylamine, RT; b) H₂, 10% Pd—C, methanol 1.5 h, RT; c) 1,1′-[(1,5-dioxopentane-1,5-diyl)bis(oxy)]dipyrrolidine-2,5-dione, N,N-diisopropylethylamine, DMF, stirring at RT overnight; d) AK2 in PBS, addition of 5 equiv. of active ester dissolved in DMSO, stirring at RT under argon for 60 min, addition of another 5 equiv. of active ester dissolved in DMSO, stirring at RT under argon for 60 min, then purification by means of PD 10 columns equilibrated with PBS buffer (pH 7.2) (Sephadex® G-25, GE Healthcare) and subsequent concentration by means of ultracentrifugation and setting of the concentration desired with PBS at pH 7.2)]

Scheme 11: Synthesis of ADC precursors with legumain-cleavable head group

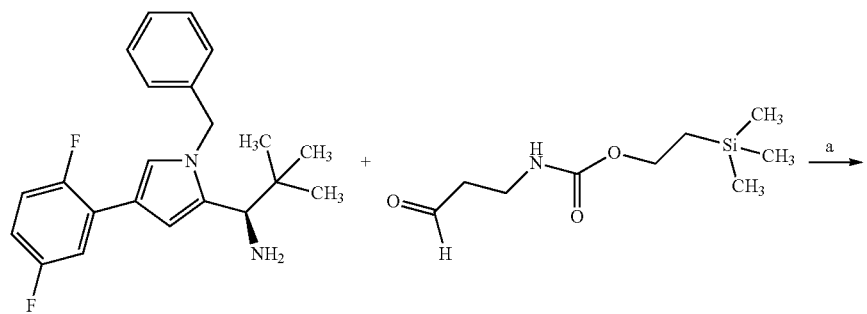

173 174
-continued
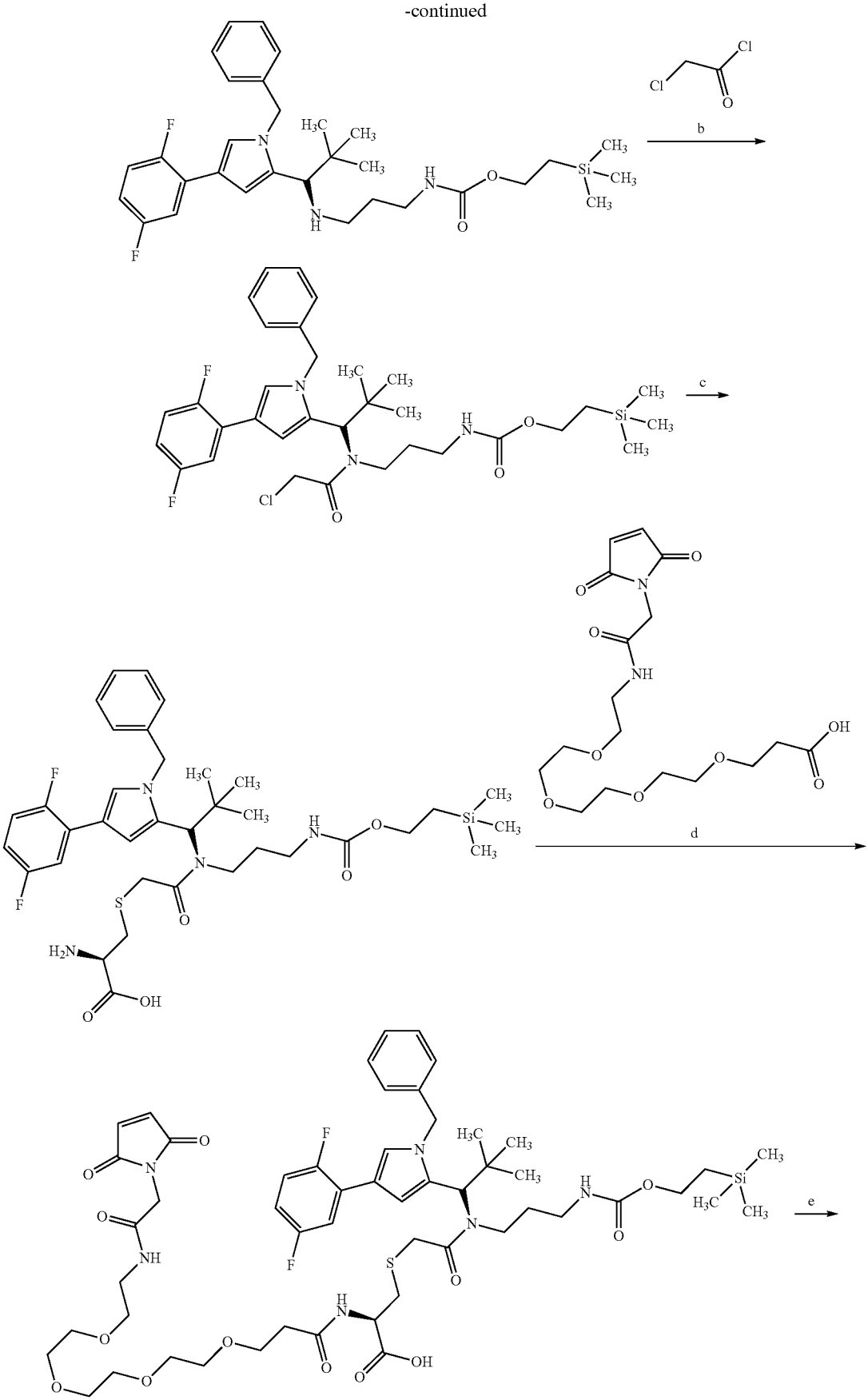

175

176

-continued

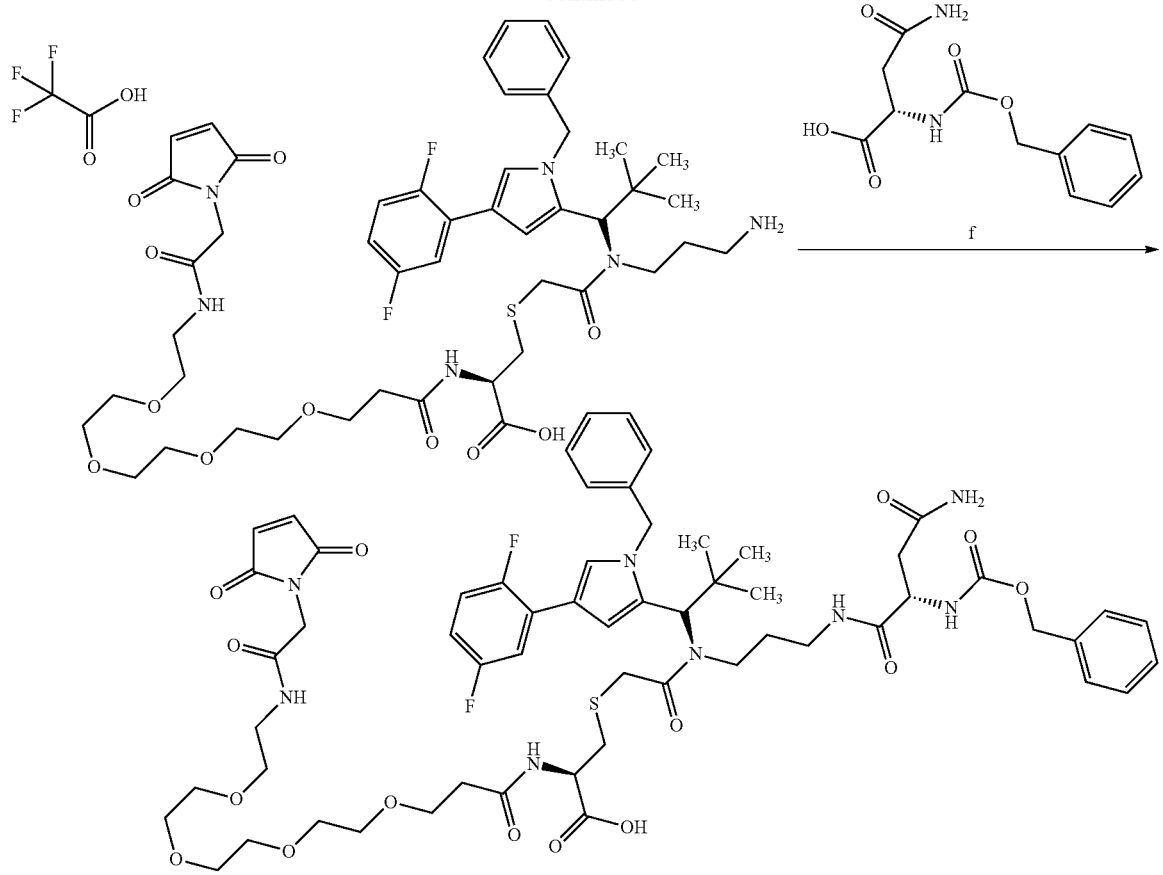

[a]: NaBH(OAc)₃, HOAc, dichloromethane, RT; b) chloroacetyl chloride, NEt₃, DCM, RT; c) L-cysteine, NaHCO₃, DBU, isopropanol/water, 50° C.; d) HATU, DMF, diisopropylethylamine, RT; e) zinc chloride, trifluoroethanol, 50° C.; f) d) HATU, DMF, diisopropylethylamine, RT]

[a]: NaBH(OAc)s, HOAc, dichloromethane, RT; b) chloroacetyl chloride, NEts, DCM, RT; c) L-cysteine, NaHCO₃, DBU, isopropanol/water, 50° C.; d) HATU, DMF, diisopropylethylamine, RT; e) zinc chloride, trifluoroethanol, 50° C.; f) d) HATU, DMF, diisopropylethylamine, RT]

Scheme 12: Synthesis of ADCs via transglutaminase coupling

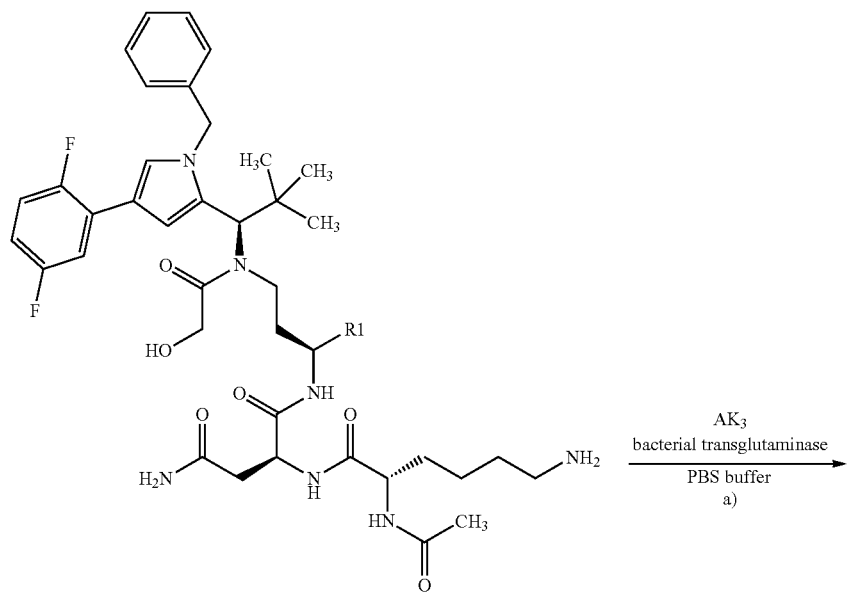

-continued

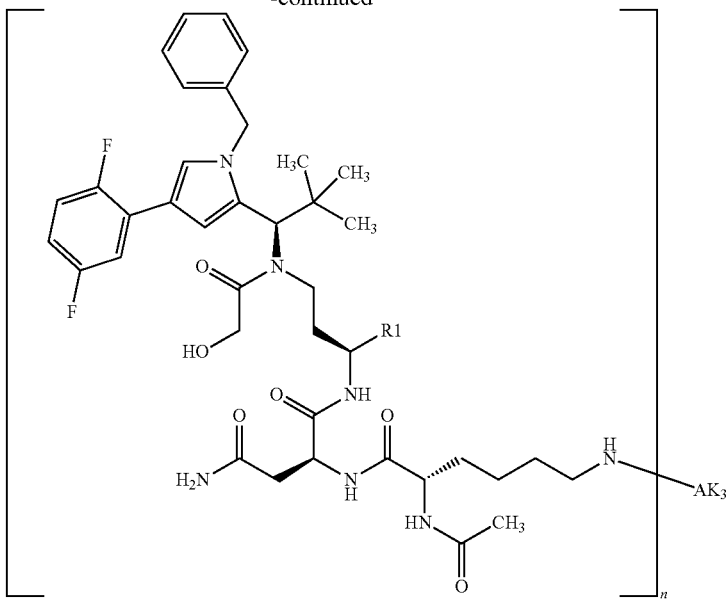

[a: 5 mg AK3 in DPBS pH 7.4 (c~10 mg/ml), 6 equivalents of a toxophore-linker precursor, add 50 μl of a solution of 12.5 μl (1.25 U) of recombinant bacterial transglutaminase solution in water (100 U/ml) and 37.5 μl of DPBS pH 7.4, incubate at 37° C. for 24 h]

A. Examples

Abbreviations and Acronyms

ABCB1 ATP-binding cassette sub-family B member 1 (synonym for P-gp and MDR1)
abs. absolute
Ac acetyl
ACN acetonitrile
aq. aqueous, aqueous solution
ATP adenosine triphosphate
BCRP breast cancer resistance protein, an efflux transporter
BEP 2-bromo-1-ethylpyridinium tetrafluoroborate
Boc tert-butoxycarbonyl
br. broad (in NMR)
Ex. Example
BxPC3 human tumour cell line
ca. circa, about
CI chemical ionization (in MS)
D doublet (in NMR)
D day(s)
DAR Drug Antibody Ratio (loading of the antibody)
TLC thin-layer chromatography
DCI direct chemical ionization (in MS)
DCM dichloromethane
Dd doublet of doublets (in NMR)
DMAP 4-N,N-dimethylaminopyridine
DME 1,2-dimethoxyethane
DMEM Dulbecco's Modified Eagle Medium (standardized nutrient medium for cell culture)
DMF N,N-dimethylformamide
DMSO dimethyl sulphoxide
DPBS, D-PBS, Dulbecco's phosphate-buffered salt solution
D/P dye (fluorescent dye)/protein ratio
PBS PBS=DPBS=D-PBS, pH 7.4, from Sigma, No D8537 Composition:
0.2 g KCl
0.2 g $KH_2PO_4$ (anhyd)
8.0 g NaCl
1.15 g $Na_2HPO_4$ (anhyd)
made up ad 1 l with $H_2O$
Dt doublet of triplets (in NMR)
DTT DL-dithiothreitol
EDC N'-(3-dimethylaminopropyl)-N-ethylcarbodiimide hydrochloride
EGFR epidermal growth factor receptor
EI electron impact ionization (in MS)
ELISA enzyme-linked immunosorbent assay
eq. equivalent(s)
ESI electrospray ionization (in MS)
ESI-MicroTofq ESI-MicroTofq (name of the mass spectrometer with Tof=time of flight and q=quadrupole)
FCS foetal calf serum
Fmoc (9H-fluoren-9-ylmethoxy)carbonyl
sat. saturated
GTP guanosine-5'-triphosphate
H hour(s)
HATU O-(7-azabenzotriazol-1-yl)-N,N,N',N'-tetramethyluronium hexafluorophosphate
HEPES 4-(2-hydroxyethyl)piperazine-1-ethanesulphonic acid
HOAc acetic acid
HOAt 1-hydroxy-7-azabenzotriazole
HOBt 1-hydroxy-1H-benzotriazole hydrate
HOSu N-hydroxysuccinimide
HPLC high-pressure, high-performance liquid chromatography
$IC_{50}$ half-maximal inhibitory concentration
i.m. intramuscularly, administration into the muscle
i.v. intravenously, administration into the vein
conc. concentrated
KPL-4 human tumour cell lines
KU-19-19 human tumour cell line LC-MS liquid chromatography-coupled mass spectrometry
LLC-PK1 cells Lewis lung carcinoma pork kidney cell line
L-MDR human MDR1 transfected LLC-PK1 cells
LoVo human tumour cell line
M multiplet (in NMR)
MDR1 Multidrug resistance protein 1
MeCN acetonitrile
Min minute(s)
MS mass spectrometry
MTT 3-(4,5-dimethylthiazol-2-yl)-2,5-diphenyl-2H-tetrazolium bromide
NCI-H292 human tumour cell line
—Nme- a methyl group bonded to the nitrogen atom
NMM N-methylmorpholine
NMP N-methyl-2-pyrrolidinone
NMR nuclear magnetic resonance spectrometry
NMRI mouse strain originating from the Naval Medical Research Institute (NMRI)
Nude mice experimental animals
NSCLC non small cell lung cancer
PBS phosphate-buffered salt solution
Pd/C palladium on activated carbon
P-gp P-glycoprotein, a transporter protein
PNGaseF enzyme for cleaving sugar
quant. quantitative (in yield)
Quart. quartet (in NMR)
Quint quintet (in NMR)
$R_f$ retention index (in TLC)
RT room temperature
$R_t$ retention time (in HPLC)
S singlet (in NMR)
s.c. subcutaneously, administration under the skin
SCID mice test mice with severe combined immunodeficiency
SK-HEP-1 human tumour cell line
t triplet (in NMR)
TBAF tetra-n-butylammonium fluoride
TCEP tris(2-carboxyethyl)phosphine
TEMPO (2,2,6,6-tetramethylpiperidin-1-yl)oxyl
Teoc trimethylsilylethoxycarbonyl
tert tertiary
TFA trifluoroacetic acid
THF tetrahydrofuran
T3P® 2,4,6-tripropyl-1,3,5,2,4,6-trioxatriphosphinane 2,4,6-trioxide
U251 human tumour cell line
UV ultraviolet spectrometry
v/v volume to volume ratio (of a solution)
Z benzyloxycarbonyl Amino Acid Abbreviations Ala=alanine
Arg=arginine
Asn=asparagine
Asp=aspartic acid
Cys=cysteine
Glu=glutamic acid
Gln=glutamine
Gly=glycine
His=histidine
Ile=isoleucine
Leu=leucine
Lys=lysine
Met=methionine
Nva=norvaline
Phe=phenylalanine
Pro=proline
Ser=serine
Thr=threonine
Trp=tryptophan
Tyr=tyrosine
Val=valine HPLC and LC-MS Methods:

Method 1 (LC-MS):
Instrument: Waters ACQUITY SQD UPLC System; column: Waters Acquity UPLC HSS T3 1.8µ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 2 (LC-MS):
MS instrument type: Waters Synapt G2S; UPLC instrument type: Waters Acquity I-CLASS; column: Waters, BEH300, 2.1×150 mm, C18 1.7 µm; eluent A: 1 l water+0.01% formic acid; eluent B: 1 l acetonitrile+0.01% formic acid; gradient: 0.0 min 2% B→1.5 min 2% B→8.5 min 95% B→10.0 min 95% B; oven: 50° C.; flow rate: 0.50 ml/min; UV detection: 220 nm Method 3 (LC-MS):
MS instrument: Waters (Micromass) QM; HPLC instrument: Agilent 1100 Series; column: Agilent ZORBAX Extend-C18 3.0×50 mm 3.5-micron; eluent A: 1 l water+0.01 mol ammonium carbonate, eluent B: 1 l acetonitrile; gradient: 0.0 min 98% A→0.2 min 98% A→3.0 min 5% A→4.5 min 5% A; oven: 40° C.; flow rate: 1.75 ml/min; UV detection: 210 nm Method 4 (LC-MS):
MS instrument type: Waters Synapt G2S; UPLC instrument type: Waters Acquity I-CLASS; column: Waters, HSST3, 2.1×50 mm, C18 1.8 µm; eluent A: 1 l water+0.01% formic acid; eluent B: 1 l acetonitrile+0.01% formic acid; gradient: 0.0 min 10% B→0.3 min 10% B→1.7 min 95% B→2.5 min 95% B; oven: 50° C.; flow rate: 1.20 ml/min; UV detection: 210 nm.

Method 5 (LC-MS):
Instrument: Waters ACQUITY SQD UPLC System; column: Waters Acquity UPLC HSS T3 1.8µ 50×1 mm; eluent A: 1 l water+0.25 ml 99% formic acid, eluent B: 1 l acetonitrile+0.25 ml 99% formic acid; gradient: 0.0 min 95% A→6.0 min 5% A→7.5 min 5% A; oven: 50° C.; flow rate: 0.35 ml/min; UV detection: 210-400 nm.

Method 6 (LC-MS):
Instrument: Micromass Quattro Premier with Waters UPLC Acquity; column: Thermo Hypersil GOLD 1.9 µ 50×1 mm; eluent A: 1 l water+0.5 ml 50% formic acid, eluent B: 1 l acetonitrile+0.5 ml 50% formic acid; gradient: 0.0 min 97% A→0.5 min 97% A→3.2 min 5% A→4.0 min 5% A; oven: 50° C.; flow rate: 0.3 ml/min; UV detection: 210 nm.

Method 7 (LC-MS):
Instrument: Agilent MS Quad 6150; HPLC: Agilent 1290; column: Waters Acquity UPLC HSS T3 1.8µ 50×2.1 mm; eluent A: 1 l water+0.25 ml 99% formic acid, eluent B: 1 l acetonitrile+0.25 ml 99% formic acid; gradient: 0.0 min 90% A→0.3 min 90% A→1.7 min 5% A→3.0 min 5% A; oven: 50° C.; flow rate: 1.20 ml/min; UV detection: 205-305 nm.

Method 8 (LC-MS):
MS instrument type: Waters Synapt G2S; UPLC instrument type: Waters Acquity I-CLASS; column: Waters, HSST3, 2.1×50 mm, C18 1.8 µm; eluent A: 1 l water+0.01% formic acid; eluent B: 1 1 acetonitrile+0.01% formic acid; gradient: 0.0 min 2% B→2.0 min 2% B→13.0 min 90% B→15.0 min 90% B; oven: 50° C.; flow rate: 1.20 ml/min; UV detection: 210 nm.

Method 9: LC-MS-Prep Purification Method for Examples 181-191 (Method LIND-LC-MS-Prep)

MS instrument: Waters; HPLC instrument: Waters; Waters X-Bridge C18 column, 19 mm×50 mm, 5 μm, eluent A: water+0.05% ammonia, eluent B: acetonitrile (ULC), with gradient; flow rate: 40 ml/min; UV detection: DAD; 210-400 nm.

or

MS instrument: Waters; HPLC instrument: Waters; Phenomenex Luna 5μ C18 100A column, AXIA Tech. 50×21.2 mm, eluent A: water+0.05% formic acid, eluent B: acetonitrile (ULC) with gradient; flow rate: 40 ml/min; UV detection: DAD; 210-400 nm.

Method 10: LC-MS Analysis Method for Examples 181-191 (LIND_SQD_SB_AQ)

Instrument MS: Waters SQD; Instrument HPLC: Waters UPLC; column: Zorbax SB-Aq (Agilent), 50 mm×2.1 mm, 1.8 μm; eluent A: water+0.025% formic acid, eluent B: acetonitrile (ULC)+0.025% formic acid; gradient: 0.0 min 98% A—0.9 min 25% A—1.0 mir 5% A—1.4 min 5% A—1.41 min 98% A—1.5 min 98% A; oven: 40° C.; flow rate: 0.600 ml/min; UV detection: DAD; 210 nm.

Method 11 (HPLC):

Instrument: HP1100 Series

Column: Merck Chromolith SpeedROD RP-18e, 50-4.6 mm, Cat. No. 1.51450.0001, Chromolith Guard Cartridge Kit precolumn, RP-18e, 5-4.6 mm, Cat. No. 1.51470.0001

Gradient: flow rate 5 ml/min injection volume 5 μl

Solvent A: HClO4 (70%) in water (4 ml/I)

Solvent B: acetonitrile

Start 20% B 0.50 Min 20% B 3.00 Min 90% B 3.50 Min 90% B 3.51 Min 20% B 4.00 Min 20% B Column temperature: 40° C.

Wavelength: 210 nm

Method 12: (LC-MS):

MS instrument type Thermo Scientific FT-MS; UHPLC+ instrument type Thermo Scientific UltiMate 3000; column Waters, HSST3, 2.1×75 mm, C18 1.8 μm; eluent A 1 1 of water+0.01% formic acid; eluent B 1 1 of acetonitrile+0.01% formic acid; gradient 0.0 min 10% B→2.5 min 95% B→3.5 min 95% B; oven 50° C.; flow rate 0.90 ml/min; UV detection 210 nm/optimum integration path 210-300 nm Method 13: (LC-MS):

MS instrument: Waters (Micromass) Quattro Micro; Instrument Waters UPLC Acquity; column: Waters BEH C18 1.7μ 50×2.1 mm; eluent A: 1 1 water+0.01 mol ammonium formate, eluent B: 1 of acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Method 14: (LC-MS) (MCW-LTQ-POROSHELL-TFA98-10 min)

MS instrument type: ThermoFisher Scientific LTQ-Orbitrap-XL; HPLC instrument type: Agilent 1200SL; column: Agilent, POROSHELL 120, 3×150 mm, SB—C18 2.7 μm; eluent A: 1 1 water+0.1% trifluoroacetic acid; eluent B: 1 1 acetonitrile+0.1% trifluoroacetic acid; gradient: 0.0 min 2% B→0.3 min 2% B→5.0 min 95% B→10.0 min 95% B; oven: 40° C.; flow rate: 0.75 ml/min; UV detection: 210 nm Starting Compounds and Intermediates Starting compounds suitable for the preparation of the compounds according to the invention and the preparation of suitable intermediates have already been described in WO2015/96982 A1 and in WO2016/96610 A1.

The intermediates C1 to C73, L1 to L73, F1 to F58 and F82 to F91, F103 to F129, F142 to F156, F163 to F180, F192 to F196, F204 to F207, F209 to F218, F235, F236, F238, F241 to F245, F247, F248 and F254 according to WO2015/96982 A1 form part of the disclosure of the present application. Further intermediates which have been described in WO2016/96610 A1 likewise form part of the disclosure of the present application. Where reference is made hereinafter to compounds having particular numbers (e.g. Intermediate C1, L1 or F1), this means the compounds having these numbers according to WO2015/96982 A1. Further starting compounds and intermediates are described hereinafter.

Intermediate C102

(2S)-4-[{(1R)-1-[1-Benzyl-4-(2,5-difluorophenyl)-1H-pyrrol-2-yl]-2,2-dimethylpropyl}(glycoloyl)amino]-2-{[(benzyloxy)carbonyl]amino}butanoic acid

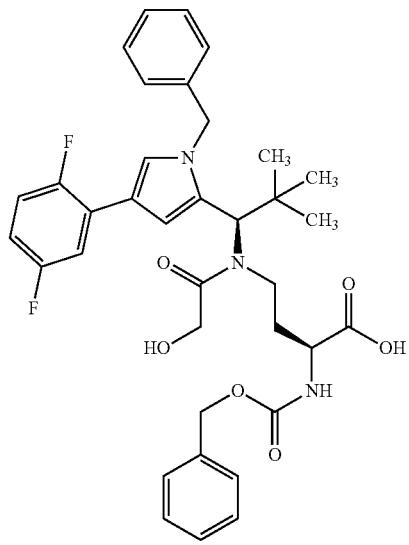 [SMILES: CC(C)(C)[C@H](c1cc(-c2cc(F)ccc2F)cn1Cc1ccccc1)N(CC[C@H](NC(=O)OCc1ccccc1)C(=O)O)C(=O)CO]

First, intermediate C52 was reductively alkylated with benzyl (2S)-2-{[(benzyloxy)carbonyl]amino}-4-oxobutanoate analogously to intermediate C2. The secondary amino group was then acylated with 2-chloro-2-oxoethyl acetate, and the two ester groups were then hydrolysed with 2M lithium hydroxide solution in methanol.

LC-MS (Method 1): $R_t$=1.31 min; MS (ESIpos): m/z=646 (M–H)⁻.

Intermediate C109

Di-tert-butyl N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-L-glutamate

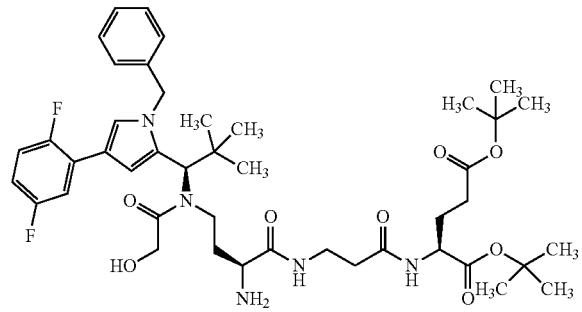 [SMILES: CC(C)(C)OC(=O)CC[C@H](NC(=O)CCNC(=O)[C@@H](N)CCN(C(=O)CO)[C@@H](c1cc(-c2cc(F)ccc2F)cn1Cc1ccccc1)C(C)(C)C)C(=O)OC(C)(C)C]

First of all, the dipeptide derivative di-tert-butyl beta-alanyl-L-glutamate was prepared by conventional methods of peptide chemistry by coupling of commercially available N-[(benzyloxy)carbonyl]-beta-alanine and di-tert-butyl L-glutamate hydrochloride (1:1) in the presence of HATU and subsequent hydrogenolytic detachment of the Z protecting group. The title compound was then prepared by coupling this intermediate with Intermediate C102 in the presence of HATU and N,N-diisopropylethylamine and subsequent detachment of the Z protecting group by hydrogenation over 10% palladium on activated carbon in methanol at RT under standard hydrogen pressure for 45 minutes.

LC-MS (Method 1): $R_t$=0.99 min; MS (ESIpos): m/z=826 [M+H]⁺.

Intermediate C111

Di-tert-butyl N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-D-glutamate

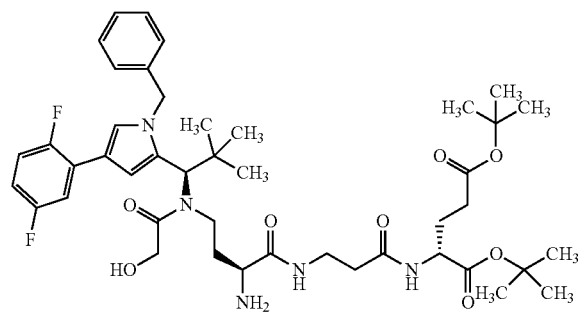 [SMILES: CC(C)(C)OC(=O)CC[C@@H](NC(=O)CCNC(=O)[C@@H](N)CCN(C(=O)CO)[C@@H](c1cc(-c2cc(F)ccc2F)cn1Cc1ccccc1)C(C)(C)C)C(=O)OC(C)(C)C]

The title compound was synthesized analogously to Intermediate C109.

LC-MS (Method 1): $R_t$=1.06 min; MS (ESIpos): m/z=826 [M+H]⁺.

Intermediate C116

Trifluoroacetic acid/$N^1$—{(2S)-4-[{(1R)-1-[1-benzyl-4-(2,5-difluorophenyl)-1H-pyrrol-2-yl]-2,2-dimethylpropyl}(glycoloyl)amino]-1-[(2-{[-(2,5-dioxo-2,5-dihydro-1H-pyrrol-1-yl)acetyl]amino}ethyl) amino]-1-oxobutan-2-yl}-L-aspartamide

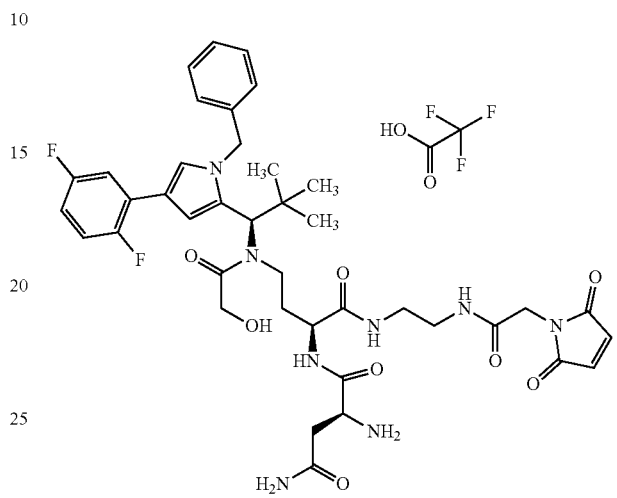

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[(2,5-dioxo-2,5-dihydro-1H-pyrrol-1-yl)acetyl]amino}ethyl)butanamide (1:1) (81.0 mg, 100 μmol) (Intermediate F104) and 2,5-dioxopyrrolidin-1-yl $N^2$-(tert-butoxycarbonyl)-L-asparaginate (43.0 mg, 131 μmol) were dissolved in 5.0 ml of DMF. The reaction mixture was stirred with N,N-diisopropylethylamine (61 μl, 350 μmol) at RT for a further 1 h, and then purified directly by preparative RP-HPLC (column: Chromatorex 125×30; 10μ, flow rate: 75 ml/min, MeCN/water, 0.1% TFA). The solvents were evaporated under reduced pressure and the residue was lyophilized. This gave 84 mg (88% of theory) of the compound tert-butyl [(2S)-4-amino-1-({(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}amino)-1,4-dioxobutan-2-yl]carbamate.

LC-MS (Method 1): $R_t$=1.09 min; MS (ESIpos): m/z=907 [M+H]⁺ tert-Butyl [(2S)-4-amino-1-({(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}amino)-1,4-dioxobutan-2-yl]carbamate (83.0 mg, 91.5 μmol) was dissolved in 5.0 ml of trifluoroethanol. The reaction mixture was admixed with zinc chloride (74.8 mg, 549 μmol) and stirred at 50° C. for 15 min. The mixture was admixed with ethylenediamine-N,N,N',N'-tetraacetic acid (160 mg, 549 μmol) and diluted with 5.0 ml of acetonitrile/water, TFA (20 μl) was added and the mixture was stirred for a further 10 min. The mixture was filtered through a syringe filter and purified by preparative RP-HPLC (column: Chromatorex 125×30; 10μ, flow rate: 75 ml/min, MeCN/water, 0.1% TFA). The solvents were evaporated under reduced pressure and the residue was dried under high vacuum. This gave 50 mg (58% of theory) of the title compound.

LC-MS (Method 1): $R_t$=0.81 min; MS (ESIpos): m/z=807 [M+H]+

Intermediate C118 tert-Butyl N-[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9-dioxo-5-oxa-7,10-diaza-2-siladodecan-12-yl]-D-alpha-glutaminate

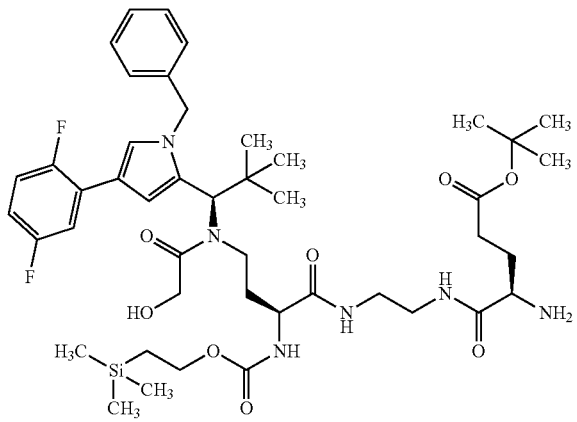 [SMILES: CC(C)(C)OC(=O)CC[C@@H](N)C(=O)NCCNC(=O)[C@H](CCN(C(=O)CO)[C@@H](c1cc(-c2cc(F)ccc2F)cn1Cc1ccccc1)C(C)(C)C)NC(=O)OCC[Si](C)(C)C]

The title compound was prepared by conventional methods of peptide chemistry by coupling Intermediate L119 and Intermediate C58 in the presence of HATU, followed by hydrogenolytic detachment of the Z protecting group.

LC-MS (Method 1): $R_t$=1.05 min; MS (ESIpos): m/z=885 (M+H)+.

Intermediate C119 tert-Butyl glycyl N-[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9-dioxo-5-oxa-7,10-diaza-2-siladodecan-12-yl]-D-alpha-glutaminate

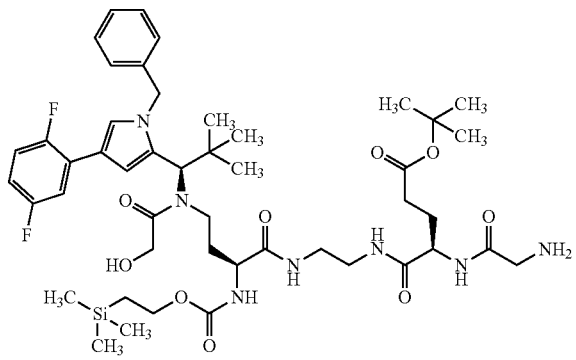 [SMILES: CC(C)(C)OC(=O)CC[C@@H](NC(=O)CN)C(=O)NCCNC(=O)[C@H](CCN(C(=O)CO)[C@@H](c1cc(-c2cc(F)ccc2F)cn1Cc1ccccc1)C(C)(C)C)NC(=O)OCC[Si](C)(C)C]

Intermediate C119 was prepared by conventional methods of peptide chemistry by coupling 2,5-dioxopyrrolidin-1-yl N-[(benzyloxy)carbonyl]glycinate and Intermediate C118 in the presence of HATU, followed by detachment of the Z protecting group, hydrogenation over 10% palladium on activated carbon in methanol/dichloromethane at RT under standard hydrogen pressure.

LC-MS (Method 1): $R_t$=1.03 min; MS (ESIpos): m/z=942 (M+H)+.

Intermediate C121

Dibenzyl N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-D-glutamate

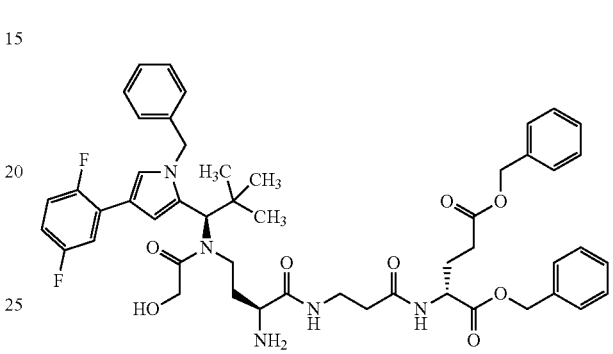

The title compound was prepared by coupling dibenzyl D-glutamate, which had been released beforehand from its p-toluenesulphonic acid salt by partitioning between ethyl acetate and 5% sodium hydrogencarbonate solution, with Intermediate C61 in the presence of HATU and N,N-diisopropylethylamine and subsequent detachment of the Teoc protecting group with zinc chloride in trifluoroethanol.

LC-MS (Method 1): $R_t$=1.05 min; MS (ESIpos): m/z=894 [M+H]+.

Intermediate C122 tert-Butyl N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-$N^2$-(tert-butoxycarbonyl)-D-alpha-glutaminate

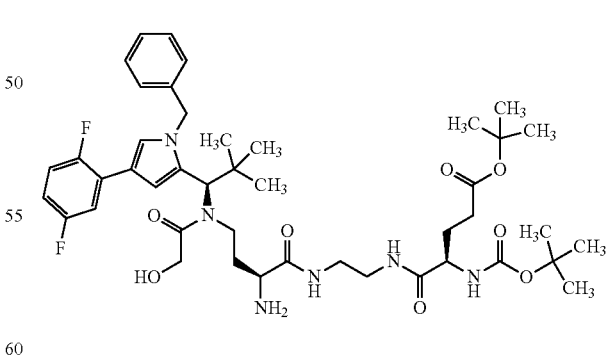

The title compound was prepared by coupling tert-butyl N-(2-aminoethyl)-$N^2$-(tert-butoxycarbonyl)-alpha-glutaminate trifluoroacetate with Intermediate C102 in the presence of HATU and N,N-diisopropylethylamine and subsequent hydrogenolytic detachment of the Z protecting group.

LC-MS (Method 1): $R_t$=1.06 min; MS (ESIpos): m/z=841 [M+H]+.

Intermediate C123 tert-Butyl N-[2-({(2S)-2-(L-asparaginylamino)-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N²-(tert-butoxycarbonyl)-D-alpha-glutaminate

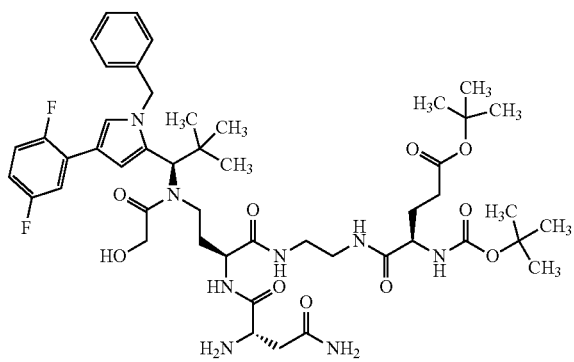 [SMILES: CC(C)(C)OC(=O)CC[C@@H](NC(=O)OC(C)(C)C)C(=O)NCCNC(=O)[C@H](CCN(C(=O)CO)[C@@H](c1cc(-c2cc(F)ccc2F)cn1Cc1ccccc1)C(C)(C)C)NC(=O)[C@@H](N)CC(N)=O]

The title compound was prepared by coupling of 4-nitrophenyl N²-[(benzyloxy)carbonyl]-L-asparaginate to Intermediate C122 in DMF in the presence of N,N-diisopropylethylamine and subsequent detachment of the Z protecting group by hydrogenation over 10% palladium on activated carbon in DCM/methanol 1:1 under standard hydrogen pressure at RT.

LC-MS (Method 1): $R_t$=0.98 min; MS (ESIpos): m/z=955 [M+H]⁺.

Intermediate C130

9H-Fluoren-9-ylmethyl {3-[{(1R)-1-[1-benzyl-4-(2,5-difluorophenyl)-1H-pyrrol-2-yl]-2,2-dimethylpropyl}(chloroacetyl)amino]propyl}carbamate

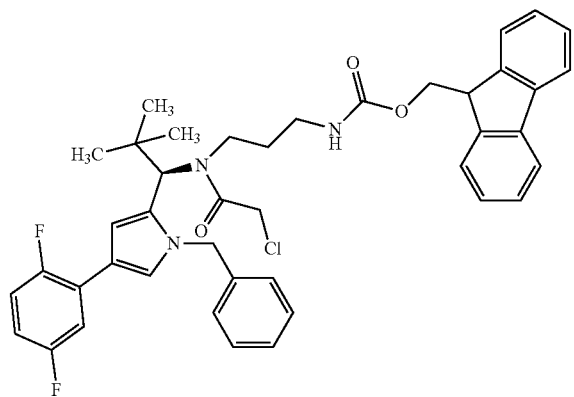 [SMILES: CC(C)(C)[C@H](c1cc(-c2cc(F)ccc2F)cn1Cc1ccccc1)N(CCCNC(=O)OCC1c2ccccc2-c2ccccc21)C(=O)CCl]

9H-Fluoren-9-ylmethyl [3-({(1R)-1-[1-benzyl-4-(2,5-difluorophenyl)-1H-pyrrol-2-yl]-2,2-dimethylpropyl}amino)propyl]carbamate (2.50 g, 3.94 mmol) (Intermediate C67) and triethylamine (1.6 ml, 12 mmol) were initially charged in dichloromethane (200 ml). Chloroacetyl chloride (2.23 g, 19.7 mmol) was added and the reaction was stirred at room temperature for 5 h. The reaction mixture was diluted with ethyl acetate and the organic phase was washed with 10% citric acid solution, water, saturated sodium hydrogencarbonate solution and saturated sodium chloride solution. The organic phase was then dried over magnesium sulphate, filtered and concentrated. The residue was used further without further purification. 1.7 g of the title compound were obtained.

Intermediate C131 tert-Butyl S-{2-[{(1R)-1-[1-benzyl-4-(2,5-difluorophenyl)-1H-pyrrol-2-yl]-2,2-dimethylpropyl}(3-{[(9H-fluoren-9-ylmethoxy)carbonyl]amino}propyl)amino]-2-oxoethyl}-L-cysteinate

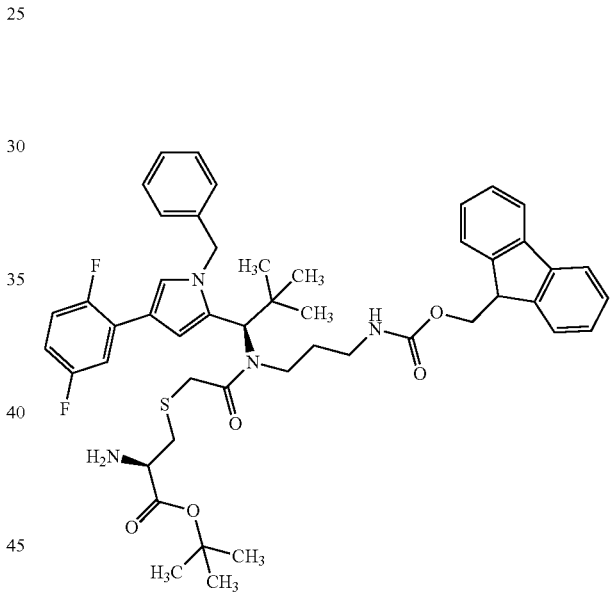

To an initial charge of di-tert-butyl L-cystinate dihydrochloride (135 mg, 317 μmol) in 6.0 ml of water and 7.5 ml of iso-propanol under argon was added TCEP (303 mg, 1.06 mmol). The reaction mixture was stirred at RT for 30 min. Subsequently, a solution of 9H-fluoren-9-ylmethyl {3-[{(1R)-1-[1-benzyl-4-(2,5-difluorophenyl)-1H-pyrrol-2-yl]-2,2-dimethylpropyl}(chloroacetyl)amino]propyl}carbamate (300 mg, 422 μmol) and 1,8-diazabicyclo(5.4.0)undec-7-ene (760 μl, 5.1 mmol) in 1.5 ml of iso-propanol was added and the reaction mixture was stirred at 50° C. for 1 h. It was diluted with ethyl acetate and the organic phase was washed with water and sat. sodium chloride solution. The organic phase was dried over magnesium sulphate and the solvent was evaporated under reduced pressure. The residue was used further without purification. 360 mg of the title compound were obtained.

LC-MS (Method 1): $R_t$=1.17 min; MS (ESIpos): m/z=851 [M+H]⁺

Intermediate C132 tert-Butyl S-{2-[{(1R)-1-[1-benzyl-4-(2,5-difluorophenyl)-1H-pyrrol-2-yl]-2,2-dimethylpropyl}(3-{[(9H-fluoren-9-ylmethoxy)carbonyl]amino}propyl)amino]-2-oxoethyl}-N-(2,2-dimethyl-4,20-dioxo-3,8,11,14,17-pentaoxa-5-azaicosan-20-yl)-L-cysteinate N,N-diisopropylethylamine (300 µl, 1.7 mmol), and the reaction was stirred at RT for 5 min. The mixture was quenched with 1 ml of water+0.1% TFA and purified directly via prep. HPLC (eluent: ACN/water+0.1% TFA, gradient). 167 mg of the target compound were obtained.

LC-MS (Method 1): R$_t$=1.56 min; MS (ESIpos): m/z=1198 [M+H]$^+$

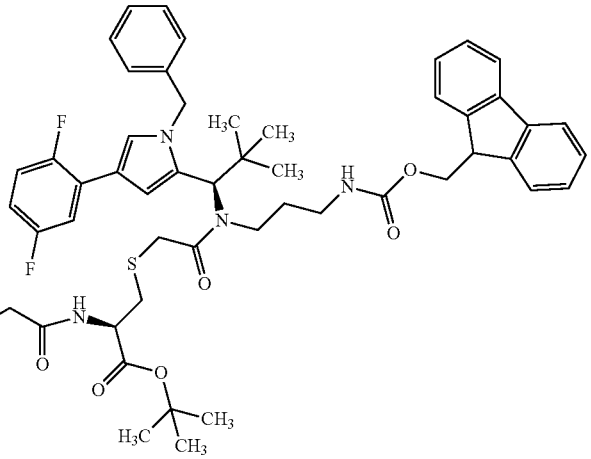

tert-Butyl S-{2-[{(1R)-1-[1-benzyl-4-(2,5-difluorophenyl)-1H-pyrrol-2-yl]-2,2-dimethylpropyl}(3-{[(9H-fluoren-9-ylmethoxy)carbonyl]amino}propyl)amino]-2-oxoethyl}-L-cysteinate (361 mg, 424 µmol) were dissolved in absolute DMF (3 ml) and added to 2,2-dimethyl-4-oxo-3,8,11,14,17-pentaoxa-5-azaicosan-20-oic acid (186 mg, 509 µmol). To the mixture were added HATU (193 mg, 509 µmol) and

Intermediate C133 tert-Butyl S-{2-[(3-aminopropyl){(1R)-1-[1-benzyl-4-(2,5-difluorophenyl)-1H-pyrrol-2-yl]-2,2-dimethylpropyl}amino]-2-oxoethyl}-N-(2,2-dimethyl-4,20-dioxo-3,8,11,14,17-pentaoxa-5-azaicosan-20-yl)-L-cysteinate

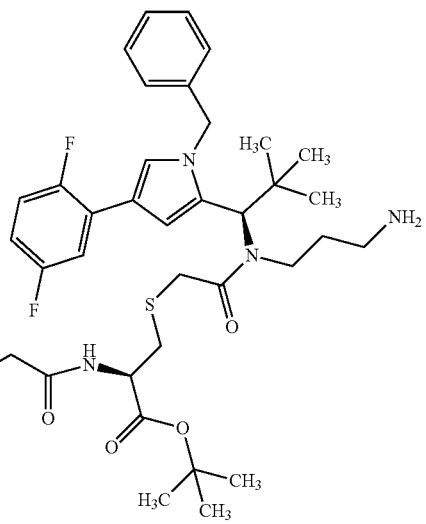

To a solution of tert-butyl S-{2-[{(1R)-1-[1-benzyl-4-(2,5-difluorophenyl)-1H-pyrrol-2-yl]-2,2-dimethylpropyl}(3-{[(9H-fluoren-9-ylmethoxy)carbonyl]amino}propyl)amino]-2-oxoethyl}-N-(2,2-dimethyl-4,20-dioxo-3,8,11,14,17-pentaoxa-5-azaicosan-20-yl)-L-cysteinate (214 mg, 178 µmol) in DMF (5 ml) was added morpholine (160 µl, 1.8 mmol), and the mixture was stirred at room temperature for 5 hours. The mixture was quenched with water+0.1% TFA and purified directly via prep. HPLC (acetonitrile/water+0.1% TFA gradient). 111 mg of the target compound were obtained.

LC-MS (Method 1): $R_t$=1.03 min; MS (ESIpos): m/z=976 [M+H]$^+$

Intermediate C134 tert-Butyl S-{2-[{(1R)-1-[1-benzyl-4-(2,5-difluorophenyl)-1H-pyrrol-2-yl]-2,2-dimethylpropyl}(3-{[N2-(pyridin-4-ylacetyl)-L-asparaginyl]amino}propyl)amino]-2-oxoethyl}-N-(2,2-dimethyl-4,20-dioxo-3,8,11,14,17-pentaoxa-5-azaicosan-20-yl)-L-cysteinate

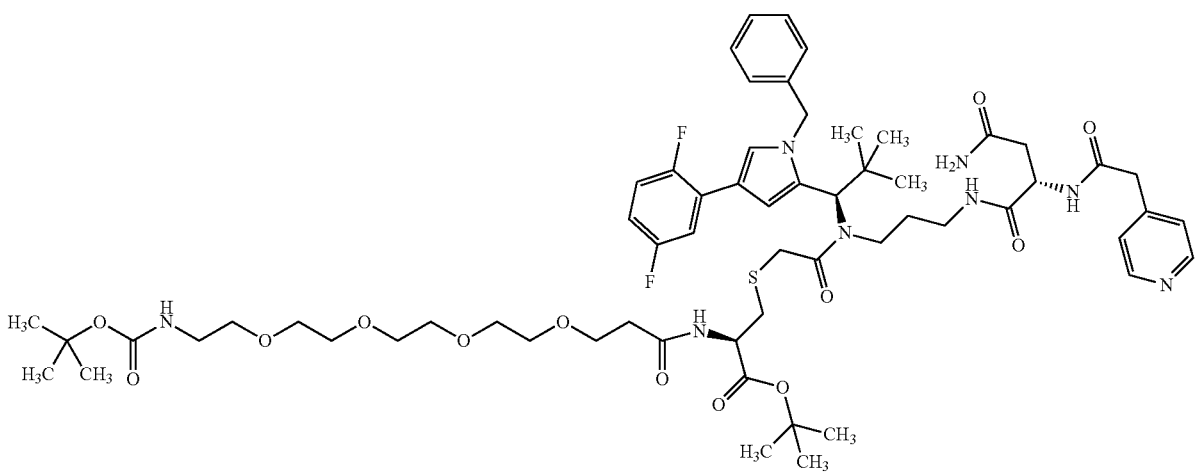 [SMILES: CC(C)(C)OC(=O)NCCOCCOCCOCCOCCC(=O)N[C@@H](CSCC(=O)N(CCCNC(=O)[C@H](CC(N)=O)NC(=O)Cc1ccncc1)[C@@H](c1cc(-c2cc(F)ccc2F)cn1Cc1ccccc1)C(C)(C)C)C(=O)OC(C)(C)C]

tert-Butyl S-{2-[(3-aminopropyl){(1R)-1-[1-benzyl-4-(2,5-difluorophenyl)-1H-pyrrol-2-yl]-2,2-dimethylpropyl}amino]-2-oxoethyl}-N-(2,2-dimethyl-4,20-dioxo-3,8,11,14,17-pentaoxa-5-azaicosan-20-yl)-L-cysteinate (27.2 mg, 27.9 µmol) and N²-(pyridin-4-ylacetyl)-L-asparagine (8.40 mg, 33.4 µmol, Intermediate L136) were dissolved in absolute DMF (3 ml), and HATU (12.7 mg, 33.4 µmol) and N,N-diisopropylethylamine (15 µl, 84 µmol) were added. The reaction was stirred at RT for 10 min. The mixture was quenched with 1 ml of water+0.1% TFA and purified directly via prep. HPLC (eluent: ACN/water+0.1% TFA, gradient). 23 mg of the target compound were obtained.

LC-MS (Method 12): $R_t$=2.12 min; MS (ESIpos): m/z=1209 [M+H]$^+$

Intermediate C135

N-(15-Amino-4,7,10,13-tetraoxapentadecan-1-oyl)-S-{2-[{(1R)-1-[1-benzyl-4-(2,5-difluorophenyl)-1H-pyrrol-2-yl]-2,2-dimethylpropyl}(3-{[N2-(pyridin-4-ylacetyl)-L-asparaginyl]amino}propyl)amino]-2-oxoethyl}-L-cysteine trifluoroacetic acid salt

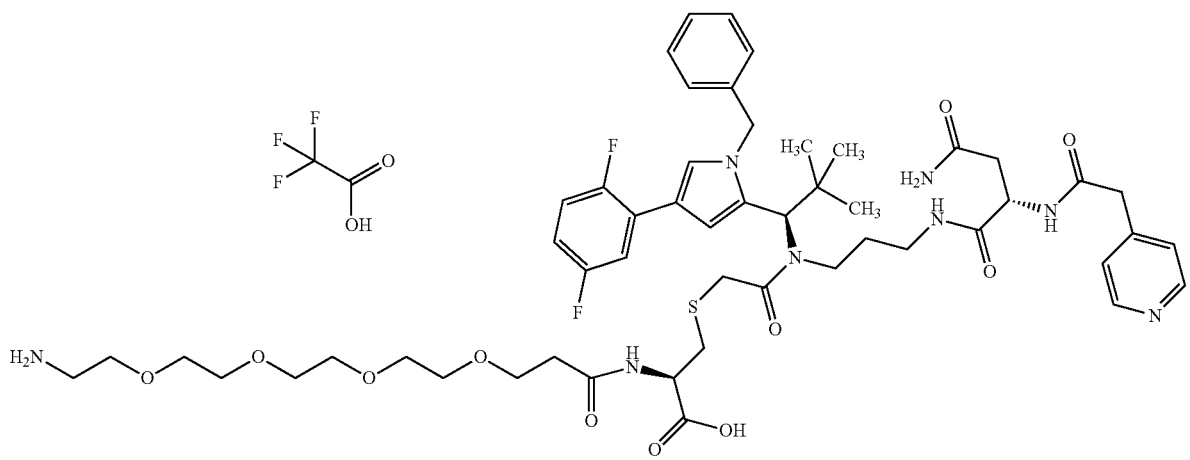 [SMILES: CC(C)(C)[C@H](c1cc(-c2cc(F)ccc2F)cn1Cc1ccccc1)N(CCCNC(=O)[C@H](CC(N)=O)NC(=O)Cc1ccncc1)C(=O)CSC[C@H](NC(=O)CCOCCOCCOCCOCCN)C(=O)O ; O=C(O)C(F)(F)F]

tert-Butyl S-{2-[{(1R)-1-[1-benzyl-4-(2,5-difluorophenyl)-1H-pyrrol-2-yl]-2,2-dimethylpropyl}(3-{[N²-(pyridin-4-ylacetyl)-L-asparaginyl]amino}propyl)amino]-2-oxoethyl}-N-(2,2-dimethyl-4,20-dioxo-3,8,11,14,17-pentaoxa-5-azaicosan-20-yl)-L-cysteinate (63.6 mg, 52.6 μmol) was dissolved in trifluoroethanol (3.0 ml, 41 mmol), and zinc chloride (43.0 mg, 316 μmol) was added. The reaction was stirred at 50° C. for 2 h 20 min. Another 6 eq. of ZnCl₂ were added and the mixture was stirred at 50° C. for 1 h. Ethylenediamine-N,N,N',N'-tetraacetic acid (184 mg, 631 μmol) was added to the mixture, which was allowed to cool down to room temperature. Water (+0.1% TFA) was added to the reaction mixture, which was filtered and purified by means of prep. RP-HPLC (flow rate: 50 ml/min, MeCN/water, 0.1% TFA). The solvents were evaporated under reduced pressure and the residue was lyophilized. 40 mg of the title compound were obtained.

LC-MS (Method 1): $R_t$=0.75 min; MS (ESIneg): m/z=1051 [M−H]⁻

Intermediate C136

Benzyl [2-({(2S)-2-(L-asparaginylamino)-4-[{(1R)-1-[1-benzyl-4-(2,5-difluorophenyl)-1H-pyrrol-2-yl]-2,2-dimethylpropyl}(glycoloyl)amino]butanoyl}amino)ethyl]carbamate trifluoroacetate

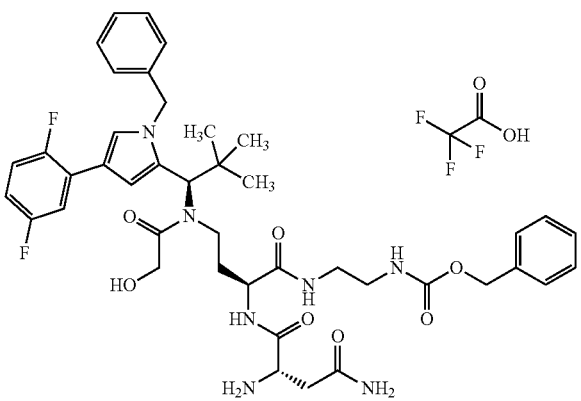 [SMILES: CC(C)(C)[C@H](c1cc(-c2cc(F)ccc2F)cn1Cc1ccccc1)N(CC[C@H](NC(=O)[C@@H](N)CC(N)=O)C(=O)NCCNC(=O)OCc1ccccc1)C(=O)CO ; O=C(O)C(F)(F)F]

Firstly, Intermediate C58 was coupled to benzyl 2-aminoethyl carbamate hydrochloride (1:1) in the presence of HATU and N,N-diisopropylethylamine. This was followed by the detachment of the Teoc protecting group by stirring at 50° C. in trifluoroethanol with 8 equiv. of zinc chloride for 2 hours. The resultant intermediate was then coupled to 2,5-dioxopyrrolidin-1-yl $N^2$-(tert-butoxycarbonyl)-L-aspartate in the presence of N,N-diisopropylethylamine. In the last step, the Boc protecting group was detached by stirring at 50° C. in trifluoroethanol with 6 equiv. of zinc chloride for 1 hour, giving the target compound.

LC-MS (Method 1): $R_t$=0.91 min; MS (ESIpos): m/z=804 [M+H]⁺.

Intermediate C137

Benzyl N-(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]sulphonyl}ethyl)-$N^2$-[(benzyloxy)carbonyl]-D-alpha-glutaminate trifluoroacetate

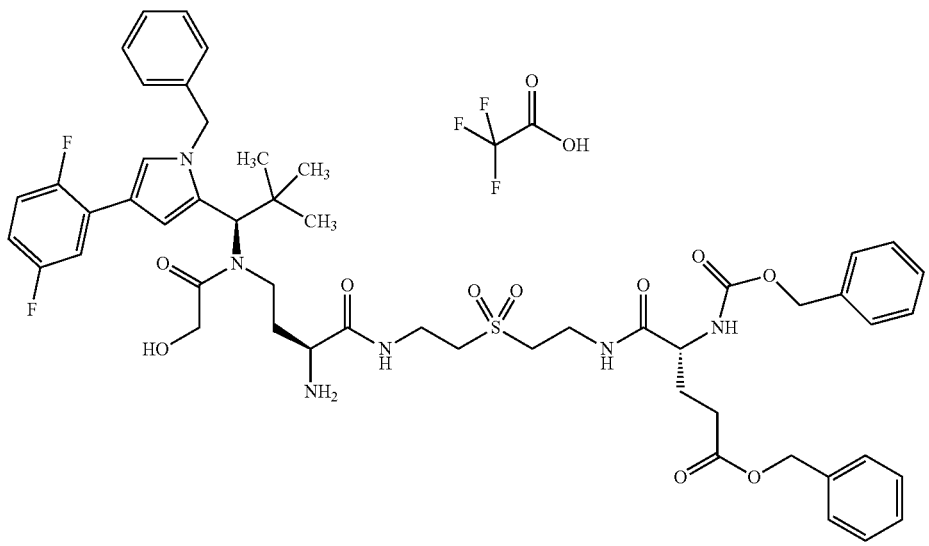 [SMILES: CC(C)(C)[C@H](c1cc(-c2cc(F)ccc2F)cn1Cc1ccccc1)N(CC[C@H](N)C(=O)NCCS(=O)(=O)CCNC(=O)[C@@H](CCC(=O)OCc1ccccc1)NC(=O)OCc1ccccc1)C(=O)CO ; O=C(O)C(F)(F)F]

The title compound was prepared proceeding from Intermediate L81 by coupling to Intermediate C58 in the presence of HATU and N,N-diisopropylethylamine. In the next step, the Z protecting group was removed by hydrogenation over 10% palladium on activated carbon in DCM/methanol 1:1 at RT under standard hydrogen pressure for 30 minutes. The deprotected intermediate was then converted to the title compound by coupling to (2R)-5-(benzyloxy)-2-{[(benzyloxy)carbonyl]amino}-5-oxopentanoic acid in the presence of 2 equiv. of HATU and 3 equiv. of N,N-diisopropylethylamine and finally by deprotection with 6 equiv. of zinc chloride (stirring at 50° C. in trifluoroethanol for 1 h).

LC-MS (Method 12): $R_t$=1.89 min; MS (ESIpos): m/z=1001 (M+H)⁺.

Intermediate C138 tert-Butyl N-[(8S)-8-{2-[{(1R)-1-[1-benzyl-4-(2,5-difluorophenyl)-1H-pyrrol-2-yl]-2,2-dimethyl propyl}(glycoloyl)amino]ethyl}-2,2-dimethyl-13,13-dioxido-6,9-dioxo-5-oxa-13lambda$^6$-thia-7,10-diaza-2-silapentadecan-15-yl]-D-alpha-glutaminate

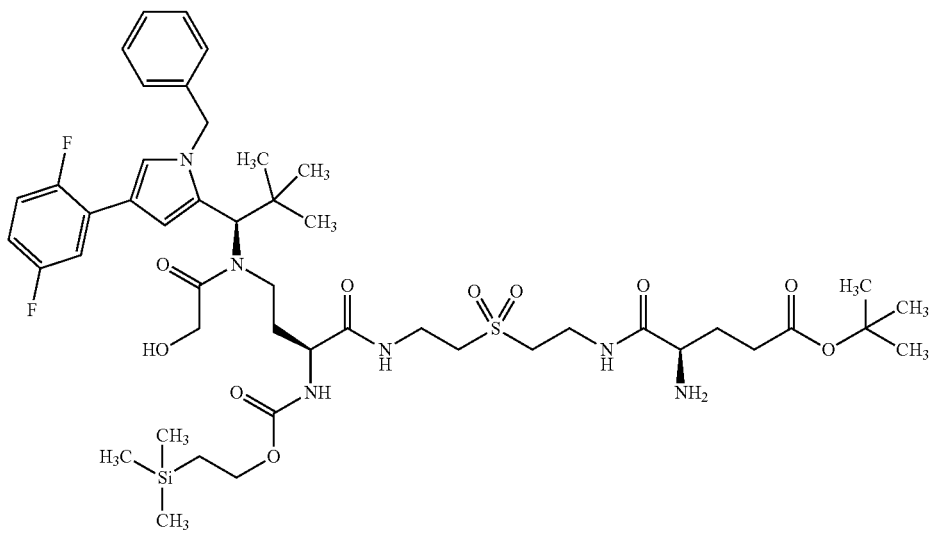 [SMILES: CC(C)(C)OC(=O)CC[C@@H](N)C(=O)NCCS(=O)(=O)CCNC(=O)[C@H](CCN(C(=O)CO)[C@@H](c1cc(-c2cc(F)ccc2F)cn1Cc1ccccc1)C(C)(C)C)NC(=O)OCC[Si](C)(C)C]

The title compound was prepared proceeding from Intermediate C58 by coupling to Intermediate L81 in the presence of HATU and N,N-diisopropylethylamine. In the next step, the Z protecting group was removed by hydrogenation over 10% palladium on activated carbon in DCM/methanol 1:1 at RT under standard hydrogen pressure for 1 hour. The deprotected intermediate was then converted to the title compound by coupling to (2R)-2-{[(benzyloxy)carbonyl]amino}-5-tert-butoxy-5-oxopentanoic acid in the presence of HATU and N,N-diisopropylethylamine and finally by detachment of the Z protecting group by hydrogenation over 10% palladium on activated carbon in DCM/methanol 1:1 at RT under standard hydrogen pressure for 2 hours.

LC-MS (Method 1): $R_t$=1.14 min; MS (ESIpos): m/z=977 (M+H)$^+$.

Intermediate C139

Di-tert-butyl N-{(2S)-2-(L-asparaginylamino)-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-D-glutamate

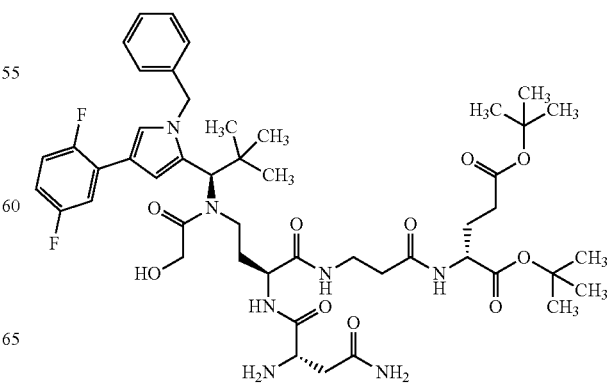

The title compound was synthesized by coupling Intermediate C111 to 1.5 equiv. of 4-nitrophenyl N²-[(benzyloxy)carbonyl]-L-aspartate in DMF in the presence of 3 equiv. of N,N-diisopropylethylamine, followed by detachment of the Z protecting group by hydrogenation over 10% palladium on activated carbon in DCM/methanol 1:1 under standard hydrogen pressure at RT for 2 hours.

LC-MS (Method 1): $R_t$=1.02 min; MS (ESIpos): m/z=940 [M+H]⁺.

Intermediate C140

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-N¹,N⁵-dibenzyl-D-glutamamide trifluoroacetate

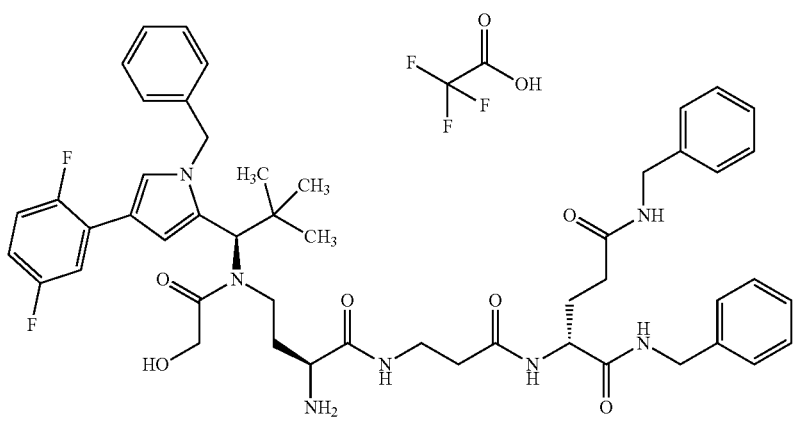 [SMILES: CC(C)(C)[C@H](c1cc(-c2cc(F)ccc2F)cn1Cc1ccccc1)N(CC[C@H](N)C(=O)NCCC(=O)N[C@H](CCC(=O)NCc1ccccc1)C(=O)NCc1ccccc1)C(=O)CO ; O=C(O)C(F)(F)F]

Firstly, N¹,N⁵-dibenzyl-D-glutamamide trifluoroacetate was prepared by coupling N-(tert-butoxycarbonyl)-D-glutamic acid to benzylamine in the presence of HATU and N,N-diisopropylethylamine, followed by detachment of the Boc protecting group with TFA. This intermediate was then coupled to Boc-β-alanine in the presence of HATU and N,N-diisopropylethylamine, and then the Boc protecting group was removed with TFA in DCM. The resultant compound was then coupled to Intermediate C58 in the presence of HATU and N,N-diisopropylethylamine and, finally, the title compound was prepared by detaching the Teoc protecting group by means of zinc chloride in trifluoroethanol.

LC-MS (Method 1): $R_t$=0.95 min; MS (ESIpos): m/z=892 [M+H]⁺.

Intermediate C141

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-L-asparagine trifluoroacetate

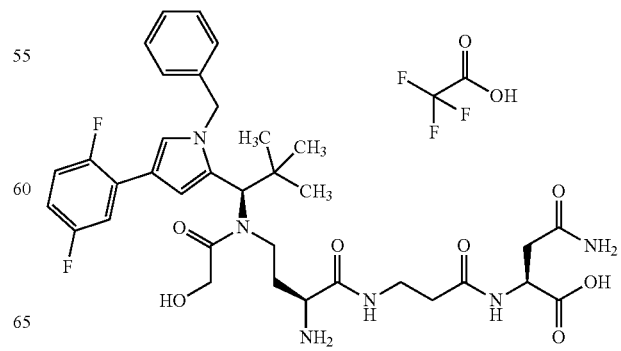

Firstly, Intermediate C61 was coupled to tert-butyl L-aspartate in the presence of 1.5 equiv. of HATU and 3 equiv. of N,N-diisopropylethylamine. Subsequently, by stirring with 6 equiv. of zinc chloride in trifluoroethanol at 50° C., the Teoc protecting group and the tert-butyl ester were removed and hence the title compound was obtained.

LC-MS (Method 1): $R_t$=0.95 min; MS (ESIpos): m/z=892 [M+H]$^+$.

Intermediate C142

Di-tert-butyl N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-beta-alanyl-D-glutamate

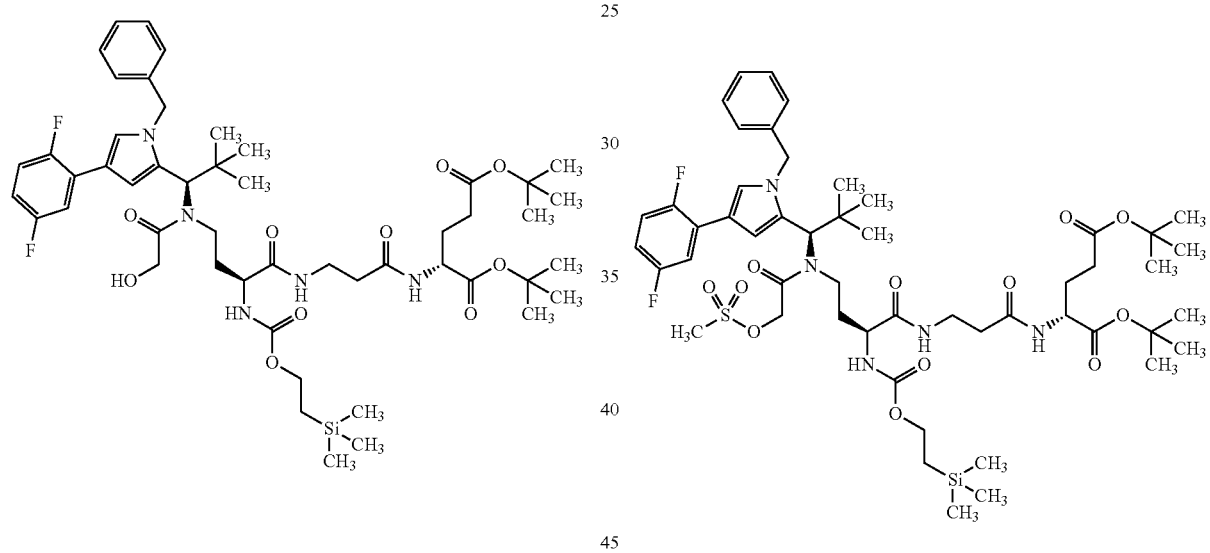

To a solution of N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-beta-alanine (745 mg, 1.02 mmol, Intermediate C61) in DMF (10 ml) were added di-tert-butyl D-glutamate hydrochloride (363 mg, 1.23 mmol), HATU (505 mg, 1.33 mmol) and N,N-diisopropylethylamine (530 µl, 3.1 mmol), and the reaction was stirred at room temperature for 10 min. The reaction mixture was admixed with ethyl acetate and washed with water and saturated sodium chloride solution. The organic phase was dried over magnesium sulphate and concentrated, and the residue was purified by means of prep. RP-HPLC (gradient, MeCN/water+0.1% TFA). The solvents were evaporated under reduced pressure and the residue was dried under high vacuum.

LC-MS (Method 1): $R_t$=1.58 min; MS (ESIpos): m/z=970 [M+H]$^+$

Intermediate C143

Di-tert-butyl N-[(2S)-4-({(1R)-1-[1-benzyl-4-(2,5-difluorophenyl)-1H-pyrrol-2-yl]-2,2-dimethylpropyl}{[(methylsulphonyl)oxy]acetyl}amino)-2-({[2-(trimethylsilyl)ethoxy]carbonyl}-amino)butanoyl]-beta-alanyl-D-glutamate

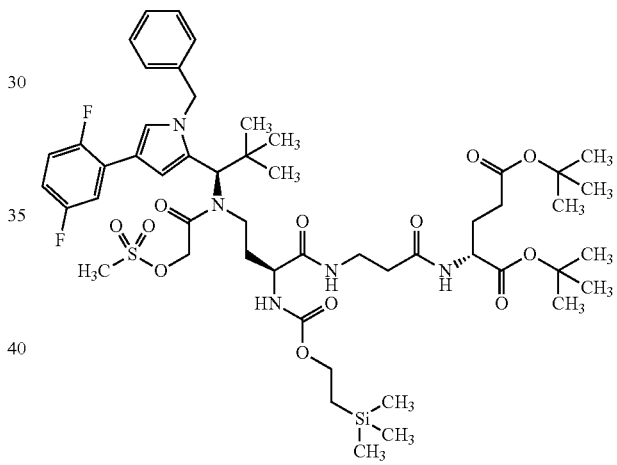

To a solution of di-tert-butyl N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}-amino)butanoyl]-beta-alanyl-D-glutamate (257 mg, 264 µmol of Intermediate C142) in dichloromethane (20 ml) were added, at 0° C., methanesulphonyl chloride (49 µl, 630 µmol) and triethylamine (92 µl, 660 µmol), and the reaction was stirred at 0° C. for 1 h. It was then diluted with dichloromethane and washed with a saturated sodium hydrogencarbonate solution (3×) and a saturated sodium chloride solution. The organic phase was dried over magnesium sulphate and concentrated, and the residue was converted further without further purification.

LC-MS (Method 1): $R_t$=1.52 min; MS (ESIpos): m/z=1048 [M+H]$^+$

Intermediate C144

Di-tert-butyl N-[(2S)-4-[({[(2R)-2-amino-3-tert-butoxy-3-oxopropyl]sulphanyl}acetyl){(1R)-1-[1-benzyl-4-(2,5-difluorophenyl)-1H-pyrrol-2-yl]-2,2-dimethylpropyl}amino]-2-({[2-(trimethyl-silyl)ethoxy]carbonyl}amino)butanoyl]-beta-alanyl-D-glutamat trifluoroacetate

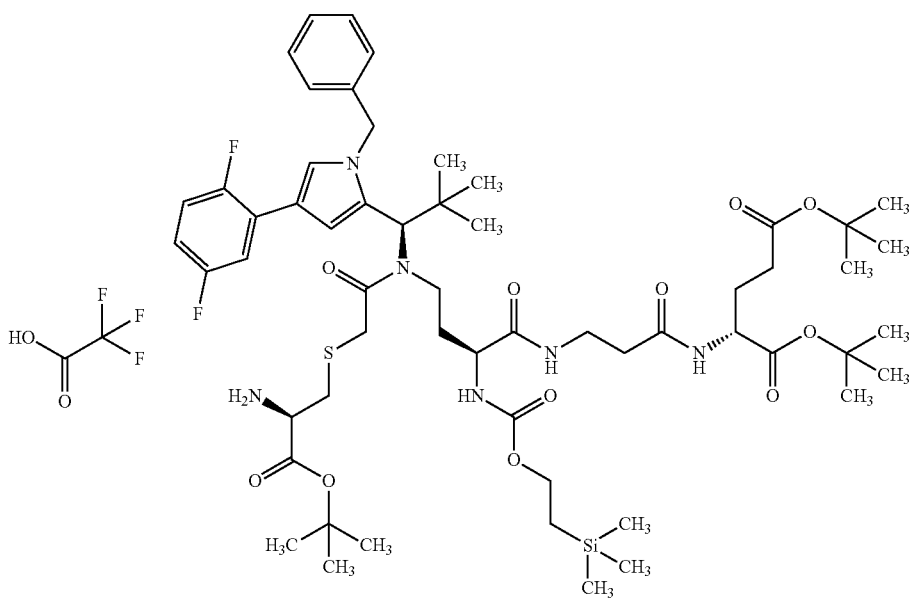

To an initial charge of di-tert-butyl L-cystinate dihydrochloride (306 mg, 719 µmol) in 25 ml of water and 50 ml of iso-propanol was added TCEP (687 mg, 2.40 mmol) under argon. The reaction mixture was stirred at RT for 30 min. Subsequently, a solution of di-tert-butyl N-[(2S)-4-({(1R)-1-[1-benzyl-4-(2,5-difluorophenyl)-1H-pyrrol-2-yl]-2,2-dimethylpropyl}{[(methyl-sulphonyl)oxy]acetyl}amino)-2-({[2-(trimethylsilyl)ethoxy]carbonyl}amino)butanoyl]-beta-alanyl-D-glutamate (1.00 g, 958 µmol of Intermediate C143) and 1,8-diazabicyclo(5.4.0)undec-7-ene (1.7 ml, 11 mmol) in 35 ml iso-propanol was added and the reaction mixture was stirred at 50° C. for 14 h. It was diluted with ethyl acetate and the organic phase was washed with water and sat. sodium chloride solution. The organic phase was dried over magnesium sulphate and the solvent was evaporated under reduced pressure. The residue was purified by means of prep. RP-HPLC (gradient, MeCN/water+0.1% TFA). The solvents were evaporated under reduced pressure and the residue was dried under high vacuum. 923 mg of the title compound were obtained.

LC-MS (Method 12): $R_f$=2.46 min; MS (ESIpos): m/z=1129 [M+H]$^+$

Intermediate C145

Di-tert-butyl N-[(2S)-4-[{(1R)-1-[1-benzyl-4-(2,5-difluorophenyl)-1H-pyrrol-2-yl]-2,2-dimethylpropyl}({[(2R)-3-tert-butoxy-2-({N²-[(9H-fluoren-9-ylmethoxy)carbonyl]-L-asparaginyl}amino)-3-oxopropyl]sulphanyl}acetyl)amino]-2-({[2-(trimethylsilyl)-ethoxy]carbonyl}amino)butanoyl]-beta-alanyl-D-glutamate

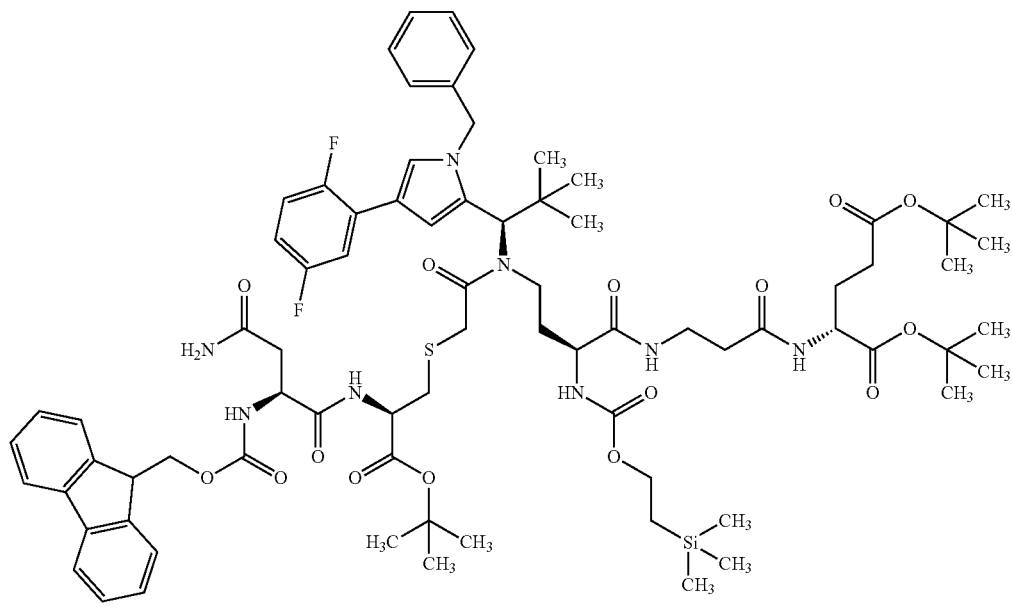 [SMILES: CC(C)(C)OC(=O)CC[C@@H](NC(=O)CCNC(=O)[C@H](CCN(C(=O)CSC[C@H](NC(=O)[C@H](CC(N)=O)NC(=O)OCC1c2ccccc2-c2ccccc21)C(=O)OC(C)(C)C)[C@@H](c1cc(-c2cc(F)ccc2F)cn1Cc1ccccc1)C(C)(C)C)NC(=O)OCC[Si](C)(C)C)C(=O)OC(C)(C)C]

To a solution of di-tert-butyl N-[(2S)-4-[({[(2R)-2-amino-3-tert-butoxy-3-oxopropyl]sulphanyl}acetyl){(1R)-1-[1-benzyl-4-(2,5-difluorophenyl)-1H-pyrrol-2-yl]-2,2-dimethylpropyl}amino]-2-({[2-(trimethylsilyl)ethoxy]carbonyl}amino)butanoyl]-beta-alanyl-D-glutamate trifluoroacetate (60.0 mg, 48.2 µmol of Intermediate C144) and N²-[(9H-fluoren-9-ylmethoxy)carbonyl]-L-asparagine (20.5 mg, 57.9 µmol) in DMF (3.0 ml) were added HATU (22.0 mg, 57.9 µmol) and N,N-diisopropylethylamine (25 µl, 140 µmol), and the reaction was stirred at room temperature for 10 min. 1 ml of water+0.1% TFA was added to the mixture, which was purified directly via prep. HPLC (eluent: ACN/water+0.1% TFA, gradient). 71 mg of the target compound were obtained.

LC-MS (Method 12): $R_f$=3.15 min; MS (ESIpos): m/z=1466 [M+H]⁺

Intermediate C146

Di-tert-butyl N-[(2S)-4-[({[(2R)-2-(L-asparaginylamino)-3-tert-butoxy-3-oxopropyl]sulphanyl}-acetyl){(1R)-1-[1-benzyl-4-(2,5-difluorophenyl)-1H-pyrrol-2-yl]-2,2-dimethylpropyl}amino]-2-({[2-(trimethylsilyl)ethoxy]carbonyl}amino)butanoyl]-beta-alanyl-D-glutamate trifluoroacetate

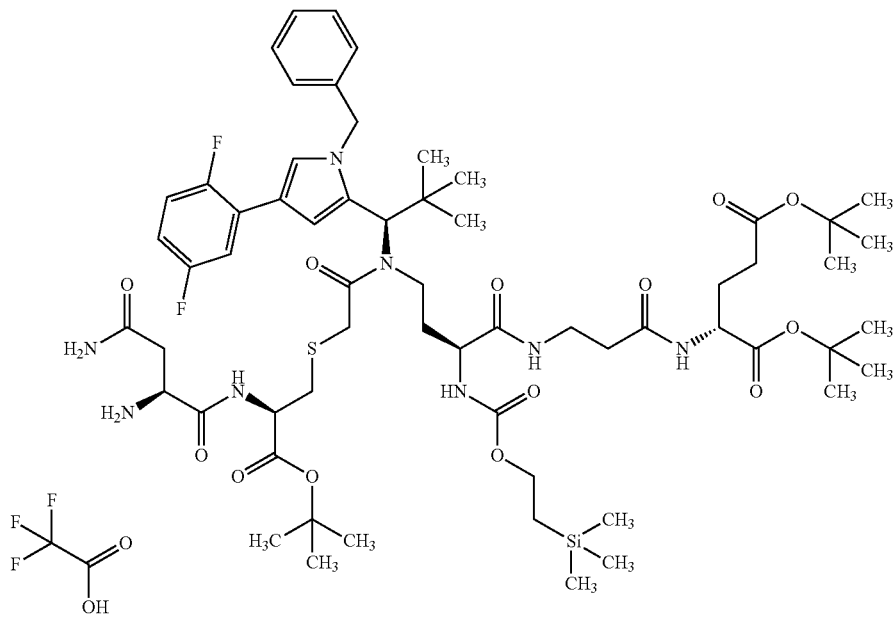 [SMILES: O=C(O)C(F)(F)F ; CC(C)(C)OC(=O)CC[C@@H](NC(=O)CCNC(=O)[C@H](CCN(C(=O)CSC[C@H](NC(=O)[C@@H](N)CC(N)=O)C(=O)OC(C)(C)C)[C@@H](c1cc(-c2cc(F)ccc2F)cn1Cc1ccccc1)C(C)(C)C)NC(=O)OCC[Si](C)(C)C)C(=O)OC(C)(C)C]

Di-tert-butyl N-[(2S)-4-[{(1R)-1-[1-benzyl-4-(2,5-difluorophenyl)-1H-pyrrol-2-yl]-2,2-dimethylpropyl}({[(2R)-3-tert-butoxy-2-({N²-[(9H-fluoren-9-ylmethoxy)carbonyl]-L-asparaginyl}amino)-3-oxopropyl]sulphanyl}acetyl)amino]-2-({[2-(trimethylsilyl)ethoxy]-carbonyl}amino)butanoyl]-beta-alanyl-D-glutamate (63.5 mg, 43.3 µmol, Intermediate C145) was initially charged in DMF (3 ml), morpholine (38 µl, 430 µmol) was added and the mixture was stirred at room temperature for 18 h. 1 ml of water+0.1% TFA was added to the mixture, which was purified directly via prep. HPLC (eluent: ACN/water+0.1% TFA, gradient). 38 mg of the target compound were obtained.

LC-MS (Method 1): $R_t$=1.25 min; MS (ESIpos): m/z=1243 [M+H]⁺

Intermediate L81

Trifluoroacetic acid/benzyl {2-[(2-aminoethyl)sulphonyl]ethyl}carbamate

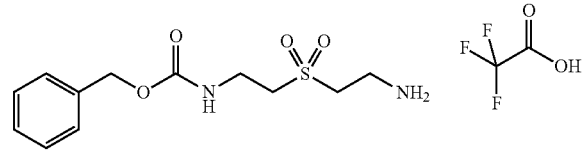 [SMILES: NCCS(=O)(=O)CCNC(=O)OCc1ccccc1 ; O=C(O)C(F)(F)F]

250 mg (1.11 mmol) of 2,2'-sulphonyldiethanamine were coupled to 92.3 mg (0.37 mmol) of 1-{[(benzyloxy)carbonyl] oxy}pyrrolidine-2,5-dione in the presence of N,N-diisopropylethylamine in DMF. Subsequent purification by HPLC gave 70 mg (47% of theory) of the title compound.

C-MS (Method 12): $R_t$=0.64 min; MS (ESIpos): m/z=257.11 (M+H)⁺.

Intermediate L103

N-(Pyridin-4-ylacetyl)-L-alanyl-L-alanyl-L-asparagine trifluoroacetate

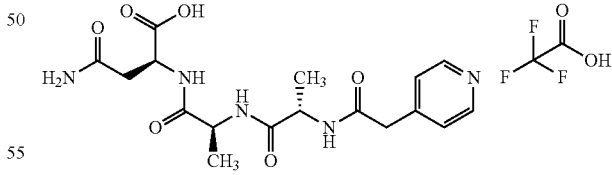

The title compound was prepared by conventional methods of peptide chemistry commencing with the coupling of 4-pyridineacetic acid with commercially available tert-butyl L-alanyl-L-alaninate in the presence of HATU and N,N-diisopropylethylamine, followed by deprotection with trifluoroacetic acid, coupling to tert-butyl L-asparaginate and subsequent deprotection of the carboxyl group with trifluoroacetic acid.

LC-MS (Method 1): $R_t$=0.15 min; MS (ESIpos): m/z=394 (M+H)⁺.

Intermediate L119

Trifluoroacetic acid tert-butyl N-(2-aminoethyl)-N²-[(benzyloxy)carbonyl]-D-alpha-glutaminate salt

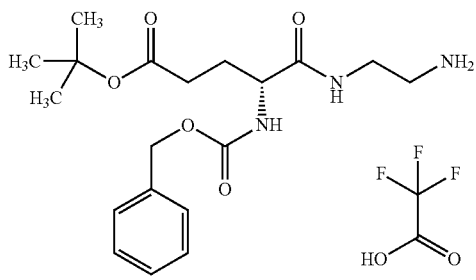 [SMILES: CC(C)(C)OC(=O)CC[C@@H](NC(=O)OCc1ccccc1)C(=O)NCCN ; O=C(O)C(F)(F)F]

Intermediate L119 was prepared by conventional methods of peptide chemistry by coupling commercially available (2R)-2-{[(Benzyloxy)carbonyl]amino}-5-tert-butoxy-5-oxopentanoic acid (1.00 g, 2.96 mmol) and tert-butyl (2-aminoethyl)carbamate (560 µl, 3.6 mmol) in the presence of HATU, followed by acidic detachment of the Boc protecting group with TFA in dichloromethane.

LC-MS (Method 1): $R_t$=0.62 min; MS (ESI-pos): m/z=380 (M+H)⁺.

Intermediate L136

N²-(Pyridin-4-ylacetyl)-L-asparagine

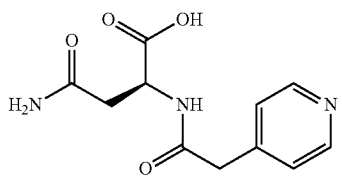 [SMILES: NC(=O)C[C@H](NC(=O)Cc1ccncc1)C(=O)O]

The title compound was prepared by coupling pyridin-4-ylacetic acid hydrochloride to tert-butyl L-aspartate in the presence of HATU and N,N-diisopropylethylamine, followed by detachment of the t-butyl protecting group by means of trifluoroacetic acid in dichloromethane.

LC-MS (Method 12): $R_t$=0.65 min; MS (ESIneg): m/z=250 [M−H]⁻

Intermediate L137

N²-(Pyridin-4-ylacetyl)-L-glutamine

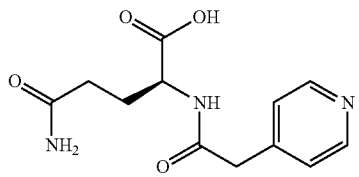 [SMILES: NC(=O)CC[C@H](NC(=O)Cc1ccncc1)C(=O)O]

The title compound was prepared by coupling pyridin-4-ylacetic acid hydrochloride (1:1) to tert-butyl L-glutaminate in the presence of HATU and N,N-diisopropylethylamine, followed by detachment of the t-butyl protecting group by means of trifluoroacetic acid in dichloromethane.

LC-MS (Method 12): $R_t$=0.59 min; MS (ESIneg): m/z=264 [M−H]⁻

Intermediate L138

1-Bromo-2-oxo-6,9,12,15-tetraoxa-3-azaoctadecan-18-oic acid

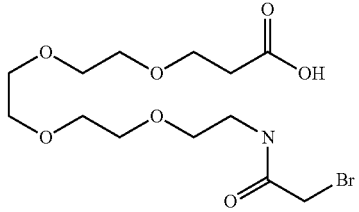 [SMILES: O=C(O)CCOCCOCCOCCOCCNC(=O)CBr]

The title compound was prepared by coupling 1-amino-3,6,9,12-tetraoxapentadecan-15-oic acid to bromoacetic anhydride in the presence of N,N-diisopropylethylamine.

LC-MS (Method 5): $R_t$=1.05 min; MS (ESIpos): m/z=386 and 388 (M+H)⁺.

Intermediate F104

Trifluoroacetic acid (2S)-2-amino-4-[{(1R)-1-[1-benzyl-4-(2,5-difluorphenyl)-1H-pyrrol-2-yl]-2,2-dimethylpropyl}(glycoloyl)amino]-N-(2-{[(2,5-dioxo-2,5-dihydro-1H-pyrrol-1-yl)acetyl]-amino}ethyl)butanamide

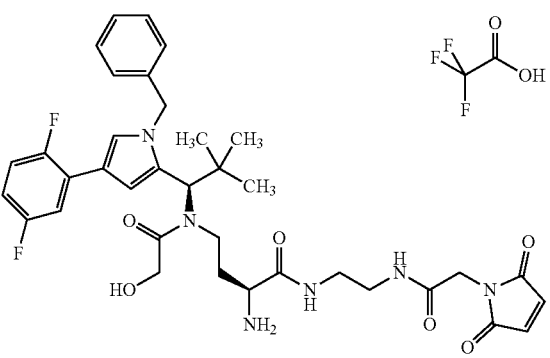 [SMILES: CC(C)(C)[C@H](c1cc(-c2cc(F)ccc2F)cn1Cc1ccccc1)N(CC[C@H](N)C(=O)NCCNC(=O)CN1C(=O)C=CC1=O)C(=O)CO ; O=C(O)C(F)(F)F]

The title compound was prepared proceeding from Intermediate C58. 15 mg (0.023 mmol) of Intermediate C58 were first reacted with 11 mg (0.036 mmol) of Intermediate L1 in the presence of 13 mg (0.034 mmol) of HATU and 10 µl of N,N-diisopropylethylamine. After stirring at RT for 60 min, the mixture was concentrated and the residue was purified by preparative HPLC. 12.3 mg (63% of theory) of the protected intermediate were obtained.

LC-MS (Method 1): $R_t$=1.3 min; MS (EIpos): m/z=837 [M+H]⁺.

In the second step, this intermediate was dissolved in 3 ml of 2,2,2-trifluoroethanol. 12 mg (0.088 mmol) of zinc chloride were added and the mixture was stirred at 50° C. for 2 h. Subsequently, 26 mg (0.088 mmol) of ethylenediamine-N,N,N',N'-tetraacetic acid and 2 ml of a 0.1% aqueous trifluoroacetic acid solution were added. The mixture was purified by means of preparative HPLC. After concentration of the appropriate fractions and lyophilization of the residue from acetonitrile/water, 8.1 mg (68% of theory) of the title compound were obtained.

LC-MS (Method 1): $R_t$=0.89 min; MS (ESIpos): m/z=693 (M+H)$^+$.

General Method for Synthesis of the APDC or ADC Precursors (Intermediate Series S)

The intermediates of the F series (F1-F305) described previously in prior disclosures WO2015/96982 A1 and WO2016/096610 A1 can, optionally after adaptation of the synthesis route or of the protecting group strategy, be converted to the APDC precursor S. As shown in Scheme 1a and Scheme 1b by way of example, in the case of release of the N-terminal amino group of the legumain-cleavable asparagine in the APDC precursor molecule, this can be modified in the last step with substituted acyl radicals or alkyl radicals of various structures to improve the profile of properties. The protein-reactive group (for example maleimide or active ester) can optionally be introduced into the synthesis at later times.

An illustrative method is described here:

0.037 mmol of an intermediate F1-Fx is taken up in 1-20 ml, preferably 5-10 ml, of a suitable solvent, for example DMF, DMSO, DCM, chloroform, toluene, THF, methanol or a mixture thereof, and 0.039 mmol of an N-terminally modified aspartic acid derivative, for example Intermediate L136, is added, as are 0.041 mmol of a standard coupling reagent, for example HATU, EDCI/HOBT, BEP etc., and 0.11 mmol of a standard base, for example N,N-diisopropylethylamine, triethylamine, 4-methylmorpholine etc. After stirring at RT for 5 min, the mixture is acidified with 2 drops of trifluoroacetic acid and concentrated. The residue is purified by preparative HPLC. The appropriate fractions are concentrated under reduced pressure and the residue is lyophilized from acetonitrile/water.

When said N-terminal modification of the attached tripeptide derivative is a protecting group, this can subsequently be detached by known methods, for example a Z protecting group preferably by means of hydrogenolysis, a Boc protecting group by means of acid hydrolysis, an Fmoc protecting group by base hydrolysis or a Teoc group by means of fluorides or with zinc chloride.

Finally, the amino group thus released can be acylated or alkylated to improve the profile of properties, for example with amine-reactive groups such as active esters, acid chlorides, isocyanates, etc., or by coupling to carboxylic acid derivatives in the presence of a standard coupling reagent, for example HATU, EDCI/HOBT, BEP etc., and of a standard base, for example N,N-diisopropylethylamine, triethylamine, 4-methylmorpholine etc. If they are still present, further protecting groups in the molecule may be removed in a last step.

Scheme 1a

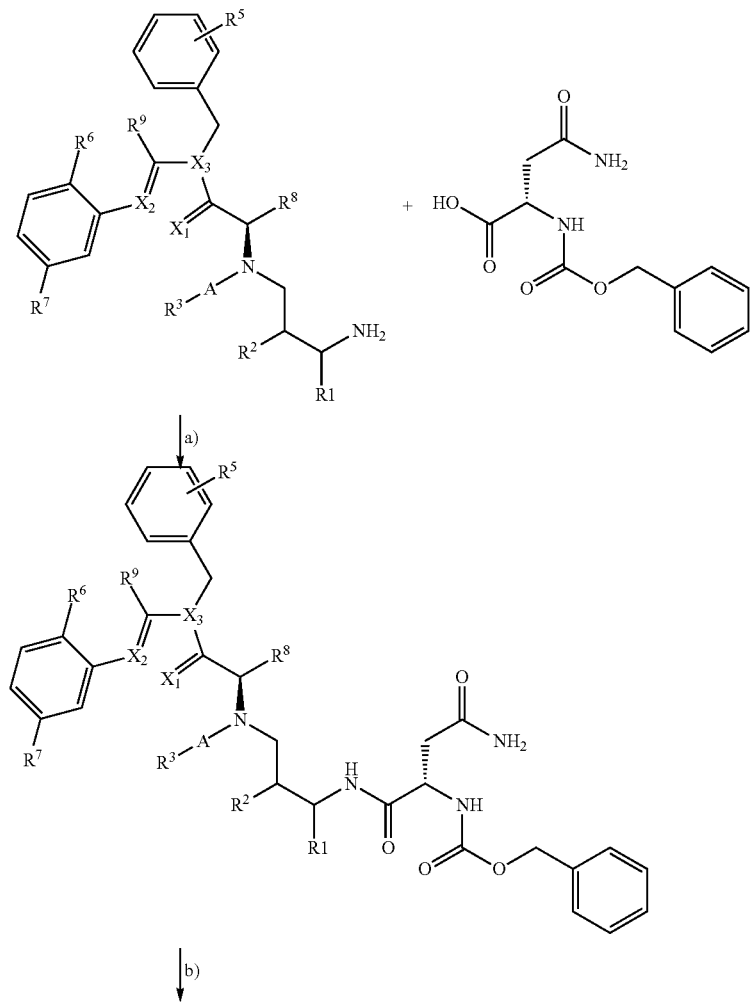

213
-continued
214
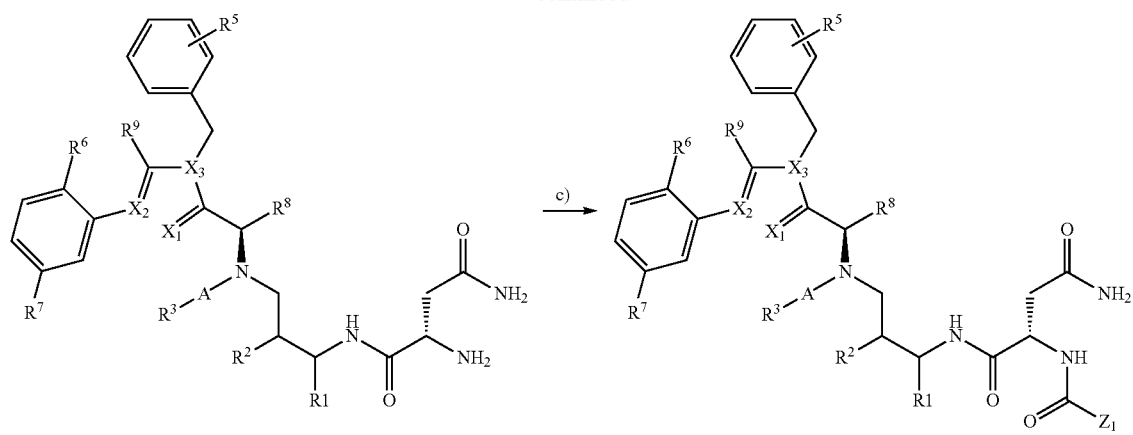
[a]: HATU, DMF, N,N-diisopropylethylamine, RT or EDCl, HOBT, N,N-diisopropylethylamine, DMF, RT b) H$_2$, 10% Pd—C, MeOH, RT; c) Z$_1$—COOH, EDCl, HOBT, N,N-diisopropylethylamine, DMF, RT or Z$_1$—COOH, HATU, N,N-diisopropylethylamine, DMF, RT or Z$_1$—COOSu, N,N-diisopropylethylamine, DMF, RT]
Scheme 1b
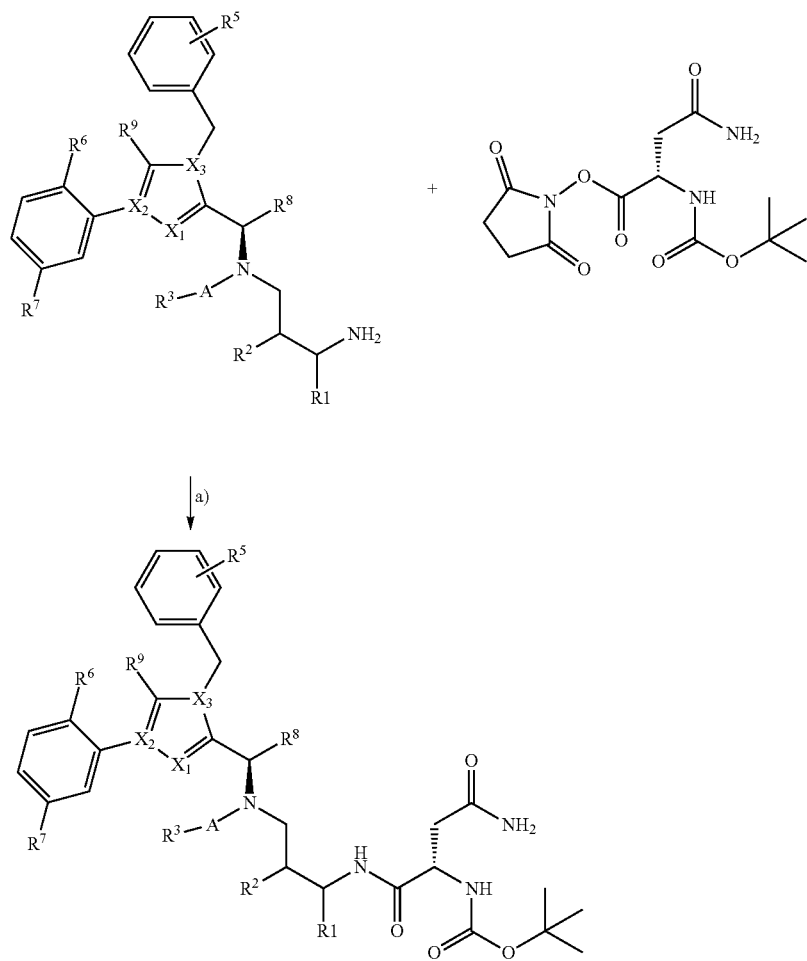

215

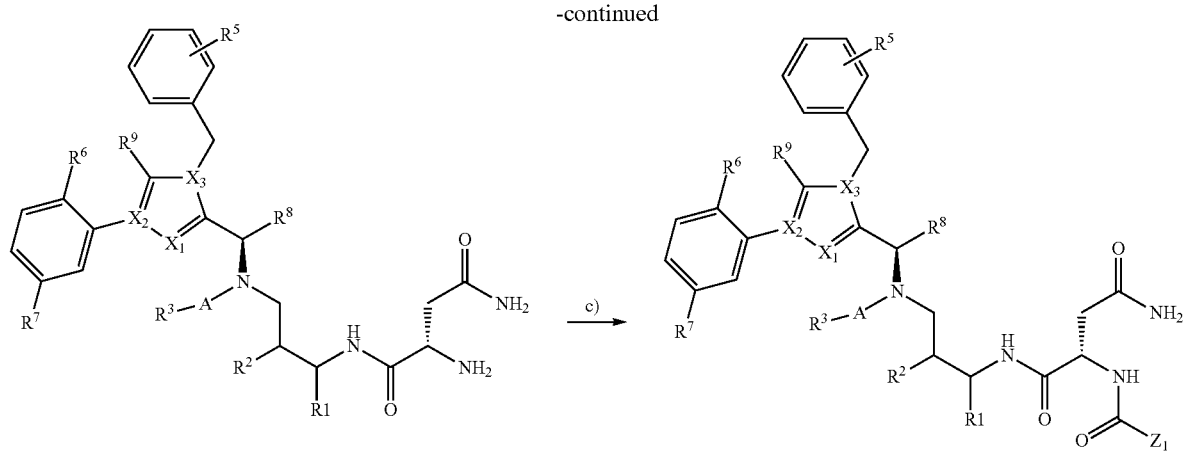

[a]: 2,5-dioxopyrrolidin-1-yl N²-(tert-butoycarbonyl)-L-aspartate, DMF, N,N-diisopropylethylamine, RT; b) ZnCl₂, trifluoroethanol, 50° C.; c) $Z_1$—COOH, EDCl, HOBT, N,N-diisopropylethylamine, DMF, RT or $Z_1$—COOH, HATU, N,N-diisopropylethylamine, DMF, RT or $Z_1$—COOSu, N,N-diisopropylethylamine, DMF, RT]

In addition, other intermediates according to Schemes 2a and 3a can be converted to legumain-cleavable ADC precursors:

Scheme 2a

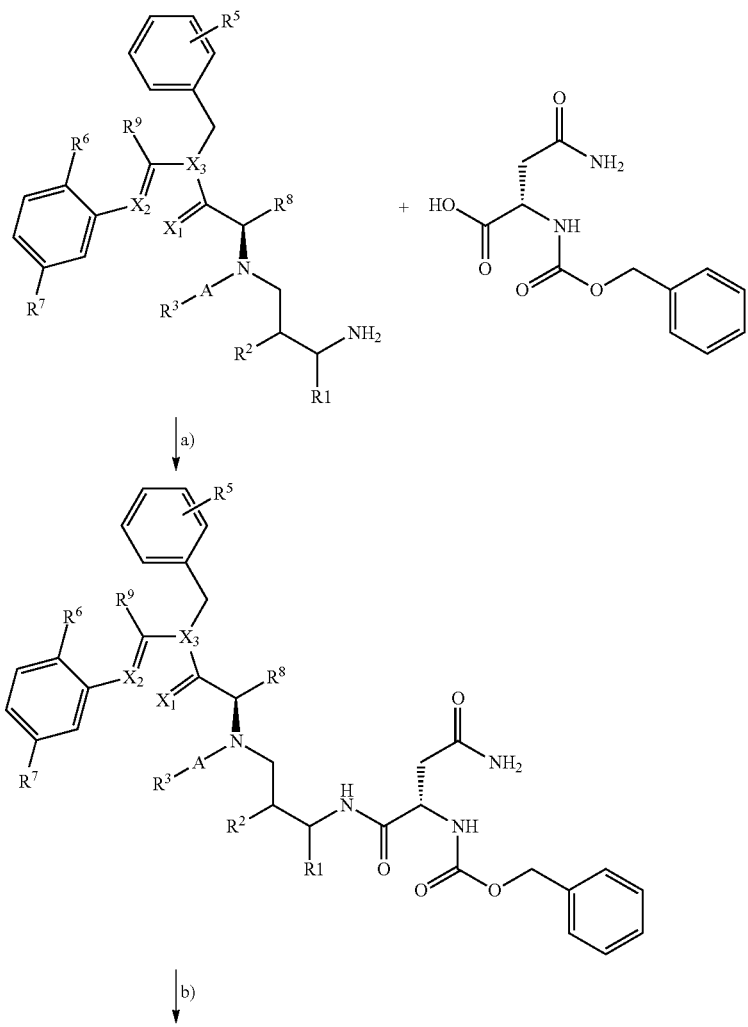

-continued

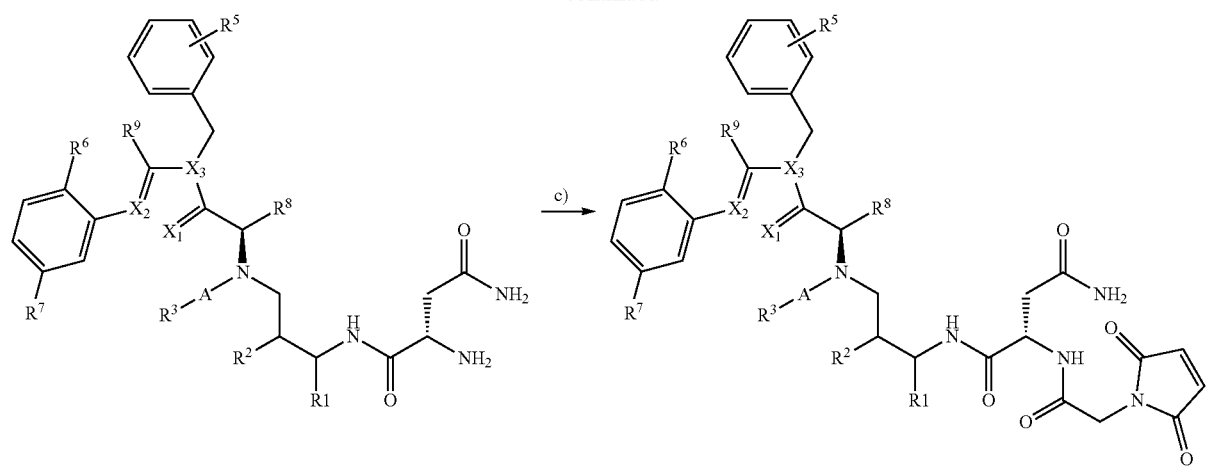

[a]: HATU, DMF, N,N-diisopropylethylamine, RT or EDCl, HOBT, N,N-diisopropylethylamine, DMF, RT; alternatively, the acylation can for example also be effected with 2,5-dioxopyrrolidin-1-yl $N^2$-[(benzyloxy)carbonyl]-L-aspartate in the presence of N,N-diisopropyethylamine in DMF; b) $H_2$, 10% Pd—C, MeOH, RT; c) 1,1′-[(1,5-dioxopentane-1,5-diyl)bis(oxy)]dipyrrolidine-2,5-dione, N,N-diisopropylethylamine, DMF, RT]

Scheme 3a

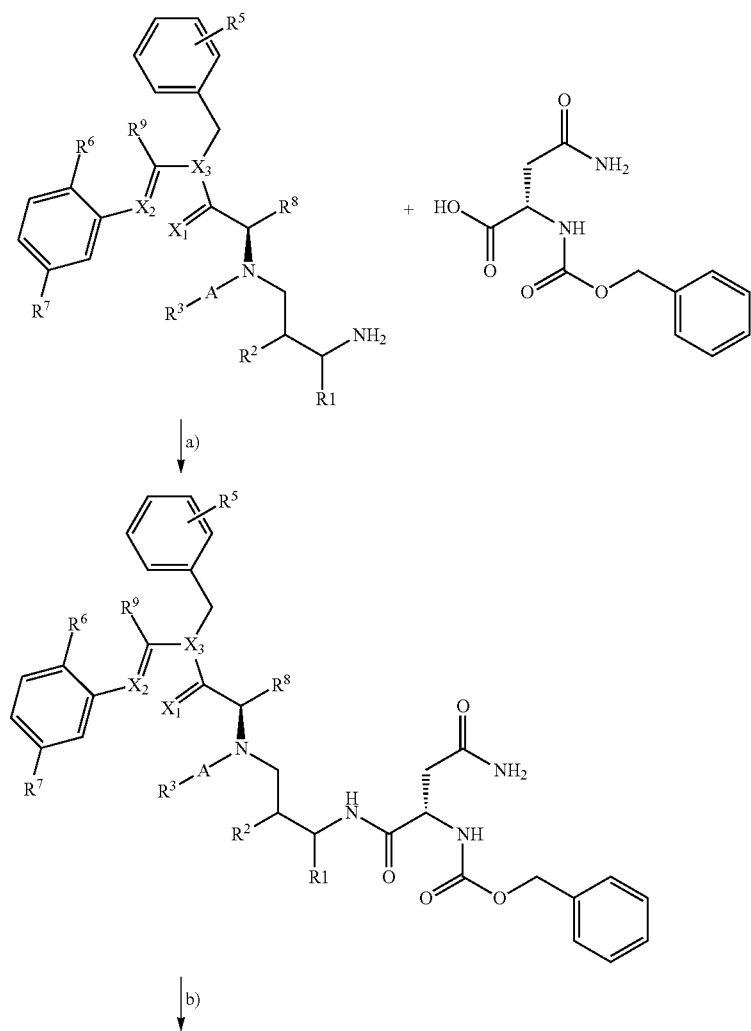

-continued

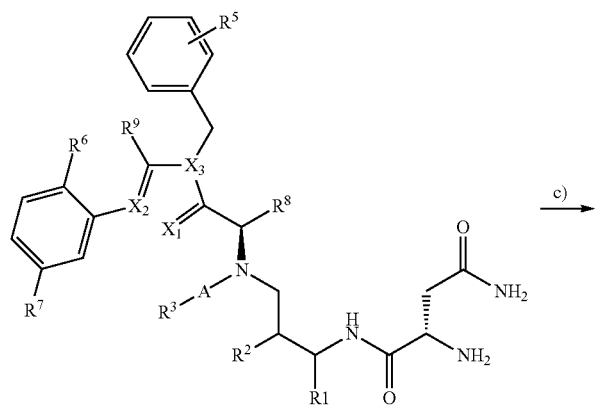

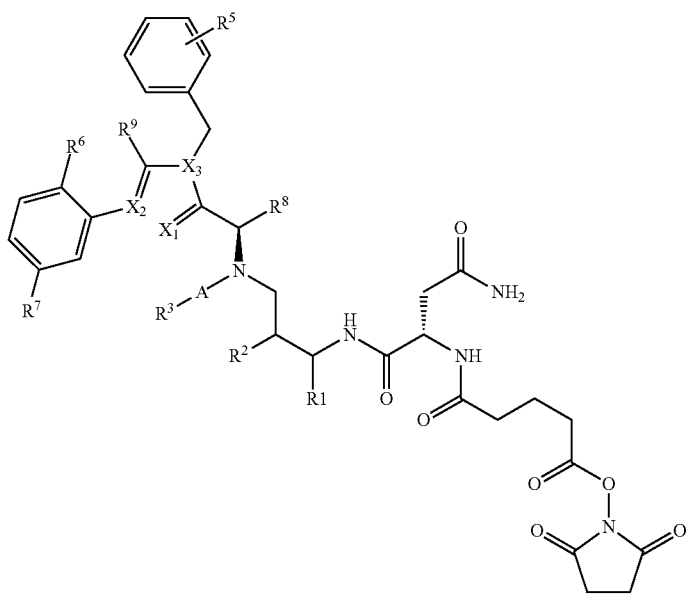

[a]: HATU, DMF, N,N-diisopropylethylamine, RT or EDCl, HOBT, N,N-diisopropylethylamine, DMF, RT; alternatively, the acylation can for example also be effected with 2,5-dioxopyrrolidin-1-yl N²-[(benzyloxy)carbonyl]-L-asparate in the presence of N,N-diisopropyethylamine in DMF; b) H₂, 10% Pd—C, MeOH, RT; c) 1,1′-[(1,5-dioxopentane-1,5-diyl)bis(oxy)]dipyrrolidine-2,5-dione, N,N-diisopropylethylamine, DMF, RT]

As an alternative to the benzyloxycarbonyl group shown in Schemes 1-3, it is possible to use other protecting groups established in peptide chemistry and detach them by corresponding methods that are likewise known. The selection of the protecting group strategy is made according to requirements known to those skilled in the art relating to compatibility with other structural elements that occur in the molecule. If they are still present, further protecting groups in the molecule may be removed in a last step.

The syntheses may also optionally be rearranged in terms of their sequence.

In addition, the protein-reactive group in the context of the linker structures L1-L2 may be varied within the scope of the claims.

Intermediate S1

N¹—{(2S)-4-[{(1R)-1-[1-Benzyl-4-(2,5-difluoro-phenyl)-1H-pyrrol-2-yl]-2,2-dimethylpropyl}(gly-coloyl)amino]-1-[(2-{[(2,5-dioxo-2,5-dihydro-1H-pyrrol-1-yl)acetyl]amino}ethyl)amino]-1-oxobutan-2-yl}-N²-(pyridin-4-ylacetyl)-L-aspartamide

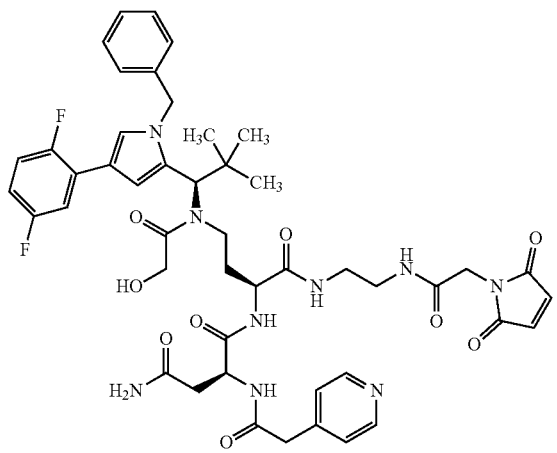 [SMILES: CC(C)(C)[C@H](c1cc(-c2cc(F)ccc2F)cn1Cc1ccccc1)N(CC[C@H](NC(=O)[C@H](CC(N)=O)NC(=O)Cc1ccncc1)C(=O)NCCNC(=O)CN1C(=O)C=CC1=O)C(=O)CO]

5 mg (0.0062 mmol) of Intermediate F104 were dissolved in 2 ml of DMF and coupled to 1.9 mg (0.0074 mmol) of Intermediate L136 in the presence of 3.5 mg (0.0093 mmol) of HATU and 3 μl of N,N-diisopropylethylamine. After stirring at RT for 16 h and purification by means of preparative HPLC, 2.8 mg (49% of theory) of the title compound were obtained.

LC-MS (Method 1): $R_t$=0.86 min; MS (ESIpos): m/z=926 (M+H)⁺.

Intermediate S2

N²-Acetyl-N1-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2,5-dioxo-2,5-dihydro-1H-pyrrol-1-yl)acetyl]amino}ethyl)amino]-1-oxobutan-2-yl}-L-aspartamide

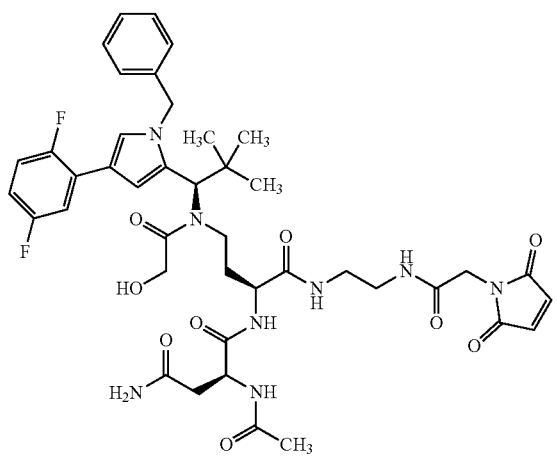 [SMILES: CC(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)CN1C(=O)C=CC1=O]

6 mg (0.0065 mmol) of Intermediate C116 in 2 ml of DMF were coupled to 2 mg (0.013 mmol) of 1-acetoxypyr-rolidine-2,5-dione in the presence of 3 μl of N,N-diisopro-pylethylamine. After purification by means of preparative HPLC, 5 mg (90% of theory) of the title compound were obtained.

LC-MS (Method 1): $R_t$=0.95 min; MS (ESIpos): m/z=849 (M+H)⁺.

Intermediate S3

Benzyl [(2S)-4-amino-1-({(2S)-4-[{(1R)-1-[1-ben-zyl-4-(2,5-difluorophenyl)-1H-pyrrol-2-yl]-2,2-dim-ethylpropyl}(glycoloyl)amino]-1-[(2-{[(2,5-dioxo-2,5-dihydro-1H-pyrrol-1-yl)acetyl]-amino}ethyl)amino]-1-oxobutan-2-yl}amino)-1,4-dioxobutan-2-yl]carbamate

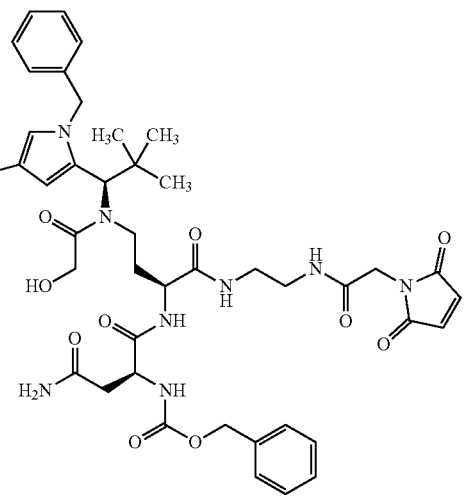

10 mg (0.0124 mmol) of Intermediate F104 in DMF were coupled to 3.6 mg (0.0136 mmol) of N2-[(benzyloxy)car-bonyl]-L-asparagine in the presence of 5.7 mg (0.0149 mmol) of HATU and 9 μl of N,N-diisopropylethylamine. After stirring at RT for 30 min and purification by means of preparative HPLC, 6 mg (51% of theory) of the title compound were obtained.

LC-MS (Method 12): $R_t$=2.06 min: MS (ESIneg): m/z=939 (M–H)⁻.

Intermediate S4

N-[2-({(2S)-2-[(N²-Acetyl-L-asparaginyl)amino]-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N²-[(2,5-dioxo-2,5-dihydro-1H-pyrrol-1-yl)acetyl]-D-alpha-glutamine

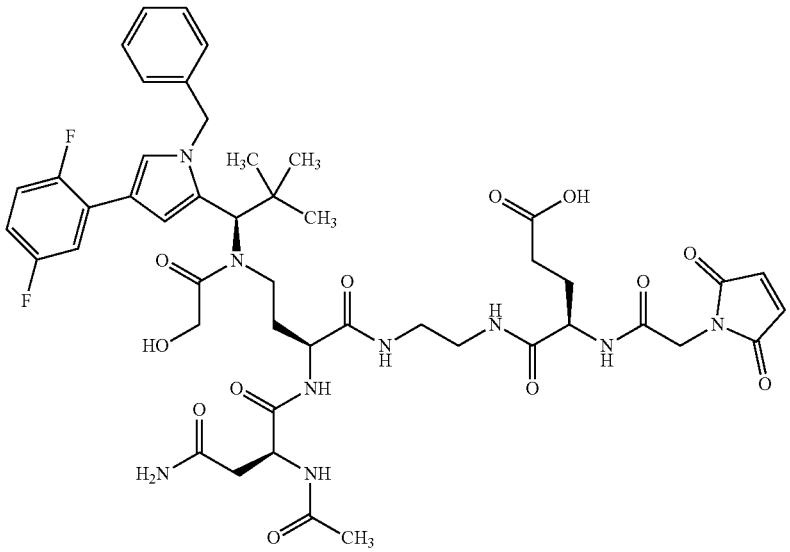 [SMILES: CC(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCNC(=O)[C@@H](CCC(=O)O)NC(=O)CN1C(=O)C=CC1=O]

15 mg (0.016 mmol) of Intermediate C123 in 3 ml of DMF were coupled to 7.4 mg (0.047 mmol) of 1-acetoxypyrrolidine-2,5-dione in the presence of 8 μl of N,N-diisopropylethylamine. After purification by means of preparative HPLC, 10 mg (64% of theory) of the protected intermediate were obtained. Then the tert-butyl ester and the Boc protecting group were detached by stirring at 50° C. with 6 equivalents of zinc chloride in trifluoroethanol for 3 h. In the last step, 6 mg (0.006 mmol) of the resultant intermediate were converted to the title compound by coupling to 1.9 mg (0.008 mmol) of 1-{2-[(2,5-dioxopyrrolidin-1-yl)oxy]-2-oxoethyl}-1H-pyrrole-2,5-dione in DMF in the presence of 3 μl of N,N-diisopropylethylamine. After purification by means of preparative HPLC, 3 mg (49% of theory) of the title compound were obtained.

LC-MS (Method 1): $R_t$=0.91 min; MS (ESIpos): m/z=978 (M+H)⁺.

Intermediate S5

N-(2-{[(2S)-4-[{(1R)-1-[1-Benzyl-4-(2,5-difluorophenyl)-1H-pyrrol-2-yl]-2,2-dimethylpropyl}(glycoloyl)amino]-2-{[N²-(pyridin-4-ylacetyl)-L-asparaginyl]amino}butanoyl]-amino}ethyl)-N²-[(2,5-dioxo-2,5-dihydro-1H-pyrrol-1-yl)acetyl]-D-alpha-glutamine

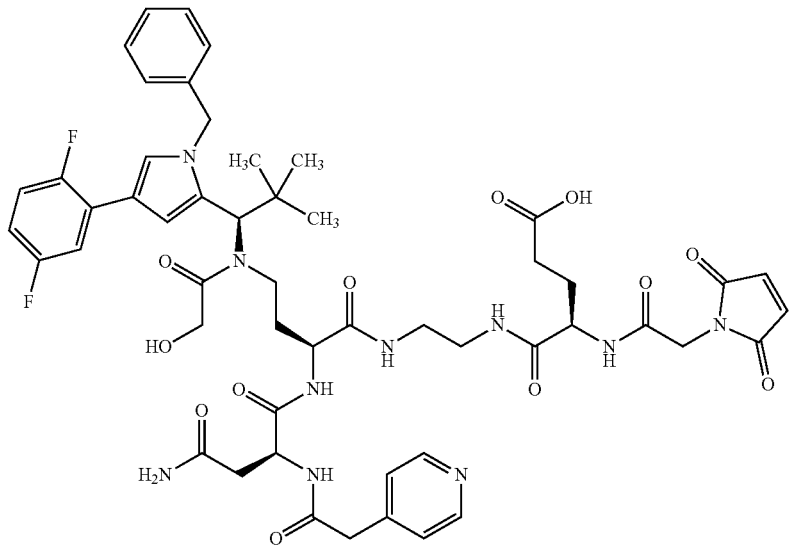 [SMILES: CC(C)(C)[C@H](c1cc(-c2cc(F)ccc2F)cn1Cc1ccccc1)N(CC[C@H](NC(=O)[C@H](CC(N)=O)NC(=O)Cc1ccncc1)C(=O)NCCNC(=O)[C@@H](CCC(=O)O)NC(=O)CN1C(=O)C=CC1=O)C(=O)CO]

15 mg (0.016 mmol) of Intermediate C123 in 5.6 ml of DMF were coupled to 3.3 mg (0.019 mmol) of pyridin-4-ylacetic acid hydrochloride (1:1) in the presence of 7.2 mg (0.019 mmol) of HATU and 14 µl of N,N-diisopropylethylamine. After purification by means of preparative HPLC, 11 mg (63% of theory) of the protected intermediate were obtained. Then the tert-butyl ester and the Boc protecting group were detached by stirring at 50° C. with 6 equivalents of zinc chloride in trifluoroethanol for 3 h. In the last step, 6.5 mg (0.006 mmol) of the resultant intermediate were converted to the title compound by coupling to 1.2 mg (0.008 mmol) of 1-{2-[(2,5-dioxopyrrolidin-1-yl)oxy]-2-oxoethyl}-1H-pyrrole-2,5-dione in 2 ml of DMF in the presence of 3.3 µl of N,N-diisopropylethylamine. After purification by means of preparative HPLC, 3 mg (49% of theory) of the title compound were obtained.

LC-MS (Method 1): $R_t$=0.82 min; MS (ESIpos): m/z=1055 (M+H)$^+$.

Intermediate S6

N-{(2S)-4-[{(1R)-1-[1-Benzyl-4-(2,5-difluorophe-nyl)-1H-pyrrol-2-yl]-2,2-dimethylpropyl}(glycoloyl)amino]-2-[(N$^2$-{5-[(2,5-dioxopyrrolidin-1-yl)oxy]-5-oxopentanoyl}-L-asparaginyl) amino]butanoyl}-beta-alanyl-D-glutamic acid

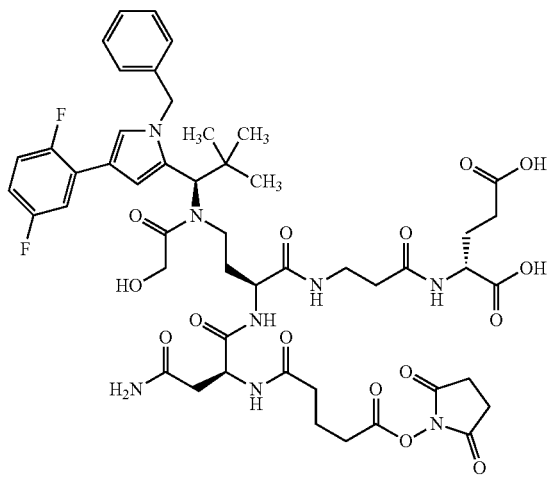 [SMILES: CC(C)(C)[C@H](c1cc(-c2cc(F)ccc2F)cn1Cc1ccccc1)N(CC[C@H](NC(=O)[C@H](CC(N)=O)NC(=O)CCCC(=O)ON1C(=O)CCC1=O)C(=O)NCCC(=O)N[C@H](CCC(=O)O)C(=O)O)C(=O)CO]

The title compound was prepared proceeding from compound C121 by first coupling to 2,5-dioxopyrrolidin-1-yl N$^2$-(tert-butoxycarbonyl)-L-aspartate in DMF in the presence of N,N-diisopropylethylamine. Then the Boc protecting group was detached by stirring at 50° C. with 6 equivalents of zinc chloride in trifluoroethanol for 1 h. In the next step, the benzyl ester was removed by hydrogenation over 10% palladium on activated carbon in ethanol under standard hydrogen pressure at RT, and the deprotected intermediate was then converted to the title compound by reaction with 1,1'-[(1,5-dioxopentane-1,5-diyl)bis(oxy)]dipyrrolidine-2,5-dione in the presence of N,N-diisopropylethylamine in DMF.

LC-MS (Method 1): $R_t$=0.92 min; MS (ESIpos): m/z=1039 [M+H]$^+$.

Intermediate S7

N-[(2S)-4-[{(1R)-1-[1-Benzyl-4-(2,5-difluorophe-nyl)-1H-pyrrol-2-yl]-2,2-dimethylpropyl}(glycoloyl)amino]-2-({N$^2$-[6-(2,5-dioxo-2,5-dihydro-1H-pyrrol-1-yl)hexanoyl]-L-asparaginyl}amino)butanoyl]-beta-alanyl-D-glutamic acid

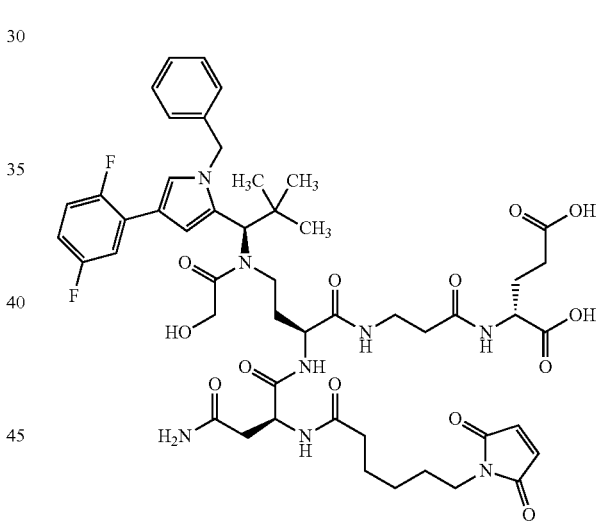

The title compound was prepared proceeding from compound C121 by first coupling to 2,5-dioxopyrrolidin-1-yl N$^2$-(tert-butoxycarbonyl)-L-aspartate in DMF in the presence of N,N-diisopropylethylamine. Then the Boc protecting group was detached by stirring at 50° C. with 6 equivalents of zinc chloride in trifluoroethanol for 1 h. In the next step, the benzyl ester was removed by hydrogenation over 10% palladium on activated carbon in ethanol under standard hydrogen pressure at RT and the deprotected intermediate was then converted to the title compound by reaction with 1.5 equivalents of 1-{6-[(2,5-dioxopyrrolidin-1-yl)oxy]-6-oxohexyl}-1H-pyrrole-2,5-dione in the presence of 3 equivalents of N,N-diisopropylethylamine in DMF.

LC-MS (Method 12): $R_t$=1.81 min; MS (ESIneg): m/z=1019 [M−H]$^−$.

Intermediate S8

N¹-{3-[{(1R)-1-[1-Benzyl-4-(2,5-difluorophenyl)-1H-pyrrol-2-yl]-2,2-dimethylpropyl}(glycoloyl)amino]propyl}-N²-{5-[(2,5-dioxopyrrolidin-1-yl)oxy]-5-oxopentanoyl}-L-aspartamide

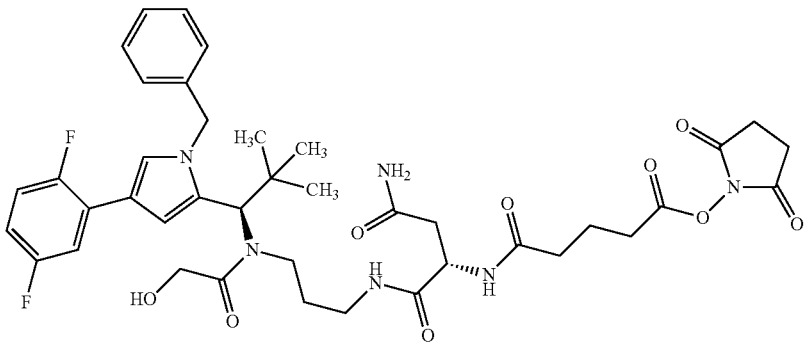 [SMILES: CC(C)(C)[C@H](c1cc(-c2cc(F)ccc2F)cn1Cc1ccccc1)N(CCCNC(=O)[C@H](CC(N)=O)NC(=O)CCCC(=O)ON1C(=O)CCC1=O)C(=O)CO]
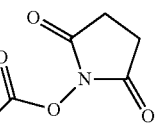

The title compound was prepared proceeding from example 98 described in WO 2015096982:

First of all, the compound from example 98 was coupled to 1.8 equivalents of 4-nitrophenyl N²-[(benzyloxy)carbonyl]-L-aspartate in DMF in the presence of 2 equivalents of N,N-diisopropylethylamine. Then the Z protecting group was detached by hydrogenation over 10% palladium on activated carbon in ethanol under standard hydrogen pressure at RT. In the last step, the title compound was prepared by reaction with 1,1'-[(1,5-dioxopentane-1,5-diyl)bis(oxy)]dipyrrolidine-2,5-dione in the presence of N,N-diisopropylethylamine in DMF.

LC-MS (Method 1): $R_t$=1.03 min; MS (ESIpos): m/z=795 [M+H]⁺.

Intermediate S9

(8S,11S)-11-(2-Amino-2-oxoethyl)-8-{2-[{(1R)-1-[1-benzyl-4-(2,5-difluorophenyl)-1H-pyrrol-2-yl]-2,2-dimethylpropyl}(glycoloyl)amino]ethyl}-1-(2,5-dioxo-2,5-dihydro-1H-pyrrol-1-yl)-2,7,10,13-tetraoxo-3,6,9,12-tetraazahexadecan-16-oic acid

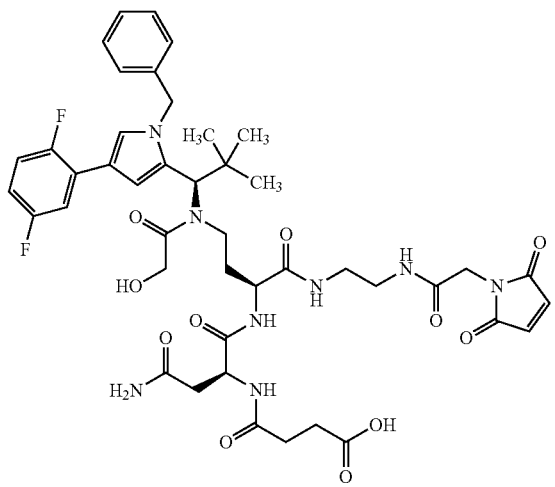 [SMILES: CC(C)(C)[C@H](c1cc(-c2cc(F)ccc2F)cn1Cc1ccccc1)N(CC[C@H](NC(=O)[C@H](CC(N)=O)NC(=O)CCC(=O)O)C(=O)NCCNC(=O)CN1C(=O)C=CC1=O)C(=O)CO]

First of all, Intermediate C136 was coupled to 1.4 equiv. of dihydrofuran-2,5-dione in the presence of 3 equiv. of N,N-diisopropylethylamine. In the next step, the benzyl ester and the Z protecting group were removed by hydrogenation over 10% palladium on activated carbon in ethanol-DCM under standard hydrogen pressure at RT. In the last step, the title compound was obtained by reaction with 1-{2-[(2,5-dioxopyrrolidin-1-yl)oxy]-2-oxoethyl}-1H-pyrrole-2,5-dione in the presence of 3 equiv. of N,N-diisopropylethylamine.

LC-MS (Method 1): $R_t$=0.93 min; MS (ESIpos): m/z=907 [M+H]⁺.

Intermediate S10

N-[(2S)-4-[{(1R)-1-[1-Benzyl-4-(2,5-difluorophenyl)-1H-pyrrol-2-yl]-2,2-dimethylpropyl}(glycoloyl)amino]-2-({N2-[(2,5-dioxo-2,5-dihydro-1H-pyrrol-1-yl)acetyl]-L-asparaginyl}-amino)butanoyl]-beta-alanyl-D-glutamic acid

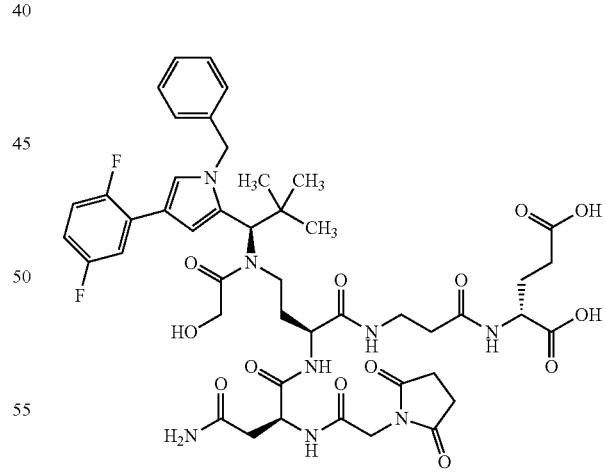

The title compound was prepared in analogy to Intermediate S6, except that, in the last step, in place of 1,1'-[(1,5-dioxopentane-1,5-diyl)bis(oxy)]dipyrrolidine-2,5-dione, the coupling was effected with 1.5 equiv. of 1-{2-[(2,5-dioxopyrrolidin-1-yl)oxy]-2-oxoethyl}-1H-pyrrole-2,5-dione in the presence of 3 equiv. of N,N-diisopropylethylamine.

LC-MS (Method 1): $R_t$=0.90 min; MS (ESIpos): m/z=965 [M+H]⁺.

Intermediate S11

N-(2-{[2-({(2S)-2-[(N²-Acetyl-L-asparaginyl)amino]-4-[{(1R)-1-[1-benzyl-4-(2,5-difluorophenyl)-1H-pyrrol-2-yl]-2,2-dimethylpropyl}(glycoloyl)amino]butanoyl}amino)ethyl]sulphonyl}ethyl)-N²-[(2,5-dioxo-2,5-dihydro-1H-pyrrol-1-yl)acetyl]-D-alpha-glutamine

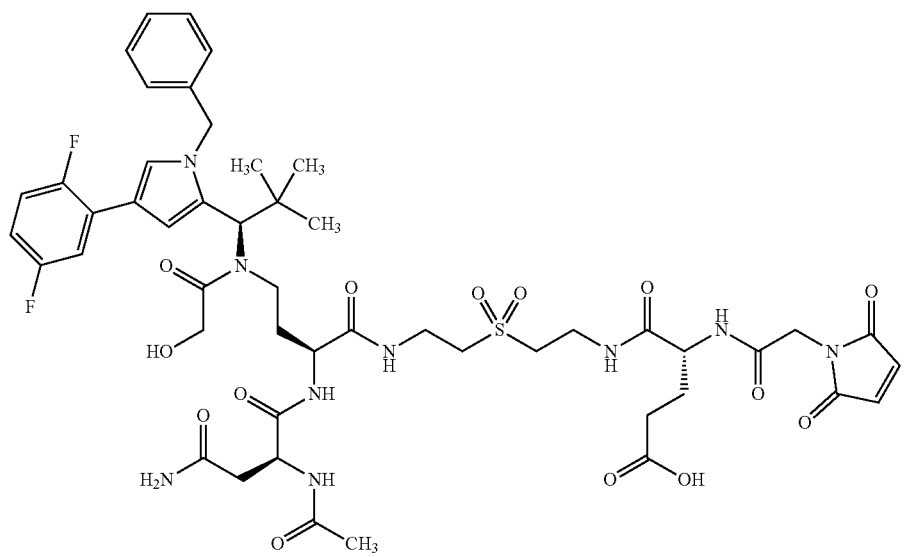 [SMILES: CC(=O)N[C@@H](CC(N)=O)C(=O)N[C@@H](CCN(C(=O)CO)[C@@H](c1cc(-c2cc(F)ccc2F)cn1Cc1ccccc1)C(C)(C)C)C(=O)NCCS(=O)(=O)CCNC(=O)[C@@H](CCC(=O)O)NC(=O)CN1C(=O)C=CC1=O]

First of all, Intermediate C137 was coupled to 1.3 equiv. of 2,5-dioxopyrrolidin-1-yl N²-(tert-butoxycarbonyl)-L-aspartate in the presence of 3 equiv. of N,N-diisopropylethylamine. The Boc group was then detached by stirring with 6 equiv. of zinc chloride in trifluoroethanol at 50° C. for 3 hours. The reaction product was coupled to 2 equiv. of 1-acetoxypyrrolidine-2,5-dione in the presence of 3 equiv. of N,N-diisopropylethylamine. Then the Z protecting group was removed by hydrogenation over 10% palladium on activated carbon in ethanol under standard hydrogen pressure at RT. In the last step, finally, the title compound was obtained by reaction with 1-{2-[(2,5-dioxopyrrolidin-1-yl)oxy]-2-oxoethyl}-1H-pyrrole-2,5-dione in the presence of 3 equiv. of N,N-diisopropylethylamine.

LC-MS (Method 12): $R_t$=1.66 min; MS (ESIpos): m/z=1070 [M+H]⁺.

Intermediate S12

N-[(2S)-4-[{(1R)-1-[1-Benzyl-4-(2,5-difluorophenyl)-1H-pyrrol-2-yl]-2,2-dimethylpropyl}(glycoloyl)amino]-2-{[N²-(bromoacetyl)-L-asparaginyl]amino}butanoyl]-beta-alanyl-D-glutamic acid

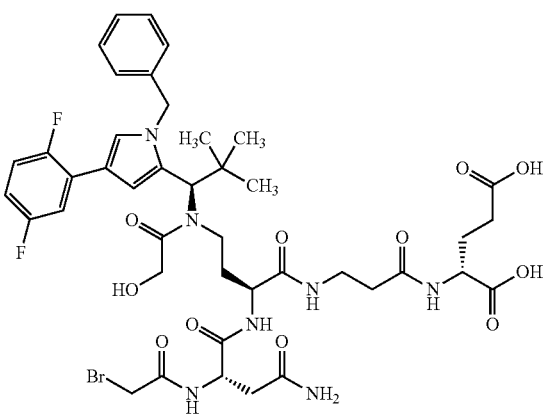 [SMILES: CC(C)(C)[C@H](c1cc(-c2cc(F)ccc2F)cn1Cc1ccccc1)N(CC[C@H](NC(=O)[C@H](CC(N)=O)NC(=O)CBr)C(=O)NCCC(=O)N[C@H](CCC(=O)O)C(=O)O)C(=O)CO]

The title compound was prepared in analogy to Intermediate S10, except that the reaction in the last step was with 3 equiv. of 1-(2-bromoacetoxy)pyrrolidine-2,5-dione instead of 1-{2-[(2,5-dioxopyrrolidin-1-yl)oxy]-2-oxoethyl}-1H-pyrrole-2,5-dione in the presence of 2 equiv. of N,N-diisopropylethylamine.

LC-MS (Method 1): $R_t$=0.93 min; MS (ESIpos): m/z=948 and 950 [M+H]$^+$.

Intermediate S13

N-[(2S)-4-[{(1R)-1-[1-Benzyl-4-(2,5-difluorophenyl)-1H-pyrrol-2-yl]-2,2-dimethylpropyl}(glycoloyl)amino]-2-({N²-[1-(2,5-dioxo-2,5-dihydro-1H-pyrrol-1-yl)-2,18-dioxo-6,9,12,15-tetraoxa-3-azaoctadecan-18-yl]-L-asparaginyl}amino)butanoyl]-beta-alanyl-D-glutamic acid

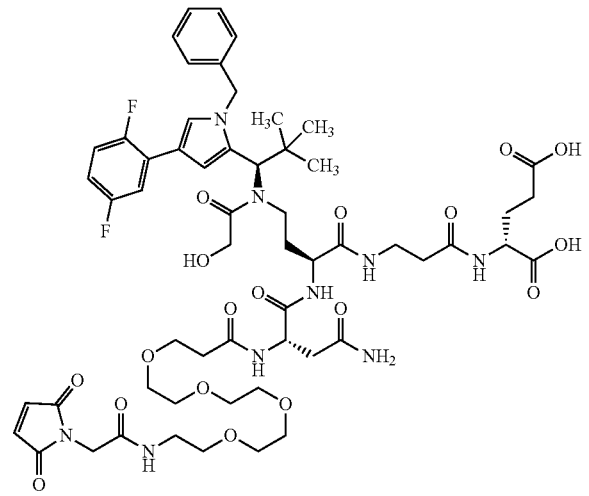 [SMILES: CC(C)(C)[C@H](c1cc(-c2cc(F)ccc2F)cn1Cc1ccccc1)N(CC[C@H](NC(=O)[C@H](CC(N)=O)NC(=O)CCOCCOCCOCCOCCNC(=O)CN1C(=O)C=CC1=O)C(=O)NCCC(=O)N[C@H](CCC(=O)O)C(=O)O)C(=O)CO]

The title compound was prepared proceeding from compound C121 by first coupling to 2,5-dioxopyrrolidin-1-yl N²-(tert-butoxycarbonyl)-L-aspartate in DMF in the presence of N,N-diisopropylethylamine. Then the Boc protecting group was detached by stirring at 50° C. with 6 equivalents of zinc chloride in trifluoroethanol for 1 h.

In the next step, the resultant intermediate was coupled to 3-oxo-1-phenyl-2,7,10,13,16-pentaoxa-4-azanonadecan-19-oic acid in the presence of 1.2 equiv. of HATU and 3 equiv. of N,N-diisopropylethylamine in DMF. Then the benzyl ester and the Z protecting group were removed by hydrogenation over 10% palladium on activated carbon in methanol/DCM 1:1 under standard hydrogen pressure at RT and the deprotected intermediate was then converted to the title compound by reaction with 1-{2-[(2,5-dioxopyrrolidin-1-yl)oxy]-2-oxoethyl}-1H-pyrrole-2,5-dione in the presence of N,N-diisopropylethylamine in DMF.

LC-MS (Method 1): $R_t$=0.89 min; MS (ESIpos): m/z=1212 [M+H]$^+$.

Intermediate S14

N-[(2S)-4-[{(1R)-1-[1-Benzyl-4-(2,5-difluorophenyl)-1H-pyrrol-2-yl]-2,2-dimethylpropyl}(glycoloyl)amino]-2-({N2-[1-(2,5-dioxo-2,5-dihydro-1H-pyrrol-1-yl)-6,22-dioxo-3,10,13,16,19-pentaoxa-7-azadocosan-22-yl]-L-asparaginyl}amino)butanoyl]-beta-alanyl-D-glutamic acid

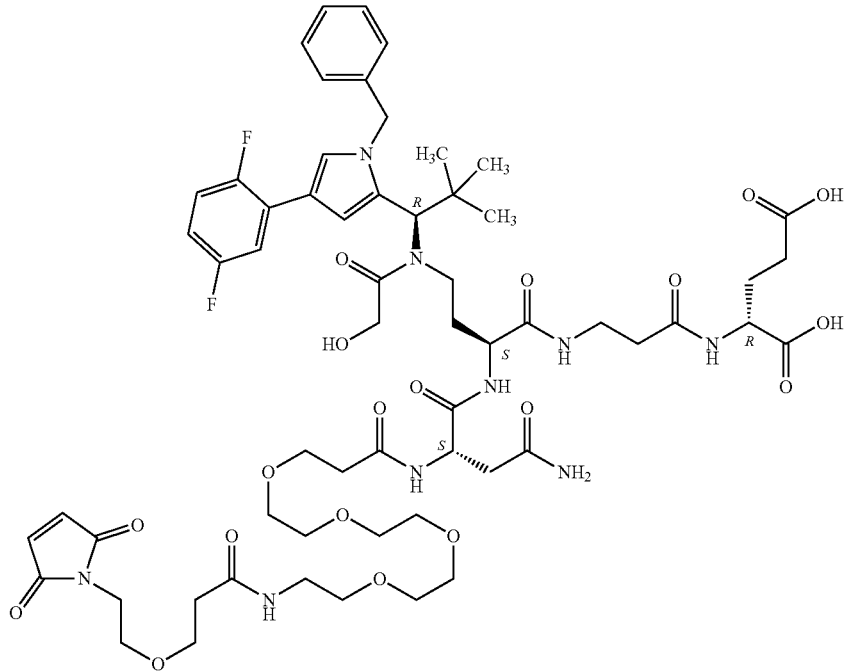

The title compound was prepared in analogy to Intermediate S13, except that the reaction in the last step was with 3 equiv. of 1-(2-{3-[(2,5-dioxopyrrolidin-1-yl)oxy]-3-oxopropoxy}ethyl)-1H-pyrrole-2,5-dione instead of 1-{2-[(2,5-dioxopyrrolidin-1-yl)oxy]-2-oxoethyl}-1H-pyrrole-2,5-dione in the presence of 3 equiv. of N,N-diisopropylethylamine.

LC-MS (Method 1): $R_t$=0.89 min; MS (ESIpos): m/z=1270 [M+H]$^+$.

Intermediate S15

N$^2$-[(2,5-Dioxo-2,5-dihydro-1H-pyrrol-1-yl)acetyl]-L-asparaginyl-N-(2-{[2-({(2S)-2-amino-4-[{(1R)-1-[1-benzyl-4-(2,5-difluorophenyl)-1H-pyrrol-2-yl]-2,2-dimethylpropyl}(glycoloyl) amino] butanoyl}amino)ethyl]sulphonyl}ethyl)-D-alpha-glutamine trifluoroacetate

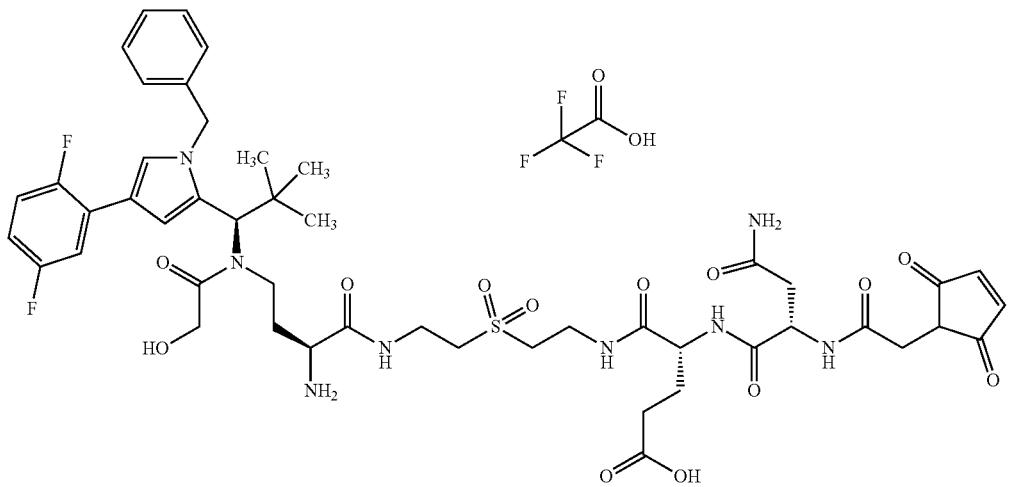 [SMILES: CC(C)(C)[C@H](c1cc(-c2cc(F)ccc2F)cn1Cc1ccccc1)N(CC[C@H](N)C(=O)NCCS(=O)(=O)CCNC(=O)[C@@H](CCC(=O)O)NC(=O)[C@H](CC(N)=O)NC(=O)CC1C(=O)C=CC1=O)C(=O)CO ; O=C(O)C(F)(F)F]

The synthesis of the title compound commenced firstly with the coupling of Intermediate C138 to 4-nitrophenyl N$^2$-[(benzyloxy)carbonyl]-L-aspartate in DMF in the presence of 2 equiv. of N,N-diisopropylethylamine. This was followed by the detachment of the Z protecting group by hydrogenation over 10% palladium on activated carbon in DCM/methanol 1:1 under standard hydrogen pressure at RT for 2 hours. Then reaction was effected with 1.2 equiv. of 1-{2-[(2,5-dioxopyrrolidin-1-yl)oxy]-2-oxoethyl}-1H-pyrrole-2,5-dione in the presence of 3 equiv. of N,N-diisopropylethylamine in DMF. In the last step, the title compound was obtained by stirring at 50° C. with 6 equivalents of zinc chloride in trifluoroethanol for 2 h.

LC-MS (Method 1): $R_t$=0.79 min; MS (ESIpos): m/z=1028 [M+H]$^+$.

Intermediate S16

N-[(2S)-4-[{(1R)-1-[1-Benzyl-4-(2,5-difluorophenyl)-1H-pyrrol-2-yl]-2,2-dimethylpropyl}(glycoloyl) amino]-2-{[N$^2$-(18-bromo-17-oxo-4,7,10,13-tetraoxa-16-azaoctadecan-1-oyl)-L-asparaginyl] amino}butanoyl]-beta-alanyl-D-glutamic acid

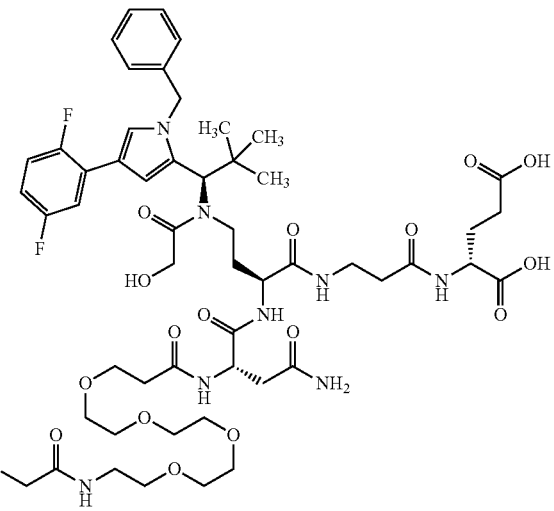

The title compound was synthesized by first coupling Intermediate C139 to Intermediate L138 in DMF in the presence of 1.2 equiv. of HATU and 3 equiv. of N,N-diisopropylethylamine. Then the tert-butyl ester groups were detached by stirring at 50° C. with 18 equivalents of zinc chloride in trifluoroethanol for 1 h. LC-MS (Method 1): $R_t$=0.91 min; MS (ESI-neg): m/z=1193 and 1195 [M–H]⁻.

Intermediate S17

S-{2-[{(1R)-1-[1-Benzyl-4-(2,5-difluorophenyl)-1H-pyrrol-2-yl]-2,2-dimethylpropyl}(3-{[N2-(pyridin-4-ylacetyl)-L-asparaginyl]amino}propyl)amino]-2-oxoethyl}-N-[1-(2,5-dioxo-2,5-dihydro-1H-pyrrol-1-yl)-2,18-dioxo-6,9,12,15-tetraoxa-3-azaoctadecan-18-yl]-L-cysteine

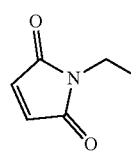
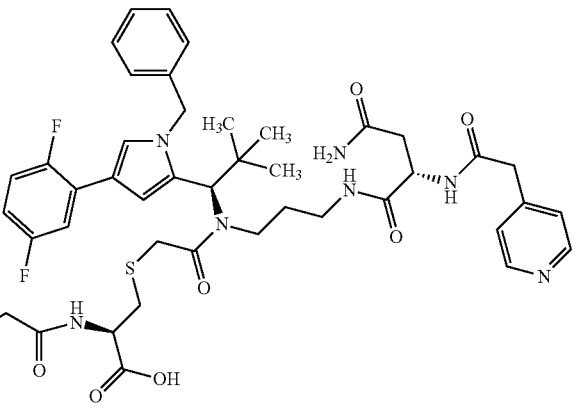

To a solution of N-(15-amino-4,7,10,13-tetraoxapentadecan-1-oyl)-S-{2-[{(1R)-1-[1-benzyl-4-(2,5-difluorophenyl)-1H-pyrrol-2-yl]-2,2-dimethylpropyl}(3-{[N2-(pyridin-4-ylacetyl)-L-asparaginyl]amino}propyl)amino]-2-oxoethyl}-L-cysteine trifluoroacetic acid salt (10.0 mg, 8.57 µmol) and 1-{2-[(2,5-dioxopyrrolidin-1-yl)oxy]-2-oxoethyl}-1H-pyrrole-2,5-dione (2.38 mg, 9.42 µmol) in DMF (1 ml) was added 4-methylmorpholine (2.8 µl, 26 µmol), and the reaction was stirred at room temperature for 18 hours. One drop of acetic acid was added to the reaction mixture, which was purified by means of prep. RP-HPLC (flow rate: 50 ml/min, MeCN/water, 0.1% TFA). The solvents were evaporated under reduced pressure and the residue was lyophilized. This gave 2.2 mg of the title compound.

LC-MS (Method 12): $R_t$=1.62 min; MS (ESIpos): m/z=1190 [M+H]⁺

Intermediate S18

S-{2-[{(1R)-1-[1-Benzyl-4-(2,5-difluorophenyl)-1H-pyrrol-2-yl]-2,2-dimethylpropyl}(3-{[N2-(pyridin-4-ylacetyl)-L-asparaginyl]amino}propyl)amino]-2-oxoethyl}-N-{21-[(2,5-dioxo-pyrrolidin-1-yl)oxy]-17,21-dioxo-4,7,10,13-tetraoxa-16-azahenicosan-1-oyl}-L-cysteine

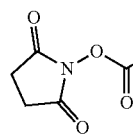
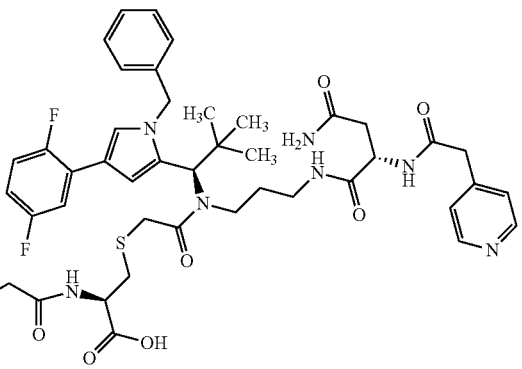

To a solution of N-(15-amino-4,7,10,13-tetraoxapentadecan-1-oyl)-S-{2-[{(1R)-1-[1-benzyl-4-(2,5-difluorophenyl)-1H-pyrrol-2-yl]-2,2-dimethylpropyl}(3-{[N2-(pyridin-4-ylacetyl)-L-asparaginyl]amino}propyl)amino]-2-oxoethyl}-L-cysteine trifluoroacetic acid salt (10.6 mg, 9.08 µmol) in DMF (1 ml) were added 1,1'-[(1,5-dioxopentane-1,5-diyl)bis(oxy)]dipyrrolidine-2,5-dione (7.41 mg, 22.7 µmol) and N,N-diisopropylethylamine (6.3 µl, 36 µmol), and the reaction mixture was stirred at room temperature until conversion was complete. The mixture was admixed with water+0.1% TFA, filtered and purified directly via prep. HPLC (eluent: ACN/water+0.1% TFA, gradient). 1.2 mg of the target compound were obtained.

LC-MS (Method 1): $R_t$=0.89 min; MS (ESIpos): m/z=1263 [M−H]$^+$

Intermediate S19

N-{(2S)-2-Amino-4-[{(1R)-1-[1-benzyl-4-(2,5-difluorophenyl)-1H-pyrrol-2-yl]-2,2-dimethylpropyl}({[(2R)-2-carboxy-2-({N²-[(2,5-dioxo-2,5-dihydro-1H-pyrrol-1-yl)acetyl]-L-asparaginyl}amino)ethyl]sulphanyl}acetyl)amino]butanoyl}-beta-alanyl-D-glutamic acid trifluoroacetate To a solution of di-tert-butyl N-[(2S)-4-[({[(2R)-2-(L-asparaginylamino)-3-tert-butoxy-3-oxopropyl]sulphanyl}acetyl){(1R)-1-[1-benzyl-4-(2,5-difluorophenyl)-1H-pyrrol-2-yl]-2,2-dimethylpropyl}amino]-2-({[2-(trimethylsilyl)ethoxy]carbonyl}amino)butanoyl]-beta-alanyl-D-glutamate trifluoroacetate (12.0 mg, 8.84 µmol, Intermediate C146) and 1-{2-[(2,5-dioxopyrrolidin-1-yl)oxy]-2-oxoethyl}-1H-pyrrole-2,5-dione (2.45 mg, 9.72 µmol) in DMF (1.0 ml) was added N,N-diisopropylethylamine (6.2 µl, 35 µmol), and the reaction was stirred at room temperature for 2 h. Subsequently, 1-{2-[(2,5-dioxopyrrolidin-1-yl)oxy]-2-oxoethyl}-1H-pyrrole-2,5-dione (2.45 mg, 9.72 µmol) was added and the mixture was stirred at room temperature for a further 2 h. The mixture was admixed with 1 ml of water+0.1% TFA and purified directly via prep. HPLC (eluent: ACN/water+0.1% TFA, gradient). Subsequently, the protecting groups were detached by stirring at 50° C. with 12 equivalents of zinc chloride in trifluoroethanol for 4 h.

LC-MS (Method 1): $R_t$=0.83 min; MS (ESIpos): m/z=1068 [M+H]$^+$

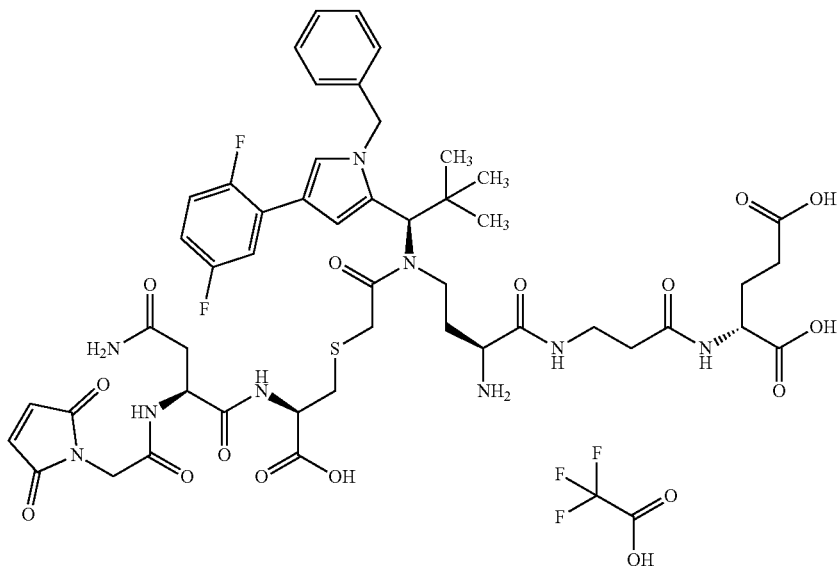 [SMILES: CC(C)(C)[C@H](c1cc(-c2cc(F)ccc2F)cn1Cc1ccccc1)N(CC[C@H](N)C(=O)NCCC(=O)N[C@H](CCC(=O)O)C(=O)O)C(=O)CSC[C@H](NC(=O)[C@H](CC(N)=O)NC(=O)CN1C(=O)C=CC1=O)C(=O)O ; O=C(O)C(F)(F)F]

Intermediate S20

N-{(2S)-4-[{(1R)-1-[1-Benzyl-4-(2,5-difluorophenyl)-1H-pyrrol-2-yl]-2,2-dimethylpropyl}-(glycoloyl)amino]-2-[(N²-{5-[(2,5-dioxopyrrolidin-1-yl)oxy]-5-oxopentanoyl}-L-asparaginyl)-amino]butanoyl}-beta-alanyl-L-asparagine

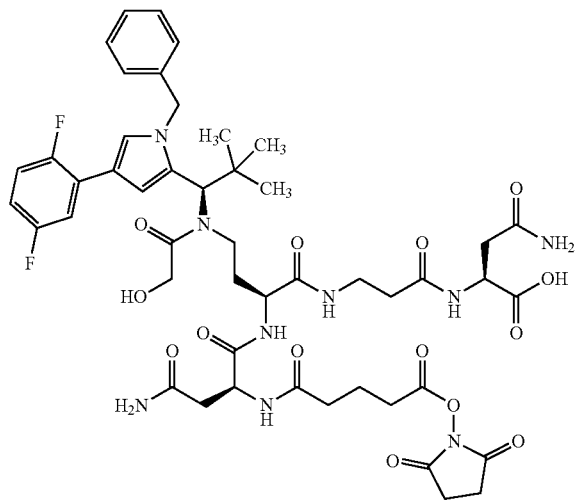 [SMILES: CC(C)(C)[C@H](c1cc(-c2cc(F)ccc2F)cn1Cc1ccccc1)N(CC[C@H](NC(=O)[C@H](CC(N)=O)NC(=O)CCCC(=O)ON1C(=O)CCC1=O)C(=O)NCCC(=O)N[C@@H](CC(N)=O)C(=O)O)C(=O)CO]

First of all, Intermediate C141 was coupled to 1.8 equivalents of 4-nitrophenyl N²-[(benzyloxy)carbonyl]-L-aspartate in DMF in the presence of 12 equivalents of N,N-diisopropylethylamine. Then the Z protecting group was detached by hydrogenation over 10% palladium on activated carbon in DCM/methanol 1:1 under standard hydrogen pressure at RT. In the last step, the title compound was prepared by reaction with 1,1'-[(1,5-dioxopentane-1,5-diyl)bis(oxy)]dipyrrolidine-2,5-dione in the presence of N,N-diisopropylethylamine in DMF.

LC-MS (Method 1): $R_t$=0.91 min; MS (ESIpos): m/z=1024 [M+H]⁺.

Intermediate S21

N-[(2S)-4-[{(1R)-1-[1-Benzyl-4-(2,5-difluorophenyl)-1H-pyrrol-2-yl]-2,2-dimethylpropyl}-(glycoloyl)amino]-2-({N²-[(2,5-dioxo-2,5-dihydro-1H-pyrrol-1-yl)acetyl]-L-asparaginyl}-amino)butanoyl]-beta-alanyl-L-asparagine

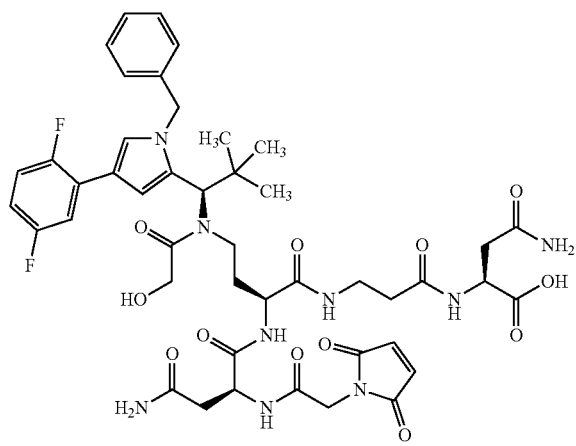 [SMILES: CC(C)(C)[C@H](c1cc(-c2cc(F)ccc2F)cn1Cc1ccccc1)N(CC[C@H](NC(=O)[C@H](CC(N)=O)NC(=O)CN1C(=O)C=CC1=O)C(=O)NCCC(=O)N[C@@H](CC(N)=O)C(=O)O)C(=O)CO]

First of all, Intermediate C141 was coupled to 1.8 equivalents of 4-nitrophenyl N²-[(benzyloxy)carbonyl]-L-aspartate in DMF in the presence of 12 equivalents of N,N-diisopropylethylamine. Then the Z protecting group was detached by hydrogenation over 10% palladium on activated carbon in DCM/methanol 1:1 under standard hydrogen pressure at RT. In the last step, the title compound was prepared by reaction with 2.5 equiv. of 1-{2-[(2,5-dioxopyrrolidin-1-yl)oxy]-2-oxoethyl}-1H-pyrrole-2,5-dione in the presence of 4 equiv. of N,N-diisopropylethylamine in DMF.

LC-MS (Method 1): $R_t$=0.90 min; MS (ESIpos): m/z=950 [M+H]⁺.

Intermediate S22

N-{(2S)-4-[{(1R)-1-[1-Benzyl-4-(2,5-difluorophenyl)-1H-pyrrol-2-yl]-2,2-dimethylpropyl}(glycoloyl)amino]-2-[(N²-{16-[(2,5-dioxopyrrolidin-1-yl)oxy]-16-oxo-4,7,10,13-tetraoxa-hexadecan-1-oyl}-L-asparaginyl)amino]butanoyl}-beta-alanyl-D-glutamic acid

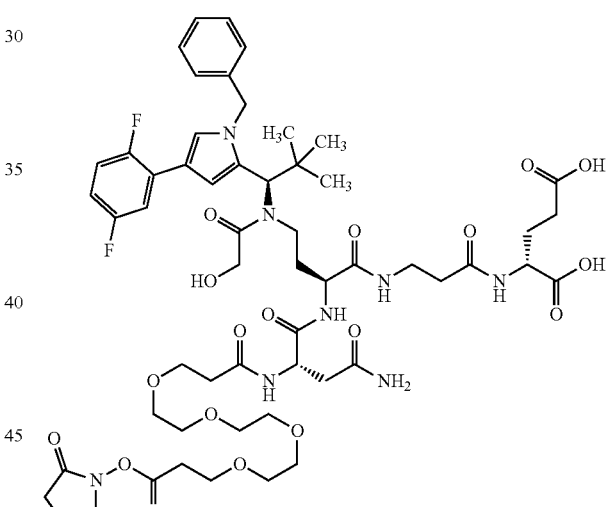

The title compound was prepared proceeding from compound C121 by first coupling to 2,5-dioxopyrrolidin-1-yl N²-(tert-butoxycarbonyl)-L-aspartate in DMF in the presence of N,N-diisopropylethylamine. Then the Boc protecting group was detached by stirring with 6 equivalents of zinc chloride in trifluoroethanol at 50° C. for 1 h. In the next step, the benzyl ester was removed by hydrogenation over 10% palladium on activated carbon in DCM/methanol 1:1 under standard hydrogen pressure at RT and the deprotected intermediate was then converted to the title compound by reaction with 3 equiv. of 1,1'-[(1,19-dioxo-4,7,10,13,16-pentaoxanonadecane-1,19-diyl)bis(oxy)]dipyrrolidine-2,5-dione in the presence of 3 equiv. of N,N-diisopropylethylamine in DMF.

LC-MS (Method 1): $R_t$=0.96 min; MS (ESIpos): m/z=1245 [M+H]⁺.

B: Preparation of Antibody-Drug Conjugates (ADC)

B-1. General Method for Generation of Antibodies

The protein sequence (amino acid sequence) of the antibodies used, for example TPP-2090, TPP-2658, TPP-5442, TPP-8825, TPP-7006, TPP-7007, TPP-10334, TPP-10335, TPP-10336, TPP-10337, TPP-1015, TPP-7510, TPP-7511, TPP-8382 and TPP-8567, was transformed into a DNA sequence that encodes the protein by a method well known to those skilled in the art and inserted into an expression vector suitable for transient mammalian cell culture (as described by Tom et al., Chapter 12 in Methods Express: Expression Systems, edited by Michael R. Dyson and Yves Durocher, Scion Publishing Ltd, 2007).

B-2. General Method for Expression of Antibodies in Mammalian Cells

The antibodies, for example TPP-2090, TPP-2658, TPP-5442, TPP-8825, TPP-7006, TPP-7007, TPP-10334, TPP-10335, TPP-10336, TPP-10337, TPP-1015, TPP-7510, TPP-7511, TPP-8382 and TPP-8567, were produced in transient mammalian cell cultures, as described by Tom et al., Chapter 12 in Methods Express: Expression Systems, edited by Michael R. Dyson and Yves Durocher, Scion Publishing Ltd, 2007.

B-3. General Method for Purification of Antibodies from Cell Supernatants

The antibodies, for example TPP-2090, TPP-2658, TPP-5442, TPP-8825, TPP-7006, TPP-7007, TPP-10334, TPP-10335, TPP-10336, TPP-10337, TPP-1015, TPP-7510, TPP-7511, TPP-8382 and TPP-8567, were obtained from the cell culture supernatants. The cell supernatants were clarified by centrifugation of cells. The cell supernatant was then purified by affinity chromatography on a MabSelect Sure (GE Healthcare) chromatography column. To this end, the column was equilibrated in DPBS pH 7.4 (Sigma/Aldrich), the cell supernatant was applied and the column was washed with about 10 column volumes of DPBS pH 7.4+500 mM sodium chloride. The antibodies were eluted in 50 mM sodium acetate pH 3.5+500 mM sodium chloride and then purified further by gel filtration chromatography on a Superdex 200 column (GE Healthcare) in DPBS pH 7.4.

The commercially available antibodies were purified by standard chromatography methods (protein A chromatography, preparative gel filtration chromatography (SEC—size exclusion chromatography)).

B-4. General Method for Coupling to Cysteine Side Chains

The following antibodies were used in the coupling reactions:

Examples a: cetuximab (anti-EGFR AK)
Examples e: TPP-1015 (anti-Her2 AK)
Examples k: anti-TWEAKR AK (TPP-7007)
Examples k: anti-TWEAKR AK (TPP-2658)

The coupling reactions were usually carried out under argon.

Between 2 and 5 equivalents of tris(2-carboxyethyl)phosphine hydrochloride (TCEP), dissolved in PBS buffer, were added to a solution of the appropriate antibody in PBS buffer in the concentration range between 1 mg/ml and 20 mg/ml, preferably in the range of about 10 mg/ml to 15 mg/ml, and the mixture was stirred at RT for 30 min to 1 h. For this purpose, the solution of the respective antibody used can be employed at the concentrations stated in the working examples, or it may optionally also be diluted with PBS buffer to about half of the stated starting concentrations in order to get into the preferred concentration range. Subsequently, depending on the intended loading, from 2 to 20 equivalents, preferably about 5-10 equivalents of the maleimide precursor compound or halide precursor compound to be coupled were added as a solution in DMSO. In order to achieve higher DARs, it is also possible to use 15-20 equivalents. Here, the amount of DMSO should not exceed 10% of the total volume. The mixture was stirred in the case of maleimide precursors for 60-240 min at RT and in the case of halide precursors between 8 and 24 h at RT and then applied to PBS-equilibrated PD 10 columns (Sephadex© G-25, GE Healthcare) and eluted with PBS buffer. Generally, unless indicated otherwise, 5 mg of the antibody in question in PBS buffer were used for the reduction and the subsequent coupling. Purification on the PD10 column thus in each case afforded solutions of the respective ADCs in 3.5 ml PBS buffer. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution. The respective protein concentrations, stated in the working examples, of the ADC solutions were determined. Furthermore, antibody loading (drug/mAb ratio) was determined using the methods described under B-7.

Depending on the linker, the ADCs shown in the examples may also be present to a lesser or higher degree in the form of the hydrolysed open-chain succinamides linked to the antibodies.

Particularly the KSP-I-ADCs linked via the linker substructure

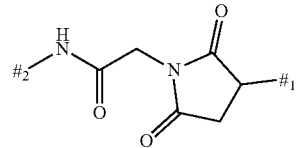

to thiol groups of the antibodies can optionally also be prepared selectively by rebuffering after the coupling and stirring at pH 8 for about 20-24 h according to Schemes 4 and 9 via the ADCs linked via open-chain succinamides.

1 represents the sulphur bridge to the antibody, and #2 the point of attachment to the modified KSP inhibitor Such ADCs where the linker is attached to the antibodies through hydrolysed open-chain succinamides can optionally also be prepared selectively by an illustrative method as follows:

Small-Scale Coupling:

Between 2 and 5 equivalents of tris(2-carboxyethyl)phosphine hydrochloride (TCEP), dissolved in PBS buffer, were added to a solution of 2-5 mg of the appropriate antibody in PBS buffer in the concentration range between 1 mg/ml and 20 mg/ml, preferably in the range of about 5 mg/ml to 15 mg/ml, and the mixture was stirred at RT for 30 min to 1 h. Subsequently, depending on the intended loading, from 2 to 20 equivalents, preferably about 5-10 equivalents of the maleimide precursor compound to be coupled were added as a solution in DMSO. In order to achieve higher DARs, it is also possible to use 15-20 equivalents. Here, the amount of DMSO should not exceed 10% of the total volume. The mixture was stirred at RT for 60-240 min and then diluted to a volume of 2.5-7.5 ml with PBS buffer which had been adjusted to pH 8 beforehand and then passed through a PD column (Sephadex© G-25, GE Healthcare) equilibrated with PBS buffer pH 8, and eluted with PBS buffer pH 8. The eluate was stirred at RT under argon overnight. Subsequently, the solution was concentrated by ultracentrifugation and rediluted with PBS buffer (pH 7.2).

Medium-Scale Coupling:

Under argon, a solution of 2-5 equivalents, preferably 3 equivalents, of TCEP in PBS buffer (c~0.2-0.8 mg/ml, preferably 0.5 mg/ml) were added to 20-200 mg of the antibody in question in PBS buffer (c~5-15 mg/ml). The mixture was stirred at RT for 30 min, and then 2-20, preferably 5-10, equivalents of a maleimide precursor compound dissolved in DMSO were added. In order to achieve higher DARs, it is also possible to use 15-20 equivalents. After stirring at RT for a further 1.5 h-2 h, the mixture was diluted with PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was diluted with PBS buffer pH 8 to a concentration of 1-7 mg/ml. This solution was stirred at RT under argon overnight. If required, the solution was then rebuffered to pH 7.2. The ADC solution was concentrated by ultracentrifugation, rediluted with PBS buffer (pH 7.2) and then optionally concentrated again to a concentration of about 10 mg/ml.

Other potentially hydrolysis-sensitive thianylsuccinimide bridges to the antibody in the working examples contain the following linker substructures, where #1 represents the thioether linkage to the antibody and #1 the linkage site to the modified KSP inhibitor:

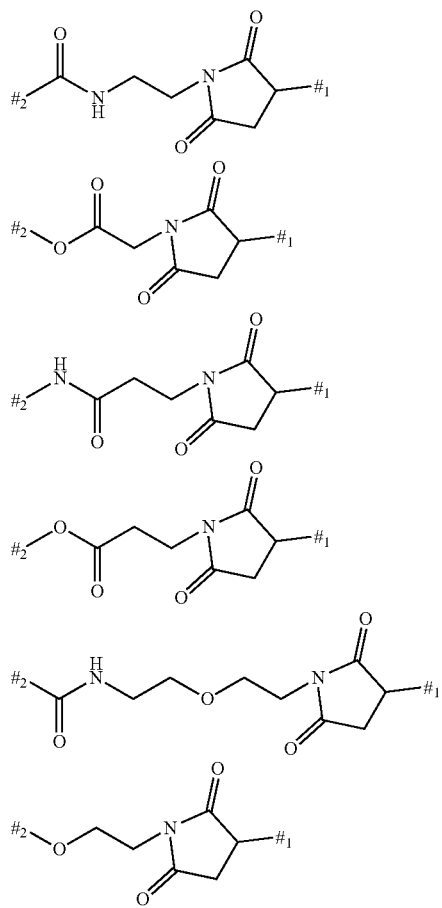

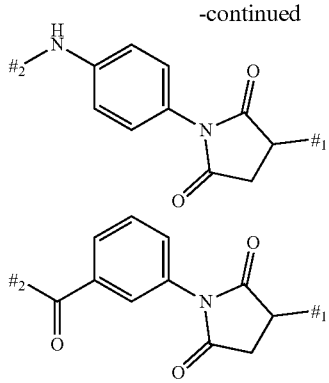

These linker substructures represent the linking unit to the antibody and have (in addition to the further linker composition) a significant effect on the structure and the profile of the metabolites formed in the tumour cells.

In the structural formulae shown, $AK_1$ has the meaning
Examples a: cetuximab (partially reduced)-S §$^1$
Examples e: anti-HER2 AK (TPP-1015 partially reduced)-S §$^1$
Examples k: anti-TWEAKR AK (TPP-7007 partially reduced)-S §$^1$
Examples k: anti-TWEAKR AK (TPP-2658 partially reduced)-S §$^1$
where
§$^1$ represents the linkage to the succinimide group or to any isomeric hydrolysed open-chain succinamides or the alkylene radical resulting therefrom,
and
S represents the sulphur atom of a cysteine residue of the partially reduced antibody.

B-5. General Process for Coupling to Lysine Side Chains

The following antibodies were used for the coupling reactions:
Examples a: cetuximab (anti-EGFR AK)
Examples e: TPP-1015 (anti-Her2 AK)
Examples k: anti-TWEAKR antibody (TPP-7007)
Examples k: anti-TWEAKR antibody (TPP-2658)

The coupling reactions were usually carried out under argon.

From 2 to 10 equivalents of the precursor compound to be coupled were added as a solution in DMSO to a solution of the antibody in question in PBS buffer in a concentration range between 1 mg/ml and 20 mg/ml, preferably about 10 mg/ml, depending on the intended loading. After stirring at RT for 30 min to 6 h, the same amount of precursor compound in DMSO was added again. Here, the amount of DMSO should not exceed 10% of the total volume. After stirring at RT for a further 30 min to 6 h, the mixture was applied to PD 10 columns (Sephadex® G-25, GE Healthcare) equilibrated with PBS and eluted with PBS buffer. Generally, unless indicated otherwise, 5 mg of the antibody in question in PBS buffer were used for the coupling. Purification on the PD10 column thus in each case afforded solutions of the respective ADCs in 3.5 ml PBS buffer. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution.

The respective protein concentrations, stated in the working examples, of the ADC solutions were determined. Furthermore, antibody loading (drug/mAb ratio) was determined using the methods described under B-7.

In the structural formulae shown, $AK_2$ has the meaning
Examples a: cetuximab-NH§ $^2$
Examples e: anti-HER2 AK (TPP-1015)-NH§ $^2$
Examples k: anti-TWEAKR antibody (TPP-7007)-NH§ $^2$
Examples k: anti-TWEAKR antibody (TPP-2658)-NH§ $^2$
where
§ $^2$ represents the linkage to the carbonyl group
and
NH represents the side-chain amino group of a lysine residue of the antibody.

B-5a. General Method for ADC Synthesis by Means of Bacterial Transglutaminase

In the coupling reactions with bacterial transglutaminase, the antibodies which follow may be used (the antibody-HC-N297Z nomenclature which follows means the antibody where the amino acid N297 (Kabat numbering) has been exchanged for the amino acid Z in both heavy chains, the TPP-xxxx-HC-Q295N-HC-N297Q nomenclature means the antibody with the TPP-XXXX where the amino acid Q295 (Kabat numbering) has been exchanged for the amino acid N and the amino acid N297 (Kabat numbering) has been exchanged for the amino acid Q in both heavy chains. The antibody name of the original antibody may either be reported as the name (for example trastuzumab) or as TPP-XXXX (antibody with the TPP number XXXX)):

$AK_{3a}$: anti-TWEAKR antibody (TPP-2658) (corresponding to TPP-2090-HC—N297A)
$AK_{3b}$: anti-TWEAKR antibody (TPP-5442) (corresponding to TPP-2090-HC—N297Q)
$AK_{3c}$: anti-TWEAKR antibody (TPP-8225) (corresponding to TPP-2090-HC-Q295N—HC—N297Q)
$AK_{3d}$: anti-HER2 antibody (TPP-7510) (corresponding to TPP-1015-HC—N297A)
$AK_{3e}$: anti-HER2 antibody (TPP-7511) (corresponding to TPP-1015-HC—N297Q)

General Procedure to Achieve a Maximum DAR of 2:

To a solution of 5 mg of the corresponding aglyco antibody variant (HC—N297A) in DPBS pH 7.4 (c~5-15 mg/ml) were added 20 µl (6 equivalents) of a solution of a suitable toxophore linker precursor (e.g. Intermediates $R^{50}$ and $R^{51}$; 10 mM solution in DMSO). After incubation at 37° C. for 5 min, 50 µl of a solution of recombinant bacterial transglutaminase solution in water (product number T001 from Zedira GmbH, Darmstadt, Germany) (25 U/ml) were added and incubation was continued at 37° C. for a further 24 h. Then the reaction mixture was diluted with DPBS pH 7.4 to a total volume of 2.5 ml and passed by gel filtration through DPBS-equilibrated PD 10 columns (Sephadex® G-25, GE Healthcare) and eluted with DPBS buffer at pH 7.4. Subsequently, the ADC solution was concentrated by means of Amicon Ultracel-30K centrifugation (Millipore), and it was rediluted again with DPBS to a volume of about 2.5 ml. Finally, 0.00625 µmol of the b-transglutaminase blocker Zedira C100 in 12.5 µl of DPBS was added to the solution. The respective protein concentrations, stated in the working examples, of the ADC solutions were determined. Furthermore, antibody loading (drug/mAb ratio) was determined using the methods described under B-7.

General Procedure to Achieve a Maximum DAR of 4:

To a solution of 5 mg of the corresponding aglyco antibody variant (HC-N297Q) in DPBS pH 7.4 (c~5-15 mg/ml) were added 16-24 equivalents of a solution of suitable toxophore linker precursor (e.g. Intermediate R50 and R51; 10 mM solution in DMSO). After incubation at 37° C. for 5 min, 400 µl (10 U) of a solution of recombinant bacterial transglutaminase solution in water (product number T001 from Zedira GmbH, Darmstadt, Germany) (25 U/ml) were added and incubation was continued at 37° C. for a further 24 h. Then the reaction mixture was diluted with DPBS pH 7.4 to a total volume of 2.5 ml and passed by gel filtration through DPBS-equilibrated PD 10 columns (Sephadex® G-25, GE Healthcare) and eluted with DPBS buffer at pH 7.4. Subsequently, the ADC solution was concentrated by means of Amicon Ultracel-30K centrifugation (Millipore), and it was rediluted again with DPBS to a volume of about 2.5 ml. Finally, 0.1 µmol of the b-transglutaminase blocker Zedira C100 in 200 µl of DPBS was added to the solution. The respective protein concentrations, stated in the working examples, of the ADC solutions were determined. Furthermore, antibody loading (drug/mAb ratio) was determined using the methods described under B-7.

General Procedure for Transglutaminase-Mediated Coupling on a Larger Scale to Obtain a Maximum DAR of 2:

To a solution of 30 mg of the aglycosylated variant (HC—N297A) of the particular antibody in DPBS pH 7.4 (c~5-15 mg/ml) were added 6 equivalents of a solution of the appropriate toxophore linker precursor (10 mM in DMSO). After incubation at 37° C. for 5 min, 200 µl (7.5 U) of a solution of recombinant bacterial transglutaminase in water (product number T001 from Zedira GmbH, Darmstadt, Germany) (25 U/ml) were added and incubation was continued at 37° C. for a further 24 h. The reaction mixture was purified via gel filtration chromatography on a Superdex 200 column (GE Healthcare) in DPBS pH 7.4, in order to separate small molecules and the transglutaminase from the ADC. Subsequently, the ADC solution was concentrated to final concentrations of 5-25 mg/ml using Amicon Ultracel-30K centrifugation tubes (Millipore). The solution was then sterile-filtered.

The respective concentrations of the ADC solutions reported in the working examples were determined. The loading was determined by the methods described in Chapter B7. The ADC batches were characterized as indicated in the working examples.

General Procedure for Transglutaminase-Mediated Coupling on a Larger Scale to Obtain a Maximum DAR of 4:

To a solution of 30 mg of the aglycosylated variant (HC—N297Q) of the particular antibody in DPBS pH 7.4 (c~5-15 mg/ml) were added 16-24 equivalents of a solution of the appropriate toxophore linker precursor (10 mM in DMSO). After incubation at 37° C. for 5 min, 2400 µl (60 U) of a solution of recombinant bacterial transglutaminase in water (product number T001 from Zedira GmbH, Darmstadt, Germany) (25 U/ml) were added and incubation was continued at 37° C. for a further 24 h. The reaction mixture was purified via gel filtration chromatography on a Superdex 200 column (GE Healthcare) in DPBS pH 7.4, in order to separate small molecules and the transglutaminase from the ADC. Subsequently, the ADC solution was concentrated to final concentrations of 5-25 mg/ml using Amicon Ultracel-30K centrifugation tubes (Millipore). The solution was then sterile-filtered.

The respective concentrations of the ADC solutions reported in the working examples were determined. The loading was determined by the methods described in Chapter B7. The ADC batches were characterized as indicated in the working examples.

$AK_3$ in each case has the following meaning:
$AK_{3a}$: anti-TWEAKR antibody (TPP-2658) (corresponding to TPP-2090-HC—N297A)-CO— § 2

AK$_{3b}$: anti-TWEAKR antibody (TPP-5442) (corresponding to TPP-2090-HC—N297Q)-CO— § 2

AK$_{3c}$: anti-TWEAKR antibody (TPP-8825) (corresponding to TPP-2090-HC-Q295N—HC—N297Q)-CO— § 2

AK$_{3d}$: anti-HER2 antibody (TPP-7510) (corresponding to TPP-1015-HC—N297A)-CO— § 2

AK$_{3e}$: anti-HER2 antibody (TPP-7511) (corresponding to TPP-1015-HC—N297Q)-CO— § 2 where

§ $^2$ denotes the linkage to the amino group of a toxophore linker precursor, and CO represents the side-chain carbonyl group of a glutamine residue of the antibody.

Potentially suitable substrates for bacterial transglutaminase for the purposes of the application are:

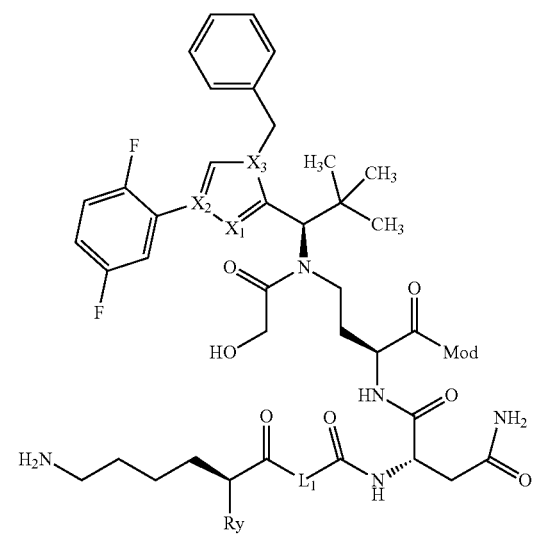

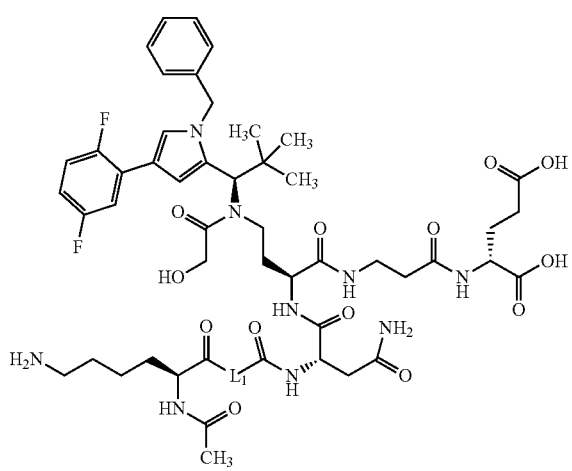

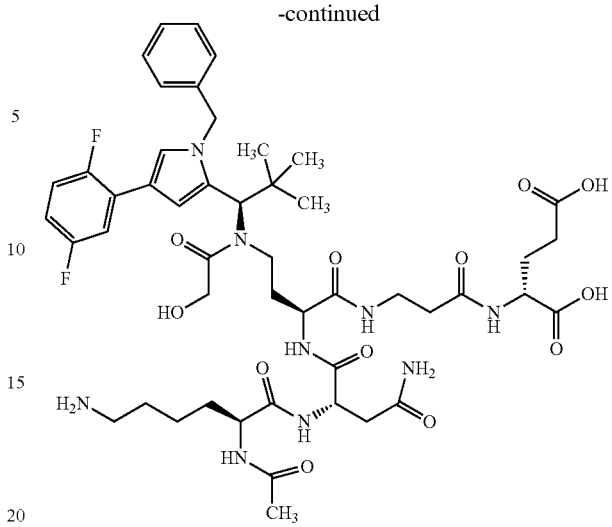

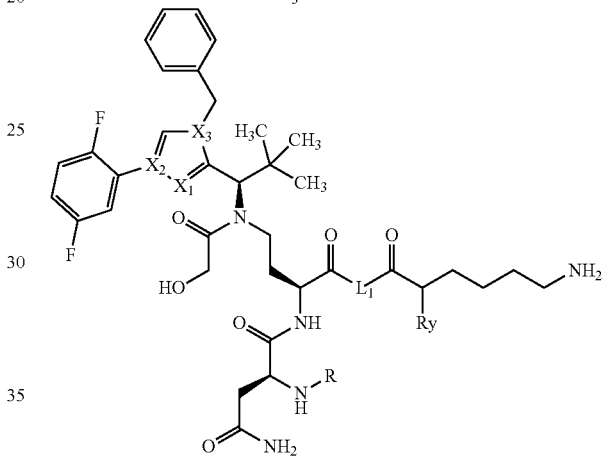

B-6a. General Method for Preparation of Closed Succinimide-Cysteine Adducts:

In an illustrative embodiment, 10 μmol of the above-described maleimide precursor compounds were taken up in 3-5 ml of DMF, and 2.1 mg (20 μmol) of L-cysteine were added. The reaction mixture was stirred at RT for 2 h to 24 h, then concentrated under reduced pressure and then purified by preparative HPLC.

B-6Aa. General Method for Preparation of Isomeric Open Succinamide-Cysteine Adducts:

In an illustrative embodiment, 68 μmol of the maleimide precursor compounds described above were taken up in 15 ml of DMF, and 36 mg (136 μmol) of N-{[2-(trimethylsilyl)ethoxy]carbonyl}-L-cysteine were added. The reaction mixture was stirred at RT for ~20 h, then concentrated under reduced pressure and then purified by preparative HPLC. The appropriate fractions were combined and the solvents were evaporated under reduced pressure, and the residue was then dissolved in 15 ml of THF/water 1:1. 131 μl of a 2M aqueous lithium hydroxide solution were added and the mixture was stirred at RT for 1 h. The reaction was then neutralized with a 1M hydrochloric acid, the solvent was evaporated under reduced pressure and the residue was purified by preparative HPLC. This gave ~50% of theory of the regioisomeric protected intermediates as a colourless foam.

In the last step, 0.023 mmol of these regioisomeric hydrolysis products were dissolved in 3 ml of 2,2,2-trifluoroethanol. 12.5 mg (0.092 mmol) of zinc chloride were added, and the reaction mixture was stirred at 50° C. for 4 h. 27 mg (0.092 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave the hydrolysed open sulphanylsuccinamides as a regioisomer mixture.

Further Purification and Characterization of the Conjugates According to the Invention After the reaction, in some instances the reaction mixture was concentrated, for example by ultrafiltration, and then desalted and purified by chromatography, for example using a Sephadex® G-25 column. Elution was carried out, for example, with phosphate-buffered saline (PBS). The solution was then sterile filtered and frozen. Alternatively, the conjugate can be lyophilized.

B-7. Determination of the Antibody, the Toxophore Loading and the Proportion of Open Cysteine Adducts For protein identification in addition to molecular weight determination after deglycosylation and/or denaturing, a tryptic digestion was carried out which, after denaturing, reduction and derivatization, confirms the identity of the protein via the tryptic peptides found.

The toxophore loading of the PBS buffer solutions obtained of the conjugates described in the working example was determined as follows:

Determination of toxophore loading of lysine-linked ADCs was carried out by mass spectrometry determination of the molecular weights of the individual conjugate species. Here, the antibody conjugates were first deglycosylated with PNGaseF, and the sample was acidified and, after HPLC separation/desalting, analysed by mass spectrometry using ESI-MicroTof$_Q$ (Bruker Daltonik). All spectra over the signal in the TIC (Total Ion Chromatogram) were added and the molecular weight of the different conjugate species was calculated based on MaxEnt deconvolution. The DAR (=drug/antibody ratio) was then calculated after signal integration of the different species. For this purpose, the sum total of the integration results for all species weighted by the toxophore count was divided by the sum of the simply weighted integration results for all species.

The toxophore loading of cysteine-linked conjugates was determined by reversed-phase chromatography of the reduced and denatured ADCs. Guanidinium hydrochloride (GuHCl) (28.6 mg) and a solution of DL-dithiothreitol (DTT) (500 mM, 3 µl) were added to the ADC solution (1 mg/ml, 50 µl). The mixture was incubated at 55° C. for one hour and analysed by HPLC.

HPLC analysis was carried out on an Agilent 1260 HPLC system with detection at 220 nm. A Polymer Laboratories PLRP-S polymeric reversed-phase column (catalogue number PL1912-3802) (2.1×150 mm, 8 µm particle size, 1000 Å) was used at a flow rate of 1 ml/min with the following gradient: 0 min, 25% B; 3 min, 25% B; 28 min, 50% B. Eluent A consisted of 0.05% trifluoroacetic acid (TFA) in water, eluent B of 0.05% trifluoroacetic acid in acetonitrile.

The detected peaks were assigned by retention time comparison with the light chain (L0) and the heavy chain (H0) of the non-conjugated antibody. Peaks detected exclusively in the conjugated sample were assigned to the light chain with one toxophore (L1) and the heavy chains with one, two and three toxophores (H1, H2, H3).

Average loading of the antibody with toxophores was calculated from the peak areas determined by integration as double the sum of HC load and LC load, where LC load is calculated from the sum of the toxophore number-average weighed integration results of all LC peaks divided by the sum of the singly weighed integration results of all LC peaks, and where the HC load is calculated from the sum of the toxophore number-average weighed integration results of all HC peaks divided by the sum of the singly weighed integration results of all HC peaks. In individual cases, it was be possible that, owing to co-elution of some peaks, it was not possible to determine toxophore loading accurately.

In the cases where light and heavy chains could not be separated sufficiently by HPLC, determination of toxophore loading of cysteine-linked conjugates was carried out by mass spectrometry determination of the molecular weights of the individual conjugate species at light and heavy chain.

For this purpose, guanidinium hydrochloride (GuHCl) (28.6 mg) and a solution of DL-dithiothreitol (DTT) (500 mM, 3 µl) were added to the ADC solution (1 mg/ml, 50 µl). The mixture was incubated for one hour at 55° C. and analysed by mass spectrometry after online desalting using ESI-MicroTofQ (Bruker Daltonik).

For the DAR determination, all spectra were added over the signal in the TIC (Total Ion Chromatogram), and the molecular weight of the different conjugate species at light and heavy chain was calculated based on MaxEnt deconvolution. The average loading of the antibody with toxophores was determined from the peak areas determined by integration as twice the sum total of the HC loading and the LC loading. In this context, the LC loading is calculated from the sum total of the integration results for all LC peaks weighted by the toxophore count, divided by the sum total of the simply weighted integration results for all LC peaks, and the HC loading from the sum total of the integration results for all HC peaks weighted by the toxophore count, divided by the sum total of the simply weighted integration results for all HC peaks.

In the case of the open constructs, to determine the proportion of the open cysteine adduct, the molecular weight area ratio of closed to open cysteine adduct (molecular weight delta 18 daltons) of all singly conjugated light and heavy chain variants was determined. The mean of all variants yielded the proportion of the open cysteine adduct.

The toxophore loading of glutamine-linked conjugates was determined by reversed-phase chromatography of the reduced and denatured ADCs. Guanidinium hydrochloride (GuHCl) (28.6 mg) and a solution of DL-dithiothreitol (DTT) (500 mM, 3 µl) were added to the ADC solution (1 mg/ml, 50 µl). The mixture was incubated at 55° C. for one hour and analysed by HPLC.

HPLC analysis was carried out on an Agilent 1260 HPLC system with detection at 220 nm. A Polymer Laboratories PLRP-S polymeric reversed-phase column (catalogue number PL1912-3802) (2.1×150 mm, 8 µm particle size, 1000 Å) was used at a flow rate of 1 ml/min with the following gradient: 0 min, 31% B; 1 min, 31% B; 14 min, 38% B, 16 min, 95% B. Eluent A consisted of 0.05% trifluoroacetic acid (TFA) in water, eluent B of 0.05% trifluoroacetic acid in acetonitrile.

The detected peaks were assigned by retention time comparison with the light chain (L0) and the heavy chain (H0) of the non-conjugated antibody. Peaks detected exclusively in the conjugated sample were assigned to the heavy chains with one and two toxophores (H1, H2).

Average loading of the antibody with toxophores was calculated from the peak areas determined by integration as double the sum of HC load and LC load, where LC load is calculated from the sum of the toxophore number-average weighed integration results of all LC peaks divided by the sum of the singly weighed integration results of all LC peaks, and where the HC load is calculated from the sum of the toxophore number-average weighed integration results of all HC peaks divided by the sum of the singly weighed integration results of all HC peaks.

Alternatively, the toxophore loading of glutamine-linked ADCs was determined by mass spectrometry determination of the molecular weights of the individual conjugate species. In this case, the sample was acidified and, after HPLC separation/desalting, analysed by mass spectrometry using ESI-MicroTof$_Q$ (Bruker Daltonik). All spectra over the signal in the TIC (Total Ion Chromatogram) were added and the molecular weight of the different conjugate species was calculated based on MaxEnt deconvolution. The DAR (=drug/antibody ratio) was then calculated after signal integration of the different species. For this purpose, the sum total of the integration results for all species weighted by the toxophore count was divided by the sum total of the simply weighted integration results for all species.

Alternatively, the toxophore loading was determined independently of the bonding site via UV absorption during size exclusion chromatography (SEC), abbreviated hereinafter to SEC-UV. For this purpose, 50 µl of the ADC solution were analysed via SEC. The analysis was conducted on an Agilent 1260 HPLC system with detection at 280 nm and detection at 260 nm. A Superdex 200 10/300 GL column from GE Healthcare (Lot No: 10194037) (10×310 mm, particle size 1 µm) was used with a flow rate of 1 ml/min under isocratic conditions. The mobile phase consisted of PBS buffer (pH 7.2). For the determination of the drug load from the HPLC chromatogram, the ratio R of the peak areas of the monomer peak at 260 nm and at 280 nm was determined. This ratio was used to ascertain the drug load (DAR) as follows:

$$DAR = \frac{\varepsilon_{Ab}^{\lambda_{drug}} - R \cdot \varepsilon_{Ab}^{280}}{R \cdot \varepsilon_{D}^{280} - \varepsilon_{D}^{\lambda_{drug}}}$$

In this formula, E is the molar extinction coefficient of the antibody (Ab) and the drug (D). $\lambda_{drug}$ represents the wavelength 260 nm, while 280 represents 280 nm. The extinction coefficients of the antibodies at 280 nm and at 260 nm were determined experimentally. The mean value from these determinations for various antibodies was used for the DAR calculation. For the KSP toxophore as well, the molar extinction coefficients at 280 nm and at 260 nm were determined experimentally. The following wavelengths and extinction coefficients were used for the DAR calculations:

|  | ($\lambda_{drug}$) (nm) | ε(280 nm) [1/µM] | ε(260 nm) [1/µM] |
|---|---|---|---|
| Antibody |  | 0.2284 | 0.1163 |
| KSP | 260 | 0.010 | 0.014 |

The concentration of ADCs was determined via the determination of the UV absorption at 280 nm. The concentration was determined using the molar absorption coefficient of the respective antibody. In order likewise to take account of the absorption of the toxophore at 280 nm, the concentration measured at 280 nm was corrected using the following equation:

concentration=preliminary concentration/(1+DAR$_{UV}$*
($\square_{Toxophore\ 280\ nm}$/$\square_{Antibody\ 280\ nm}$))

In this formula, "preliminary concentration" represents the concentration that has been calculated using the absorption coefficient of the antibody only, DAR$_{UV}$ is the DAR of the respective ADC determined via SEC-UV, and $\square_{Toxophore\ 280\ nm}$ and $\square_{Antibody\ 280\ nm}$ are the respective extinction coefficients of the toxophore and the antibody at 280 nm.

B-8. Verification of the Antigen Binding of the ADCs

The capability of the binder of binding to the target molecule was checked after coupling had taken place. The person skilled in the art is familiar with various methods which can be used for this purpose; for example, the affinity of the conjugate can be checked using ELISA technology or surface plasmon resonance analysis (BIAcore™ measurement). The conjugate concentration can be measured by the person skilled in the art using customary methods, for example for antibody conjugates by protein determination. (see also Doronina et al.; Nature Biotechnol. 2003; 21:778-784 and Polson et al., Blood 2007; 1102:616-623).

Working Examples of APDCs and ADCs

The APDCs and ADCs shown in the structural formulae of the Working examples, which were coupled to the cysteine side chains of the antibodies via maleimide radicals, are, depending on the linker and the coupling procedure, mainly present in the ring-opened or ring-closed forms shown in each case. However, the preparation may comprise a small proportion of the respective other form.

The coupling reactions were carried out under argon.

Example 1

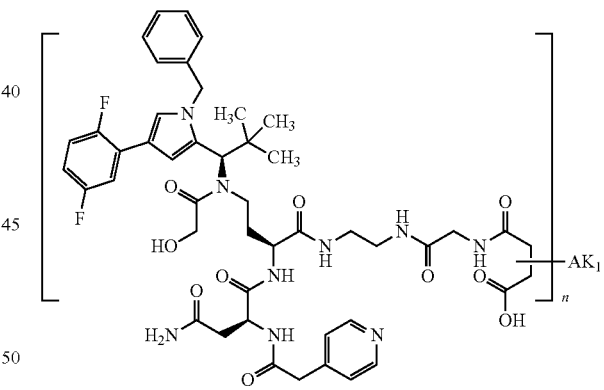

Illustrative Procedure A:

Under argon, a solution of 0.029 mg of TCEP in 0.05 ml of PBS buffer was added to 5 mg of the appropriate antibody in 0.4 ml of PBS (c=12.5 mg/ml). The mixture was stirred at RT for 30 min, and then 0.22 mg (0.00023 mmol) of Intermediate S1 dissolved in 50 µl of DMSO was added. After stirring at RT for a further 90 min, the mixture was diluted to 2.5 ml with PBS buffer which had been adjusted to pH 8 beforehand and then passed through a PD 10 column (Sephadex® G-25, GE Healthcare) equilibrated with PBS buffer pH 8, and eluted with PBS buffer pH 8. The eluate was then stirred at RT under argon overnight. This was followed by concentration by ultracentrifugation and redilution with PBS buffer (pH 7.2).

| Example | Target | Antibody TPP- | Procedure | C [mg/mL] | DAR |
|---|---|---|---|---|---|
| 1a-981 | EGFR | 981 | A | 1.93 | 3.3 |
| 1e-1015 | HER2 | 1015 | A | 1.69 | 3.7 |
| 1k-7007 | TWEAKR | 7007 | A | 1.90 | 3.4 |

Example 2

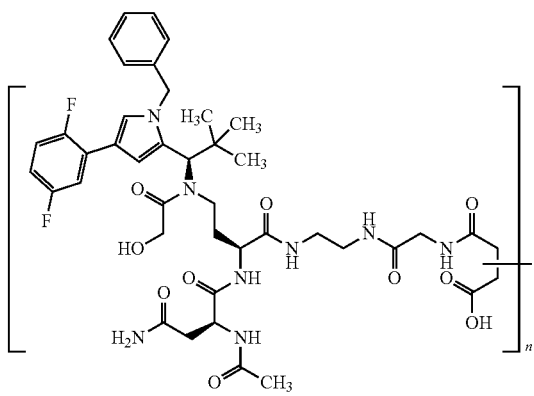

Illustrative Procedure A:

Under argon, a solution of 0.029 mg of TCEP in 0.05 ml of PBS buffer was added to 5 mg of the appropriate antibody in 0.4 ml of PBS (c=12.5 mg/ml). The mixture was stirred at RT for 30 min, and then 0.2 mg (0.00023 mmol) of Intermediate S2 dissolved in 50 µl of DMSO was added. After stirring at RT for a further 90 min, the reaction mixture was diluted to a volume of 2.5 ml with PBS buffer which had been adjusted to pH 8 beforehand and then applied to a PD 10 column (Sephadex® G-25, GE Healthcare) which had been equilibrated with PBS buffer pH 8 and was eluted with PBS buffer pH 8. The eluate was stirred at RT under argon overnight. This was followed by concentration by ultracentrifugation and redilution with PBS buffer (pH 7.2).

Illustrative Procedure B:

Under argon, a solution of 0.172 mg of TCEP in 0.2 ml of PBS buffer was added to 30 mg of the appropriate antibody in 2.52 ml of PBS (c=11.9 mg/ml). The mixture was stirred at RT for 30 min, and then 1.2 mg (0.0014 mmol) of Intermediate S2 dissolved in 200 µl of DMSO was added. After stirring at RT for a further 90 min, the reaction mixture was diluted to a volume of 5 ml with PBS buffer which had been adjusted to pH 8 beforehand, then applied to a PD 10 column (Sephadex® G-25, GE Healthcare) which had been equilibrated with PBS buffer pH 8 and was eluted with PBS buffer pH 8. The eluate was diluted to a volume of 7.5 ml with PBS buffer pH 8 and then stirred at RT under argon overnight. This was followed by concentration by ultracentrifugation and redilution with PBS buffer (pH 7.2).

| Example | Target | Antibody TPP- | Procedure | C [mg/mL] | DAR |
|---|---|---|---|---|---|
| 2a-981 | EGFR | 981 | A | 2.44 | 3.0 |
| 2e-1015 | HER2 | 1015 | A | 1.48 | 3.5 |
| 2k-7007 | TWEAKR | 7007 | A | 1.88 | 3.7 |
| 2k*-7007 | TWEAKR | 7007 | B | 8.61 | 3.2 |

For Example 2k*-7007, the percentage of the ring-opened from was determined as 87.4% by mass spectrometry.

Example 3

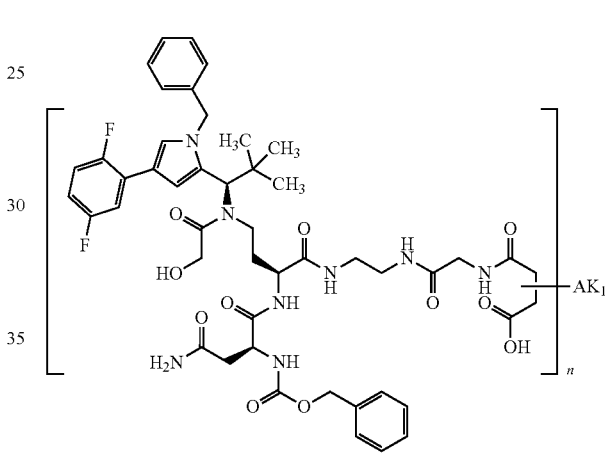

Illustrative Procedure A:

Under argon, a solution of 0.029 mg of TCEP in 0.05 ml of PBS buffer was added to 5 mg of the corresponding antibody in 0.5 ml of PBS (c=10 mg/ml). The mixture was stirred at RT for 30 min, and then 0.22 mg (0.00023 mmol) of Intermediate S3 dissolved in 50 µl of DMSO was added. After stirring at RT for a further 90 min, the mixture was diluted to a volume of 2.5 ml with PBS buffer which had been adjusted to pH 8 beforehand and then passed through a PD 10 column (Sephadex® G-25, GE Healthcare) equilibrated with PBS buffer pH 8, and eluted with PBS buffer pH 8. The eluate was stirred under argon at RT overnight. This was followed by concentration by ultracentrifugation and redilution with PBS buffer (pH 7.2).

| Example | Target | Antibody TPP- | Procedure | C [mg/mL] | DAR |
|---|---|---|---|---|---|
| 3a-981 | EGFR | 981 | A | 1.93 | 4.3 |
| 3e-1015 | HER2 | 1015 | A | 1.9 | 4.8 |
| 3k-2658 | TWEAKR | 2658 | A | 1.88 | 3.6 |

Example 4

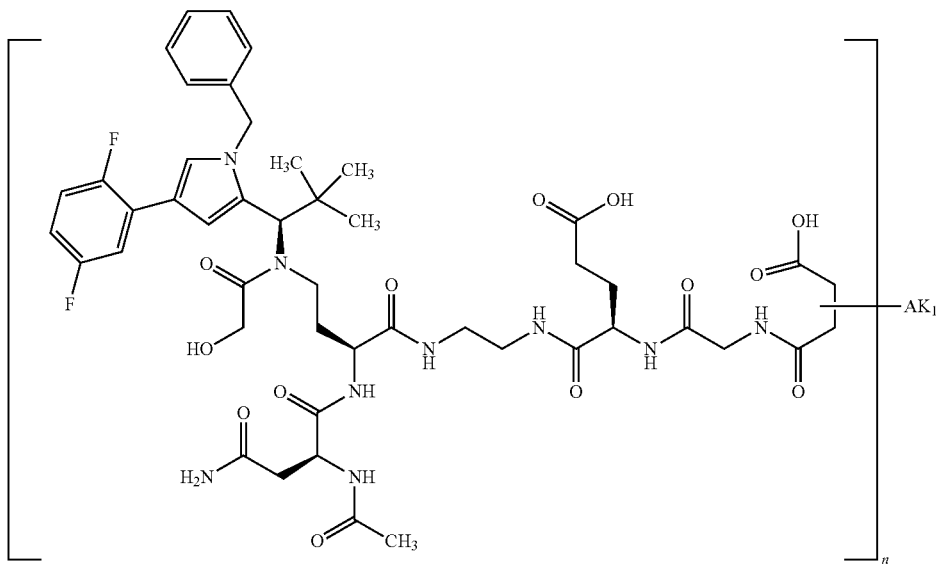

Illustrative Procedure A:

Under argon, a solution of 0.029 mg of TCEP in 0.05 ml of PBS buffer was added to 5 mg of the appropriate antibody in 0.5 ml of PBS (c=10 mg/ml). The mixture was stirred at RT for 30 min, and then 0.23 mg (0.00023 mmol) of Intermediate S4 dissolved in 50 μl of DMSO was added. After stirring at RT for a further 90 min, the mixture was diluted to a volume of 2.5 ml with PBS buffer which had been adjusted to pH 8 beforehand and then passed through a PD 10 column (Sephadex® G-25, GE Healthcare) equilibrated with PBS buffer pH 8, and eluted with PBS buffer pH 8. The eluate was stirred at RT under argon overnight. This was followed by concentration by ultracentrifugation and redilution with PBS buffer (pH 7.2).

| Example | Target | Antibody TPP- | Procedure | C [mg/mL] | DAR |
|---|---|---|---|---|---|
| 4a-981 | EGFR | 981 | A | 1.79 | 2.8 |
| 4e-1015 | HER2 | 1015 | A | 2.22 | 3.2 |
| 4k-7007 | TWEAKR | 7007 | A | 1.84 | 2.8 |

Example 5

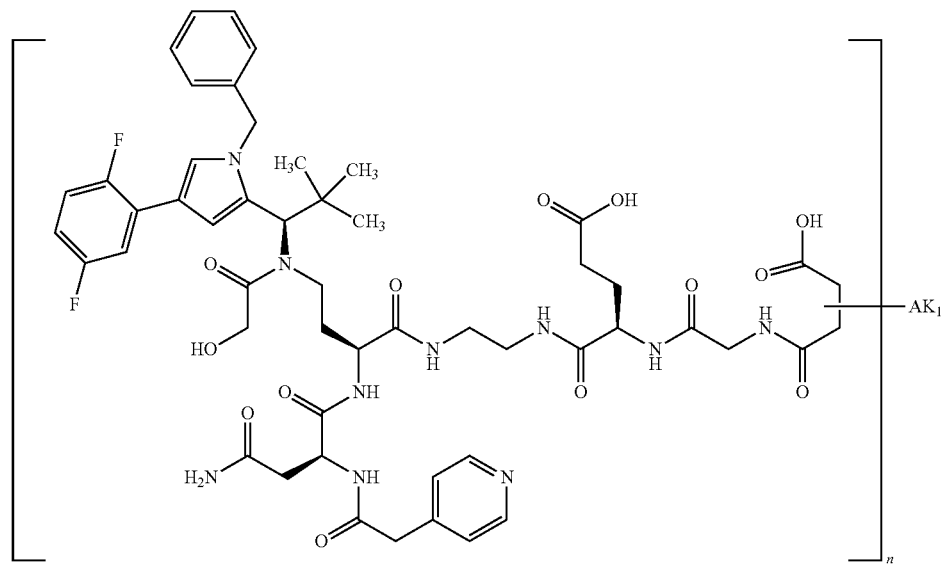

Illustrative Procedure A:

Under argon, a solution of 0.029 mg of TCEP in 0.05 ml of PBS buffer was added to 5 mg of the appropriate antibody in 0.5 ml of PBS (c=10 mg/ml). The mixture was stirred at RT for 30 min, and then 0.23 mg (0.00019 mmol) of Intermediate S5 dissolved in 50 μl of DMSO was added. After stirring at RT for a further 90 min, the reaction mixture was diluted to a volume of 2.5 ml with PBS buffer which had been adjusted to pH 8 beforehand, and then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by concentration by ultracentrifugation and redilution with PBS buffer (pH 7.2).

| Example | Target | Antibody TPP- | Procedure | C [mg/mL] | DAR |
|---|---|---|---|---|---|
| 5a-981 | EGFR | 981 | A | 1.87 | 3.5 |
| 5e-1015 | HER2 | 1015 | A | 1.79 | 3.6 |
| 5k-7007 | TWEAKR | 7007 | A | 1.73 | 3.5 |

Example 6

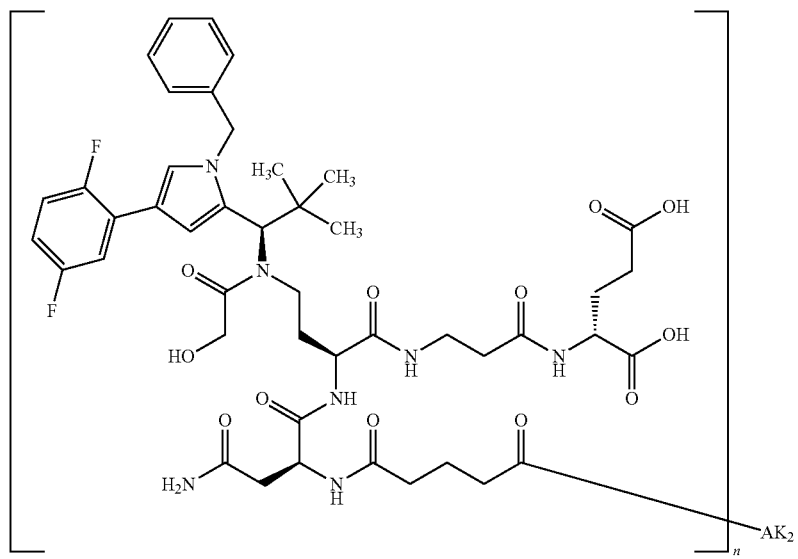

Illustrative Procedure A:

Under argon, 5 eq (0.18 mg) of Intermediate S6 dissolved in 50 μl of DMSO were added to 5 mg of the respective antibody in 0.4 ml of PBS (c=12.5 mg/ml). After stirring at RT for 1 h the same amount was added again and the mixture was stirred at RT for a further hour. The reaction mixture was subsequently diluted to 2.5 ml with PBS buffer (pH 7.2), purified on a Sephadex column, then concentrated by ultracentrifugation and rediluted with PBS (pH 7.2).

Illustrative Procedure B:

To 80 mg of the antibody in question in 5.58 ml of PBS (c=14.3 mg/ml; the concentration may generally also be between 3 and 20 mg/ml) under argon were added 5 eq (2.8 mg) of Intermediate S6 dissolved in 500 μl of DMSO. After stirring at RT for 1 h, the same amount again was added and the mixture was stirred at RT for a further hour. Subsequently, the mixture was diluted with PBS buffer (pH 7.2) to 7.5 ml, purified by means of a Sephadex column and then concentrated by ultracentrifugation and rediluted with PBS (pH 7.2).

| Example | Target | Antibody TPP- | Procedure | C [mg/mL] | DAR |
|---|---|---|---|---|---|
| 6a-981 | EGFR | 981 | A | 2.6 | 5.9 |
| 6e-1015 | HER2 | 1015 | A | 2.32 | 6.9 |
| 6k-7007 | TWEAKR | 7007 | A | 2.53 | 5.3 |

Example 7

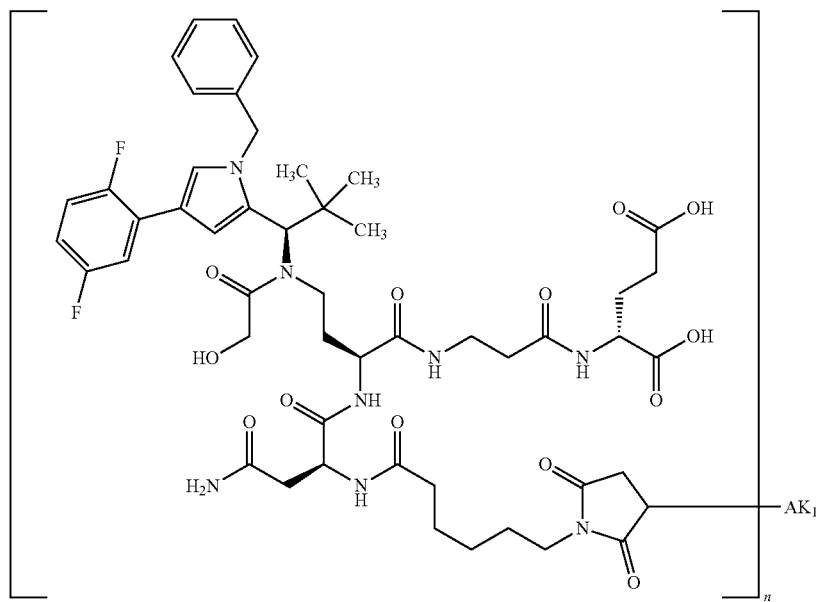

Illustrative Procedure A:

To 5 mg of the antibody in question in 0.4 ml of PBS buffer (pH 7.2) (c=12.5 mg/ml) under argon was added a solution of 0.029 mg of TCEP in 0.05 ml of PBS buffer. The mixture was stirred at RT for 30 min and then 0.24 mg (0.00023 mmol) of Intermediate S7 dissolved in 50 μl of DMSO was added. After stirring at RT for a further 90 min, the mixture was diluted with PBS buffer to a total volume of 2.5 ml. This solution was then passed through a PD 10 column (Sephadex® G-25, GE Healthcare) equilibrated with PBS buffer (pH 7.2) and eluted with PBS buffer (pH 7.2). Subsequently, the mixture was concentrated by ultracentrifugation and rediluted with PBS buffer (pH 7.2).

| Example | Target | Antibody TPP- | Procedure | c [mg/mL] | DAR |
|---|---|---|---|---|---|
| 7a-981 | EGFR | 981 | A | 2.13 | 3.6 |
| 7e-1015 | HER2 | 1015 | A | 2.02 | 3.9 |
| 7k-7007 | TWEAKR | 7007 | A | 2.12 | 3.8 |

Example 8

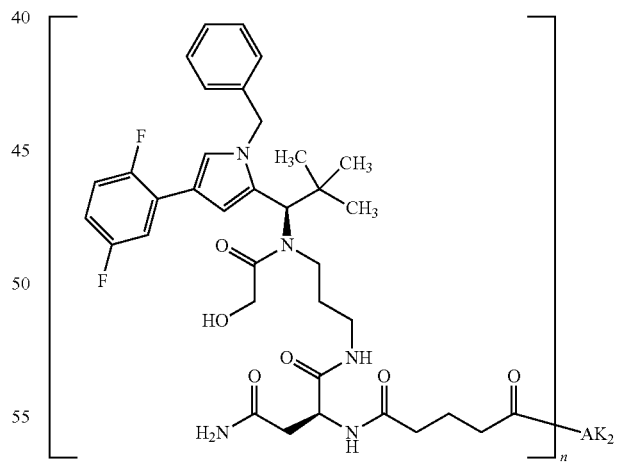

Illustrative Procedure A:

Under argon, 5 eq (0.14 mg) of Intermediate S8 dissolved in 50 μl of DMSO were added to 5 mg of the respective antibody in 0.4 ml of PBS (c=12.5 mg/ml). After stirring at RT for 1 h the same amount again was added and the mixture was stirred at RT for a further hour. The reaction was subsequently diluted to 2.5 ml with PBS buffer (pH 7.2), purified on a Sephadex column, then concentrated by ultracentrifugation and rediluted with PBS (pH 7.2).

| Example | Target | Antibody TPP- | Procedure | C [mg/mL] | DAR |
|---|---|---|---|---|---|
| 8a-981 | EGFR | 981 | A | 1.23 | 3.8 |
| 8e-1015 | HER2 | 1015 | A | 1.59 | 4.5 |
| 8k-7007 | TWEAKR | 7007 | A | 2.22 | 3.1 |

Example 9

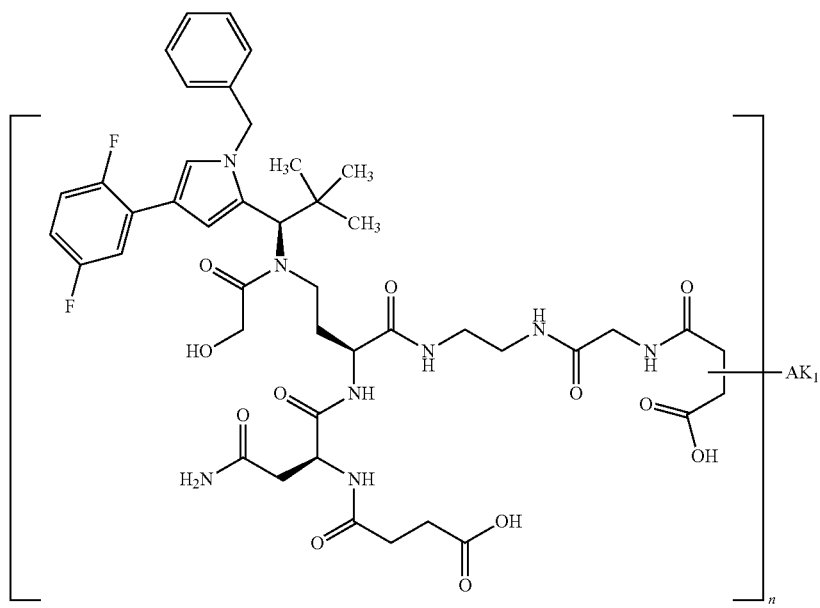

Illustrative Procedure A:

Under argon, a solution of 0.029 mg of TCEP in 0.05 ml of PBS buffer was added to 5 mg of the appropriate antibody in 0.5 ml of PBS (c=10 mg/ml). The mixture was stirred at RT for 30 min, and then 0.22 mg (0.00023 mmol) of Intermediate S9 dissolved in 50 μl of DMSO was added. After stirring at RT for a further 90 min, the reaction mixture was diluted to a volume of 2.5 ml with PBS buffer which had been adjusted to pH 8 beforehand, then applied to a PD 10 column (Sephadex® G-25, GE Healthcare) which had been equilibrated with PBS buffer pH 8 and was eluted with PBS buffer pH 8. The eluate was stirred under argon at RT overnight. This was followed by concentration by ultracentrifugation and redilution with PBS buffer (pH 7.2).

| Example | Target | Antibody TPP- | Procedure | C [mg/mL] | DAR |
|---|---|---|---|---|---|
| 9a-981 | EGFR | 981 | A | 2.06 | 3.4 |
| 9e-1015 | HER2 | 1015 | A | 1.92 | 3.6 |
| 9k-7007 | TWEAKR | 7007 | A | 2.05 | 3.1 |

Example 10

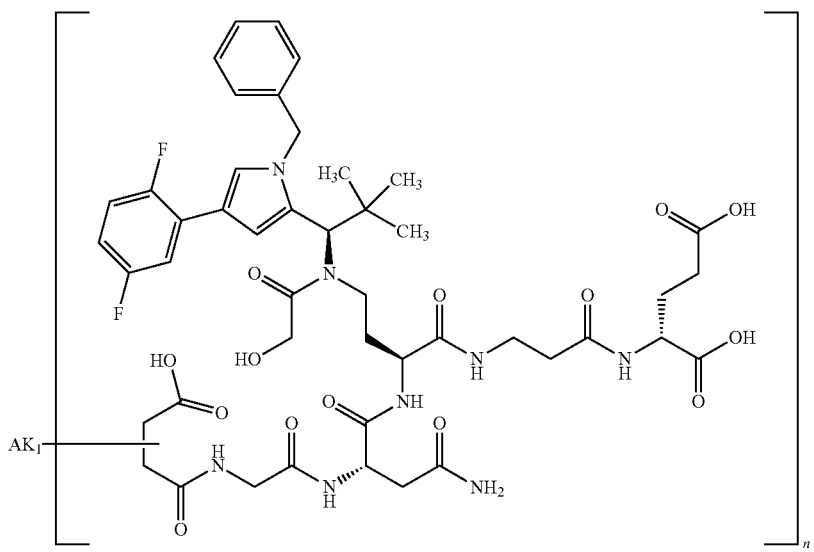

Illustrative Procedure A:

Under argon, a solution of 0.029 mg of TCEP in 0.05 ml of PBS buffer was added to 5 mg of the corresponding antibody in 0.4 ml of PBS buffer (pH 7.2) (c=12.5 mg/ml). The mixture was stirred at RT for 30 min and then 0.23 mg (0.00023 mmol) of Intermediate S10 dissolved in 50 μl of DMSO was added. After stirring at RT for a further 90 min, the mixture was diluted to a total volume of 2.5 ml with PBS buffer, then applied to a PD 10 column (Sephadex® G-25, GE Healthcare) which had been equilibrated with PBS buffer pH 8 and was eluted with PBS buffer pH 8. The eluate was stirred at RT under argon overnight. This was followed by concentration by ultracentrifugation and redilution with PBS buffer (pH 7.2).

| Example | Target | Antibody TPP- | Procedure | C [mg/mL] | DAR |
|---|---|---|---|---|---|
| 10a-981 | EGFR | 981 | A | 2.13 | 3.0 |
| 10e-1015 | HER2 | 1015 | A | 1.8 | 3.1 |
| 10k-7007 | TWEAKR | 7007 | A | 2.02 | 2.6 |

Example 11

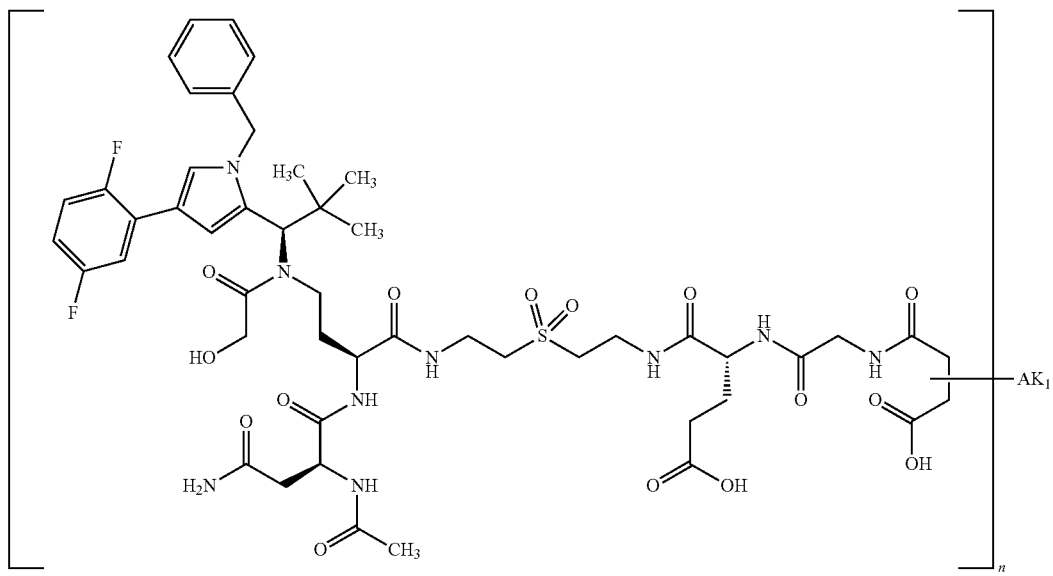

Illustrative Procedure A:

To 5 mg of the appropriate antibody in 0.4 ml of PBS (c=12.5 mg/ml) under argon was added a solution of 0.029 mg of TCEP in 0.05 ml of PBS buffer. The mixture was stirred at RT for 30 min and then 0.23 mg (0.00023 mmol) of Intermediate S11 dissolved in 50 μl of DMSO were added. After stirring at RT for a further 90 min, the mixture was diluted to a volume of 2.5 ml with PBS buffer that had been adjusted to pH 8 beforehand, then passed through a PD 10 column (Sephadex® G-25, GE Healthcare) equilibrated with PBS buffer pH 8 and eluted with PBS buffer pH 8. The eluate was stirred at RT under argon overnight. Subsequently, the mixture was concentrated by ultracentrifugation and rediluted with PBS buffer (pH 7.2).

| Example | Target | Antibody TPP- | Procedure | C [mg/ml] | DAR |
|---------|--------|---------------|-----------|-----------|-----|
| 11a-981 | EGFR | 981 | A | 1.90 | 3.2 |
| 11e-1015 | HER2 | 1015 | A | 1.77 | 3.5 |
| 11k-7007 | TWEAKR | 7007 | A | 1.99 | 3.4 |

Illustrative Procedure A:

To 5 mg of the antibody in question in 0.4 ml of PBS buffer (pH 7.2) (c=12.5 mg/ml) under argon was added a solution of 0.029 mg of TCEP in 0.05 ml of PBS buffer. The mixture was stirred at RT for 30 min and then 0.22 mg (0.00023 mmol) of Intermediate S12 dissolved in 50 μl of DMSO was added and the mixture was stirred at RT overnight. The mixture was then diluted to a total volume of 2.5 ml with PBS buffer. This solution was passed through a PD 10 column (Sephadex® G-25, GE Healthcare) equilibrated with PBS buffer and eluted with PBS buffer. Subsequently, the mixture was concentrated by ultracentrifugation and rediluted with PBS buffer (pH 7.2).

| Example | Target | Antibody TPP- | Procedure | C [mg/ml] | DAR |
|---------|--------|---------------|-----------|-----------|-----|
| 12a-981 | EGFR | 981 | A | 1.92 | 2.2 |
| 12e-1015 | HER2 | 1015 | A | 1.66 | 2.5 |
| 12k-7007 | TWEAKR | 7007 | A | 1.84 | 2.5 |

Example 12

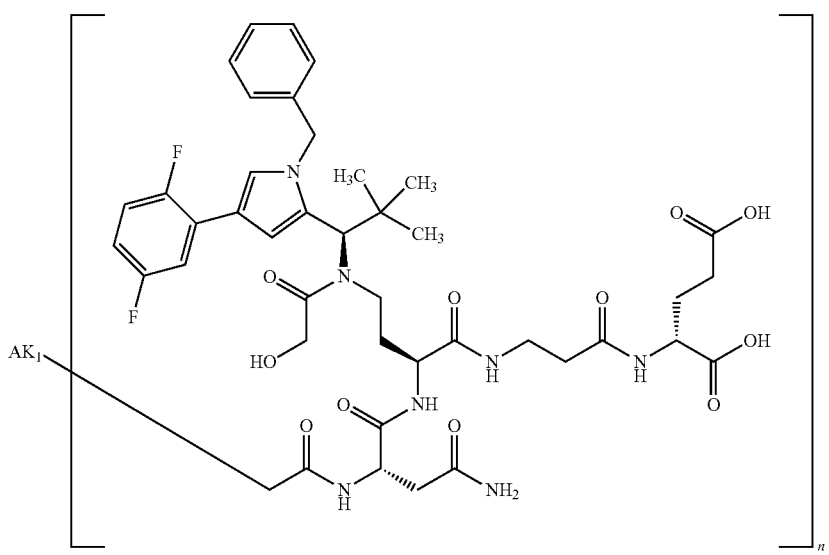

Example 13

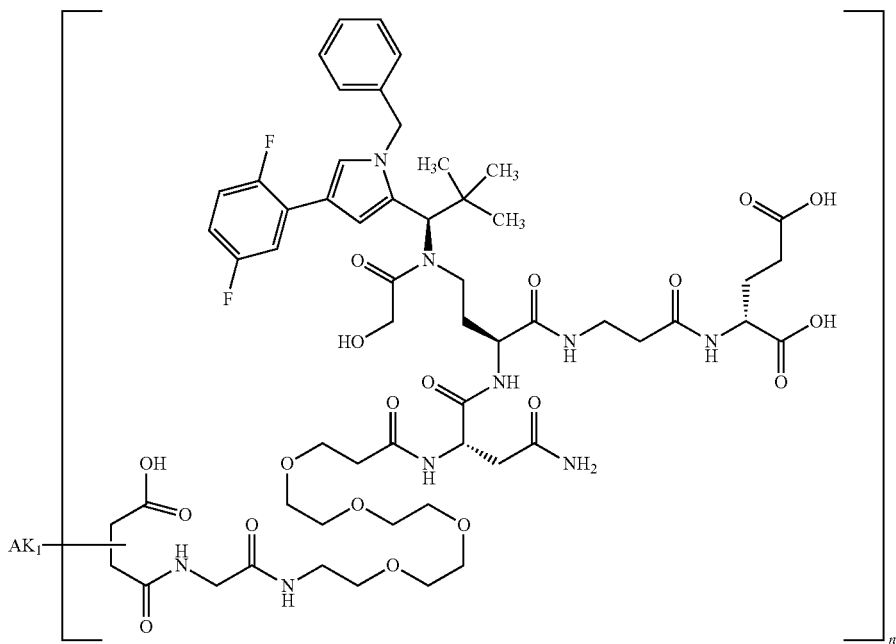

Illustrative Procedure A:

To 5 mg of the antibody in question in 0.5 ml of PBS buffer (pH 7.2) (c=10 mg/ml) under argon was added a solution of 0.029 mg of TCEP in 0.05 ml of PBS buffer. The mixture was stirred at RT for 30 min and then 0.28 mg (0.00023 mmol) of Intermediate S13 dissolved in 50 µl of DMSO was added. After stirring at RT for a further 90 min, the mixture was diluted to a total volume of 2.5 ml with PBS buffer, then passed through a PD column (Sephadex® G-25, GE Healthcare) equilibrated with PBS buffer pH 8 and eluted with PBS buffer pH 8. The eluate was stirred at RT under argon overnight. Subsequently, the mixture was concentrated by ultracentrifugation and rediluted with PBS buffer (pH 7.2).

| Example | Target | Antibody TPP- | Procedure | C [mg/ml] | DAR |
|---|---|---|---|---|---|
| 13a-981 | EGFR | 981 | A | 1.72 | 3.0 |
| 13e-1015 | HER2 | 1015 | A | 1.67 | 3.0 |
| 13k-7007 | TWEAKR | 7007 | A | 1.73 | 2.3 |

Example 14

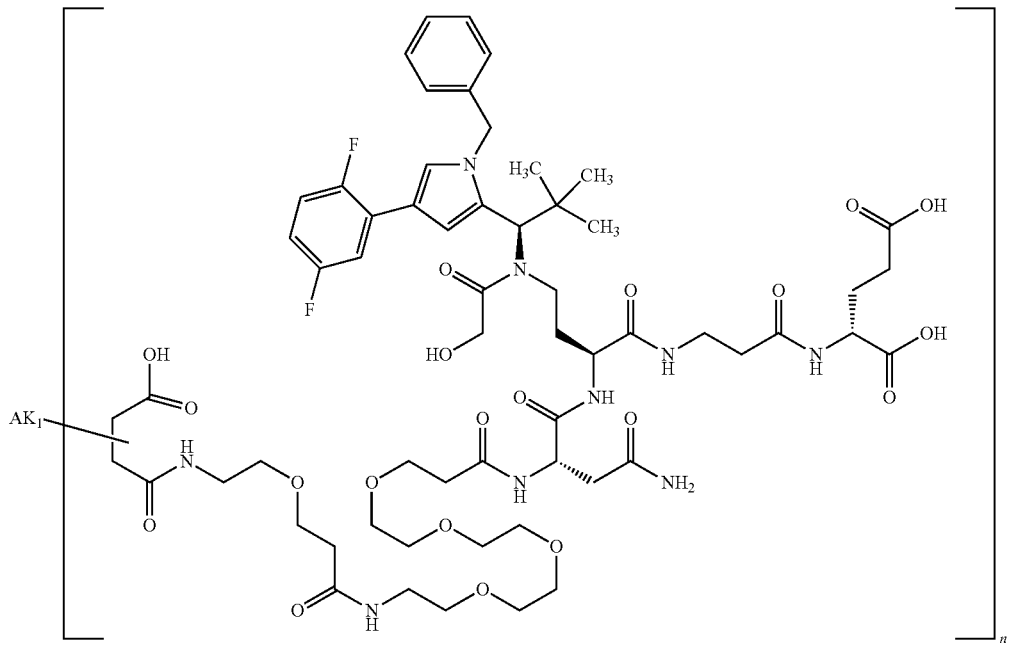

Illustrative Procedure A:

To 5 mg of the antibody in question in 0.5 ml of PBS buffer (pH 7.2) (c=10 mg/ml) under argon was added a solution of 0.029 mg of TCEP in 0.05 ml of PBS buffer. The mixture was stirred at RT for 30 min and then 0.3 mg (0.00023 mmol) of Intermediate S14 dissolved in 50 µl of DMSO was added. After stirring at RT for a further 90 min, the mixture was diluted to a total volume of 2.5 ml with PBS buffer that had been adjusted to pH 8. This solution was passed through a PD 10 column (Sephadex® G-25, GE Healthcare) equilibrated with PBS buffer (pH 8), eluted with PBS buffer (pH 8) and stirred at RT overnight. Subsequently, the mixture was concentrated by ultracentrifugation and rediluted with PBS buffer (pH 7.2).

| Example | Target | Antibody TPP- | Procedure | C [mg/ml] | DAR |
|---|---|---|---|---|---|
| 14a-981 | EGFR | 981 | A | 1.77 | 3.3 |
| 14e-1015 | HER2 | 1015 | A | 1.65 | 3.4 |
| 14k-7007 | TWEAKR | 7007 | A | 1.65 | 2.5 |

In the case of the ADCs from Example 14 that had been prepared under these conditions and with this linker, the ring opening was incomplete. They still contained relatively large fractions (more than 50%) in which the linkage to the antibody was via the ring-closed succinimide form (cf. Example 7).

Example 15

Illustrative Procedure A:

To 5 mg of the appropriate antibody in 0.5 ml of PBS (c=10 mg/ml) under argon was added a solution of 0.029 mg of TCEP in 0.05 ml of PBS buffer. The mixture was stirred at RT for 30 min and then 0.27 mg (0.00023 mmol) of Intermediate S15 dissolved in 50 µl of DMSO was added and the mixture was stirred at RT for a further 90 min. The solution was then diluted to 2.5 ml with PBS buffer that had been adjusted to pH 8 beforehand, then passed through a PD 10 column (Sephadex® G-25, GE Healthcare) equilibrated with PBS buffer pH 8 and eluted with PBS buffer pH 8. The eluate was stirred at RT under argon overnight. Subsequently, the mixture was concentrated by ultracentrifugation and rediluted with PBS buffer (pH 7.2).

| Example | Target | Antibody TPP- | Procedure | C [mg/ml] | DAR |
|---|---|---|---|---|---|
| 15a-981 | EGFR | 981 | A | 1.52 | 3.5 |
| 15e-1015 | HER2 | 1015 | A | 1.72 | 3.2 |
| 15k-7007 | TWEAKR | 7007 | A | 1.75 | 2.3 |

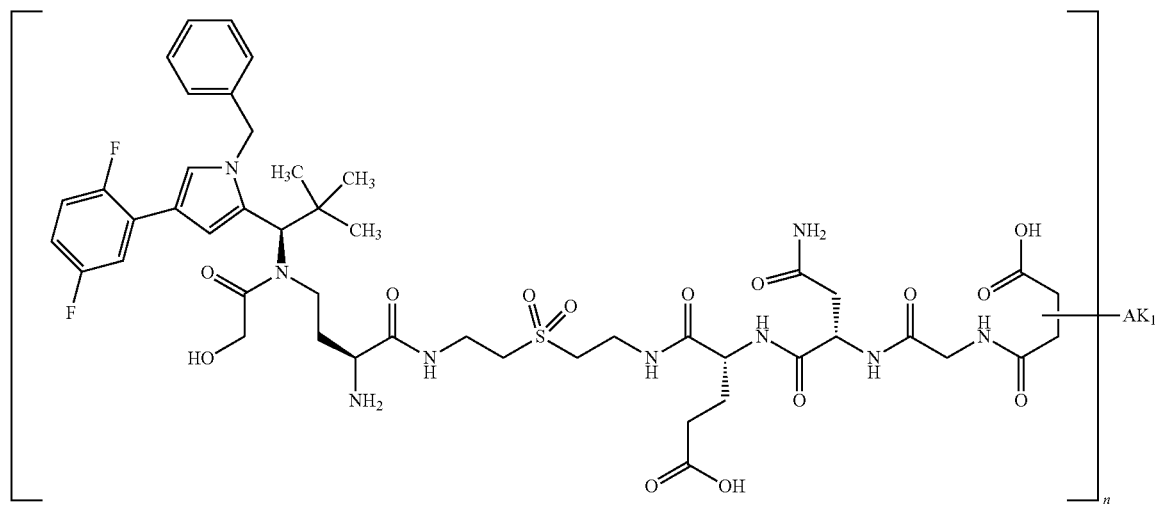

Example 16

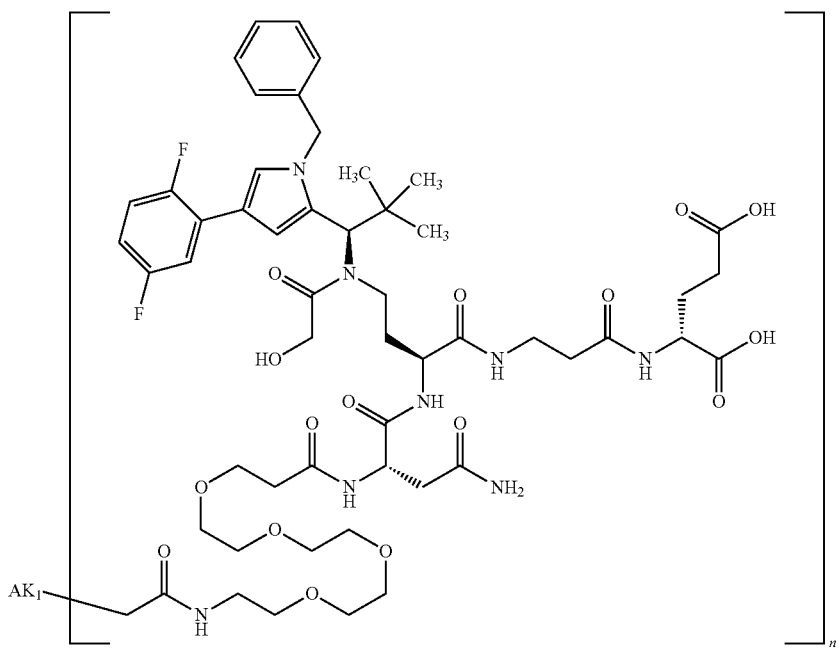

Illustrative Procedure a (for Achievement of a Higher DAR):

To 5 mg of the appropriate antibody in 0.5 ml of PBS (c=10 mg/ml) under argon was added a solution of 0.067 mg of TCEP in 0.05 ml of PBS buffer. The mixture was stirred at RT for 30 min and then 0.68 mg (0.00057 mmol) of Intermediate S16 dissolved in 50 µl of DMSO was added. After further stirring under argon at RT overnight, the mixture was diluted to a volume of 2.5 ml with PBS buffer. This solution was then passed through a PD column (Sephadex® G-25, GE Healthcare) equilibrated with PBS buffer pH 7.2 and eluted with PBS buffer pH 7.2. Subsequently, the mixture was concentrated by ultracentrifugation and rediluted with PBS buffer (pH 7.2).

| Example | Target | Antibody TPP- | Procedure | C [mg/ml] | DAR |
|---|---|---|---|---|---|
| 16e-1015 | HER2 | 1015 | A | 2.14 | 3.1 |
| 16k-7007 | TWEAKR | 7007 | A | 1.84 | 2.7 |

Example 17

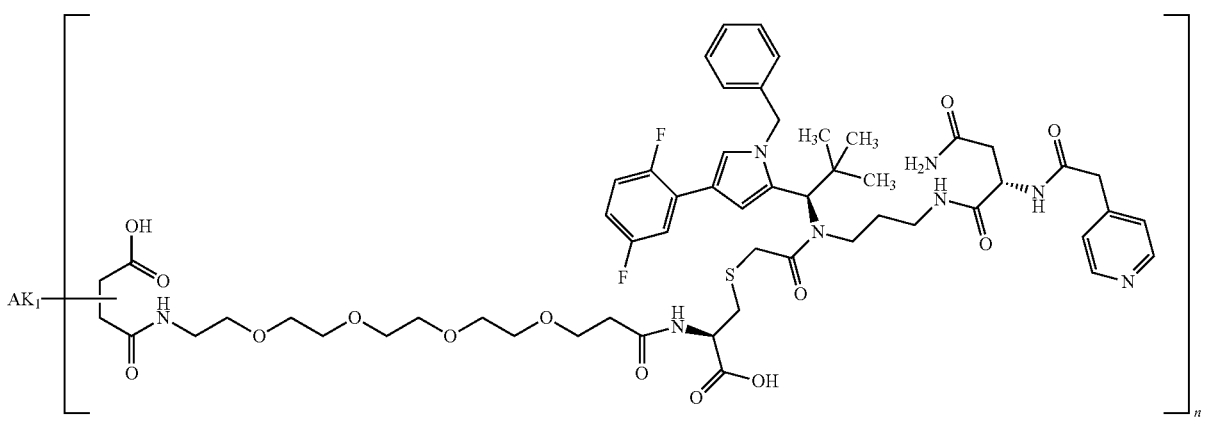

Illustrative Procedure A:

To 5 mg of the appropriate antibody in 0.45 ml of PBS (c=11 mg/ml) under argon was added a solution of 0.029 mg of TCEP in 0.05 ml of PBS buffer. The mixture was stirred at RT for 30 min and then 0.30 mg (0.00023 mmol) of Intermediate S17 dissolved in 50 μl of DMSO was added and the mixture was stirred at RT for a further 90 min. The solution was then diluted to 2.5 ml with PBS buffer that had been adjusted to pH 8 beforehand, then passed through a PD 10 column (Sephadex® G-25, GE Healthcare) equilibrated with PBS buffer pH 8 and eluted with PBS buffer pH 8. The eluate was stirred at RT under argon overnight. Subsequently, the mixture was concentrated by ultracentrifugation and rediluted with PBS buffer (pH 7.2).

| Example | Target | Antibody TPP- | Procedure | C [mg/ml] | DAR |
|---------|--------|---------------|-----------|-----------|-----|
| 17a-981 | EGFR | 981 | A | 1.45 | 3.0 |
| 17e-1015 | HER2 | 1015 | A | 0.86 | 3.0 |
| 17k-7007 | TWEAKR | 7007 | A | 1.01 | 2.5 |

Example 18

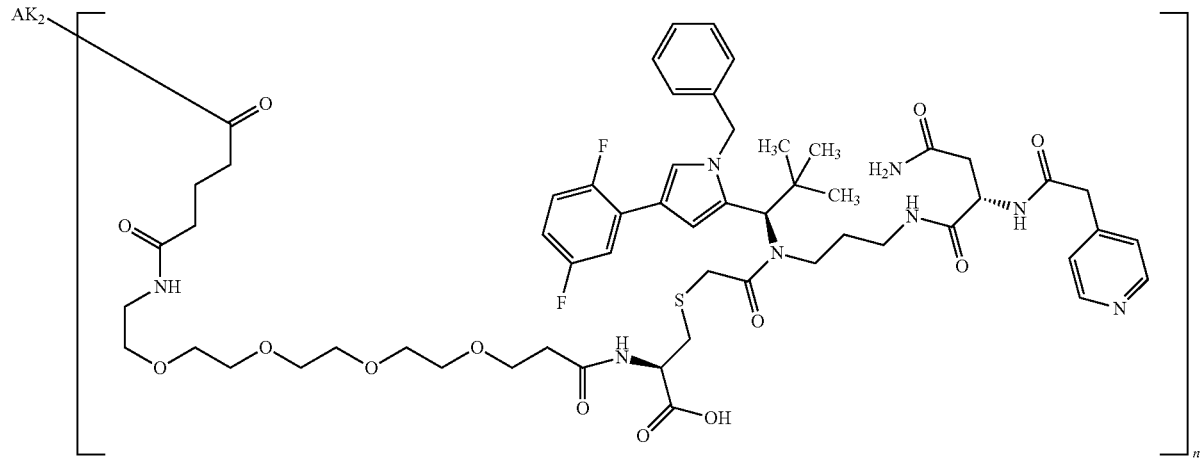

Illustrative Procedure A:

Under argon, 5 eq (0.12 mg) of Intermediate S18 dissolved in 30 μl of DMSO were added to 3 mg of the respective antibody in 0.3 ml of PBS (c=10 mg/ml). After stirring at RT for 1 h the same amount again was added and the mixture was stirred at RT for a further hour. The reaction mixture was subsequently diluted to 2.5 ml with PBS buffer (pH 7.2), purified on a Sephadex column, then concentrated by ultracentrifugation and rediluted with PBS (pH 7.2).

| Example | Target | Antibody TPP- | Procedure | C [mg/mL] | DAR |
|---------|--------|---------------|-----------|-----------|-----|
| 18a-981 | EGFR | 981 | A | 1.98 | 2.8 |
| 18e-1015 | HER2 | 1015 | A | 1.16 | 3.8 |
| 18k-7007 | TWEAKR | 7007 | A | 2.00 | 3.7 |

Example 19

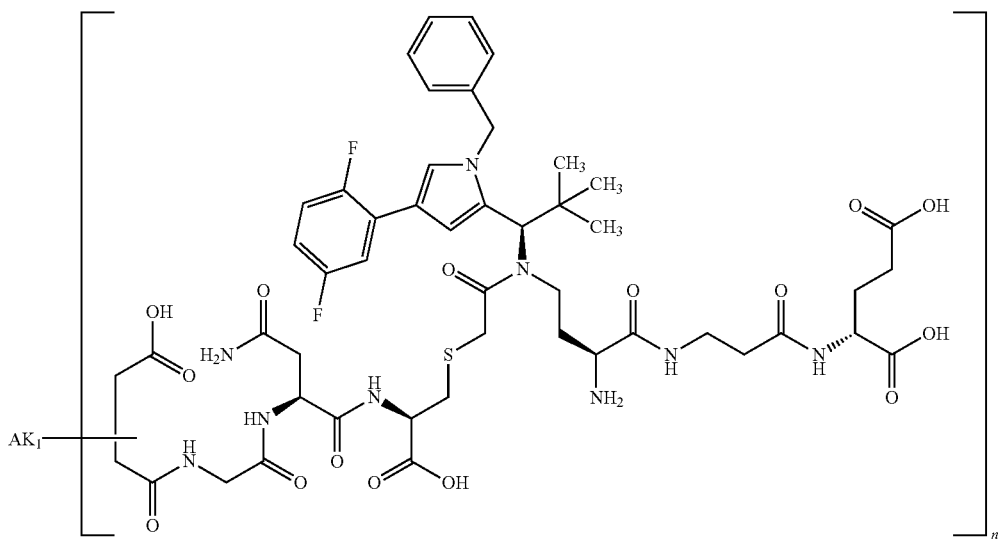

Illustrative Procedure A:

To 5 mg of the appropriate antibody in 0.45 ml of PBS (c=11 mg/ml) under argon was added a solution of 0.029 mg of TCEP in 0.05 ml of PBS buffer. The mixture was stirred at RT for 30 min and then 0.28 mg (0.00023 mmol) of Intermediate S19 dissolved in 50 µl of DMSO was added and the mixture was stirred at RT for a further 90 min. The solution was then diluted to 2.5 ml with PBS buffer that had been adjusted to pH 8 beforehand, then passed through a PD 10 column (Sephadex® G-25, GE Healthcare) equilibrated with PBS buffer pH 8 and eluted with PBS buffer pH 8. The eluate was stirred at RT under argon overnight. Subsequently, the mixture was concentrated by ultracentrifugation and rediluted with PBS buffer (pH 7.2).

| Example | Target | Antibody TPP- | Procedure | C [mg/ml] | DAR |
|---|---|---|---|---|---|
| 19a-981 | EGFR | 981 | A | 1.29 | 4.8 |
| 19e-1015 | HER2 | 1015 | A | 1.29 | 5.1 |
| 19k-7007 | TWEAKR | 7007 | A | 1.10 | 4.8 |

Example 20

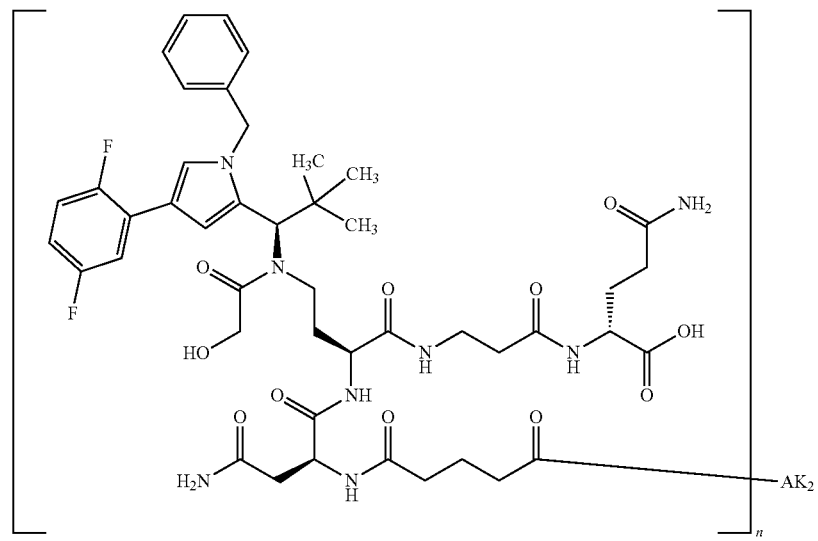

Illustrative Procedure A:

Under argon, 5 eq (0.17 mg) of Intermediate S20 dissolved in 50 μl of DMSO were added to 5 mg of the respective antibody in 0.5 ml of PBS (c=10 mg/ml). After stirring at RT for 1 h the same amount again was added and the mixture was stirred at RT for a further hour. Then the mixture was diluted to 2.5 ml with PBS buffer (pH 7.2), purified on a Sephadex column, then concentrated by ultracentrifugation and rediluted with PBS (pH 7.2).

| Example | Target | Antibody TPP- | Procedure | C [mg/mL] | DAR |
|---|---|---|---|---|---|
| 20a-981 | EGFR | 981 | A | 2.0 | 6.2 |
| 20e-1015 | HER2 | 1015 | A | 2.19 | 4.3 |
| 20k-7007 | TWEAKR | 7007 | A | 2.1 | 4.6 |

Example 21

Illustrative Procedure A:

Under argon, a solution of 0.029 mg of TCEP in 0.05 ml of PBS buffer was added to 5 mg of the relevant antibody in 0.5 ml of PBS buffer (pH 7.2) (c=10 mg/ml). The mixture was stirred at RT for 30 min, and then 0.22 mg (0.00023 mmol) of Intermediate S21 dissolved in 50 μl of DMSO was added. After stirring at RT for a further 90 min, the reaction mixture was diluted to a total volume of 2.5 ml with PBS buffer, then applied to a PD 10 column (Sephadex® G-25, GE Healthcare) which had been equilibrated with PBS buffer pH 8 and was eluted with PBS buffer pH 8. The eluate was stirred at RT under argon overnight. This was followed by concentration by ultracentrifugation and redilution with PBS buffer (pH 7.2).

| Example | Target | Antibody TPP- | Procedure | C [mg/mL] | DAR |
|---|---|---|---|---|---|
| 21a-981 | EGFR | 981 | A | 1.79 | 2.5 |
| 21e-1015 | HER2 | 1015 | A | 1.72 | 2.7 |
| 21k-7007 | TWEAKR | 7007 | A | 1.95 | 2.0 |

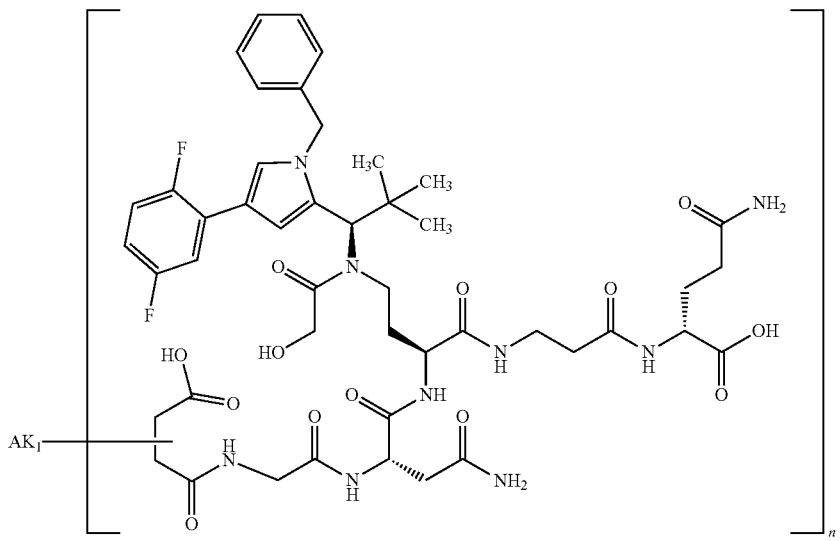

Example 22

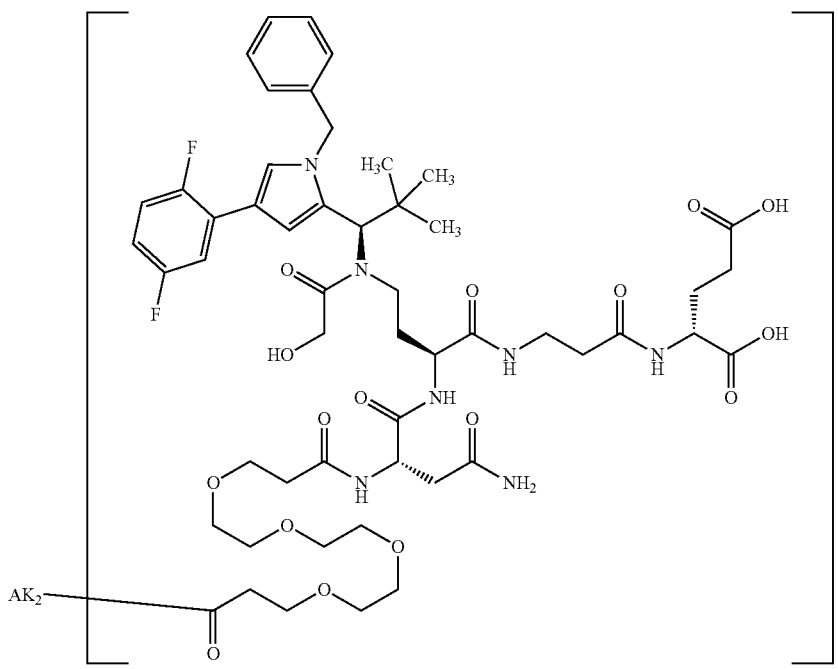

Illustrative Procedure A:

5 mg of the respective antibody in 0.5 ml of PBS (c=10 mg/ml) were admixed under argon with 5 eq (0.22 mg) of Intermediate S22 dissolved in 50 µl of DMSO. After stirring at RT for 1 h, the same amount again was added and the mixture was stirred at RT for a further hour. The reaction mixture was subsequently diluted to 2.5 ml with PBS buffer (pH 7.2), purified on a Sephadex column, then concentrated by ultracentrifugation and rediluted with PBS (pH 7.2).

| Example | Target | Antibody TPP- | Procedure | C [mg/mL] | DAR |
|---|---|---|---|---|---|
| 22a-981 | EGFR | 981 | A | 1.86 | 6.4 |
| 22e-1015 | HER2 | 1015 | A | 1.97 | 5.6 |
| 22k-7007 | TWEAKR | 7007 | A | 1.90 | 5.3 |

Working Examples of Metabolites

The metabolites formed in the tumour from the ADCs according to the invention in their various embodiments were prepared and characterized for comparative purposes. Some of them have already been described in earlier disclosures of other ADCs.

Metabolites which can be Formed, for Example, from Example 2, 3 and 9

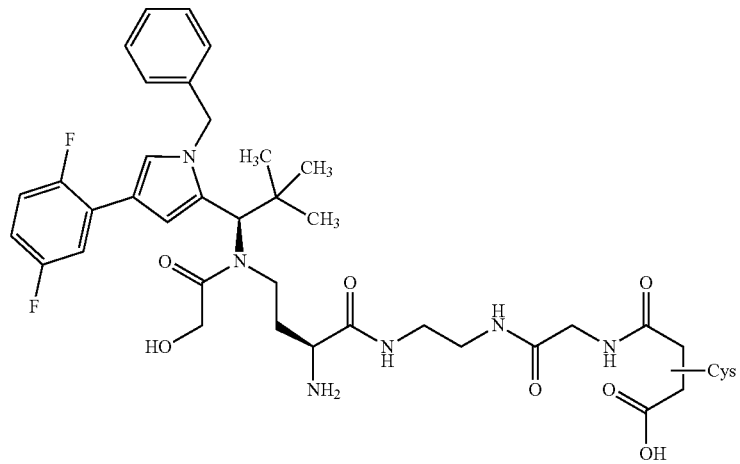

The synthesis of the 4 isomeric cysteine metabolites which can be formed from Example 1, 2, 3, 9 were described in WO2016/096610, where they were characterized as Examples M13, M14, M15 and M16.

Metabolites M1 and M2 which can be Formed, for Example, from Example 4 and 5

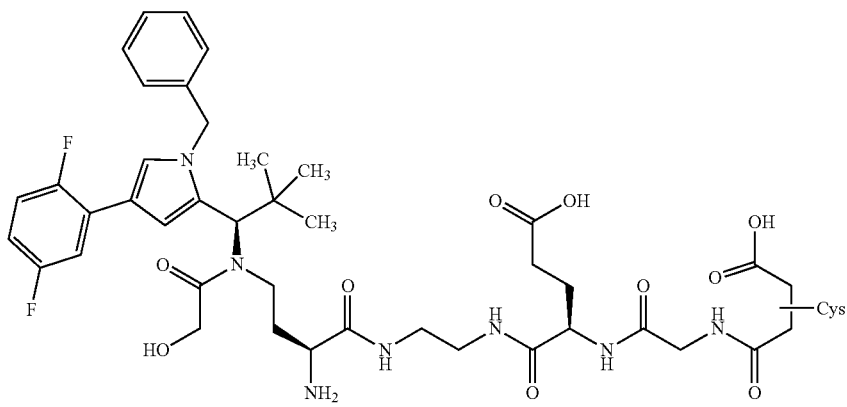

Example M1

N-(3-{[(2R)-2-Amino-2-carboxyethyl]sulphanyl}-3-carboxypropanoyl)glycyl-N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-D-alpha-glutamine trifluoroacetic acid salt Regioisomer 1, Epimer Mixture

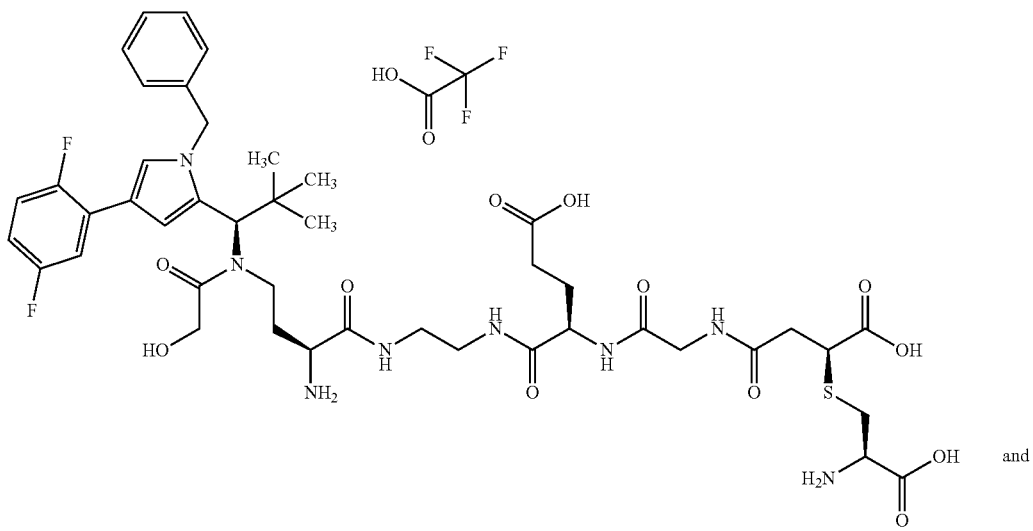

and

-continued

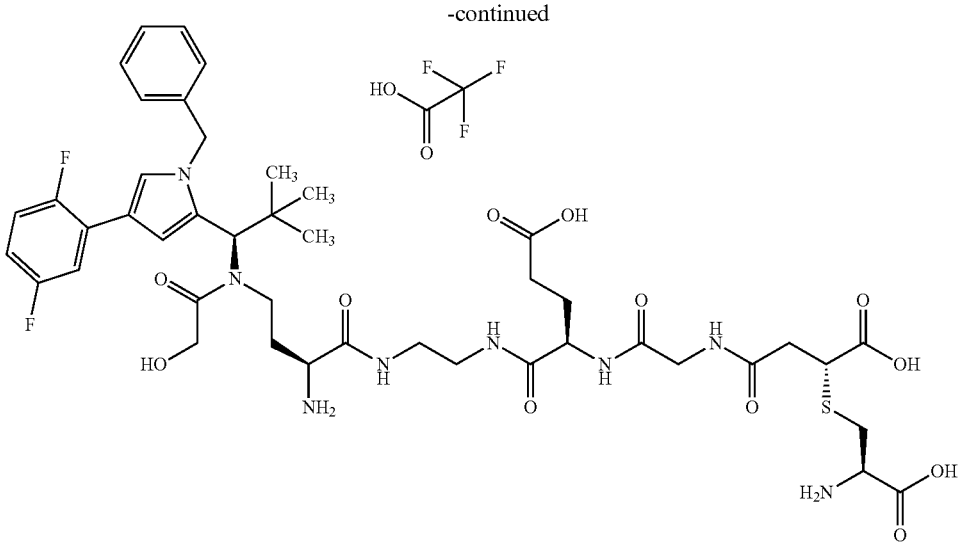

To a solution of methyl L-cysteinate hydrochloride (1:1) (5.00 g, 29.1 mmol) in 1,4-dioxane (200 ml) was added triethylamine (10 ml, 73 mmol) and then 1-({[2-(trimethylsilyl)ethoxy]-carbonyl}oxy)pyrrolidine-2,5-dione (8.31 g, 32.0 mmol). The reaction was stirred at room temperature for 20 h. Subsequently, the solids were filtered off and the filtrate was concentrated under high vacuum. The residue was purified via preparative HPLC.

To a solution of the resultant methyl N-{[2-(trimethylsilyl)ethoxy]carbonyl}-L-cysteinate (130 mg, 465 µmol) and 3-bromo-4-methoxy-4-oxobutanoic acid (393 mg, 1.86 mmol) in DMF (6.5 ml) were added 210 µl (1.4 mmol) of 1,8-diazabicyclo(5.4.0)undec-7-ene, and the reaction was stirred at room temperature for 10 min. Subsequently, the mixture was concentrated under reduced pressure and the residue was purified by preparative HPLC. The solvent was evaporated off under reduced pressure and the residue was dried under high vacuum.

This resultant intermediate was coupled by conventional methods of peptide chemistry to Intermediate C119 in the presence of HATU. Subsequently, the methyl ester was hydrolysed by treatment with a lithium hydroxide solution in THF/water (1:1).

In the last step, 22 mg of the intermediate obtained were dissolved in 10 ml of 2,2,2-trifluoroethanol. 34 mg (0.252 mmol) of zinc chloride were added and the mixture was stirred at 50° C. for 1 h. Subsequently, 74 mg (0.252 mmol) of ethylenediamine-N,N,N',N'-tetraacetic acid, 10 ml of water and 500 µl of TFA were added. The mixture was filtered and the solvent was evaporated under reduced pressure. The residue was purified by means of preparative HPLC. After concentration of the appropriate fractions and lyophilization of the residue from acetonitrile/water, 13 mg (72% of theory) of the title compound were obtained.

LC-MS (Method 5): $R_t$=2.44 min; MS (ESIneg): m/z=959 [M−H]⁻

Example M2

N-(2-{[(2R)-2-Amino-2-carboxyethyl]sulphanyl}-3-carboxypropanoyl)glycyl-N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-D-alpha-glutamine trifluoroacetic acid salt Regioisomer 2, Epimer Mixture

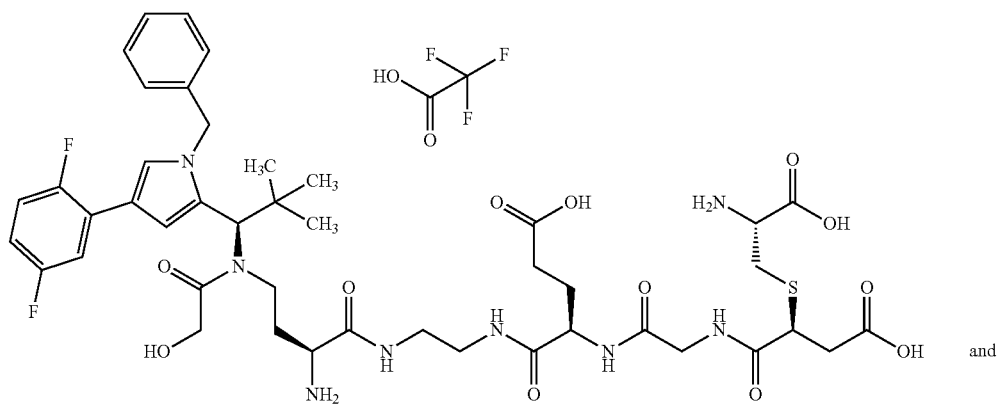

and

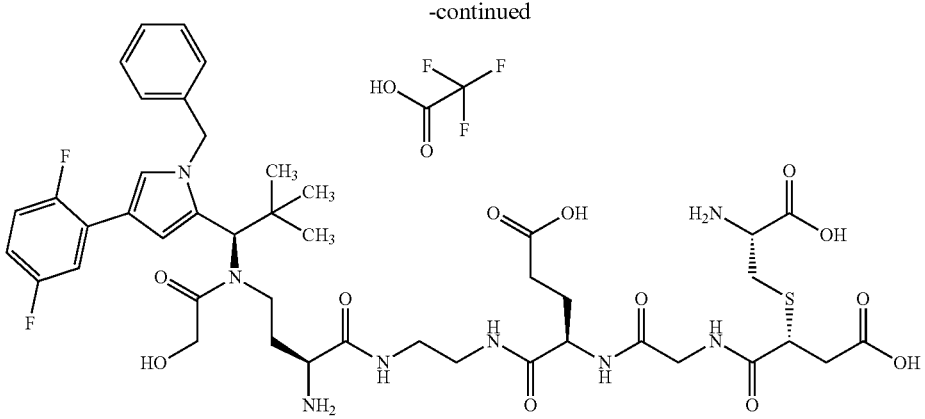

The title compounds M2 were prepared as an epimer mixture analogously to Example M1:

To a solution of methyl N-{[2-(trimethylsilyl)ethoxy]carbonyl}-L-cysteinate (1000 mg, 3.58 mmol) and 2-bromo-4-ethoxy-4-oxobutanoic acid (926 mg, 4.11 mmol) in DMF (40 ml) were added 801 µl (5.4 mmol) of 1,8-diazabicyclo(5.4.0)undec-7-ene, and the reaction was stirred at room temperature for 2 h. Subsequently, the mixture was concentrated under reduced pressure and the residue was purified by preparative HPLC.

The resultant intermediate was coupled by conventional methods of peptide chemistry to Intermediate C119 in the presence of HATU and methylmorpholine. Subsequently, the methyl ester and the ethyl ester were hydrolysed by treatment with a lithium hydroxide solution in THF/water (1:1).

In the last step, 48 mg of this intermediate were dissolved in 5 ml of 2,2,2-trifluoroethanol. 75 mg (0.550 mmol) of zinc chloride were added and the mixture was stirred at 50° C. for 3 h. Subsequently, 160 mg (0.550 mmol) of ethylenediamine-N,N,N',N'-tetraacetic acid, 2 ml of water and 20 µl of TFA were added. The solvent was concentrated under reduced pressure and the residue was purified by means of preparative HPLC. After concentration of the appropriate fractions and lyophilization of the residue from acetonitrile/water, 14 mg (39% of theory) of the title compound were obtained.

LC-MS (Method 5): $R_t$=2.41 min; MS (ESIneg): m/z=959 [M−H]⁻

Metabolite M3 which can be Formed, for Example, from Example 6, 7, 10, 12, 13, 14, 16 and 22

Example M3

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-D-glutamic acid

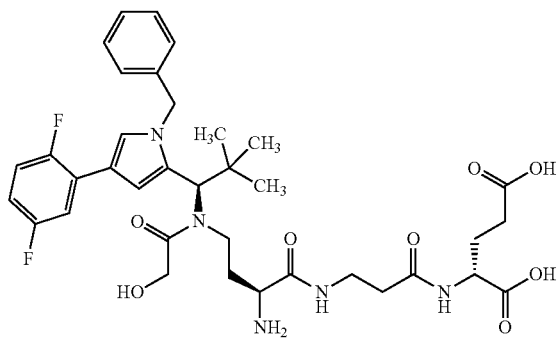 [SMILES: CC(C)(C)[C@H](c1cc(-c2cc(F)ccc2F)cn1Cc1ccccc1)N(CC[C@H](N)C(=O)NCCC(=O)N[C@H](CCC(=O)O)C(=O)O)C(=O)CO]

Intermediate C121 was converted to the title compound by hydrogenation over 10% palladium on activated carbon in ethanol under standard hydrogen pressure at RT for 1 hour.

LC-MS (Method 1): $R_t$=1.78 min; MS (ESIpos): m/z=714 [M+H]⁺.

Metabolite M4 which can be Formed, for Example, from Example 8

Example of Metabolite M4

N-(3-Aminopropyl)-N-{(1R)-1-[1-benzyl-4-(2,5-difluorophenyl)-1H-pyrrol-2-yl]-2,2-dimethylpropyl}-2-hydroxyacetamide

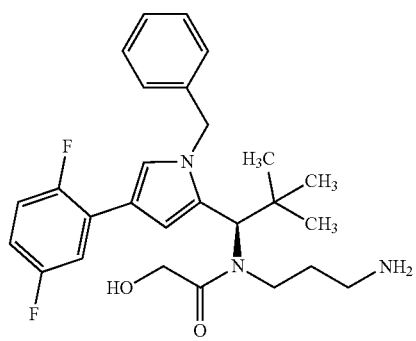 [SMILES: CC(C)(C)[C@H](c1cc(-c2cc(F)ccc2F)cn1Cc1ccccc1)N(CCCN)C(=O)CO]

The preparation and characterization of this metabolite M4 were described in WO2016/096610 as metabolite M9. This metabolite formed from the ADCs according to the invention in Example 8 shows a profile which differs from the other metabolites M1, M2 and M3 in terms of transporter substrate properties and cellular cytotoxicity.

Reference Examples: APDCs and Small Molecules

First of all, for comparative purposes, the APDC R1e and the ADC R6k were each prepared with tripeptide sequences as legumain substrate.

In addition, to examine the legumain-mediated cleavage, for comparative purposes, the legumain-cleavable prodrugs of small molecules RM-A and RM-B were prepared.

Reference Example R1e with TPP1015

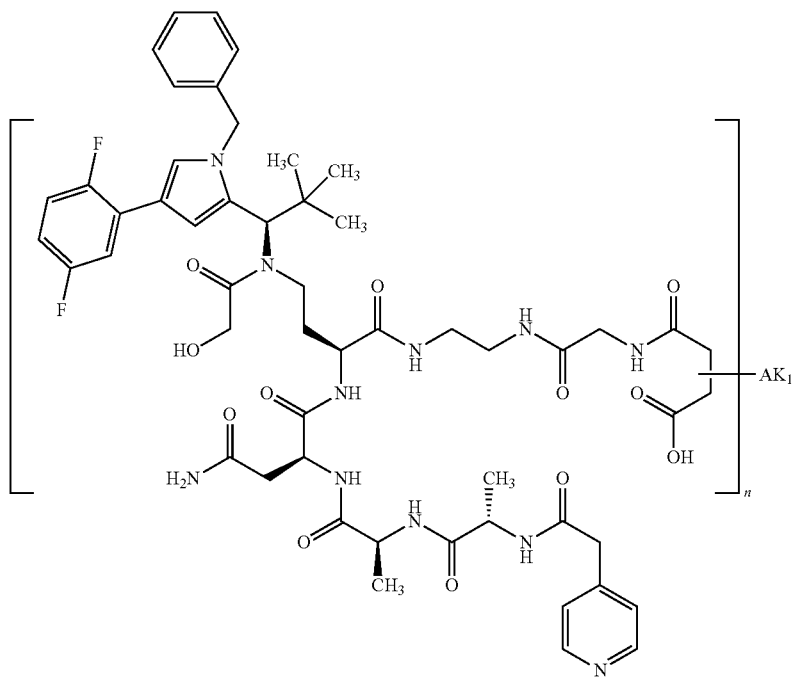

The preparation of the ADC with TPP1015 was effected analogously to Example 1.
Protein concentration: 1.7 mg/ml
Drug/mAb ratio: 3.3
The precursor was prepared analogously to Intermediate S1 by coupling Intermediate F104 with Intermediate L103 in the presence of HATU and N,N-diisopropylethylamine.

LC-MS (Method 1): $R_t$=0.83 min; MS (ESIpos): m/z=1068 (M+H)$^+$.

Reference Example R6k with TPP7007

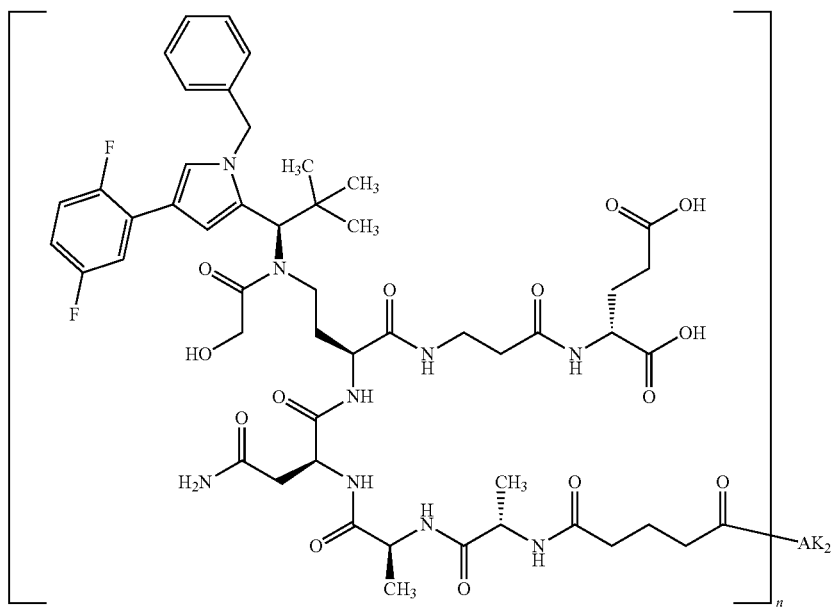

The ADC with TPP7007 was prepared in analogy to Example 6.

Protein concentration: 2.11 mg/ml
Drug/mAb ratio: 5.3

The precursor was prepared in analogy to Intermediate S6 proceeding from compound C121 by first coupling to 2,5-dioxopyrrolidin-1-yl N²-(tert-butoxycarbonyl)-L-aspartate in DMF in the presence of N,N-diisopropylethylamine. Then the Boc protecting group was detached by stirring with 6 equivalents of zinc chloride in trifluoroethanol at 50° C. for 1 h. In the next step, the resultant intermediate was coupled to N-(tert-butoxycarbonyl)-L-alanyl-L-alanine in DMF in the presence of HATU and N,N-diisopropylethylamine. Then the Boc protecting group was again detached by stirring at 50° C. with 6 equivalents of zinc chloride in trifluoroethanol for 2 h. In the next step, the benzyl ester was removed by hydrogenation over 10% palladium on activated carbon in ethanol under standard hydrogen pressure at RT, and the deprotected intermediate was then converted to the title compound by reaction with 1,1'-[(1,5-dioxopentane-1,5-diyl)bis(oxy)]dipyrrolidine-2,5-dione in the presence of N,N-diisopropylethylamine in DMF.

LC-MS (Method 1): $R_t$=0.90 min; MS (ESIpos): m/z=1181 [M+H]⁺.

RM-A (Model Compound A)

N-(Pyridin-4-ylacetyl)-L-alanyl-L-alanyl-N¹-[(2S)-4-[{(1R)-1-[1-benzyl-4-(2,5-difluorophenyl)-1H-pyrrol-2-yl]-2,2-dimethylpropyl}(glycoloyl)amino]-1-(methylamino)-1-oxobutan-2-yl]-L-aspartamide

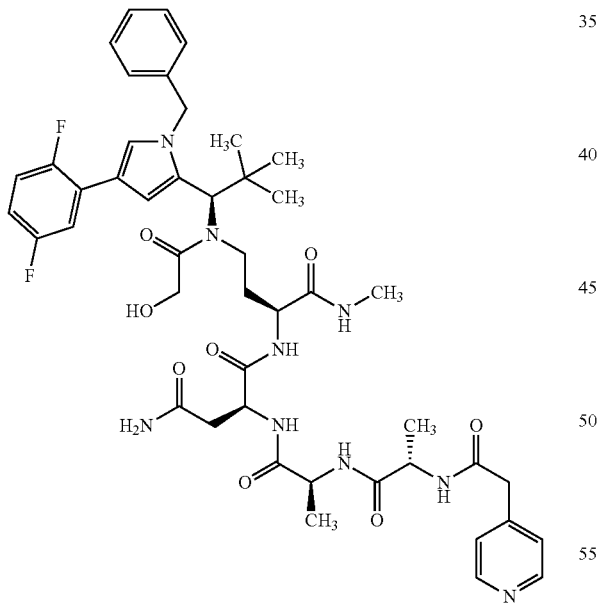

First of all, trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide (1:1) was prepared as described in WO 2015096982 A1 (Example 99). Subsequently, this intermediate was used to prepare the title compound by coupling to Intermediate L103 in DMF in the presence of HATU and of N,N-diisopropylethylamine.

LC-MS (Method 1): $R_t$=0.86 min; MS (ESIpos): m/z=902 [M+H]⁺.

RM-B (Model Compound B)

N¹-[(2S)-4-[{(1R)-1-[1-Benzyl-4-(2,5-difluorophenyl)-1H-pyrrol-2-yl]-2,2-dimethylpropyl}(glycoloyl)amino]-1-(methylamino)-1-oxobutan-2-yl]-N²-(pyridin-4-ylacetyl)-L-aspartamide

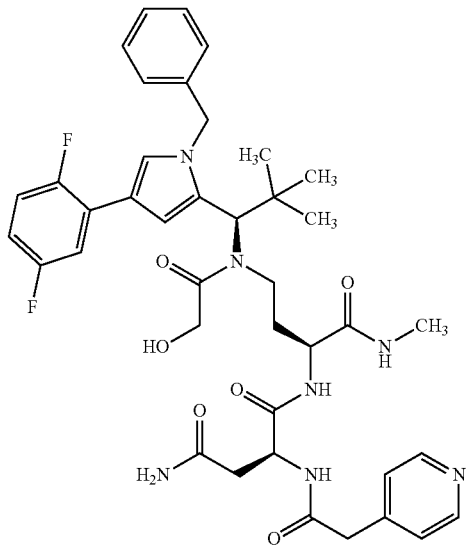 [SMILES: CNC(=O)[C@H](CCN(C(=O)CO)[C@@H](c1cc(-c2cc(F)ccc2F)cn1Cc1ccccc1)C(C)(C)C)NC(=O)[C@H](CC(N)=O)NC(=O)Cc1ccncc1]

First of all, trifluoroacetic acid (2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide (1:1) was prepared as described in WO 2015096982 A1 (Example 99). Subsequently, this intermediate was used to prepare the title compound by coupling to Intermediate L136 in DMF in the presence of HATU and of N,N-diisopropylethylamine.

LC-MS (Method 12): $R_t$=1.57 min; MS (ESIpos): m/z=760 [M+H]⁺.

RM-C (Model Compound C)

N¹-[(2S)-4-[{(1R)-1-[1-Benzyl-4-(2,5-difluorophenyl)-1H-pyrrol-2-yl]-2,2-dimethylpropyl}(glycoloyl)amino]-1-(methylamino)-1-oxobutan-2-yl]-N²-(pyridin-4-ylacetyl)-L-glutamide

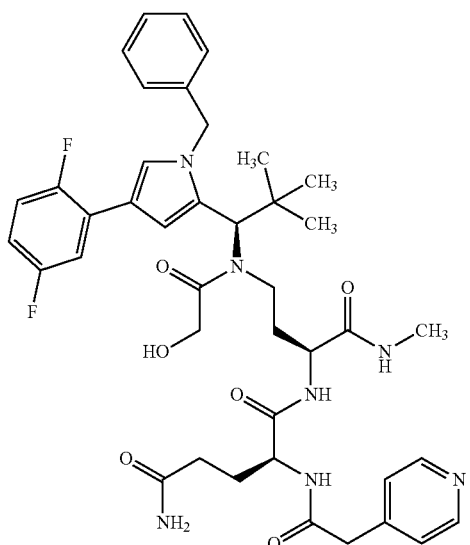

First of all, trifluoroacetic acid (2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide (1:1) was prepared as described in WO 2015096982 A1 (Example 99). Subsequently, this intermediate was used to prepare the title compound by coupling to Intermediate L137 in DMF in the presence of HATU and of N,N-diisopropylethylamine.

LC-MS (Method 12): $R_t$=1.56 min; MS (ESIpos): m/z=774 [M+H]$^+$.

C: Assessment of Biological Efficacy

The biological activity of the compounds according to the invention can be shown in the assays described below:

C-1a Determination of the Cytotoxic Effect of the ADCs

The analysis of the cytotoxic effects of the ADCs was carried out with various cell lines:

NCI-H292: human mucoepidermoid lung carcinoma cells, ATCC-CRL-1848, standard medium: RPMI 1640 (Biochrom; #FG1215, stab. glutamine)+10% FCS (Sigma; #F2442), TWEAKR-positive; EGFR-positive.

BxPC3: human pancreas carcinoma cells, ATCC-CRL-1687, standard medium: RPMI 1640 (Biochrom; #FG1215, stab. glutamine)+10% FCS (Sigma; #F2442), TWEAKR-positive.

LoVo human colorectal cancer cells, ATCC No. CCL-229, cultivation for MTT assay: standard medium: Kaighn's+L-glutamine (Invitrogen 21127)+10% heat inactivated FCS (from Gibco, No. 10500-064). Cultivation for CTG assay: RPMI 1640 (Biochrom; #FG1215, stab. glutamine)+10% FCS (Sigma #F2442). TWEAKR-positive.

KPL4: human breast cancer cell line, Bayer Pharma AG (identity checked and confirmed on 19 Jul. 2012 at DSMZ), standard medium: RPMI 1640 (from Gibco; #21875-059, stab. L-Glutamin)+10% heat inactivated FCS (from Gibco, No. 10500-064); HER2-positive.

SK-HEP-1: human liver cell cancer line, ATCC No. HTB-52, standard medium: MEM with Earle's salts+Glutamax I (Invitrogen 41090)+10% heat inactivated FCS (from Gibco, No. 10500-064); EGFR-positive, TWEAKR-positive.

KU-19-19: human bladder carcinoma cells, DMSZ, standard medium: RPMI 1640 (Biochrom; #FG1215, stab. glutamine)+10% FCS (Sigma; #F2442), TWEAKR-positive.

U251: human glioblastoma cells, standard medium: RPMI 1640 (Biochrom; #FG1215, stab. glutamine)+10% FCS (Biochrom; #S0415); B7H3-positive.

The cells were cultivated by the standard method as stated by the American Tissue Culture Collection (ATCC) or the Leibniz-Institut DSMZ-Deutsche Sammlung von Mikroorganismen und Zellkulturen GmbH (DSMZ) for the cell lines in question.

CTG Assay

The cells were cultivated by the standard method, with the growth media specified under C-1a. The test was carried out by detaching the cells with a solution of trypsin (0.05%) and EDTA (0.02%) in PBS (Biochrom AG #L2143), pelleting, resuspending in culture medium, counting and sowing into a 96-well culture plate with white bottom (Costar #3610) (at 75 μl/well, the following cell numbers per well are: NCI-H292: 2500 cells/well, BxPC3 2500 cells/well, LoVo 3000 cells/well) and incubating in an incubator at 37° C. and 5% carbon dioxide. After 24 h, the antibody drug conjugates were added in 25 μl of culture medium (concentrated four-fold) to the cells to give final antibody drug conjugate concentrations of $3\times10^{-7}$ M to $3\times10^{-1}$ M on the cells (triplicates). The cells were then incubated in an incubator at 37° C. and 5% carbon dioxide. On a parallel plate, the cell activity at the start of the drug treatment (day 0) was determined using the Cell Titer Glow (CTG) luminescent cell viability assay (Promega #G7573 and #G7571). To this end, per cell batch 100 μl of the substrate were added, the plates were then covered with aluminium foil, shaken on the plate shaker at 180 rpm for 2 minutes, allowed to stand on the laboratory bench for 8 minutes and then measured using a luminometer (Victor X2, Perkin Elmer). The substrate detects the ATP content in the living cells generating a luminescence signal whose intensity is directly proportional to the viability of the cells. After incubation with the antibody drug conjugates for 72 h, the viability of these cells was then also determined using the Cell Titer Glow luminescent cell viability assay as described above. From the data measured, the $IC_{50}$ of the growth inhibition was calculated in comparison to day 0 using the DRC (Dose Response Curve) analysis spreadsheets and a 4-parameter fit. The DRC analysis spreadsheet is a biobook spreadsheet developed by Bayer Pharma AG and Bayer Business Services on the IDBS E-WorkBook Suite platform (IDBS: ID Business Solutions Ltd., Guildford, UK).

MTT Assay

The cells were cultivated by the standard method, with the growth media specified under C-1a. The test was carried out by detaching the cells with a solution of Accutase in PBS (from Biochrom AG #L2143), pelletizing, resuspending in culture medium, counting and sowing into a 96-well culture plate with white bottom (from Costar #3610) (NCI H292: 2500 cells/well; SK-HEP-1: 1000 cells/well; KPL4: 1200 cells/well; in total volume 100 μl). The cells were then incubated in an incubator at 37° C. and 5% carbon dioxide. After 48 h, the medium was replaced. The antibody drug conjugates in 10 μl of culture medium in concentrations from $10^{-5}$M to $10^{-13}$M were then pipetted to the cells (in triplicate), and the assay was then incubated in an incubator at 37° C. and 5% carbon dioxide. After 96 h, the cell proliferation was detected using the MTT assay (ATCC, Manassas, Virginia, USA, catalogue No. 30-1010K). To this end, the MTT reagent was incubated with the cells for 4 h, followed by lysis of the cells overnight by addition of the detergent. The dye formed was detected at 570 nm (Infinite M1000 pro, Tecan). The measured data were used to calculate the $IC_{50}$ of the growth inhibition using the DRC (dose response curve). The proliferation of cells which were not treated with test substance but were otherwise identically treated was defined as the 100% figure.

The table below lists the $IC_{50}$ values for representative working examples from these assays:

TABLE 1a

| Example | NCI-H292 $IC_{50}$ [M] MTT/CTG | LoVo $IC_{50}$ [M] CTG | SKHep-1 $IC_{50}$ [M] MTT | BxPC3 $IC_{50}$ [M] CTG | KPL-4 $IC_{50}$ [M] [MTT] |
|---|---|---|---|---|---|
| 1a-981 | 4.08E−11 | | 5.29E−08 | | |
| 1e-1015 | | | | | 1.42E−10 |
| 1k-7007 | 2.96E−10 | 4.14E−11 | | 4.76E−10 | |
| 2a-981 | 7.96E−12 | | 3.30E−07 | | |
| 2e-1015 | | | | | 8.03E−11 |
| 2k-7007 | 2.48E−10 | 1.50E−11 | | 5.75E−10 | |
| 2k*-7007 | 3.99E−10 | 1.50E−11 | | 4.07E−10 | |
| 3a-981 | 9.73E−10 | | 1.69E−07 | | |
| 3e-1015 | | | | | 4.50E−10 |
| 3k-2658 | 2.44E−08 | 4.78E−10 | | 4.62E−09 | |
| 4a-981 | 1.56E−11 | | 3.18E−07 | | |

TABLE 1a-continued

| Example | NCI-H292 IC$_{50}$ [M] MTT/CTG | LoVo IC$_{50}$ [M] CTG | SKHep-1 IC$_{50}$ [M] MTT | BxPC3 IC$_{50}$ [M] CTG | KPL-4 IC$_{50}$ [M] [MTT] |
|---|---|---|---|---|---|
| 4e-1015 | | | | | 2.93E−10 |
| 4k-7007 | 3.71E−10 | 8.11E−11 | | 7.14E−10 | |
| 5a-981 | 2.63E−12 | | 5.60E−08 | | |
| 5e-1015 | | | | | 1.43E−10 |
| 5k-7007 | 2.68E−10 | 6.21E−11 | | 5.55E−10 | |
| 6a-981 | 1.00E−11 | | 5.00E−07 | | |
| 6e-1015 | | | | | 1.91E−10 |
| 6k-7007 | 7.60E−11 | 1.50E−11 | | 9.67E−11 | |
| 7a-981 | 4.29E−12 | | 1.22E−07 | | |
| 7e-1015 | | | | | 1.82E−10 |
| 7k-7007 | 2.09E−10 | 4.81E−11 | | 2.27E−10 | |
| 8a-981 | 4.50E−10 | | 4.25E−09 | | |
| 8e-1015 | | | | | 3.84E−09 |
| 8k-7007 | 5.68E−10 | 2.18E−09 | | 7.68E−10 | |
| 9a-981 | 4.50E−12 | | 4.34E−09 | | |
| 9e-1015 | | | | | 1.31E−10 |
| 9k-7007 | 2.80E−10 | 3.32E−11 | | 6.06E−10 | |
| 10a-981 | 5.15E−12 | | 8.42E−09 | | |
| 10e-1015 | | | | | 2.54E−12 |
| 10k-7007 | 1.83E−10 | 3.29E−11 | | 2.25E−10 | |
| 11a-981 | 3.25E−11 | | 8.38E−09 | | |
| 11e-1015 | | | | | 4.97E−10 |
| 11k-7007 | 9.95E−10 | 8.07E−11 | | 3.68E−09 | |
| 12a-981 | 2.50E−11 | | 2.62E−08 | | |
| 12e-1015 | | | | | 7.66E−10 |
| 12k-7007 | 7.38E−10 | 6.14E−11 | | 3.81E−10 | |
| 13a-981 | 3.71E−11 | | | | |
| 13e-1015 | | | | | 7.72E−11 |
| 13k-7007 | 2.07E−10 | 5.31E−11 | | 2.61E−10 | |
| 14a-981 | 7.81E−10 | | | | |
| 14e-1015 | | | | | 4.32E−11 |
| 14k-7007 | 6.13E−11 | 1.5E−11 | | 8.67E−11 | |
| 15a-981 | 4.13E−10 | | | | |
| 15e-1015 | | | | | 7.91E−10 |
| 15k-7007 | 9.97E−09 | 6.00E−07 | | 7.47E−09 | |
| 16e-1015 | | | | | 2.01E−11 |
| 16k-7007 | 5.45E−11 | 1.50E−11 | | 4.00E−11 | |
| 17a-981 | 1.40E−12 | | 3.16E−11 | | |
| 17e-1015 | | | | | 2.99E−11 |
| 17k-7007 | 8.95E−10 | 2.36E−10 | | 8.96E−10 | |
| 18a-981 | 1.00E−12 | | 6.01E−11 | | |
| 18e-1015 | | | | | 2.07E−11 |
| 18k-7007 | 1.62E−10 | 6.00E−07 | | 2.55E−10 | |
| 19e-1015 | | | | | 3.48E−11 |
| 19k-7007 | 1.20E−10 | 1.50E−11 | | 1.37E−10 | |
| 20e-1015 | | | | | 1.17E−11 |
| 20k-7007 | 1.54E−10 | 1.52E−10 | | 1.91E−10 | |
| 21e-1015 | | | | | 3.66E−11 |
| 21k-7007 | 3.14E−10 | 1.08E−09 | | 3.60E−10 | |
| 22e-1015 | | | | | 6.13E−11 |
| 22k-7007 | 8.26E−11 | 1.50E−11 | | 9.41E−11 | |

Table 1b below lists the IC$_{50}$ values for reference examples from these assays:

TABLE 1b

| Example | NCI-H292 IC$_{50}$ [M] MTT | LoVo IC$_{50}$ [M] CTG | BxPC3 IC$_{50}$ [M] CTG | KPL-4 IC$_{50}$ [M] [MTT] |
|---|---|---|---|---|
| R1e | | | | 9.37E−11 |
| R6k | 5.49E−11 | 1.50E−11 | 9.80E−11 | |

The activity data reported relate to the working examples described in the present experimental section, with the drug/mAB ratios indicated. The values may possibly deviate for different drug/mAB ratios. The IC50 values are means of several independent experiments or individual values. The action of the antibody drug conjugates was selective for the respective isotype control comprising the respective linker and toxophore.

C-1b Determination of the Inhibition of the Kinesin Spindle Protein KSP/Eg5 by the Active Metabolites Formed from Selected Examples The motor domain of the human kinesin spindle protein KSP/Eg5 (tebu-bio/Cytoskeleton Inc, No. 027EG01-XL) was incubated in a concentration of 10 nM with microtubuli (bovine or porcine, tebu-bio/Cytoskeleton Inc) stabilized with 50 μg/ml taxol (Sigma No. T7191-5MG) for 5 min at RT in 15 mM PIPES, pH 6.8 (5 mM MgCl$_2$ and 10 mM DTT, Sigma). The freshly prepared mixture was aliquoted into a 384 MTP (from Corning). The inhibitors to be examined at concentrations of $1.0 \times 10^{-6}$ M to $1.0 \times 10^{-13}$ M and ATP (final concentration 500 μM, Sigma) were then added. Incubation was at RT for 2 h. ATPase activity was detected by detecting the inorganic phosphate formed using malachite green (Biomol). After addition of the reagent, the assay was incubated at RT for 50 min prior to detection of the absorption at a wavelength of 620 nm. The positive controls used were monastrol (Sigma, M8515-1 mg) and ispinesib (AdooQ Bioscience A10486). The individual data of the dose-activity curve are eight-fold determinations. The IC$_{50}$ values are means of two independent experiments. The 100% control was the sample which had not been treated with inhibitors.

Table 2 below lists the IC$_{50}$ values of the active metabolites formed from the representative working examples from the assay described and summarizes the corresponding cytotoxicity data (MTT assay):

TABLE 2

| Examples | KSP assay IC$_{50}$ [M] | NCI-H292 IC$_{50}$ [M] MTT | SK-Hep-1 IC$_{50}$ [M] MTT | KPL4 IC$_{50}$ [M] MTT |
|---|---|---|---|---|
| M1 | 2.13E−09 | 5.00E−07 | 9.88E−08 | 5.00E−07 |
| M2 | 4.67E−10 | | | |
| M3 | 1.59E−09 | 1.74E−07 | 1.46E−08 | 1.73E−07 |
| M4 | 1.80E−09 | 9.24E−10 | | 5.14E−10 |

The activity data reported relate to the working examples described in the present experimental section.

C-1c Enzymatic Assays and Stability Studies

First, the cleavage of the small molecule prodrugs RM-A and RM-B was tested under various conditions:

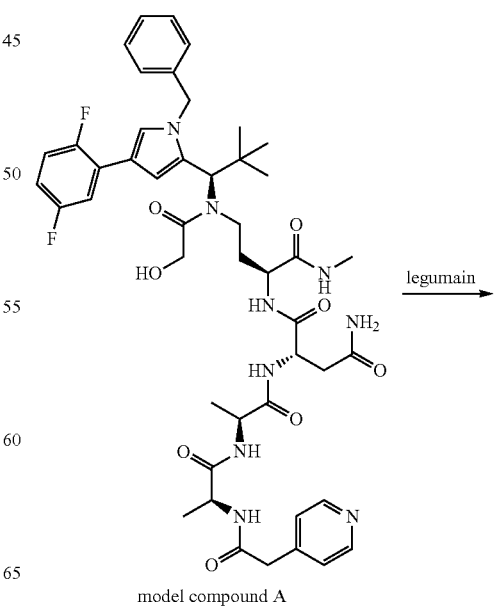

model compound A

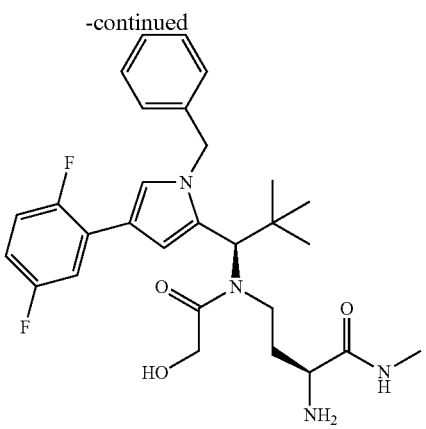

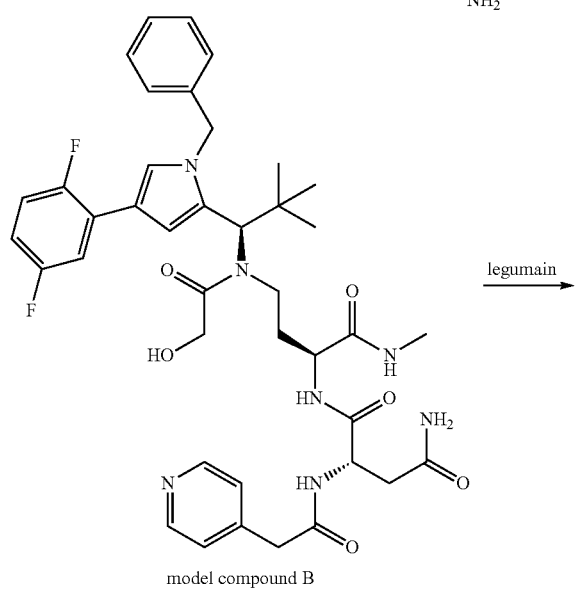

model compound B a: Legumain Assay

The legumain assay was conducted with recombinant human enzyme. The rh legumain enzyme solution (catalogue #2199-CY, R&D Systems) was diluted to the desired concentration in 50 mM Na acetate buffer/100 mM NaCl, pH4.0 and preincubated at 37° C. for 2 h. rh legumain was then adjusted to a final concentration of 1 ng/µl in 50 mM MES buffer, 250 mM NaCl, pH 5.0. For every legumain-cleavable prodrug to be examined, a mixture was made up in a micro reaction vessel (0.5 ml, from Eppendorf). For this purpose, the substrate solution was adjusted to the desired concentration (double concentration) with 50 mM MES buffer, 250 mM NaCl, pH 5.0. For the kinetic measurement of the enzymatic reaction, 250 µl of the legumain solution were first initially charged and the enzyme reaction was started by adding 250 µl of the substrate solution (final concentration: single concentration). At different times, 50 µl samples were taken. This sample was admixed immediately with 100 µl of ice-cold methanol in order to stop the enzymatic reaction and then frozen at −20° C. The times selected for sampling were after 0.5 h, 1 h, 3 h and 24 h. The samples were then analysed by means of RP-HPLC analysis and by LC-MS analysis. The determination of the toxophore released enabled the determination of the half-life $t_{1/2}$ of the enzymatic reaction (FIG. 1).

Model compound A (RM-A) was cleaved under the above-described conditions of the legumain assay to the target compound with a half-life of 0.2 h.

Model compound B (RM-B) was cleaved under the above-described conditions of the legumain assay to the target compound with a half-life of about 10 h.

Model compound C (RM-C) was not cleaved to the target compound under the above-described conditions of the legumain assay.

b: Assay for Determination of Stability in Rat Plasma

To examine the stability of compounds A and B, 1 ml of rat plasma in a 1.5 ml Eppendorf tube in each case was equilibrated to 37° C. on an Eppendorf shaker. A stock solution (9 acetonitrile/1 DMSO) having a concentration of 100 µg/ml for compound A and compound B was prepared. 10 µl in each case of the stock solution were pipetted into 1 ml of equilibrated rat plasma, so as to give a concentration of 1 µg/ml.

The samples were kept at 450 rpm and 37° C. for 24 h. At each of the sampling times of 0, 0.25 h, 0.5 h, 1 h, 2 h, 4 h, 6 h and 24 h, 50 µl were taken and pipetted into 150 µl of methanol. Internal standard was included in the initial charge of methanol at a concentration of 0.05 µg/ml. After brief vortexing, 300 µl of 10 mM ammonium acetate buffer (pH 6.8) were added and centrifuged at 1881 g for 10 min. The samples were then analysed by means of RP-HPLC analysis and by LC-MS analysis.

c: Assay for Determination of Stability in Rat Liver Lysosomes

To determine the lysosomal stability of compounds RM-A and RM-B, lysosomal enzymes were isolated from rat liver cells. Compounds A and B were each added to this lysosomal extract in order to examine stability under lysosomal conditions. The proteolytic enzyme legumain is expressed only in a very small amount, if any, in rat liver lysosomes (Chen, J-M. et al 1997). To monitor the enzymatic activity of the lysosomal enzymes, a cathepsin-specific substrate was added.

First of all, a fresh rat liver was removed, weighed and immediately placed on ice in homogenization medium (0.25 M sucrose, 1 mM EDTA, 10 mM HEPES, pH7). The liver was comminuted and a change of medium was undertaken. The rat livers were homogenized with 4 times the amount of the rat liver weight at 750 rpm in a Potter (B. Braun). The homogenate was centrifuged at 1000 g for 10 min and the supernatant was filtered. In the next step, with the aid of an ultracentrifuge, the "light mitochondrial fraction" (LMF) was centrifuged out of the supernatant at 26 500 g over 20 min. Also present in the pellet apart from mitochondria are the lysosomes. The supernatant was discarded and the pellet was resuspended with 0.8 ml/g of homogenization medium.

In order to separate the lysosomal fraction from the other cell constituents of the LMF, 6 Optiprep density gradients were prepared with a sucrose content of 8%, 12%, 16%, 19%, 22.5% and 27% in the Optiprep buffer (100 mM MOPS, 20 mM EDTA, 0.5% EtOH, pH 7.6). The sucrose was added from a 2.3 M stock solution of the particular percentage. 2.5 ml of isolated LMF were additionally added to the density stage with a sucrose content of 19%. Subsequently, the density stages were layered one on top of another in 10 ml centrifuge tubes and centrifuged at 48 500 g for 17 h. Fractions 1-8 are in the upper 5.6 ml of the gradient and were discarded. Fractions 9 and 10 are in the 1.6 ml beneath and were removed from the gradient and lysed with 1.6 ml of lysis buffer (25 mM HEPES, 150 mM NaCl, 0.1% Triton X100, pH 5) on ice for 5 min. The lysosomes are present in fractions 9 and 10. To monitor the lysis, the protein content of the lysed lysosomal fraction was monitored with the aid of a BCA assays (Pierce BCA protein assay kit).

To examine the lysosomal stability of compounds RM-A and RM-B, 6 µl of a 100 µg/ml stock solution (9 acetonitrile/1 DMSO) were added to 290 µl of 90 mM citrate buffer and 300 µl of lysosomal extract and incubated at 37° C. on an Eppendorf shaker. 50 µl each time were taken from the incubation solution after 0 h, 1 h, 2 h, 6 h, 24 h and 48 h and pipetted into 150 µl of MeOH. Internal standard was included in the initial charge at 0.05 µg/ml. For the RP-HPLC LCMS analysis, the samples were diluted with 300 µl of 10 mM ammonium acetate buffer (pH 6.8) and analysed.

Under the conditions of the lysosomal stability assay, compound A (Reference Example RM-A) was cleaved to an extent of about 80% with a half-life of about 6 h within 24 h, while compound B (Reference Example RM-B) is cleaved to an extent of only 13% over the same period. RM-B is thus markedly more stable than RM-A in the lysosomal stability assay, which means that a reduced degree of formation of active metabolites in the healthy liver can be assumed.

C-2 Internalization Assay

Internalization is a key process which enables specific and efficient provision of the cytotoxic payload in antigen-expressing cancer cells via antibody drug conjugates (ADC). This process is monitored via fluorescent labelling of specific antibodies and an isotype control antibody. First, the fluorescent dye was conjugated to lysines of the antibody. Conjugation was carried out using a two-fold molar excess of CypHer 5E mono NHS ester (Batch 357392, GE Healthcare) at pH 8.3. After the coupling, the reaction mixture was purified by gel chromatography (Zeba Spin Desalting Columns, 40K, Thermo Scientific, No. 87768; elution buffer: DULBECCO'S PBS, Sigma-Aldrich, No. D8537), to eliminate excess dye and to adjust the pH. The protein solution was concentrated using VIVASPIN 500 columns (Sartorius stedim biotec). The dye load of the antibody was determined by spectrophotometric analysis (NanoDrop) and subsequent calculation $$(D:P = A_{dye} \varepsilon_{protein} : (A_{280} - 0.16 A_{dye}) \varepsilon_{dye}).$$

The dye load of the antibodies examined here and the isotype control were of a comparable order of magnitude. In cell binding assays, it was confirmed that the coupling did not lead to any change in the affinity of the antibodies.

The labelled antibodies were used for the internalization assay. Prior to the start of the treatment, cells ($2 \times 10^4$/well) were sown in 100 µl medium in a 96-well MTP (fat, black, clear bottom No 4308776, from Applied Biosystems). After 18 h of incubation at 37° C./5% $CO_2$, the medium was replaced and labelled antibodies were added in different concentrations (10, 5, 2.5, 1, 0.1 µg/ml). The same treatment protocol was applied to the labelled isotype control (negative control). The chosen incubation times were 0 h, 0.25 h, 0.5 h, 1 h, 1.5 h, 2 h, 3 h, 6 h and 24 h. The fluorescence measurement was carried out using the InCellAnalyzer 1000 (from GE Healthcare). This was followed by kinetic evaluation via measurement of the parameters granule counts/cell and total granule intensity/cell.

Following binding to the receptor, antibodies were examined for their internalization capacity. For this purpose, cells with different receptor expression levels were chosen. A target-mediated specific internalization was observed with the antibodies described in the context of the invention, whereas the isotype control showed no internalization.

C-3 In Vitro Tests for Determining Cell Permeability

The cell permeability of a substance can be investigated by means of in vitro testing in a flux assay using Caco-2 cells [M. D. Troutman and D. R. Thakker, Pharm. Res. 20 (8), 1210-1224 (2003)]. For this purpose, the cells were cultured for 15-16 days on 24-well filter plates. For the determination of permeation, the respective test substance was applied in a HEPES buffer to the cells either apically (A) or basally (B) and incubated for 2 hours. After 0 hours and after 2 hours, samples were taken from the cis and trans compartments. The samples were separated by HPLC (Agilent 1200, Böblingen, Germany) using reverse phase columns. The HPLC system was coupled via a Turbo Ion Spray Interface to a Triple Quadropol mass spectrometer API 4000 (AB SCIEX Deutschland GmbH, Darmstadt, Germany). The permeability was evaluated on the basis of a $P_{app}$ value, which was calculated using the formula published by Schwab et al. [D. Schwab et al., J. Med. Chem. 46, 1716-1725 (2003)]. A substance was classified as actively transported when the ratio of $P_{app}$ (B-A) to $P_{app}$ (A-B) (efflux ratio) was >2 or ≤0.5.

Of critical importance for toxophors which are released intracellularly is the permeability from B to A [$P_{app}$ (B-A)] and the ratio of $P_{app}$ (B-A) to $P_{app}$ (A-B) (efflux ratio): the lower this permeability, the slower the active and passive transport processes of the substance through the monolayer of Caco-2 cells. If additionally the efflux ratio does not indicate any active transport, the substance may, following intracellular release, remain longer in the cell. Hence, there is also more time available for interaction with the biochemical target (in this case: kinesin spindle protein, KSP/Eg5).

Table 4 below sets out permeability data for representative working examples from this assay:

TABLE 4

| Working Example | $P_{app}$ (B-A) [nm/s] | Efflux ratio |
|---|---|---|
| M1 | 1.2 | 0.8 |
| M2 | 1.1 | 1.6 |
| M3 | 2.7 | 1.6 |
| M4 | 213 | 16 |

The metabolites M1, M2 and M3 which were formed from the ADCs according to the invention from various examples show both a very low level of transport from the cell and a low efflux ratio. The metabolite M4, by way of example, shows a different profile.

C-4 In Vitro Tests for Determining the Substrate Properties for P-Glycoprotein (P-gp)

Many tumour cells express transporter proteins for drugs, and this frequently accompanies the development of resistance towards cytostatics. Substances which are not substrates of such transporter proteins, such as P-glycoprotein (P-gp) or BCRP, for example, could therefore exhibit an improved activity profile.

The substrate properties of a substance for P-gp (ABCB1) were determined by means of a flux assay using LLC-PK1 cells which overexpress P-gp (L-MDR1 cells) [A. H. Schinkel et al., *J. Clin. Invest.* 96, 1698-1705 (1995)]. For this purpose, the LLC-PK1 cells or L-MDR1 cells were cultured on 96-well filter plates for 3-4 days. For determination of the permeation, the respective test substance, alone or in the presence of an inhibitor (such as ivermectin or verapamil, for example), was applied in a HEPES buffer to the cells either apically (A) or basally (B) and incubated for 2 hours. After 0 hours and after 2 hours, samples were taken from the cis and trans compartments. The samples were separated by HPLC using reverse phase columns. The HPLC system was coupled via a Turbo Ion Spray Interface to an API 4000 triple quadropole mass spectrometer (Applied Biosystems Applera, Darmstadt, Germany). The permeability was evaluated on the basis of a $P_{app}$ value, which was calculated using the formula published by Schwab et al. [D. Schwab et al., *J. Med. Chem.* 46, 1716-1725 (2003)]. A substance was classified as P-gp substrate when the efflux ratio of $P_{app}$ (B-A) to $P_{app}$ (A-B) was >2.

As further criteria for the evaluation of the P-gp substrate properties, the efflux ratios in L-MDR1 and LLC-PK1 cells or the efflux ratio in the presence or absence of an inhibitor may be compared. If these values differ by a factor of more than 2, the substance in question is a P-gp substrate.

C-5 Pharmacokinetics

C5a: Identification of the ADC Metabolites after Internalization In Vitro

Description of the Method:

Internalization studies with immunoconjugates are carried out to analyse metabolites formed intracellularly. To this end, human lung tumour cells NCI H292 ($3 \times 10^5$/well) are sown in 6-well plates and incubated overnight (37° C., 5% $CO_2$). The cells are treated with 10 µg/ml (66 nM) of the ADC to be examined. Internalization was carried out at 37° C. and 5% $CO_2$. Cell samples are taken for further analysis at various times (0, 4, 24, 48, 72 h). First of all, the supernatants (about 5 ml) are harvested and, after centrifugation (2 min, RT, 1000 rpm Heraeus Variofuge 3.0R), stored at −80° C. The cells are washed with PBS and detached with Accutase, and the cell number is determined. After another washing, a defined number of cells ($2 \times 10^5$) is treated with 100 ml of lysis buffer (Mammalian Cell Lysis Kit (Sigma MCL1) and incubated with continuous shaking (Thermomixer, 15 min, 4° C., 650 rpm) in Protein LoBind tubes (Eppendorf Cat. No. 0030 108.116). After the incubation, the lysate is centrifuged (10 min, 4° C., 12000 g, eppendorf 5415R) and the supernatant is harvested. The supernatant obtained is stored at −80° C. All samples are then analysed as follows.

Measurement of the compounds in the culture supernatant or cell lysate is carried out after precipitation of the proteins with methanol or acetonitrile by high-pressure liquid chromatography (HPLC) coupled to a triple-quadrupole mass spectrometer (MS).

For workup of 50 µl of culture supernatant/cell lysate, 150 µl of precipitation reagent (methanol) are added and the mixture is shaken for 10 seconds. The precipitation reagent contains an internal standard (ISTD) in a suitable concentration (generally in the range of 20-100 µg/l). After centrifugation at 1881 g for 10 minutes, the supernatant is transferred into an autosampler vial, made up with 300 µl of a buffer matched to the eluent and shaken again and centrifuged at 1881 g for 10 min.

The cell lysate and supernatant samples are finally analysed using the HPLC-coupled API4500 triple-quadrupole mass spectrometer from AB SCIEX Deutschland GmbH.

For calibration, blank lysate or blank supernatant is admixed with appropriate concentrations (0.1-1000 µg/l). The detection limit (LLOQ) is about 0.2 µg/l.

Quality controls for testing validity contain 4 and 40 µg/l.

C5b: Identification of the ADC Metabolites In Vivo

After i.v. administration of 10 mg/kg of various conjugates according to the invention in xenograft mice, 24 h after administration of these conjugates, it is possible to measure the plasma, tumour, liver and kidney concentrations of the antibody and potential metabolites. Under C-6 there is a more specific description of the method with regard to the xenograft model. All that are to be addressed here are the metabolite concentrations of the conjugates according to the invention. The measurements for the metabolites in the matrices mentioned additionally give information as to the extent of the metabolite load in the plasma, kidney and liver compared to the load in the tumour.

Analysis for Quantification of the Potential Metabolites

The analysis of the compounds in the plasma, tumour, liver and kidney follows after precipitation of the proteins with generally methanol by high-pressure liquid chromatography (HPLC) coupled to a triple-quadrupole mass spectrometer (MS).

For workup of 50 µl of plasma, 150 µl of precipitation reagent (generally methanol) are added and the mixture is shaken for 10 sec. The precipitation reagent contains an internal standard (ISTD) in a suitable concentration (generally in the range of 20-100 µg/l). After centrifugation at 1881 g for 10 minutes, the supernatant is transferred into an autosampler vial, made up with 300 µl of a buffer matched to the eluent and shaken again.

In the workup of tumour or organ material, the particular material is admixed with 3-20 times the amount of extraction buffer. The extraction buffer contains 50 ml of Tissue Protein Extraction Reagent (Pierce, Rockford, IL), two pellets of Complete-Protease-Inhibitor-Cocktail (Roche Diagnostics GmbH, Mannheim, Germany) and phenylmethylsulphonyl fluoride (Sigma, St. Louis, MO) in a final concentration of 1 mM. According to the tissue type (hard: tumour; soft: liver, kidney), the lysis and homogenization programme of the Prescellys 24 lysis and homogenization system (Bertin Technologies) is selected (www.prescellys-.com). The homogenized samples are left to stand at 4° C. overnight. 50 µl of the homogenizate are transferred into an autosampler vial and made up with 150 µl of methanol including ISTD, agitated for 10 sec and then left to stand for 5 min. After adding 300 µl of ammonium acetate buffer (pH 6.8) and agitating briefly, the sample is centrifuged at 1881 g for 10 minutes.

For calibration, plasma for plasma samples and corresponding blank matrix for tissue samples is admixed with concentrations of 0.6-1000 µg/l. According to the sample type or tissue type, the detection limit (LOQ) is between 1 and 20 µg/l.

The plasma and matrix samples are finally analysed using the HPLC-coupled API6500 triple-quadrupole mass spectrometer from AB SCIEX Deutschland GmbH.

Quality controls for testing validity contain 4, 40 and 400 µg/l.

C-6 Activity Test In Vivo

The activity of the conjugates according to the invention was tested, for example, using xenograft models. The person skilled in the art is familiar with methods in the prior art which allow the activity of the compounds according to the invention to be tested (see, for example, WO 2005/081711; Polson et al., Cancer Res. 2009 Mar. 15; 69(6):2358-64). To this end, a tumour cell line expressing the target molecule of the binder was implanted into rodents (for example mice). A conjugate according to the invention, an isotype antibody control conjugate, a control antibody or isotonic saline was then administered to the implant animals. The administration took place once or more than once. Following an incubation time of several days, the size of the tumour was determined by comparing conjugate-treated animals and the control group. The conjugate-treated animals displayed a smaller tumour size.

C-6a. Growth Inhibition/Regression of Experimental Tumours in the Mouse

Human tumour cells which express the antigen for the antibody-drug conjugate are inoculated subcutaneously into the flank of immunosuppressed mice, for example NMRi nude or SCID mice. 1-10 million cells are detached from the cell culture, centrifuged and resuspended in medium or medium/matrigel. The cell suspension is injected under the skin of the mouse.

Within a few days, a tumour grows. Treatment is commenced after the tumour is established, at a tumour size of approximately 40 mm². To examine the effect on larger tumours, treatment may be initiated only at a tumour size of 50-100 mm².

Treatment with APDCs and ADCs is carried out via the intravenous (i.v.) route into the tail vein of the mouse. The ADC is administered in a volume of 5 ml/kg.

The treatment protocol depends on the pharmacokinetics of the antibody. As standard, treatment takes place three times in succession every fourth day. In the case of slow-growing tumours, weekly treatment is an option. For a quick assessment, a protocol with a single treatment may be employed. However, the treatment may also be continued, or a second cycle of three treatment days may follow at a later time.

As standard, 8 animals are used per treatment group. In addition to the groups to which the active substances are administered, one group is treated as control group only with the buffer, according to the same protocol.

During the experiment, the tumour area is measured regularly in two dimensions (length/width) using a caliper. The tumour area is determined as length×width. The ratio of the mean tumour area of the treatment group to that of the control group is stated as T/C area.

When, after the end of the treatment, all groups of the experiment are terminated at the same time, the tumours can be removed and weighed. The ratio of the mean tumour weights of the treatment group to that of the control group is stated as T/C weight. C-6b. Efficacy of the Anti-TWEAKR APDCs in Various Xenograft Models The tumour cells (e.g. KU-19-19, NCI-H292, SCC4) are inoculated subcutaneously into the flank of female NMRI-nude or NOD.SCID mice (Janvier). At a tumour size of ~40 mm², intravenous treatment is effected with the antibody-drug conjugate. After the treatment, monitoring of the tumour growth continues if appropriate.

The invention claimed is:

1. A compound, or a salt, a solvate, or a salt of a solvate thereof, wherein the compound has one of the following structures:

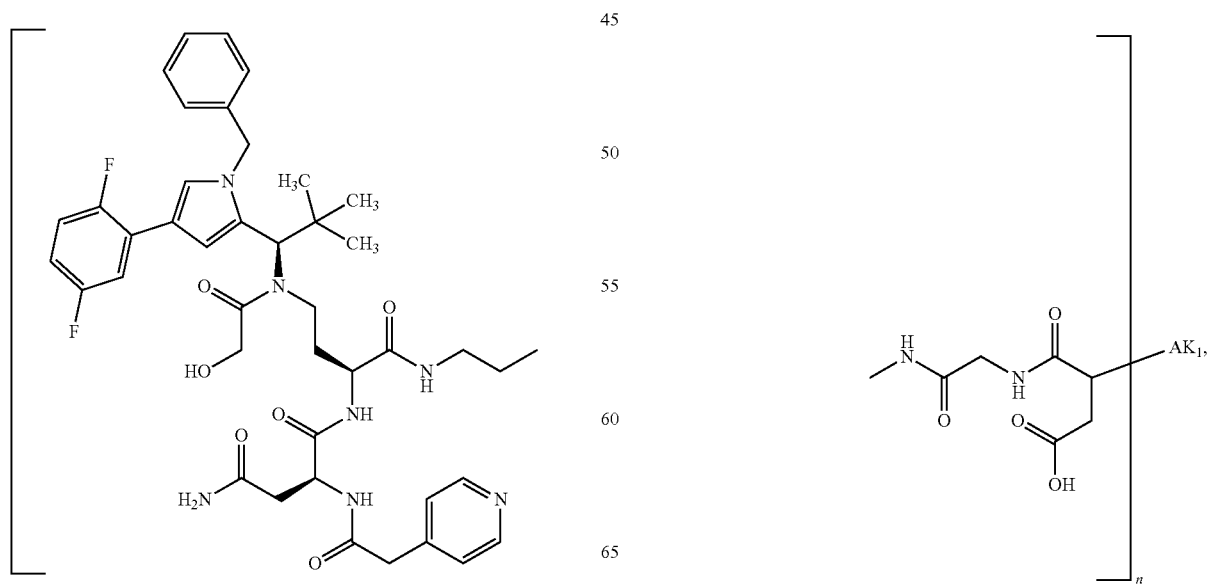

439
-continued
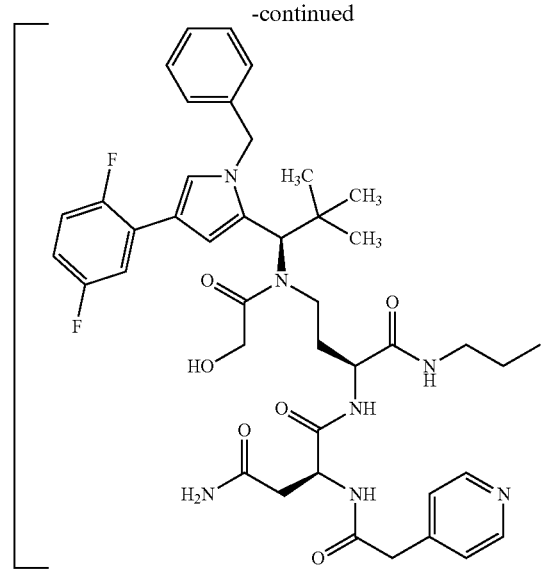
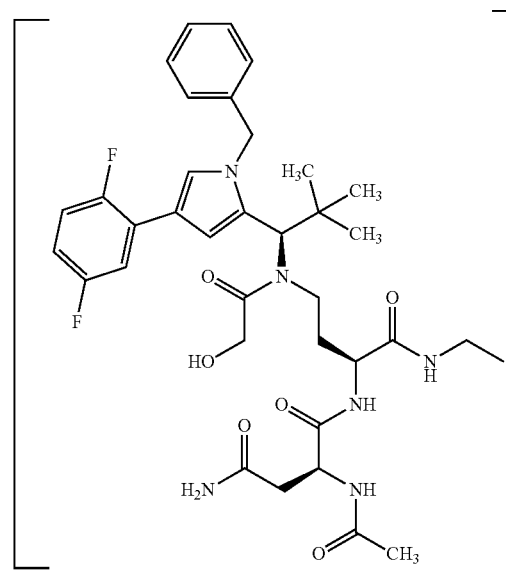
440
-continued
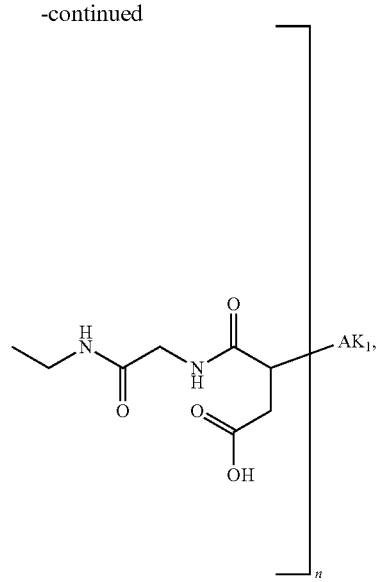
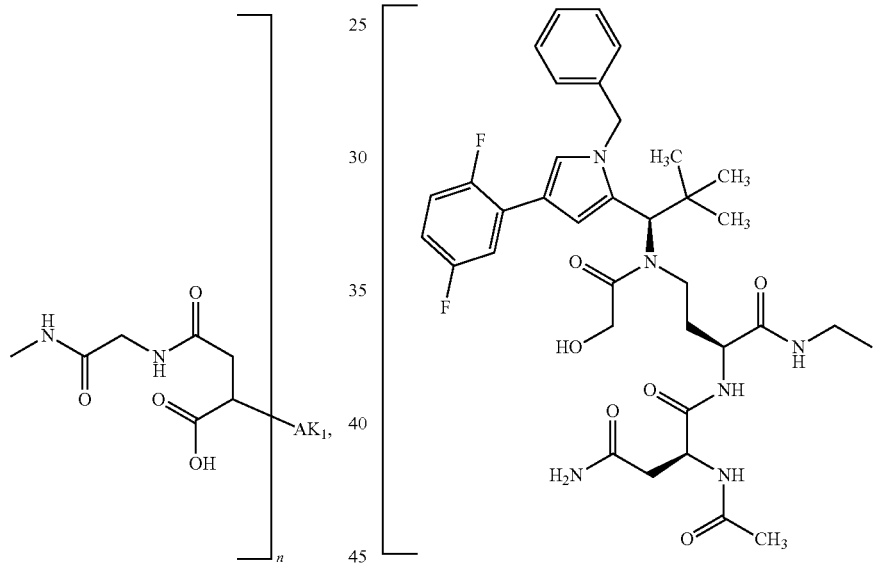
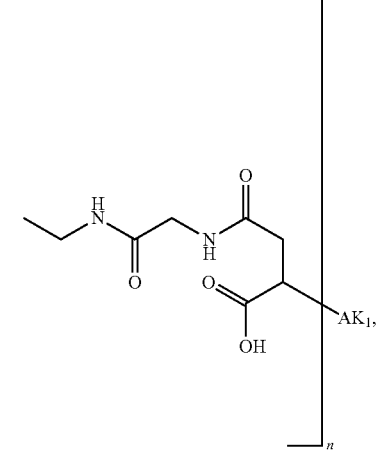

441
-continued
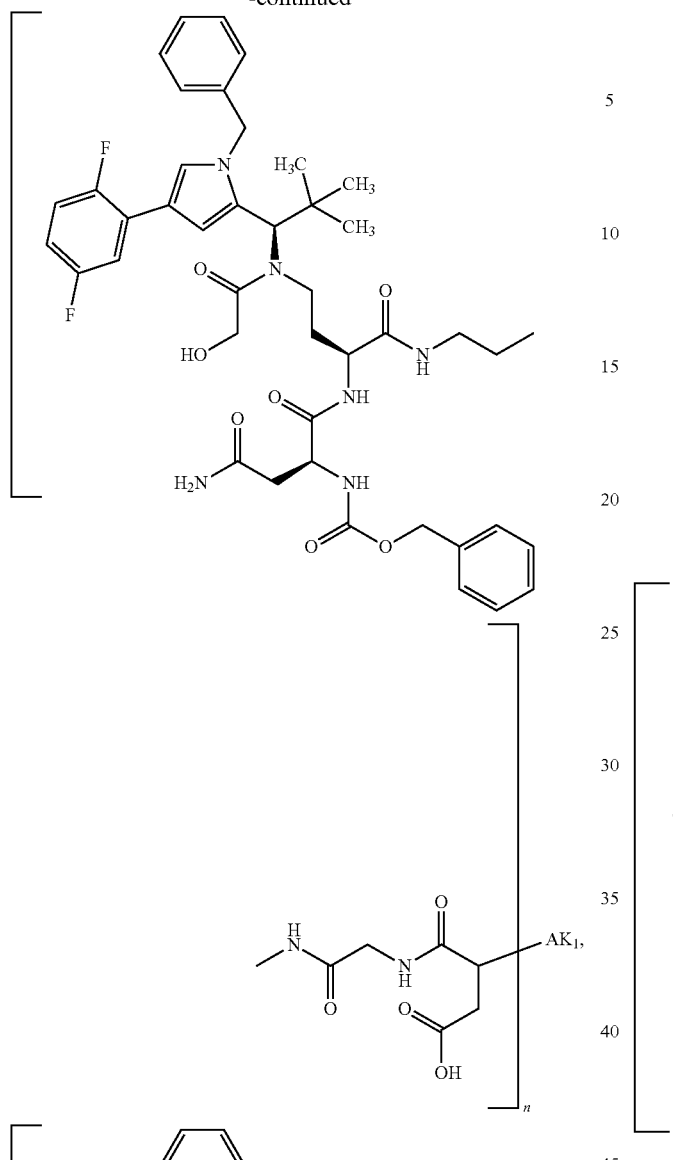
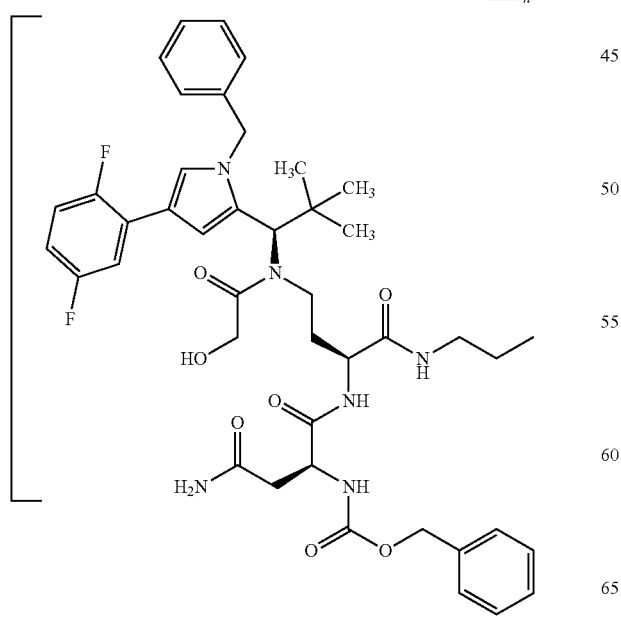
442
-continued
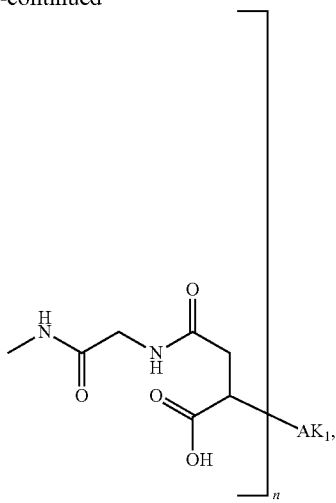
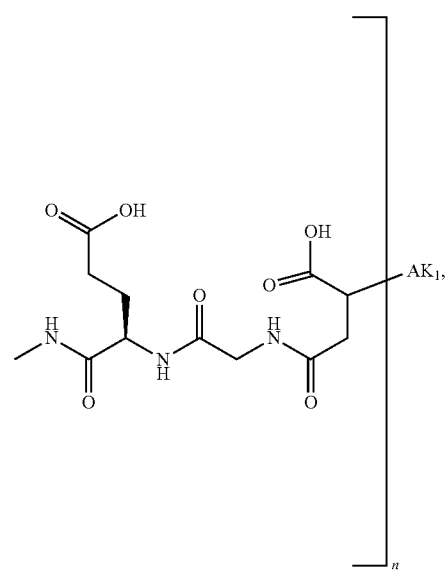

443
-continued
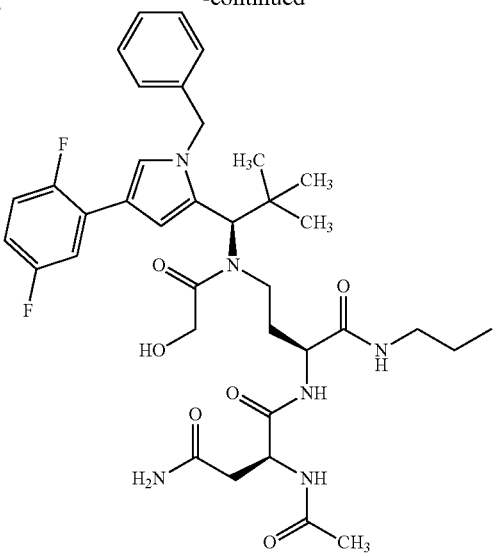
444
-continued
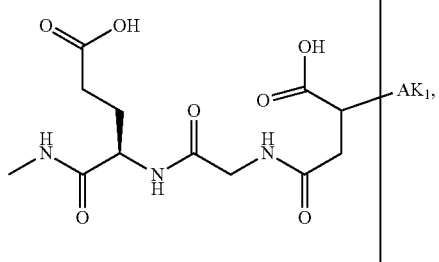
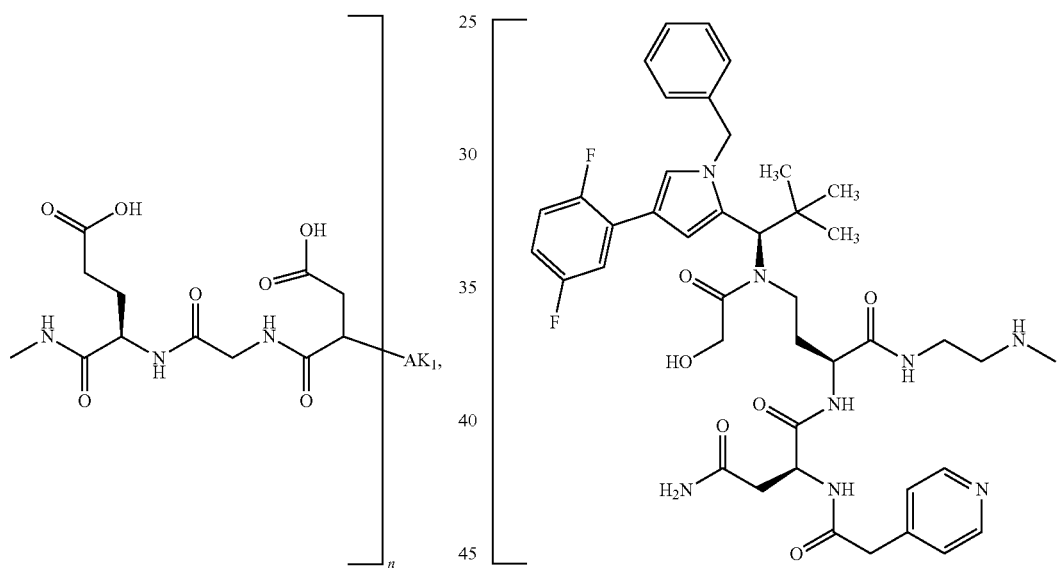
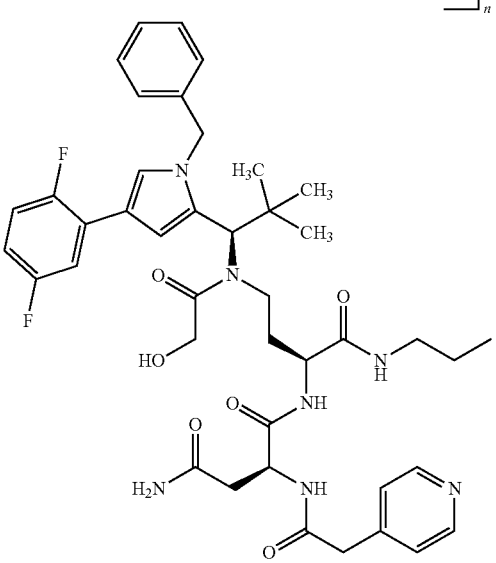
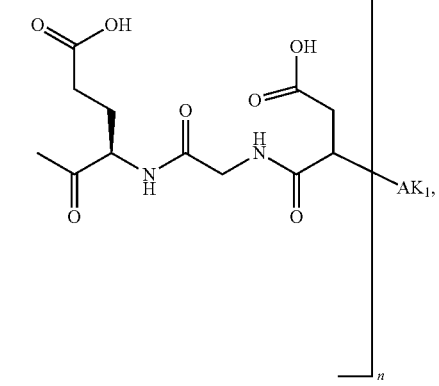

445
-continued
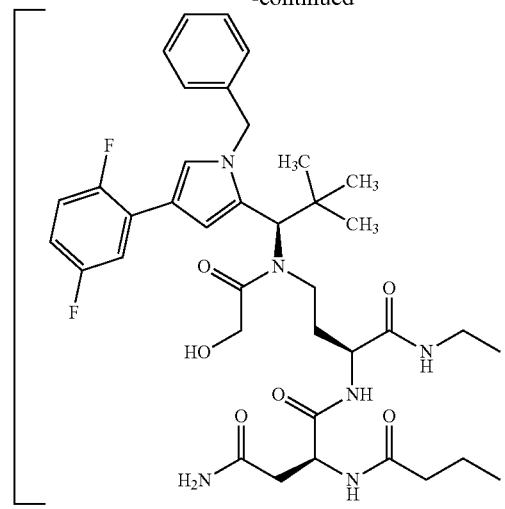
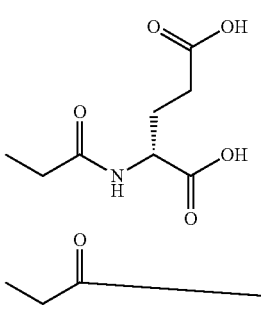
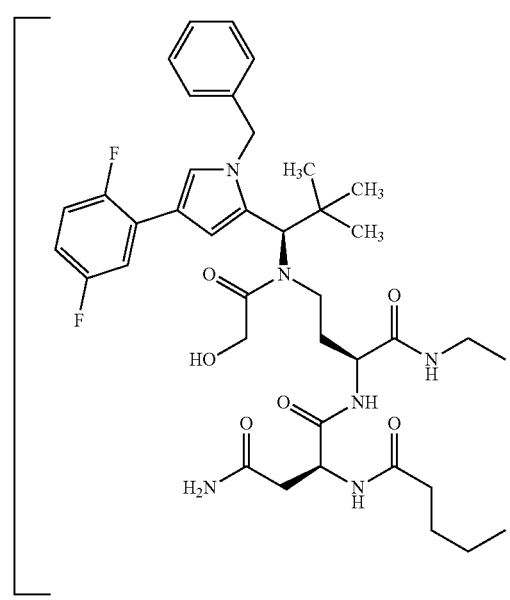
446
-continued
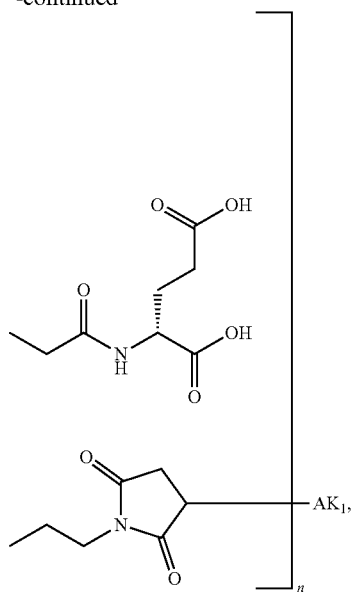
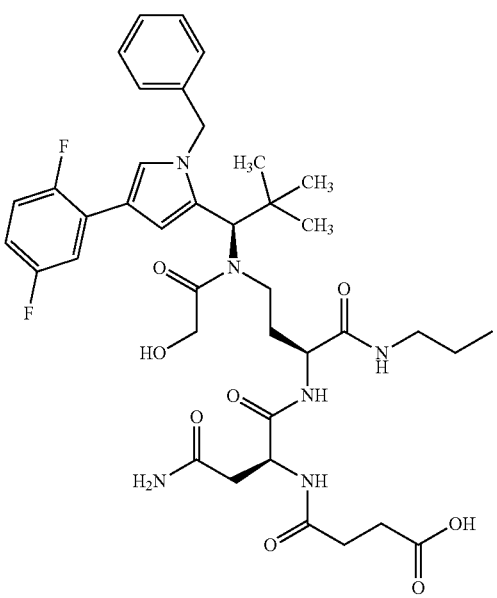
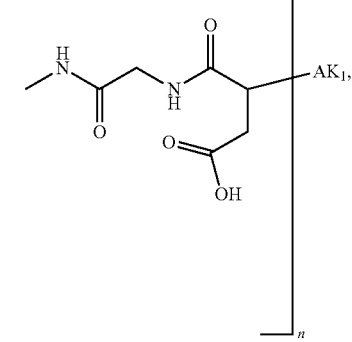

447
-continued
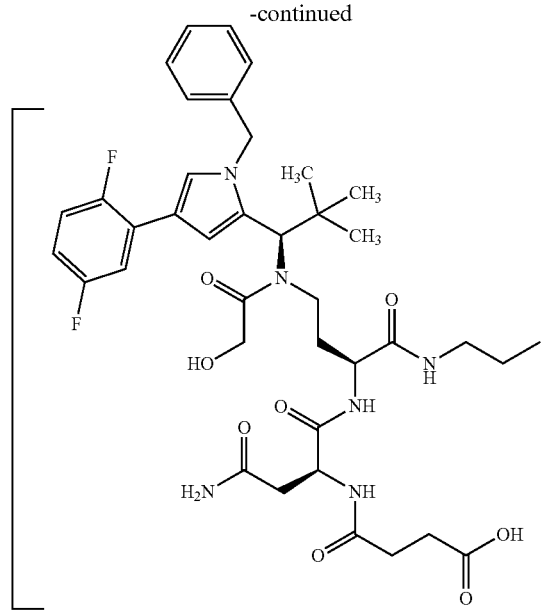
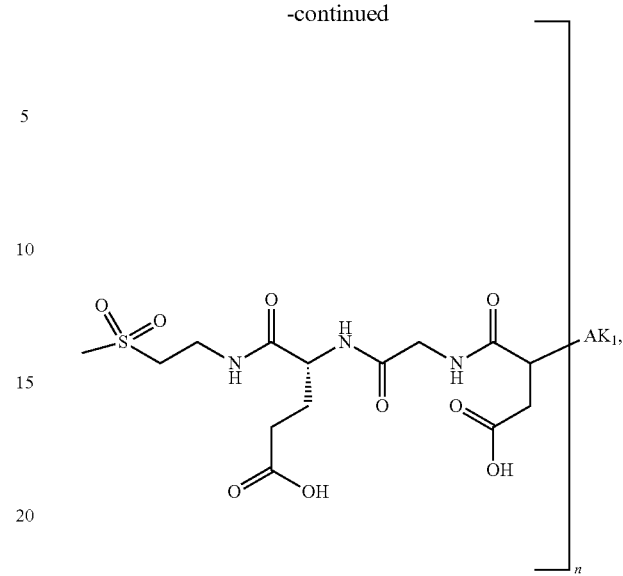
448
-continued
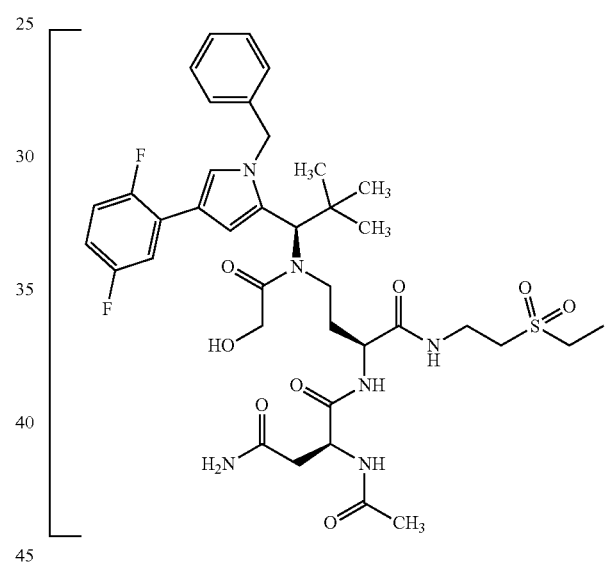
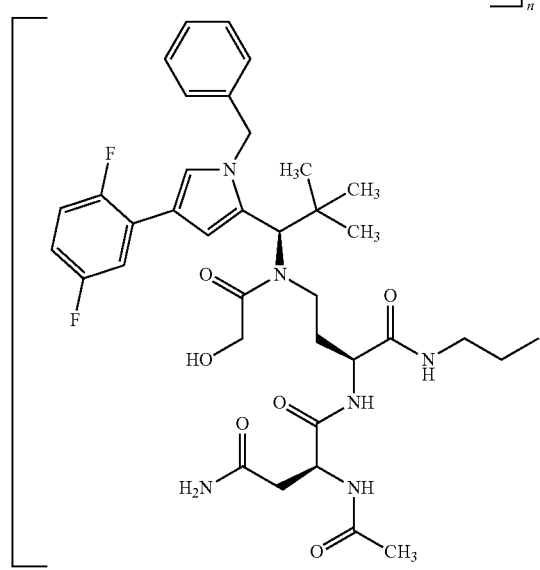
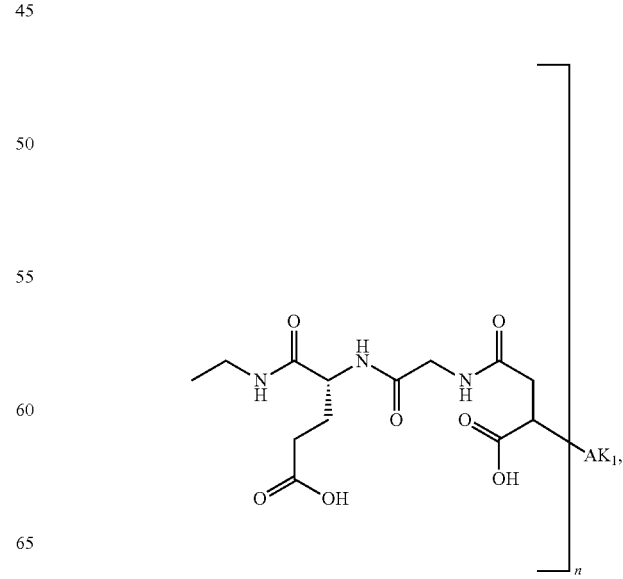

449
-continued
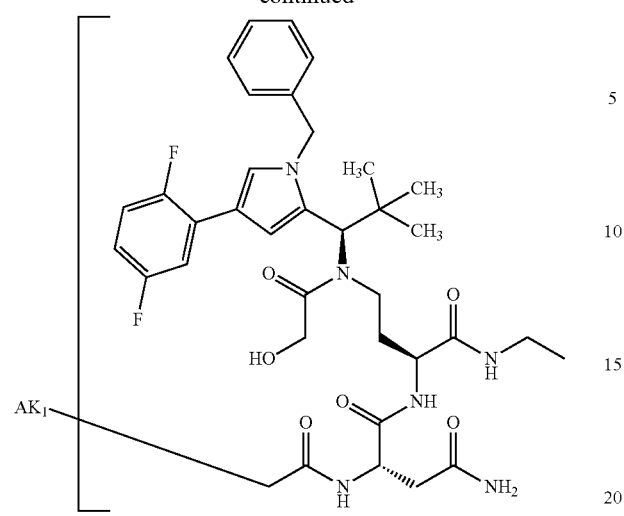
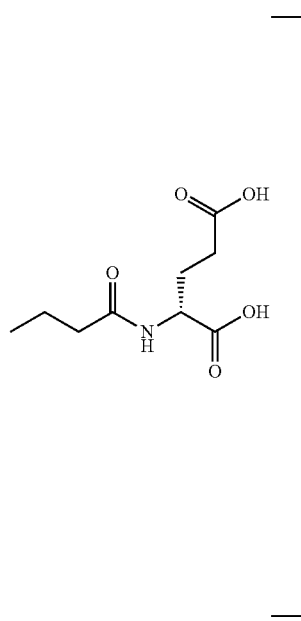
450
-continued
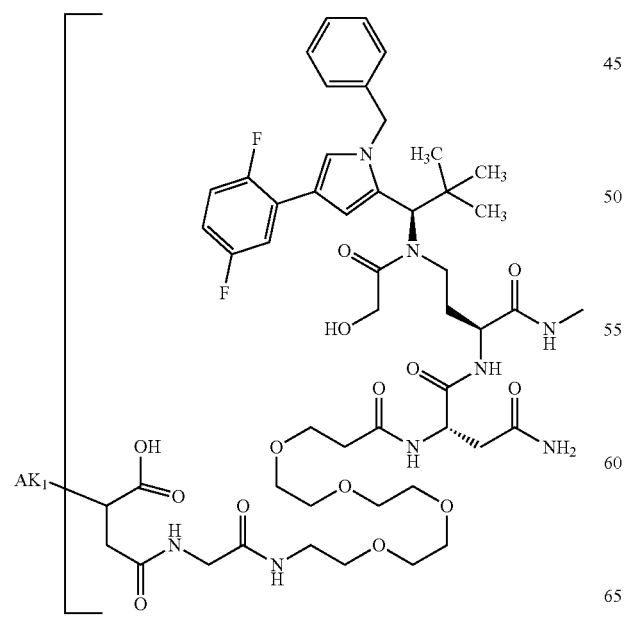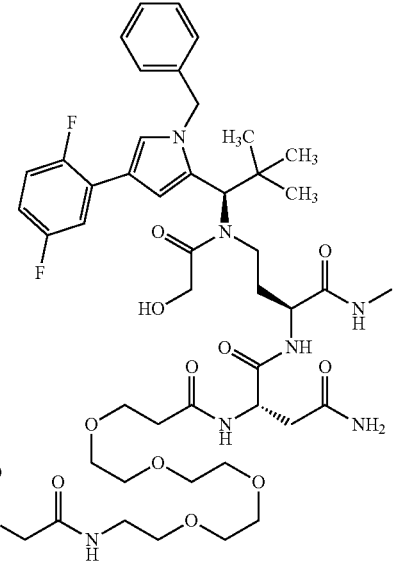

451
-continued
452
-continued
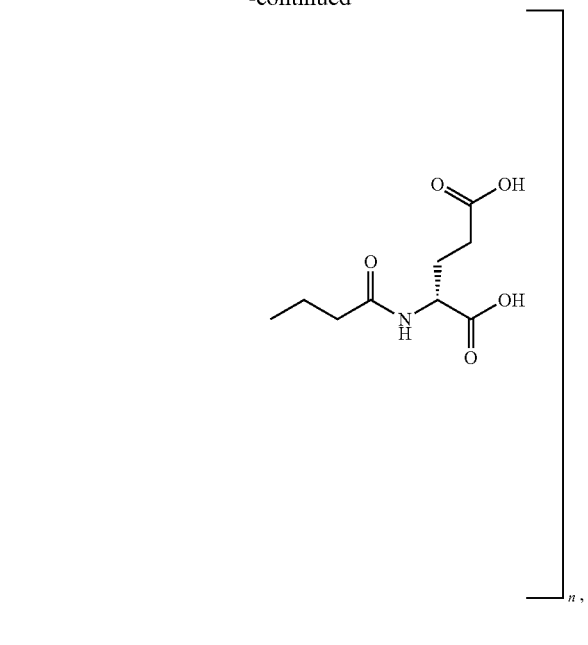
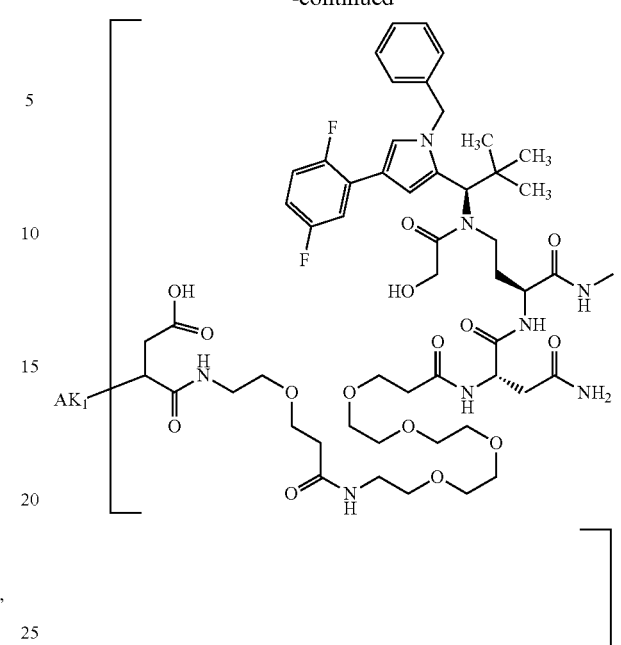
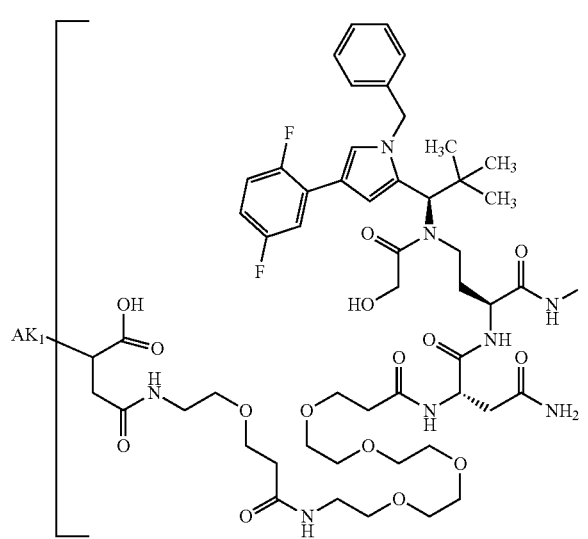
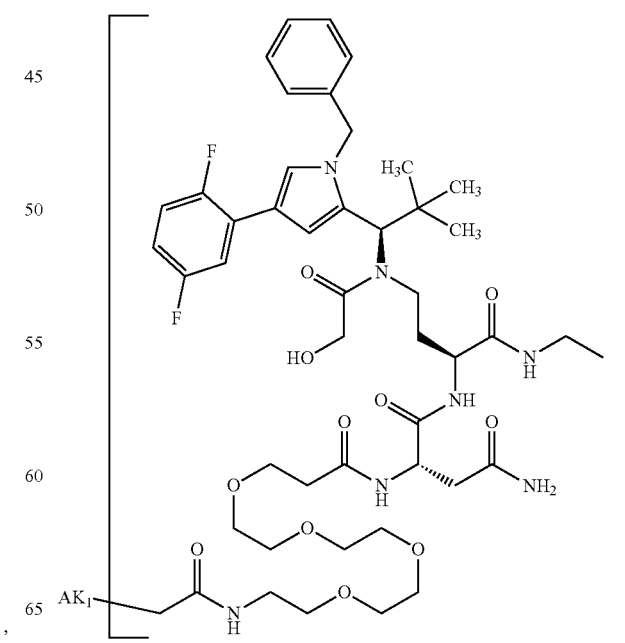

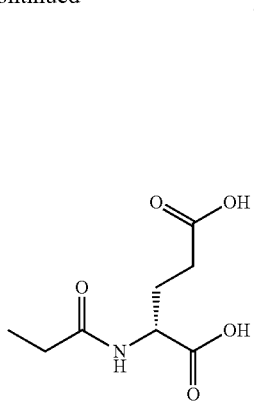

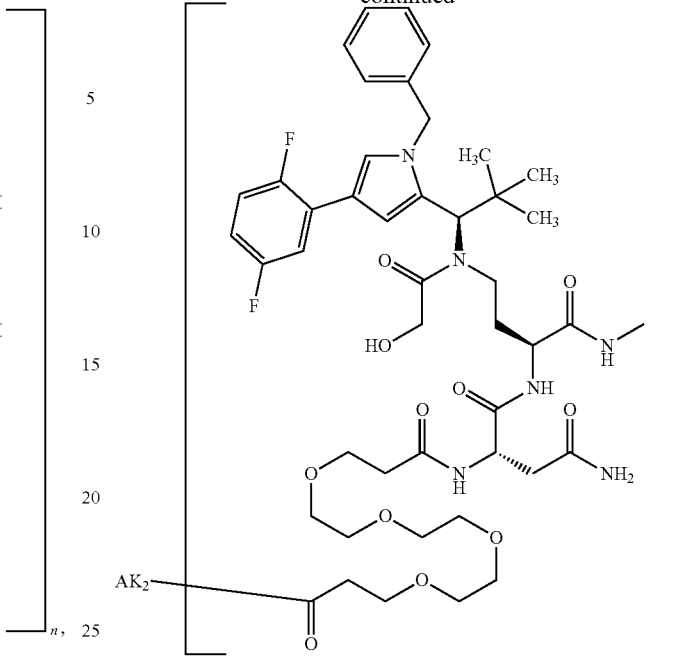

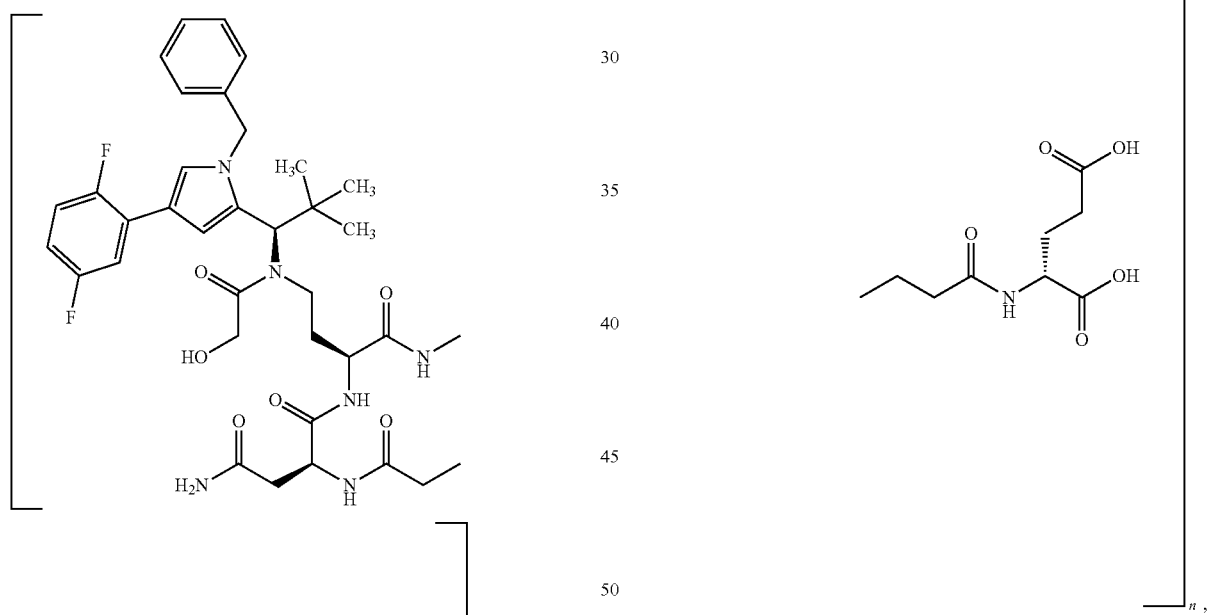

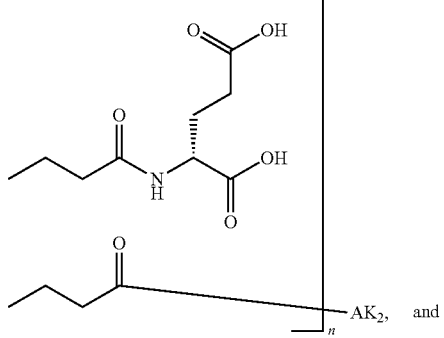

wherein
AK$_1$ and AK$_2$ is an antibody or an antigen-binding fragment thereof, and
n is a number from 1 to 50.

2. The compound according to claim 1, or a salt, a solvate, or a salt of a solvate thereof, wherein the antibody or the antigen-binding fragment thereof binds to an extracellular cancer target molecule.

3. The compound according to claim 2, or a salt, a solvate, or a salt of a solvate thereof, wherein the antibody or the antigen-binding fragment thereof, after binding to its extracellular target molecule on t-h a target cell, is internalized by the target cell through the binding.

4. The compound according to claim 1, or a salt, a solvate, or a salt of a solvate thereof, wherein the antibody is an anti-HER2 antibody, an anti-EGFR antibody, an anti-B7H3 antibody, an anti-TWEAKR antibody, or an antigen-binding fragment thereof.

5. The compound according to claim 4, or a salt, a solvate, or a salt of a solvate thereof, wherein the anti-HER2 antibody is trastuzumab.

6. The compound according to claim 1, or a salt, a solvate, or a salt of a solvate thereof, wherein the antibody (i) is an anti-EGFR antibody comprising a variable region of the heavy chain (VH) comprising the variable CDR1 sequence of the heavy chain (H-CDR1), as shown by SEQ ID NO: 2, the variable CDR2 sequence of the heavy chain (H-CDR2), as shown by SEQ ID NO: 3 and the variable CDR3 sequence of the heavy chain (H-CDR3), as shown by SEQ ID NO: 4, and a variable region of the light chain (VL) comprising the variable CDR1 sequence of the light chain (L-CDR1), as shown by SEQ ID NO: 6, the variable CDR2 sequence of the light chain (L-CDR2), as shown by SEQ ID NO: 7 and the variable CDR3 sequence of the light chain (L-CDR3), as shown by SEQ ID NO: 8, (ii) is an anti-HER2 antibody comprising a variable region of the heavy chain (VH) comprising the variable CDR1 sequence of the heavy chain (H-CDR1), as shown by SEQ ID NO: 12, the variable CDR2 sequence of the heavy chain (H-CDR2), as shown by SEQ ID NO: 13 and the variable CDR3 sequence of the heavy chain (H-CDR3), as shown by SEQ ID NO: 14, and a variable region of the light chain (VL) comprising the variable CDR1 sequence of the light chain (L-CDR1), as shown by SEQ ID NO: 16, the variable CDR2 sequence of the light chain (L-CDR2), as shown by SEQ ID NO: 17 and the variable CDR3 sequence of the light chain (L-CDR3), as shown by SEQ ID NO: 18, (iii) is an anti-TWEAKR antibody comprising a variable region of the heavy chain (VH) comprising the variable CDR1 sequence of the heavy chain (H-CDR1), as shown by SEQ ID NO: 22, the variable CDR2 sequence of the heavy chain (H-CDR2), as shown by SEQ ID NO: 23 and the variable CDR3 sequence of the heavy chain (H-CDR3), as shown by SEQ ID NO: 24, and a variable region of the light chain (VL) comprising the variable CDR1 sequence of the light chain (L-CDR1), as shown by SEQ ID NO: 26, the variable CDR2 sequence of the light chain (L-CDR2), as shown by SEQ ID NO: 27 and the variable CDR3 sequence of the light chain (L-CDR3), as shown by SEQ ID NO: 28, (iv) is an anti-TWEAKR antibody comprising a variable region of the heavy chain (VH) comprising the variable CDR1 sequence of the heavy chain (H-CDR1), as shown by SEQ ID NO: 32, the variable CDR2 sequence of the heavy chain (H-CDR2), as shown by SEQ ID NO: 33 and the variable CDR3 sequence of the heavy chain (H-CDR3), as shown by SEQ ID NO: 34, and a variable region of the light chain (VL) comprising the variable CDR1 sequence of the light chain (L-CDR1), as shown by SEQ ID NO: 36, the variable CDR2 sequence of the light chain (L-CDR2), as shown by SEQ ID NO: 37 and the variable CDR3 sequence of the light chain (L-CDR3), as shown by SEQ ID NO: 38, (v) is an anti-TWEAKR antibody comprising a variable region of the heavy chain (VH) comprising the variable CDR1 sequence of the heavy chain (H-CDR1), as shown by SEQ ID NO: 42, the variable CDR2 sequence of the heavy chain (H-CDR2), as shown by SEQ ID NO: 43 and the variable CDR3 sequence of the heavy chain (H-CDR3), as shown by SEQ ID NO: 44, and a variable region of the light chain (VL) comprising the variable CDR1 sequence of the light chain (L-CDR1), as shown by SEQ ID NO: 46, the variable CDR2 sequence of the light chain (L-CDR2), as shown by SEQ ID NO: 47 and the variable CDR3 sequence of the light chain (L-CDR3), as shown by SEQ ID NO: 48, (vi) is an anti-TWEAKR antibody comprising a variable region of the heavy chain (VH) comprising the variable CDR1 sequence of the heavy chain (H-CDR1), as shown by SEQ ID NO: 52, the variable CDR2 sequence of the heavy chain (H-CDR2), as shown by SEQ ID NO: 53 and the variable CDR3 sequence of the heavy chain (H-CDR3), as shown by SEQ ID NO: 54, and a variable region of the light chain (VL) comprising the variable CDR1 sequence of the light chain (L-CDR1), as shown by SEQ ID NO: 56, the variable CDR2 sequence of the light chain (L-CDR2), as shown by SEQ ID NO: 57 and the variable CDR3 sequence of the light chain (L-CDR3), as shown by SEQ ID NO: 58, (vii) is an anti-TWEAKR antibody comprising a variable region of the heavy chain (VH) comprising the variable CDR1 sequence of the heavy chain (H-CDR1), as shown by SEQ ID NO: 62, the variable CDR2 sequence of the heavy chain (H-CDR2), as shown by SEQ ID NO: 63 and the variable CDR3 sequence of the heavy chain (H-CDR3), as shown by SEQ ID NO: 64, and a variable region of the light chain (VL) comprising the variable CDR1 sequence of the light chain (L-CDR1), as shown by SEQ ID NO: 66, the variable CDR2 sequence of the light chain (L-CDR2), as shown by SEQ ID NO: 67 and the variable CDR3 sequence of the light chain (L-CDR3), as shown by SEQ ID NO: 68, (viii) is an anti-HER2 antibody comprising a variable region of the heavy chain (VH) comprising the variable CDR1 sequence of the heavy chain (H-CDR1), as shown by SEQ ID NO: 72, the variable CDR2 sequence of the heavy chain (H-CDR2), as shown by SEQ ID NO: 73 and the variable CDR3 sequence of the heavy chain (H-CDR3), as shown by SEQ ID NO: 74, and a variable region of the light chain (VL) comprising the variable CDR I sequence of the light chain (L-CDR1), as shown by SEQ ID NO: 76, the variable CDR2 sequence of the light chain (L-CDR2), as shown by SEQ ID NO: 77 and the variable CDR3 sequence of the light chain (L-CDR3), as shown by SEQ ID NO: 78, (ix) is an anti-HER2 antibody comprising a variable region of the heavy chain (VH) comprising the variable CDR1 sequence of the heavy chain (H-CDR1), as shown by SEQ ID NO: 82, the variable CDR2 sequence of the heavy chain (H-CDR2), as shown by SEQ ID NO: 83 and the variable CDR3 sequence of the heavy chain (H-CDR3), as shown by SEQ ID NO: 84, and a variable region of the light chain (VL) comprising the variable CDR1 sequence of the light chain (L-CDR1), as shown by SEQ ID NO: 86, the variable CDR2 sequence of the light chain (L-CDR2), as shown by SEQ ID NO: 87 and the variable CDR3 sequence of the light chain (L-CDR3), as shown by SEQ ID NO: 88, (x) is an anti-B7H3 antibody comprising a variable region of the heavy chain (VH) comprising the variable CDR1 sequence of the heavy chain (H-CDR1), as shown by SEQ ID NO: 92, the variable CDR2 sequence of the heavy chain (H-CDR2), as shown by SEQ ID NO: 93 and the variable CDR3 sequence of the heavy chain (H-CDR3), as shown by SEQ ID NO: 94, and a variable region of the light chain (VL) comprising the variable CDR1 sequence of the light chain (L-CDR1), as shown by SEQ ID NO: 96, the variable CDR2 sequence of the light chain (L-CDR2), as shown by SEQ ID NO: 97 and the variable CDR3 sequence of the light chain (L-CDR3), as shown by SEQ ID NO: 98, (xi) is an anti-B7H3 antibody comprising a variable region of the heavy chain (VH) comprising the variable CDR1 sequence of the heavy chain (H-CDR1), as shown by SEQ ID NO: 102, the variable CDR2 sequence of the heavy chain (H-CDR2), as shown by SEQ ID NO: 103 and the variable CDR3 sequence of the heavy chain (H-CDR3), as shown by SEQ ID NO: 104, and a variable region of the light chain (VL) comprising the variable CDR1 sequence of the light chain (L-CDR1), as shown by SEQ ID NO: 106, the variable CDR2 sequence of the light chain (L-CDR2), as shown by SEQ ID NO: 107 and the variable CDR3 sequence of the light chain (L-CDR3), as shown by SEQ ID NO: 108, (xii) is an anti-TWEAKR antibody comprising a variable region of the heavy chain (VH) comprising the variable CDR1 sequence of the heavy chain (H-CDR1), as shown by SEQ ID NO: 112, the variable CDR2 sequence of the heavy chain (H-CDR2), as shown by SEQ ID NO: 113 and the variable CDR3 sequence of the heavy chain (H-CDR3), as shown by SEQ ID NO: 114, and a variable region of the light chain (VL) comprising the variable CDR1 sequence of the light chain (L-CDR1), as shown by SEQ ID NO: 116, the variable CDR2 sequence of the light chain (L-CDR2), as shown by SEQ ID NO: 117 and the variable CDR3 sequence of the light chain (L-CDR3), as shown by SEQ ID NO: 118, (xiii) is an anti-TWEAKR antibody comprising a variable region of the heavy chain (VH) comprising the variable CDR1 sequence of the heavy chain (H-CDR1), as shown by SEQ ID NO: 122, the variable CDR2 sequence of the heavy chain (H-CDR2), as shown by SEQ ID NO: 123 and the variable CDR3 sequence of the heavy chain (H-CDR3), as shown by SEQ ID NO: 124, and a variable region of the light chain (VL) comprising the variable CDR1 sequence of the light chain (L-CDR1), as shown by SEQ ID NO: 126, the variable CDR2 sequence of the light chain (L-CDR2), as shown by SEQ ID NO: 127 and the variable CDR3 sequence of the light chain (L-CDR3), as shown by SEQ ID NO: 128, (xiv) is an anti-TWEAKR antibody comprising a variable region of the heavy chain (VH) comprising the variable CDR1 sequence of the heavy chain (H-CDR1), as shown by SEQ ID NO: 132, the variable CDR2 sequence of the heavy chain (H-CDR2), as shown by SEQ ID NO: 133 and the variable CDR3 sequence of the heavy chain (H-CDR3), as shown by SEQ ID NO: 134, and a variable region of the light chain (VL) comprising the variable CDR1 sequence of the light chain (L-CDR1), as shown by SEQ ID NO: 136, the variable CDR2 sequence of the light chain (L-CDR2), as shown by SEQ ID NO: 137 and the variable CDR3 sequence of the light chain (L-CDR3), as shown by SEQ ID NO: 138, (xv) is an anti-TWEAKR antibody comprising a variable region of the heavy chain (VH) comprising the variable CDR1 sequence of the heavy chain (H-CDR1), as shown by SEQ ID NO: 142, the variable CDR2 sequence of the heavy chain (H-CDR2), as shown by SEQ ID NO: 143 and the variable CDR3 sequence of the heavy chain (H-CDR3), as shown by SEQ ID NO: 144, and a variable region of the light chain (VL) comprising the variable CDR1 sequence of the light chain (L-CDR1), as shown by SEQ ID NO: 146, the variable CDR2 sequence of the light chain (L-CDR2), as shown by SEQ ID NO: 147 and the variable CDR3 sequence of the light chain (L-CDR3), as shown by SEQ ID NO: 148, or (xvi) is an anti-TWEAKR antibody comprising a variable region of the heavy chain (VH) comprising the variable CDR1 sequence of the heavy chain (H-CDR1), as shown by SEQ ID NO: 152, the variable CDR2 sequence of the heavy chain (H-CDR2), as shown by SEQ ID NO: 153 and the variable CDR3 sequence of the heavy chain (H-CDR3), as shown by SEQ ID NO: 154, and a variable region of the light chain (VL) comprising the variable CDR1 sequence of the light chain (L-CDR1), as shown by SEQ ID NO: 156, the variable CDR2 sequence of the light chain (L-CDR2), as shown by SEQ ID NO: 157 and the variable CDR3 sequence of the light chain (L-CDR3), as shown by SEQ ID NO: 158, or is an antigen-binding fragment of these antibodies.

7. The compound according to claim 1, or a salt, a solvate, or a salt of a solvate thereof, wherein the antibody (i) is an anti-EGFR antibody comprising a variable region of the heavy chain (VH) as shown by SEQ ID NO: 1 and a variable region of the light chain (VL) as shown by SEQ ID NO: 5, (ii) is an anti-HER2 antibody comprising a variable region of the heavy chain (VH) as shown by SEQ ID NO: 11 and a variable region of the light chain (VL) as shown by SEQ ID NO: 15, (iii) is an anti-TWEAKR antibody comprising a variable region of the heavy chain (VH) as shown by SEQ ID NO: 21 and a variable region of the light chain (VL) as shown by SEQ ID NO: 25, (iv) is an anti-TWEAKR antibody comprising a variable region of the heavy chain (VH) as shown by SEQ ID NO: 31 and a variable region of the light chain (VL) as shown by SEQ ID NO: 35, (v) is an anti-TWEAKR antibody comprising a variable region of the heavy chain (VH) as shown by SEQ ID NO: 41 and a variable region of the light chain (VL) as shown by SEQ ID NO: 45, (vi) is an anti-TWEAKR antibody comprising a variable region of the heavy chain (VH) as shown by SEQ ID NO: 51 and a variable region of the light chain (VL) as shown by SEQ ID NO: 55, (vii) is an anti-TWEAKR antibody comprising a variable region of the heavy chain (VH) as shown by SEQ ID NO: 61 and a variable region of the light chain (VL) as shown by SEQ ID NO: 65, (viii) is an anti-HER2 antibody comprising a variable region of the heavy chain (VH) as shown by SEQ ID NO: 71 and a variable region of the light chain (VL) as shown by SEQ ID NO: 75, (ix) is an anti-HER2 antibody comprising a variable region of the heavy chain (VH) as shown by SEQ ID NO: 81 and a variable region of the light chain (VL) as shown by SEQ IDNO: 85, (x) is an anti-B7H3 antibody comprising a variable region of the heavy chain (VH) as shown by SEQ ID NO: 91 and a variable region of the light chain (VL) as shown by SEQ IDNO: 95, (xi) is an anti-B7H3 antibody comprising a variable region of the heavy chain (VH) as shown by SEQ ID NO: 101 and a variable region of the light chain (VL) as shown by SEQ ID NO: 105,
(xii) is an anti-TWEAKR antibody comprising a variable region of the heavy chain (VH) as shown by SEQ ID NO: 111 and a variable region of the light chain (VL) as shown by SEQ ID NO: 115,
(xiii) is an anti-TWEAKR antibody comprising a variable region of the heavy chain (VH) as shown by SEQ ID NO: 121 and a variable region of the light chain (VL) as shown by SEQ ID NO: 125,
(xiv) is an anti-TWEAKR antibody comprising a variable region of the heavy chain (VH) as shown by SEQ ID NO: 131 and a variable region of the light chain (VL) as shown by SEQ ID NO: 135,
(xv) is an anti-TWEAKR antibody comprising a variable region of the heavy chain (VH) as shown by SEQ ID NO: 141 and a variable region of the light chain (VL) as shown by SEQ ID NO: 145, or
(xvi) is an anti-TWEAKR antibody comprising a variable region of the heavy chain (VH) as shown by SEQ ID NO: 151 and a variable region of the light chain (VL) as shown by SEQ ID NO: 155,
or is an antigen-binding fragment of these antibodies.

8. The compound according to claim 1, or a salt, a solvate, or a salt of a solvate thereof, wherein the antibody
(i) is an anti-EGFR antibody comprising a region of the heavy chain as shown by SEQ ID NO: 9 and a region of the light chain as shown by SEQ ID NO: 10,
(ii) is an anti-HER2 antibody comprising a region of the heavy chain as shown by SEQ ID NO: 19 and a region of the light chain as shown by SEQ ID NO: 20,
(iii) is an anti-TWEAKR antibody comprising a region of the heavy chain as shown by SEQ ID NO: 29 and a region of the light chain as shown by SEQ ID NO: 30,
(iv) is an anti-TWEAKR antibody comprising a region of the heavy chain as shown by SEQ ID NO: 39 and a region of the light chain as shown by SEQ ID NO: 40,
(v) is an anti-TWEAKR antibody comprising a region of the heavy chain as shown by SEQ ID NO: 49 and a region of the light chain as shown by SEQ ID NO: 50,
(vi) is an anti-TWEAKR antibody comprising a region of the heavy chain as shown by SEQ ID NO: 59 and a region of the light chain as shown by SEQ ID NO: 60,
(vii) is an anti-TWEAKR antibody comprising a region of the heavy chain as shown by SEQ ID NO: 69 and a region of the light chain as shown by SEQ ID NO: 70,
(viii) is an anti-HER2 antibody comprising a region of the heavy chain as shown by SEQ ID NO: 79 and a region of the light chain as shown by SEQ ID NO: 80,
(ix) is an anti-HER2 antibody comprising a region of the heavy chain as shown by SEQ ID NO: 89 and a region of the light chain as shown by SEQ ID NO: 90,
(x) is an anti-B7H3 antibody comprising a region of the heavy chain as shown by SEQ ID NO: 99 and a region of the light chain as shown by SEQ ID NO: 100,
(xi) is an anti-B7H3 antibody comprising a region of the heavy chain as shown by SEQ ID NO: 109 and a region of the light chain as shown by SEQ ID NO: 110,
(xii) is an anti-TWEAKR antibody comprising a region of the heavy chain as shown by SEQ ID NO: 119 and a region of the light chain as shown by SEQ ID NO: 120,
(xiii) is an anti-TWEAKR antibody comprising a region of the heavy chain as shown by SEQ ID NO: 129 and a region of the light chain as shown by SEQ ID NO: 130,
(xiv) is an anti-TWEAKR antibody comprising a region of the heavy chain as shown by SEQ ID NO: 139 and a region of the light chain as shown by SEQ ID NO: 140,
(xv) is an anti-TWEAKR antibody comprising a region of the heavy chain as shown by SEQ ID NO: 149 and a region of the light chain as shown by SEQ ID NO: 150, or
(xvi) is an anti-TWEAKR antibody comprising a region of the heavy chain as shown by SEQ ID NO: 159 and a region of the light chain as shown by SEQ ID NO: 160,
or is an antigen-binding fragment of these antibodies.

9. A pharmaceutical composition comprising the compound according to claim 1, or a salt, a solvate, or a salt of a solvate thereof, in combination with an inert non-toxic pharmaceutically suitable excipient.

10. A method for treatment of hyperproliferative and/or angiogenic disorders, comprising administering to a human in need thereof an effective amount of the compound according to claim 1, or a salt, a solvate, or a salt of a solvate thereof.

11. A method for treatment of cancer and tumors, comprising administering to a human in need thereof an effective amount of the compound according to claim 1, or a salt, a solvate, or a salt of a solvate thereof.

12. A method for treatment of cancer and tumors, comprising administering to a human in need thereof an effective amount of the compound according to claim 1, or a salt, a solvate, or a salt of a solvate thereof, in combination with one or more therapeutic approaches for cancer immunotherapy or with one or more drugs directed against a molecular target from cancer immunotherapy.

13. The compound according to claim 1, or a salt, a solvate, or a salt of a solvate thereof, wherein the AK1 antibody or antigen-binding fragment thereof is bound via a cysteine residue of the antibody or antigen-binding fragment thereof, or the AK2 antibody or antigen-binding fragment thereof is bound via a lysine residue of the antibody or antigen-binding fragment thereof.

14. The compound according to claim 13, or a salt, a solvate, or a salt of a solvate thereof, wherein the AK1 antibody or antigen-binding fragment thereof is bound via a cysteine residue of the antibody or antigen-binding fragment thereof.

15. The compound according to claim 13, or a salt, a solvate, or a salt of a solvate thereof, wherein the AK2 antibody or antigen-binding fragment thereof is bound via a lysine residue of the antibody or antigen-binding fragment thereof.

* * * * *